US012577206B2

(12) United States Patent
Johnson et al.

(10) Patent No.: US 12,577,206 B2
(45) Date of Patent: Mar. 17, 2026

(54) PYRAZOLONE FORMYL PEPTIDE 2 RECEPTOR AGONISTS

(71) Applicant: BRISTOL-MYERS SQUIBB COMPANY, Princeton, NJ (US)

(72) Inventors: James A. Johnson, Pennington, NJ (US); Zulan Pi, Pennington, NJ (US); Nicholas R. Wurtz, Pennington, NJ (US); Joanne M. Smallheer, Hernando, FL (US); Meriah Neissel Valente, Bedminister, NJ (US); Ellen K. Kick, Pennington, NJ (US); Charles G. Clark, Cherry Hill, NJ (US); Pravin Sudhakar Shirude, Bangalore (IN); Balaji Seshadri, Hosur (IN); Amit Kumar Chattopadhyay, Bangalore (IN)

(73) Assignee: Bristol-Myers Squibb Company, Princeton, NJ (US)

( * ) Notice: Subject to any disclaimer, the term of this patent is extended or adjusted under 35 U.S.C. 154(b) by 556 days.

(21) Appl. No.: 18/004,722

(22) PCT Filed: Jul. 8, 2021

(86) PCT No.: PCT/US2021/040793
§ 371 (c)(1),
(2) Date: Jan. 9, 2023

(87) PCT Pub. No.: WO2022/011083
PCT Pub. Date: Jan. 13, 2022

(65) Prior Publication Data

US 2023/0250063 A1 Aug. 10, 2023

Related U.S. Application Data

(60) Provisional application No. 63/049,831, filed on Jul. 9, 2020.

(51) Int. Cl.

| | |
|---|---|
| *C07D 231/50* | (2006.01) |
| *C07D 401/04* | (2006.01) |
| *C07D 401/14* | (2006.01) |
| *C07D 405/14* | (2006.01) |
| *C07D 413/14* | (2006.01) |
| *C07D 451/02* | (2006.01) |

(52) U.S. Cl.
CPC ......... *C07D 231/50* (2013.01); *C07D 401/04* (2013.01); *C07D 401/14* (2013.01); *C07D 405/14* (2013.01); *C07D 413/14* (2013.01); *C07D 451/02* (2013.01)

(58) Field of Classification Search
CPC .. C07D 231/50; C07D 401/04; C07D 401/14; C07D 405/14; C07D 413/14; C07D 451/02; C07D 403/04; C07D 407/14; C07D 413/06; C07D 487/08; C07D 491/10; C07D 231/44; A61P 9/00; A61P 11/00
See application file for complete search history.

(56) References Cited

U.S. PATENT DOCUMENTS

| | | | |
|---|---|---|---|
| 9,822,069 B2 | 11/2017 | Takahashi et al. |
| 2009/0069340 A1 | 3/2009 | Balestra et al. |
| 2010/0056505 A1 | 3/2010 | Lee et al. |
| 2017/0088545 A1 | 3/2017 | Arista et al. |

FOREIGN PATENT DOCUMENTS

| | | | |
|---|---|---|---|
| CN | 106661012 | A | 5/2017 |
| WO | 2004106306 | A1 | 12/2004 |
| WO | 2016189876 | A1 | 12/2016 |
| WO | 2016189877 | A1 | 12/2016 |
| WO | 2017091496 | A1 | 6/2017 |
| WO | 2017100390 | A1 | 6/2017 |
| WO | 2018217684 | A1 | 11/2018 |
| WO | 2018227058 | A9 | 12/2018 |
| WO | 2018227061 | A1 | 12/2018 |
| WO | 2018227065 | A1 | 12/2018 |
| WO | 2018227067 | A1 | 12/2018 |
| WO | 2019173182 | A1 | 9/2019 |
| WO | 2020112583 | A1 | 6/2020 |

OTHER PUBLICATIONS

CAS Registry No. 306280-34-2, entered STN on Dec. 4, 2000 (Year: 2000).*

(Continued)

*Primary Examiner* — Joseph K Mckane
*Assistant Examiner* — Anna Grace Kuckla
(74) *Attorney, Agent, or Firm* — Hong Liu

(57) ABSTRACT

The disclosure relates to compounds of formula I, which are formyl peptide 2 (FPR2) receptor agonists. The disclosure also provides compositions and methods of using the compounds, for example, for the treatment of atherosclerosis, heart failure, chronic obstructive pulmonary disease (COPD), and related diseases.

I

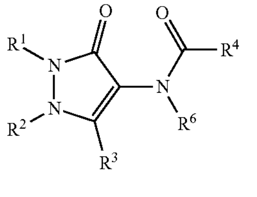

27 Claims, No Drawings

(56) References Cited

OTHER PUBLICATIONS

Boström J, Hogner A, Llinás A, Wellner E, Plowright AT. Oxadiazoles in medicinal chemistry. J Med Chem. Mar. 8, 2012;55(5):1817-30. doi: 10.1021/jm2013248. Epub Jan. 13, 2012. PMID: 22185670. (Year: 2012).*

Shalini K, Kumar N, Drabu S, Sharma PK. Advances in synthetic approach to and antifungal activity of triazoles. Beilstein J Org Chem. 2011;7:668-77. doi: 10.3762/bjoc.7.79. Epub May 25, 2011. PMID: 21804864; PMCID: PMC3135122. (Year: 2011).*

Allen, Jr., Loyd V., "Remington: The Science and Practice of Pharmacy, vol. I and vol. II. Twenty-second edition", Pharmaceutical Press, 2012, p. 2724.

Burli et al., "Potent hFPRLI (ALXR) agonists as potential anti-inflammatory agents", Bioorganic & Medicinal Chemistry Letters, vol. 16(14), pp. 3713-3718 (2006).

Cattaneo et al., "Distinct Signaling Cascades Elicited by Different Formyl Peptide Receptor 2 (FPR2) Agonists" Int. J. Mol. Sci., vol. 14, pp. 7193-7230 (2013).

Chandrasekharan et al., "Lipoxins: nature's way to resolve inflammation", Journal of Inflammation Research, 2015:8 181-192.

Chen et al., "Regulation of inflammation by members of the formyl-peptide receptor family", Journal of Autoimmunity vol. 85, pp. 64-77 (2017).

Fredman et al.,"Targeted nanoparticles containing the pro resolving peptide Ac2-26 protect against advanced atherosclerosis in hypercholesterolemic mice", Sci. Trans. Med., vol. 7(275) 2015.

Gavins, Felicity N.E., "Are formyl peptide receptors novel targets for therapeutic intervention ischaemia-reperfusion injury?" Trends in Pharmacological Sciences, vol. 31(6), pp. 266-276 (2010).

Greene, T.W. et al., Protecting Groups in Organic Synthesis, 4th Edition, Wiley (2007).

Kain et al., "Resolvin D1 activates the inflammation resolving response at splenic and ventricular site following myocardial infarction leading to improved ventricular function", Journal of Molecular and Cellular Cardiology, vol. 84, pp. 24-35 (2015).

Kirpotina et al., "Identification of Novel Small-Molecule Agonists for Human Formyl Peptide Receptors and Pharmacophore Models of Their Recognition", Molecular Pharmacology, vol. 77(2), pp. 159-170 (2010).

Liu et al., "Lipoxin A4 ameliorates ischemia/reperfusion induced spinal cord injury in rabbit model", Int. J. Clin.Exp. Medicine, Vo. 8(8), pp. 12826-12833 (2015.

Perretti, et al., "Resolution Pharmacology: Opportunities for Therapeutic Innovationin Inflammation", Trends in Pharmacological Sciences, vol. 36(11) 2015.

Petri et al., "The role of the FPR2/ALX receptor in atherosclerosis development and plaque stability", Cardiovascular Research, vol. 105, pp. 65-74 (2015).

Romano et al., "Lipoxins and aspirin-triggered lipoxinsin resolution of inflammation", European Journal of Pharmacology vol. 760 pp. 49-63 (2015).

Stepniewski et al., "Non-peptide ligand binding to the formyl peptide receptor FPR2-A comparison to peptide ligand binding modes", Bioorg Med Chem., vol. 23, pp. 4072-4081 (2015).

Ye et al., "International Union of Basic and Clinical Pharmacology. LXXIII. Nomenclature for the Formyl Peptide Receptor (FPR) Family", Pharmacological Reviews, vol. 61(2), 2009.

* cited by examiner

PYRAZOLONE FORMYL PEPTIDE 2 RECEPTOR AGONISTS

CROSS REFERENCE TO RELATED APPLICATIONS

This application is a 371 application of PCT/US2021/040793, filed Jul. 8, 2021, which is entitled to priority pursuant to 35 U.S.C. § 119(e) to U.S. provisional patent application No. 63/049,831, filed Jul. 9, 2020, which is incorporated herein in its entirety.

BACKGROUND OF THE INVENTION

The present invention relates to novel pyrazolone compounds of formula I which are formyl peptide 2 (FPR2) receptor agonists, and also relates to compositions containing them, and methods of using them, for example, for the treatment of atherosclerosis, heart failure, chronic obstructive pulmonary disease (COPD), and related diseases.

Formyl peptide receptor 2 (FPR2) belongs to a small group of seven-transmembrane domain, G protein-coupled receptors that are expressed in multiple human tissues including immune cells and are known to be important in host defense and inflammation. FPR2 shares significant sequence homology with FPR1 and FPR3 (Chen K, et. al., Journal of Autoimmunity 85, 2017, 64-77). Collectively, these receptors bind a number of structurally diverse agonists, including N-formyl and non-formyl peptides which act as chemo attractants and activate phagocytes. The endogenous peptide Annexin A1 and its N-terminal fragments are examples of ligands that bind human FPR1 and FPR2. Fatty acids such as the eicosanoid lipoxin A4, which belongs to a class of small pro-resolution mediators (SPMs), has also been reported as an agonist for FPR2 (Ye R D., et al., Pharmacol. Rev., 2009, 61, 119-61).

Endogenous FPR2 pro-resolution ligands, such as lipoxin A4 and Annexin A1, have been reported to trigger a wide array of cytoplasmatic cascades such as Gi coupling, $Ca^{2+}$ mobilization and β-arrestin recruitment. (Cattaneo, F, et. al., Int J Mol Sci. 2013 April; 14(4): 7193-7230). FPR2 regulates both innate and adaptive immune systems including neutrophils, macrophages, T-, and B-cells. In neutrophils, FPR2 ligands modulate movement, cytotoxicity and life span. In macrophages, agonism of FPR2 prevents apoptosis and enhances efferocytosis. (Chandrasekharan J A, Sharma-Walia N, J. Inflamm. Res., 2015, 8, 181-92). The initiation of resolution of inflammation by FPR2 agonism is responsible for enhancing anti-fibrotic wound healing and returning of the injured tissue to homeostasis (Romano M., et al., Eur. J. Pharmacol., 2015, 5, 49-63).

Chronic inflammation is part of the pathway of pathogenesis of many human diseases and stimulation of resolution pathways with FPR2 agonists may have both protective and reparative effects. Ischemia-reperfusion (I/R) injury is a common feature of several diseases associated with high morbidity and mortality, such as myocardial infarction and stroke. Non-productive wound healing associated with cardiomyocyte death and pathological remodeling resulting from ischemia-reperfusion injury leads to scar formation, fibrosis, and progressive loss of heart function. FPR2 modulation is proposed to enhance myocardial wound healing post injury and diminish adverse myocardial remodeling (Kain V., et al., J. Mol. Cell. Cardiol., 2015, 84, 24-35). In addition, FPR2 pro-resolution agonists, in the central nervous system, may be useful therapeutics for the treatment of a variety of clinical I/R conditions, including stroke in brain (Gavins F N., Trends Pharmacol. Sci., 2010, 31, 266-76) and I/R induced spinal cord injury (Liu Z Q., et al., Int. J. Clin. Exp. Med., 2015, 8, 12826-33).

In addition to beneficial effects of targeting the FPR2 receptor with novel pro-resolution agonists for treatment of I/R induced injury, utility of these ligands can also be applied to other diseases. In the cardiovascular system both the FPR2 receptor and its pro-resolution agonists were found to be responsible for atherogenic-plaque stabilization and healing (Petri M H., et al., Cardiovasc. Res., 2015, 105, 65-74; and Fredman G., et al., Sci. Trans. Med., 2015, 7(275); 275ra20). FPR2 agonists also have been shown to be beneficial in preclinical models of chronic inflammatory human diseases, including: infectious diseases, psoriasis, dermatitis, inflammatory bowel syndrome, Crohn's disease, ocular inflammation, sepsis, pain, metabolic/diabetes diseases, cancer, COPD, asthma and allergic diseases, cystic fibrosis, acute lung injury and fibrosis, rheumatoid arthritis and other joint diseases, Alzheimer's disease, kidney fibrosis, and organ transplantation (Romano M., et al., Eur. J. Pharmacol., 2015, 5, 49-63, Perrett, M., et al., Trends in Pharm. Sci., 2015, 36, 737-755).

SUMMARY OF THE INVENTION

The present invention provides novel pyrazolones, and their analogues thereof, which are useful as FPR2 agonists, including stereoisomers, tautomers, pharmaceutically acceptable salts, or solvates thereof.

The present invention also provides processes and intermediates for making the compounds of the present invention or stereoisomers, tautomers, pharmaceutically acceptable salts, or solvates thereof.

The present invention also provides pharmaceutical compositions comprising a pharmaceutically acceptable carrier and at least one of the compounds of the present invention or stereoisomers, tautomers, pharmaceutically acceptable salts, or solvates thereof.

The compounds of the invention may be used in therapy.

The compounds of the invention may be used in the treatment and/or prophylaxis of multiple diseases or disorders associated with FPR2, such as inflammatory diseases, heart diseases, chronic airway diseases, cancers, septicemia, allergic symptoms, HIV retrovirus infection, circulatory disorders, neuroinflammation, nervous disorders, pains, prion diseases, amyloidosis, and immune disorders. The heart diseases are selected from the group consisting of angina pectoris, unstable angina, myocardial infarction, acute coronary disease, cardiac iatrogenic damage, and heart failure including, but not limited to, acute heart failure, chronic heart failure of ischemic and non-ischemic origin, systolic heart failure, diastolic heart failure, heart failure with reduced ejection fraction ($HF_REF$), and heart failure with preserved ejection fraction ($HF_PEF$).

The compounds of the invention can be used alone, in combination with other compounds of the present invention, or in combination with one or more other agent(s).

Other features and advantages of the invention will be apparent from the following detailed description and claims.

DESCRIPTION OF THE INVENTION

The invention encompasses compounds of formula I, which are formyl peptide 2 (FPR2) receptor agonists, compositions containing them, and methods of using them, for example, in the treatment of atherosclerosis, heart failure, chronic obstructive pulmonary disease (COPD), and related diseases.

One aspect of the invention is a compound of formula I

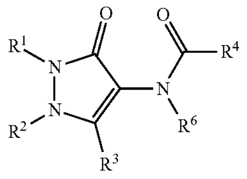

I or a pharmaceutically acceptable salt thereof, wherein $R^1$ is alkyl, haloalkyl, hydroxyalkyl, alkoxyalkyl, alkoxycarbonylalkyl, cycloalkyl, ($Ar^1$)alkyl, or $Ar^1$;

$Ar^1$ is cycloalkyl, piperidinyl, phenyl, pyridinyl, pyridazinyl, pyrimidinyl, pyrazinyl, pyrrolyl, furanyl, thienyl, pyrazolyl, isoxazolyl, isothiazolyl, imidazolyl, oxazolyl, thiazolyl, triazolyl, oxadiazolyl, thiadiazolyl, quinolinyl, isoquinolinyl, or quinoxalinyl and, is substituted with 0-2 $R^{5a}$ and 0-2 $R^{5b}$;

$R^2$ is alkyl or haloalkyl;

$R^3$ is phenyl or pyridinyl and, is substituted with 1 $R^{3a}$ and 0-2 $R^{3b}$;

$R^{3a}$ is halo, alkyl, haloalkyl, alkoxy, deuteroalkoxy, haloalkoxy, or cycloalkyl substituent in the para-position with respect to the pyrazol-3-one moiety;

$R^{3b}$ is halo, alkyl, hydroxy, or haloalkyl;

or $R^{3a}$ and the adjacent $R^{3b}$, together with the two carbon atoms they are attached to, form a 3-6 membered heterocycle comprising carbon atoms and 1-3 heteroatoms selected from N, NH, O, S, and substituted with 0-3 halo, hydroxy, alkyl, haloalkyl, or alkoxycarbonyl;

$R^4$ is phenyl or pyridinyl and, is substituted with 1 $R^{4a}$ and 0-2 $R^{4b}$;

$R^{4a}$ is halo, alkyl, cycloalkyl, haloalkyl, alkoxy, haloalkoxy, or pyrazolyl substituent in the para-position with respect to the amide moiety;

$R^{4b}$ is halo or haloalkyl;

$R^{5a}$ and $R^{5b}$ are independently cyano, halo, alkyl, haloalkyl, alkoxyalkyl, hydroxy, hydroxyalkyl, alkoxy, alkoxyalkoxy, hydroxyalkoxy, haloalkoxy, hydroxyhaloalkoxy, hydroxyalkoxyalkoxy, alkyl sulfonylalkoxy, carboxamide, alkoxycarbonyl, alkylaminoalkyl, alkoxycarbonylalkoxy, hydroxyalkylcycloalkylalkyl, alkylsulfonyl, aminocarbonylalkyl, —$NR^7R^8$, cycloalkyl substituted with 0-3 halo, hydroxy, alkyl, or alkoxy, phenyl substituted with 0-3 halo, hydroxy, or alkyl, 4-8 membered heterocyclyl comprising carbon atoms and 1-3 heteroatoms selected from N, NH, O, S, and substituted with 0-3 halo, alkyl, hydroxyalkyl, haloalkyl, alkoxycarbonyl, or alkylsulfonyl, heterocyclyloxy, heterocyclylalkyl, or heterocyclylalkoxy wherein the heterocyclyl moiety of the heterocyclyloxy, heterocyclylalkyl, and heterocyclylalkoxy comprises 4-8 carbon atoms and 1-3 heteroatoms selected from N, NH, O, S, and substituted with 0-3 halo, hydroxy, hydroxyalkyl, alkyl, or haloalkyl;

$R^6$ is hydrogen or lower alkyl;

$R^7$ and $R^8$ are independently hydrogen, alkyl, haloalkyl, hydroxyalkyl, halohydroxyalkyl, alkoxyalkyl, aminocarbonylalkyl, alkyl sulfonyl; alkylaminocarbonylalkyl, cycloalkylaminocarbonylalkyl, cycloalkylalkyl, hydroxycycloalkylalkyl, hydroxyalkylcycloalkylalkyl, cycloalkylalkyl, cycloalkyl, wherein each cycloalkyl is substituted with 0-3 halo, hydroxy, or alkyl, or hydroxyalkyl, or 5-8 membered heterocyclyl comprising carbon atoms and 1-3 heteroatoms selected from N, NH, O, S, and substituted with 0-3 halo, hydroxy, alkyl, haloalkyl, or alkoxycarbonyl;

or $R^7$ and $R^8$, together with the nitrogen to which they are attached, form a 5-12 membered heterocycle comprising carbon atoms and 0-3 additional heteroatoms selected from N, NH, O, S and substituted with 0-5 halo, hydroxy, alkyl, alkoxy, oxo, haloalkyl, cycloalkylalkyl, hydroxyalkyl, alkoxyalkyl, alkylsulfonyl, alkylsulfonylalkyl, aminocarbonyl, or alkoxycarbonyl.

Another aspect of the invention is a compound of formula I, or a pharmaceutically acceptable salt thereof, wherein $R^1$ is $Ar^1$.

Another aspect of the invention is a compound of formula I, or a pharmaceutically acceptable salt thereof, wherein $R^2$ is alkyl or haloalkyl.

Another aspect of the invention is a compound of formula I, or a pharmaceutically acceptable salt thereof, wherein $R^3$ is phenyl substituted with 1 $R^{3a}$ and 0-2 $R^{3b}$;

$R^{3a}$ is halo, alkyl, haloalkyl, alkoxy, or deuteroalkoxy substituent in the para-position with respect to the pyrazol-3-one moiety; and $R^{3b}$ is halo or haloalkyl.

Another aspect of the invention is a compound of formula I, or a pharmaceutically acceptable salt thereof, wherein $R^3$ is pyridinyl substituted with 1 halo, haloalkyl alkoxy, or haloalkoxy substituent in the 4-position with respect to the pyrazol-3-one moiety and 0-2 additional halo or haloalkyl substituents.

Another aspect of the invention is a compound of formula I, or a pharmaceutically acceptable salt thereof, wherein $R^4$ is phenyl or pyridinyl substituted with 1 $R^{4a}$ in the para-position with respect to the amide moiety and 0-2 $R^{4b}$;

$R^{4a}$ is halo, alkyl, cycloalkyl, haloalkyl, alkoxy, or haloalkoxy; and $R^{4b}$ is halo or haloalkyl.

Another aspect of the invention is a compound of formula I, or a pharmaceutically acceptable salt thereof, wherein $R^4$ is pyridinyl substituted 1 halo, alkyl, cycloalkyl, haloalkyl, alkoxy, haloalkoxy, or pyrazolyl substituent in the 4-position with respect to the amide moiety and 0-2 additional halo or haloalkyl substituents.

Another aspect of the invention is a compound of formula I, or a pharmaceutically acceptable salt thereof, wherein $Ar^1$ is phenyl substituted with 0-3 substituents selected from cyano, halo, alkyl, cycloalkyl, haloalkyl, alkoxy, hydroxyalkyl, carboxamide, haloalkoxy, and phenyl.

Another aspect of the invention is a compound of formula I, or a pharmaceutically acceptable salt thereof, wherein $Ar^1$ is pyridinyl substituted with 0-3 substituents selected from cyano, halo, alkyl, cycloalkyl, haloalkyl, alkoxy, hydroxyalkyl, carboxamide, haloalkoxy, and phenyl.

Another aspect of the invention is a compound of formula II

II

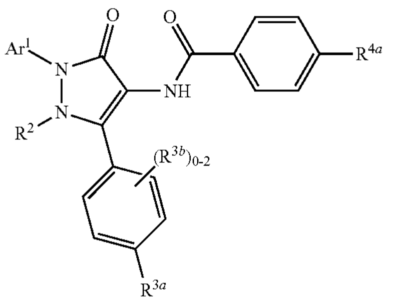

or a pharmaceutically acceptable salt thereof, wherein $Ar^1$ is

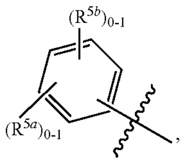
,
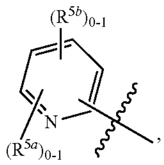
, or
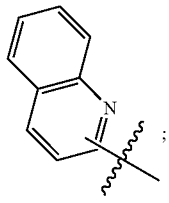
;

$R^2$ is alkyl or haloalkyl;

$R^{3a}$ is halo, alkyl, haloalkyl, alkoxy, deuteroalkoxy, haloalkoxy or cycloalkyl;

$R^{3b}$ is halo, alkyl, hydroxy, or haloalkyl;

or $R^{3a}$ and the adjacent $R^{3b}$, together with the two carbon atoms they are attached to, form a 3-6 membered heterocycle comprising carbon atoms and 1-3 heteroatoms selected from N, NH, O, S, and substituted with 0-3 halo, hydroxy, alkyl, haloalkyl, or alkoxycarbonyl;

$R^{4a}$ is halo, alkyl, cycloalkyl, haloalkyl, alkoxy, haloalkoxy, or pyrazolyl;

$R^{5a}$ and $R^{5b}$ are independently cyano, halo, alkyl, haloalkyl, alkoxyalkyl, hydroxy, hydroxyalkyl, alkoxy, alkoxyalkoxy, hydroxyalkoxy, haloalkoxy, hydroxyhaloalkoxy, hydroxyalkoxyalkoxy, alkylsulfonylalkoxy, carboxamide, alkoxycarbonyl, alkylaminoalkyl, alkoxycarbonylalkoxy, hydroxyalkylcycloalkylalkyl, alkylsulfonyl, —$NR^7R^8$, cycloalkyl substituted with 0-3 halo, hydroxy, alkyl, or alkoxy, phenyl substituted with 0-3 halo, hydroxy, or alkyl, 4-8 membered heterocyclyl comprising carbon atoms and 1-3 heteroatoms selected from N, NH, O, S, and substituted with 0-3 halo, alkyl, hydroxyalkyl, haloalkyl, alkoxycarbonyl, or alkylsulfonyl, heterocyclyloxy, heterocyclylalkyl or heterocyclylalkoxy wherein the heterocyclyl moiety of the heterocyclyloxy and heterocyclylalkoxy comprises 4-8 carbon atoms and 1-3 heteroatoms selected from N, NH, O, S, and substituted with 0-3 halo, hydroxy, hydroxyalkyl, alkyl, or haloalkyl; and $R^7$ and $R^8$ are independently hydrogen, alkyl, haloalkyl, hydroxyalkyl, halohydroxyalkyl, alkoxyalkyl, aminocarbonylalkyl, alkylsulfonyl; alkylaminocarbonylalkyl, cycloalkylaminocarbonylalkyl, cycloalkylalkyl, hydroxycycloalkylalkyl, hydroxyalkylcycloalkylalkyl, cycloalkylalkyl, cycloalkyl, wherein each cycloalkyl is substituted with 0-3 halo, hydroxy, or alkyl, or hydroxyalkyl, or 5-8 membered heterocyclyl comprising carbon atoms and 1-3 heteroatoms selected from N, NH, O, S, and substituted with 0-3 halo, hydroxy, alkyl, haloalkyl, or alkoxycarbonyl;

or $R^7$ and $R^8$, together with the nitrogen to which they are attached, form a 5-12 membered heterocycle comprising carbon atoms and 0-3 additional heteroatoms selected from N, NH, O, S and substituted with 0-5 halo, hydroxy, alkyl, alkoxy, oxo, haloalkyl, cycloalkylalkyl, hydroxyalkyl, alkoxyalkyl, alkylsulfonyl, alkylsulfonylalkyl, aminocarbonyl, or alkoxycarbonyl.

Another aspect of the invention is a compound of formula II, or a pharmaceutically acceptable salt thereof, wherein $Ar^1$ is;

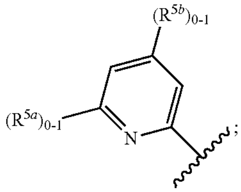
;

$R^{5a}$ is cyano, halo, alkyl, haloalkyl, alkoxyalkyl, hydroxyalkyl, alkoxy, haloalkoxy, carboxamide, alkoxycarbonyl, —$NR^7R^8$, cycloalkyl substituted with 0-1 halo, hydroxy, alkyl, or alkoxy, phenyl substituted with 0-1 halo, hydroxy, or alkyl, or 5-8 membered heterocyclyl comprising carbon atoms and 1-3 heteroatoms selected from N, NH, O, S, and substituted with 0-1 halo, hydroxy, or alkyl;

$R^{5b}$ is cyano, halo, alkyl, haloalkyl, alkoxyalkyl, hydroxyalkyl, alkoxy, haloalkoxy, carboxamide, alkoxycarbonyl, or cycloalkyl; and $R^7$ and $R^8$ are independently hydrogen, alkyl, haloalkyl, or hydroxyalkyl; or $R^7$ and $R^8$, together with the nitrogen to which they are attached, form a heterocycle with 0-3 additional heteroatoms selected from N, NH, O, S, and substituted with 0-3 halo, hydroxy, alkyl, alkoxy, or oxo;

other variables are as defined in formula II above.

Another aspect of the invention is a compound of formula II, or a pharmaceutically acceptable salt thereof, wherein $Ar^1$ is;

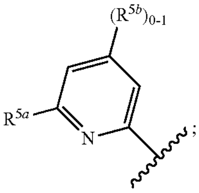
;

$R^{5a}$ is alkyl, hydroxyalkyl, —$NR^7R^8$, cyclobutyl substituted with 0-1 halo, hydroxy, alkyl, alkoxy, or phenyl;

$R^{5b}$ is alkoxy; and $R^7$ and $R^8$ are independently alkyl or hydroxyalkyl; or $R^7$ and $R^8$, together with the nitrogen to which they are attached, form a heterocycle with 0-2 additional nitrogen atoms and substituted with 0-3 halo, hydroxy, alkyl, alkoxy, or oxo;

other variables are as defined in formula II above.

Another aspect of the invention is a compound of formula II, or a pharmaceutically acceptable salt thereof, wherein $R^{5a}$ is —$NR^7R^8$; and $R^7$ and $R^8$ are independently alkyl or hydroxyalkyl; or $R^7$ and $R^8$, together with the nitrogen to which they are attached form

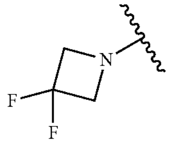,
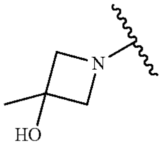,
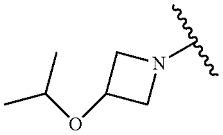,
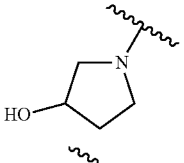,
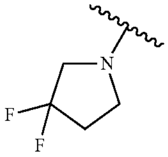,
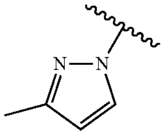,
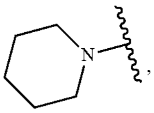,
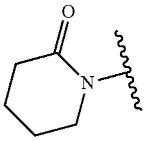,
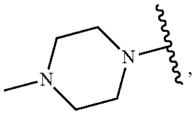,
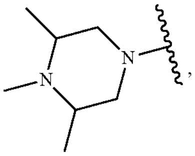,
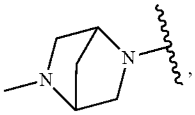,
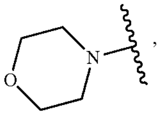, or
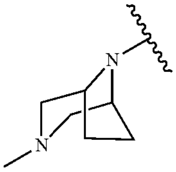;

other variables are as defined in formula II above.

Another aspect of the invention is a compound of formula II, or a pharmaceutically acceptable salt thereof, wherein $Ar^1$ is

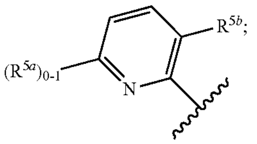

$R^{5a}$ is cyano, halo, alkyl, haloalkyl, hydroxyalkyl, alkoxy, haloalkoxy, —$NR^7R^8$, or cycloalkyl substituted with 0-1 alkoxy;

$R^{5b}$ is cyano, halo, alkyl, dimethylamino or haloalkyl; and $R^7$ and $R^8$ are independently alkyl or hydroxyalkyl; or $R^7$ and $R^8$, together with the nitrogen to which they are attached, form a heterocycle selected from

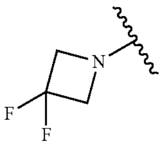,
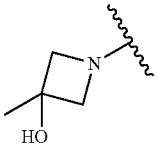,
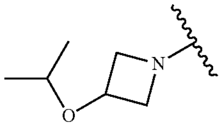,
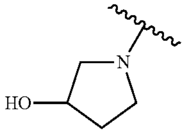,
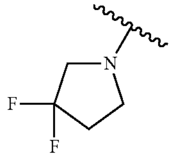,
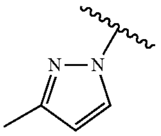,
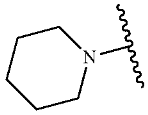,
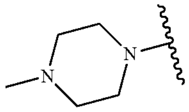,
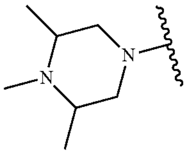,
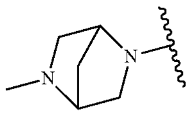,
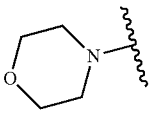, and
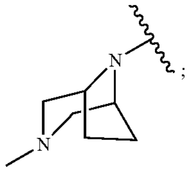;

other variables are as defined in formula II above.

Another aspect of the invention is a compound of formula II, or a pharmaceutically acceptable salt thereof, wherein $Ar^1$ is;

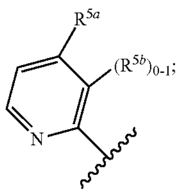

$R^{5a}$ is cyano, halo, alkyl, haloalkyl, alkoxyalkyl, hydroxyalkyl, alkoxy, or haloalkoxy; and $R^{5b}$ is cyano, halo, alkyl, haloalkyl, alkoxyalkyl, hydroxyalkyl, alkoxy, or haloalkoxy;

other variables are as defined in formula II above.

Another aspect of the invention is a compound of formula II, or a pharmaceutically acceptable salt thereof, wherein Ar[1] is

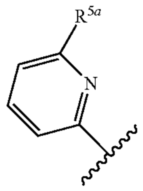

or

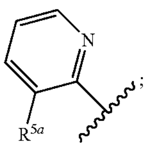

and $R^{5a}$ is alkyl, haloalkyl, hydroxyalkyl, alkoxy, haloalkoxy, or cycloalkyl;

other variables are as defined in formula II above.

Another aspect of the invention is a compound of formula II, or a pharmaceutically acceptable salt thereof, wherein Ar[1] is

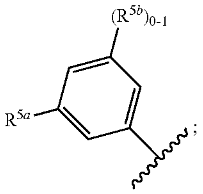

$R^{5a}$ is halo, alkoxy, haloalkoxy, carboxamide, alkoxycarbonyl, or cycloalkyl substituted with 0-1 hydroxy; and $R^{5b}$ is cyano, halo, alkyl, haloalkyl, alkoxyalkyl, hydroxyalkyl, alkoxy, haloalkoxy, carboxamide, alkoxycarbonyl, or cycloalkyl;

other variables are as defined in formula II above.

Another aspect of the invention is a compound of formula II, or a pharmaceutically acceptable salt thereof, wherein Ar[1] is

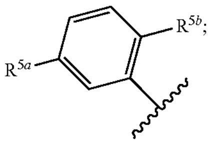

$R^{5a}$ is cyano, halo, alkyl, haloalkyl, alkoxyalkyl, hydroxyalkyl, or alkoxy; and $R^{5b}$ is cyano, halo, alkyl, or haloalkyl;

other variables are as defined in formula II above.

Another aspect of the invention is a compound of formula II, or a pharmaceutically acceptable salt thereof, wherein Ar[1] is

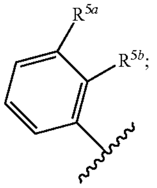

$R^{5a}$ is halo; and $R^{5b}$ is halo;

other variables are as defined in formula II above.

Another aspect of the invention is a compound of formula II, or a pharmaceutically acceptable salt thereof, wherein Ar[1] is

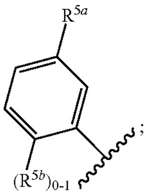

$R^{5a}$ is halo, alkyl, alkoxy, or haloalkoxy; and $R^{5b}$ is halo, alkyl, haloalkyl, alkoxyalkyl, hydroxyalkyl, alkoxy, or haloalkoxy;

other variables are as defined in formula II above.

Another aspect of the invention is a compound of formula III

III

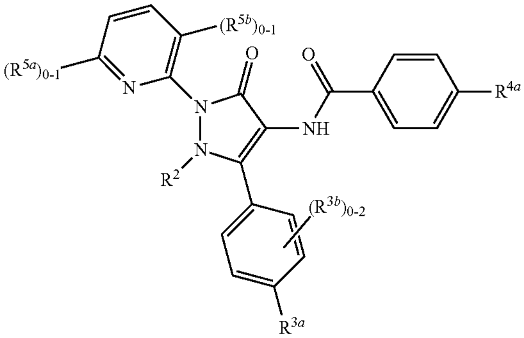

or a pharmaceutically acceptable salt thereof, wherein $R^2$ is alkyl or haloalkyl;

$R^{3a}$ is halo, alkyl, haloalkyl, alkoxy, deuteraroalkoxy, haloalkoxy, or cycloalkyl;

$R^{3b}$ is halo, alkyl, hydroxy, or haloalkyl; or $R^{3a}$ and the adjacent $R^{3b}$, together with the two carbon atoms they are attached to, form a 3-6 membered heterocycle comprising carbon atoms and 1-3 heteroatoms selected from N, NH, O, S, and substituted with 0-3 halo, hydroxy, alkyl, haloalkyl, or alkoxycarbonyl;

$R^{4a}$ is halo, alkyl, cycloalkyl, haloalkyl, alkoxy, haloalkoxy, or pyrazolyl;

$R^{5a}$ is halo, alkoxy, alkoxyalkoxy, hydroxyalkyl, hydroxyalkoxy, alkylaminoalkyl, alkoxycarbonylalkoxy, hydroxyalkylcycloalkylalkyl, alkylsulfonyl, —$NR^7R^8$, 5-8 membered heterocyclyl comprising carbon atoms and 1-3 heteroatoms selected from N, NH, O, S, and substituted with 0-3 halo, hydroxy, alkyl, haloalkyl, alkoxycarbonyl, or alkylsulfonyl, or heterocyclylalkyl wherein the heterocyclyl comprises 5-8 carbon atoms and 1-3 heteroatoms selected from N, NH, O, S, and substituted with 0-3 halo, hydroxy, alkyl, or haloalkyl;

$R^{5b}$ is cyano, halo, allyl, alkoxy, or haloalkyl;

$R^7$ and $R^8$ are independently hydrogen, alkyl, haloalkyl, hydroxyalkyl, halohydroxyalkyl, alkoxyalkyl, aminocarbonylalkyl, alkylsulfonyl; alkylaminocarbonylalkyl, cycloalkylaminocarbonylalkyl, cycloalkylalkyl, hydroxycycloalkylalkyl, hydroxyalkylcycloalkylalkyl, cycloalkylalkyl, cycloalkyl, wherein each cycloalkyl is substituted with 0-3 halo, hydroxy, or alkyl, or hydroxyalkyl, or 5-8 membered heterocyclyl comprising carbon atoms and 1-3 heteroatoms selected from N, NH, O, S, and substituted with 0-3 halo, hydroxy, alkyl, haloalkyl, or alkoxycarbonyl;

or $R^7$ and $R^8$, together with the nitrogen to which they are attached, form a 5-12 membered heterocycle comprising carbon atoms and 0-3 additional heteroatoms selected from N, NH, O, S and substituted with 0-5 halo, hydroxy, alkyl, alkoxy, oxo, haloalkyl, cycloalkylalkyl, hydroxyalkyl, alkoxyalkyl, alkylsulfonyl, alkylsulfonylalkyl, aminocarbonyl, or alkoxycarbonyl.

Another aspect of the invention is a compound of formula IV

IV

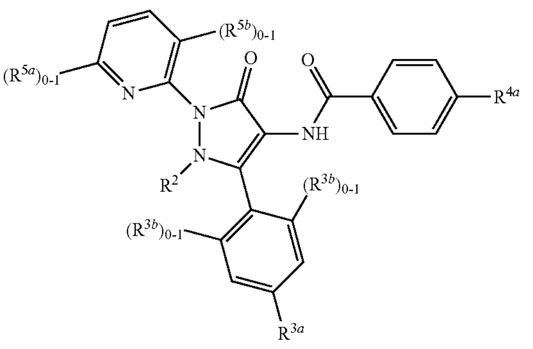

or a pharmaceutically acceptable salt thereof, wherein $R^{5a}$ is halo, alkoxy, alkoxyalkoxy, hydroxyalkyl, hydroxyalkoxy, aminocarbonylalkyl, hydroxyalkylcycloalkylalkyl, —$NR^7R^8$, or

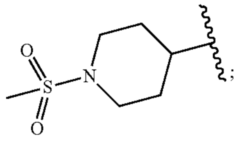 [SMILES: *C1CCN(S(C)(=O)=O)CC1];

$R^{5b}$ is halo or haloalkyl;

$R^7$ and $R^8$ are independently hydrogen, alkyl, hydroxyalkyl, halohydroxyalkyl, alkoxyalkyl, aminocarbonylalkyl, hydroxycycloalkylalkyl, hydroxyalkylcycloalkylalkyl, cycloalkylalkyl, cycloalkyl,

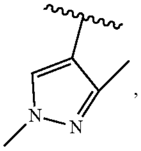, or 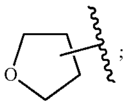;

or $R^7$ and $R^8$, together with the nitrogen to which they are attached, form a heterocyclyl selected from

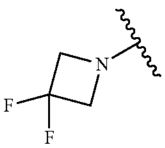, 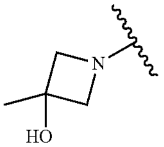,

-continued

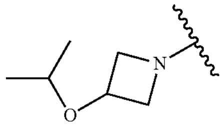, 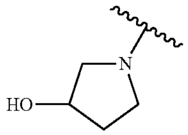,

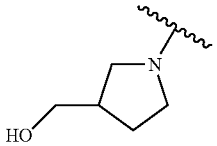, 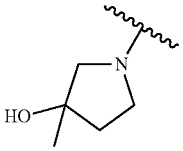,

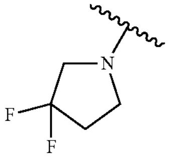, 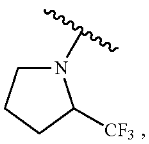, 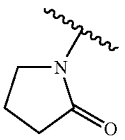,

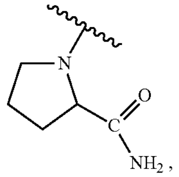, 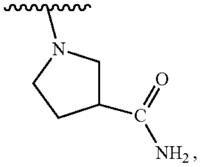,

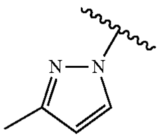, 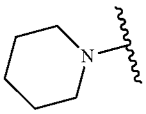, 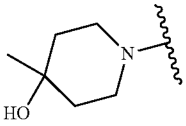,

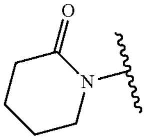, 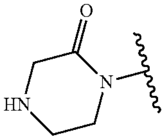, 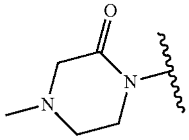,

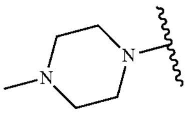, 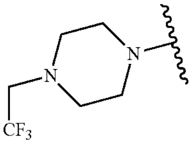,

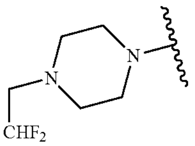, 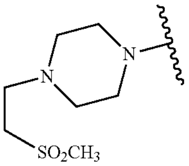,

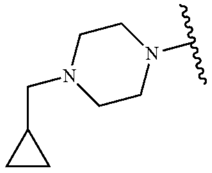, 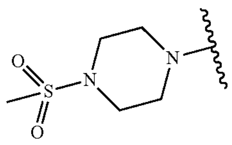,

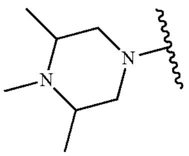, 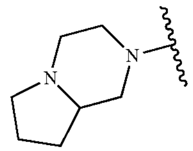, or

-continued

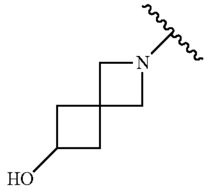;

and other variables are as defined in formula III above.

Another aspect of the invention is a compound of formula V

V

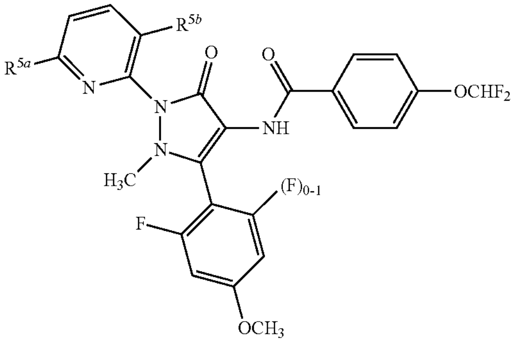

or a pharmaceutically acceptable salt thereof, wherein $R^{5a}$ is halo, alkoxyalkoxy, hydroxyalkyl, hydroxyalkoxy, —$NR^7R^8$, or

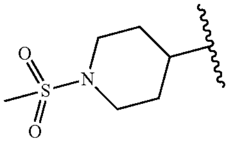;

$R^{5b}$ is Cl or $CF_3$;

$R^7$ is hydrogen;

$R^8$ is alkyl, hydroxyalkyl, halohydroxyalkyl, alkoxyalkyl, aminocarbonylalkyl, hydroxycycloalkylalkyl, hydroxyalkylcycloalkylalkyl, cycloalkylalkyl, cycloalkyl,

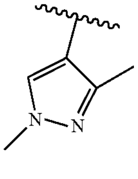, or 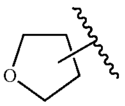;

or $R^7$ and $R^8$, together with the nitrogen to which they are attached form a heterocyclyl selected from

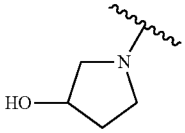, 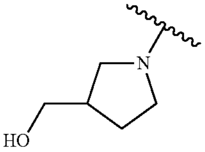,

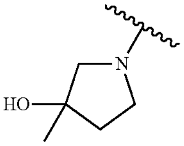, 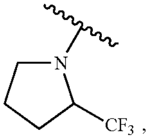, 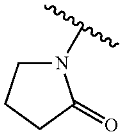,

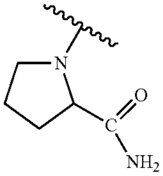, 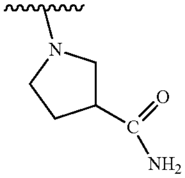,

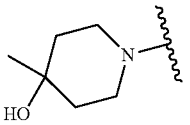, 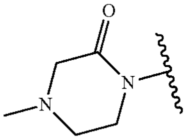,

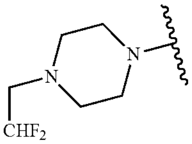, 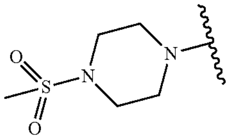, or

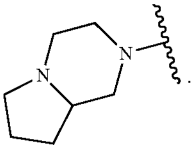.

Another aspect of the invention is a compound of formula VI

VI

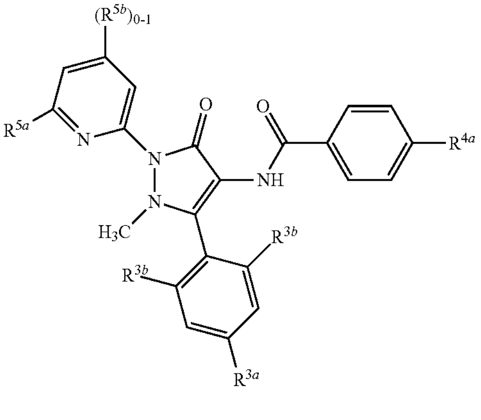

or a pharmaceutically acceptable salt thereof, wherein $R^{3a}$ is halo, alkyl, alkoxy, or deuteroalkoxy;

$R^{3b}$ is halo;

$R^{4a}$ is haloalkoxy;

$R^{5a}$ is cyano, halo, alkyl, haloalkyl, hydroxyalkyl, alkoxyalkoxy, hydroxyalkoxy, hydroxyhaloalkoxy, hydroxyalkoxyalkoxy, alkylsylfonylalkoxy, 5-8 membered heterocyclyl comprising carbon atoms and 1-3 heteroatoms selected from N, NH, O, S, and substituted with 0-3 halo, alkyl, hydroxyalkyl, haloalkyl, or alkylsulfonyl, or heterocyclylalkoxy wherein the heterocyclyl comprises 5-8 carbon atoms and 1-3 heteroatoms selected from N, NH, O, S, and substituted with 0-3 halo, hydroxy, hydroxyalkyl, alkyl, or haloalkyl; and $R^{5b}$ is cano, alkyl, hydroxyalkyl, alkoxy, hydroxyalkoxy, 5-8 membered heterocyclyl comprising carbon atoms and 1-3 heteroatoms selected from N, NH, O, S, and substituted with 0-3 halo, alkyl, or heterocyclyloxy wherein the heterocyclyl moiety comprises 5-8 carbon atoms and 1-3 heteroatoms selected from N, NH, O, S, and substituted with alkyl, heterocyclyl substituted with 0-1 alkyl.

Another aspect of the invention is a compound of formula VI, or a pharmaceutically acceptable salt thereof, wherein $R^{5a}$ is

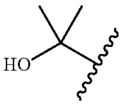, 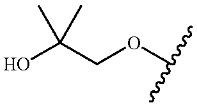, 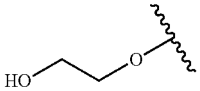, 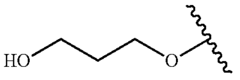, 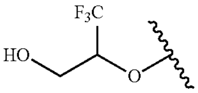, 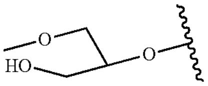, 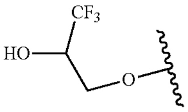, 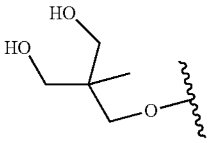, 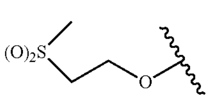, 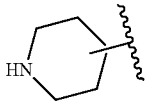, 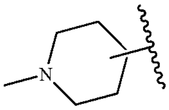, 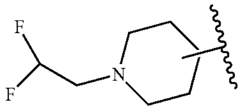, 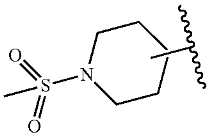, 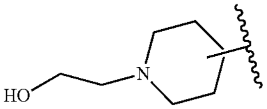, 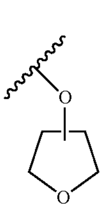, 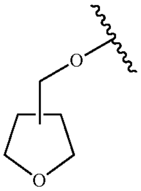, or 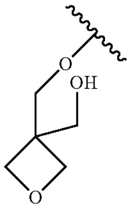;

$R^{5b}$ is $-OCH_3$ or $CH_3$ and other variables are as defined in formula VI above.

Another aspect of the invention is a compound of formula VII

VII

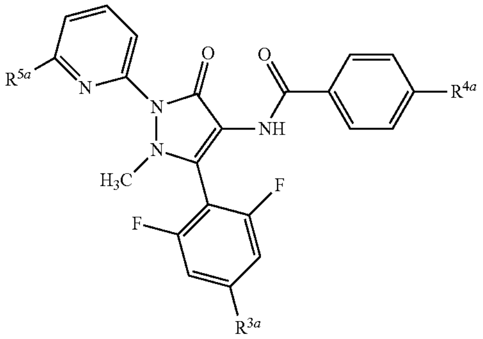

or a pharmaceutically acceptable salt thereof, wherein $R^{3a}$ is Cl, $CF_3$, $CH_3$, $CH_3CH_2$, $CD_3$, $OCH_3$, $OCF_3$, $OCF_2$, or $OCD_3$;

$R^{4a}$ is $OCF_3$ or $OCF_2$; and $R^{5a}$ is

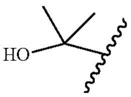, 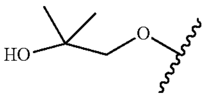, or 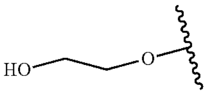.

Another aspect of the invention is a compound of formula VIII

VIII

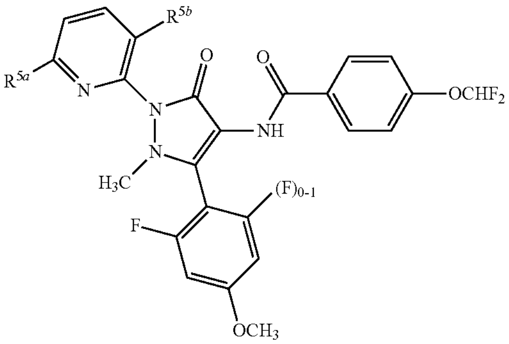

or a pharmaceutically acceptable salt thereof, wherein $R^{5a}$ is cyano, alkyl, hydroxyalkyl, alkoxy, hydroxyalkoxy, $-NR^7R^8$,

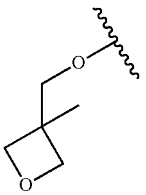, or 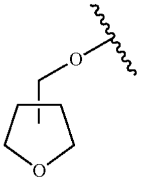;

$R^{5b}$ is cyano, alkyl, or haloalkyl;

$R^7$ is hydrogen or alkyl; and $R^8$ is alkyl or hydroxyalky.

For a compound of Formulae I-VIII, the scope of any instance of a variable substituent can be used independently with the scope of any other instance of a variable substituent. As such, the invention includes combinations of the different aspects.

In one non-limiting embodiment, for a compound of Formula (I), $R^1$ is $Ar^1$ or ($Ar^1$)alkyl; $Ar^1$ is phenyl substituted with 0-2 $R^{5a}$ or 0-2 $R^{5b}$; $R^{5a}$ and $R^{5b}$ are independently halo, alkyl, hydroxyalkyl, haloalkyl, alkoxy, alkoxycarbonyl; $R^2$ is lower alkyl; $R^3$ is phenyl substituted with 1 $R^{3a}$ and 0-2 $R^{3b}$; $R^{3a}$ is alkoxy; $R^{3b}$ is halo; $R^4$ is phenyl substituted with 1 $R^{4a}$; $R^{4a}$ is haloalkyl or haloalkoxy; and $R^6$ is hydrogen.

In another non-limiting embodiment, for a compound of Formula (I), $R^1$ is $Ar^1$; $Ar^1$ is cycloalkyl substituted with 0-2 $R^{5a}$ or 0-2 $R^{5b}$; $R^{5a}$ and $R^{5b}$ are independently halo, alkyl, hydroxyalkyl, haloalkyl, alkoxy, alkoxycarbonyl; $R^2$ is lower alkyl; $R^3$ is phenyl substituted with 1 $R^{3a}$ and 0-2 $R^{3b}$; $R^{3a}$ is alkoxy; $R^{3b}$ is halo; $R^4$ is phenyl substituted with 1 $R^{4a}$; $R^{4a}$ is haloalkyl or haloalkoxy; and $R^6$ is hydrogen.

In another non-limiting embodiment, for a compound of Formula (I), $R^1$ is $Ar^1$; $Ar^1$ is quinolinyl substituted with 0-2 $R^{5a}$ or 0-2 $R^{5b}$; $R^{5a}$ and $R^{5b}$ are independently halo, alkyl, hydroxyalkyl, haloalkyl, alkoxy, alkoxycarbonyl; $R^2$ is lower alkyl; $R^3$ is phenyl substituted with 1 $R^{3a}$ and 0-2 $R^{3b}$; $R^{3a}$ is alkoxy; $R^{3b}$ is halo; $R^4$ is phenyl substituted with 1 $R^{4a}$; $R^{4a}$ is haloalkyl or haloalkoxy; and $R^6$ is hydrogen.

In one non-limiting embodiment, for a compound of Formula (I), $R^1$ is $Ar^1$; $Ar^1$ is pyridinyl substituted with 1 $R^{5a}$; $R^{5a}$ is halo, alkyl, hydroxyalkyl, haloalkyl, alkoxy, alkoxycarbonyl; $R^2$ is lower alkyl; $R^3$ is phenyl substituted with 1 $R^{3a}$ and 0-2 $R^{3b}$; $R^{3a}$ is alkoxy; $R^{3b}$ is halo; $R^4$ is phenyl substituted with 1 $R^{4a}$; $R^{4a}$ is haloalkyl or haloalkoxy; and $R^6$ is hydrogen.

In another non-limiting embodiment, for a compound of Formula (I), $R^1$ is $Ar^1$; $Ar^1$ is pyridinyl substituted with 1 $R^{5a}$; $R^{5a}$ is F, Cl, $—CHF_2$, $—CF_3$, $—CH_2OH$, $—C(CH_3)_2OH$, $—OCH_3$, $—OCH(CH_3)_2$, $—O(CH_3)_2OH$, $—OCH_2C(CH_3)_2OH$, or $—C(CH_3)_2OH$; $R^2$ is $—CH_3$; $R^3$ is phenyl substituted with 1 $R^{3a}$ and 0-2 $R^{3b}$; $R^{3a}$ is methoxy, ethoxy, deuteromethoxy or deuteroethoxy; $R^{3b}$ is halo; $R^4$ is phenyl substituted with 1 $R^{4a}$; $R^{4a}$ is $—CF_3$, $—OCHF_2$, or $—OCF_3$; and $R^6$ is hydrogen.

In another non-limiting embodiment, for a compound of Formula (I), $R^1$ is $Ar^1$; $Ar^1$ is pyridinyl substituted with 1 $R^{5a}$; $R^{5a}$ is $—NR^7R^8$; $R^2$ is $—CH_3$; $R^3$ is phenyl substituted with 1 $R^{3a}$ and 0-2 $R^{3b}$; $R^{3a}$ is methoxy, ethoxy, deuteromethoxy, or deuteroethoxy; $R^{3b}$ is halo; $R^4$ is phenyl substituted with 1 $R^{4a}$; $R^{4a}$ is $—CF_3$, $—OCHF_2$, or $—OCF_3$; $R^6$ is hydrogen; and $R^7$ and $R^8$ are independently hydrogen, $—CH_3$, or $—CH_2CH_3$; or $R^7$ and $R^8$, together with the nitrogen to which they are attached, form or

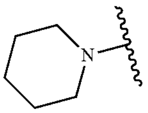 or 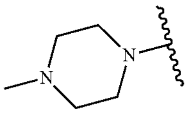.

In one non-limiting embodiment, for a compound of Formula (I), $R^1$ is $Ar^1$; $Ar^1$ is pyridyl substituted with 0-2 $R^{5a}$ or 0-2 $R^{5b}$; $R^{5a}$ and $R^{5b}$ are independently halo, alkyl, hydroxyalkyl, haloalkyl, alkoxy, alkoxycarbonyl; $R^2$ is lower alkyl; $R^3$ is phenyl substituted with 1 $R^{3a}$ and 0-2 $R^{3b}$; $R^{3a}$ is alkoxy; $R^{3b}$ is halo; $R^4$ is phenyl substituted with 1 $R^{4a}$; $R^{4a}$ is haloalkyl or haloalkoxy; and $R^6$ is hydrogen.

In another non-limiting embodiment, for a compound of Formula (I), $R^1$ is $Ar^1$; $Ar^1$ is pyridinyl substituted with 1 $R^{5a}$ or 0-1 $R^{5b}$; $R^{5a}$ and $R^{5b}$ are independently F, Cl, $—CHF_2$, or $—CF_3$, $—CH_2OH$, $—C(CH_3)_2OH$, $—CF_3$, $—OCH_3$, $—OCH(CH_3)_2$, $—O(CH_3)_2OH$, $—OCH_2C(CH_3)_2OH$, $—C(CH_3)_2OH$; $R^2$ is $CH_3$; $R^3$ is phenyl substituted with 1 $R^{3a}$ and 0-2$R^{3b}$; $R^{3a}$ is methoxy, ethoxy, deuteratomethoxy, or deuteroethoxy; $R^{3b}$ is halo; $R^4$ is phenyl substituted with 1 $R^{4a}$; $R^{4a}$ is $CF_3$, $OCHF_2$, or $OCF_3$; and $R^6$ is hydrogen.

In another non-limiting embodiment, for a compound of Formula (I), $R^1$ is $Ar^1$; $Ar^1$ is pyridinyl substituted with 1 $R^{5a}$ or 1 $R^{5b}$; $R^{5a}$ is cycloalkyl substituted with hydroxy; $R^{5b}$ is alkoxy; $R^2$ is $CH_3$; $R^3$ is phenyl substituted with 1 $R^{3a}$ and 0-2 $R^{3b}$; $R^{3a}$ is methoxy, ethoxy, deuteromethoxy, or deuteroethoxy; $R^{3b}$ is halo; $R^4$ is phenyl substituted with $1R^{4a}$; and $R^{4a}$ is $CF_3$, $OCHF_2$, or $OCF_3$; and $R^6$ is hydrogen.

In another non-limiting embodiment, for a compound of Formula (I), $R^1$ is $Ar^1$; $Ar^1$ is pyridinyl substituted with 1 $R^{5a}$ or 1 $R^{5b}$; $R^{5a}$ is $—OCH(CH_3)_2$, $—O(CH_3)_2OH$, $—OCH_2C(CH_3)_2OH$, or $—NR^7R^8$; and $R^{5b}$ is $—CF_3$ or $—OCH_3$; $R^2$ is $CH_3$; $R^3$ is phenyl substituted with 1 $R^{3a}$ and 0-2 $R^{3b}$; $R^{3a}$ is methoxy, ethoxy, deuteromethoxy, or deuteroethoxy; $R^{3b}$ is halo; $R^4$ is phenyl substituted with 1 $R^{4a}$; $R^{4a}$ is $CF_3$, $OCHF_2$, or $OCF_3$; and $R^6$ is hydrogen; $R^7$ and $R^8$ are hydrogen, $CH_3$, $CH_2CH_3—CH_2CH_2OH—CH_2CH(OH)CH_3$,

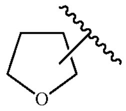, or 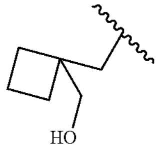;

$R^7$ and $R^8$, together with the nitrogen to which they are attached, form

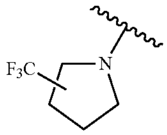 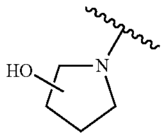 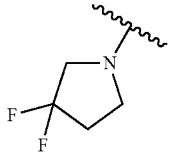,

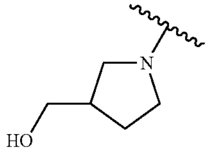, 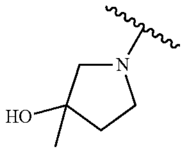,

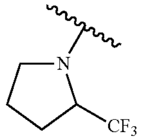, 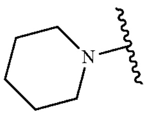 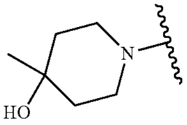,

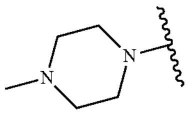 or 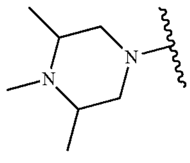.

In another non-limiting embodiment, for a compound of Formula (I), $R^1$ is $Ar^1$; $Ar^1$ is

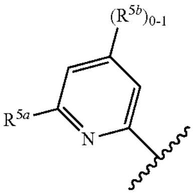

$R^{5a}$ is —$NR^7R^8$ or cycloalkyl substituted with hydroxy; $R^{5b}$ is —$OCH_3$; $R^2$ is $CH_3$; $R^3$ is phenyl substituted with 1 $R^{3a}$ and 0-2 $R^{3b}$; $R^{3a}$ is methoxy, ethoxy deuteroethoxy, or deuteroethoxy; $R^{3b}$ is halo; $R^4$ is phenyl substituted with 1 $R^{4a}$; and $R^{4a}$ is $CF_3$, $OCHF_2$, or $OCF_3$; $R^7$ and $R^8$ are hydrogen, $CH_3$, $CH_2CH_3$—$CH_2CH_2OH$—$CH_2CH(OH)CH_3$,

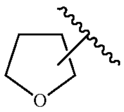, or 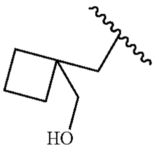;

and $R^6$ is hydrogen; $R^7$ and $R^8$, together with the nitrogen to which they are attached, form

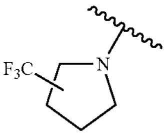, 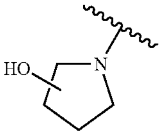, 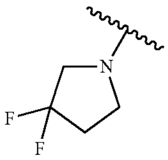, 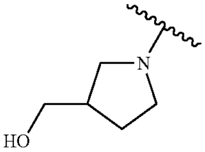, 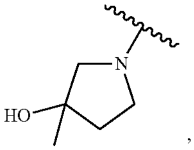, 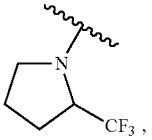, 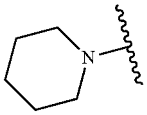, 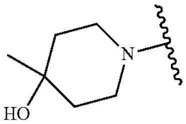, 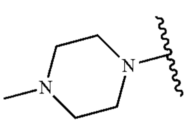 or 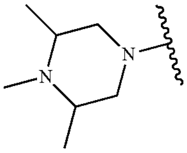.

In another non-limiting embodiment, for a compound of Formula (I), $R^1$ is $Ar^1$; $Ar^1$ is

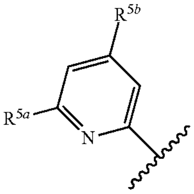

$R^{5a}$ is

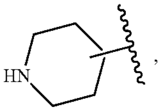, 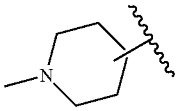, $R^{5b}$ is —$CH_3$ or —$OCH_3$; $R^2$ is —$CH_3$; $R^3$ is phenyl substituted with 1 $R^{3a}$ and 0-2 $R^{3b}$; $R^{3a}$ is methoxy, ethoxy, deuteromethoxy, or deuteroethoxy; $R^{3b}$ is halo; $R^4$ is phenyl substituted with 1 $R^{4a}$; and $R^{4a}$ is $CF_3$, $OCHF_2$, or $OCF_3$; and $R^6$ is hydrogen.

In another non-limiting embodiment, for a compound of Formula (I), $R^1$ is $Ar^1$; $Ar^1$ is

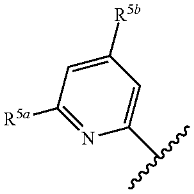

$R^{5a}$ is —$CH_3$, —$OCH_2CH_2OH$, —$OCH_2C(OH)CF_3$, —$OCH(CF_3)CH_2OH$, $OCH_2CH_2S(O)_2CH_3$,

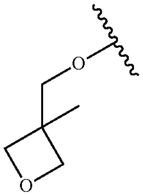, 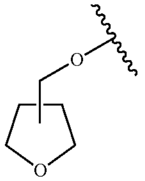, 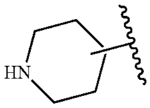, 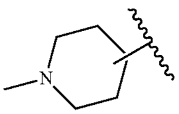, 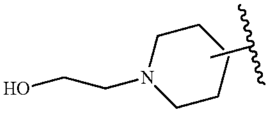, or —$NR^7R^8$; $R^{5b}$ is $CH_3$ or —$OCH_3$; $R^2$ is $CH_3$; $R^3$ is phenyl substituted with 1 $R^{3a}$ and 0-2 $R^{3b}$; $R^{3a}$ is methoxy, ethoxy, deuteromethoxy, or deuteroethoxy; $R^{3b}$ is halo; $R^4$ is phenyl substituted with 1 $R^{4a}$; and $R^{4a}$ is $CF_3$, $OCHF_2$, or $OCF_3$; $R^6$ is hydrogen; $R^7$ and $R^8$, together with the nitrogen to which they are attached form

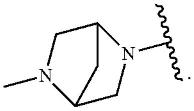 [SMILES: *N1CC2CC1CN2C].

In another non-limiting embodiment, for a compound of Formula (I), $R^1$ is $Ar^1$; $Ar^1$ is

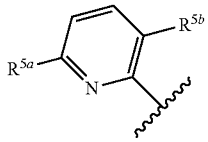

$R^{5a}$ is F, Cl, $—OCH_2C(CH_3)_2OH$ or $—NR^7R^8$; $R^{5b}$ is $—CF_3$; $R^2$ is $CH_3$; $R^3$ is phenyl substituted with 1 $R^{3a}$ and 0-2 $R^{3b}$; $R^{3a}$ is methoxy, ethoxy, deuteromethoxy, or deuteroethoxy; $R^{3b}$ is absent or halo; $R^4$ is phenyl substituted with 1 $R^{4a}$; and $R^{4a}$ is $CF_3$, $OCHF_2$, or $OCF_3$; $R^6$ is hydrogen; $R^7$ is hydrogen; $R^8$ is $CH_3$, $CH_2CH_3—$ $CH_2CH_2OH$, $—CH_2CH(CH_3)OH$, $—CH_2C(CH_3)_2OH$, $—CH_2CH(OH)CH_3$,

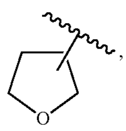, 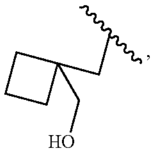, or 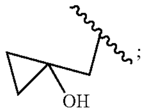;

$R^7$ and $R^8$, together with the nitrogen to which they are attached, form

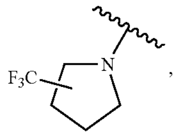, 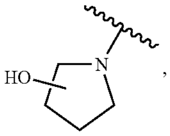, 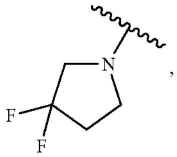,

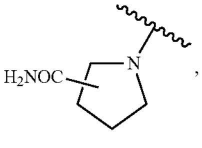, 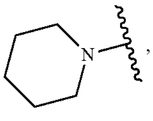, 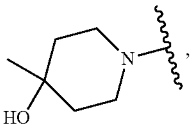,

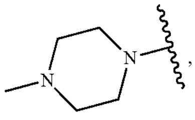, 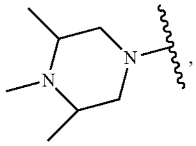, or

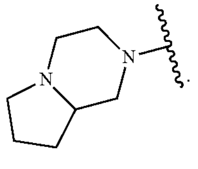.

In another embodiment, the compounds of the present invention are selected from the compounds having FPR2 $EC_{50}$ values≥0.1 μM.

In another embodiment, the compounds of the present invention are selected from the compounds having FPR2 $EC_{50}$ values≥0.01 μM<0.1 μM.

In another embodiment, the compounds of the present invention are selected from the compounds having FPR2 $EC_{50}$ values≥0.006 μM<0.01 μM.

In another embodiment, the compounds of the present invention are selected from the compounds having FPR2 $EC_{50}$ values≥0.001 μM<0.006 μM.

In another embodiment, the compounds of the present invention are selected from the compounds having FPR2 $EC_{50}$ values<0.001 μM.

Unless specified otherwise, these terms have the following meanings.

A dash "-" that is not between two letters or symbols is used to indicate a point of attachment for a substituent. For example, $—CONH_2$ is attached through the carbon atom.

A bond pointing to a wave line, such as

, as used in structural formulas herein, depicts the bond that is the point of attachment of the moiety or substituent to the core or backbone structure.

"Cyano" means —CN.

"Hydroxy" means —OH.

"Alkyl" means a straight or branched alkyl group composed of 1 to 6 carbons. "Lower alkyl: means a straight or branched alkyl group composed of 1 to 3 carbons.

"Alkenyl" means a straight or branched alkyl group composed of 2 to 6 carbons with at least one double bond.

"Alkynyl" means a straight or branched alkyl group composed of 2 to 6 carbons with at least one triple bond.

"Cycloalkyl" means a monocyclic ring system composed of 3 to 7 carbons. Terms with a hydrocarbon moiety (e.g. alkoxy) include straight and branched isomers for the hydrocarbon portion.

"Halo" refers to fluoro, chloro, bromo, and iodo.

"Haloalkyl" refers to halo substituted alkyl groups. Haloalkyl includes all halogenated isomers from monohalo to perhalo.

"Alkoxy" means an alkyl group attached via an oxygen linkage to the rest of the molecule. Representative examples of such groups are $—OCH_3$ and $—OC_2H_5$. Unless set forth or recited to the contrary, all alkoxy groups described or claimed herein may be straight chain or branched. The term "deuteroalkoxy" refers to an alkoxy group wherein from one to five hydrogen atoms have been replaced by deuterium. An example of a "deuteroalkoxy" group is $—OCD_3$.

"Alkoxyalkoxy" refers to an alkoxy group wherein at least one of the hydrogen atoms of the alkoxy group has been replaced by another alkoxy group.

"Hydroxyalkoxyalkoxy" refers to an alkyoxyalkoxy group wherein at least one of the hydrogen atoms of the alkoxyalkoxy group has been replaced by a hydroxy group.

"Hydroxyhaloalkoxy" refers to an alkoxy group wherein at least one of the hydrogen atoms of the alkoxy group has been replaced by a halo group and at least one of the hydrogen atoms of the alkoxy group has been replaced by a hydroxy group.

"Alkylsulfonylalkoxy" refers to an alkoxy group wherein at least one of the hydrogen atoms of the alkoxy group has been replaced by an alkylsulfonyl group.

"Heterocyclylalkoxy" refers to refers to an alkoxy group wherein at least one of the hydrogen atoms of the alkoxy group has been replaced by a heterocyclyl group.

"Alkylsulfonyl" refers to a group $—SO_2$-alkyl wherein alkyl is as herein defined.

"Hydroxyalkyl" refers to an alkyl group that has at least one hydrogen atom substituted with a hydroxy group.

"Alkoxyalkyl" refers to an alkyl group that has at least one hydrogen atom substituted with an alkoxy group.

"Haloalkoxy" refers to halo substituted alkyl groups linked through the oxygen atom. Haloalkoxy include mono-substituted as well as multiple halo substituted alkoxy groups, up to perhalo substituted alkoxy. For example trifluoromethoxy, chloromethoxy, and bromomethoxy are included. “Alkoxycarbonyl” refers to an alkoxy substituted carbonyl radical (such as —C(O)OR), wherein R represents an optionally substituted alkyl, aryl, aralkyl, cycloalkyl, cycloalkylalkyl or similar moiety.

“Aminocarbonylalkyl” refers to a group “-alkyl-C(O)NRR,” wherein each R represents hydrogen or an optionally substituted alkyl, aryl, aralkyl, cycloalkyl, cycloalkylalkyl or similar moiety.

“Aryl” refers to a monocyclic or bicyclic aromatic hydrocarbon groups having 6 to 12 carbon atoms, or a bicyclic fused ring system wherein one or both of the rings is aromatic. Bicyclic fused ring systems consist of a phenyl group fused to a four- to seven-membered aromatic or non-aromatic carbocyclic ring. Representative examples of aryl groups include but are not limited to phenyl, indanyl, indenyl, naphthyl, and tetrahydronaphthyl.

“Heteroaryl” refers to a 5 to 7 membered monocyclic or 8 to 11 membered bicyclic aromatic ring system with 1-5 heteroatoms independently selected from nitrogen, oxygen, and sulfur.

“Heterocyclyl” or “heterocycle” refers to a 5 to 7 membered monocyclic or 8 to 11 polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N→O and $S(O)_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term “heterocycle” is used, it is intended to include heteroaryl.

“Heterocyclyloxy” refers to a group —O-heterocyclyl wherein the heterocyclyl is as herein defined.

“Heterocyclylalkyl” refers to an alkyl group that has at least one hydrogen atom substituted with a heterocyclyl group as herein defined.

Where a bonding attachment location is not specified, the bonding may be attached at any appropriate location as understood by practitioners in the art. Combinations of substituents and bonding patterns are only those that result in stable compounds as understood by practitioners in the art. Parenthetic and multiparenthetic terms are intended to clarify bonding relationships to those skilled in the art. For example, a term such as ((R)alkyl) means an alkyl substituent further substituted with the substituent R.

Some examples of compounds where Ria is substituted in the para-position with respect to the pyrazol-3-one are illustrated below.

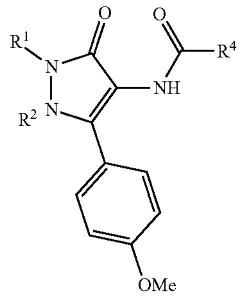

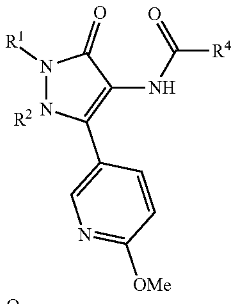

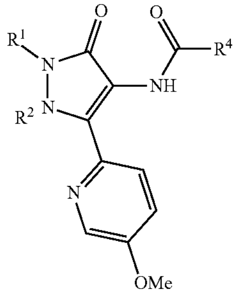

Some examples of compounds where $R^{4a}$ is substituted in the para-position with respect to the amide moiety are illustrated below.

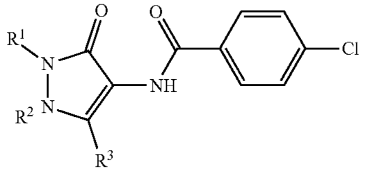

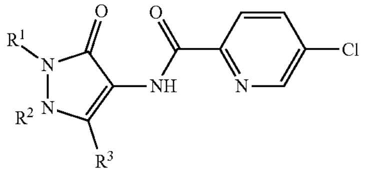

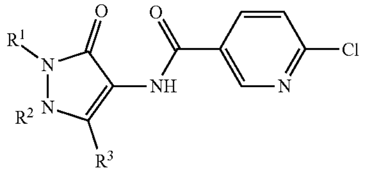

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention exist in stereoisomeric forms including the structure below with the indicated carbon. The invention includes all stereoisomeric forms of the compounds including enantiomers and diastereomers. Methods of making and separating stereoisomers are known in the art. The invention includes all tautomeric forms of the compounds. The invention includes atropisomers and rotational isomers.

The invention is intended to include all isotopes of atoms occurring in the compounds. Isotopes include those atoms having the same atomic number but different mass numbers. By way of general example and without limitation, isotopes of hydrogen include deuterium (D) and tritium (T). Isotopes of carbon include $^{11}C$, $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

BIOLOGICAL METHODS

N-formyl peptide receptors (FPRs) are a family of chemo attractant receptors that facilitate leukocyte response during inflammation. FPRs belong to the seven-transmembrane G protein-coupled receptor superfamily and are linked to inhibitory G-proteins (Gi). Three family members (FPR1, FPR2 and FPR3) have been identified in humans and are predominantly found in myeloid cells with varied distribution and have also been reported in multiple organs and tissues. After agonist binding, the FPRs activate a multitude of physiological pathways, such as intra cellular signaling transduction, $Ca^{2+}$ mobilization and transcription. The family interacts with a diverse set of ligands that includes proteins, polypeptides and fatty acid metabolites which activate both pro-inflammatory and pro-resolution downstream responses. FPR2 and FPR1 Cyclic Adenosine Monophosphate (cAMP) Assays were used to measure the in vitro activity of the compounds disclosed in this application.

FPR2 and FPR1 Cyclic Adenosine Monophosphate (cAMP) Assays. A mixture of forskolin (5 μM final for FPR2 or 10 μM final for FPR1) and IBMX (200 μM final) were added to 384-well Proxiplates (Perkin-Elmer) pre-dotted with test compounds in DMSO (1% final) at final concentrations in the range of 0.020 nM to 100 μM. Chinese Hamster Ovary cells (CHO) overexpressing human FPR1 or human FPR2 receptors were cultured in F-12 (Ham's) medium supplemented with 10% qualified FBS, 250 μg/mL zeocin and 300 μg/mL hygromycin (Life Technologies). Reactions were initiated by adding 2,000 human FPR2 cells per well or 4,000 human FPR1 cells per well in Dulbecco's PBS (with calcium and magnesium) (Life Technologies) supplemented with 0.1% BSA (Perkin-Elmer). The reaction mixtures were incubated for 30 min at rt. The level of intracellular cAMP was determined using the HTRF HiRange cAMP assay reagent kit (Cisbio) according to manufacturer's instruction. Solutions of cryptate conjugated anti-cAMP and d2 flurorophore-labeled cAMP were made in a supplied lysis buffer separately. Upon completion of the reaction, the cells were lysed with equal volume of the d2-cAMP solution and anti-cAMP solution. After a 1-h room temperature incubation, time-resolved fluorescence intensity was measured using the Envision (Perkin-Elmer) at 400 nm excitation and dual emission at 590 nm and 665 nm. A calibration curve was constructed with an external cAMP standard at concentrations ranging from 1 μM to 0.1 μM by plotting the fluorescent intensity ratio from 665 nm emission to the intensity from the 590 nm emission against cAMP concentrations. The potency and activity of a compound to inhibit cAMP production was then determined by fitting to a 4-parametric logistic equation from a plot of cAMP level versus compound concentrations.

The examples disclosed below were tested in the FPR2 and FPR1 cAMP assay described above and found having FPR2 and/or FPR1 agonist activity. Table 1 below lists $EC_{50}$ values in the FPR2 and FPR1 cAMP assays.

TABLE 1

| Example | hFPR2 cAMP2 $EC_{50}$ (μM) | hFPR1 cAMP2 $EC_{50}$ (μM) |
|---|---|---|
| 1 | 0.012 | 2.4 |
| 2 | 0.005 | 0.21 |
| 3 | 0.008 | 1.90 |
| 4 | 0.008 | 1.30 |
| 5 | 0.010 | 2.9 |
| 6 | 0.010 | 0.55 |
| 7 | 0.010 | 0.30 |
| 8 | 0.010 | 0.26 |
| 9 | 0.011 | >10 |
| 10 | 0.014 | 0.92 |
| 11 | 0.015 | 1.1 |
| 12 | 0.017 | 1.6 |
| 13 | 0.022 | 2.4 |
| 14 | 0.023 | >10 |
| 15 | 0.030 | >10 |
| 16 | 0.030 | >10 |
| 17 | 0.051 | 1.7 |
| 18 | 0.053 | 4.1 |
| 19 | 0.066 | 4.2 |
| 20 | 0.12 | >10 |
| 21 | 0.14 | >10 |
| 22 | 0.14 | >10 |
| 23 | 0.15 | 3.0 |
| 24 | 0.22 | >10 |
| 25 | 0.28 | >10 |
| 26 | 0.009 | 1.1 |
| 27 | 0.010 | >10 |
| 28 | 0.010 | 2.5 |
| 29 | 0.012 | >10 |
| 30 | 0.018 | >10 |
| 31 | 0.020 | >10 |
| 32 | 0.008 | 6.5 |
| 33 | 0.007 | 9.8 |
| 34 | 0.004 | 1.9 |
| 35 | 0.006 | 1.7 |
| 36 | 0.009 | 0.27 |
| 37 | 0.019 | >10 |
| 38 | 0.042 | 0.50 |
| 39 | 0.014 | 3.0 |
| 40 | 0.012 | 2.4 |
| 41 | 0.007 | 2.1 |
| 42 | 0.018 | 6.2 |
| 43 | 0.041 | >10 |
| 44 | 0.016 | >10 |
| 45 | 0.006 | 2.8 |
| 46 | 0.022 | >10 |
| 47 | 0.006 | 0.46 |
| 48 | 0.043 | >10 |
| 49 | 0.055 | 6.8 |
| 50 | 0.018 | 1.3 |
| 51 | 0.018 | 1.1 |
| 52 | 0.009 | 0.19 |
| 53 | 0.059 | 0.61 |
| 54 | 0.019 | 3.3 |
| 55 | 0.008 | 9.6 |
| 56 | 0.007 | >10 |
| 57 | 0.15 | 0.38 |
| 58 | 0.23 | >10 |

TABLE 1-continued

| Example | hFPR2 cAMP2 $EC_{50}$ (μM) | hFPR1 cAMP2 $EC_{50}$ (μM) |
|---|---|---|
| 59 | 0.008 | >10 |
| 60 | 0.003 | 0.21 |
| 61 | 0.011 | 1.6 |
| 62 | 0.006 | >10 |
| 63 | 0.007 | >10 |
| 64 | 0.011 | 0.80 |
| 65 | 0.008 | >10 |
| 66 | 0.008 | 2.5 |
| 67 | 0.009 | 3.4 |
| 68 | 0.008 | 1.0 |
| 69 | 0.005 | 0.005 |
| 70 | 0.003 | 0.005 |
| 71 | 0.020 | 2.6 |
| 72 | 0.0027 | 0.18 |
| 73 | 0.013 | 0.95 |
| 74 | 0.006 | 0.82 |
| 75 | 0.007 | 2.3 |
| 76 | 0.012 | 10.0 |
| 77 | 0.017 | 0.62 |
| 78 | 0.010 | 9.5 |
| 79 | 0.010 | >10 |
| 80 | 0.002 | 1.3 |
| 81 | 0.017 | >10 |
| 82 | 0.002 | 0.52 |
| 83 | 0.002 | >10 |
| 84 | 0.005 | 0.082 |
| 85 | 0.005 | 0.75 |
| 86 | 0.010 | 1.4 |
| 87 | 0.004 | 0.78 |
| 88 | 0.002 | 6.3 |
| 89 | 0.003 | 0.9 |
| 90 | 0.008 | 10.0 |
| 91 | 0.020 | 10.0 |
| 92 | 0.016 | 2.1 |
| 93 | 0.002 | 1.8 |
| 94 | 0.006 | 10.0 |
| 95 | 0.008 | 10.0 |
| 96 | 0.007 | 10.0 |
| 97 | 0.003 | 3.4 |
| 98 | 0.006 | 10.0 |
| 99 | 0.004 | 10.0 |
| 100 | 0.002 | 1.6 |
| 101 | 0.003 | 10.0 |
| 102 | 0.002 | 1.0 |
| 103 | 0.001 | 5.0 |
| 104 | 0.003 | 6.2 |
| 105 | 0.001 | 10.0 |
| 106 | 0.005 | 5.0 |
| 107 | 0.005 | 10.0 |
| 108 | 0.003 | 10.0 |
| 109 | 0.011 | 8.1 |
| 110 | 0.009 | 0.037 |
| 111 | 0.004 | 0.002 |
| 112 | 0.005 | 0.003 |
| 113 | 0.002 | 0.002 |
| 114 | 0.004 | 0.050 |
| 115 | 0.005 | 0.28 |
| 116 | 0.021 | 2.0 |
| 117 | 0.008 | >10 |
| 118 | 0.006 | 0.003 |
| 119 | 0.008 | 0.065 |
| 120 | 0.004 | 6.0 |
| 121 | 0.006 | >10 |
| 122 | 0.021 | >10 |
| 123 | 0.019 | >10 |
| 124 | 0.004 | >10 |
| 125 | 0.004 | 2.0 |
| 126 | 0.009 | 1.2 |
| 127 | 0.008 | >10 |
| 128 | 0.007 | 0.019 |
| 129 | 0.024 | 2.2 |
| 130 | 0.020 | 1.9 |
| 131 | 0.011 | >10 |
| 132 | 0.006 | 0.083 |
| 133 | 0.003 | 0.55 |
| 134 | 0.010 | >10 |
| 135 | 0.003 | 2.4 |
| 136 | 0.003 | 6.8 |
| 137 | 0.016 | 7.1 |
| 138 | 0.004 | 4.8 |
| 139 | 0.003 | >10 |
| 140 | 0.004 | 1.5 |
| 141 | 0.007 | 3.3 |
| 142 | 0.017 | 3.1 |
| 143 | 0.010 | 3.7 |
| 144 | 0.022 | >10 |
| 145 | 0.003 | 2.9 |
| 146 | 0.006 | >10 |
| 147 | 0.003 | 0.73 |
| 148 | 0.004 | 1.5 |
| 149 | 0.006 | 4.7 |
| 150 | 0.013 | 1.5 |
| 151 | 0.013 | 2.7 |
| 152 | 0.010 | >10 |
| 153 | 0.005 | 4.2 |
| 154 | 0.004 | >10 |
| 155 | 0.009 | 2.2 |
| 156 | 0.015 | 4.0 |
| 157 | 0.004 | >10 |
| 158 | 0.013 | >10 |
| 159 | 0.007 | >10 |
| 160 | 0.003 | >10 |
| 161 | 0.004 | >10 |
| 162 | 0.012 | >10 |
| 163 | 0.004 | >10 |
| 164 | 0.015 | >10 |
| 165 | 0.015 | >10 |
| 166 | 0.020 | >10 |
| 167 | 0.004 | 0.46 |
| 168 | 0.012 | >10 |
| 169 | 0.015 | 1.4 |
| 170 | 0.008 | >10 |
| 171 | 0.012 | >10 |
| 172 | 0.013 | 3.3 |
| 173 | 0.020 | >10 |
| 174 | 0.007 | >10 |
| 175 | 0.025 | >10 |
| 176 | 0.009 | >10 |
| 177 | 0.003 | 0.003 |
| 178 | 0.006 | >10 |
| 179 | 0.023 | 0.3 |
| 180 | 0.008 | >10 |
| 181 | 0.006 | 0.14 |
| 182 | 0.012 | >10 |
| 183 | 0.011 | 3.9 |
| 184 | 0.008 | >10 |
| 185 | 0.005 | >10 |
| 186 | 0.010 | >10 |
| 187 | 0.004 | 2.2 |
| 188 | 0.014 | >10 |
| 189 | 0.005 | 0.19 |
| 190 | 0.003 | >10 |
| 191 | 0.002 | 4.8 |
| 192 | 0.004 | >10 |
| 193 | 0.005 | >10 |
| 194 | 0.005 | >10 |
| 195 | 0.014 | >10 |
| 196 | 0.009 | >10 |
| 197 | 0.016 | >10 |
| 198 | 0.013 | >10 |
| 199 | 0.005 | 0.90 |
| 200 | 0.011 | >10 |
| 201 | 0.004 | >10 |
| 202 | 0.032 | 2.5 |
| 203 | 0.005 | >10 |
| 204 | 0.015 | >10 |
| 205 | 0.025 | >10 |
| 206 | 0.044 | >5 |
| 207 | 0.003 | 0.14 |
| 208 | 0.003 | >10 |
| 209 | 0.003 | >10 |
| 210 | 0.011 | 4.8 |
| 211 | 0.012 | >10 |
| 212 | 0.009 | >10 |

TABLE 1-continued

| Example | hFPR2 cAMP2 $EC_{50}$ (μM) | hFPR1 cAMP2 $EC_{50}$ (μM) |
|---|---|---|
| 213 | 0.016 | >10 |
| 214 | 0.004 | 0.15 |
| 215 | 0.005 | >10 |
| 216 | 0.006 | >10 |
| 217 | 0.006 | >10 |
| 218 | 0.021 | 1.5 |
| 219 | 0.010 | 3.2 |
| 220 | 0.002 | 0.56 |
| 221 | 0.141 | >5 |
| 222 | 0.005 | >10 |
| 223 | 0.166 | >5 |
| 224 | 0.015 | >5 |
| 225 | 0.003 | >10 |
| 226 | 0.013 | >10 |
| 227 | 0.003 | >5 |
| 228 | 0.001 | >5 |
| 229 | 0.003 | >10 |
| 230 | 0.010 | >10 |
| 231 | 0.005 | >10 |
| 232 | 0.005 | >10 |
| 233 | 0.008 | >10 |
| 234 | 0.003 | 2.9 |
| 235 | 0.001 | >10 |
| 236 | 0.009 | >10 |
| 237 | 0.001 | >5 |
| 238 | 0.003 | >10 |
| 239 | 0.005 | 2.7 |
| 240 | 0.002 | 1.3 |
| 241 | 0.002 | >10 |
| 242 | 0.020 | >10 |
| 243 | 0.006 | >10 |
| 244 | 0.035 | >10 |
| 245 | 0.020 | 1.2 |
| 246 | 0.315 | >10 |
| 247 | 0.005 | 0.63 |
| 248 | 0.008 | >10 |
| 249 | 0.038 | 0.51 |
| 250 | 0.013 | 0.97 |
| 251 | 0.002 | >10 |
| 252 | 0.012 | >10 |
| 253 | 0.005 | >10 |
| 254 | 0.004 | >10 |
| 255 | 0.002 | >10 |
| 256 | 0.003 | >10 |
| 257 | 0.010 | >10 |
| 258 | 0.009 | >5 |
| 259 | 0.010 | >10 |
| 260 | 0.010 | >10 |
| 261 | 0.002 | >5 |
| 262 | 0.025 | 2.0 |
| 263 | 0.008 | 1.7 |
| 264 | 0.002 | >5 |
| 265 | 0.002 | >10 |
| 266 | 0.004 | >10 |
| 267 | 0.002 | 7.1 |
| 268 | 0.002 | 1.5 |
| 269 | 0.003 | 3.3 |
| 270 | 0.006 | 3.4 |
| 271 | 0.003 | >10 |
| 272 | 0.001 | >10 |
| 273 | 0.003 | >5 |
| 274 | 0.002 | >5 |
| 275 | 0.005 | >10 |
| 276 | 0.004 | 2.89 |
| 277 | 0.017 | 0.73 |
| 278 | 0.002 | >10 |
| 279 | 0.002 | >10 |
| 280 | 0.002 | 2.7 |
| 281 | 0.018 | 0.50 |
| 282 | 0.002 | 2.1 |
| 283 | 0.001 | >10 |
| 284 | 0.002 | 1.8 |
| 285 | 0.002 | >10 |
| 286 | 0.003 | >5 |
| 287 | 0.013 | >5 |
| 288 | 0.001 | >10 |
| 289 | 0.004 | >10 |

TABLE 1-continued

| Example | hFPR2 cAMP2 $EC_{50}$ (μM) | hFPR1 cAMP2 $EC_{50}$ (μM) |
|---|---|---|
| 290 | 0.001 | >10 |
| 291 | 0.002 | >10 |
| 292 | 0.002 | 4.1 |
| 293 | 0.009 | 1.2 |
| 294 | 0.032 | 1.4 |
| 295 | 0.001 | 1.5 |
| 296 | 0.033 | >10 |
| 297 | 0.002 | 0.38 |
| 298 | 0.014 | 0.44 |
| 299 | 0.008 | >5 |
| 300 | 0.007 | >5 |
| 301 | 0.006 | 0.14 |
| 302 | 0.001 | 2.2 |
| 303 | 0.001 | >10 |
| 304 | 0.021 | 0.11 |
| 305 | 0.002 | 3.9 |
| 306 | 0.001 | 2.3 |
| 307 | 0.005 | >10 |
| 308 | 0.003 | >10 |
| 309 | 0.010 | 2.2 |
| 310 | 0.007 | >10 |
| 311 | 0.005 | >10 |
| 312 | 0.012 | 2.0 |
| 313 | 0.001 | 0.21 |
| 314 | 0.001 | 2.7 |
| 315 | 0.030 | 0.29 |
| 316 | 0.002 | >5 |
| 317 | 0.014 | 1.8 |
| 318 | 0.007 | >10 |
| 319 | 0.002 | >10 |
| 320 | 0.002 | 0.99 |
| 321 | 0.004 | 0.39 |
| 322 | 0.007 | >10 |
| 323 | 0.014 | >10 |
| 324 | 0.005 | >10 |
| 325 | 0.003 | >10 |
| 326 | 0.058 | 1.6 |
| 327 | 0.023 | 0.059 |
| 328 | 0.015 | 1.6 |
| 329 | 0.004 | >10 |
| 330 | 0.006 | >10 |
| 331 | 0.003 | >10 |
| 332 | 0.003 | >10 |
| 333 | 0.014 | 1.3 |
| 334 | 0.007 | 0.49 |
| 335 | 0.003 | >10 |
| 336 | 0.024 | >10 |
| 337 | 0.015 | >10 |
| 338 | 0.002 | >10 |
| 339 | 0.008 | >10 |
| 340 | 0.010 | >10 |
| 341 | 0.010 | 2.6 |
| 342 | 0.002 | >10 |
| 343 | 0.001 | >10 |
| 344 | 0.002 | 2.4 |
| 345 | 0.005 | >10 |
| 346 | 0.005 | >10 |
| 347 | 0.004 | >10 |
| 348 | 0.020 | 2.2 |
| 349 | 0.022 | 0.094 |
| 350 | 0.009 | >10 |
| 351 | 0.002 | >10 |
| 352 | 0.006 | >10 |
| 353 | 0.002 | 1.6 |
| 354 | 0.002 | >10 |
| 355 | 0.004 | >10 |
| 356 | 0.005 | >10 |
| 357 | 0.005 | >10 |
| 358 | 0.009 | >10 |
| 359 | 0.005 | >10 |
| 360 | 0.004 | >10 |
| 361 | 0.001 | >10 |
| 362 | 0.010 | >10 |
| 363 | 0.003 | >10 |
| 364 | 0.062 | 2.1 |
| 365 | 0.014 | >10 |
| 366 | 0.007 | >10 |

TABLE 1-continued

| Example | hFPR2 cAMP2 $EC_{50}$ (μM) | hFPR1 cAMP2 $EC_{50}$ (μM) |
|---|---|---|
| 367 | 0.001 | >10 |
| 368 | 0.007 | >10 |
| 369 | 0.005 | >10 |
| 370 | 0.005 | >10 |
| 371 | 0.006 | 0.24 |
| 372 | 0.006 | >10 |
| 373 | 0.016 | >10 |
| 374 | 0.022 | 0.32 |
| 375 | 0.003 | >10 |
| 376 | 0.005 | >10 |
| 377 | 0.008 | 0.47 |
| 378 | 0.000 | 0.025 |
| 379 | 0.007 | >10 |
| 380 | 0.002 | 2.3 |
| 381 | 0.002 | 1.9 |
| 382 | 0.008 | >10 |
| 383 | 0.001 | 2.5 |
| 384 | 0.007 | >10 |
| 385 | 0.003 | >10 |
| 386 | 0.009 | >10 |
| 387 | 0.008 | >10 |
| 388 | 0.004 | 3.6 |
| 389 | 0.006 | 4.5 |
| 390 | 0.010 | 2.2 |
| 391 | 0.006 | 0.24 |
| 392 | 0.022 | 0.83 |
| 393 | 0.015 | 2.8 |
| 394 | 0.005 | 0.74 |
| 395 | 0.061 | >10 |
| 396 | 0.002 | 0.30 |
| 397 | 0.008 | >10 |
| 398 | 0.024 | 0.59 |
| 399 | 0.011 | 0.55 |
| 400 | 0.057 | >10 |
| 401 | 0.103 | 1.8 |
| 402 | 0.005 | >10 |
| 403 | 0.006 | 1.7 |
| 404 | 0.007 | 1.5 |
| 405 | 0.008 | 0.39 |
| 406 | 0.012 | 1.6 |
| 407 | 0.023 | >10 |
| 408 | 0.007 | 1.1 |

Pharmaceutical Compositions and Methods of Use

The compounds of the present invention may be administered to mammals, preferably humans, for the treatment of a variety of conditions and disorders including atherosclerosis, heart failure, lung diseases including asthma, COPD, and cystic fibrosis; neuroinflammatory diseases including multiple sclerosis, Alzheimer's disease, and stroke; and chronic inflammatory diseases such as inflammatory bowel disease, rheumatoid arthritis, psoriasis, sepsis, and kidney fibrosis.

Unless otherwise specified, the following terms have the stated meanings. The term "subject" refers to any human or other mammalian species that could potentially benefit from treatment with a FPR2 and/or FPR1 agonist as understood by practitioners in this field. Some subjects include human beings of any age with risk factors for cardiovascular disease. Common risk factors include age, sex, weight, family history, sleep apnea, alcohol or tobacco use, physical inactivity arrthymia or signs of insulin resistance such as acanthosis nigricans, hypertension, dyslipidemia, or polycystic ovary syndrome (PCOS). The term "patient" means a person suitable for therapy as determined by practitioners in the field. "Treating" or "treatment" cover the treatment of a patient or subject as understood by practitioners in this field. "Preventing" or "prevention" cover the preventive treatment (i.e., prophylaxis and/or risk reduction) of a subclinical disease-state in a patient or subject aimed at reducing the probability of the occurrence of a clinical disease-state as understood by practitioners in this field. Patients are selected for preventative therapy based on factors that are known to increase risk of suffering a clinical disease state compared to the general population. "Therapeutically effective amount" means an amount of a compound that is effective as understood by practitioners in this field.

Another aspect of the invention are pharmaceutical compositions comprising a therapeutically effective amount of a compound of formulae I-VIII in combination with a pharmaceutical carrier.

Another aspect of the invention are pharmaceutical compositions comprising a therapeutically effective amount of a compound of formulae I-VIII in combination with at least one other therapeutic agent and a pharmaceutical carrier.

"Pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, anti-bacterial agents, anti-fungal agents, lubricating agents and dispensing agents, depending on the nature of the mode of administration and dosage forms.

Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, Allen, L. V., Jr. et al., *Remington: The Science and Practice of Pharmacy* (2 Volumes), 22nd Edition, Pharmaceutical Press (2012).

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

Another aspect of the invention is a method for treating heart disease comprising administering a therapeutically effective amount of a compound of formulae I-VIII to a patient.

Another aspect of the invention is a method for treating heart disease wherein the heart disease is selected from the group consisting of angina pectoris, unstable angina, myocardial infarction, heart failure, acute coronary disease, acute heart failure, chronic heart failure, and cardiac iatrogenic damage.

It will be understood that treatment or prophylaxis of heart failure may involve treatment or prophylaxis of a cardiovascular event as well. Treatment or prophylaxis as referred to herein may refer to treatment or prophylaxis of certain negative symptoms or conditions associated with or arising as a result of a cardiovascular event. By way of example, treatment or prophylaxis may involve reducing or preventing negative changes in fractional shortening, heart weight, lung weight, myocyte cross sectional area, pressure overload induced cardiac fibrosis, stress induced cellular senescence, and/or cardiac hypertrophy properties, or any combination thereof, associated with or arising as a result of a cardiovascular event. Treatment may be administered in preparation for or in response to a cardiovascular event to alleviate negative effects. Prevention may involve a pro-active or prophylactic type of treatment to prevent the cardiovascular event or to reduce the onset of negative effects of a cardiovascular event.

In one embodiment, the present invention provides the use of a compound of Formulae I-VIII or a pharmaceutically acceptable salt thereof for the preparation of a pharmaceutical composition for the treatment or prophylaxis of heart failure, for example, heart failure results from hypertension, an ischemic heart disease, a non-ischemic heart disease, exposure to a cardiotoxic compound, myocarditis, Kawasaki's disease, Type I and Type II diabetes, thyroid disease, viral infection, gingivitis, drug abuse, alcohol abuse, pericarditis, atherosclerosis, vascular disease, hypertrophic cardiomyopathy, dilated cardiomyopathy, myocardial infarction, atrial fibrosis, left ventricular systolic dysfunction, left ventricular diastolic dysfunction, coronary bypass surgery, pacemaker implantation surgery, starvation, an eating disorder, muscular dystrophies, and a genetic defect. Preferably, the heart failure to be treated is diastolic heart failure, heart failure with reduced ejection fraction ($HF_REF$), heart failure with preserved ejection fraction ($HF_PEF$), acute heart failure, and chronic heart failure of ischemic and non-ischemic origin.

In one embodiment, the present invention provides the use of a compound of Formulae I-VIII to treat systolic and/or diastolic dysfunction, wherein the compound is administered in a therapeutically effective amount to increase the ability of the cardiac muscle cells to contract and relax thereby increasing the filling and emptying of both the right and left ventricles, preferably, the left ventricle.

In another embodiment, the present invention provides the use of a compound of Formulae I-VIII to treat heart failure wherein the compound is administered in a therapeutically effective amount to increase ejection fraction in the left ventricle.

In still another embodiment, the present invention provides the use of a compound of Formulae I-VIII to treat heart failure wherein the compound is administered in a therapeutically effective amount to reduce fibrosis in heart tissue.

Another aspect of the invention is a method for treating heart disease wherein the treatment is post myocardial infarction.

Another aspect of the invention is a method for treating heart disease comprising administering a therapeutically effective amount of a compound of formula I to a patient in conjunction with other therapeutic agents.

The compounds of this invention can be administered by any suitable means, for example, orally, such as tablets, capsules (each of which includes sustained release or timed release formulations), pills, powders, granules, elixirs, tinctures, suspensions (including nanosuspensions, microsuspensions, spray-dried dispersions), syrups, and emulsions; sublingually; bucally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired.

By way of general guidance, the daily oral dosage of each active ingredient, when used for the indicated effects, will range between about 0.01 to about 5000 mg per day, preferably between about 0.1 to about 1000 mg per day, and most preferably between about 0.1 to about 250 mg per day. Intravenously, the most preferred doses will range from about 0.01 to about 10 mg/kg/minute during a constant rate infusion. Compounds of this invention may be administered in a single daily dose, or the total daily dosage may be administered in divided doses of two, three, or four times daily.

Dosage forms (pharmaceutical compositions) suitable for administration may contain from about 1 milligram to about 2000 milligrams of active ingredient per dosage unit. In these pharmaceutical compositions the active ingredient will ordinarily be present in an amount of about 0.1-95% by weight based on the total weight of the composition. A typical capsule for oral administration contains at least one of the compounds of the present invention (250 mg), lactose (75 mg), and magnesium stearate (15 mg). The mixture is passed through a 60 mesh sieve and packed into a No. 1 gelatin capsule. A typical injectable preparation is produced by aseptically placing at least one of the compounds of the present invention (250 mg) into a vial, aseptically freeze-drying and sealing. For use, the contents of the vial are mixed with 2 mL of physiological saline, to produce an injectable preparation.

The compounds of the present invention may be employed in combination with other suitable therapeutic agents useful in the treatment of the aforementioned diseases or disorders including: anti-atherosclerotic agents, anti-dyslipidemic agents, anti-diabetic agents, anti-hyperglycemic agents, anti-hyperinsulinemic agents, anti-thrombotic agents, anti-retinopathic agents, anti-neuropathic agents, anti-nephropathic agents, anti-ischemic agents, anti-hypertensive agents, anti-obesity agents, anti-hyperlipidemic agents, anti-hypertriglyceridemic agents, anti-hypercholesterolemic agents, anti-restenotic agents, anti-pancreatic agents, lipid lowering agents, anorectic agents, memory enhancing agents, anti-dementia agents, cognition promoting agents, appetite suppressants, agents for treating heart failure, agents for treating peripheral arterial disease, agents for treating malignant tumors, and anti-inflammatory agents.

The compounds of the invention may be used with at least one of the following heart failure agents selected from loop diuretics, angiotensin converting enzyme (ACE) inhibitors, angiotensin II receptor blockers (ARBs), angiotensin receptor-neprilysin inhibitors (ARNI), beta blockers, mineralocorticoid receptor antagonists, nitroxyl donors, RXFP1 agonists, APJ agonists, SGLT2 inhibitors, HCN potassium-sodium channel inhibitors, myosin modulators, calcium channel inhibitors, chymase inhibitors and cardiotonic agents. These agents include, but are not limited to furosemide, bumetanide, torsemide, sacubitrial-valsartan, thiazide diruetics, captopril, enalapril, lisinopril, carvedilol, metopolol, bisoprolol, serelaxin, spironolactone, eplerenone, ivabradine, candesartan, eprosartan, irbestarain, losartan, olmesartan, telmisartan, and valsartan.

The compounds of the present invention may be employed in combination with at least one of the following therapeutic agents in treating atherosclerosis: anti-hyperlipidemic agents, plasma HDL-raising agents, anti-hypercholesterolemic agents, cholesterol biosynthesis inhibitors (such as HMG CoA reductase inhibitors), LXR agonist, probucol, raloxifene, nicotinic acid, niacinamide, cholesterol absorption inhibitors, bile acid sequestrants (such as anion exchange resins, or quaternary amines (e.g., cholestyramine or colestipol)), low density lipoprotein receptor inducers, clofibrate, fenofibrate, benzofibrate, cipofibrate, gemfibrizol, vitamin $B_6$, vitamin $B_{12}$, anti-oxidant vitamins, β-blockers, anti-diabetes agents, angiotensin II antagonists, angiotensin converting enzyme inhibitors, platelet aggregation inhibitors, fibrinogen receptor antagonists, aspirin and fabric acid derivatives.

The compounds of the present invention may be employed in combination at least one of the following therapeutic agents in treating cholesterol biosynthesis inhibitor, particularly an HMG-CoA reductase inhibitor. Examples of suitable HMG-CoA reductase inhibitors include, but are not limited to, lovastatin, simvastatin, pravastatin, fluvastatin, atorvastatin, and rosuvastatin.

The compounds of the invention may be used in combination with at least one of the following anti-diabetic agents depending on the desired target therapy. Studies indicate that diabetes and hyperlipidemia modulation can be further improved by the addition of a second agent to the therapeutic regimen. Examples of anti-diabetic agents include, but are not limited to, sulfonylureas (such as chlorpropamide, tolbutamide, acetohexamide, tolazamide, glyburide, gliclazide, glynase, glimepiride, and glipizide), biguanides (such as metformin), thiazolidinediones (such as ciglitazone, pioglitazone, troglitazone, and rosiglitazone), and related insulin sensitizers, such as selective and non-selective activators of PPARα, PPARβ and PPARγ; dehydroepiandrosterone (also referred to as DHEA or its conjugated sulphate ester, DHEA-$SO_4$); anti-glucocorticoids; TNFα inhibitors; dipeptidyl peptidase IV (DPP4) inhibitor (such as sitagliptin, saxagliptin), GLP-1 agonists or analogs (such as exenatide), α-glucosidase inhibitors (such as acarbose, miglitol, and voglibose), pramlintide (a synthetic analog of the human hormone amylin), other insulin secretagogues (such as repaglinide, gliquidone, and nateglinide), insulin, as well as the therapeutic agents discussed above for treating atherosclerosis.

The compounds of the invention may be used in combination with at least one of the following anti-obesity agents selected from phenylpropanolamine, phentermine, diethylpropion, mazindol, fenfluramine, dexfenfluramine, phentiramine, $\beta_3$-adrenoreceptor agonist agents; sibutramine, gastrointestinal lipase inhibitors (such as orlistat), and leptins. Other agents used in treating obesity or obesity-related disorders include neuropeptide Y, enterostatin, cholecytokinin, bombesin, amylin, histamine $H_3$ receptors, dopamine $D_2$ receptor modulators, melanocyte stimulating hormone, corticotrophin releasing factor, galanin and gamma amino butyric acid (GABA).

The compounds of the present invention are also useful as standard or reference compounds, for example as a quality standard or control, in tests or assays involving the FPR2. Such compounds may be provided in a commercial kit, for example, for use in pharmaceutical research involving FPR2 activity. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness. The compounds of the present invention may also be used in diagnostic assays involving FPR2.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises a first therapeutic agent, comprising a compound of the present invention or a pharmaceutically acceptable salt form thereof; and, (c) a package insert stating that the pharmaceutical composition can be used for the treatment of dyslipidemias and the sequelae thereof. In another embodiment, the package insert states that the pharmaceutical composition can be used in combination (as defined previously) with a second therapeutic agent for the treatment of dyslipidemias and the sequelae thereof. The article of manufacture can further comprise: (d) a second container, wherein components (a) and (b) are located within the second container and component (c) is located within or outside of the second container. Located within the first and second containers means that the respective container holds the item within its boundaries. The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product. The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached. The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Chemistry Methods

The disclosed compounds can be made by various methods known in the art including those of the following schemes and in the specific embodiments section. The structure numbering and variable numbering shown in the synthetic schemes are distinct from and should not be confused with the structure or variable numbering in the claims or the rest of the specification. The variables in the schemes are meant only to illustrate how to make some of the compounds of this invention.

A consideration in the planning of any synthetic route in this field is the choice of the protecting group used for protection of the reactive functional groups present in the compounds described in this invention. An authoritative account describing the many alternatives to the trained practitioner is Greene, T. W. et al., *Protecting Groups in Organic Synthesis,* 4th Edition, Wiley (2007)).

The abbreviations used below are standard organic chemistry abbreviations known by those skilled in this art.

ABBREVIATIONS

AcOH or HOAc acetic acid
ACN acetonitrile
ADDP 1,1'-(azodicarbonyl) dipiperidine
$CDCl_3$ deutero-chloroform
$CD_3OD$ deutero-methanol
CDI 1,1'-carbonyldiimidazole
cone concentrated
DCM dichloromethane
DIEA or DIPEA diisopropylethylamine
DMF dimethyl formamide
DMSO dimethyl sulfoxide
DMSO-$d_6$ deutero-dimethyl sulfoxide
$Et_3N$ or TEA triethylamine EtOAc ethyl acetate
EtOH ethanol
HATU 1-[bis(dimethylamino)methylene]-1H-1,2,3-triazolo[4,5-b]pyridinium 3-oxide hexafluorophosphate
HCl hydrochloric acid
HPLC high-performance liquid chromatography
$K_2HPO_4$ potassium hydrogenphosphate
LCMS liquid chromatography mass spectrometry
MeOH methanol
$MgSO_4$ magnesium sulfate
NMP N-methyl-2-pyrrolidone
NaCl sodium chloride
$Na_2CO_3$ sodium carbonate
$NaHCO_3$ sodium bicarbonate
NaOH sodium hydroxide
$Na_2SO_4$ sodium sulfate
$NH_4Cl$ ammonium chloride
$NH_4OAc$ ammonium acetate
$Pd(OAc)_2$ palladium(II) acetate
$Pd(PPh_3)_4$ tetrakis(triphenylphosphine)palladium(0)
Rt retention time
$SiO_2$ silica oxide
$SOCl_2$ thionyl chloride
TEA triethylamine
TFA trifluoroacetic acid
THF tetrahydrofuran
T3P® 1-propanephosphonic acid cyclic anhydride Normal phase chromatography was carried out using prepacked $SiO_2$ cartridges. Reverse phase preparative HPLC of Examples was carried out using Waters)(Bridge C18 column (19×200 mm, 5-μm particles) with UV and LCMS detection using variable gradients of mobile phase A (95% water, 5% ACN) and mobile phase B (5% water, 95% ACN) containing 0.1% TFA or 10 mM $NH_4OAc$. Reverse phase analytical HPLC/MS of Examples was performed on a Waters Acquity system coupled with a Waters MICROMASS® ZQ Mass Spectrometer.

Method A: Linear gradient of 0 to 100% B over 3 min, with 0.75 min hold time at 100% B;
UV visualization at 220 nm
Column: Waters BEH C18 2.1×50 mm
Flow rate: 1.0 mL/min
Solvent A: 10 mM $NH_4OAc$, 95% water, 5% ACN
Solvent B: 10 mM $NH_4OAc$, 5% water, 95% ACN Method B: Linear gradient of 0 to 100% B over 3 min, with 0.75 min hold time at 100% B;
UV visualization at 220 nm
Column: Waters BEH C18 2.1×50 mm
Flow rate: 1.0 mL/min
Solvent A: 0.1% TFA, 95% water, 5% ACN
Solvent B: 0.1% TFA, 5% water, 95% ACN Method C: Linear gradient of 2 to 98% B over 1 min, with 0.50 min hold time at 100% B;
UV visualization at 220 nm
Column: Waters BEH C18 2.1×50 mm
Flow rate: 0.8 mL/min
Solvent A: water containing 0.05% TFA
Solvent B: ACN containing 0.05% TFA Method D: Linear gradient of 0 to 100% B over 10 min, with 5 min hold at 100% B
UV visualization at 254 nm
Column: SunFire C18; 3.5 μm; 4.6×150 mm
Flow rate: 1 mL/min
Solvent A: 10% acetonitrile, 90% water, 0.05% TFA
Solvent B: 10% water, 90% acetonitrile, 0.05% TFA Method E: Linear gradient of 0 to 100% B over 3 min, with 0.5 min hold at 100% B Detection: MS and UV (220 nm)

Column: Waters)(Bridge C18, 2.1 mm×50 mm, 1.7 μm particles

Flow rate: 1 mL/min (Method A)

Temperature: 50° C.

Solvent A: 5:95 acetonitrile:water with 10 mM ammonium acetate

Solvent B: 95:5 acetonitrile:water with 10 mM ammonium acetate

Some compounds of formula I can be prepared as described in Scheme 1.

Scheme 1.

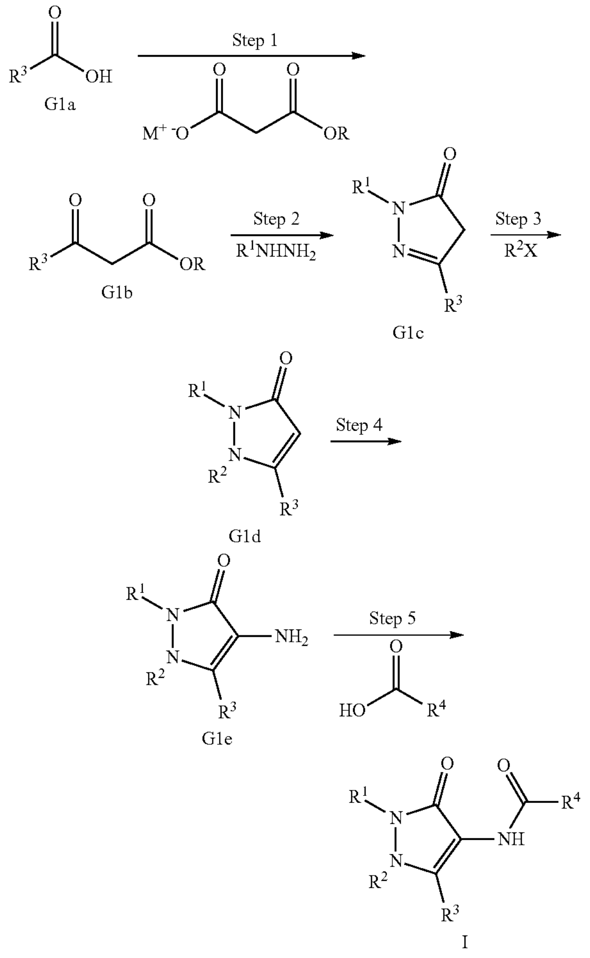

Step 1 describes the preparation of compounds of Formula G1b by condensing an acid of Formula G1a, which has been activated using reagents (e.g. CDI or SOC12), with a metal salt (e.g. potassium or sodium) of an alkyl malonate. Step 2 describes the preparation of compounds of Formula G1c by condensation of compounds of Formula G1b with a hydrazine $R^1NHNH_2$. Step 3 describes the preparation of compounds of Formula G1 d from compounds of Formula G1c by alkylation using $R^2X$, where X represents a leaving group (e.g. halogens or sulfonates). Step 4 describes the preparation of compounds of Formula G1e by amination of compounds of Formula G1d. The conversion of compounds of Formula G1d to compounds of G1e is generally a two step process: nitrosation followed by reduction of the intermediate nitroso compound. Step 5 describes the preparation of compounds of Formula I by condensing compounds of Formula G1e with an acid $R^4CO_2H$ or activated equivalent.

Example 1. N-[5-(2,6-difluoro-4-methoxyphenyl)-1-methyl-3-oxo-2-phenyl-2,3-dihydro-1H-pyrazol-4-yl]-4-(difluoromethoxy)benzamide

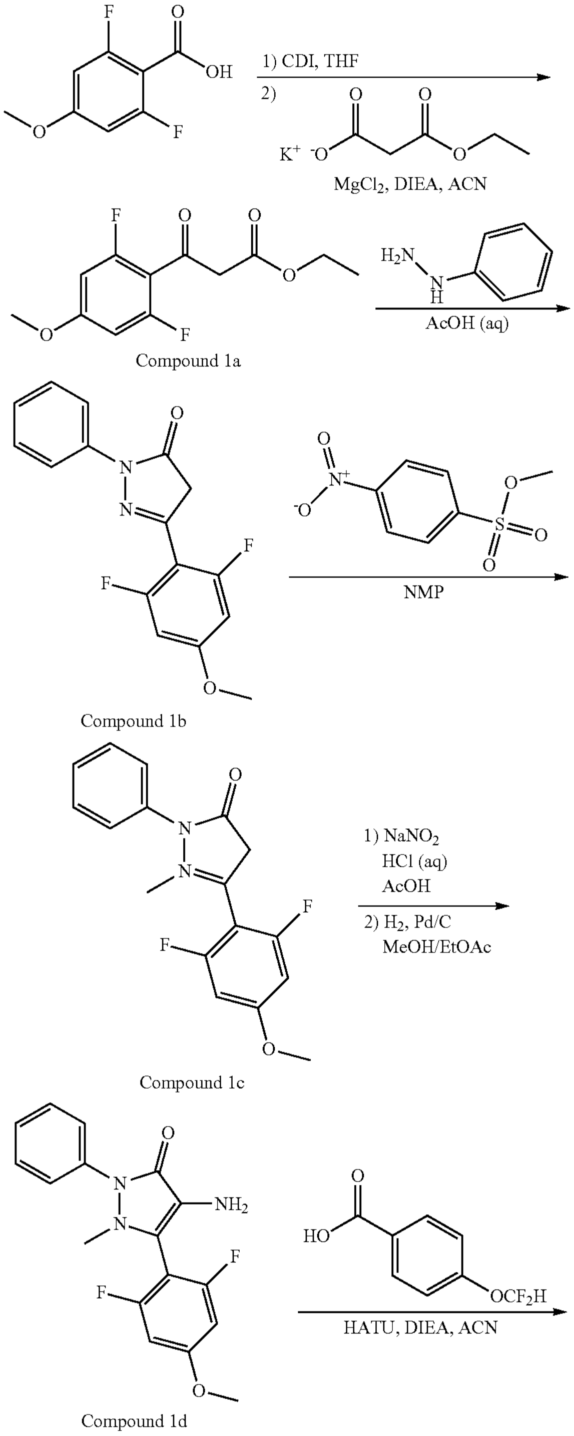

-continued

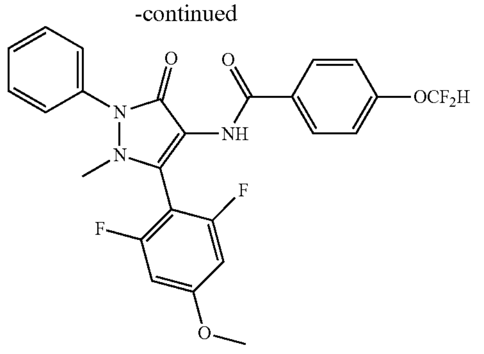

Example 1

Compound 1a. ethyl 3-(2,6-difluoro-4-methoxyphenyl)-3-oxopropanoate: (i) CDI (1.18 g, 7.28 mmol) was added in portions to a mixture of 2,6-difluoro-4-methoxybenzoic acid (1.14 g, 6.07 mmol) and anhydrous THF (7.5 mL), and the mixture stirred for 8 h. (ii) Magnesium chloride (1.45 g, 15.2 mmol) was added in portions to a mixture of ethyl potassium malonate (2.07 g, 12.2 mmol), DIEA (3.18 mL, 18.2 mmol) and anhydrous ACN (30 mL) keeping the temperature below 20° C. The mixture was stirred at rt for 4 h then cooled in an ice-bath. The solution from step (i) was added dropwise, and the mixture was stirred at rt for 16 h. The mixture was concentrated under reduced pressure then toluene (20 mL) added. The mixture was cooled in an ice bath, and 4 M HCl (8 mL) was slowly added. The mixture was allowed to warm to rt, diluted with EtOAc and water, and the layers were separated. The aqueous layer was extracted with EtOAc then the combined organic layers were washed with water and brine, dried ($Na_2SO_4$), filtered and concentrated under reduced pressure. The residue was purified by silica gel chromatography, eluting with 0 to 20% EtOAc/hexanes to give Compound 1a (1.22 g, 4.71 mmol, 78% yield) as a clear colorless oil. LCMS (Method C) Rt=0.98 min, m/z=259.1 (M+H). Compound appears to exist as a 3:1 ratio of keto/enol tautomers. Major tautomer: $^1$H NMR (500 MHz, $CDCl_3$) δ 6.51 (d, J=10.5 Hz, 2H), 4.22 (q, J=7.2 Hz, 2H), 3.90 (s, 2H), 3.87 (s, 2H), 1.27 (t, J=7.2 Hz, 3H).

Compound 1b. 5-(2,6-difluoro-4-methoxyphenyl)-2-phenyl-2,4-dihydro-3H-pyrazol-3-one. To a solution of Compound 1a (680 mg, 2.63 mmol) in 50% aq AcOH (20 mL) was added phenylhydrazine (0.26 mL, 2.6 mmol), and the mixture was heated at 115° C. for 2 h. The mixture was allowed to cool to rt then poured into brine and extracted with EtOAc (3×). The combined extracts were dried ($Na_2SO_4$), filtered and concentrated under reduced pressure. The residue was purified by silica gel chromatography eluting with 5 to 45% EtOAc/hexanes to give Compound 1b (510 mg, 1.7 mmol, 65% yield) as a white solid. LCMS (Method C) Rt=0.87 min, m/z=303.1 (M+H). $^1$H NMR (500 MHz, $CDCl_3$) δ 7.98 (d, J=7.7 Hz, 2H), 7.45 (t, J=8.0 Hz, 2H), 7.27-7.20 (m, 1H), 6.59 (d, J=10.7 Hz, 2H), 3.94 (s, 2H), 3.88 (s, 3H).

Compound 1c. 5-(2,6-difluoro-4-methoxyphenyl)-1-methyl-2-phenyl-1,2-dihydro-3H-pyrazol-3-one. To a solution of Compound 1b (250 mg, 0.83 mmol) in NMP (2 mL) was added methyl 4-nitrobenzenesulfonate (540 mg, 2.5 mmol), and the mixture was heated at 160° C. for 1 h. The mixture was cooled to rt, poured into water and extracted with 50% EtOAc/hexanes (3×). The combined extracts were washed with brine, dried ($Na_2SO_4$), filtered and concentrated under reduced pressure. The residue was purified by silica gel chromatography eluting with 5 to 60% EtOAc/DCM to give Compound 1c (150 mg, 0.47 mmol, 57% yield). LCMS (Method C) Rt=0.79 min, m/z=317.1 (M+H). $^1$H NMR (500 MHz, $CDCl_3$) δ 7.56-7.46 (m, 4H), 7.39-7.31 (m, 1H), 6.63 (d, J=9.6 Hz, 2H), 8 Compound 1d. 4-amino-5-(2,6-difluoro-4-methoxyphenyl)-1-methyl-2-phenyl-1,2-dihydro-3H-pyrazol-3-one. To a solution of Compound 1c (550 mg, 1.7 mmol) in a mixture of acetic acid (6.5 mL) and conc HCl (1.3 mL) in an ice bath was added dropwise a solution of sodium nitrite (480 mg, 7.0 mmol) in water (0.80 mL), and the mixture stirred for 2 h. The mixture was poured into ice water and extracted with DCM (3×). The combined extracts were washed with brine, dried ($Na_2SO_4$), filtered and evaporated under reduced pressure. The residue was dissolved in a 1:1 mixture of EtOAc/MeOH (20 mL), and 10% Pd/C (catalytic amount) was added. The mixture was stirred under a balloon of $H_2$ for 16 h. The mixture was filtered, evaporated under reduced pressure, and the residue was purified by silica gel chromatography eluting with 0 to 85% EtOAc/hexanes to give Compound 1d (290 mg, 0.88 mmol, 50% yield) as an off-white solid. LCMS (Method C) Rt=0.76 min, m/z=322.2 (M+H). $^1$H NMR (500 MHz, $CDCl_3$) δ 7.70-7.55 (m, 2H), 7.48 (t, J=8.0 Hz, 2H), 7.34-7.20 (m, 1H), 6.63 (d, J=9.9 Hz, 2H), 3.87 (s, 3H), 3.41 (br s, 2H), 2.73 (s, 3H).

Example 1. N-[5-(2,6-difluoro-4-methoxyphenyl)-1-methyl-3-oxo-2-phenyl-2,3-dihydro-1H-pyrazol-4-yl]-4-(difluoromethoxy)benzamide. To a solution of Compound 1d (7.8 mg, 0.024 mmol) and 4-(difluoromethoxy)benzoic acid (5.8 mg, 0.031 mmol) in ACN (0.25 mL) was added DIEA (6.2 μL, 0.035 mmol) followed by HATU (10.7 mg, 0.028 mmol), and the mixture stirred at 80° C. for 4 h. The mixture was cooled to rt, and evaporated under reduced pressure. The residue was purified by silica gel chromatography eluting with 10 to 90% EtOAc/hexanes to give Example 1 (9.0 mg, 0.018 mmol, 75% yield) as a white solid. LCMS (Method C) Rt=0.86 min, m/z=502.1 (M+H). $^1$H NMR (500 MHz, $CD_3OD$) δ 7.84 (br d, J=8.3 Hz, 2H), 7.56-7.50 (m, 2H), 7.49-7.45 (m, 2H), 7.43-7.37 (m, 1H), 7.13 (br d, J=8.5 Hz, 2H), 6.60 (t, J=73.5 Hz, 1H), 6.58 (d, J=9.9 Hz, 2H), 3.81 (s, 3H), 3.04 (s, 3H).

Examples 2-33 (Table 2) were prepared as described for Example 1.

Example 34. N-[2-(2,3-dichlorophenyl)-5-(2,6-difluoro-4-methoxyphenyl)-1-methyl-3-oxo-2,3-dihydro-1H-pyrazol-4-yl]-4-(difluoromethoxy)benzamide

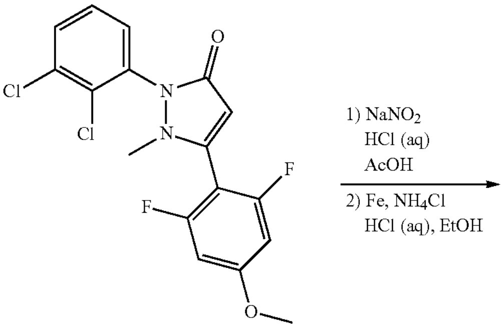

Compound 34a

-continued

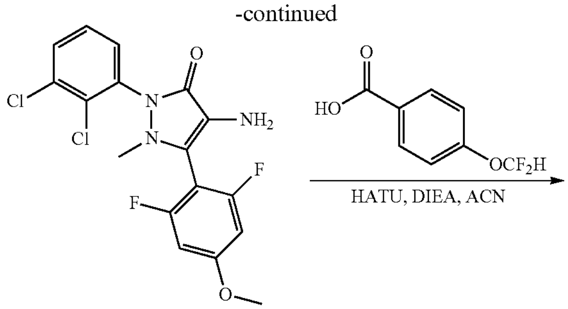

Compound 34b

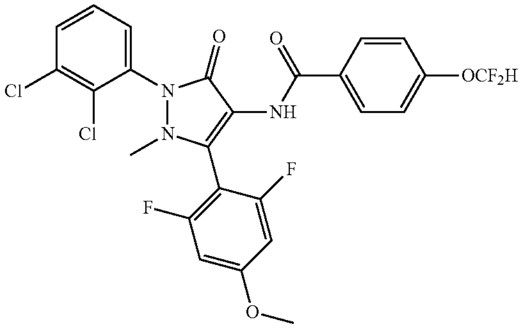

Example 34

Compound 34b. 4-amino-2-(2,3-dichlorophenyl)-5-(2,6-difluoro-4-methoxyphenyl)-1-methyl-1,2-dihydro-3H-pyrazol-3-one. To a solution of Compound 34a (89 mg, 0.23 mmol, prepared as described for Compound 1c) in AcOH (0.86 mL) and conc HCl (0.17 mL) at ice bath temperature was added dropwise a solution of sodium nitrite (64 mg, 0.92 mmol) in water (0.12 mL), and the mixture stirred for 0.5 h. The mixture was poured into ice water and extracted with DCM (3×). The combined extracts were washed with brine, dried ($Na_2SO_4$), filtered and evaporated under reduced pressure. The residue was dissolved in a 4:1 mixture of EtOH/water (3 mL). Ammonium chloride (38 mg, 0.72 mmol) was added, followed by iron (39 mg, 0.69 mmol) and conc HCl (19 μl, 0.23 mmol), and the mixture was heated at 90° C. for 15 min. The mixture was cooled to rt then poured into 1.5N $K_2HPO_4$ and extracted with DCM (3×). The combined extracts were dried ($Na_2SO_4$), filtered and evaporated under reduced pressure. The residue was purified by silica gel chromatography eluting with 0 to 60% EtOAc/DCM to give Compound 34b (33 mg, 0.082 mmol, 36% yield) as an off-white solid. LCMS (Method C) Rt=0.85 min, m/z=400.0 (M+H).

Example 34. N-[2-(2,3-dichlorophenyl)-5-(2,6-difluoro-4-methoxyphenyl)-1-methyl-3-oxo-2,3-dihydro-1H-pyrazol-4-yl]-4-(difluoromethoxy)benzamide Prepared from Compound 34b as described for Example 1. LCMS (Method A) Rt=1.86 min, m/z=570.2 (M+H). $^1H$ NMR (500 MHz, DMSO-$d_6$) δ 9.58 (br s, 1H), 7.89 (br d, J=7.9 Hz, 2H), 7.82 (d, J=8.1 Hz, 1H), 7.59 (t, J=8.0 Hz, 1H), 7.55-7.50 (m, 1H), 7.42-7.06 (m, 3H), 6.86 (br d, J=10.9 Hz, 2H), 3.82 (s, 3H), 2.92 (s, 3H).

Examples 35 to 38 (Table 2) were prepared as described for Example 34.

Example 39. N-[2-(6-chloropyridin-2-yl)-5-(2,6-difluoro-4-methoxyphenyl)-1-methyl-3-oxo-2,3-dihydro-1H-pyrazol-4-yl]-4-(difluoromethoxy)benzamide

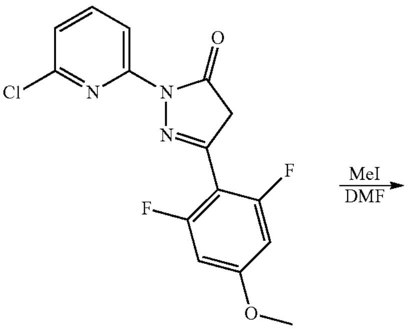

Compound 39a

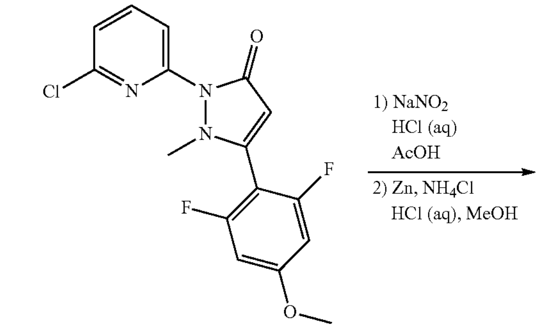

Compound 39b

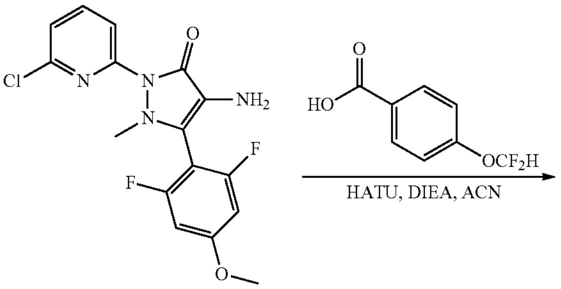

Compound 39c

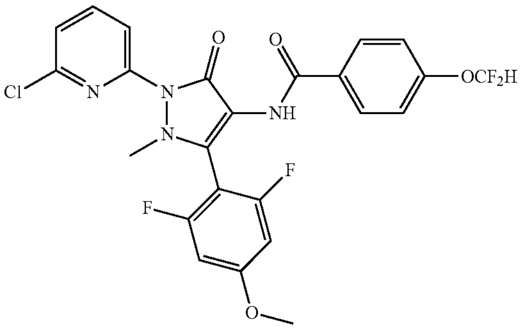

Example 39

Compound 39b. 2-(6-chloropyridin-2-yl)-5-(2,6-difluoro-4-methoxyphenyl)-1-methyl-1,2-dihydro-3H-pyrazol-3-one. To a solution of Compound 39a (460 mg, 1.4 mmol, prepared as described for Compound 1b) in DMF (3.5 mL) was added methyl iodide (0.13 mL, 2.0 mmol), and the mixture was heated at 100° C. for 16 h. Additional methyl iodide (0.065 mL, 1.0 mmol) was added, and the mixture was heated at 100° C. for 4 h. The mixture was cooled to rt, diluted with EtOAc, washed with brine (3×), dried ($Na_2SO_4$), filtered and evaporated under reduced pressure. The residue was purified by silica gel chromatography eluting with 0-100% EtOAc/DCM to give Compound 39b (354 mg, 1.01 mmol, 74% yield) as an off-white solid. LCMS (Method C) Rt=0.81 min, m/z=352.0 (M+H).

Compound 39c. 4-amino-2-(6-chloropyridin-2-yl)-5-(2,6-difluoro-4-methoxyphenyl)-1-methyl-1,2-dihydro-3H-pyrazol-3-one. To a solution of Compound 39b (300 mg, 0.85 mmol) in AcOH (6.5 mL) and cone HCl (1.3 mL) at ice bath temp was added dropwise a solution of sodium nitrite (160 mg, 2.3 mmol) in water (0.8 mL), and the mixture was stirred for 0.5 h. The mixture was poured into ice water and extracted with DCM (3×). The combined extracts were washed with brine, dried ($Na_2SO_4$), filtered, and evaporated under reduced pressure. The residue was suspended in a 4:1 mixture of MeOH/water (10 mL), cooled in an ice bath, and then treated with cone HCl (71 μL, 0.85 mmol), ammonium chloride (141 mg, 2.64 mmol) and zinc (167 mg, 2.56 mmol). The mixture was warmed to rt and stirred for 15 min. The mixture was concentrated under reduced pressure. The residue was dissolved in EtOAc, washed with sat. $NaHCO_3$, dried ($Na_2SO_4$), filtered and evaporated under reduced pressure. The residue was purified by silica gel chromatography eluting with 0-100% EtOAc/DCM to give Compound 39c (150 mg, 0.41 mmol, 48% yield) as a white solid. LCMS (Method C) Rt=0.76 min, m/z=367.0 (M+H).

Example 39. N-[2-(6-chloropyridin-2-yl)-5-(2,6-difluoro-4-methoxyphenyl)-1-methyl-3-oxo-2,3-dihydro-1H-pyrazol-4-yl]-4-(difluoromethoxy)benzamide. Prepared from Compound 39c as described for Example 1. LCMS (Method A) Rt=1.84 min, m/z=537.4 (M+H). $^1H$ NMR (500 MHz, $CD_3OD$) δ 8.00-7.94 (m, 1H), 7.92-7.84 (m, 3H), 7.41 (d, J=7.7 Hz, 1H), 7.19 (d, J=8.6 Hz, 2H), 7.05-6.72 (m, 3H), 3.87 (s, 3H), 3.33 (s, 3H).

Example 40-41 (Table 2) were prepared as described for Example 39.

Example 42. N-[2-(5-chloropyridin-2-yl)-5-(2,6-difluoro-4-methoxyphenyl)-1-methyl-3-oxo-2,3-dihydro-1H-pyrazol-4-yl]-4-(difluoromethoxy)benzamide

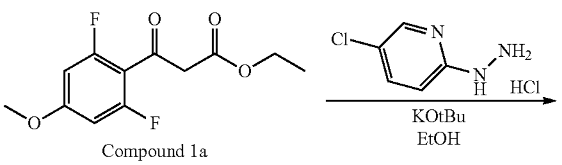

Compound 1a

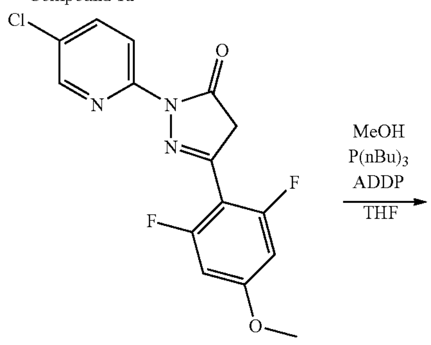

Compound 42a

-continued

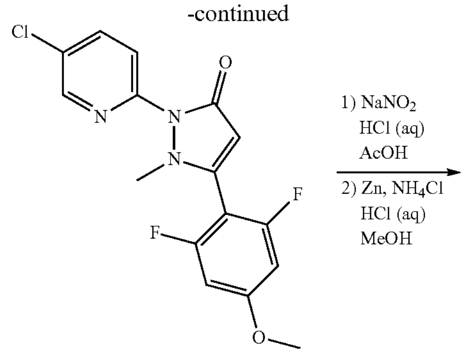

Compound 42b

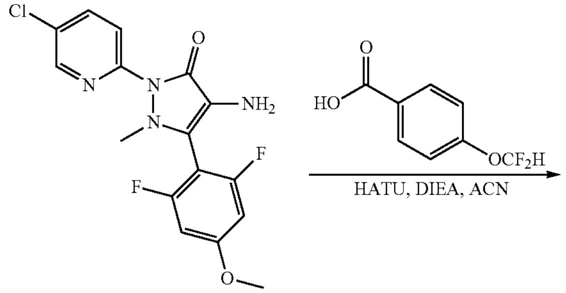

Compound 42c

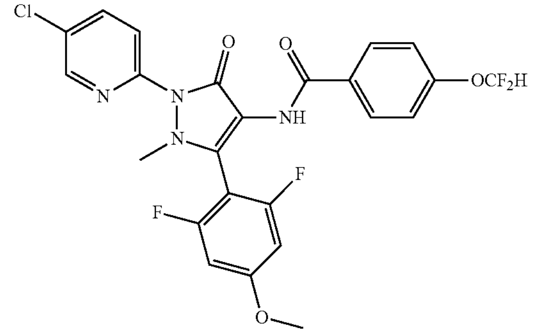

Example 42

Compound 42a. 2-(5-chloropyridin-2-yl)-5-(2,6-difluoro-4-methoxyphenyl)-2,4-dihydro-3H-pyrazol-3-one. A mixture of 5-chloro-2-hydrazinylpyridine hydrochloride (450 mg, 2.5 mmol) and potassium tert-butoxide (280 mg, 2.5 mmol) in EtOH (3.2 mL) was stirred for 15 min then Compound 1a was added. The mixture was stirred at 90° C. for 16 h. The mixture was cooled to rt, then quenched with saturated $NH_4Cl$, and the mixture was extracted with EtOAc (3×). The combined extracts were dried ($Na_2SO_4$), filtered and evaporated under reduced pressure. The residue was purified by silica gel chromatography eluting with 0 to 100% EtOAc/hexane to give Compound 42a (215 mg, 0.64 mmol, 66% yield) as an off-white solid. LCMS (Method C) Rt=1.12 min, m/z=338.1 (M+H).

Compound 42b. 2-(5-chloropyridin-2-yl)-5-(2,6-difluoro-4-methoxyphenyl)-1-methyl-1,2-dihydro-3H-pyrazol-3-one. To a solution of Compound 39a (210 mg, 0.63 mmol) in THF (6.3 mL) was added MeOH (0.26 mL, 6.3 mmol), tri-n-butylphosphine (0.32 mL, 1.3 mmol) and ADDP (190 mg, 0.76 mmol), and the mixture stirred for 16 h. The mixture was diluted with brine and extracted with EtOAc. The extract was washed with brine, dried ($Na_2SO_4$), filtered and evaporated under reduced pressure. The residue was treated with DCM and diethyl ether, and the solid was removed by filtration. The filtrate was concentrated, and the residue was purified by silica gel chromatography eluting with 0-100% EtOAc/hexanes to give Compound 42b (100 mg, 0.28 mmol, 45% yield) as a white solid. LCMS (Method C) Rt=0.95 min, m/z=352.1 (M+H). $^1$H NMR (500 MHz, DMSO-d6) δ 8.62 (d, J=2.5 Hz, 1H), 8.12 (dd, J=8.8, 2.8 Hz, 1H), 7.95 (d, J=8.8 Hz, 1H), 7.03 (d, J=10.2 Hz, 2H), 5.74 (s, 1H), 3.89 (s, 3H), 3.19 (s, 3H).

Compound 42c. 4-amino-2-(5-chloropyridin-2-yl)-5-(2,6-difluoro-4-methoxyphenyl)-1-methyl-1,2-dihydro-3H-pyrazol-3-one. Prepared from Compound 42b as described for Compound 39c. LCMS (Method C) Rt=0.78 min, m/z=367.0 (M+H).

Example 42. N-[2-(5-chloropyridin-2-yl)-5-(2,6-difluoro-4-methoxyphenyl)-1-methyl-3-oxo-2,3-dihydro-1H-pyrazol-4-yl]-4-(difluoromethoxy)benzamide. Prepared from Compound 42c as described for Example 1. LCMS (Method A) Rt=1.85 min, m/z=537.2 (M+H). $^1$H NMR (500 MHz, $CD_3OD$) δ 8.57 (d, J=2.4 Hz, 1H), 8.02 (dd, 2.5 Hz, 1H), 7.96-7.91 (m, 1H), 7.90-7.84 (m, 2H), 7.27-7.14 (m, 2H), 7.05-6.71 (m, 3H), 3.86 (m, 3H), 3.31 (s, 3H)

Example 43 (Table 2) was prepared as described for Example 42.

Example 44. N-[5-(2,6-difluoro-4-methoxyphenyl)-1-methyl-3-oxo-2-(pyridin-2-yl)-2,3-dihydro-1H-pyrazol-4-yl]-4-(difluoromethoxy)benzamide

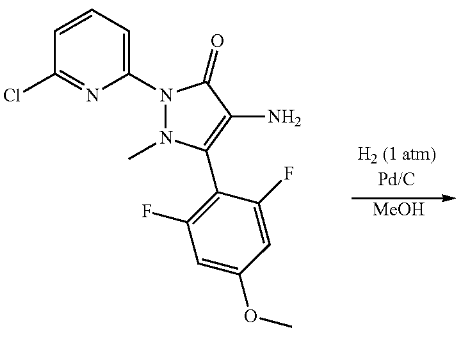

Compound 39c

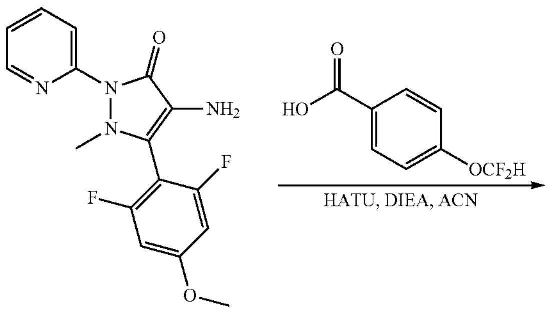

Compound 44c

-continued

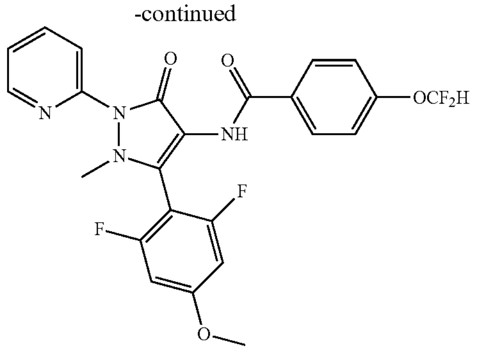

Example 44

Compound 44a. 4-amino-5-(2,6-difluoro-4-methoxyphenyl)-1-methyl-2-(pyridin-2-yl)-1,2-dihydro-3H-pyrazol-3-one. To a solution of Compound 39c (24 mg, 0.065 mmol) in MeOH (3 mL) was added 10% Pd/C (10 mg). The mixture was stirred under a balloon of hydrogen for 16 h. The mixture was filtered through celite, and the filtrate was evaporated under reduced pressure to give Compound 44a (22 mg, 0.065 mmol, 100% yield). LCMS (Method C) Rt=0.64 min, m/z=333.1 (M+H).

Example 44. N-[5-(2,6-difluoro-4-methoxyphenyl)-1-methyl-3-oxo-2-(pyridin-2-yl)-2,3-dihydro-1H-pyrazol-4-yl]-4-(difluoromethoxy)benzamide. Prepared from Compound 44a as described for Example 1. LCMS (Method A) Rt=1.50 min, m/z=503.2 (M+H). $^1$H NMR (500 MHz, $CD_3OD$) δ 8.59 (br d, J=4.1 Hz, 1H), 8.00 (br d, J=1.3 Hz, 1H), 7.88 (br d, J=8.2 Hz, 3H), 7.40 (dd, 5.2 Hz, 1H), 7.19 (d, J=8.7 Hz, 2H), 7.06-6.69 (m, 3H), 3.86 (s, 3H), 3.30 (s, 3H).

Example 45. N-[2-(6-cyclopropylpyridin-2-yl)-5-(2,6-difluoro-4-methoxyphenyl)-1-methyl-3-oxo-2,3-dihydro-1H-pyrazol-4-yl]-4-(difluoromethoxy)benzamide

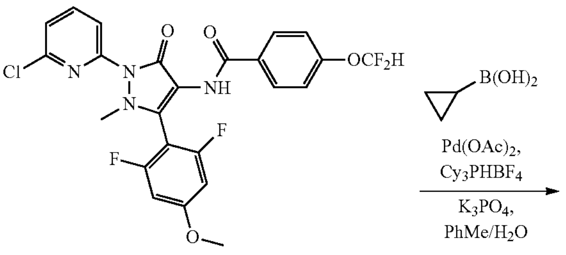

Example 39

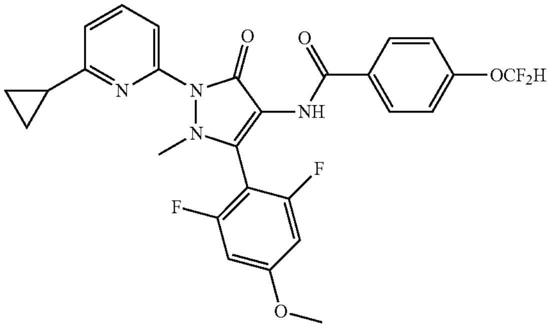

Example 45

Example 45. N-[2-(6-cyclopropylpyridin-2-yl)-5-(2,6-difluoro-4-methoxyphenyl)-1-methyl-3-oxo-2,3-dihydro-1H-pyrazol-4-yl]-4-(difluoromethoxy)benzamide. To a solution of Example 39 (130 mg, 0.24 mmol) in toluene (2.5 mL) and water (0.50 mL) was added cyclopropylboronic acid (125 mg, 1.45 mmol), palladium(II) acetate (11 mg, 0.048 mmol), tricyclohexylphosphonium tetrafluoroborate (36 mg, 0.097 mmol) and phosphoric acid, potassium salt (210 mg, 0.97 mmol). The reaction mixture was degassed and heated at 140° C. for 1 h. The mixture was filtered through celite and evaporated under reduced pressure. The residue was purified by preparative HPLC to give Example 45 (91 mg, 0.17 mmol, 69% yield) as an off-white solid. LCMS (Method C) Rt=0.88 min, m/z=543.1 (M+H). $^1$H NMR (500 MHz, $CD_3OD$) δ 7.92 (d, J=8.8 Hz, 2H), 7.84 (t, J=7.8 Hz, 1H), 7.63 (d, J=7.7 Hz, 1H), 7.30 (d, J=7.4 Hz, 1H), 7.22 (d, J=8.8 Hz, 2H), 6.96 (t, J=73.5 Hz, 1H), 6.81 (d, J=10.2 Hz, 2H), 3.89 (s, 3H), 3.33 (s 3H), 2.25-2.11 (m, 1H), 1.13-1.00 (m, 4H).

Examples 46-53 (Table 2) were prepared as described for Example 45.

Example 54. N-[2-(5-cyanopyridin-2-yl)-5-(2,6-difluoro-4-methoxyphenyl)-1-methyl-3-oxo-2,3-dihydro-1H-pyrazol-4-yl]-4-(difluoromethoxy)benzamide

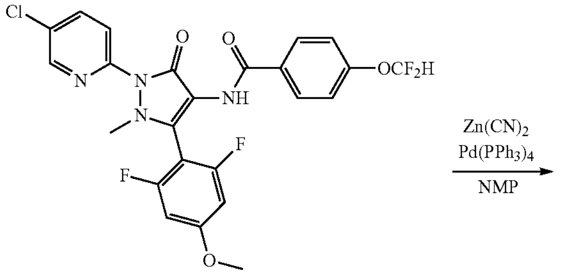

Example 42

-continued

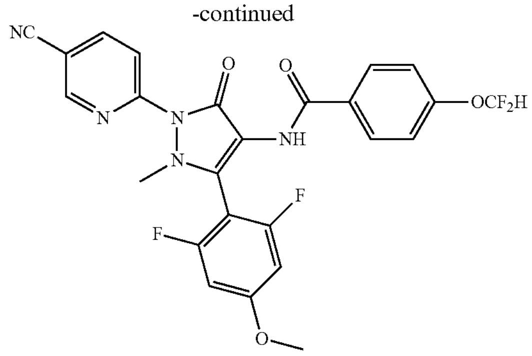

Example 54

Example 54. N-[2-(5-cyanopyridin-2-yl)-5-(2,6-difluoro-4-methoxyphenyl)-1-methyl-3-oxo-2,3-dihydro-1H-pyrazol-4-yl]-4-(difluoromethoxy)benzamide. To a solution of Example 42 (17 mg, 0.029 mmol) in degassed NMP (0.3 mL) was added dicyanozinc (6.9 mg, 0.058 mmol) and $Pd(PPh_3)_4$ (3.4 mg, 2.9 μmol). The solution was placed under nitrogen and stirred at 110° C. for 16 h. The mixture was cooled to rt, filtered, and the residue was purified by preparative HPLC to give Example 54 (7.6 mg, 0.014 mmol, 48% yield). LCMS (Method A) Rt=1.83 min, m/z=528.0 (M+H). $^1$H NMR (500 MHz, $CD_3OD$) δ 8.90 (d, J=1.4 Hz, 1H), 8.35-8.18 (m, 2H), 7.88 (br d, J=8.6 Hz, 2H), 7.20 (s, 2H), 7.07-6.69 (m, 3H), 3.87 (s, 3H), 3.35 (s, 3H).

Examples 55-56 (Table 2) were prepared as described for Example 54.

Example 57. N-[5-(2,6-difluoro-4-methoxyphenyl)-1-methyl-3-oxo-2-{[5-(propan-2-yl)-1,3,4-oxadiazol-2-yl]methyl}-2,3-dihydro-1H-pyrazol-4-yl]-4-(difluoromethoxy)benzamide

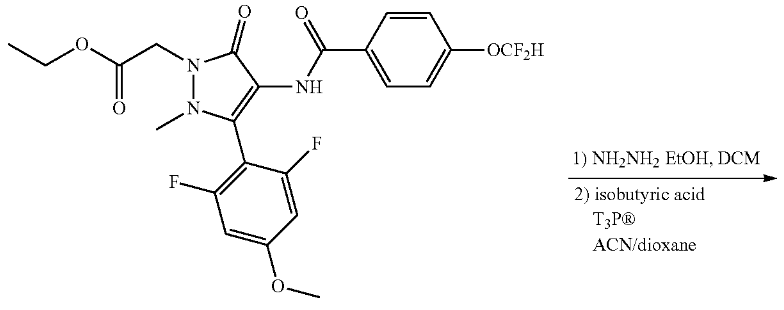

Example 21

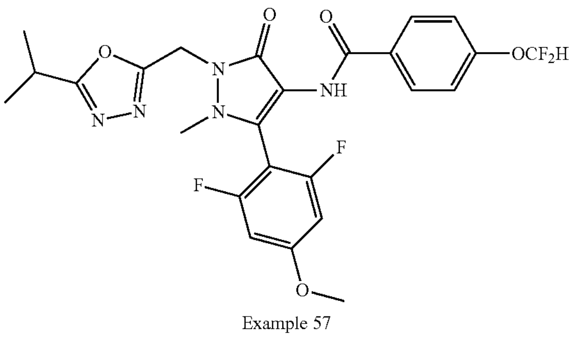

Example 57

Example 57. N-[5-(2,6-difluoro-4-methoxyphenyl)-1-methyl-3-oxo-2-{[5-(propan-2-yl)-1,3,4-oxadiazol-2-yl] methyl}-2,3-dihydro-1H-pyrazol-4-yl]-4-(difluoromethoxy) benzamide. To a solution of Example 21 (27 mg, 0.053 mmol) in 10% EtOH/DCM (0.5 mL) was added hydrazine (17 μL, 0.53 mmol), and the mixture stirred for 16 h. The mixture was diluted with $Et_2O$ and filtered to give the intermediate hydrazide, N-(5-(2,6-difluoro-4-methoxyphenyl)-2-(2-hydrazinyl-2-oxoethyl)-1-methyl-3-oxo-2,3-dihydro-1H-pyrazol-4-yl)-4-(difluoromethoxy)benzamide (26 mg, 0.052 mmol, 99% yield), as a white solid. LCMS (Method C) Rt=0.64 min, m/z=498.0 (M+H). The intermediate hydrazide (13 mg, 0.026 mmol) and isobutyric acid (2.7 μL, 0.029 mmol) were dissolved in dioxane (0.2 mL), and 50% T3P® in ACN (0.062 mL, 0.11 mmol) was added followed by DIEA (0.018 mL, 0.11 mmol). The mixture was heated at 70° C. for 16 h. The mixture was cooled to rt, filtered, and the residue was purified by preparative HPLC to give Example 57 (1.6 mg, 0.0028 mmol, 11% yield). LCMS (Method A) Rt=1.62 min, m/z=550.3 (M+H). $^1$H NMR (500 MHz, DMSO-$d_6$) δ 9.62 (br s, 1H), 7.89 (br d, J=8.2 Hz, 2H), 7.33 (t, J=73.6 Hz, 1H), 7.23 (br d, J=8.2 Hz, 2H), 6.88 (br d, J=10.4 Hz, 2H), 5.38 (s, 2H), 3.81 (s, 3H), 3.18 (br d, J=4.9 Hz, 1H), 3.14 (s, 3H), 1.30 (d, J=6.7 Hz, 6H)

Example 58. N-[5-(2,6-difluoro-4-methoxyphenyl)-2-(2-hydroxyethyl)-1-methyl-3-oxo-2,3-dihydro-1H-pyrazol-4-yl]-4-(difluoromethoxy)benzamide

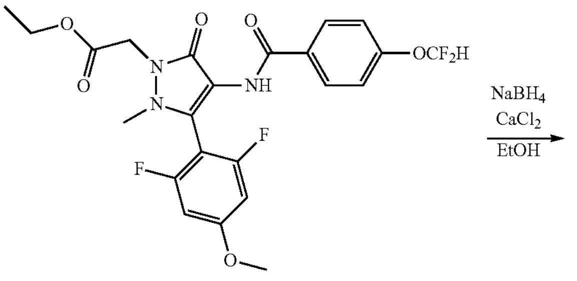

Example 21

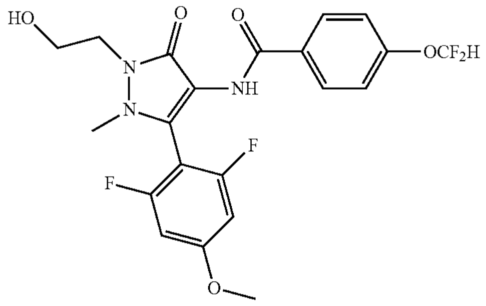

Example 58

Example 58. N-[5-(2,6-difluoro-4-methoxyphenyl)-2-(2-hydroxyethyl)-1-methyl-3-oxo-2,3-dihydro-1H-pyrazol-4-yl]-4-(difluoromethoxy)benzamide. To a solution of Example 21 (10 mg, 0.020 mmol) in EtOH (0.25 mL) was added calcium chloride (4.3 mg, 0.039 mmol) followed by sodium borohydride (1.5 mg, 0.039 mmol), and the mixture was stirred for 3 h. The mixture was diluted with water and extracted with DCM (3×). The combined extracts were dried ($Na_2SO_4$), filtered and concentrated under reduced pressure. The residue was purified by preparative HPLC to give Example 58 (5.9 mg, 0.012 mmol, 62% yield). LCMS (Method A) Rt=1.40 min, m/z=469.9 (M+H). $^1$H NMR (500 MHz, DMSO-$d_6$) δ 7.87 (br d, J=8.1 Hz, 2H), 7.26 (t, J=72.8 Hz, 1H), 7.21 (br d, J=8.4 Hz, 2H), 6.83 (br d, J=10.4 Hz, 2H), 3.95 (t, J=5.9 Hz, 2H), 3.82 (s, 3H), 3.63 (br t, J=5.7 Hz, 2H), 3.19 (s, 3H).

Example 59. N-[5-(2,6-difluoro-4-methoxyphenyl)-2-(4-methoxypyridin-2-yl)-1-methyl-3-oxo-2,3-dihydro-1H-pyrazol-4-yl]-4-(difluoromethoxy)benzamide

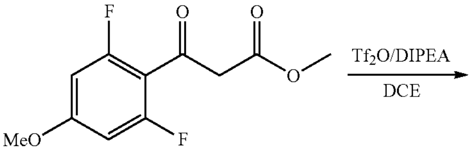

Compound 1a

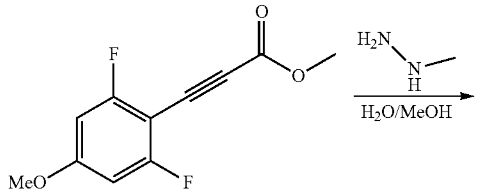

Compound 59a

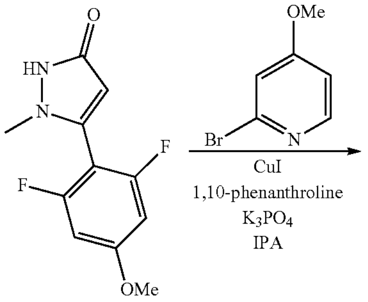

Compound 59b

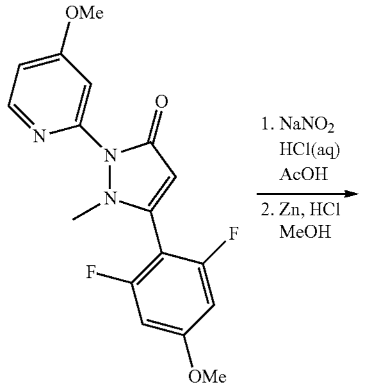

Compound 59c

-continued

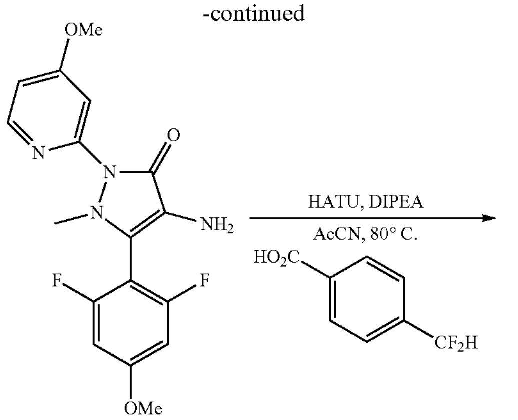

Compound 59d

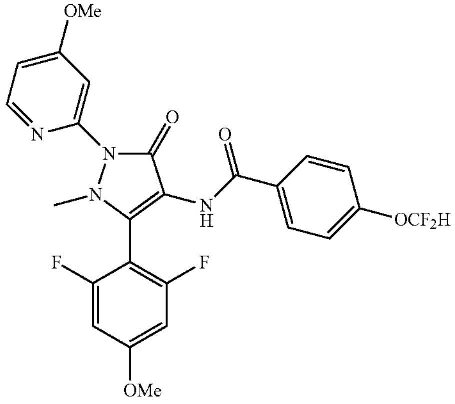

Example 59

Compound 59a. Methyl 3-(2,6-difluoro-4-methoxyphenyl)propiolate: To compound 1a (0.71 g, 2.9 mmol) in DCE (3.6 mL) under nitrogen was added triflic anhydride (0.54 mL, 3.2 mmol). The mixture was stirred for 15 min, then a solution of DIPEA (1.3 mL, 7.3 mmol) was added dropwise over a period of 15 min, resulting in an exothermic reaction. The reaction mixture was stirred for 30 min. The reaction was quenched with water, extracted with EtOAc, washed with 1N HCl and brine, dried over $Na_2SO_4$ and concentrated. The crude residue was purified by silica gel chromatography eluting with 0-100% EtOAc/hexanes to give compound 59a (430 mg, 1.9 mmol, 65% yield). MS (ESI) m/z 226.9 (M+H).

Compound 59b. 5-(2,6-difluoro-4-methoxyphenyl)-1-methyl-1,2-dihydro-3H-pyrazol-3-one: To a solution of compound 59a (425 mg, 1.88 mmol) in MeOH (2 mL) was added $H_2O$ (2 mL) followed by methylhydrazine (0.109 mL, 2.07 mmol), and the mixture heated at 50° C. overnight. The reaction mixture was cooled to rt, concentrated, and then poured into water and extracted with EtOAc. The combined extracts were washed with brine, dried over $Na_2SO_4$, filtered and evaporated. The residue was suspended in DCM, and the resulting solid was collected by filtration to give compound 59b as a white solid (155 mg, 0.646 mmol, 34.3% yield). NMR (500 MHz, DMSO-d6) δ 9.72 (br s, 1H), 6.92 (d, J=9.6 Hz, 2H), 5.59 (s, 1H), 3.85 (s, 3H), 3.44 (s, 3H).

Compound 59c. 5-(2,6-difluoro-4-methoxyphenyl)-2-(4-methoxypyridin-2-yl)-1-methyl-1,2-dihydro-3H-pyrazol-3-one: A mixture of 2-bromo-4-methoxypyridine (47.0 mg, 0.250 mmol), compound 59b (60 mg, 0.25 mmol), 1,10-phenanthroline (4.1 mg, 0.023 mmol), $K_3PO_4$ (74.2 mg, 0.350 mmol) and copper(I) iodide (2.38 mg, 0.012 mmol) and iPrOH (0.5 mL) in a pressure vial was flushed with nitrogen, then sealed and heated at 110° C. overnight. The reaction mixture was cooled to rt, diluted with water, then extracted with DCM (3×). The combined extracts were dried over $Na_2SO_4$, filtered and evaporated. The residue was purified by silica gel chromatography, eluting with 0-100% EtOAc/hexanes to provide compound 59c (45 mg, 0.13 mmol, 52%) $^1H$ NMR (500 MHz, $CDCl_3$) δ 8.34 (d, J=5.8 Hz, 1H), 7.65 (d, J=2.2 Hz, 1H), 6.74 (dd, J=5.8, 2.2 Hz, 1H), 6.68-6.57 (m, 2H), 5.73 (s, 1H), 3.96 (s, 3H), 3.89 (s, 3H), 3.30 (s, 3H) and the O-arylated by-product, 2-((5-(2,6-difluoro-4-methoxyphenyl)-1-methyl-1H-pyrazol-3-yl)oxy)-4-methoxypyridine (24 mg, 0.069 mmol, 27.4%). $^1H$ NMR (500 MHz, $CDCl_3$) δ 8.06 (d, J=6.1 Hz, 1H), 6.67-6.55 (m, 3H), 6.53 (d, J=2.2 Hz, 1H), 6.18 (s, 1H), 3.87 (s, 3H), 3.86 (s, 3H), 3.72 (s, 3H).

Compound 59d. 4-amino-5-(2,6-difluoro-4-methoxyphenyl)-2-(4-methoxypyridin-2-yl)-1-methyl-1,2-dihydro-3H-pyrazol-3-one: Compound 59d was prepared from compound 59c using the procedure described for Compound 1d.

Example 59. N-(5-(2,6-difluoro-4-methoxyphenyl)-2-(4-methoxypyridin-2-yl)-1-methyl-3-oxo-2,3-dihydro-1H-pyrazol-4-yl)-4-(difluoromethoxy)benzamide: Example 59 was prepared from compound 59d using the procedure described for Example 1. LCMS (Method C) Rt=1.59 min, m/z=533.2 (M+H). $^1H$ NMR (500 MHz, DMSO-d6) δ 9.69 (s, 1H), 8.41 (d, J=5.5 Hz, 1H), 7.91 (d, J=8.2 Hz, 2H), 7.49-7.41 (m, 1H), 7.37-7.15 (m, 3H), 7.00 (dd, J=5.8, 2.4 Hz, 1H), 6.94 (d, J=10.4 Hz, 2H), 3.92 (s, 3H), 3.83 (s, 3H), 3.18 (s, 3H).

Examples 60-84 (Table 2) were prepared as described for Example 59. In the case of trifluoromethoxyamide examples, trifluoromethoxybenzoic acid was used in place of difluoromethoxybenzoic acid for the amide formation.

Example 85

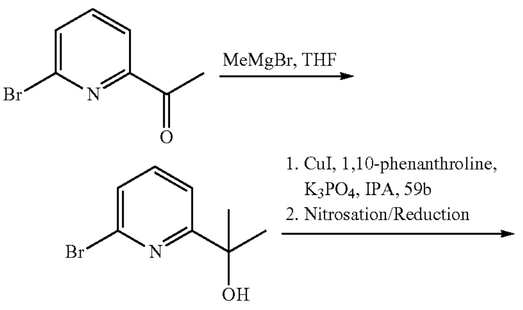

compound 85a

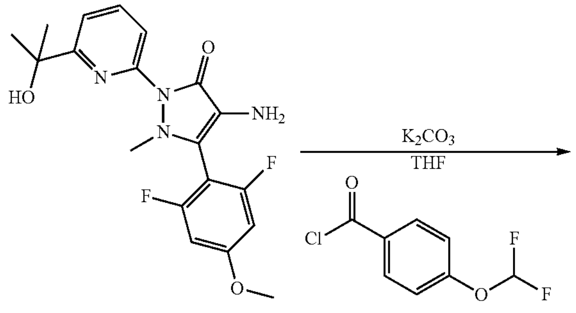

compound 85b

-continued

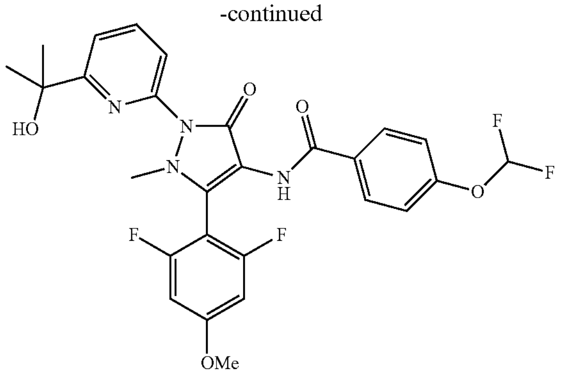

Example 85

Compound 85a. 2-(6-bromopyridin-2-yl)propan-2-ol: A solution of methylmagnesium bromide, 3M in $Et_2O$ (570 μL, 1.71 mmol) was added dropwise to a cooled solution of 1-(6-bromopyridin-2-yl)ethan-1-one (285 mg, 1.42 mmol) in anhydrous THF (2.8 mL) at 0° C. for 1.5 hr, then at rt ON. The reaction mixture was quenched with aq. $NH_4Cl$ solution and extracted twice with EtOAc. The combine extracts were dried over $Na_2SO_4$, filtered and evaporated. The crude product was used without further purification in the next step. MS (ESI) 215.9 (M+H).

Compound 85b. 4-amino-5-(2,6-difluoro-4-methoxyphenyl)-2-(6-(2-hydroxypropan-2-yl)pyridin-2-yl)-1-methyl-1,2-dihydro-3H-pyrazol-3-one: Compound 85b was prepared from compound 59b and compound 85a using the methods described for compounds 59c and 59d. MS (ESI) m/z 391.3 (M+H).

Example 85. A mixture of compound 85b and $K_2CO_3$ (49.6 mg, 0.359 mmol) under nitrogen was stirred in an ice bath, and 4-(difluoromethoxy)benzoyl chloride (26.0 μL, 0.172 mmol) was added. The reaction mixture was stirred for 10 min in the ice bath, then at rt overnight. The reaction mixture was diluted with ~1 mL DMF and purified by RP-HPLC to provide Example 85 (32.4 mg, 0.057 mmol, 40.0% yield). LCMS (Method A) Rt=1.64 min, m/z 561.4 (M+H). $^1H$ NMR (500 MHz, DMSO-d6) δ 9.70 (s, 1H), 7.98 (t, J=7.9 Hz, 1H), 7.89 (d, J=8.3 Hz, 2H), 7.70 (d, J=7.7 Hz, 1H), 7.60 (d, J=7.7 Hz, 1H), 7.25 (d, J=8.3 Hz, 2H), 7.50-7.12 (m, 1H), 6.92 (d, J=10.6 Hz, 2H), 5.57-5.43 (m, 1H), 3.82 (s, 3H), 3.22 (s, 3H), 1.49 (s, 6H).

Example 87. N-(5-(2,6-difluoro-4-methoxyphenyl)-2-(6-(1-hydroxycyclobutyl)pyridin-2-yl)-1-methyl-3-oxo-2,3-dihydro-1H-pyrazol-4-yl)-4-(difluoromethoxy)benzamide

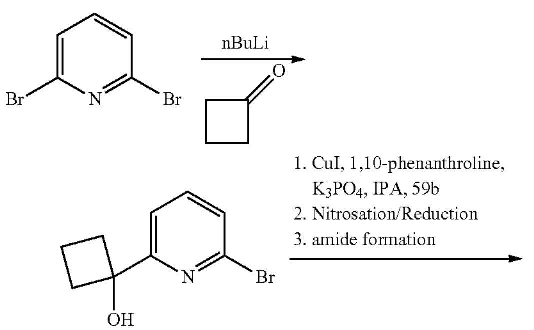

compound 87a

-continued

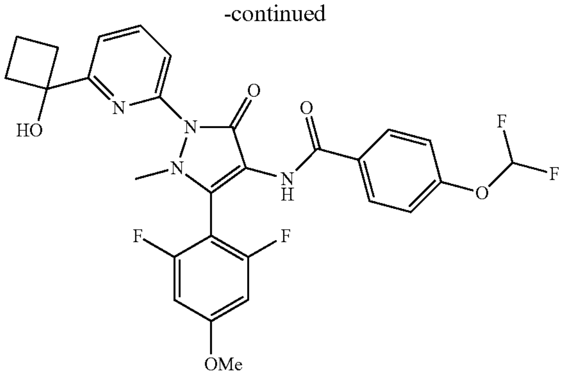

Example 87

Compound 87a. 1-(6-bromopyridin-2-yl)cyclobutan-1-ol: 2,6-Dibromopyridine (0.300 g, 1.27 mmol) was dissolved in anhydrous DCM (7.5 mL) under an atmosphere of nitrogen. The solution was cooled to −78° C. and a solution of nBuLi, 1.6M in hexanes (0.863 mL, 1.38 mmol) was added very slowly via a syringe. After the addition was complete, the reaction mixture was stirred at −78° C. for 1 hr. A solution of cyclobutanone (0.089 g, 1.3 mmol) in anhydrous DCM (1.0 mL) was then added dropwise via a syringe. The reaction mixture was stirred at −78° C. and allowed to slowly warm to rt overnight. The reaction was quenched with saturated $NaHCO_3$ solution and extracted twice with DCM. The combined organic layers were washed with brine, dried over anhydrous $Na_2SO_4$, and evaporated. The residue was purified by silica gel chromatography, eluting with 0-30% MeOH/DCM to yield compound 87a (210 mg, 0.922 mmol, 72.8% yield). $^1H$ NMR (500 MHz, $CDCl_3$) δ 7.67-7.58 (m, 1H), 7.54 (d, J=7.7 Hz, 1H), 7.42 (d, J=8.0 Hz, 1H), 4.33 (s, 1H), 2.57-2.47 (m, 4H), 2.16-2.03 (m, 1H), 1.88 (dquin, J=11.7, 8.6 Hz, 1H).

Example 87 was prepared from compound 87a using the methods described for Example 85. LCMS (Method B) Rt=1.68 min. m/z 573.3 (M+H). $^1H$ NMR (500 MHz, DMSO-d6) δ 9.72 (s, 1H), 7.99-7.88 (m, 3H), 7.74 (d, J=7.9 Hz, 1H), 7.53-7.43 (m, 1H), 7.35-7.14 (m, 3H), 6.95 (d, J=10.4 Hz, 2H), 3.82 (s, 3H), 3.27 (s, 3H), 2.61-2.56 (m, 2H), 2.37-2.25 (m, 2H), 2.01-1.82 (m, 2H). OH proton not observed.

Example 88. N-(2-(6-cyclopropyl-4-methoxypyridin-2-yl)-5-(2,6-difluoro-4-methoxyphenyl)-1-methyl-3-oxo-2,3-dihydro-1H-pyrazol-4-yl)-4-(difluoromethoxy)benzamide

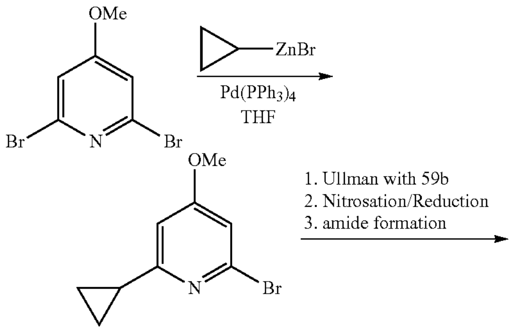

compound 88a

-continued

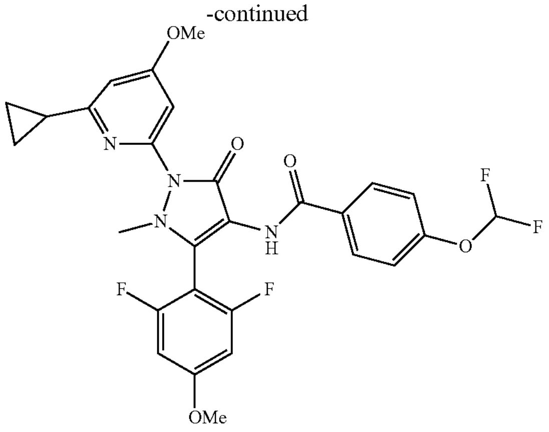

Example 88

Compound 88a. 2-bromo-6-cyclopropyl-4-methoxypyridine: A stirred solution of 2,6-dibromo-4-methoxypyridine (152 mg, 0.569 mmol) and $(Ph_3P)_4Pd$ (32.9 mg, 0.028 mmol) in THF (2.2 mL) was bubbled with $N_2$ for a few minutes, after which cyclopropylzinc(II) bromide, 0.5M in THF (1.34 mL, 0.672 mmol) was added. The mixture was stirred at rt ON. The reaction mixture was partitioned between EtOAc and saturated aqueous $NaHCO_3$ solution. The organic phase was dried over $Na_2SO_4$, filtered and evaporated. The residue was purified silica gel chromatography, eluting with 0-100% EtOAc/hexanes to provide compound 88a (37.4 mg, 0.164 mmol, 28.8% yield). $^1H$ NMR (400 MHz, $CDCl_3$-d) δ 6.78 (d, J=2.2 Hz, 1H), 6.59 (d, J=2.0 Hz, 1H), 3.84 (s, 3H), 2.03-1.88 (m, 1H), 1.06-0.95 (m, 4H).

Example 88 was prepared from compound 88a using the methods described for Example 85. LCMS (Method B) Rt=1.92 min. m/z 573.0 (M+H). $^1H$ NMR (500 MHz, DMSO-d6) δ 9.65 (s, 1H), 7.89 (d, J=8.5 Hz, 2H), 7.24 (d, J=8.5 Hz, 2H), 7.18 (d, J=1.8 Hz, 1H), 7.30 (t, J=73.9 Hz, 1H), 6.95-6.85 (m, 3H), 3.88 (s, 3H), 3.82 (s, 3H), 3.16 (s, 3H), 2.16-2.06 (m, 1H), 1.00-0.90 (m, 4H).

Example 91. N-(5-(2,6-difluoro-4-methoxyphenyl)-2-(4-methoxy-6-(pyrrolidin-1-yl)pyridin-2-yl)-1-methyl-3-oxo-2,3-dihydro-1H-pyrazol-4-yl)-4-(difluoromethoxy)benzamide

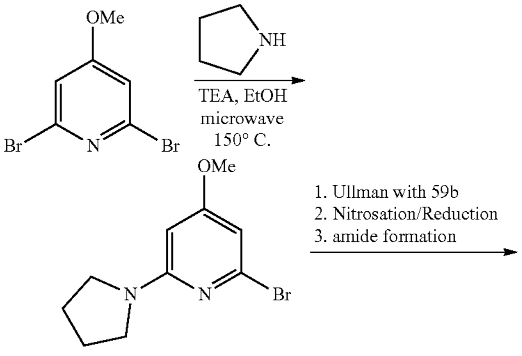

compound 91a

-continued

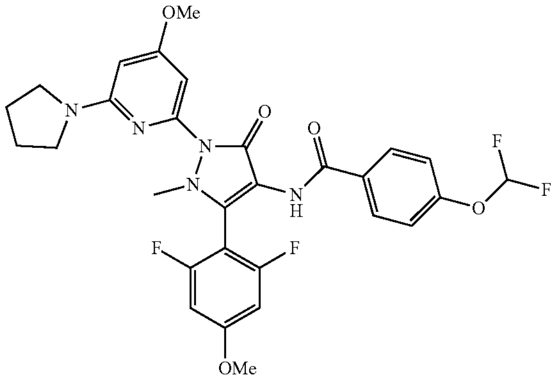

Example 91

Compound 91a. 2-bromo-4-methoxy-6-(pyrrolidin-1-yl) pyridine: A mixture of 2,6-dibromo-4-methoxypyridine (300 mg, 1.12 mmol), pyrrolidine (0.103 mL, 1.24 mmol) and TEA (0.172 mL, 1.24 mmol) in EtOH (1.5 mL) was heated to 150° C. in a sealed tube under microwave irradiation for 1 h. The reaction mixture was partitioned between water and EtOAc, and the organic phase was dried ($Na_2SO_4$), filtered and evaporated. The residue was purified by silica gel chromatography, eluting with 0-100% EtOAc/hexanes to provide compound 91a (235 mg, 0.914 mmol, 81% yield). MS (ESI) m/z 259.0 (M+H).

Example 91 was prepared from compound 91a using the methods described for Example 85. LCMS (Method B) Rt=1.73 min. m/z 602.1 (M+H). $^1H$ NMR (500 MHz, DMSO-d6) δ 9.63 (s, 1H), 7.91 (d, J=7.6 Hz, 2H), 7.27-7.21 (m, 2H), 7.52-7.17 (m, 1H), 7.13 (s, 1H), 7.02 (s, 1H), 6.92 (d, J=10.4 Hz, 2H), 3.84 (s, 3H), 3.82 (s, 3H), 3.92-3.78 (m, 4H), 3.25 (s, 3H), 1.98-1.93 (m, 4H).

Examples 86, 89-90, 92-107 (Table 2) were prepared using methods described for Examples 85, 87-88 or 91.

Example 108. N-[3,5-dimethoxyphenyl)-5-(2,6-difluoro-4-methoxyphenyl)-1-methyl-3-oxo-2,3-dihydro-1H-pyrazol-4-yl]-4-(difluoromethoxy)benzamide

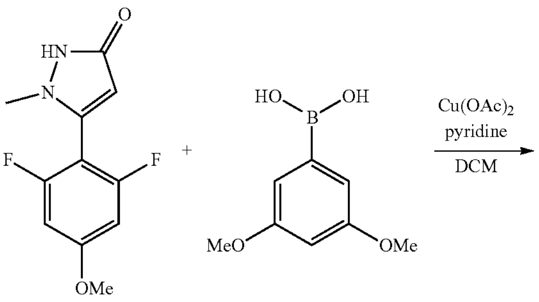

Compound 59c

-continued

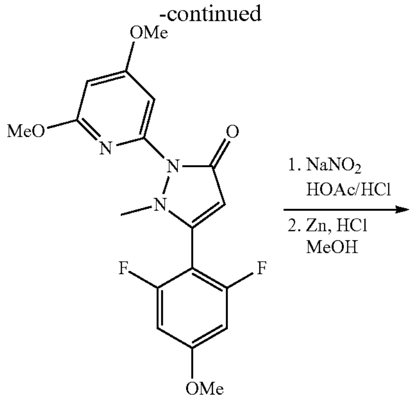

Compound 108a

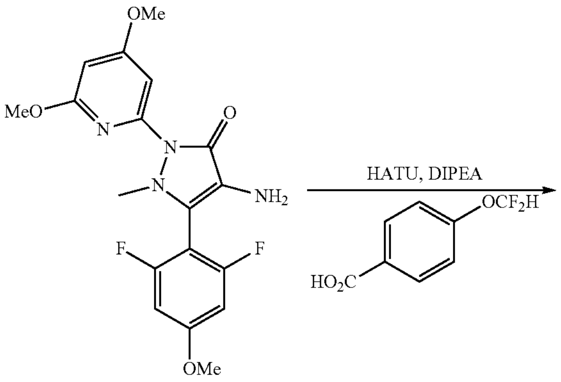

Compound 108b

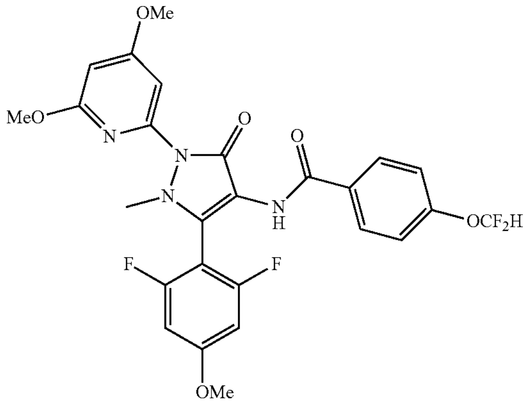

Example 108

Compound 108a. 5-(2,6-difluoro-4-methoxyphenyl)-2-(3,5-dimethyoxyphenyl)-1-methyl-1,2-dihydro-3H-pyrazol-3-one: A mixture of compound 59c (100 mg, 0.416 mmol), (3,5-dimethoxyphenyl)boronic acid (152 mg, 0.833 mmol), copper (II) acetate (113 mg, 0.624 mmol) and pyridine (0.067 mL, 0.83 mmol) in DCM (3 mL) was stirred overnight under an air atmosphere. The reaction mixture was diluted with DCM and water, and the aqueous layer was reextracted with DCM. The combined extracts were washed with brine, dried over $Na_2SO_4$, filtered and evaporated. The residue was purified by silica gel chromatography, eluting with 0-100% EtOAc/hexanes to provide compound 108a (78 mg, 0.21 mmol, 50% yield). LCMS (ESI) m/z: 377.1 (M+H). $^1$H NMR (400 MHz, $CDCl_3$) δ 6.67 (d, J=2.2 Hz, 2H), 6.63-6.55 (m, 2H), 6.42 (t, J=2.3 Hz, 1H), 5.76 (s, 1H), 3.86 (s, 3H), 3.83 (s, 6H), 3.00 (s, 3H).

Example 108 was obtained in two steps from compound 108a using the methods described for compound 1d and Example 1. LCMS (Method C) Rt=1.77 min, m/z=562.3 (M+H). $^1$H NMR (500 MHz, DMSO-d6) δ 9.72 (s, 1H), 7.89 (br d, J=8.2 Hz, 2H), 7.24 (br d, J=8.5 Hz, 2H), 7.31 (t, J=74.0 Hz, 1H), 6.91 (br d, J=10.7 Hz, 2H), 6.63-6.46 (m, 3H), 3.82 (s, 3H), 3.80 (s, 6H), 2.94 (s, 3H).

Examples 109-134 (Table 2) were prepared using the methods described for Example 108.

Example 135. N-[5-(2,6-difluoro-4-methoxyphenyl)-1-methyl-2-[6-(4-methylpiperazin-1-yl)-3-(trifluoromethyl)pyridin-2-yl]-3-oxo-2,3-dihydro-1H-pyrazol-4-yl]-4-(difluoromethoxy)benzamide

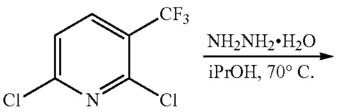

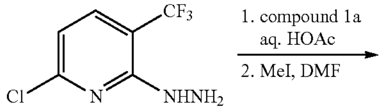

Compound 135a

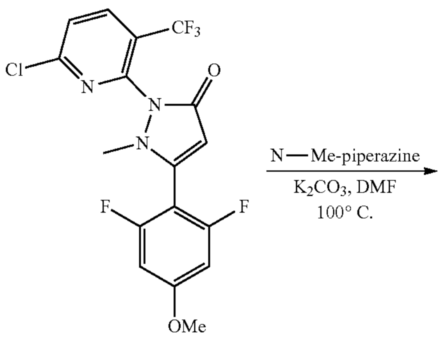

Compound 135b

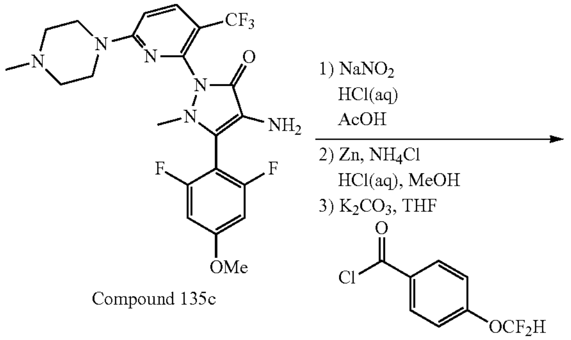

Compound 135c

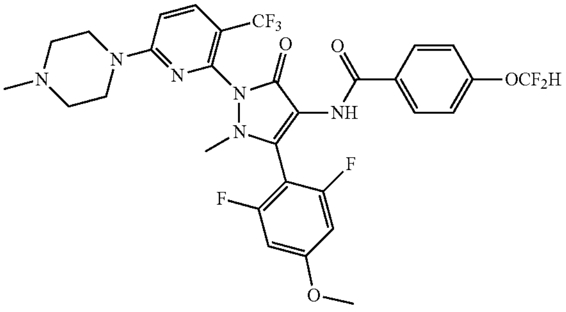

Example 135

Compound 135a. A mixture of 2,6-dichloro-3-(trifluoromethyl)pyridine (2.49 mL, 23.2 mmol) and hydrazine hydrate (4.49 mL, 93.0 mmol) in iPrOH (42 mL) was heated at 100° C. under reflux with stirring overnight under nitrogen. The reaction mixture was cooled to rt and partially concentrated. The concentrate was diluted with water and extracted EtOAc (5×). The combined extracts were washed with brine, dried over $Na_2SO_4$, filtered and evaporated. The residue was purified by silica gel chromatography, eluting with 0/100% EtOAc/hexanes to give compound 135a (minor regioisomer; 0.78 g, 0.3.7 mmol, 16% yield). 41 NMR (500 MHz, DMSO-d6) δ 8.17 (br s, 1H), 7.80 (d, J=7.7 Hz, 1H), 6.73 (d, J=8.0 Hz, 1H), 4.41 (br s, 2H).

Compound 135b. 2-(6-chloro-3-(trifluoromethyl)pyridin-2-yl)-5-(2,6-difluoro-4-methoxyphenyl)-1-methyl-1,2-dihydro-3H-pyrazol-3-one: Compound 135b was prepared from compound 135a and ethyl 3-(2,6-difluoro-4-methoxyphenyl)-3-oxopropanoate using the procedure described for compound 1b, followed by the procedure described for compound 39b. MS (ESI) m/z: 419.9 (M+H).

Compound 135c. 5-(2,6-difluoro-4-methoxyphenyl)-1-methyl-2-(6-(4-methylpiperazin-1-yl)-3-(trifluoromethyl) pyridin-2-yl)-1,2-dihydro-3H-pyrazol-3-one: A mixture of compound 135b (286 mg, 0.681 mmol), 1-methylpiperazine (0.378 mL, 3.41 mmol) and $K_2CO_3$ (330 mg, 2.38 mmol) in NMP (2.2 mL) was heated in a pressure vial at 100° C. overnight with stirring. The reaction mixture was cooled to rt, diluted with water and extracted with EtOAc (3×). The combined extracts were washed with water (2×) and with brine, dried over anhydrous $Na_2SO_4$, filtered and evaporated. Residue was purified by silica gel chromatography, eluting with 0-20% DCM/MeOH to provide compound 135c as a white foam (215 mg, 0.445 mmol, 65.3% yield). MS (ESI) m/z: 484.1 (M+H)

Example 135 was prepared from compound 135c using the steps shown in the scheme, procedures for which have been described above. LCMS (Method A) Rt=1.79 min, m/z 669.0 (M+H). $^1H$ NMR (500 MHz, $CD_3CN$) δ 8.01 (br s, 1H), 7.90 (d, J=9.1 Hz, 1H), 7.85-7.75 (m, 2H), 7.17 (d, J=8.8 Hz, 2H), 6.88 (d, J=9.1 Hz, 1H), 6.79-6.66 (m, 2H), 6.82 (t, J=74.0 Hz, 1H), 3.83 (s, 3H), 3.65 (br d, J=3.3 Hz, 4H), 3.03 (s, 3H), 2.44 (t, J=5.1 Hz, 4H), 2.26 (s, 3H).

Examples 136-141 (Table 2) were prepared using the methods described for Example 135 and/or modifications thereof known to one skilled in the art.

Example 241: N-[5-(2,6-difluoro-4-methoxyphenyl)-1-methyl-2-[6-(N-methylmethanesulfonamido)-3-(trifluoromethyl)pyridin-2-yl]-3-oxo-2,3-dihydro-1H-pyrazol-4-yl]-4-(difluoromethoxy)benzamide

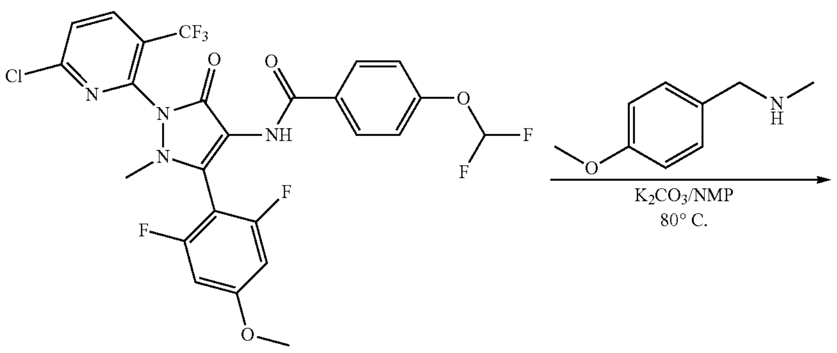

Example 222

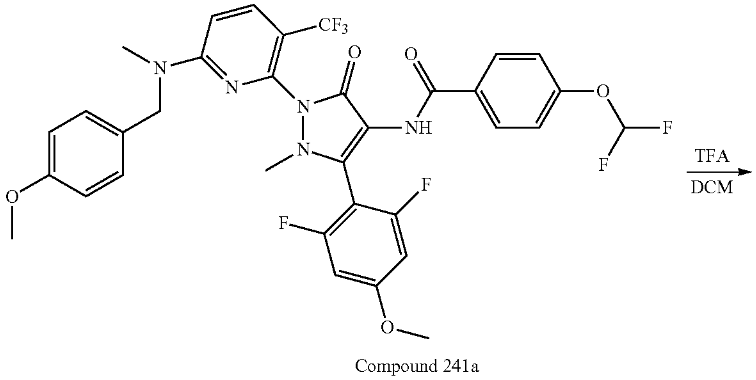

Compound 241a

-continued

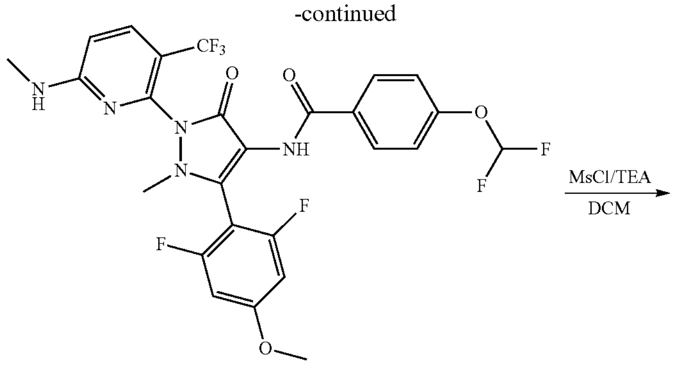

Compound 241b

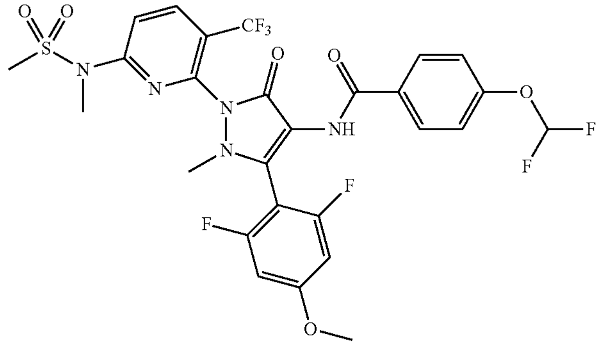

Example 241

Compound 241a. N-(5-(2,6-difluoro-4-methoxyphenyl)-2-(6-((4-methoxybenzyl)(methyl)amino)-3-(trifluoromethyl)pyridin-2-yl)-1-methyl-3-oxo-2,3-dihydro-1H-pyrazol-4-yl)-4-(difluoromethoxy)benzamide: A vial equipped with a stirring bar and pressure release septa was charged with Example 222 (15.1 mg, 25.0 μmol) and potassium carbonate (5.2 mg, 38 μmol). The vial was purged with nitrogen, a solution of 1-(4-methoxyphenyl)-N-methylmethanamine (3.8 mg, 25 μmol) in NMP (1.0 mL) introduced and the mixture was heated to 80° C. for overnight. The reaction mixture was diluted with water and EtOAc, the phases separated, aq. extracted twice more with EtOAc, all combined organics washed with brine, dried ($Na_2SO_4$), filtered and evaporated to give the title compound (17.2 mg, 96% yield) which was used without further purification. MS (ESI) m/z: 720.3 (M+H)+.

Compound 241b. N-(5-(2,6-difluoro-4-methoxyphenyl)-1-methyl-2-(6-(methylamino)-3-(trifluoromethyl)pyridin-2-yl)-3-oxo-2,3-dihydro-1H-pyrazol-4-yl)-4-(difluoromethoxy)benzamide, TFA: A vial equipped with a stirring bar and pressure release septa was charged with Example 241a (17.2 mg, 0.024 mmol) and DCM (2 mL) to which was added TFA (0.4 mL) and the mixture stirred for 4 h at ambient temperature. The reaction mixture was evaporated under reduced pressure, EtOAc was added and evaporated, this was repeated twice more to give the title compound which was used without further purification. MS (ESI) m/z: 600.3 (M+H)+.

Example 241. N-(5-(2,6-difluoro-4-methoxyphenyl)-1-methyl-2-(6-(N-methylmethylsulfonamido)-3-(trifluoromethyl)pyridin-2-yl)-3-oxo-2,3-dihydro-1H-pyrazol-4-yl)-4-(difluoromethoxy)benzamide: A vial equipped with a stirring bar and pressure release septa was charged with Example 241b (17.1 mg, 24 μmol) to which was added DCM (1 mL) and TEA (0.017 mL, 120 μmol) followed by MSCl (2.8 μl, 36 μmol) and the mixture stirred at ambient temperature for overnight. The reaction mixture was quenched with water, the phases were separated, the aqueous was extracted thrice with DCM, all combined organics dried ($Na_2SO_4$), filtered and evaporated to a residue. The crude material was purified via preparative LC/MS to yield the title compound (0.8 mg, 5% yield). MS (ESI) m/z: 678.1 (M+H)+. $^1H$ NMR (500 MHz, DMSO-$d_6$) δ 9.74 (s, 1H), 8.42 (d, J=9.0 Hz, 1H), 7.91 (br d, J=8.0 Hz, 2H), 7.64 (br d, J=8.8 Hz, 1H), 7.23 (br d, J=8.8 Hz, 2H), 7.33 (br t, J=73.8 Hz, 1H), 6.93 (br dd, J=28.2, 10.2 Hz, 2H), 3.82 (s, 3H), 3.45 (s, 3H), 3.42 (s, 3H), 3.04 (s, 3H).

Example 318: N-(5-(2,6-difluoro-4-methoxyphenyl)-1-methyl-2-(6-(methylsulfonyl)-3-(trifluoromethyl)pyridin-2-yl)-3-oxo-2,3-dihydro-1H-pyrazol-4-yl)-4-(difluoromethoxy)benzamide

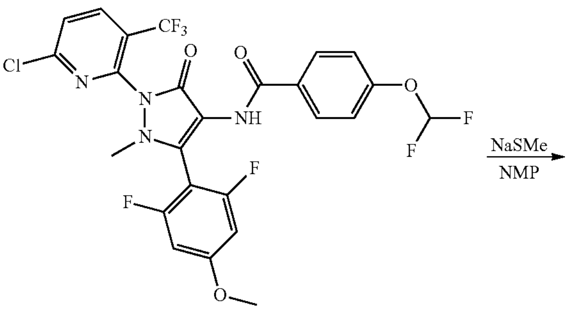

Example 222

-continued

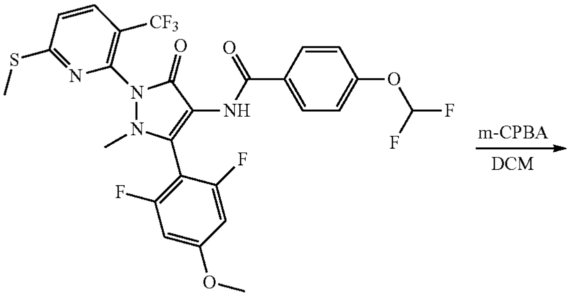

compound 318a

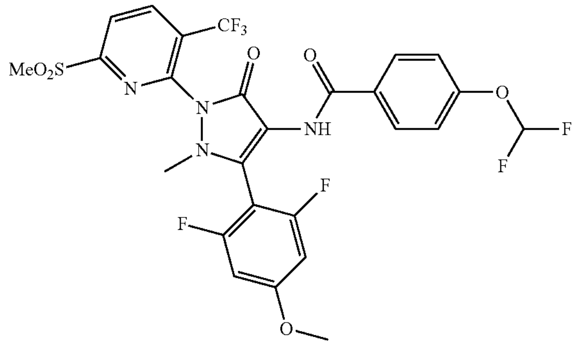

Example 318

Compound 318a. N-(5-(2,6-difluoro-4-methoxyphenyl)-1-methyl-2-(6-(methylthio)-3-(trifluoromethyl)pyridin-2-yl)-3-oxo-2,3-dihydro-1H-pyrazol-4-yl)-4-(difluoromethoxy)benzamide: A 1 dram vial equipped with a stirring bar and pressure release septa was charged with Example 222 (30 mg, 50 μmol). The vial was purged with nitrogen, then NMP (0.5 mL) was added, followed by sodium methanethiolate (3.9 mg, 5 μmol) and the reaction mixture was stirred at rt overnight. The reaction mixture was diluted with water and EtOAc, the phases were separated, and the aqueous layer was extracted with EtOAc (2×). The organic layers were combined, washed with brine, dried ($Na_2SO_4$), filtered and evaporated to a residue (29 mg).

Example 318: Compound 318a (29 mg, 47 μmol) was dissolved in a mixture of DCM (0.5 mL) and AcOH (0.005 mL). To this solution was added m-CPBA (23.7 mg, 104 μmol) and the reaction mixture was stirred at rt overnight. The reaction mixture was quenched with sat'd aqeuous $Na_2SO_3$, and diluted with $NaHCO_3$. The phases were separated, and the aqeuous layer was extracted with DCM (2×). The organic layers were combined, dried ($Na_2SO_4$), filtered and concentrated. The crude material was purified via preparative LC/MS to yield the title compound (6.1 mg, 19%). MS (ESI) m/z: 649.3 (M+H)+. 1H NMR (500 MHz, DMSO-$d_6$) δ 9.75 (s, 1H), 8.84 (d, J=8.2 Hz, 1H), 8.35 (d, J=7.9 Hz, 1H), 7.90 (br d, J=8.5 Hz, 2H), 7.23 (br d, J=8.2 Hz, 2H), 7.32 (br t, J=73.5 Hz, 1H), 7.02-6.86 (m, 2H), 3.82 (s, 3H), 3.37 (s, 3H), 3.05 (s, 3H).

Example 319: tert-butyl 6-(3-(2,6-difluoro-4-methoxyphenyl)-4-(4-(difluoromethoxy)benzamido)-2-methyl-5-oxo-2,5-dihydro-1H-pyrazol-1-yl)-5-(trifluoromethyl)-3',6'-dihydro-[2,4'-bipyridine]-1'(2'H)-carboxylate

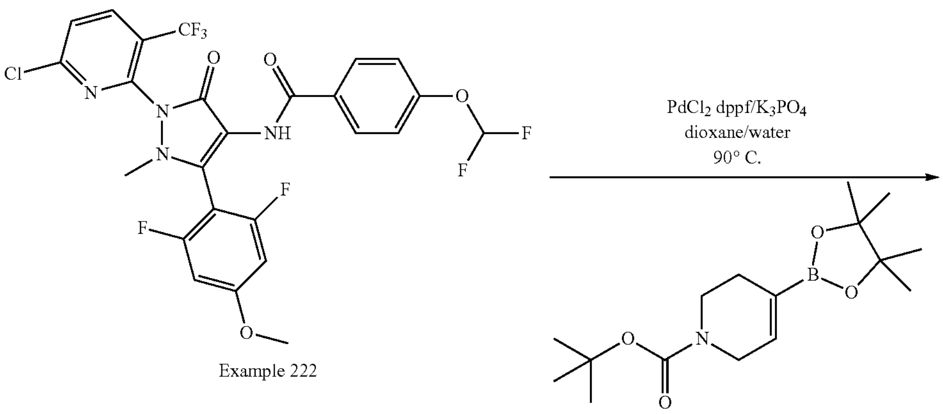

Example 222

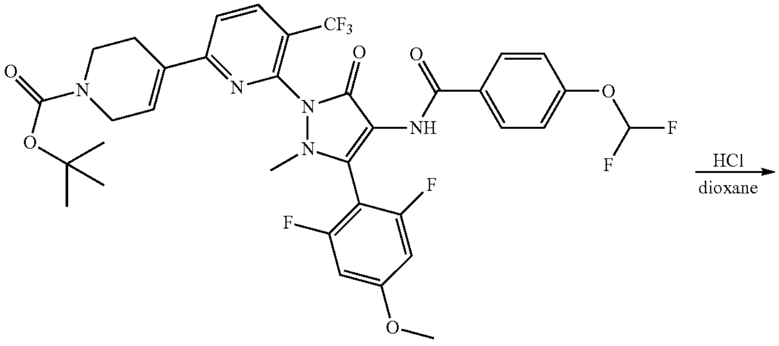

compound 222a

-continued

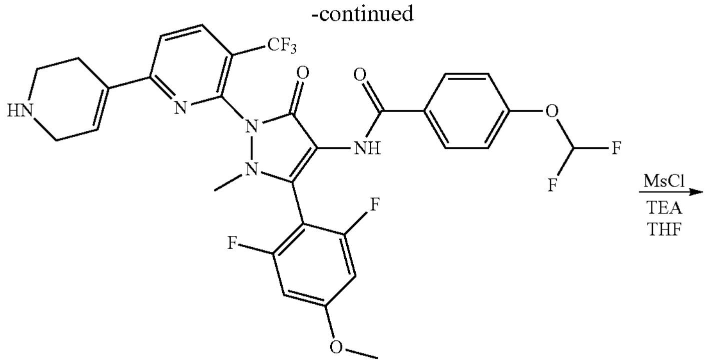

compound 222b

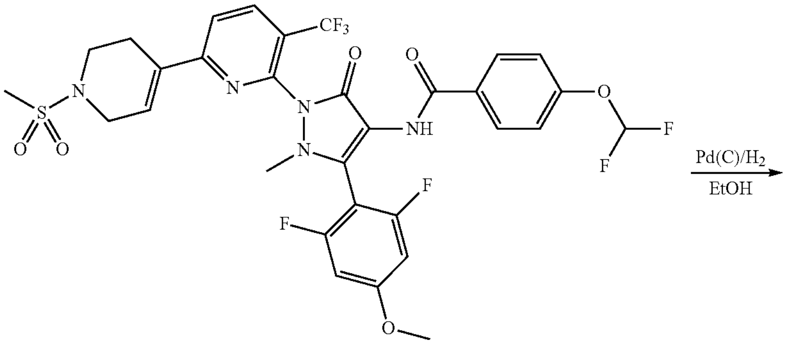

compound 222c

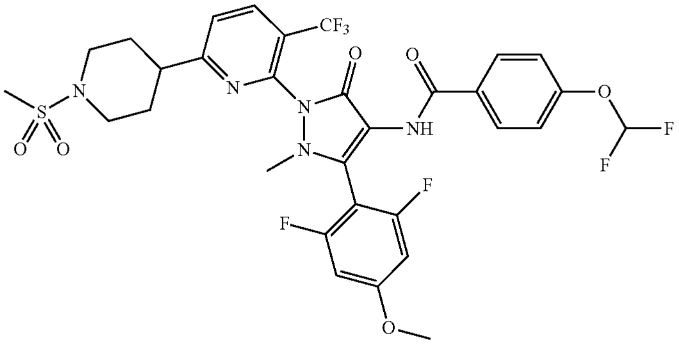

Example 319

Compound 222a. tert-butyl 6-(3-(2,6-difluoro-4-methoxyphenyl)-4-(4-(difluoromethoxy)benzamido)-2-methyl-5-oxo-2,5-dihydro-1H-pyrazol-1-yl)-5-(trifluoromethyl)-3',6'-dihydro-[2,4'-bipyridine]-1'(2'H)-carboxylate: A 2 dram vial equipped with a stirring bar and pressure release septa was charged with Example 222 (61 mg, 0.10 mmol), tert-butyl 4-(4,4,5,5-tetramethyl-1,3,2-dioxaborolan-2-yl)-3,6-dihydropyridine-1(2H)-carboxylate (47 mg, 0.15 mmol), $PdCl_2$(dppf) (11 mg, 0.015 mmol) and tripotassium phosphate (64 mg, 0.30 mmol). The vial was purged with nitrogen and a degassed mixture of 1,4-dioxane (0.9 mL)/water (0.1 mL) was added. The vial was capped and heated at 90° C. with stirring overnight. After cooling to room temperature, the reaction mixture was diluted with EtOAc/water, and the phases were separated. The aqueous layer was extracted with EtOAc (3×). The organics were combined, washed with brine, dried ($Na_2SO_4$), filtered and concentrated. The crude product was purified via silica gel chromatography (0-100% EtOAc in n-hexanes) to afford the title compound (36 mg, 48%) as a colorless solid. MS (ESI) m/z: 752.0 $(M+H)^+$. 1H NMR (400 MHz, $CDCl_3$) δ 8.13 (d, J=8.4 Hz, 1H), 7.80 (br d, J=7.9 Hz, 2H), 7.74-7.63 (m, 1H), 7.57 (br d, J=8.1 Hz, 1H), 7.13 (d, J=8.6 Hz, 2H), 6.88 (br s, 1H), 6.64-6.56 (m, 2H), 6.55 (br t, J=73.3 Hz, 1H), 4.19 (br d, J=1.3 Hz, 2H), 3.84 (s, 3H), 3.74-3.58 (m, 2H), 3.03 (s, 3H), 2.66 (br d, J=14.1 Hz, 2H), 1.51 (s, 9H).

Compound 222b: N-(5-(2,6-difluoro-4-methoxyphenyl)-1-methyl-3-oxo-2-(5-(trifluoromethyl)-1',2',3',6'-tetrahydro-[2,4'-bipyridin]-6-yl)-2,3-dihydro-1H-pyrazol-4-yl)-4-(difluoromethoxy)benzamide, HCl: To a 1 dram vial equipped with a stirring bar and pressure release septa was charged tert-butyl 6-(3-(2,6-difluoro-4-methoxyphenyl)-4-(4-(difluoromethoxy)benzamido)-2-methyl-5-oxo-2,5-dihydro-1H-pyrazol-1-yl)-5-(trifluoromethyl)-3',6'-dihydro-[2,4'-bipyridine]-1'(2'H)-carboxylate (36.1 mg, 0.048 mmol) and dioxane (1 mL). To this solution was added hydrogen chloride (4 M in dioxane, 1.0 mL, 4.0 mmol) and the reaction mixture was stirred at rt overnight. The reaction mixture was diluted with $H_2O$ and was evaporated under reduced pressure several times from EtOAc to give a light yellow solid (32 mg, 98%). The material was used for next step without further purification. MS (ESI) m/z: 652.3 (M+H)+. 1H NMR (500 MHz, DMSO-$d_6$) δ 9.71 (s, 1H), 8.37 (d, J=8.2 Hz, 1H), 7.91 (d, J=8.2 Hz, 2H), 7.85 (d, J=8.2 Hz, 1H), 7.23 (d, J=8.2 Hz, 2H), 7.33 (t, J=73.7 Hz, 1H), 7.02 (s, 1H), 6.99-6.86 (m, 2H), 3.82 (s, 3H), 2.98 (s, 3H), 2.95-2.89 (m, 1H), 2.47-2.40 (m, 2H), 1.68 (s, 3H). (Peaks missing due to water suppression).

Compound 222c. N-(5-(2,6-difluoro-4-methoxyphenyl)-1-methyl-2-(1'-(methylsulfonyl)-5-(trifluoromethyl)-1',2',3',6'-tetrahydro-[2,4'-bipyridin]-6-yl)-3-oxo-2,3-dihydro-1H-pyrazol-4-yl)-4-(difluoromethoxy)benzamide: To a mixture of N-(5-(2,6-difluoro-4-methoxyphenyl)-1-methyl-3-oxo-2-(5-(trifluoromethyl)-1',2',3',6'-tetrahydro-[2,4'-bipyridin]-6-yl)-2,3-dihydro-1H-pyrazol-4-yl)-4-(difluoromethoxy)benzamide, HCl (11 mg, 0.016 mmol) in THF (2.0 mL) under nitrogen was added TEA (11 µl, 0.078 mmol), followed by methanesulfonyl chloride (1.3 µl, 0.017 mmol). The reaction mixture was stirred under nitrogen at rt overnight. The reaction mixture was diluted with water and EtOAc, and the phases were separated. The aqeuous layer was extracted with DCM (3×). The organics were combined, washed with brine, dried ($Na_2SO_4$), filtered and evaporated to give the title compound (11 mg) as a tan solid. The material was used for next step without further purification. MS (ESI) m/z: 730.1 (M+H)+.

Example 319: To a solution of N-(5-(2,6-difluoro-4-methoxyphenyl)-1-methyl-2-(1'-(methylsulfonyl)-5-(trifluoromethyl)-1',2',3',6'-tetrahydro-[2,4'-bipyridin]-6-yl)-3-oxo-2,3-dihydro-1H-pyrazol-4-yl)-4-(difluoromethoxy) benzamide (11 mg, 0.015 mmol) in EtOH (3 mL) under nitrogen was charged 10% Pd on carbon (3.2 mg, 3.0 µmol). The mixture was thrice purged with nitrogen (evacuate/$N_2$ backfill), and the reaction mixture was stirred at rt under hydrogen overnight. The reaction mixture was filtered through a pad of Celite, the pad was washed with MeOH. The combined filtrate was evaporated to a residue. The crude material was purified via preparative LC/MS to yield the title compound (5.5 mg, 50%). MS (ESI) m/z: 732.2 $(M+H)^+$. 1H NMR (500 MHz, DMSO-$d_6$) δ 9.69 (s, 1H), 8.41 (d, J=8.2 Hz, 1H), 7.91 (d, J=8.2 Hz, 2H), 7.74 (d, J=8.2 Hz, 1H), 7.23 (d, J=8.5 Hz, 2H), 7.32 (t, J=73.5 Hz, 1H), 6.99-6.86 (m, 2H), 3.82 (s, 3H), 3.68 (br d, J=11.9 Hz, 2H), 3.08-3.00 (m, 1H), 2.98 (s, 3H), 2.90 (s, 3H), 2.89-2.83 (m, 2H), 2.09-2.00 (m, 2H), 1.85-1.72 (m, 2H).

Examples 142-408 (Table 2) were prepared using the methods described in the above methods and/or modifications thereof known to one skilled in the art.

TABLE 2

$^1$H NMR data for the examples in Table 2:

| Ex. No. | Name | Structure | LC/MS Rt (min) Method M + H |
|---|---|---|---|
| 2 | N-[5-(2,6-difluoro-4-methoxyphenyl)-2-(3-fluorophenyl)-1-methyl-3-oxo-2,3-dihydro-1H-pyrazol-4-yl]-4-(trifluoromethoxy)benzamide | 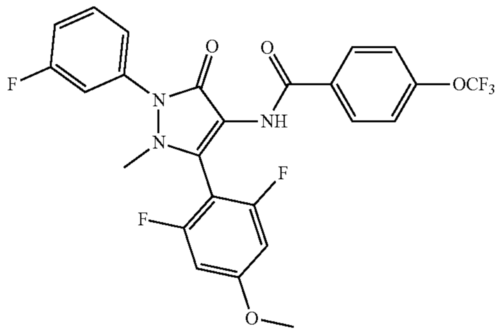 [SMILES: COc1cc(F)c(-c2c(NC(=O)c3ccc(OC(F)(F)F)cc3)c(=O)n(-c3cccc(F)c3)n2C)c(F)c1] | 1.94<br>A<br>538.3 |
| 3 | N-[5-(2,6-difluoro-4-methoxyphenyl)-2-(2,3-dimethylphenyl)-1-methyl-3-oxo-2,3-dihydro-1H-pyrazol-4-yl]-4-(difluoromethoxy)benzamide | 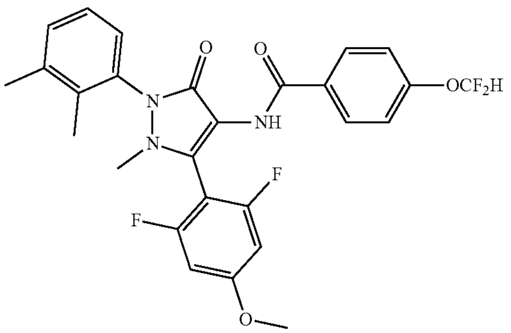 | 1.82<br>A<br>530.3 |

TABLE 2-continued

| $^1$H NMR data for the examples in Table 2: | | | |
|---|---|---|---|
| Ex. No. | Name | Structure | LC/MS Rt (min) Method M + H |
| 4 | N-[5-(2,6-difluoro-4-methoxyphenyl)-1-methyl-3-oxo-2-phenyl-2,3-dihydro-1H-pyrazol-4-yl]-4-(trifluoromethoxy)benzamide | 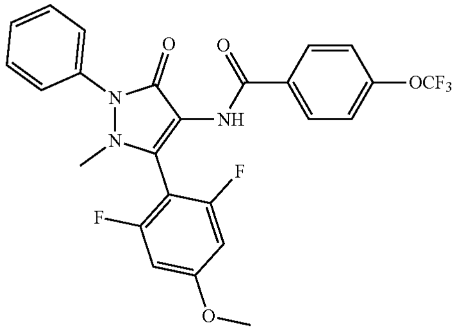 [SMILES: COc1cc(F)c(-c2c(NC(=O)c3ccc(OC(F)(F)F)cc3)c(=O)n(-c3ccccc3)n2C)c(F)c1] | 1.88<br>A<br>520.3 |
| 5 | N-[5-(2,6-difluoro-4-methoxyphenyl)-1-methyl-3-oxo-2-phenyl-2,3-dihydro-1H-pyrazol-4-yl]-4-(trifluoromethyl)benzamide | 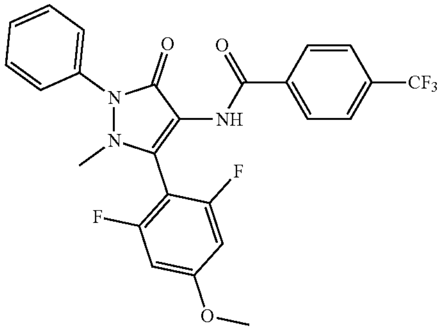 [SMILES: COc1cc(F)c(-c2c(NC(=O)c3ccc(C(F)(F)F)cc3)c(=O)n(-c3ccccc3)n2C)c(F)c1] | 1.82<br>A<br>504.3 |
| 6 | N-[2-benzyl-5-(2,6-difluoro-4-methoxyphenyl)-1-methyl-3-oxo-2,3-dihydro-1H-pyrazol-4-yl]-4-(difluoromethoxy)benzamide | 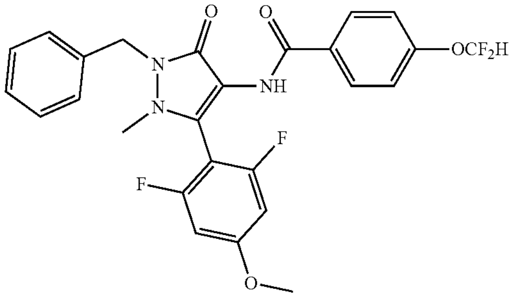 | 1.74<br>A<br>516.3 |
| 7 | 4-(difluoromethoxy)-N-[5-(4-methoxyphenyl)-1-methyl-3-oxo-2-phenyl-2,3-dihydro-1H-pyrazol-4-yl]benzamide | 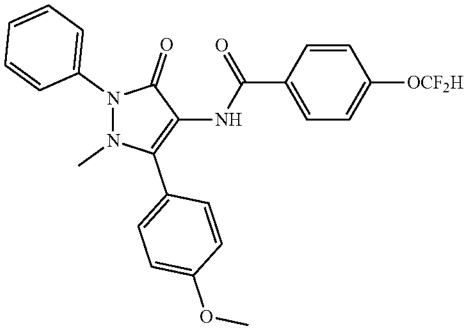 | 1.64<br>B<br>466.3 |

TABLE 2-continued

$^1$H NMR data for the examples in Table 2:

| Ex. No. | Name | Structure | LC/MS Rt (min) Method M + H |
|---|---|---|---|
| 8 | N-[5-(2,6-difluoro-4-methoxyphenyl)-2-(3-fluorophenyl)-1-methyl-3-oxo-2,3-dihydro-1H-pyrazol-4-yl]-4-(difluoromethoxy)benzamide | 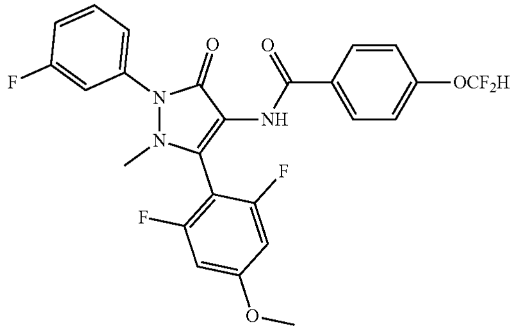 | 1.77 A 520.3 |
| 9 | 4-chloro-N-[5-(2,6-difluoro-4-methoxyphenyl)-1-methyl-3-oxo-2-phenyl-2,3-dihydro-1H-pyrazol-4-yl]benzamide | 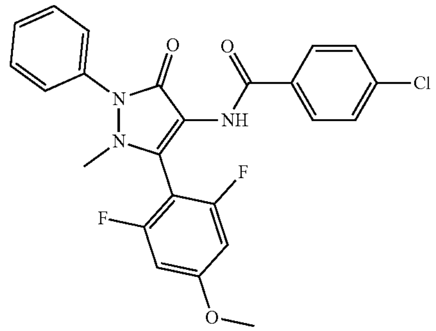 [SMILES: COc1cc(F)c(-c2c(NC(=O)c3ccc(Cl)cc3)c(=O)n(-c3ccccc3)n2C)c(F)c1] | 1.79 B 470.14 |
| 10 | N-[5-(2,6-difluoro-4-methoxyphenyl)-2-(4-fluorophenyl)-1-methyl-3-oxo-2,3-dihydro-1H-pyrazol-4-yl]-4-(trifluoromethoxy)benzamide | 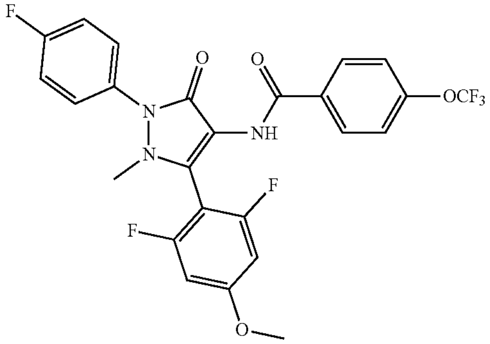 [SMILES: COc1cc(F)c(-c2c(NC(=O)c3ccc(OC(F)(F)F)cc3)c(=O)n(-c3ccc(F)cc3)n2C)c(F)c1] | 2.01 A 538.3 |
| 11 | 4-chloro-N-[5-(2,6-difluoro-4-methoxyphenyl)-2-(3-fluorophenyl)-1-methyl-3-oxo-2,3-dihydro-1H-pyrazol-4-yl]benzamide | 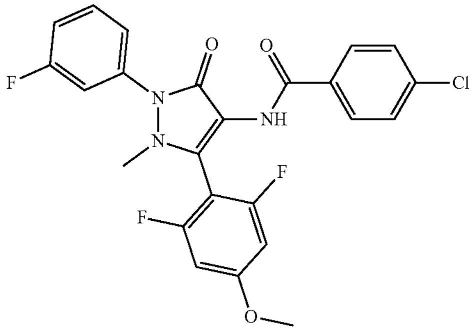 [SMILES: COc1cc(F)c(-c2c(NC(=O)c3ccc(Cl)cc3)c(=O)n(-c3cccc(F)c3)n2C)c(F)c1] | 1.79 A 488.2 |

TABLE 2-continued

| $^1$H NMR data for the examples in Table 2: | | | |
|---|---|---|---|
| Ex. No. | Name | Structure | LC/MS Rt (min) Method M + H |
| 12 | N-[5-(2,6-difluoro-4-methoxyphenyl)-2-(4-fluorophenyl)-1-methyl-3-oxo-2,3-dihydro-1H-pyrazol-4-yl]-4-(difluoromethoxy)benzamide | 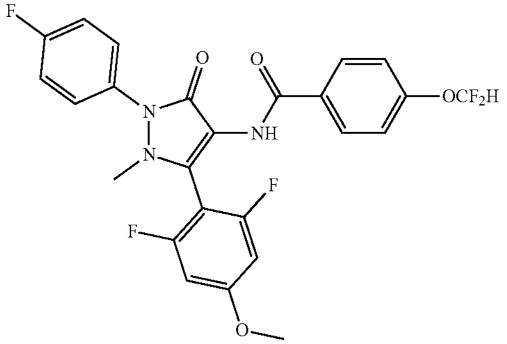 | 1.85 B 519.9 |
| 13 | N-[2-cyclopropyl-5-(2,6-difluoro-4-methoxyphenyl)-1-methyl-3-oxo-2,3-dihydro-1H-pyrazol-4-yl]-4-(difluoromethoxy)benzamide | 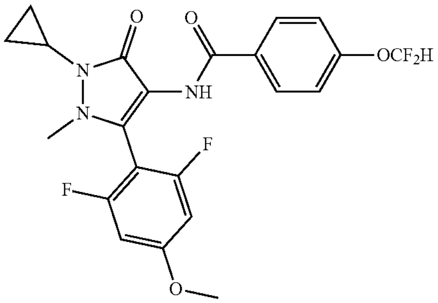 | 1.42 B 466.2 |
| 14 | N-[5-(2,6-difluoro-4-methoxyphenyl)-2-(5-fluoro-2-methylphenyl)-1-methyl-3-oxo-2,3-dihydro-1H-pyrazol-4-yl]-4-(difluoromethoxy)benzamide | 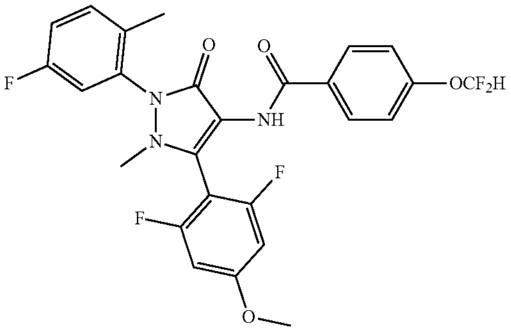 | 1.78 A 534.3 |
| 15 | 4-chloro-N-[5-(2,6-difluoro-4-methoxyphenyl)-2-(4-fluorophenyl)-1-methyl-3-oxo-2,3-dihydro-1H-pyrazol-4-yl]benzamide | 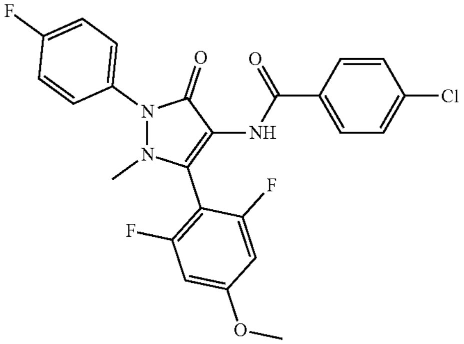 [SMILES: COc1cc(F)c(-c2c(NC(=O)c3ccc(Cl)cc3)c(=O)n(-c3ccc(F)cc3)n2C)c(F)c1] | 1.83 A 488.2 |

TABLE 2-continued

$^1$H NMR data for the examples in Table 2:

| Ex. No. | Name | Structure | LC/MS Rt (min) Method M + H |
|---|---|---|---|
| 16 | 4-cyclopropyl-N-[5-(2,6-difluoro-4-methoxyphenyl)-1-methyl-3-oxo-2-phenyl-2,3-dihydro-1H-pyrazol-4-yl]benzamide | 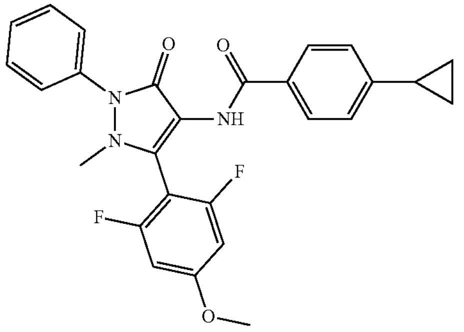 [SMILES: COc1cc(F)c(-c2c(NC(=O)c3ccc(C4CC4)cc3)c(=O)n(-c3ccccc3)n2C)c(F)c1] | 1.86<br>A<br>476.0 |
| 17 | N-[5-(2,6-difluoro-4-methoxyphenyl)-2-(4-fluorophenyl)-1-methyl-3-oxo-2,3-dihydro-1H-pyrazol-4-yl]-4-(trifluoromethyl)benzamide | 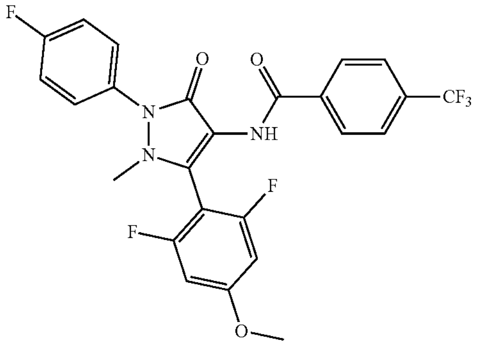 [SMILES: COc1cc(F)c(-c2c(NC(=O)c3ccc(C(F)(F)F)cc3)c(=O)n(-c3ccc(F)cc3)n2C)c(F)c1] | 1.94<br>A<br>521.9 |
| 18 | N-[5-(2,6-difluoro-4-methoxyphenyl)-1-methyl-3-oxo-2-(propan-2-yl)-2,3-dihydro-1H-pyrazol-4-yl]-4-(difluoromethoxy)benzamide | 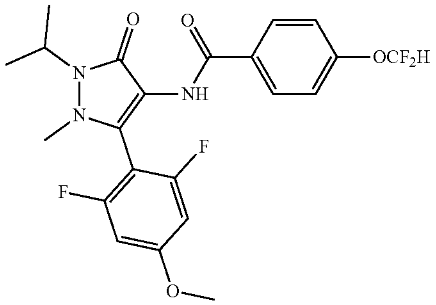 | 1.55<br>B<br>467.9 |
| 19 | N-[5-(2,6-difluoro-4-methoxyphenyl)-1-methyl-3-oxo-2-phenyl-2,3-dihydro-1H-pyrazol-4-yl]-4-(difluoromethyl)benzamide | 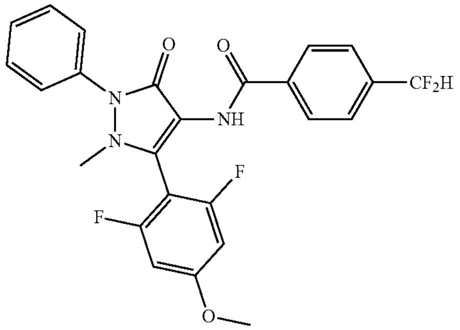 [SMILES: COc1cc(F)c(-c2c(NC(=O)c3ccc(C(F)F)cc3)c(=O)n(-c3ccccc3)n2C)c(F)c1] | 1.68<br>A<br>486.3 |

TABLE 2-continued

| $^1$H NMR data for the examples in Table 2: | | | |
|---|---|---|---|
| Ex. No. | Name | Structure | LC/MS Rt (min) Method M + H |
| 20 | N-[5-(2,6-difluoro-4-methoxyphenyl)-1-methyl-3-oxo-2-phenyl-2,3-dihydro-1H-pyrazol-4-yl]-4-fluorobenzamide | 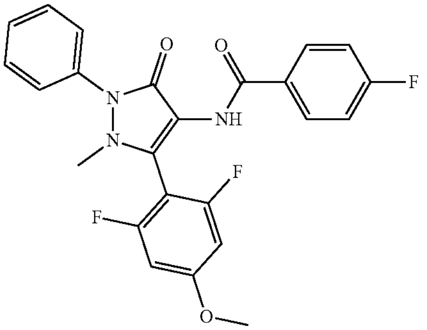 [SMILES: COc1cc(F)c(-c2c(NC(=O)c3ccc(F)cc3)c(=O)n(-c3ccccc3)n2C)c(F)c1] | 1.67 B 454.2 |
| 21 | ethyl 2-[3-(2,6-difluoro-4-methoxyphenyl)-4-[4-(difluoromethoxy)benzamido]-2-methyl-5-oxo-2,5-dihydro-1H-pyrazol-1-yl]acetate | 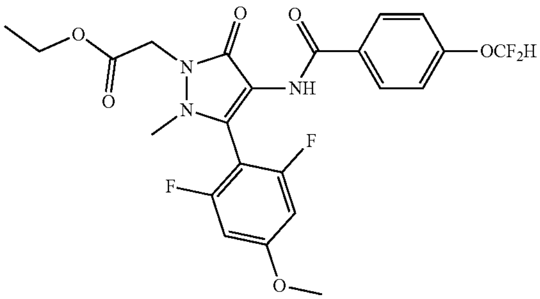 | 0.77 C 512.1 |
| 22 | N-[5-(2,6-difluoro-4-methoxyphenyl)-1-methyl-3-oxo-2-phenyl-2,3-dihydro-1H-pyrazol-4-yl]-4-methoxybenzamide | 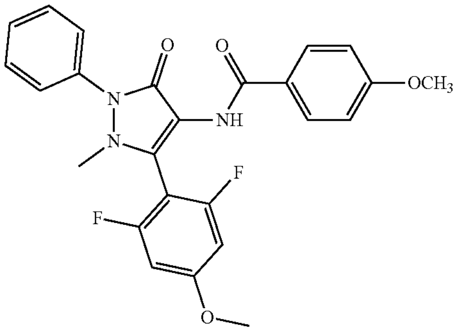 [SMILES: COc1ccc(C(=O)Nc2c(-c3c(F)cc(OC)cc3F)n(C)n(-c3ccccc3)c2=O)cc1] | 1.64 A 466.3 |
| 23 | N-[5-(2,6-difluoro-4-methoxyphenyl)-1-methyl-3-oxo-2-phenyl-2,3-dihydro-1H-pyrazol-4-yl]-4-(1H-pyrazol-1-yl)benzamide | 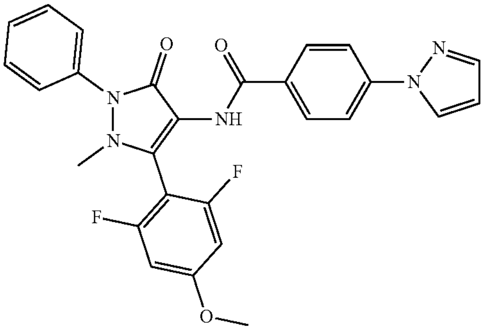 [SMILES: COc1cc(F)c(-c2c(NC(=O)c3ccc(-n4cccn4)cc3)c(=O)n(-c3ccccc3)n2C)c(F)c1] | 1.75 A 502.0 |

TABLE 2-continued

| $^1$H NMR data for the examples in Table 2: | | | |
|---|---|---|---|
| Ex. No. | Name | Structure | LC/MS Rt (min) Method M + H |
| 24 | N-[5-(2,6-difluoro-4-methoxyphenyl)-1-methyl-3-oxo-2-phenyl-2,3-dihydro-1H-pyrazol-4-yl]-5-(trifluoromethoxy)pyridine-2-carboxamide | 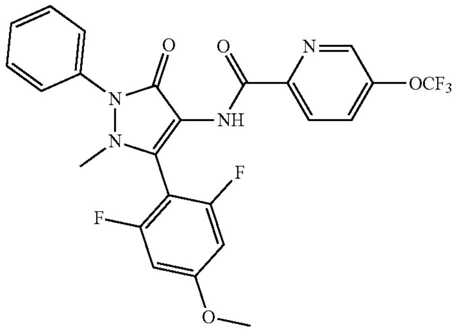 [SMILES: COc1cc(F)c(-c2c(NC(=O)c3ccc(OC(F)(F)F)cn3)c(=O)n(-c3ccccc3)n2C)c(F)c1] | 1.79<br>A<br>521.1 |
| 25 | 6-chloro-N-[5-(2,6-difluoro-4-methoxyphenyl)-1-methyl-3-oxo-2-phenyl-2,3-dihydro-1H-pyrazol-4-yl]pyridin-3-carboxamide | 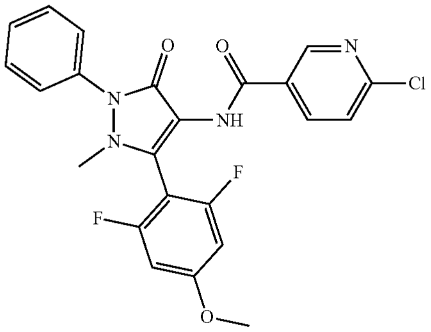 [SMILES: COc1cc(F)c(-c2c(NC(=O)c3ccc(Cl)nc3)c(=O)n(-c3ccccc3)n2C)c(F)c1] | 1.50<br>A<br>471.3 |
| 26 | N-[5-(2,6-difluoro-4-methoxyphenyl)-2-(2,6-difluorophenyl)-1-methyl-3-oxo-2,3-dihydro-1H-pyrazol-4-yl]-4-(trifluoromethoxy)benzamide | 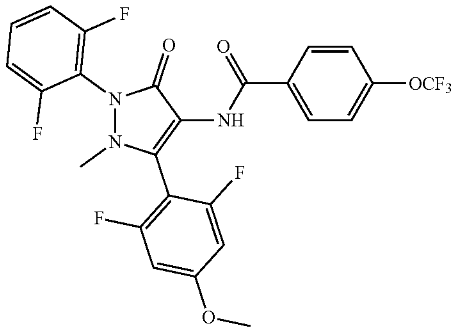 [SMILES: COc1cc(F)c(-c2c(NC(=O)c3ccc(OC(F)(F)F)cc3)c(=O)n(-c3c(F)cccc3F)n2C)c(F)c1] | 1.93<br>A<br>556.2 |
| 27 | N-[5-(2,6-difluoro-4-methoxyphenyl)-2-(2,6-difluorophenyl)-1-methyl-3-oxo-2,3-dihydro-1H-pyrazol-4-yl]-4-(difluoromethoxy)benzamide | 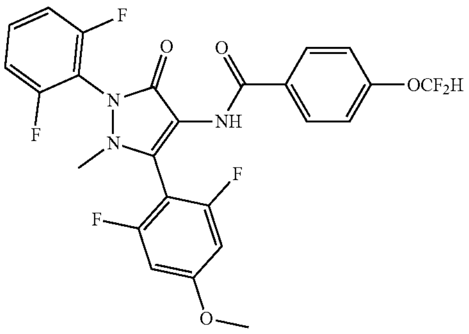 | 1.70<br>A<br>538.0 |

TABLE 2-continued

| $^1$H NMR data for the examples in Table 2: | | | |
|---|---|---|---|
| Ex. No. | Name | Structure | LC/MS Rt (min) Method M + H |
| 28 | N-[5-(2,6-difluoro-4-methoxyphenyl)-2-(2-fluorophenyl)-1-methyl-3-oxo-2,3-dihydro-1H-pyrazol-4-yl]-4-(trifluoromethoxy)benzamide | 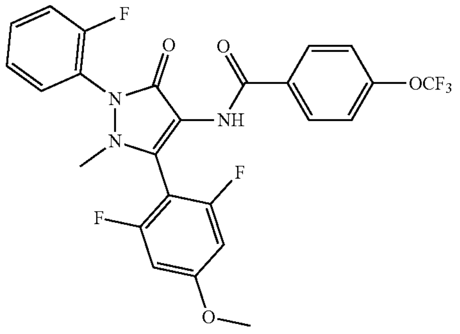 [SMILES: COc1cc(F)c(-c2c(NC(=O)c3ccc(OC(F)(F)F)cc3)c(=O)n(-c3ccccc3F)n2C)c(F)c1] | 1.90<br>A<br>538.2 |
| 29 | N-[5-(2,6-difluoro-4-methoxyphenyl)-2-(2-fluorophenyl)-1-methyl-3-oxo-2,3-dihydro-1H-pyrazol-4-yl]-4-(difluoromethoxy)benzamide | 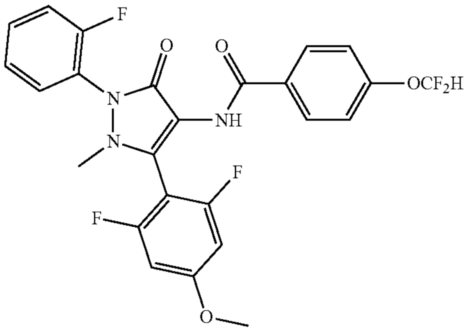 | 1.63<br>A<br>520.1 |
| 30 | 4-chloro-4-N-[5-(2,6-difluoro-4-methoxyphenyl)-2-(2-fluorophenyl)-1-methyl-3-oxo-2,3-dihydro-1H-pyrazol-4-yl]benzamide | 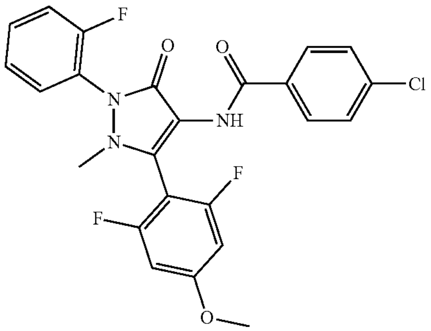 [SMILES: COc1cc(F)c(-c2c(NC(=O)c3ccc(Cl)cc3)c(=O)n(-c3ccccc3F)n2C)c(F)c1] | 1.68<br>A<br>488.2 |
| 31 | 4-chloro-N-[5-(2,6-difluoro-4-methoxyphenyl)-2-(2,6-difluorophenyl)-1-methyl-3-oxo-2,3-dihydro-1H-pyrazol-4-yl]benzamide | 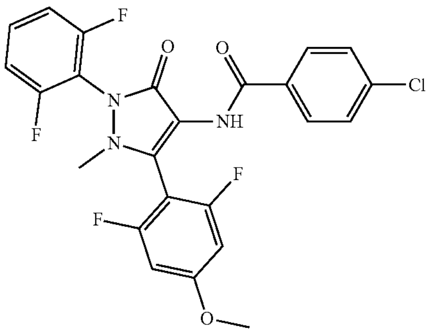 [SMILES: COc1cc(F)c(-c2c(NC(=O)c3ccc(Cl)cc3)c(=O)n(-c3c(F)cccc3F)n2C)c(F)c1] | 1.71<br>A<br>506.2 |

TABLE 2-continued

| Ex. No. | Name | Structure | LC/MS Rt (min) Method M + H |
|---|---|---|---|
| | $^1$H NMR data for the examples in Table 2: | | |
| 32 | N-[5-(2,6-difluoro-4-methoxyphenyl)-2-(3-fluoropyridin-2-yl)-1-methyl-3-oxo-2,3-dihydro-1H-pyrazol-4-yl]-4-(trifluoromethoxy)benzamide | 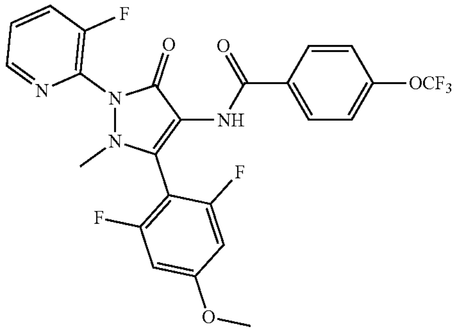 [SMILES: COc1cc(F)c(-c2c(NC(=O)c3ccc(OC(F)(F)F)cc3)c(=O)n(-c3ncccc3F)n2C)c(F)c1] | 1.68<br>A<br>539.0 |
| 33 | N-[5-(2,6-difluoro-4-methoxyphenyl)-1-methyl-3-oxo-2-[4-(trifluoromethyl)pyridin-2-yl]-2,3-dihydro-1H-pyrazol-4-yl]-4-(difluoromethoxy)benzamide | 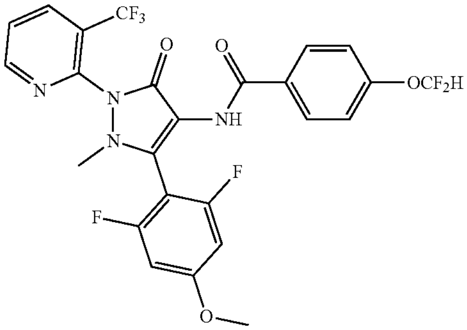 | 1.75<br>A<br>571.0 |
| 35 | N-[2-(2,3-dichlorophenyl)-5-(2,6-difluoro-4-methoxyphenyl)-1-methyl-3-oxo-2,3-dihydro-1H-pyrazol-4-yl]-4-(trifluoromethoxy)benzamide | 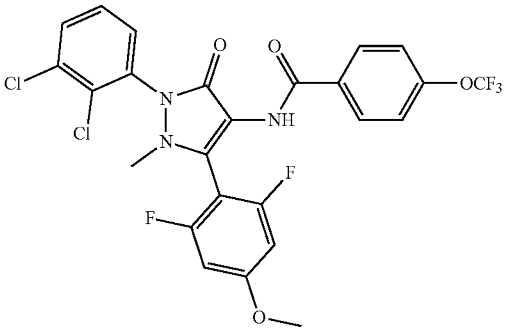 [SMILES: COc1cc(F)c(-c2c(NC(=O)c3ccc(OC(F)(F)F)cc3)c(=O)n(-c3cccc(Cl)c3Cl)n2C)c(F)c1] | 2.12<br>B<br>588.0 |
| 36 | 4-chloro-N-[2-(4-chlorophenyl)-5-(2,6-difluoro-4-methoxyphenyl)-1-methyl-3-oxo-2,3-dihydro-1H-pyrazol-4-yl]benzamide | 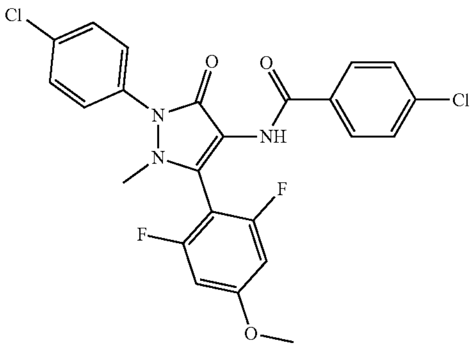 [SMILES: COc1cc(F)c(-c2c(NC(=O)c3ccc(Cl)cc3)c(=O)n(-c3ccc(Cl)cc3)n2C)c(F)c1] | 2.00<br>B<br>504.0 |

TABLE 2-continued

| $^1$H NMR data for the examples in Table 2: | | | |
|---|---|---|---|
| Ex. No. | Name | Structure | LC/MS Rt (min) Method M + H |
| 37 | N-[2-(3-chloro-2-methylphenyl)-5-(2,6-difluoro-4-methoxyphenyl)-1-methyl-3-oxo-2,3-dihydro-1H-pyrazol-4-yl]-4-(difluoromethoxy)benzamide | 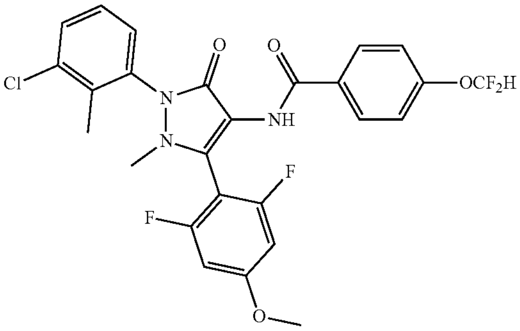 | 1.88 A 550.3 |
| 38 | N-[5-(4-chloro-2,6-difluorophenyl)-1-methyl-3-oxo-2-phenyl-2,3-dihydro-1H-pyrazol-4-yl]-4-(trifluoromethoxy)benzamide | 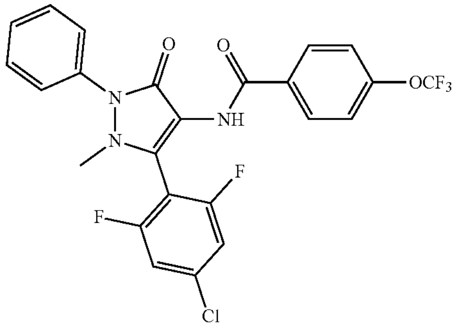 [SMILES: Cn1c(-c2c(F)cc(Cl)cc2F)c(NC(=O)c2ccc(OC(F)(F)F)cc2)c(=O)n1-c1ccccc1] | 2.12 A 524.2 |
| 40 | N-[2-(5-bromopyridin-2-yl)-5-(2,6-difluoro-4-methoxyphenyl)-1-methyl-3-oxo-2,3-dihydro-1H-pyrazol-4-yl]-4-(difluoromethoxy)benzamide | 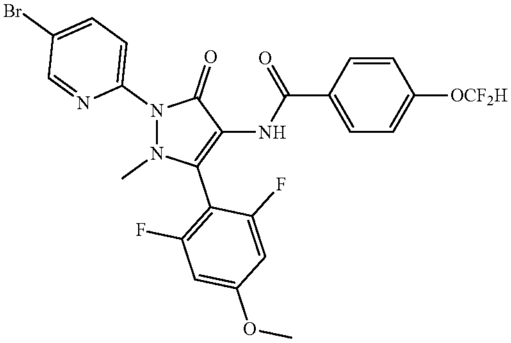 | 1.93 A 580.9 |
| 41 | N-[2-(3-chloropyridin-2-yl)-5-(2,6-difluoro-4-methoxyphenyl)-1-methyl-3-oxo-2,3-dihydro-1H-pyrazol-4-yl]-4-(trifluoromethoxy)benzamide | 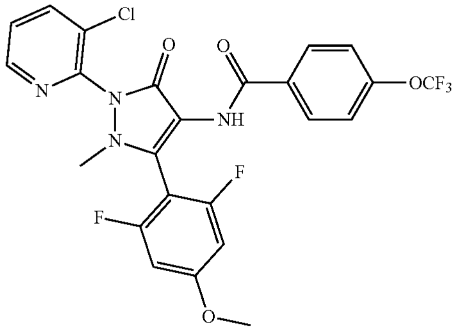 | 1.76 B 555.0 |

TABLE 2-continued

| Ex. No. | Name | Structure | LC/MS Rt (min) Method M + H |
|---|---|---|---|
| $^1$H NMR data for the examples in Table 2: | | | |
| 43 | 4-chloro-N-[2-(5-chloropyridin-2-yl)-5-(2,6-difluoro-4-methoxyphenyl)-1-methyl-3-oxo-2,3-dihydro-1H-pyrazol-4-yl]benzamide | 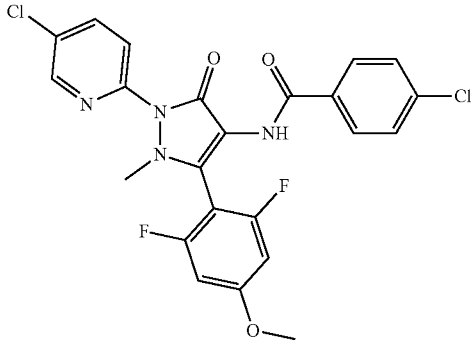 [SMILES: COc1cc(F)c(-c2c(NC(=O)c3ccc(Cl)cc3)c(=O)n(-c3ccc(Cl)cn3)n2C)c(F)c1] | 1.86<br>A<br>505.2 |
| 46 | N-[5-(2,6-difluoro-4-methoxyphenyl)-1-methyl-2-(6-methylpyridin-2-yl)-3-oxo-2,3-dihydro-1H-pyrazol-4-yl]-4-(difluoromethoxy)benzamide | 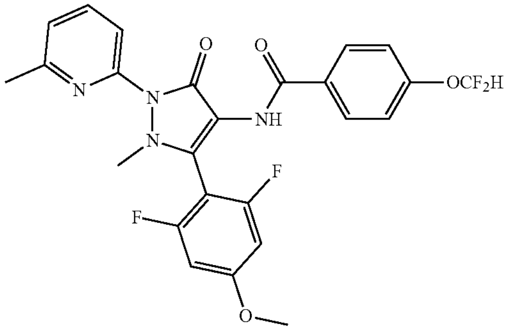 | 1.68<br>A<br>517.3 |
| 47 | N-[2-(5-cyclopropylpyridin-2-yl)-5-(2,6-difluoro-4-methoxyphenyl)-1-methyl-3-oxo-2,3-dihydro-1H-pyrazol-4-yl]-4-(difluoromethoxy)benzamide | 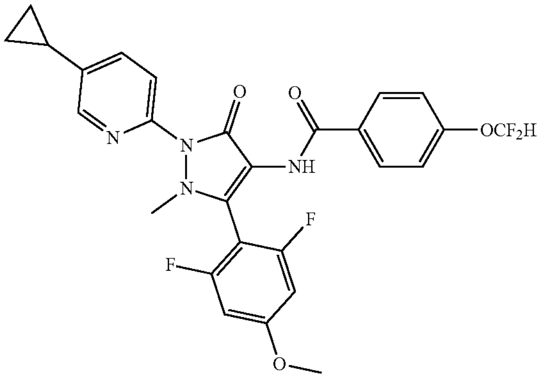 | 1.90<br>B<br>543.1 |
| 48 | 4-chloro-N-[5-(2,6-difluoro-4-methoxyphenyl)-1-methyl-2-(5-methylpyridin-2-yl)-3-oxo-2,3-dihydro-1H-pyrazol-4-yl]benzamide | 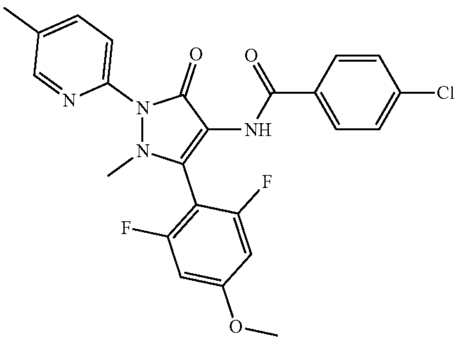 [SMILES: COc1cc(F)c(-c2c(NC(=O)c3ccc(Cl)cc3)c(=O)n(-c3ccc(C)cn3)n2C)c(F)c1] | 1.75<br>A<br>484.9 |

TABLE 2-continued

| Ex. No. | Name | Structure | LC/MS Rt (min) Method M + H |
|---|---|---|---|
| | $^1$H NMR data for the examples in Table 2: | | |
| 49 | N-[5-(2,6-difluoro-4-methoxyphenyl)-1-methyl-2-(5-methylpyridin-2-yl)-3-oxo-2,3-dihydro-1H-pyrazol-4-yl]-4-(difluoromethoxy)benzamide | 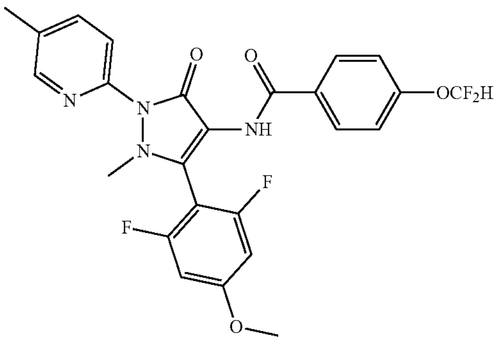 | 1.74 A 517.3 |
| 50 | N-[5-(2,6-difluoro-4-methoxyphenyl)-1-methyl-2-(5-methylpyridin-2-yl)-3-oxo-2,3-dihydro-1H-pyrazol-4-yl]-4-(trifluoromethoxy)benzamide | 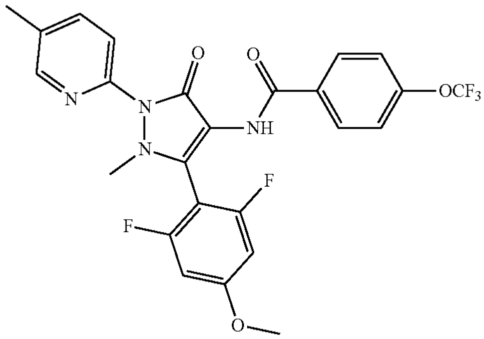 [SMILES: COc1cc(F)c(-c2c(NC(=O)c3ccc(OC(F)(F)F)cc3)c(=O)n(-c3ccc(C)cn3)n2C)c(F)c1] | 1.90 A 535.3 |
| 51 | N-[5-(2,6-difluoro-4-methoxyphenyl)-1-methyl-3-oxo-2-(5-phenylpyridin-2-yl)-2,3-dihydro-1H-pyrazol-4-yl]-4-(difluoromethoxy)benzamide | 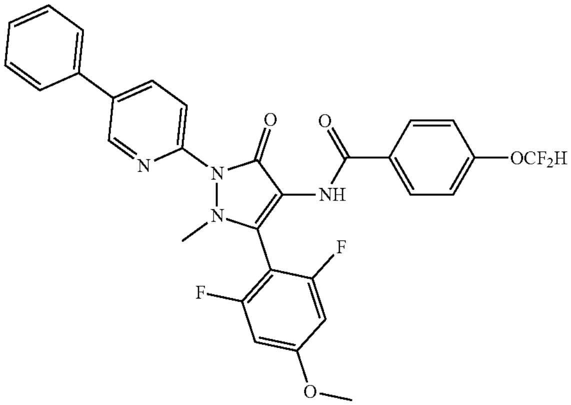 | 2.00 A 579.3 |
| 52 | N-[2-(5-cyclopropylpyridin-2-yl)-5-(2,6-difluoro-4-methoxyphenyl)-1-methyl-3-oxo-2,3-dihydro-1H-pyrazol-4-yl]-4-(trifluoromethoxy)benzamide | 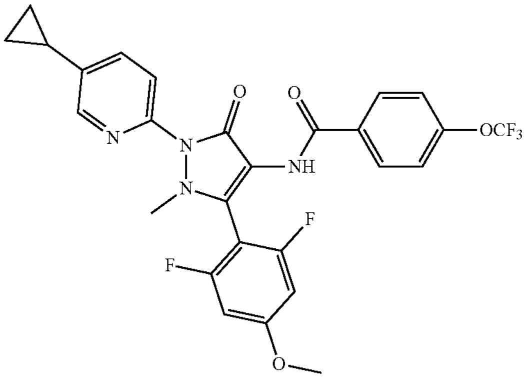 [SMILES: COc1cc(F)c(-c2c(NC(=O)c3ccc(OC(F)(F)F)cc3)c(=O)n(-c3ccc(C4CC4)cn3)n2C)c(F)c1] | 1.90 A 561.2 |

TABLE 2-continued

| $^1$H NMR data for the examples in Table 2: | | | |
|---|---|---|---|
| Ex. No. | Name | Structure | LC/MS Rt (min) Method M + H |
| 53 | 4-cyclopropyl-N-[2-(5-cyclopropylpyridin-2-yl)-5-(2,6-difluoro-4-methoxyphenyl)-1-methyl-3-oxo-2,3-dihydro-1H-pyrazol-4-yl]benzamide | 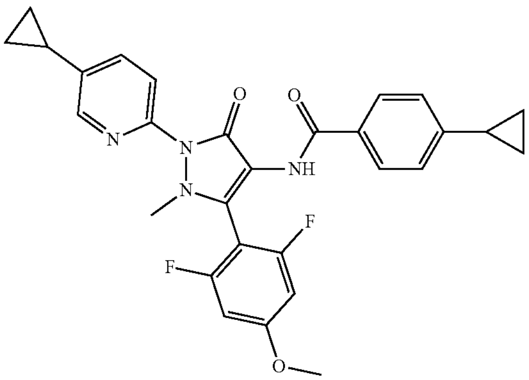 [SMILES: COc1cc(F)c(-c2c(NC(=O)c3ccc(C4CC4)cc3)c(=O)n(-c3ccc(C4CC4)cn3)n2C)c(F)c1] | 1.86 A 517.0 |
| 55 | N-[2-(3-cyanopyridin-2-yl)-5-(2,6-difluoro-4-methoxyphenyl)-1-methyl-3-oxo-2,3-dihydro-1H-pyrazol-4-yl]-4-(difluoromethoxy)benzamide | 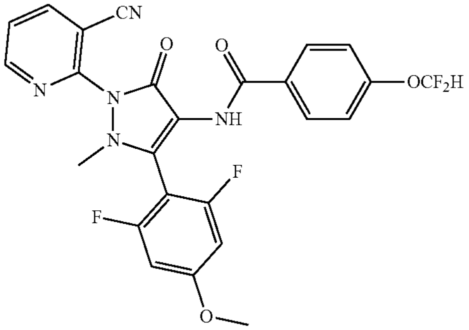 | 1.59 A 527.9 |
| 56 | N-[2-(3-cyanopyridin-2-yl)-5-(2,6-difluoro-4-methoxyphenyl)-1-methyl-3-oxo-2,3-dihydro-1H-pyrazol-4-yl]-4-(trifluoromethoxy)benzamide | 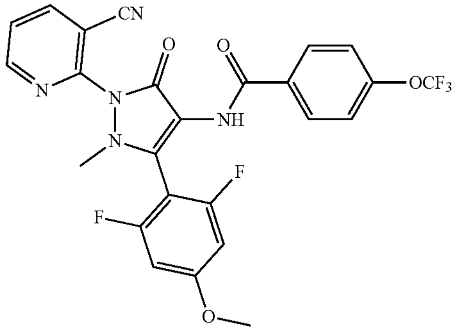 [SMILES: COc1cc(F)c(-c2c(NC(=O)c3ccc(OC(F)(F)F)cc3)c(=O)n(-c3ncccc3C#N)n2C)c(F)c1] | 1.84 A 546.2 |
| 60 | N-[5-(2,6-difluoro-4-methoxyphenyl)-1-methyl-3-oxo-2-(quinolin-2-yl)-2,3-dihydro-1H-pyrazol-4-yl]-4-(difluoromethoxy)benzamide | 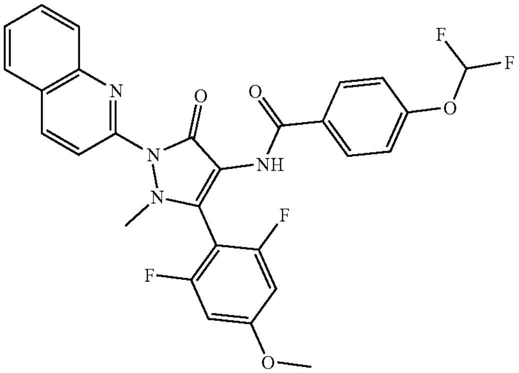 [SMILES: COc1cc(F)c(-c2c(NC(=O)c3ccc(OC(F)F)cc3)c(=O)n(-c3ccc4ccccc4n3)n2C)c(F)c1] | 1.96 B 553.1 |

TABLE 2-continued

| $^1$H NMR data for the examples in Table 2: | | | |
|---|---|---|---|
| Ex. No. | Name | Structure | LC/MS Rt (min) Method M + H |
| 61 | N-[5-(2,6-difluoro-4-methoxyphenyl)-1-methyl-2-(6-methylpyrazin-2-yl)-3-oxo-2,3-dihydro-1H-pyrazol-4-yl]-4-(difluoromethoxy)benzamide | 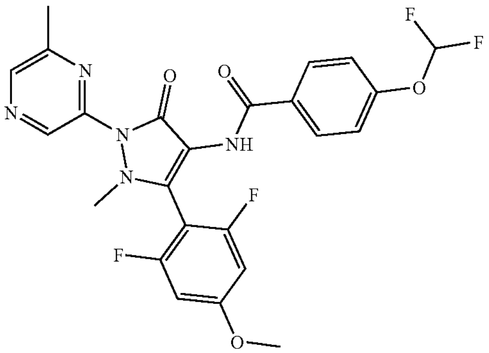 [SMILES: COc1cc(F)c(-c2c(NC(=O)c3ccc(OC(F)F)cc3)c(=O)n(-c3cncc(C)n3)n2C)c(F)c1] | 1.62<br>A<br>518.1 |
| 62 | N-[5-(2,6-difluoro-4-methoxyphenyl)-1-methyl-3-oxo-2-[4-(trifluoromethyl)pyridin-2-yl]-2,3-dihydro-1H-pyrazol-4-yl]-4-(difluoromethoxy)benzamide | 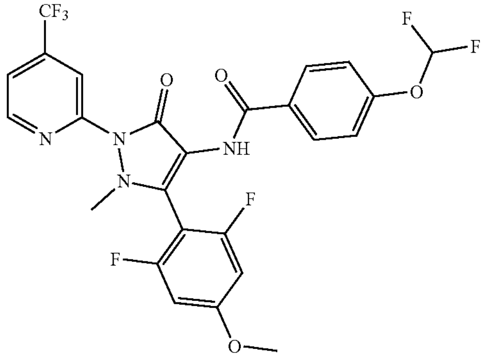 [SMILES: COc1cc(F)c(-c2c(NC(=O)c3ccc(OC(F)F)cc3)c(=O)n(-c3cc(C(F)(F)F)ccn3)n2C)c(F)c1] | 1.90<br>B<br>571.2 |
| 63 | N-[5-(2,6-difluoro-4-methoxyphenyl)-1-methyl-3-oxo-2-[4-(trifluoromethyl)pyridin-2-yl]-2,3-dihydro-1H-pyrazol-4-yl]-4-(trifluoromethoxy)benzamide | 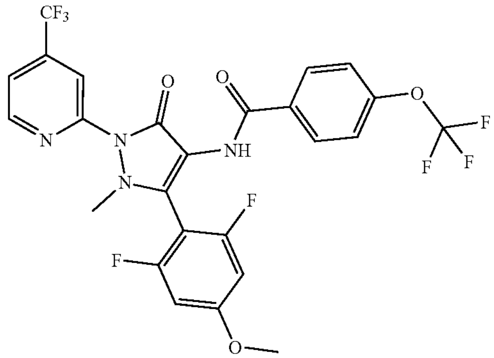 [SMILES: COc1cc(F)c(-c2c(NC(=O)c3ccc(OC(F)(F)F)cc3)c(=O)n(-c3cc(C(F)(F)F)ccn3)n2C)c(F)c1] | 2.06<br>B<br>589.2 |
| 64 | N-[5-(2,6-difluoro-4-methoxyphenyl)-1-methyl-3-oxo-2-(quinoxalin-2-yl)-2,3-dihydro-1H-pyrazol-4-yl]-4-(difluoromethoxy)benzamide | 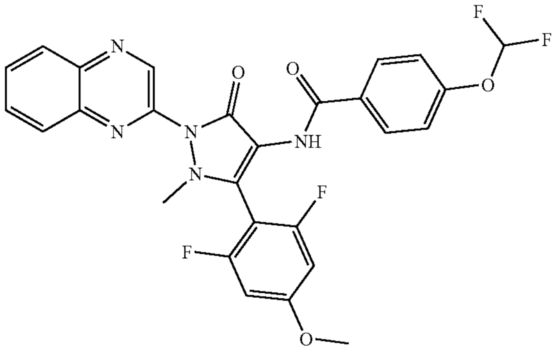 [SMILES: COc1cc(F)c(-c2c(NC(=O)c3ccc(OC(F)F)cc3)c(=O)n(-c3cnc4ccccc4n3)n2C)c(F)c1] | 1.84<br>B<br>554.2 |

TABLE 2-continued

| $^1$H NMR data for the examples in Table 2: | | | |
|---|---|---|---|
| Ex. No. | Name | Structure | LC/MS Rt (min) Method M + H |
| 65 | N-[5-(2,6-difluoro-4-methoxyphenyl)-2-(4,6-dimethylpyridin-2-yl)-1-methyl-3-oxo-2,3-dihydro-1H-pyrazol-4-yl]-4-(difluoromethoxy)benzamide | 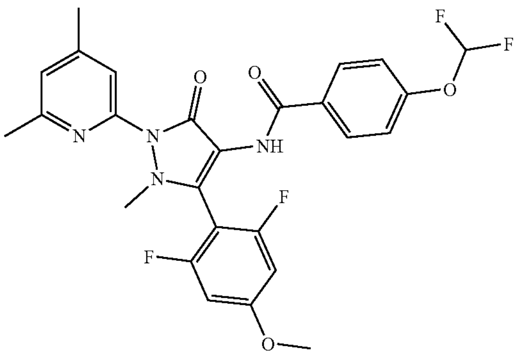 [SMILES: COc1cc(F)c(-c2c(NC(=O)c3ccc(OC(F)F)cc3)c(=O)n(-c3cc(C)cc(C)n3)n2C)c(F)c1] | 1.7<br>B<br>531.4 |
| 66 | N-[5-(2,6-difluoro-4-methoxyphenyl)-2-(4,6-dimethylpyridin-2-yl)-1-methyl-3-oxo-2,3-dihydro-1H-pyrazol-4-yl]-4-(trifluoromethoxy)benzamide | 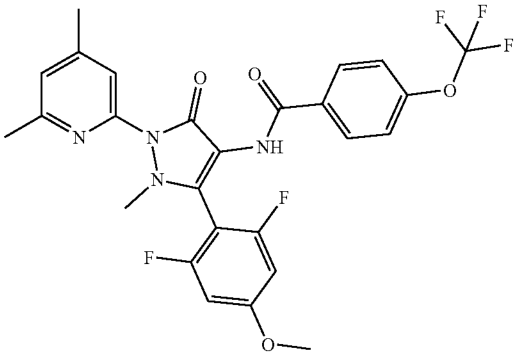 [SMILES: COc1cc(F)c(-c2c(NC(=O)c3ccc(OC(F)(F)F)cc3)c(=O)n(-c3cc(C)cc(C)n3)n2C)c(F)c1] | 1.86<br>B<br>549.3 |
| 67 | N-[5-(2,6-difluoro-4-methoxyphenyl)-2-[6-(difluoromethyl)pyridin-2-yl]-1-methyl-3-oxo-2,3-dihydro-1H-pyrazol-4-yl]-4-(difluoromethoxy)benzamide | 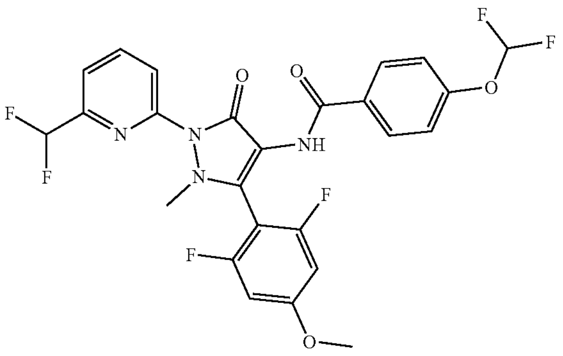 [SMILES: COc1cc(F)c(-c2c(NC(=O)c3ccc(OC(F)F)cc3)c(=O)n(-c3cccc(C(F)F)n3)n2C)c(F)c1] | 1.76<br>A<br>553.3 |
| 68 | N-[5-(2,6-difluoro-4-methoxyphenyl)-2-[6-(difluoromethyl)pyridin-2-yl]-1-methyl-3-oxo-2,3-dihydro-1H-pyrazol-4-yl]-4-(trifluoromethoxy)benzamide | 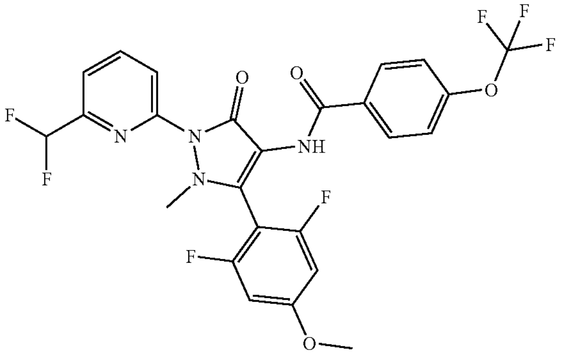 [SMILES: COc1cc(F)c(-c2c(NC(=O)c3ccc(OC(F)(F)F)cc3)c(=O)n(-c3cccc(C(F)F)n3)n2C)c(F)c1] | 1.92<br>A<br>571.2 |

TABLE 2-continued

| <sup></sup> | | | |
|---|---|---|---|

¹H NMR data for the examples in Table 2:

| Ex. No. | Name | Structure | LC/MS Rt (min) Method M + H |
|---|---|---|---|
| 69 | N-[5-(2,6-difluoro-4-methoxyphenyl)-1-methyl-2-[6-(3-methyl-1H-pyrazol-1-yl)pyridin-2-yl]-3-oxo-2,3-dihydro-1H-pyrazol-4-yl]-4-(difluoromethoxy)benzamide | 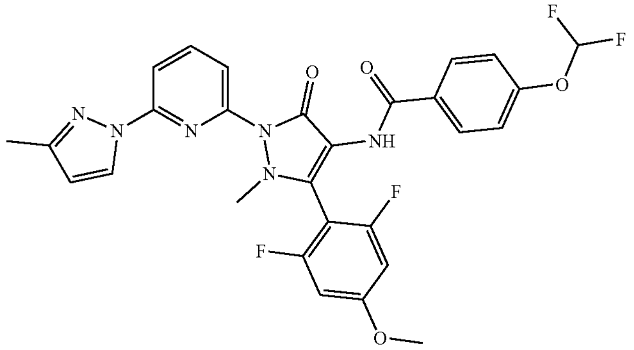 [SMILES: COc1cc(F)c(-c2c(NC(=O)c3ccc(OC(F)F)cc3)c(=O)n(-c3cccc(-n4ccc(C)n4)n3)n2C)c(F)c1] | 1.90<br>A<br>583.3 |
| 70 | N-[5-(2,6-difluoro-4-methoxyphenyl)-1-methyl-2-[6-(3-methyl-1H-pyrazol-1-yl)pyridin-2-yl]-3-oxo-2,3-dihydro-1H-pyrazol-4-yl]-4-(trifluoromethoxy)benzamide | 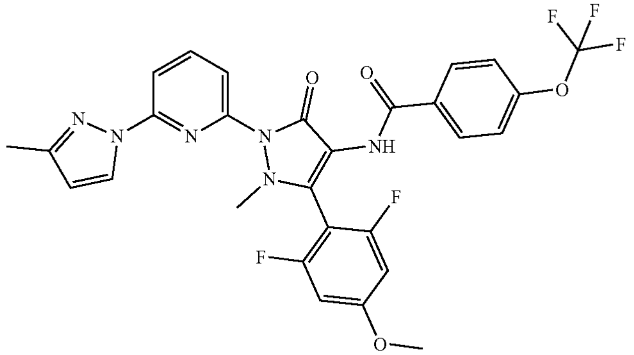 [SMILES: COc1cc(F)c(-c2c(NC(=O)c3ccc(OC(F)(F)F)cc3)c(=O)n(-c3cccc(-n4ccc(C)n4)n3)n2C)c(F)c1] | 2.05<br>B<br>601.2 |
| 71 | N-[5-(2,6-difluoro-4-methoxyphenyl)-2-(6-methoxypyrazin-2-yl)-1-methyl-3-oxo-2,3-dihydro-1H-pyrazol-4-yl]-4-(difluoromethoxy)benzamide | 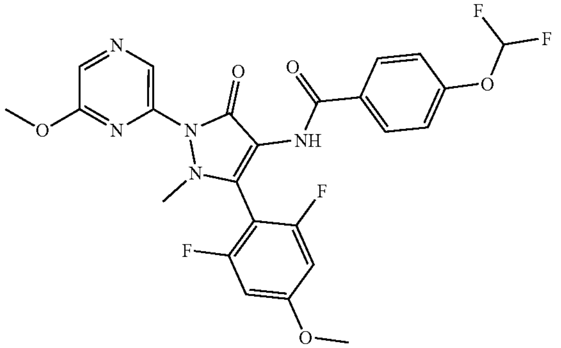 [SMILES: COc1cc(F)c(-c2c(NC(=O)c3ccc(OC(F)F)cc3)c(=O)n(-c3cncc(OC)n3)n2C)c(F)c1] | 1.71<br>B<br>534.1 |
| 72 | N-[5-(2,6-difluoro-4-methoxyphenyl)-1-methyl-3-oxo-2-(6-phenylpyridin-2-yl)-2,3-dihydro-1H-pyrazol-4-yl]-4-(difluoromethoxy)benzamide | 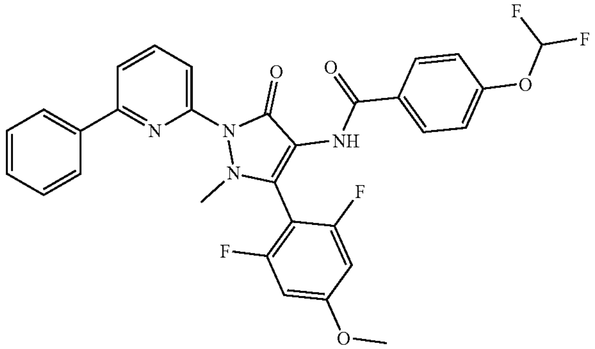 [SMILES: COc1cc(F)c(-c2c(NC(=O)c3ccc(OC(F)F)cc3)c(=O)n(-c3cccc(-c4ccccc4)n3)n2C)c(F)c1] | 2.00<br>B<br>579.3 |

TABLE 2-continued

| $^1$H NMR data for the examples in Table 2: | | | |
|---|---|---|---|
| Ex. No. | Name | Structure | LC/MS Rt (min) Method M + H |
| 73 | N-[5-(2,6-difluoro-4-methoxyphenyl)-1-methyl-3-oxo-2-(6-phenylpyridin-2-yl)-2,3-dihydro-1H-pyrazol-4-yl]-4-(trifluoromethoxy)benzamide | 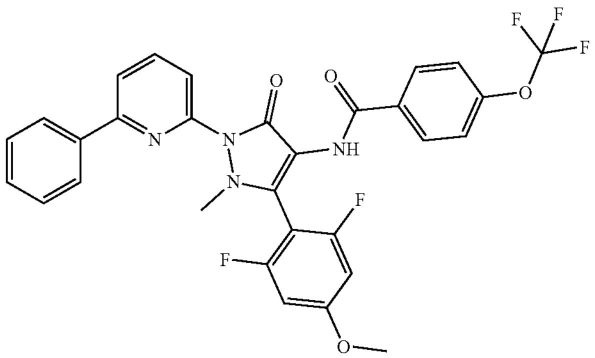 [SMILES: COc1cc(F)c(-c2c(NC(=O)c3ccc(OC(F)(F)F)cc3)c(=O)n(-c3cccc(-c4ccccc4)n3)n2C)c(F)c1] | 2.18 A 597.3 |
| 74 | N-[5-(2,6-difluoro-4-methoxyphenyl)-2-(6-methoxypyridin-2-yl)-1-methyl-3-oxo-2,3-dihydro-1H-pyrazol-4-yl]-4-(trifluoromethoxy)benzamide | 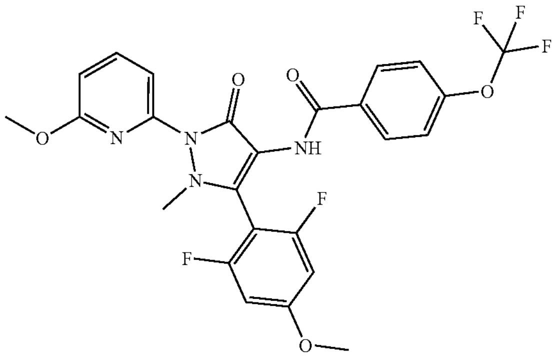 [SMILES: COc1cc(F)c(-c2c(NC(=O)c3ccc(OC(F)(F)F)cc3)c(=O)n(-c3cccc(OC)n3)n2C)c(F)c1] | 1.91 B 551.2 |
| 75 | N-[5-(2,6-difluoro-4-methoxyphenyl)-2-(6-methoxypyridin-2-yl)-1-methyl-3-oxo-2,3-dihydro-1H-pyrazol-4-yl]-4-(difluoromethoxy)benzamide | 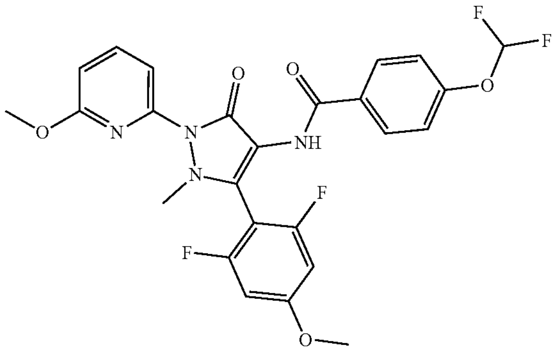 [SMILES: COc1cc(F)c(-c2c(NC(=O)c3ccc(OC(F)F)cc3)c(=O)n(-c3cccc(OC)n3)n2C)c(F)c1] | 1.75 B 533.2 |
| 76 | N-[5-(2,6-difluoro-4-methoxyphenyl)-2-[4-(difluoromethyl)pyridin-2-yl]-1-methyl-3-oxo-2,3-dihydro-1H-pyrazol-4-yl]-4-(difluoromethoxy)benzamide | 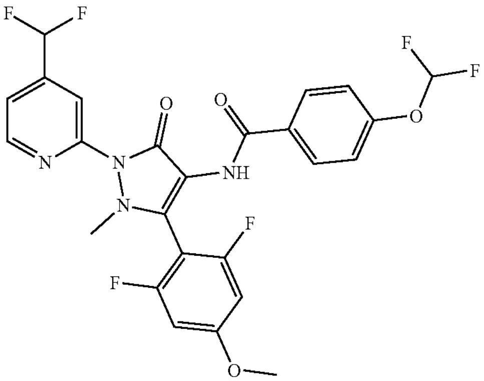 [SMILES: COc1cc(F)c(-c2c(NC(=O)c3ccc(OC(F)F)cc3)c(=O)n(-c3cc(C(F)F)ccn3)n2C)c(F)c1] | 1.72 B 553.3 |

TABLE 2-continued

| $^1$H NMR data for the examples in Table 2: | | | |
|---|---|---|---|
| Ex. No. | Name | Structure | LC/MS Rt (min) Method M + H |
| 77 | N-[5-(2,6-difluoro-4-methoxyphenyl)-2-(4-methoxy-5-methylpyridin-2-yl)-1-methyl-3-oxo-2,3-dihydro-1H-pyrazol-4-yl]-4-(difluoromethoxy)benzamide | 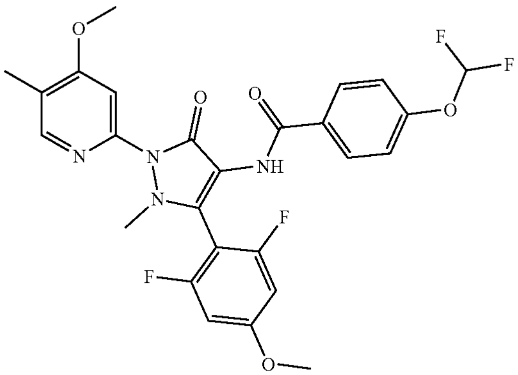 [SMILES: COc1cc(F)c(-c2c(NC(=O)c3ccc(OC(F)F)cc3)c(=O)n(-c3cc(OC)c(C)cn3)n2C)c(F)c1] | 1.79 A 547.3 |
| 78 | N-[5-(2,6-difluoro-4-methoxyphenyl)-2-(4-ethoxypyridin-2-yl)-1-methyl-3-oxo-2,3-dihydro-1H-pyrazol-4-yl]-4-(difluoromethoxy)benzamide | 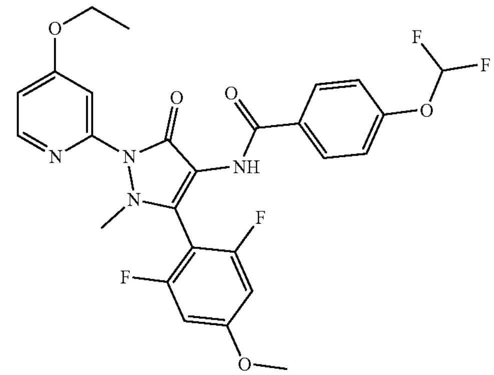 [SMILES: CCOc1ccnc(-n2c(=O)c(NC(=O)c3ccc(OC(F)F)cc3)c(-c3c(F)cc(OC)cc3F)n2C)c1] | 1.93 A 547.2 |
| 79 | N-[5-(2,6-difluoro-4-methoxyphenyl)-1-methyl-2-[6-(morpholin-4-yl)pyridin-2-yl]-3-oxo-2,3-dihydro-1H-pyrazol-4-yl]-4-(difluoromethoxy)benzamide | 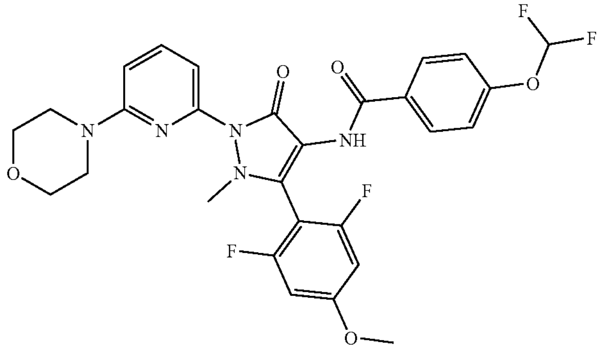 [SMILES: COc1cc(F)c(-c2c(NC(=O)c3ccc(OC(F)F)cc3)c(=O)n(-c3cccc(N4CCOCC4)n3)n2C)c(F)c1] | 1.67 B 588.1 |
| 80 | N-[5-(2,6-difluoro-4-methoxyphenyl)-1-methyl-3-oxo-2-[6-(piperidin-1-yl)pyridin-2-yl]-2,3-dihydro-1H-pyrazol-4-yl]-4-(difluoromethoxy)benzamide | 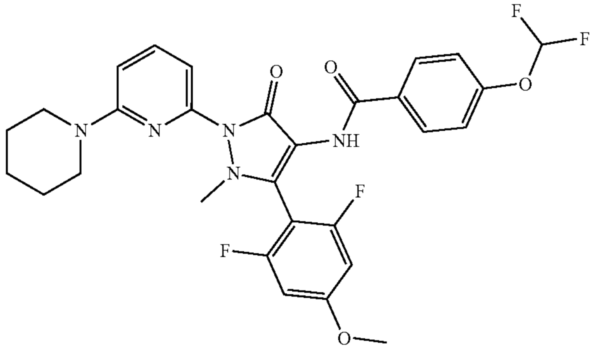 [SMILES: COc1cc(F)c(-c2c(NC(=O)c3ccc(OC(F)F)cc3)c(=O)n(-c3cccc(N4CCCCC4)n3)n2C)c(F)c1] | 2.14 A 586.2 |

TABLE 2-continued

$^1$H NMR data for the examples in Table 2:

| Ex. No. | Name | Structure | LC/MS Rt (min) Method M + H |
|---|---|---|---|
| 81 | N-[5-(2,6-difluoro-4-methoxyphenyl)-2-[6-(hydroxymethyl)pyridin-2-yl]-1-methyl-3-oxo-2,3-dihydro-1H-pyrazol-4-yl]-4-(difluoromethoxy)benzamide | 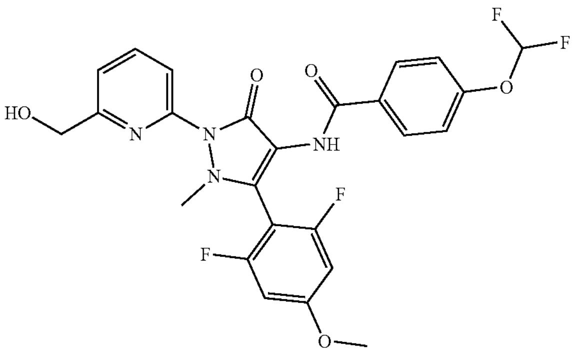 [SMILES: COc1cc(F)c(-c2c(NC(=O)c3ccc(OC(F)F)cc3)c(=O)n(-c3cccc(CO)n3)n2C)c(F)c1] | 1.51 A 533.1 |
| 82 | N-[5-(2,6-difluoro-4-methoxyphenyl)-2-[6-(dimethylamino)pyridin-2-yl]-1-methy-3-oxo-2,3-dihydro-1H-pyrazol-4-yl]-4-(difluoromethoxy)benzamide | 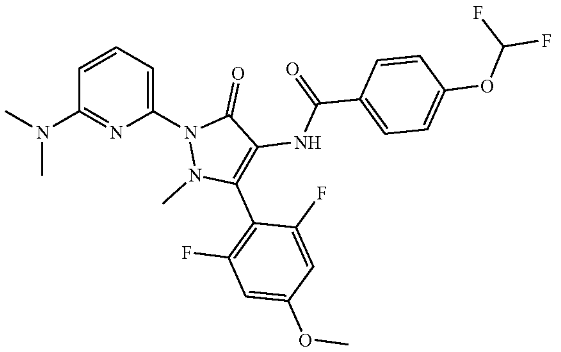 [SMILES: COc1cc(F)c(-c2c(NC(=O)c3ccc(OC(F)F)cc3)c(=O)n(-c3cccc(N(C)C)n3)n2C)c(F)c1] | 1.78 A 546.4 |
| 83 | N-[5-(2,6-difluoro-4-methoxyphenyl)-1-methyl-2-[6-(4-methylpiperazin-1-yl)pyridin-2-yl]-3-oxo-2,3-dihydro-1H-pyrazol-4-yl]-4-(difluoromethoxy)benzamide | 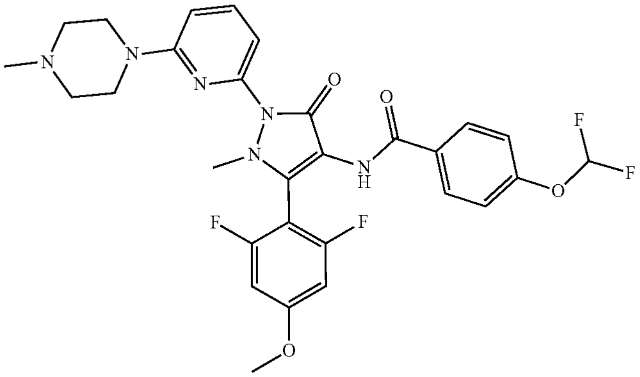 [SMILES: COc1cc(F)c(-c2c(NC(=O)c3ccc(OC(F)F)cc3)c(=O)n(-c3cccc(N4CCN(C)CC4)n3)n2C)c(F)c1] | 1.45 A 601.4 |
| 84 | N-[5-(2,6-difluoro-4-methoxyphenyl)-2-[6-(2,2-dimethylpropanamido)pyridin-2-yl]-1-methyl-3-oxo-2,3-dihydro-1H-pyrazol-4-yl]-4-(difluoromethoxy)benzamide | 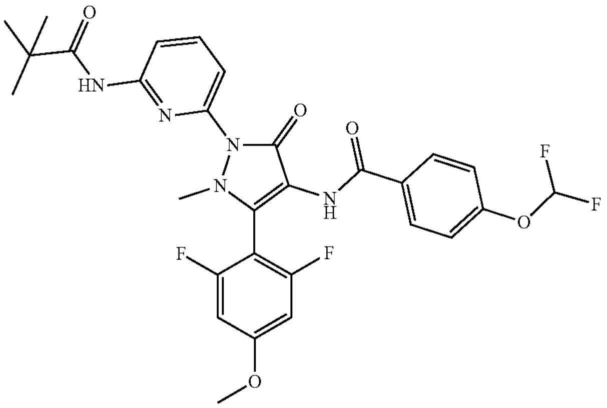 [SMILES: COc1cc(F)c(-c2c(NC(=O)c3ccc(OC(F)F)cc3)c(=O)n(-c3cccc(NC(=O)C(C)(C)C)n3)n2C)c(F)c1] | 1.88 A 602.4 |

TABLE 2-continued

| Ex. No. | Name | Structure | LC/MS Rt (min) Method M + H |
|---|---|---|---|
| | $^1$H NMR data for the examples in Table 2: | | |
| 86 | N-[5-(2,6-difluoro-4-methoxyphenyl)-2-[6-(1-hydroxyethyl)pyridin-2-yl]-1-methyl-3-oxo-2,3-dihydro-1H-pyrazol-4-yl]-4-(difluoromethoxy)benzamide | 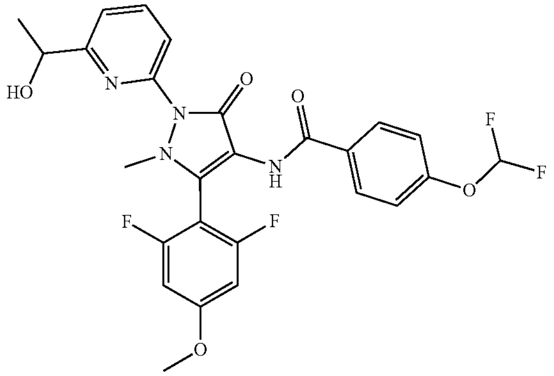 [SMILES: COc1cc(F)c(-c2c(NC(=O)c3ccc(OC(F)F)cc3)c(=O)n(-c3cccc(C(C)O)n3)n2C)c(F)c1] | 1.5<br>A<br>547.3 |
| 89 | N-[5-(2,6-difluoro-4-methoxyphenyl)-2-[6-(2-hydroxypropan-2-yl)-4-methoxypyridin-2-yl]-1-methyl-3-oxo-2,3-dihydro-1H-pyrazol-4-yl]-4-(difluoromethoxy)benzamide | 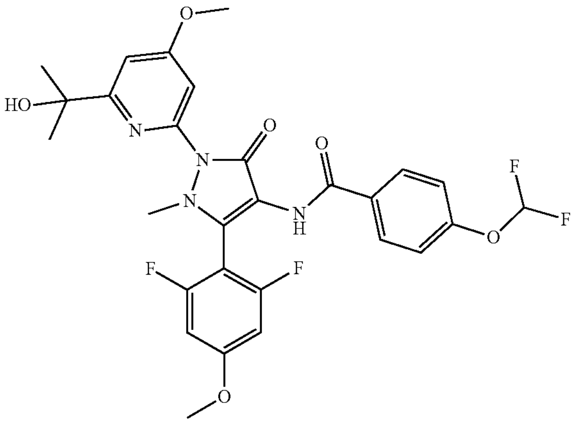 [SMILES: COc1cc(-n2c(=O)c(NC(=O)c3ccc(OC(F)F)cc3)c(-c3c(F)cc(OC)cc3F)n2C)nc(C(C)(C)O)c1] | 1.64<br>A<br>591.3 |
| 90 | N-[5-(2,6-difluoro-4-methoxyphenyl)-2-[6-(hydroxymethyl)-4-methoxypyridin-2-yl]-1-methyl-3-oxo-2,3-dihydro-1H-pyrazol-4-yl]-4-(difluoromethoxy)benzamide | 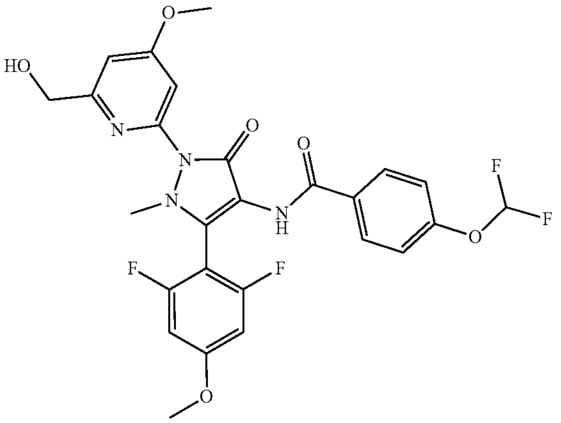 [SMILES: COc1cc(CO)nc(-n2c(=O)c(NC(=O)c3ccc(OC(F)F)cc3)c(-c3c(F)cc(OC)cc3F)n2C)c1] | 1.45<br>A<br>563.2 |

TABLE 2-continued

| $^1$H NMR data for the examples in Table 2: | | | |
|---|---|---|---|
| Ex. No. | Name | Structure | LC/MS Rt (min) Method M + H |
| 92 | N-[5-(2,6-difluoro-4-methoxyphenyl)-2-{6-[(2R,6S)-2,6-dimethylmorpholin-4-yl]-4-methoxypyridin-2-yl}-1-methyl-3-oxo-2,3-dihydro-1H-pyrazol-4-yl]-4-(difluoromethoxy)benzamide | 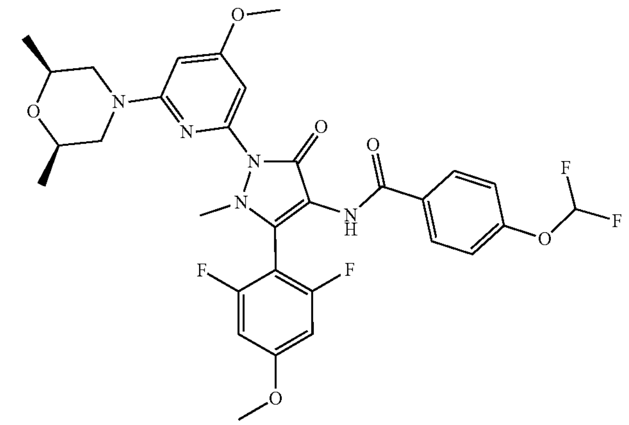 [SMILES: COc1cc(N2C[C@@H](C)O[C@@H](C)C2)nc(-n2c(=O)c(NC(=O)c3ccc(OC(F)F)cc3)c(-c3c(F)cc(OC)cc3F)n2C)c1] | 2.00 A 646.1 |
| 93 | N-[5-(2,6-difluoro-4-methoxyphenyl)-2-{4-methoxy-6-[(3R,5S)-3,4,5-trimethylpiperazin-1-yl]pyridin-2-yl}-1-methyl-3-oxo-2,3-dihydro-1H-pyrazol-4-yl]-4-(difluoromethoxy)benzamide | 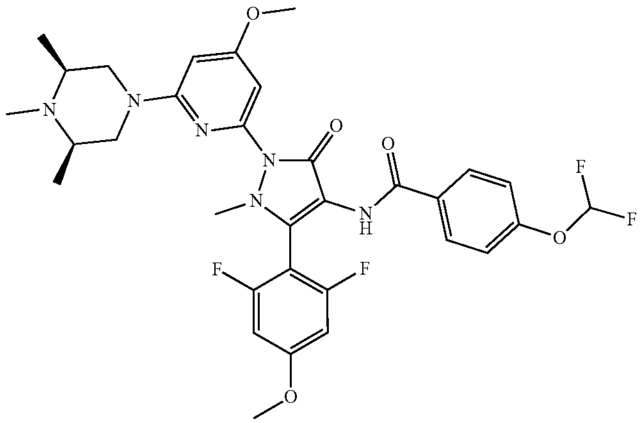 [SMILES: COc1cc(N2C[C@@H](C)N(C)[C@@H](C)C2)nc(-n2c(=O)c(NC(=O)c3ccc(OC(F)F)cc3)c(-c3c(F)cc(OC)cc3F)n2C)c1] | 1.73 A 659.4 |
| 94 | N-[5-(2,6-difluoro-4-methoxyphenyl)-2-{6-[(2-hydroxyethyl)amino]-4-methoxypyridin-2-yl}-1-methyl-3-oxo-2,3-dihydro-1H-pyrazol-4-yl]-4-(difluoromethoxy)benzamide | 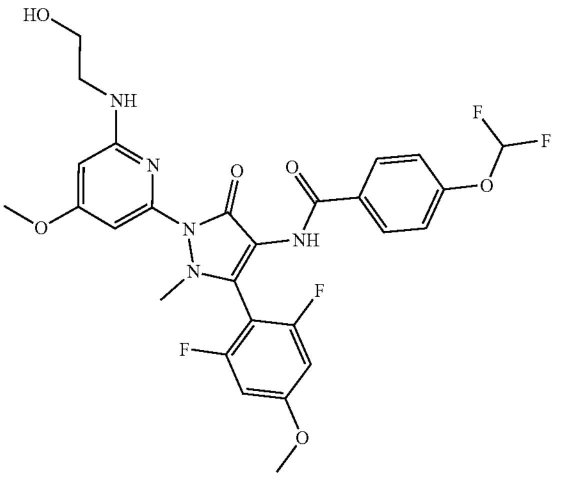 [SMILES: COc1cc(NCCO)nc(-n2c(=O)c(NC(=O)c3ccc(OC(F)F)cc3)c(-c3c(F)cc(OC)cc3F)n2C)c1] | 1.52 A 592.4 |

TABLE 2-continued

| $^1$H NMR data for the examples in Table 2: | | | |
|---|---|---|---|
| Ex. No. | Name | Structure | LC/MS Rt (min) Method M + H |
| 95 | N-[5-(2,6-difluoro-4-methoxyphenyl)-2-{6-[(3R)-3-hydroxypyrrolidin-1-yl]-4-methoxypyridin-2-yl}-1-methyl-3-oxo-2,3-dihydro-1H-pyrazol-4-yl]-4-(difluoromethoxy)benzamide | 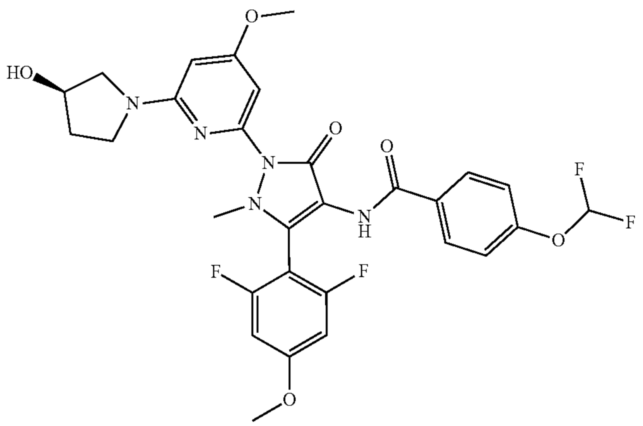 [SMILES: COc1cc(N2CC[C@@H](O)C2)nc(-n2c(=O)c(NC(=O)c3ccc(OC(F)F)cc3)c(-c3c(F)cc(OC)cc3F)n2C)c1] | 1.62 A 618.4 |
| 96 | N-[5-(2,6-difluoro-4-methoxyphenyl)-2-[6-(3-hydroxy-3-methylazetidin-1-yl)-4-methoxypyridin-2-yl]-1-methyl-3-oxo-2,3-dihydro-1H-pyrazol-4-yl]-4-(difluoromethoxy)benzamide | 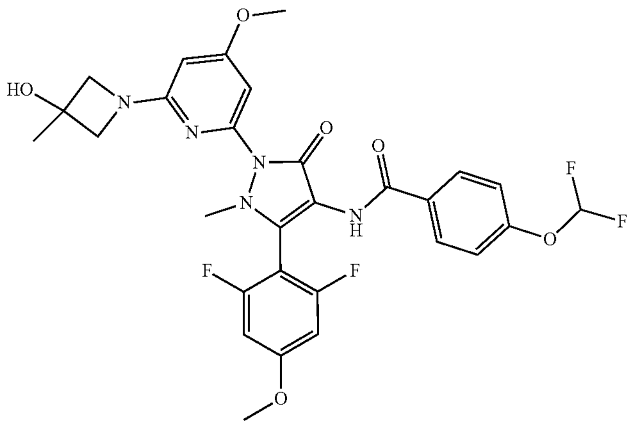 [SMILES: COc1cc(N2CC(C)(O)C2)nc(-n2c(=O)c(NC(=O)c3ccc(OC(F)F)cc3)c(-c3c(F)cc(OC)cc3F)n2C)c1] | 1.70 A 618.3 |
| 97 | N-[5-(2,6-difluoro-4-methoxyphenyl)-2-{6-[(3S)-3-hydroxypyrrolidin-1-yl]-4-methoxypyridin-2-yl}-1-methyl-3-oxo-2,3-dihydro-1H-pyrazol-4-yl]-4-(difluoromethoxy)benzamide | 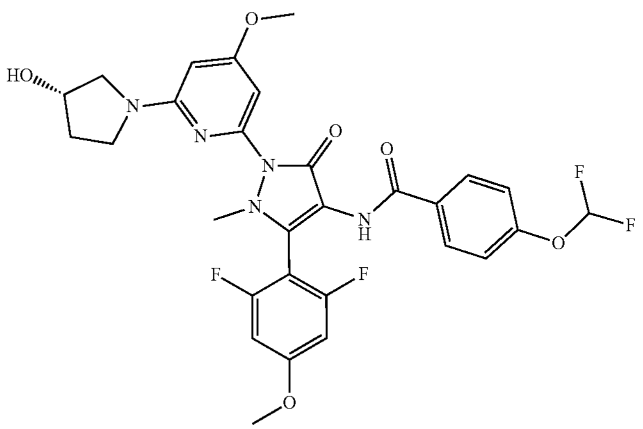 [SMILES: COc1cc(N2CC[C@H](O)C2)nc(-n2c(=O)c(NC(=O)c3ccc(OC(F)F)cc3)c(-c3c(F)cc(OC)cc3F)n2C)c1] | 1.72 A 618.0 |

TABLE 2-continued

| $^1$H NMR data for the examples in Table 2: | | | |
|---|---|---|---|
| Ex. No. | Name | Structure | LC/MS Rt (min) Method M + H |
| 98 | N-[5-(2,6-difluoro-4-methoxyphenyl)-2-{6-[(3S)-3-fluoropyrrolidin-1-yl]-4-methoxypyridin-2-yl}-1-methyl-3-oxo-2,3-dihydro-1H-pyrazol-4-yl]-4-(difluoromethoxy)benzamide | 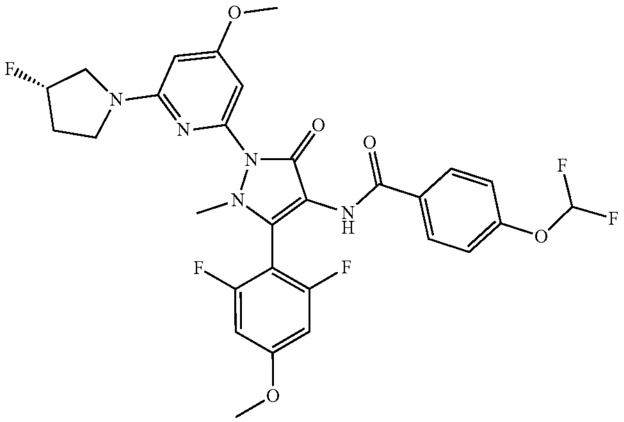 [SMILES: COc1cc(N2CC[C@H](F)C2)nc(-n2c(=O)c(NC(=O)c3ccc(OC(F)F)cc3)c(-c3c(F)cc(OC)cc3F)n2C)c1] | 1.97 A 620.0 |
| 99 | N-[5-(2,6-difluoro-4-methoxyphenyl)-2-[6-(3,3-difluoropyrrolidin-1-yl)-4-methoxypyridin-2-yl]-1-methyl-3-oxo-2,3-dihydro-1H-pyrazol-4-yl]-4-(difluoromethoxy)benzamide | 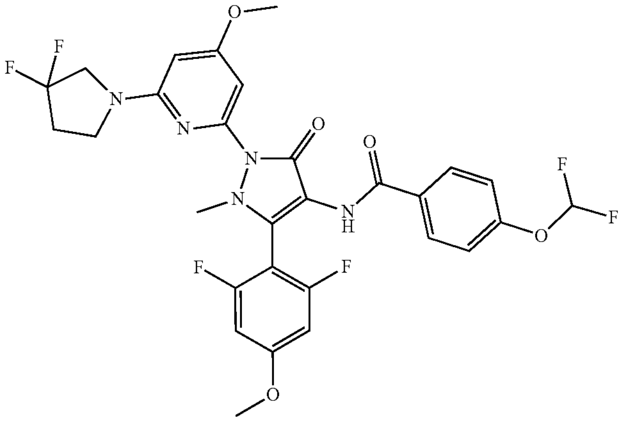 [SMILES: COc1cc(N2CCC(F)(F)C2)nc(-n2c(=O)c(NC(=O)c3ccc(OC(F)F)cc3)c(-c3c(F)cc(OC)cc3F)n2C)c1] | 1.97 A 638.0 |
| 100 | N-[5-(2,6-difluoro-4-methoxyphenyl)-2-[6-(1-hydroxycyclobutyl)-4-methoxypyridin-2-yl]-1-methyl-3-oxo-2,3-dihydro-1H-pyrazol-4-yl]-4-(difluoromethoxy)benzamide | 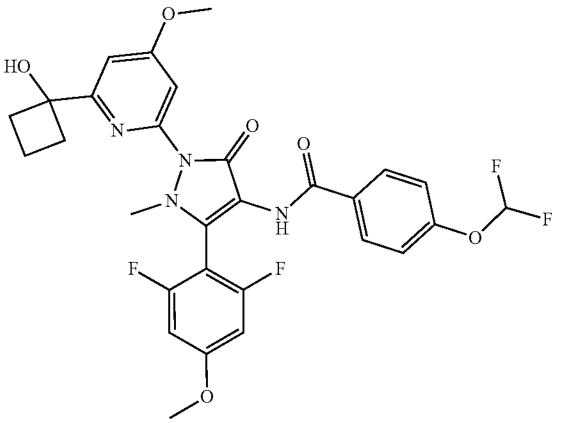 [SMILES: COc1cc(-n2c(=O)c(NC(=O)c3ccc(OC(F)F)cc3)c(-c3c(F)cc(OC)cc3F)n2C)nc(C2(O)CCC2)c1] | 1.73 A 603.4 |

TABLE 2-continued

| $^{1}$H NMR data for the examples in Table 2: | | | |
|---|---|---|---|
| Ex. No. | Name | Structure | LC/MS Rt (min) Method M + H |
| 101 | N-[5-(2,6-difluoro-4-methoxyphenyl)-2-[4-methoxy-6-(4-methylpiperazin-1-yl)pyridin-2-yl]-1-methyl-3-oxo-2,3-dihydro-1H-pyrazol-4-yl]-4-(difluoromethoxy)benzamide | 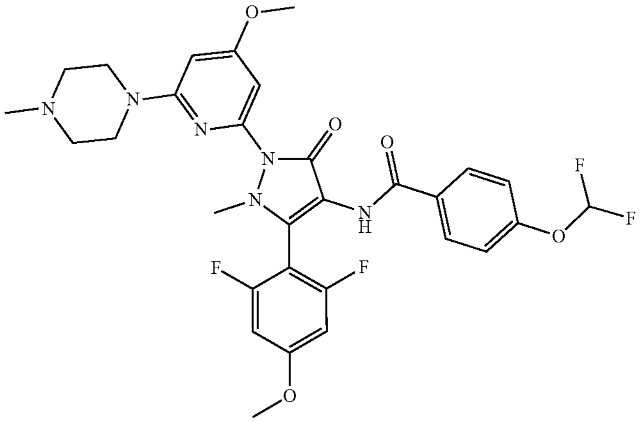 [SMILES: COc1cc(N2CCN(C)CC2)nc(-n2c(=O)c(NC(=O)c3ccc(OC(F)F)cc3)c(-c3c(F)cc(OC)cc3F)n2C)c1] | 1.72<br>A<br>631.3 |
| 102 | N-[5-(2,6-difluoro-4-methoxyphenyl)-2-{6-[(3S)-3-hydroxypyrrolidin-1-yl]pyridin-2-yl}-1-methyl-3-oxo-2,3-dihydro-1H-pyrazol-4-yl]-4-(difluoromethoxy)benzamide | 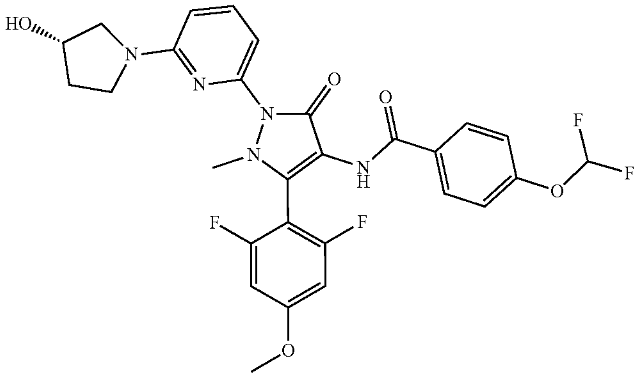 [SMILES: COc1cc(F)c(-c2c(NC(=O)c3ccc(OC(F)F)cc3)c(=O)n(-c3cccc(N4CC[C@H](O)C4)n3)n2C)c(F)c1] | 1.63<br>B<br>588.3 |
| 103 | N-[5-(2,6-difluoro-4-methoxyphenyl)-1-methyl-3-oxo-2-{6-[(3R,5S)-3,4,5-trimethylpiperazin-1-yl]pyridin-2-yl}-2,3-dihydro-1H-pyrazol-4-yl]-4-(difluoromethoxy)benzamide | 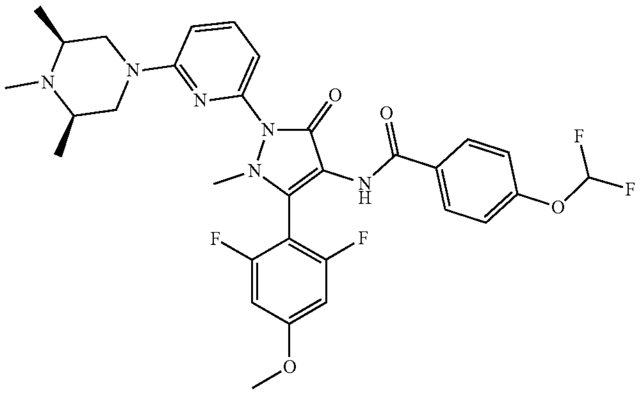 [SMILES: COc1cc(F)c(-c2c(NC(=O)c3ccc(OC(F)F)cc3)c(=O)n(-c3cccc(N4C[C@@H](C)N(C)[C@@H](C)C4)n3)n2C)c(F)c1] | 1.49<br>A<br>629.3 |

TABLE 2-continued

| $^1$H NMR data for the examples in Table 2: | | | |
|---|---|---|---|
| Ex. No. | Name | Structure | LC/MS Rt (min) Method M + H |
| 104 | N-[5-(2,6-difluoro-4-methoxyphenyl)-2-[6-(3,3-difluoroazetidin-1-yl)pyridin-2-yl]-1-methyl-3-oxo-2,3-dihydro-1H-pyrazol-4-yl]-4-(difluoromethoxy)benzamide | 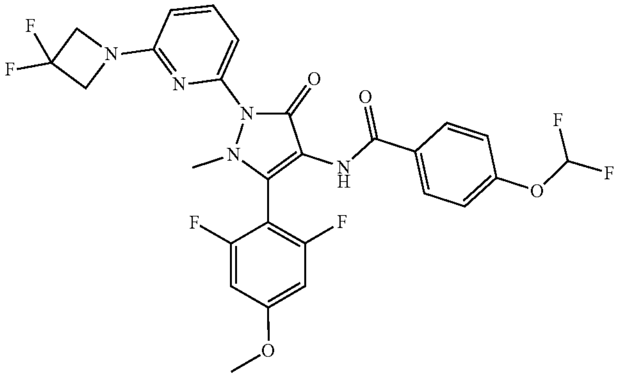 [SMILES: COc1cc(F)c(-c2c(NC(=O)c3ccc(OC(F)F)cc3)c(=O)n(-c3cccc(N4CC(F)(F)C4)n3)n2C)c(F)c1] | 1.95 B 594.0 |
| 105 | N-[5-(2,6-difluoro-4-methoxyphenyl)-2-(4-methoxy-6-{3-methyl-3,8-diazabicyclo[3.2.1]octan-8-yl}pyridin-2-yl)-1-methyl-3-oxo-2,3-dihydro-1H-pyrazol-4-yl]-4-(difluoromethoxy)benzamide | 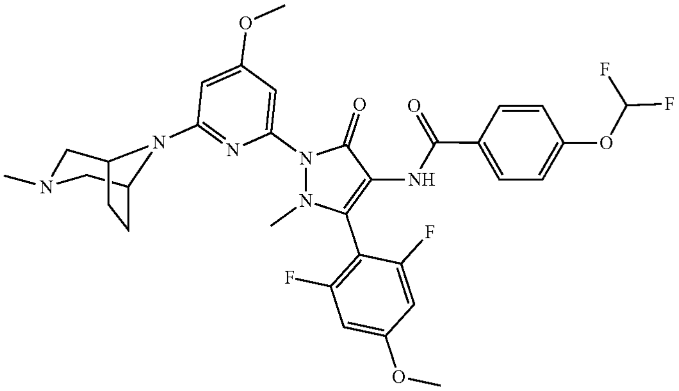 [SMILES: COc1cc(N2C3CCC2CN(C)C3)nc(-n2c(=O)c(NC(=O)c3ccc(OC(F)F)cc3)c(-c3c(F)cc(OC)cc3F)n2C)c1] | 1.56 B 657.4 |
| 106 | N-[5-(2,6-difluoro-4-methoxyphenyl)-2-{4-methoxy-6-[3-(propan-2-yloxy)azetidin-1-yl]pyridin-2-yl}-1-methyl-3-oxo-2,3-dihydro-1H-pyrazol-4-yl]-4-(difluoromethoxy)benzamide | 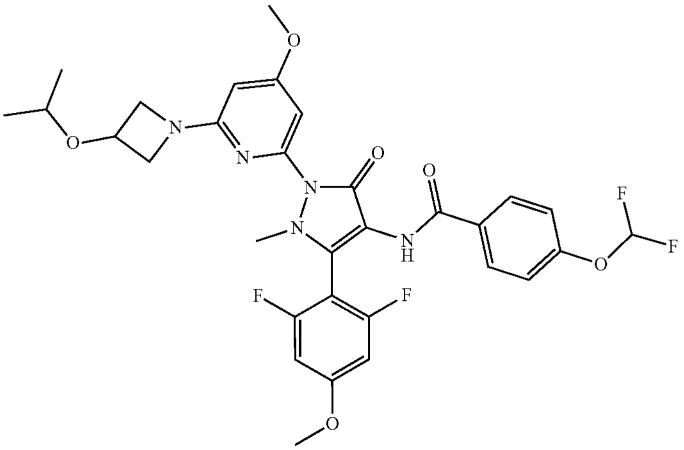 [SMILES: COc1cc(N2CC(OC(C)C)C2)nc(-n2c(=O)c(NC(=O)c3ccc(OC(F)F)cc3)c(-c3c(F)cc(OC)cc3F)n2C)c1] | 1.97 B 646.2 |

TABLE 2-continued

| $^1$H NMR data for the examples in Table 2: | | | |
|---|---|---|---|
| Ex. No. | Name | Structure | LC/MS Rt (min) Method M + H |
| 107 | N-[5-(2,6-difluoro-4-methoxyphenyl)-2-{6-[4-(2-hydroxyethyl)piperazin-1-yl]pyridin-2-yl}-1-methyl-3-oxo-2,3-dihydro-1H-pyrazol-4-yl]-4-(difluoromethoxy)benzamide | 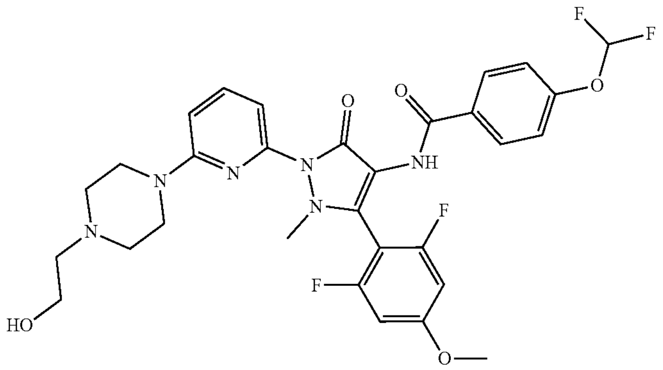 [SMILES: COc1cc(F)c(-c2c(NC(=O)c3ccc(OC(F)F)cc3)c(=O)n(-c3cccc(N4CCN(CCO)CC4)n3)n2C)c(F)c1] | 1.43 B 631.3 |
| 109 | N-[5-(2,6-difluoro-4-methoxyphenyl)-2-(3,5-dimethylphenyl)-1-methyl-3-oxo-2,3-dihydro-1H-pyrazol-4-yl]-4-(difluoromethoxy)benzamide | 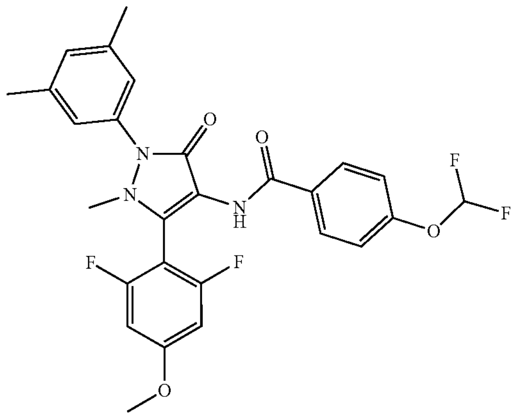 [SMILES: COc1cc(F)c(-c2c(NC(=O)c3ccc(OC(F)F)cc3)c(=O)n(-c3cc(C)cc(C)c3)n2C)c(F)c1] | 1.88 A 530.3 |
| 110 | N-[2-(3-cyanophenyl)-5-(2,6-difluoro-4-methoxyphenyl)-1-methyl-3-oxo-2,3-dihydro-1H-pyrazol-4-yl]-4-(difluoromethoxy)benzamide | 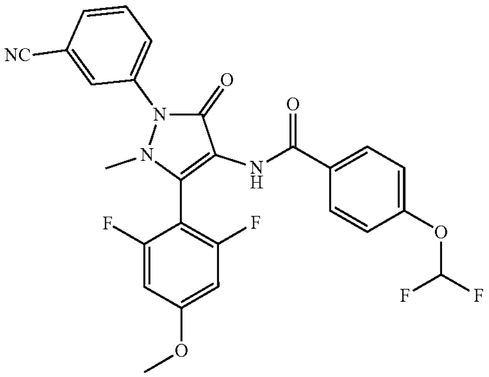 [SMILES: COc1cc(F)c(-c2c(NC(=O)c3ccc(OC(F)F)cc3)c(=O)n(-c3cccc(C#N)c3)n2C)c(F)c1] | 1.66 A 527.3 |
| 111 | N-[2-(3-cyclopropylphenyl)-5-(2,6-difluoro-4-methoxyphenyl)-1-methyl-3-oxo-2,3-dihydro-1H-pyrazol-4-yl]-4-(difluoromethoxy)benzamide | 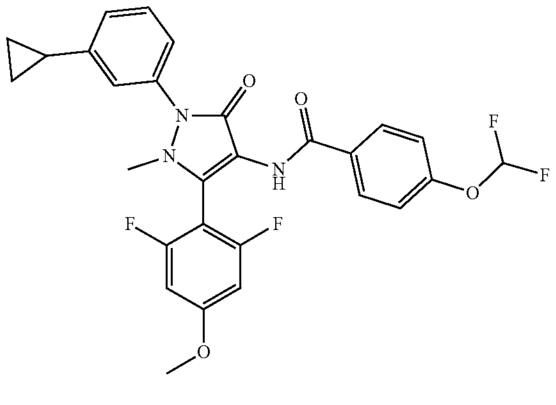 [SMILES: COc1cc(F)c(-c2c(NC(=O)c3ccc(OC(F)F)cc3)c(=O)n(-c3cccc(C4CC4)c3)n2C)c(F)c1] | 1.89 A 542.4 |

TABLE 2-continued

| $^1$H NMR data for the examples in Table 2: | | | |
|---|---|---|---|
| Ex. No. | Name | Structure | LC/MS Rt (min) Method M + H |
| 112 | N-[5-(2,6-difluoro-4-methoxyphenyl)-2-(3-methoxyphenyl)-1-methyl-3-oxo-2,3-dihydro-1H-pyrazol-4-yl]-4-(difluoromethoxy)benzamide | 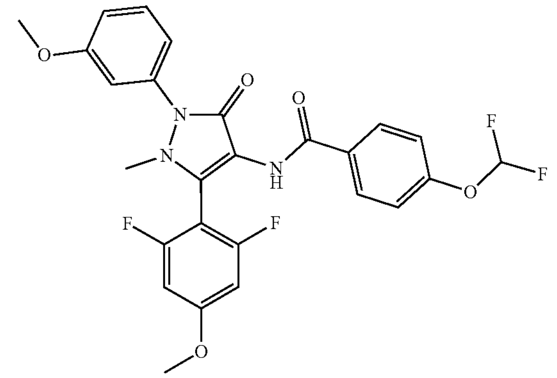 [SMILES: COc1cccc(-n2c(=O)c(NC(=O)c3ccc(OC(F)F)cc3)c(-c3c(F)cc(OC)cc3F)n2C)c1] | 1.75<br>A<br>532.3 |
| 113 | methyl 3-[3-(2,6-difluoro-4-methoxyphenyl)-4-[4-(difluoromethoxy)benzamido]-2-methyl-5-oxo-2,5-dihydro-1H-pyrazol-1-yl]benzoate | 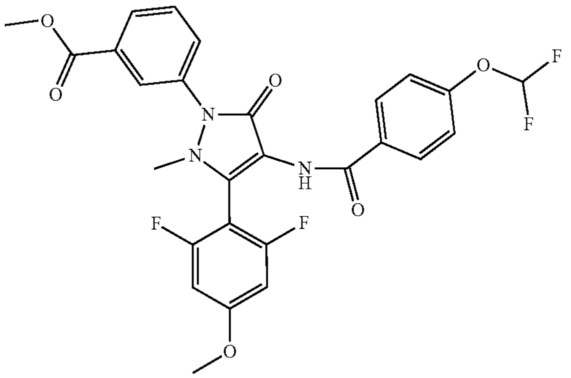 [SMILES: COC(=O)c1cccc(-n2c(=O)c(NC(=O)c3ccc(OC(F)F)cc3)c(-c3c(F)cc(OC)cc3F)n2C)c1] | 1.8<br>B<br>560.3 |
| 114 | N-[2-(3-chlorophenyl)-5-(2,6-difluoro-4-methoxyphenyl)-1-methyl-3-oxo-2,3-dihydro-1H-pyrazol-4-yl]-4-(difluoromethoxy)benzamide | 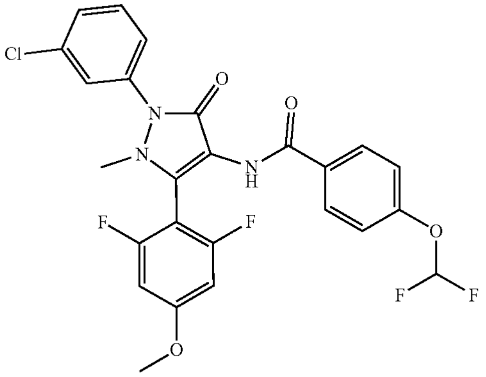 [SMILES: COc1cc(F)c(-c2c(NC(=O)c3ccc(OC(F)F)cc3)c(=O)n(-c3cccc(Cl)c3)n2C)c(F)c1] | 1.89<br>B<br>536.1 |
| 115 | N-[5-(2,6-difluoro-4-methoxyphenyl)-2-(2-methoxypyridin-4-yl)-1-methyl-3-oxo-2,3-dihydro-1H-pyrazol-4-yl]-4-(difluoromethoxy)benzamide | 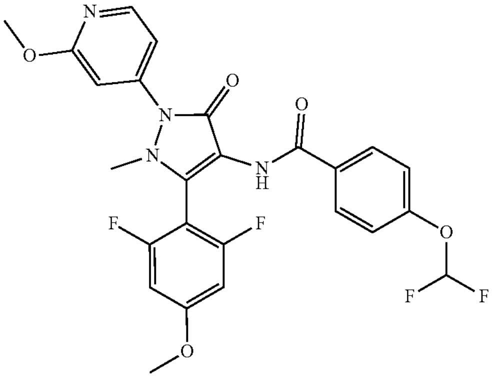 [SMILES: COc1cc(F)c(-c2c(NC(=O)c3ccc(OC(F)F)cc3)c(=O)n(-c3ccnc(OC)c3)n2C)c(F)c1] | 1.69<br>B<br>532.9 |

TABLE 2-continued

| $^1$H NMR data for the examples in Table 2: | | | |
|---|---|---|---|
| Ex. No. | Name | Structure | LC/MS Rt (min) Method M + H |
| 116 | N-[2-(2-chloropyridin-4-yl)-5-(2,6-difluoro-4-methoxyphenyl)-1-methyl-3-oxo-2,3-dihydro-1H-pyrazol-4-yl]-4-(difluoromethoxy)benzamide | 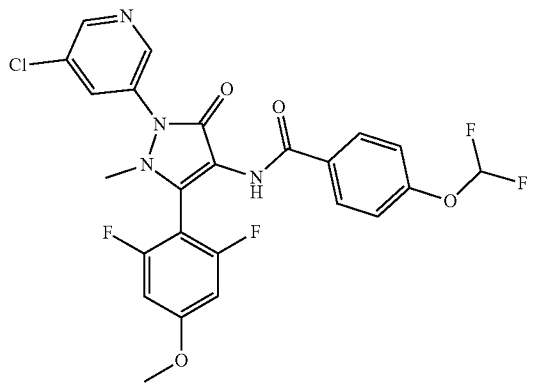 [SMILES: COc1cc(F)c(-c2c(NC(=O)c3ccc(OC(F)F)cc3)c(=O)n(-c3cncc(Cl)c3)n2C)c(F)c1] | 1.78 A 537.0 |
| 117 | N-[5-(2,6-difluoro-4-methoxyphenyl)-2-[3-methoxy-5-(trifluoromethyl)phenyl]-1-methyl-3-oxo-2,3-dihydro-1H-pyrazol-4-yl]-4-(difluoromethoxy)benzamide | 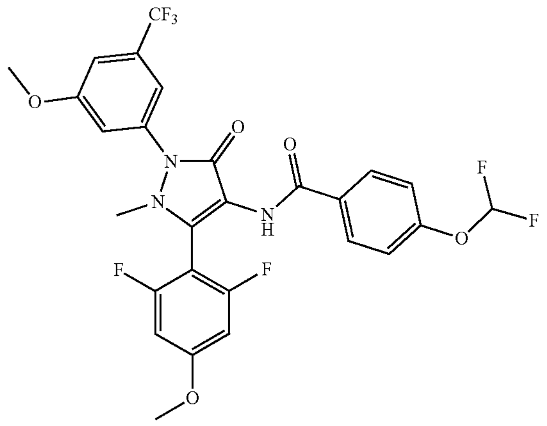 [SMILES: COc1cc(-n2c(=O)c(NC(=O)c3ccc(OC(F)F)cc3)c(-c3c(F)cc(OC)cc3F)n2C)cc(C(F)(F)F)c1] | 2.08 B 600.1 |
| 118 | N-[5-(2,6-difluoro-4-methoxyphenyl)-2-(3-ethoxyphenyl)-1-methyl-3-oxo-2,3-dihydro-1H-pyrazol-4-yl]-4-(difluoromethoxy)benzamide | 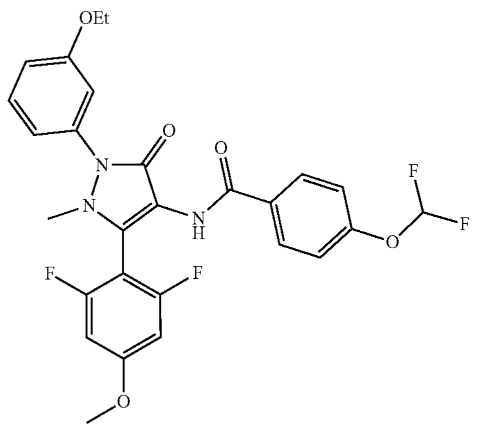 [SMILES: CCOc1cccc(-n2c(=O)c(NC(=O)c3ccc(OC(F)F)cc3)c(-c3c(F)cc(OC)cc3F)n2C)c1] | 1.92 A 545.9 |

TABLE 2-continued

| $^1$H NMR data for the examples in Table 2: | | | |
|---|---|---|---|
| Ex. No. | Name | Structure | LC/MS Rt (min) Method M + H |
| 119 | N-{2-[3-cyano-5-(propan-2-yl)phenyl]-5-(2,6-difluoro-4-methoxyphenyl)-1-methyl-3-oxo-2,3-dihydro-1H-pyrazol-4-yl}-4-(difluoromethoxy)benzamide | 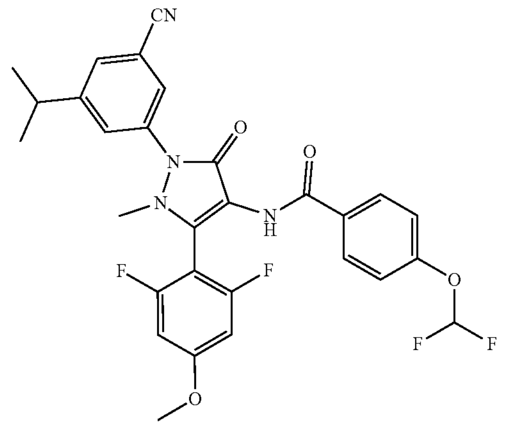 [SMILES: COc1cc(F)c(-c2c(NC(=O)c3ccc(OC(F)F)cc3)c(=O)n(-c3cc(C#N)cc(C(C)C)c3)n2C)c(F)c1] | 2.03 A 569.4 |
| 120 | methyl 3-chloro-5-[3-(2,6-difluoro-4-methoxyphenyl)-4-[4-(difluoromethoxy)benzamido]-2-methyl-5-oxo-2,5-dihydro-1H-pyrazol-1-yl]benzoate | 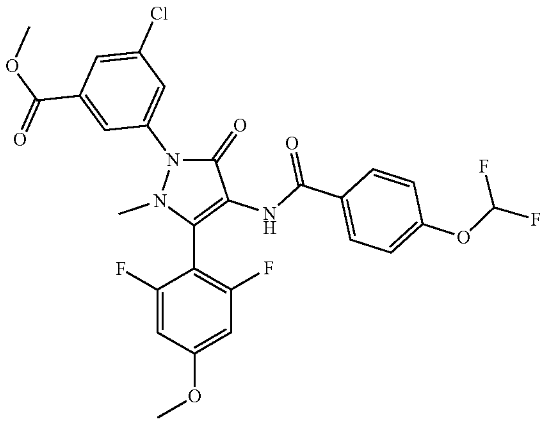 [SMILES: COC(=O)c1cc(Cl)cc(-n2c(=O)c(NC(=O)c3ccc(OC(F)F)cc3)c(-c3c(F)cc(OC)cc3F)n2C)c1] | 1.94 A 594.2 |
| 121 | N-[5-(2,6-difluoro-4-methoxyphenyl)-2-(3-methoxy-5-methylphenyl)-1-methyl-3-oxo-2,3-dihydro-1H-pyrazol-4-yl]-4-(difluoromethoxy)benzamide | 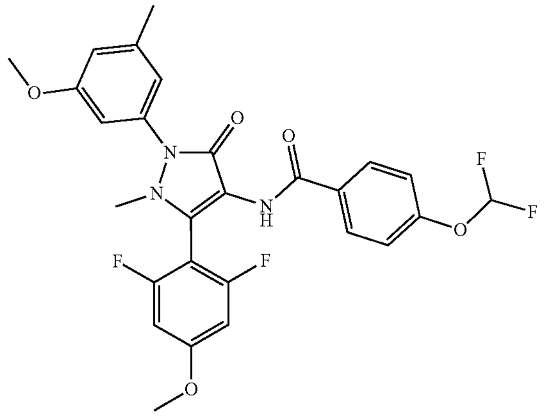 [SMILES: COc1cc(C)cc(-n2c(=O)c(NC(=O)c3ccc(OC(F)F)cc3)c(-c3c(F)cc(OC)cc3F)n2C)c1] | 1.90 A 546.3 |

TABLE 2-continued

$^1$H NMR data for the examples in Table 2:

| Ex. No. | Name | Structure | LC/MS Rt (min) Method M + H |
|---|---|---|---|
| 122 | N-[5-(2,6-difluoro-4-methoxyphenyl)-2-[3-ethoxy-5-(trifluoromethyl)phenyl]-1-methyl-3-oxo-2,3-dihydro-1H-pyrazol-4-yl]-4-(difluoromethoxy)benzamide | 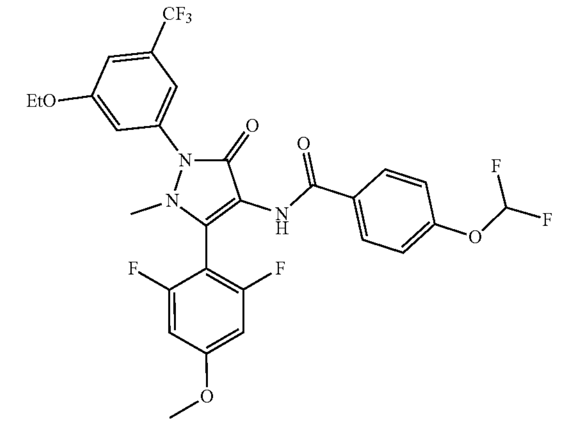 [SMILES: CCOc1cc(-n2c(=O)c(NC(=O)c3ccc(OC(F)F)cc3)c(-c3c(F)cc(OC)cc3F)n2C)cc(C(F)(F)F)c1] | 2.12<br>B<br>614.2 |
| 123 | N-{2-[3-chloro-5-(trifluoromethoxy)phenyl]-5-(2,6-difluoro-4-methoxyphenyl)-1-methyl-3-oxo-2,3-dihydro-1H-pyrazol-4-yl}-4-(difluoromethoxy)benzamide | 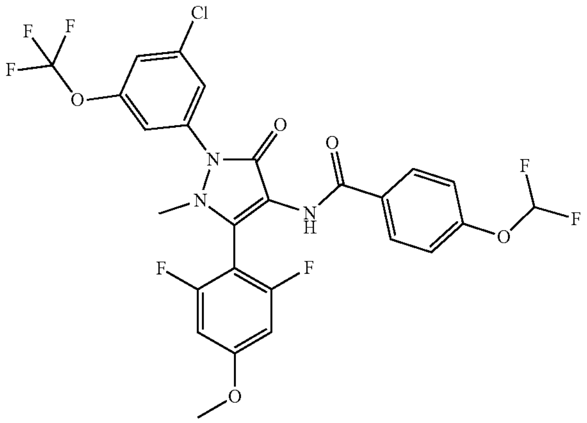 [SMILES: COc1cc(F)c(-c2c(NC(=O)c3ccc(OC(F)F)cc3)c(=O)n(-c3cc(Cl)cc(OC(F)(F)F)c3)n2C)c(F)c1] | 2.17<br>B<br>620.2 |
| 124 | N-[2-(3-chloro-5-methoxyphenyl)-5-(2,6-difluoro-4-methoxyphenyl)-1-methyl-3-oxo-2,3-dihydro-1H-pyrazol-4-yl]-4-(difluoromethoxy)benzamide | 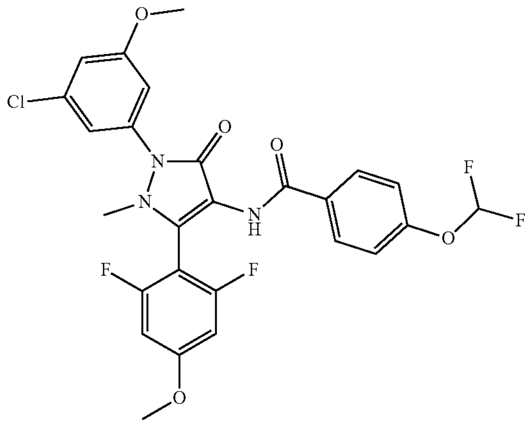 [SMILES: COc1cc(Cl)cc(-n2c(=O)c(NC(=O)c3ccc(OC(F)F)cc3)c(-c3c(F)cc(OC)cc3F)n2C)c1] | 1.92<br>A<br>566.3 |

TABLE 2-continued

| $^1$H NMR data for the examples in Table 2: | | | |
|---|---|---|---|
| Ex. No. | Name | Structure | LC/MS Rt (min) Method M + H |
| 125 | N-[5-(2,6-difluoro-4-methoxyphenyl)-2-[3-fluoro-5-(propan-2-yloxy)phenyl]-1-methyl-3-oxo-2,3-dihydro-1H-pyrazol-4-yl]-4-(difluoromethoxy)benzamide | 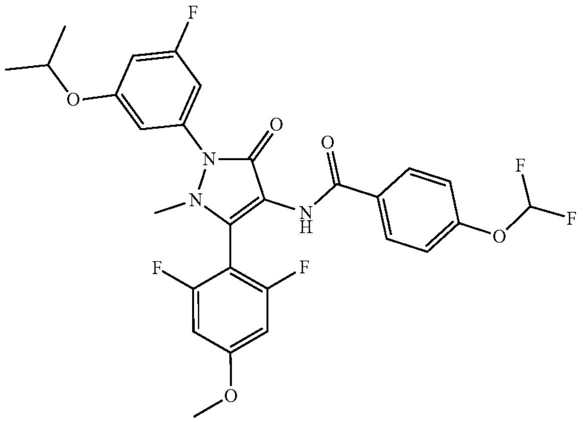 [SMILES: COc1cc(F)c(-c2c(NC(=O)c3ccc(OC(F)F)cc3)c(=O)n(-c3cc(F)cc(OC(C)C)c3)n2C)c(F)c1] | 2.03<br>A<br>578.3 |
| 126 | 3-chloro-5-[3-(2,6-difluoro-4-methoxyphenyl)-4-[4-(difluoromethoxy)benzamido]-2-methyl-5-oxo-2,5-dihydro-1H-pyrazol-1-yl]-N,N-dimethylbenzamide | 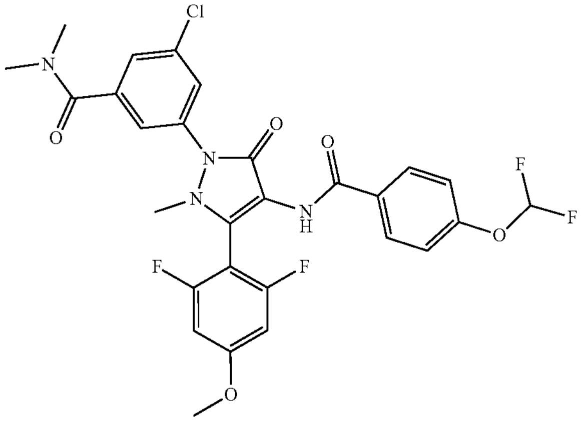 [SMILES: COc1cc(F)c(-c2c(NC(=O)c3ccc(OC(F)F)cc3)c(=O)n(-c3cc(Cl)cc(C(=O)N(C)C)c3)n2C)c(F)c1] | 1.71<br>A<br>607.3 |
| 127 | N-[2-(3,5-dichlorophenyl)-5-(2,6-difluoro-4-methoxyphenyl)-1-methyl-3-oxo-2,3-dihydro-1H-pyrazol-4-yl]-4-(difluoromethoxy)benzamide | 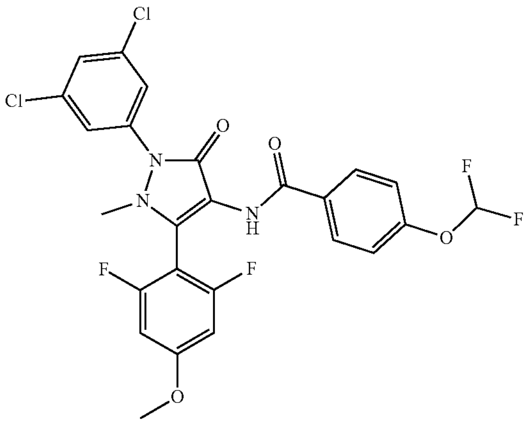 [SMILES: COc1cc(F)c(-c2c(NC(=O)c3ccc(OC(F)F)cc3)c(=O)n(-c3cc(Cl)cc(Cl)c3)n2C)c(F)c1] | 2.12<br>A<br>570.2 |

TABLE 2-continued

| Ex. No. | Name | Structure | LC/MS Rt (min) Method M + H |
|---|---|---|---|
| | $^1$H NMR data for the examples in Table 2: | | |
| 128 | methyl 5-[3-(2,6-difluoro-4-methoxyphenyl)-4-[4-(difluoromethoxy)benzamido]-2-methyl-5-oxo-2,3-dihydro-1H-pyrazol-1-yl]pyridine-3-carboxylate | 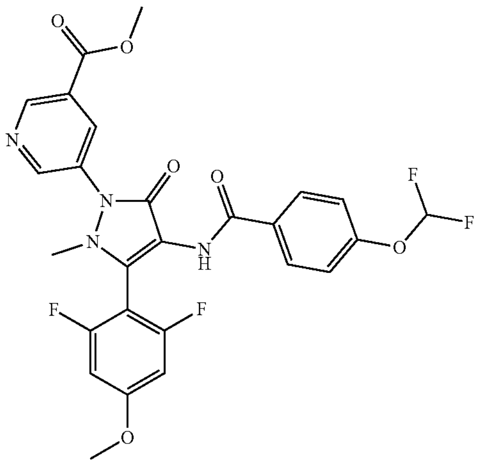 [SMILES: COC(=O)c1cncc(-n2c(=O)c(NC(=O)c3ccc(OC(F)F)cc3)c(-c3c(F)cc(OC)cc3F)n2C)c1] | 1.62<br>A<br>561.1 |
| 129 | N-[5-(2,6-difluoro-4-methoxyphenyl)-2-(5-methoxypyridin-3-yl)-1-methyl-3-oxo-2,3-dihydro-1H-pyrazol-4-yl]-4-(difluoromethoxy)benzamide | 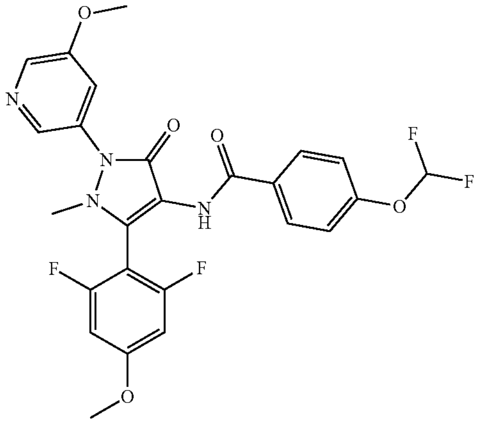 [SMILES: COc1cncc(-n2c(=O)c(NC(=O)c3ccc(OC(F)F)cc3)c(-c3c(F)cc(OC)cc3F)n2C)c1] | 1.56<br>A<br>533.3 |
| 130 | N-[2-(5-chloropyridin-3-yl)-5-(2,6-difluoro-4-methoxyphenyl)-1-methyl-3-oxo-2,3-dihydro-1H-pyrazol-4-yl]-4-(difluoromethoxy)benzamide | 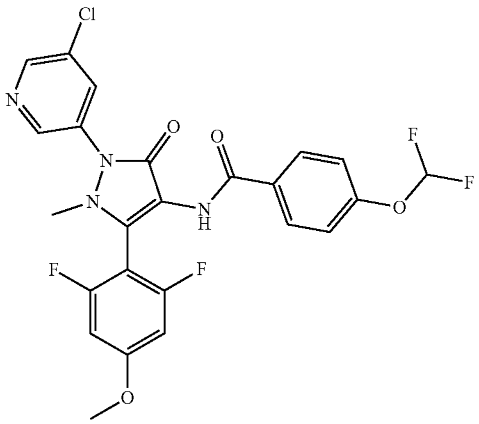 [SMILES: COc1cc(F)c(-c2c(NC(=O)c3ccc(OC(F)F)cc3)c(=O)n(-c3cncc(Cl)c3)n2C)c(F)c1] | 1.68<br>B<br>537.2 |

TABLE 2-continued

| $^1$H NMR data for the examples in Table 2: | | | |
|---|---|---|---|
| Ex. No. | Name | Structure | LC/MS Rt (min) Method M + H |
| 131 | N-{2-[3-chloro-5-(trifluoromethyl)phenyl]-5-(2,6-difluoro-4-methoxyphenyl)-1-methyl-3-oxo-2,3-dihydro-1H-pyrazol-4-yl}-4-(difluoromethoxy)benzamide | 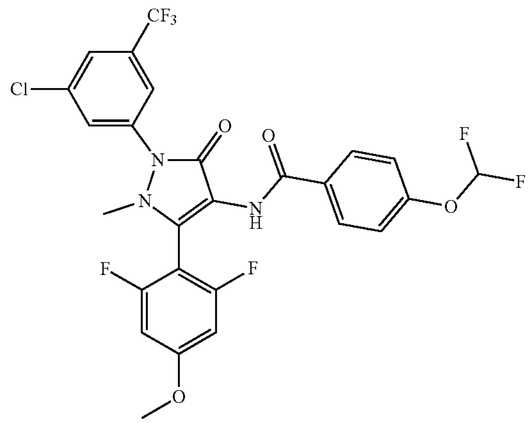 [SMILES: COc1cc(F)c(-c2c(NC(=O)c3ccc(OC(F)F)cc3)c(=O)n(-c3cc(Cl)cc(C(F)(F)F)c3)n2C)c(F)c1] | 2.17 A 604.2 |
| 132 | N-[5-(2,6-difluoro-4-methoxyphenyl)-2-(3-fluoro-5-methoxyphenyl)-1-methyl-3-oxo-2,3-dihydro-1H-pyrazol-4-yl]-4-(difluoromethoxy)benzamide | 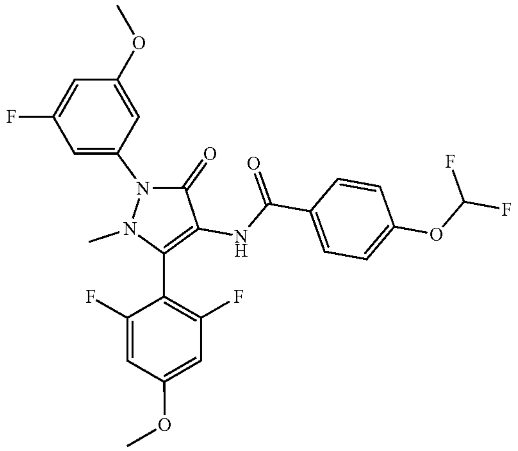 [SMILES: COc1cc(F)cc(-n2c(=O)c(NC(=O)c3ccc(OC(F)F)cc3)c(-c3c(F)cc(OC)cc3F)n2C)c1] | 1.88 B 550.2 |
| 133 | ethyl 3-[3-(2,6-difluoro-4-methoxyphenyl)-4-[4-(difluoromethoxy)benzamido]-2-methyl-5-oxo-2,5-dihydro-1H-pyrazol-1-yl]-5-fluorobenzoate | 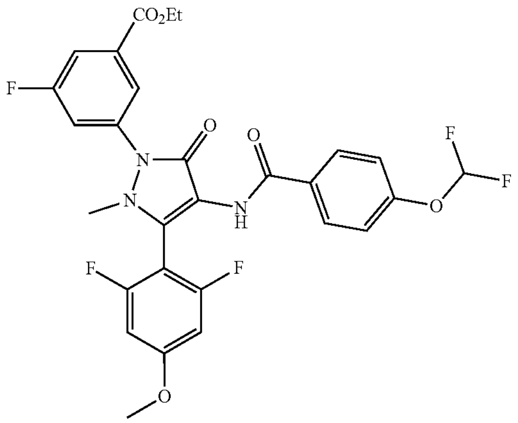 [SMILES: CCOC(=O)c1cc(F)cc(-n2c(=O)c(NC(=O)c3ccc(OC(F)F)cc3)c(-c3c(F)cc(OC)cc3F)n2C)c1] | 1.91 A 592.2 |

TABLE 2-continued $^1$H NMR data for the examples in Table 2:

| Ex. No. | Name | Structure | LC/MS Rt (min) Method M + H |
|---|---|---|---|
| 134 | N-[2-(3-chloro-5-methylphenyl)-5-(2,6-difluoro-4-methoxyphenyl)-1-methyl-3-oxo-2,3-dihydro-1H-pyrazol-4-yl]-4-(difluoromethoxy)benzamide | 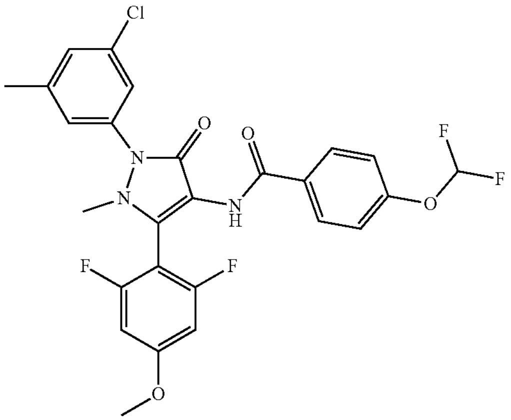 [SMILES: COc1cc(F)c(-c2c(NC(=O)c3ccc(OC(F)F)cc3)c(=O)n(-c3cc(C)cc(Cl)c3)n2C)c(F)c1] | 2.05 A 550.3 |
| 136 | N-[5-(2,6-difluoro-4-methoxyphenyl)-2-[6-(dimethylamino)-3-(trifluoromethyl)pyridin-2-yl]-1-methyl-3-oxo-2,3-dihydro-1H-pyrazol-4-yl]-4-(difluoromethoxy)benzamide | 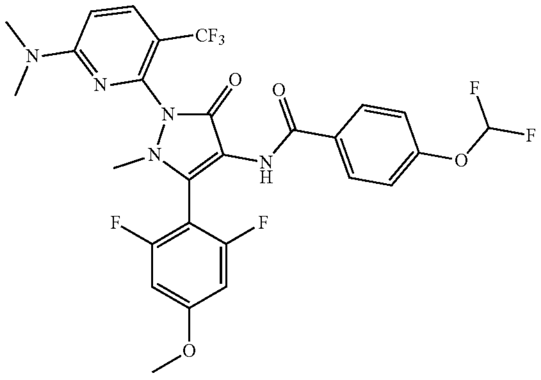 [SMILES: COc1cc(F)c(-c2c(NC(=O)c3ccc(OC(F)F)cc3)c(=O)n(-c3nc(N(C)C)ccc3C(F)(F)F)n2C)c(F)c1] | 1.91 A 614 |
| 137 | N-[5-(2,6-difluoro-4-methoxyphenyl)-1-methyl-2-(6-{3-methyl-3,8-diazabicyclo[3.2.1]octan-8-yl}-3-(trifluoromethyl)pyridin-2-yl)-3-oxo-2,3-dihydro-1H-pyrazol-4-yl]-4-(difluoromethoxy)benzamide | 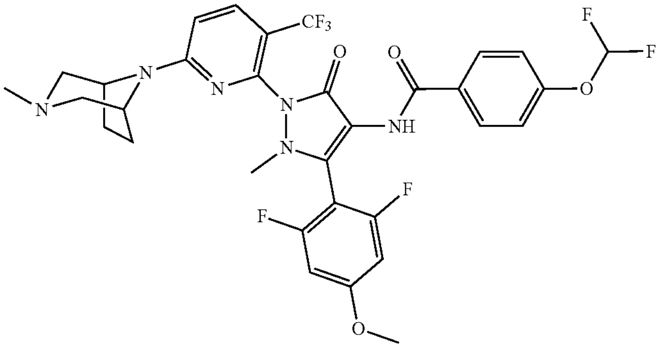 [SMILES: COc1cc(F)c(-c2c(NC(=O)c3ccc(OC(F)F)cc3)c(=O)n(-c3nc(N4C5CCC4CN(C)C5)ccc3C(F)(F)F)n2C)c(F)c1] | 1.54 A 695.3 |
| 138 | N-[5-(2,6-difluoro-4-methoxyphenyl)-2-[6-(3-hydroxy-3-methylazetidin-1-yl)-3-(trifluoromethyl)pyridin-2-yl]-1-methyl-3-oxo-2,3-dihydro-1H-pyrazol-4-yl]-4-(difluoromethoxy)benzamide | 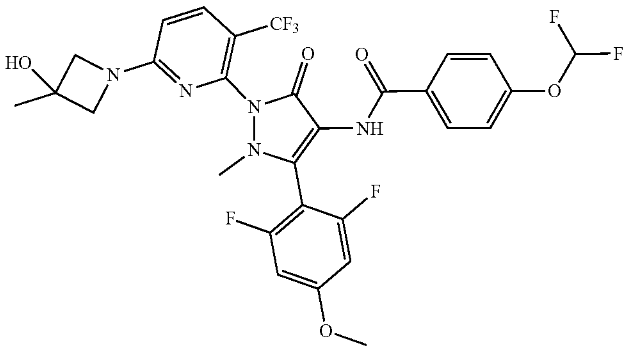 [SMILES: COc1cc(F)c(-c2c(NC(=O)c3ccc(OC(F)F)cc3)c(=O)n(-c3nc(N4CC(C)(O)C4)ccc3C(F)(F)F)n2C)c(F)c1] | 1.73 A 656.1 |

TABLE 2-continued

| $^1$H NMR data for the examples in Table 2: | | | |
|---|---|---|---|
| Ex. No. | Name | Structure | LC/MS Rt (min) Method M + H |
| 139 | N-(2-{6-[bis(2-hydroxyethyl)amino]-3-(trifluoromethyl)pyridin-2-yl}-5-(2,6-difluoro-4-methoxyphenyl)-1-methyl-3-oxo-2,3-dihydro-1H-pyrazol-4-yl)-4-(difluoromethoxy)benzamide | 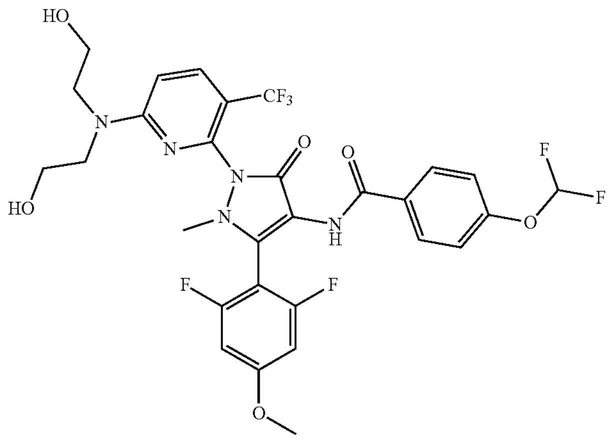 [SMILES: COc1cc(F)c(-c2c(NC(=O)c3ccc(OC(F)F)cc3)c(=O)n(-c3nc(N(CCO)CCO)ccc3C(F)(F)F)n2C)c(F)c1] | 1.69 B 674.2 |
| 140 | N-[5-(2,6-difluoro-4-methoxyphenyl)-1-methyl-3-oxo-2-{6-[3-(propan-2-yloxy)azetidin-1-yl]-3-(trifluoromethyl)pyridin-2-yl}-2,3-dihydro-1H-pyrazol-4-yl]-4-(difluoromethoxy)benzamide | 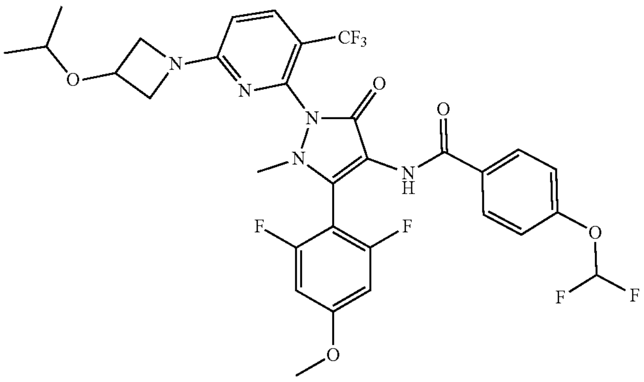 [SMILES: COc1cc(F)c(-c2c(NC(=O)c3ccc(OC(F)F)cc3)c(=O)n(-c3nc(N4CC(OC(C)C)C4)ccc3C(F)(F)F)n2C)c(F)c1] | 2.05 A 684.1 |
| 141 | 4-chloro-N-[5-(2,6-difluoro-4-methoxyphenyl)-1-methyl-3-oxo-2-{6-[3-(propan-2-yloxy)azetidin-1-yl]-3-(trifluoromethyl)pyridin-2-yl}-2,3-dihydro-1H-pyrazol-4-yl]benzamide | 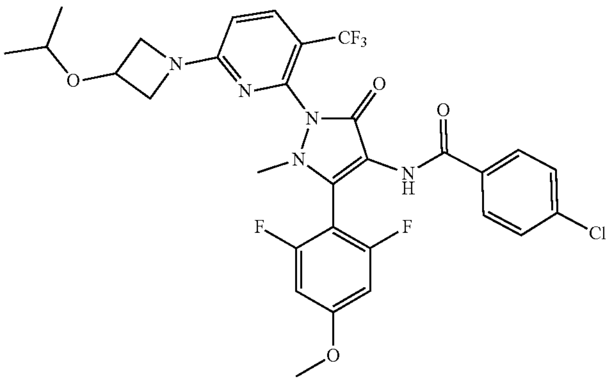 [SMILES: COc1cc(F)c(-c2c(NC(=O)c3ccc(Cl)cc3)c(=O)n(-c3nc(N4CC(OC(C)C)C4)ccc3C(F)(F)F)n2C)c(F)c1] | 2.07 A 652.1 |

TABLE 2-continued

| $^1$H NMR data for the examples in Table 2: | | | |
|---|---|---|---|
| Ex. No. | Name | Structure | LC/MS Rt (min) Method M + H |
| 142 | N-[5-(2,6-difluoro-4-methoxyphenyl)-2-[3-(dimethylamino)pyridin-2-yl]-1-methyl-3-oxo-2,3-dihydro-1H-pyrazol-4-yl]-4-(difluoromethoxy)benzamide | 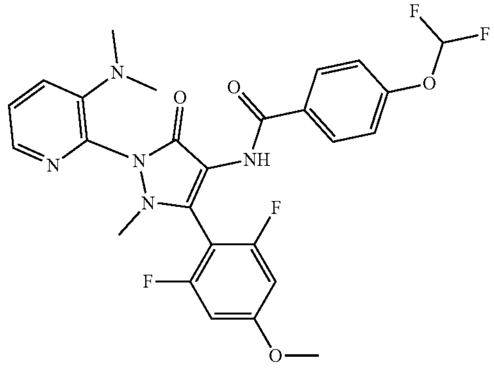 [SMILES: COc1cc(F)c(-c2c(NC(=O)c3ccc(OC(F)F)cc3)c(=O)n(-c3ncccc3N(C)C)n2C)c(F)c1] | 7.77<br>D<br>545.7 |
| 143 | N-{2-[3-chloro-6-(4-methylpiperazin-1-yl)pyridin-2-yl]-5-(2,6-difluoro-4-methoxyphenyl)-1-methyl-3-oxo-2,3-dihydro-1H-pyrazol-4-yl}-4-(difluoromethoxy)benzamide | 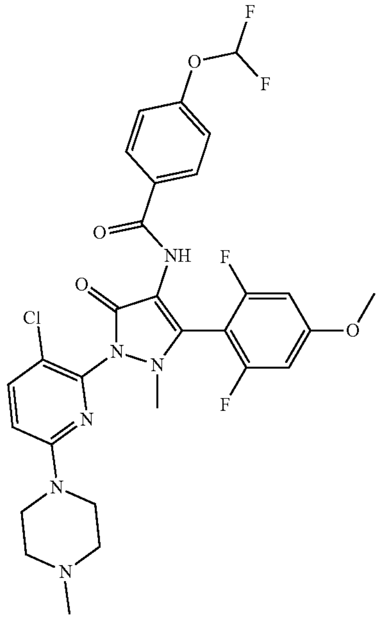 [SMILES: COc1cc(F)c(-c2c(NC(=O)c3ccc(OC(F)F)cc3)c(=O)n(-c3nc(N4CCN(C)CC4)ccc3Cl)n2C)c(F)c1] | 1.70<br>A<br>635.2 |
| 144 | N-[2-(6-chloro-3-{2-oxa-6-azaspiro[3.3]heptan-6-yl}pyridin-2-yl)-5-(2,6-difluoro-4-methoxyphenyl)-1-methyl-3-oxo-2,3-dihydro-1H-pyrazol-4-yl]-4-(difluoromethoxy)benzamide | 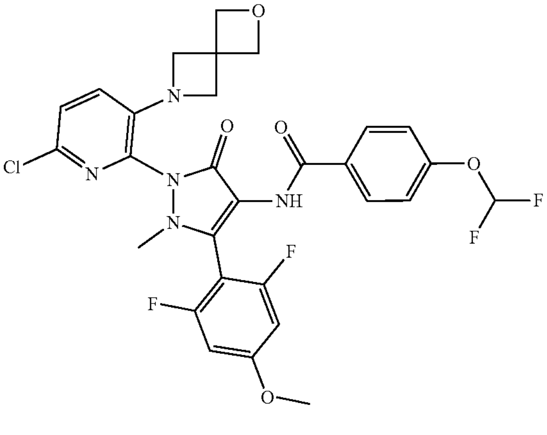 [SMILES: COc1cc(F)c(-c2c(NC(=O)c3ccc(OC(F)F)cc3)c(=O)n(-c3nc(Cl)ccc3N3CC4(COC4)C3)n2C)c(F)c1] | 1.72<br>B<br>634.1 |

TABLE 2-continued

| $^1$H NMR data for the examples in Table 2: | | | |
|---|---|---|---|
| Ex. No. | Name | Structure | LC/MS Rt (min) Method M + H |
| 145 | N-{2-[3-chloro-6-(3,3-difluoroazatidin-1-yl)pyridin-4-methoxyphenyl)-1-methyl-3-oxo-2,3-dihydro-1H-pyrazol-4-yl}-4-(difluoromethoxy)benzamide | 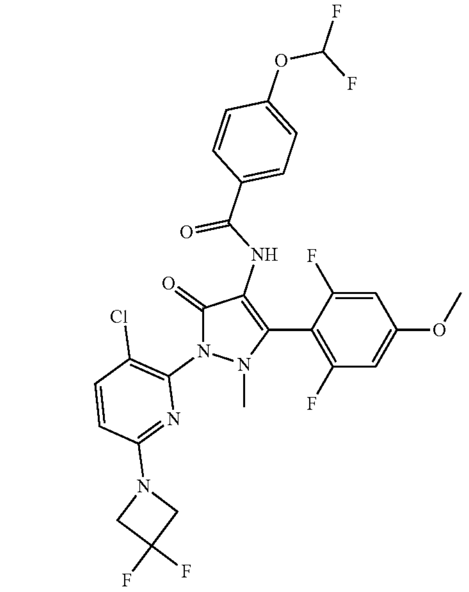 [SMILES: COc1cc(F)c(-c2c(NC(=O)c3ccc(OC(F)F)cc3)c(=O)n(-c3nc(N4CC(F)(F)C4)ccc3Cl)n2C)c(F)c1] | 1.96 A 627.9 |
| 146 | N-[2-(6-chloro-3-fluoropyridin-2-yl)-5-(2,6-difluoro-4-methoxyphenyl)-1-methyl-3-oxo-2,3-dihydro-1H-pyrazol-4-yl]-4-(difluoromethoxy)benzamide | 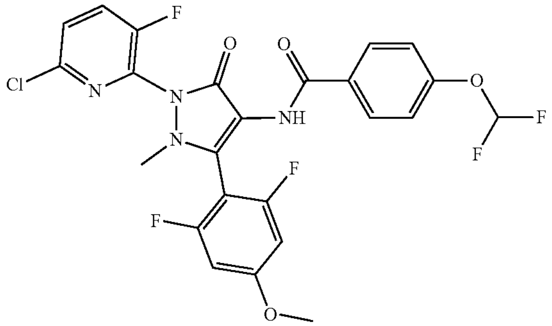 [SMILES: COc1cc(F)c(-c2c(NC(=O)c3ccc(OC(F)F)cc3)c(=O)n(-c3nc(Cl)ccc3F)n2C)c(F)c1] | 8.39 D 554.9 |
| 147 | N-{2-[3-chloro-6-(dimethylamino)pyridin-2-yl]-5-(2,6-difluoro-4-methoxyphenyl)-1-methyl-3-oxo-2,3-dihydro-1H-pyrazol-4-yl}-4-(difluoromethoxy)benzamide | 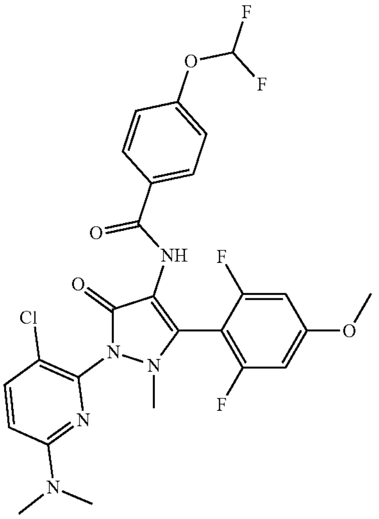 [SMILES: COc1cc(F)c(-c2c(NC(=O)c3ccc(OC(F)F)cc3)c(=O)n(-c3nc(N(C)C)ccc3Cl)n2C)c(F)c1] | 1.87 A 580.2 |

TABLE 2-continued

| $^1$H NMR data for the examples in Table 2: | | | |
|---|---|---|---|
| Ex. No. | Name | Structure | LC/MS Rt (min) Method M + H |
| 148 | N-[5-(2,6-difluoro-4-methoxyphenyl)-2-[3-fluoro-5-(2-hydroxypropan-2-yl)phenyl]-1-methyl-3-oxo-2,3-dihydro-1H-pyrazol-4-yl]-4-(difluoromethoxy)benzamide | 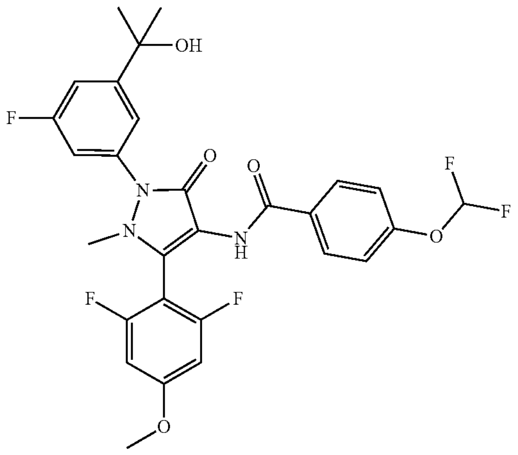 [SMILES: COc1cc(F)c(-c2c(NC(=O)c3ccc(OC(F)F)cc3)c(=O)n(-c3cc(F)cc(C(C)(C)O)c3)n2C)c(F)c1] | 1.83 A 578.3 |
| 149 | N-(2-{3-chloro-5-[(1R,4R)-2,5-diazabicyclo[2.2.1]heptan-2-yl]phenyl}-5-(2,6-difluoro-4-methoxyphenyl)-1-methyl-3-oxo-2,3-dihydro-1H-pyrazol-4-yl)-4-(difluoromethoxy)benzamide | 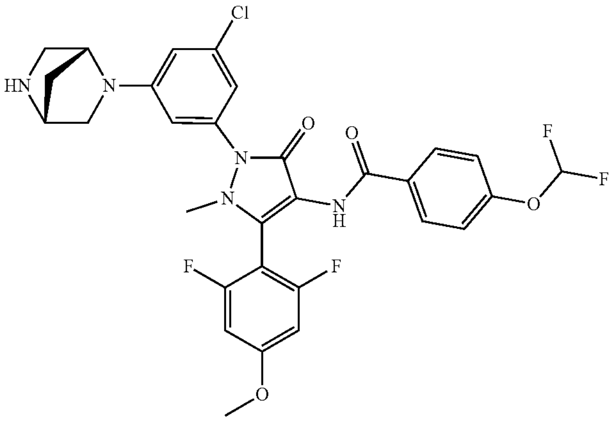 [SMILES: COc1cc(F)c(-c2c(NC(=O)c3ccc(OC(F)F)cc3)c(=O)n(-c3cc(Cl)cc(N4C[C@H]5C[C@@H]4CN5)c3)n2C)c(F)c1] | 1.62 A 632.3 |
| 150 | N-[5-(2,6-difluoro-4-methoxyphenyl)-1-methyl-3-oxo-2-[6-(2-oxopiperidin-1-yl)pyridin-2-yl]-2,3-dihydro-1H-pyrazol-4-yl]-4-(difluoromethoxy)benzamide | 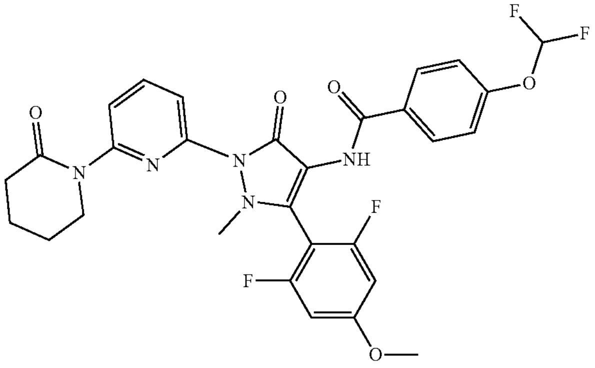 [SMILES: COc1cc(F)c(-c2c(NC(=O)c3ccc(OC(F)F)cc3)c(=O)n(-c3cccc(N4CCCCC4=O)n3)n2C)c(F)c1] | 1.75 A 600.3 |

TABLE 2-continued $^{1}$H NMR data for the examples in Table 2:

| Ex. No. | Name | Structure | LC/MS Rt (min) Method M + H |
|---|---|---|---|
| 151 | N-[5-(2,6-difluoro-4-methoxyphenyl)-1-methyl-2-(4-methylpyridin-2-yl)-3-oxo-2,3-dihydro-1H-pyrazol-4-yl]-4-(trifluoromethoxy)benzamide | 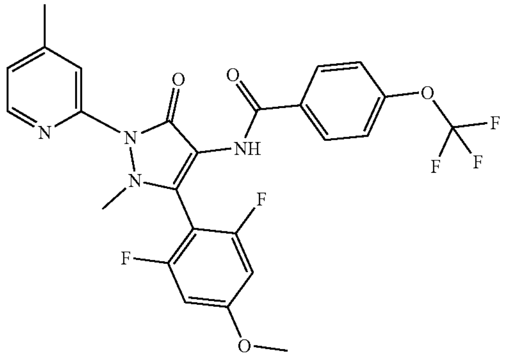 [SMILES: COc1cc(F)c(-c2c(NC(=O)c3ccc(OC(F)(F)F)cc3)c(=O)n(-c3cc(C)ccn3)n2C)c(F)c1] | 8.90<br>D<br>535.1 |
| 152 | N-[2-(4-chloropyridin-2-yl)-5-(2,6-difluoro-4-methoxyphenyl)-1-methyl-3-oxo-2,3-dihydro-1H-pyrazol-4-yl]-4-(difluoromethoxy)benzamide | 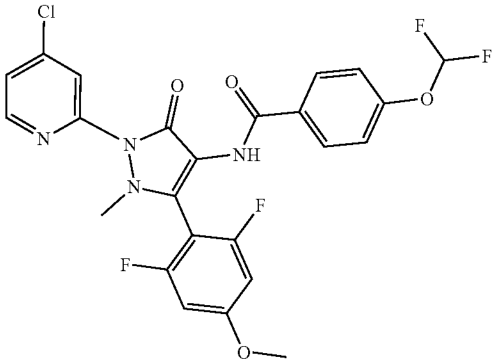 [SMILES: COc1cc(F)c(-c2c(NC(=O)c3ccc(OC(F)F)cc3)c(=O)n(-c3cc(Cl)ccn3)n2C)c(F)c1] | 8.84<br>D<br>537.1 |
| 153 | N-[2-(4-chloropyridin-2-yl)-5-(2,6-difluoro-4-methoxyphenyl)-1-methyl-3-oxo-2,3-dihydro-1H-pyrazol-4-yl]-4-(trifluoromethoxy)benzamide | 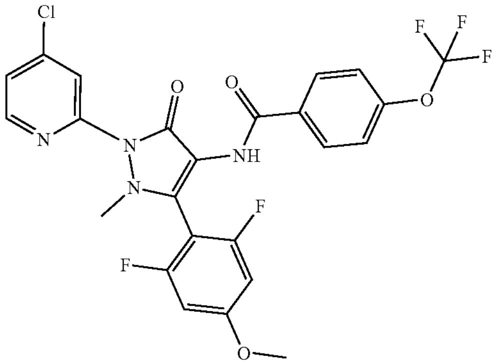 [SMILES: COc1cc(F)c(-c2c(NC(=O)c3ccc(OC(F)(F)F)cc3)c(=O)n(-c3cc(Cl)ccn3)n2C)c(F)c1] | 555.2<br>D<br>9.32 |
| 154 | N-[5-(2,6-difluoro-4-methoxyphenyl)-1-methyl-3-oxo-2-[3-(trifluoromethyl)pyridin-2-yl]-2,3-dihydro-1H-pyrazol-4-yl]-4-(trifluoromethoxy)benzamide | 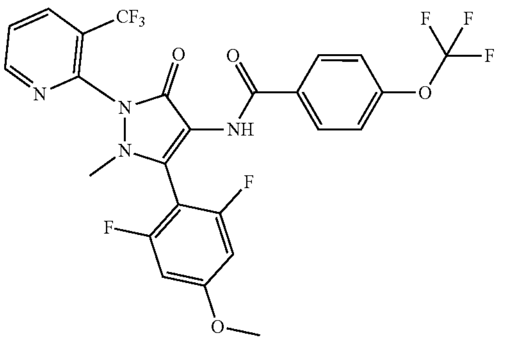 [SMILES: COc1cc(F)c(-c2c(NC(=O)c3ccc(OC(F)(F)F)cc3)c(=O)n(-c3ncccc3C(F)(F)F)n2C)c(F)c1] | 1.87<br>A<br>589.5 |

TABLE 2-continued

$^1$H NMR data for the examples in Table 2:

| Ex. No. | Name | Structure | LC/MS Rt (min) Method M + H |
|---|---|---|---|
| 155 | N-[5-(2,6-difluoro-4-methoxyphenyl)-1-methyl-3-oxo-2-[6-(trifluoromethyl)pyridin-2-yl]-2,3-dihydro-1H-pyrazol-4-yl]-4-(trifluoromethoxy)benzamide | 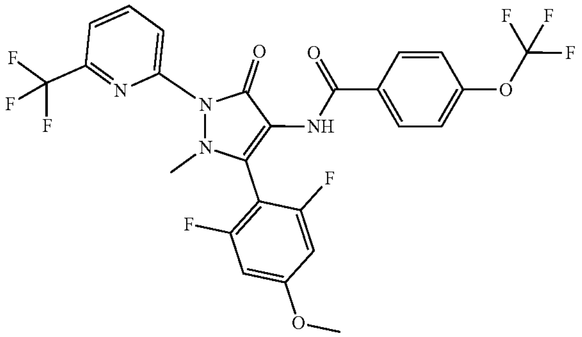 [SMILES: COc1cc(F)c(-c2c(NC(=O)c3ccc(OC(F)(F)F)cc3)c(=O)n(-c3cccc(C(F)(F)F)n3)n2C)c(F)c1] | 2.14<br>A<br>589.3 |
| 156 | N-[5-(2,6-difluoro-4-methoxyphenyl)-1-methyl-3-oxo-2-[6-(trifluoromethyl)pyridin-2-yl]-2,3-dihydro-1H-pyrazol-4-yl]-4-(difluoromethoxy)benzamide | 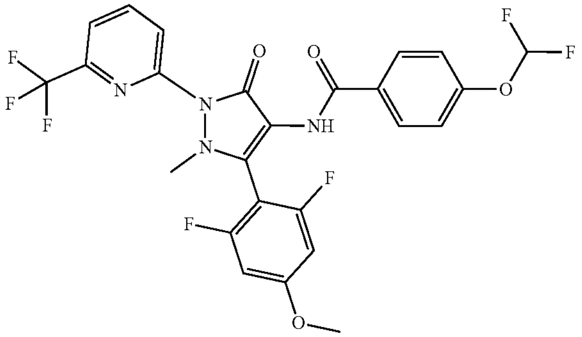 [SMILES: COc1cc(F)c(-c2c(NC(=O)c3ccc(OC(F)F)cc3)c(=O)n(-c3cccc(C(F)(F)F)n3)n2C)c(F)c1] | 1.92<br>A<br>571.2 |
| 157 | N-{2-[3-cyano-6-(trifluoromethyl)pyridin-2-yl]-5-(2,6-difluoro-4-methoxyphenyl)-1-methyl-3-oxo-2,3-dihydro-1H-pyrazol-4-yl}-4-(difluoromethoxy)benzamide | 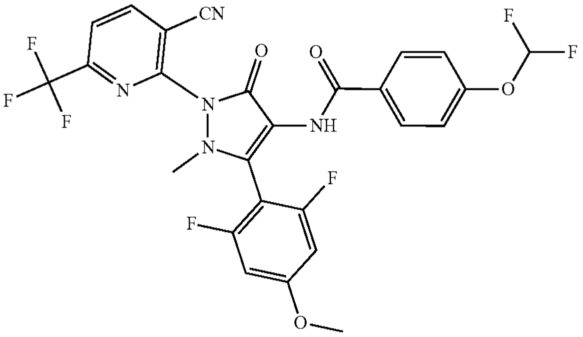 [SMILES: COc1cc(F)c(-c2c(NC(=O)c3ccc(OC(F)F)cc3)c(=O)n(-c3nc(C(F)(F)F)ccc3C#N)n2C)c(F)c1] | 1.96<br>A<br>596.3 |
| 158 | N-[5-(2,6-difluoro-4-methoxyphenyl)-2-[3-(difluoromethoxy)pyridin-2-yl]-1-methyl-3-oxo-2,3-dihydro-1H-pyrazol-4-yl]-4-(difluoromethoxy)benzamide | 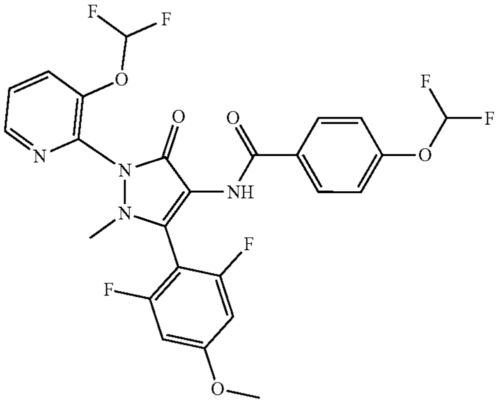 [SMILES: COc1cc(F)c(-c2c(NC(=O)c3ccc(OC(F)F)cc3)c(=O)n(-c3ncccc3OC(F)F)n2C)c(F)c1] | 1.62<br>A<br>569.0 |

TABLE 2-continued

| $^1$H NMR data for the examples in Table 2: | | | |
|---|---|---|---|
| Ex. No. | Name | Structure | LC/MS Rt (min) Method M + H |
| 159 | N-{2-[3-bromo-6-(trifluoromethyl)pyridin-2-yl]-5-(2,6-difluoro-4-methoxyphenyl)-1-methyl-3-oxo-2,3-dihydro-1H-pyrazol-4-yl}-4-(difluoromethoxy)benzamide | 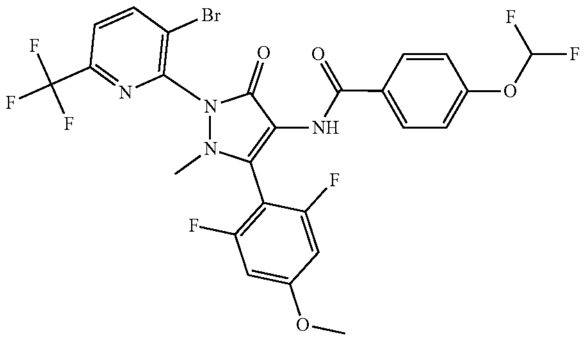 [SMILES: COc1cc(F)c(-c2c(NC(=O)c3ccc(OC(F)F)cc3)c(=O)n(-c3nc(C(F)(F)F)ccc3Br)n2C)c(F)c1] | 0.92 C 649.0 |
| 160 | N-[2-(3-bromo-6-cyclopropylpyridin-2-yl)-5-(2,6-difluoro-4-methoxyphenyl)-1-methyl-3-oxo-2,3-dihydro-1H-pyrazol-4-yl]-4-(difluoromethoxy)benzamide | 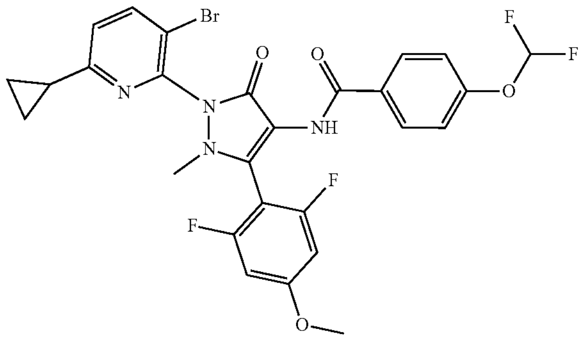 [SMILES: COc1cc(F)c(-c2c(NC(=O)c3ccc(OC(F)F)cc3)c(=O)n(-c3nc(C4CC4)ccc3Br)n2C)c(F)c1] | 0.89 C 621.2 |
| 161 | N-[2-(3-cyano-6-cyclopropylpyridin-2-yl)-5-(2,6-difluoro-4-methoxyphenyl)-1-methyl-3-oxo-2,3-dihydro-1H-pyrazol-4-yl]-4-(difluoromethoxy)benzamide | 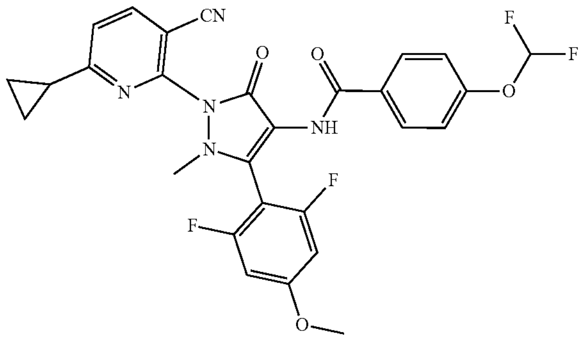 [SMILES: COc1cc(F)c(-c2c(NC(=O)c3ccc(OC(F)F)cc3)c(=O)n(-c3nc(C4CC4)ccc3C#N)n2C)c(F)c1] | 0.88 C 568.2 |
| 162 | N-[5-(2,6-difluoro-4-methoxyphenyl)-2-[4-methoxy-6-(trifluoromethyl)pyridin-2-yl]-1-methyl-3-oxo-2,3-dihydro-1H-pyrazol-4-yl]-4-(difluoromethoxy)benzamide | 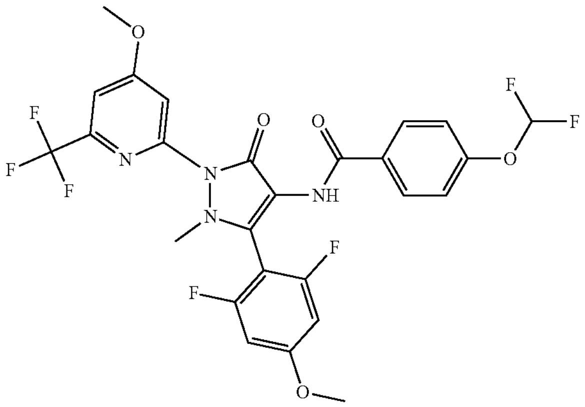 [SMILES: COc1cc(-n2c(=O)c(NC(=O)c3ccc(OC(F)F)cc3)c(-c3c(F)cc(OC)cc3F)n2C)nc(C(F)(F)F)c1] | |

TABLE 2-continued

| $^{1}$H NMR data for the examples in Table 2: | | | |
|---|---|---|---|
| Ex. No. | Name | Structure | LC/MS Rt (min) Method M + H |
| 163 | N-[5-(2,6-difluoro-4-methoxyphenyl)-2-(6-ethylpyridin-2-yl)-1-methyl-3-oxo-2,3-dihydro-1H-pyrazol-4-yl]-4-(difluoromethoxy)benzamide | 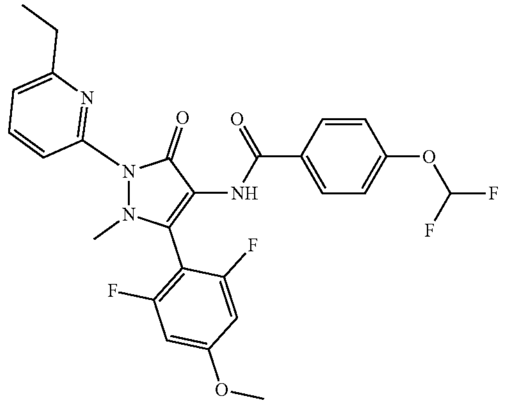 [SMILES: CCc1cccc(-n2c(=O)c(NC(=O)c3ccc(OC(F)F)cc3)c(-c3c(F)cc(OC)cc3F)n2C)n1] | 1.90<br>A<br>531.1 |
| 164 | 4-chloro-N-[2-(3-chloropyridin-2-yl)-5-(2,6-difluoro-4-methoxyphenyl)-1-methyl-3-oxo-2,3-dihydro-1H-pyrazol-4-yl]benzamide | 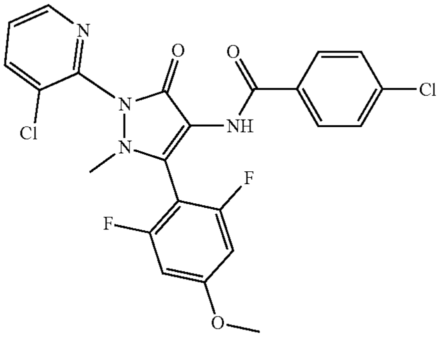 [SMILES: COc1cc(F)c(-c2c(NC(=O)c3ccc(Cl)cc3)c(=O)n(-c3ncccc3Cl)n2C)c(F)c1] | 1.61<br>A<br>505.3 |
| 165 | N-[2-(3-bromopyridin-2-yl)-5-(2,6-difluoro-4-methoxyphenyl)-1-methyl-3-oxo-2,3-dihydro-1H-pyrazol-4-yl]-4-(difluoromethoxy)benzamide | 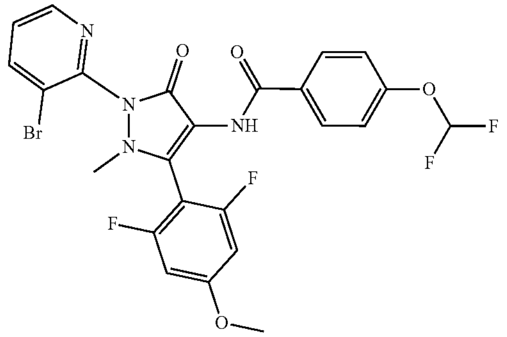 [SMILES: COc1cc(F)c(-c2c(NC(=O)c3ccc(OC(F)F)cc3)c(=O)n(-c3ncccc3Br)n2C)c(F)c1] | 1.65<br>B<br>582.2 |
| 166 | N-[5-(2,6-difluoro-4-methoxyphenyl)-2-(3-ethylpyridin-2-yl)-1-methyl-3-oxo-2,3-dihydro-1H-pyrazol-4-yl]-4-(difluoromethoxy)benzamide | 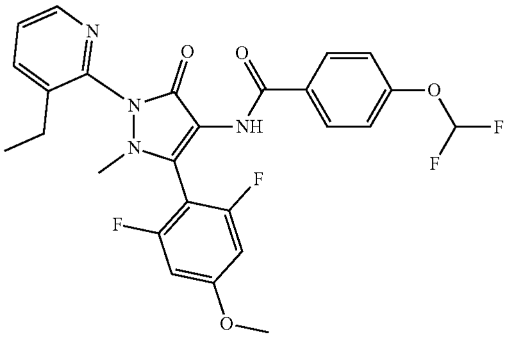 [SMILES: CCc1cccnc1-n1c(=O)c(NC(=O)c2ccc(OC(F)F)cc2)c(-c2c(F)cc(OC)cc2F)n1C] | 1.62<br>A<br>530.9 |

TABLE 2-continued

| $^1$H NMR data for the examples in Table 2: | | | |
|---|---|---|---|
| Ex. No. | Name | Structure | LC/MS Rt (min) Method M + H |
| 167 | N-[2-(6-cyclopropylpyridin-2-yl)-5-(2,6-difluoro-4-methoxyphenyl)-1-methyl-3-oxo-2,3-dihydro-1H-pyrazol-4-yl]-4-(trifluoromethoxy)benzamide | 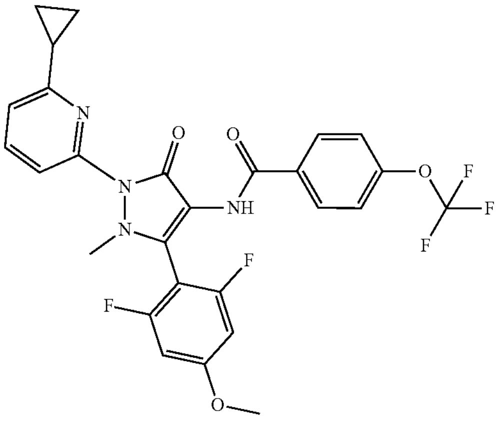 [SMILES: COc1cc(F)c(-c2c(NC(=O)c3ccc(OC(F)(F)F)cc3)c(=O)n(-c3cccc(C4CC4)n3)n2C)c(F)c1] | 2.05<br>B<br>561.3 |
| 168 | N-[5-(2,6-difluoro-4-methoxyphenyl)-2-[6-(difluoromethoxy)pyridin-2-yl]-1-methyl-3-oxo-2,3-dihydro-1H-pyrazol-4-yl]-4-(difluoromethoxy)benzamide | 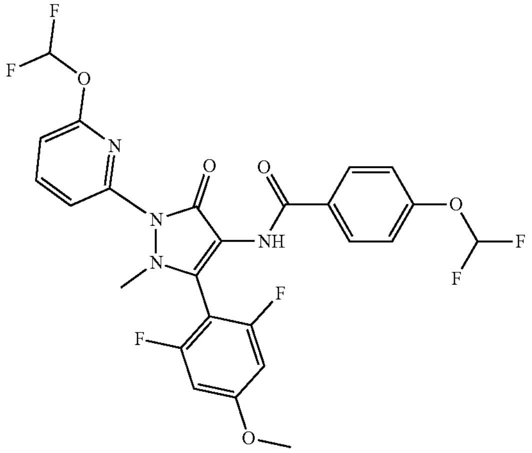 | 1.96<br>B<br>569.4 |
| 169 | N-[5-(2,6-difluoro-4-methoxyphenyl)-2-[6-(difluoromethoxy)pyridin-2-yl]-1-methyl-3-oxo-2,3-dihydro-1H-pyrazol-4-yl]-4-(trifluoromethoxy)benzamide | 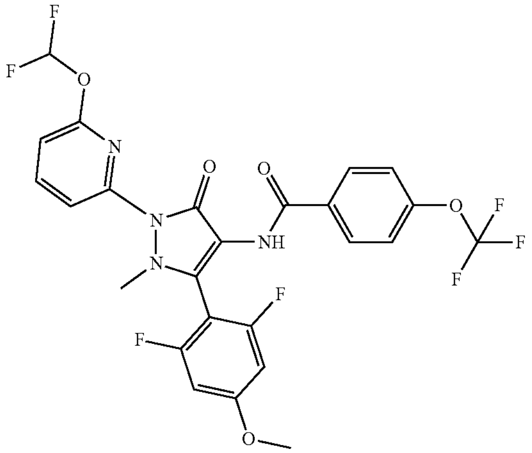 [SMILES: COc1cc(F)c(-c2c(NC(=O)c3ccc(OC(F)(F)F)cc3)c(=O)n(-c3cccc(OC(F)F)n3)n2C)c(F)c1] | 2.1<br>B<br>587.3 |

TABLE 2-continued

| $^1$H NMR data for the examples in Table 2: | | | |
|---|---|---|---|
| Ex. No. | Name | Structure | LC/MS Rt (min) Method M + H |
| 170 | N-[2-(2-cyanopyridin-3-yl)-5-(2,6-difluoro-4-methoxyphenyl)-1-methyl-3-oxo-2,3-dihydro-1H-pyrazol-4-yl]-4-(trifluoromethoxy)benzamide | 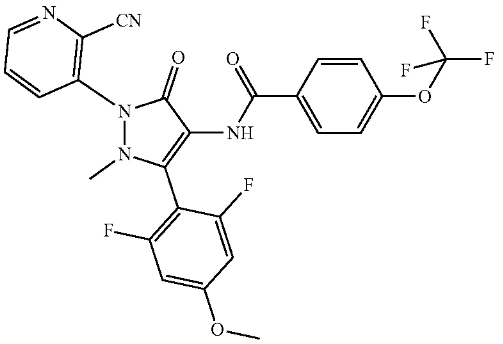 [SMILES: COc1cc(F)c(-c2c(NC(=O)c3ccc(OC(F)(F)F)cc3)c(=O)n(-c3cccnc3C#N)n2C)c(F)c1] | 1.78 A 546.1 |
| 171 | N-[2-(2-chlorophenyl)-5-(2,6-difluoro-4-methoxyphenyl)-1-methyl-3-oxo-2,3-dihydro-1H-pyrazol-4-yl]-4-(difluoromethoxy)benzamide | 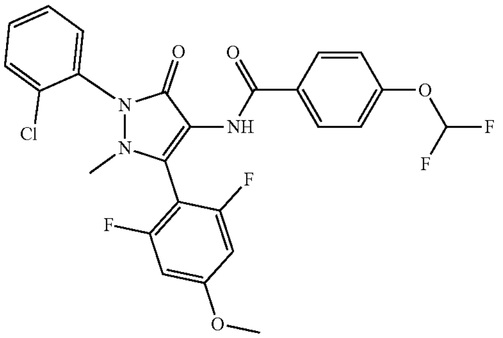 [SMILES: COc1cc(F)c(-c2c(NC(=O)c3ccc(OC(F)F)cc3)c(=O)n(-c3ccccc3Cl)n2C)c(F)c1] | 1.7 A 536.2 |
| 172 | N-[2-(2-chlorophenyl)-5-(2,6-difluoro-4-methoxyphenyl)-1-methyl-3-oxo-2,3-dihydro-1H-pyrazol-4-yl]-4-(trifluoromethoxy)benzamide | 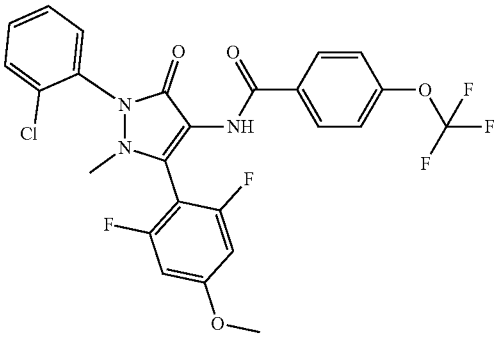 [SMILES: COc1cc(F)c(-c2c(NC(=O)c3ccc(OC(F)(F)F)cc3)c(=O)n(-c3ccccc3Cl)n2C)c(F)c1] | 1.86 A 554.1 |
| 173 | N-[2-(2-cyanophenyl)-5-(2,6-difluoro-4-methoxyphenyl)-1-methyl-3-oxo-2,3-dihydro-1H-pyrazol-4-yl]-4-(difluoromethoxy)benzamide | 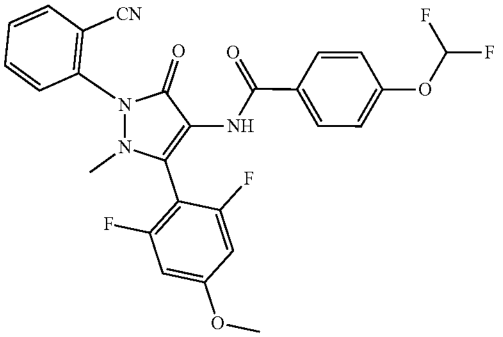 [SMILES: COc1cc(F)c(-c2c(NC(=O)c3ccc(OC(F)F)cc3)c(=O)n(-c3ccccc3C#N)n2C)c(F)c1] | 1.64 A 527.1 |

TABLE 2-continued

| $^1$H NMR data for the examples in Table 2: | | | |
|---|---|---|---|
| Ex. No. | Name | Structure | LC/MS Rt (min) Method M + H |
| 174 | N-[2-(2-cyanophenyl)-5-(2,6-difluoro-4-methoxyphenyl)-1-methyl-3-oxo-2,3-dihydro-1H-pyrazol-4-yl]-4-(trifluoromethoxy)benzamide | 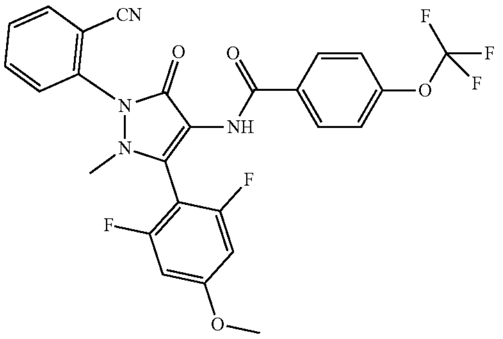 [SMILES: COc1cc(F)c(-c2c(NC(=O)c3ccc(OC(F)(F)F)cc3)c(=O)n(-c3ccccc3C#N)n2C)c(F)c1] | 1.82<br>B<br>545.2 |
| 175 | N-[2-(2-chloro-3-fluorophenyl)-5-(2,6-difluoro-4-methoxyphenyl)-1-methyl-3-oxo-2,3-dihydro-1H-pyrazol-4-yl]-4-(difluoromethoxy)benzamide | 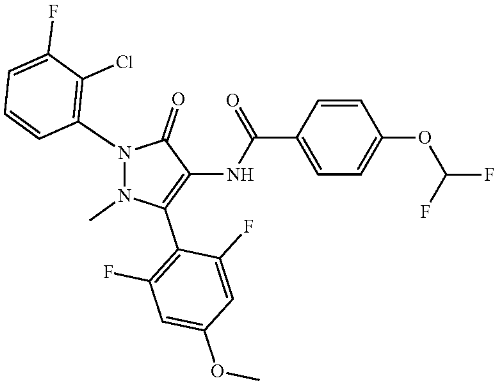 [SMILES: COc1cc(F)c(-c2c(NC(=O)c3ccc(OC(F)F)cc3)c(=O)n(-c3cccc(F)c3Cl)n2C)c(F)c1] | 1.78<br>A<br>554.2 |
| 176 | N-[2-(2,5-dichlorophenyl)-5-(2,6-difluoro-4-methoxyphenyl)-1-methyl-3-oxo-2,3-dihydro-1H-pyrazol-4-yl]-4-(difluoromethoxy)benzamide | 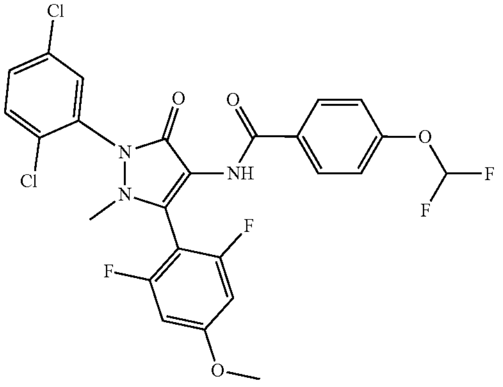 [SMILES: COc1cc(F)c(-c2c(NC(=O)c3ccc(OC(F)F)cc3)c(=O)n(-c3cc(Cl)ccc3Cl)n2C)c(F)c1] | 1.83<br>A<br>570.1 |

TABLE 2-continued

| $^1$H NMR data for the examples in Table 2: | | | |
|---|---|---|---|
| Ex. No. | Name | Structure | LC/MS Rt (min) Method M + H |
| 177 | N-[5-(2,6-difluoro-4-methoxyphenyl)-2-[3-(difluoromethoxy)phenyl]-1-methyl-3-oxo-2,3-dihydro-1H-pyrazol-4-yl]-4-(difluoromethoxy)benzamide | 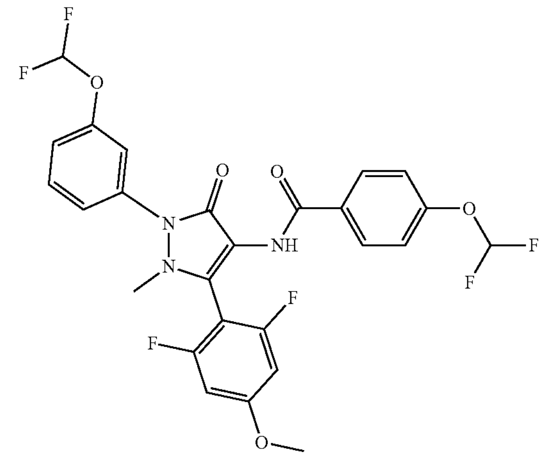 [SMILES: COc1cc(F)c(-c2c(NC(=O)c3ccc(OC(F)F)cc3)c(=O)n(-c3cccc(OC(F)F)c3)n2C)c(F)c1] | 1.89 A 568.2 |
| 178 | N-[2-(2-cyano-3-fluorophenyl)-5-(2,6-difluoro-4-methoxyphenyl)-1-methyl-3-oxo-2,3-dihydro-1H-pyrazol-4-yl]-4-(difluoromethoxy)benzamide | 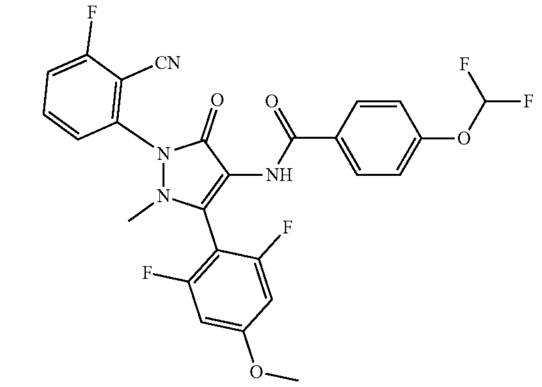 [SMILES: COc1cc(F)c(-c2c(NC(=O)c3ccc(OC(F)F)cc3)c(=O)n(-c3cccc(F)c3C#N)n2C)c(F)c1] | 1.71 A 545.3 |
| 179 | N-[2-(2,5-dicyanophenyl)-5-(2,6-difluoro-4-methoxyphenyl)-1-methyl-3-oxo-2,3-dihydro-1H-pyrazol-4-yl]-4-(difluoromethoxy)benzamide | 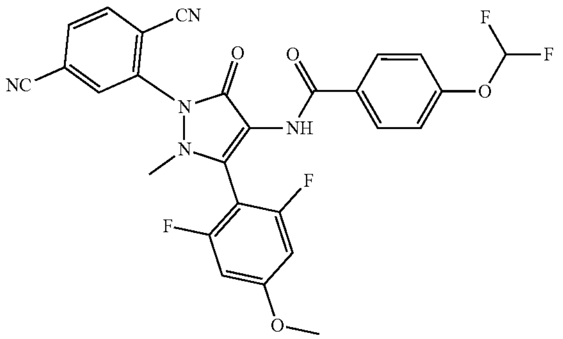 [SMILES: COc1cc(F)c(-c2c(NC(=O)c3ccc(OC(F)F)cc3)c(=O)n(-c3cc(C#N)ccc3C#N)n2C)c(F)c1] | 1.67 A 552.2 |

TABLE 2-continued

| $^1$H NMR data for the examples in Table 2: | | | |
|---|---|---|---|
| Ex. No. | Name | Structure | LC/MS Rt (min) Method M + H |
| 180 | N-[2-(3-chloro-4-methylpyridin-2-yl)-5-(2,6-difluoro-4-methoxyphenyl)-1-methyl-3-oxo-2,3-dihydro-1H-pyrazol-4-yl]-4-(difluoromethoxy)benzamide | 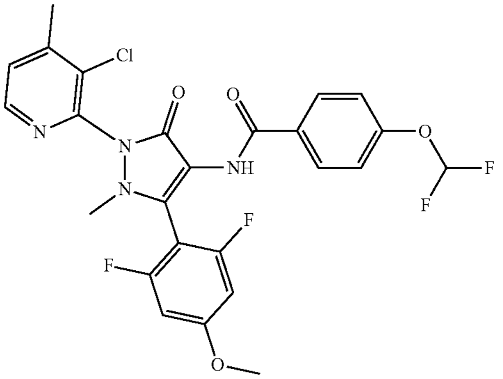 [SMILES: COc1cc(F)c(-c2c(NC(=O)c3ccc(OC(F)F)cc3)c(=O)n(-c3nccc(C)c3Cl)n2C)c(F)c1] | 1.65 B 551.2 |
| 181 | N-[2-(2-chloro-3-methoxyphenyl)-5-(2,6-difluoro-4-methoxyphenyl)-1-methyl-3-oxo-2,3-dihydro-1H-pyrazol-4-yl]-4-(difluoromethoxy)benzamide | 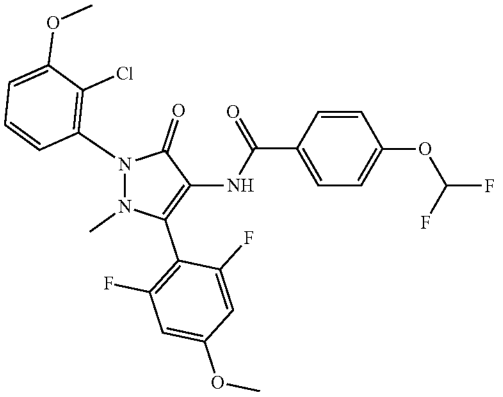 [SMILES: COc1cc(F)c(-c2c(NC(=O)c3ccc(OC(F)F)cc3)c(=O)n(-c3cccc(OC)c3Cl)n2C)c(F)c1] | 0.88 C 566.0 |
| 182 | N-[2-(3-chloro-6-methoxypyridin-2-yl)-5-(2,6-difluoro-4-methoxyphenyl)-1-methyl-3-oxo-2,3-dihydro-1H-pyrazol-4-yl]-4-(difluoromethoxy)benzamide | 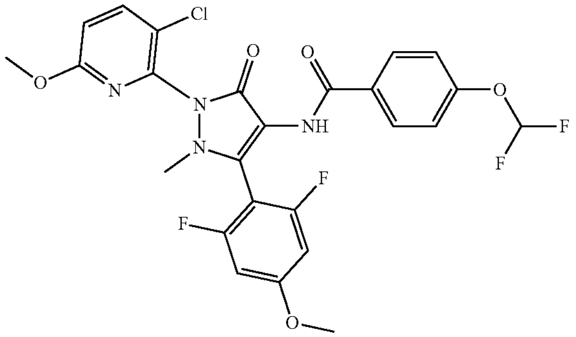 [SMILES: COc1cc(F)c(-c2c(NC(=O)c3ccc(OC(F)F)cc3)c(=O)n(-c3nc(OC)ccc3Cl)n2C)c(F)c1] | 1.75 B 567.2 |
| 183 | N-[2-(2-cyano-5-methoxyphenyl)-5-(2,6-difluoro-4-methoxyphenyl)-1-methyl-3-oxo-2,3-dihydro-1H-pyrazol-4-yl]-4-(difluoromethoxy)benzamide | 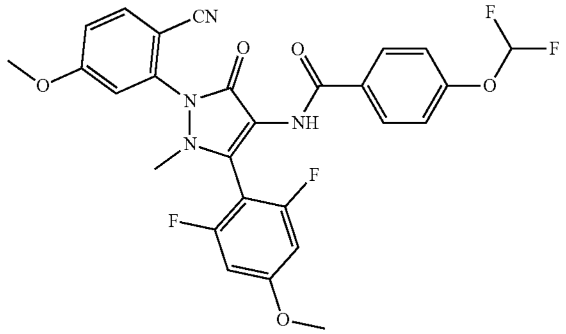 [SMILES: COc1cc(F)c(-c2c(NC(=O)c3ccc(OC(F)F)cc3)c(=O)n(-c3cc(OC)ccc3C#N)n2C)c(F)c1] | 1.69 A 557.3 |

TABLE 2-continued

| $^1$H NMR data for the examples in Table 2: | | | |
|---|---|---|---|
| Ex. No. | Name | Structure | LC/MS Rt (min) Method M + H |
| 184 | N-[2-(2-cyano-3-methoxyphenyl)-5-(2,6-difluoro-4-methoxyphenyl)-1-methyl-3-oxo-2,3-dihydro-1H-pyrazol-4-yl]-4-(difluoromethoxy)benzamide | 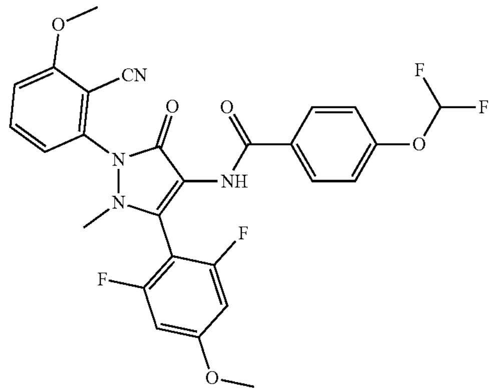 [SMILES: COc1cc(F)c(-c2c(NC(=O)c3ccc(OC(F)F)cc3)c(=O)n(-c3cccc(OC)c3C#N)n2C)c(F)c1] | 1.7 B 557.3 |
| 185 | N-[2-(3-cyano-6-methoxypyridin-2-yl)-5-(2,6-difluoro-4-methoxyphenyl)-1-methyl-3-oxo-2,3-dihydro-1H-pyrazol-4-yl]-4-(difluoromethoxy)benzamide | 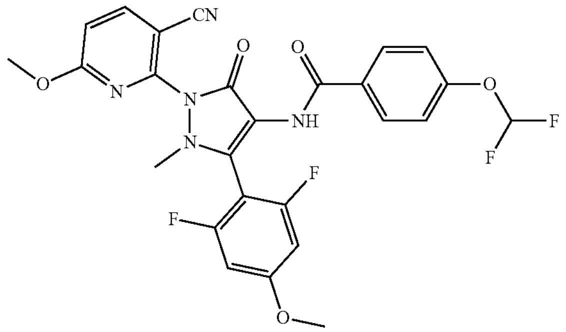 [SMILES: COc1cc(F)c(-c2c(NC(=O)c3ccc(OC(F)F)cc3)c(=O)n(-c3nc(OC)ccc3C#N)n2C)c(F)c1] | 1.75 B 558.0 |
| 186 | N-[2-(2-chloro-5-fluorophenyl)-5-(2,6-difluoro-4-methoxyphenyl)-1-methyl-3-oxo-2,3-dihydro-1H-pyrazol-4-yl]-4-(difluoromethoxy)benzamide | 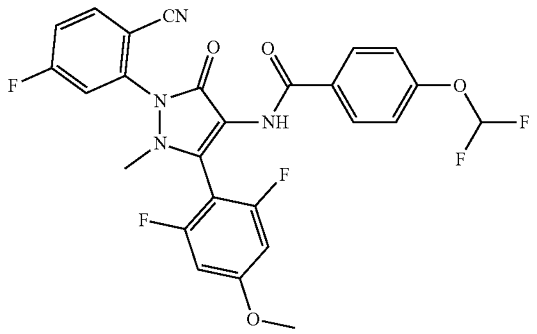 [SMILES: COc1cc(F)c(-c2c(NC(=O)c3ccc(OC(F)F)cc3)c(=O)n(-c3cc(F)ccc3C#N)n2C)c(F)c1] | 1.83 A 554.1 |
| 187 | N-[2-(3-chloro-2-fluorophenyl)-5-(2,6-difluoro-4-methoxyphenyl)-1-methyl-3-oxo-2,3-dihydro-1H-pyrazol-4-yl]-4-(difluoromethoxy)benzamide | 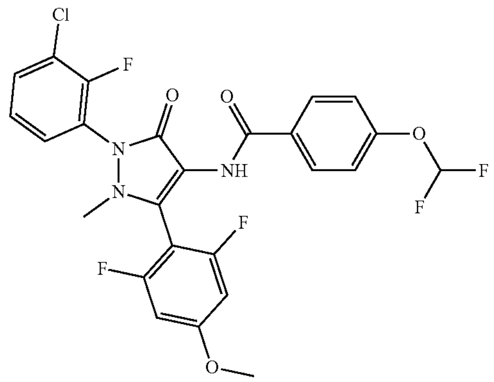 [SMILES: COc1cc(F)c(-c2c(NC(=O)c3ccc(OC(F)F)cc3)c(=O)n(-c3cccc(Cl)c3F)n2C)c(F)c1] | 1.78 B 554.3 |

TABLE 2-continued

$^1$H NMR data for the examples in Table 2:

| Ex. No. | Name | Structure | LC/MS Rt (min) Method M + H |
|---|---|---|---|
| 188 | N-[2-(2-cyano-5-fluorophenyl)-5-(2,6-difluoro-4-methoxyphenyl)-1-methyl-3-oxo-2,3-dihydro-1H-pyrazol-4-yl]-4-(difluoromethoxy)benzamide | 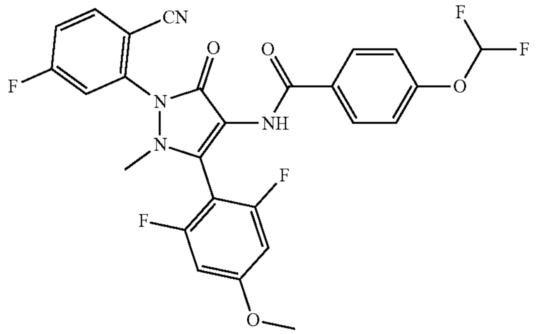 [SMILES: COc1cc(F)c(-c2c(NC(=O)c3ccc(OC(F)F)cc3)c(=O)n(-c3cc(F)ccc3C#N)n2C)c(F)c1] | 1.69 B 545.0 |
| 189 | N-[2-(3-cyano-2-fluorophenyl)-5-(2,6-difluoro-4-methoxyphenyl)-1-methyl-3-oxo-2,3-dihydro-1H-pyrazol-4-yl]-4-(difluoromethoxy)benzamide | 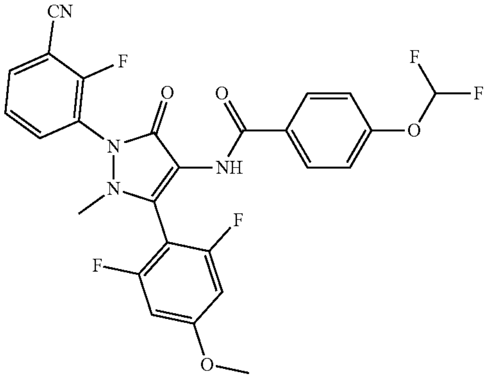 [SMILES: COc1cc(F)c(-c2c(NC(=O)c3ccc(OC(F)F)cc3)c(=O)n(-c3cccc(C#N)c3F)n2C)c(F)c1] | 1.76 A 545.0 |
| 190 | N-[2-(6-tert-butyl-3-cyanopyridin-2-yl)-5-(2,6-difluoro-4-methoxyphenyl)-1-methyl-3-oxo-2,3-dihydro-1H-pyrazol-4-yl]-4-(difluoromethoxy)benzamide | 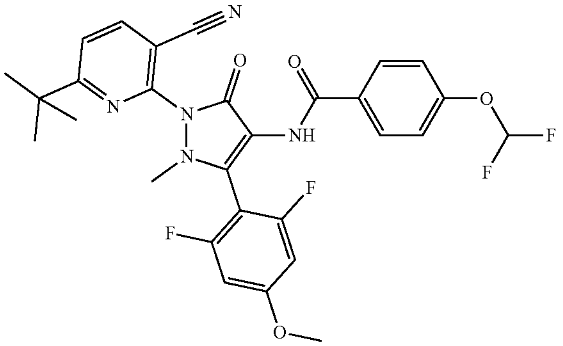 [SMILES: COc1cc(F)c(-c2c(NC(=O)c3ccc(OC(F)F)cc3)c(=O)n(-c3nc(C(C)(C)C)ccc3C#N)n2C)c(F)c1] | 2.06 B 584.4 |
| 191 | N-(2-(3-cyano-6-cyclobutylpyridin-2-yl)-5-(2,6-difluoro-4-methoxyphenyl)-1-methyl-3-oxo-2,3-dihydro-1H-pyrazol-4-yl)-4-(difluoromethoxy)benzamide | 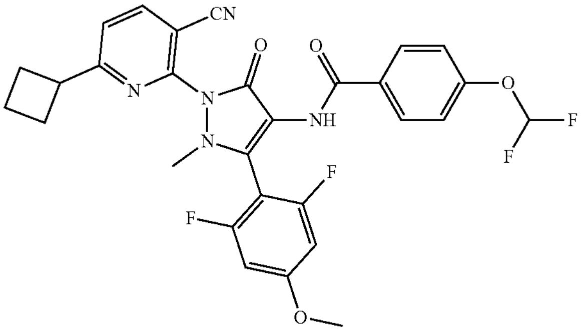 [SMILES: COc1cc(F)c(-c2c(NC(=O)c3ccc(OC(F)F)cc3)c(=O)n(-c3nc(C4CCC4)ccc3C#N)n2C)c(F)c1] | 1.80 B 582.1 |

TABLE 2-continued

| $^1$H NMR data for the examples in Table 2: | | | |
|---|---|---|---|
| Ex. No. | Name | Structure | LC/MS Rt (min) Method M + H |
| 192 | N-{2-[3-cyano-6-(1-ethoxycyclopropyl)pyridin-2-yl]-5-(2,6-difluoro-4-methoxyphenyl)-1-methyl-3-oxo-2,3-dihydro-1H-pyrazol-4-yl}-4-(difluoromethoxy)benzamide | 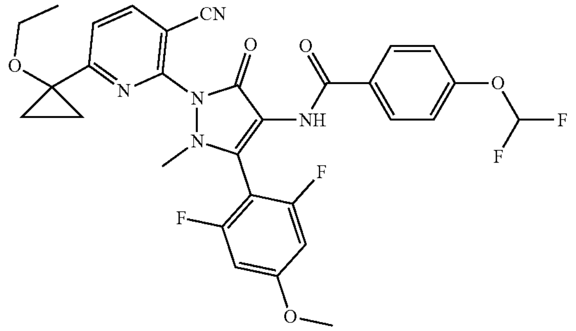 [SMILES: CCOC1(c2ccc(C#N)c(-n3c(=O)c(NC(=O)c4ccc(OC(F)F)cc4)c(-c4c(F)cc(OC)cc4F)n3C)n2)CC1] | 1.99 B 612.1 |
| 193 | N-{2-[3-cyano-4-(methoxymethyl)pyridin-2-yl]-5-(2,6-difluoro-4-methoxyphenyl)-1-methyl-3-oxo-2,3-dihydro-1H-pyrazol-4-yl}-4-(difluoromethoxy)benzamide | 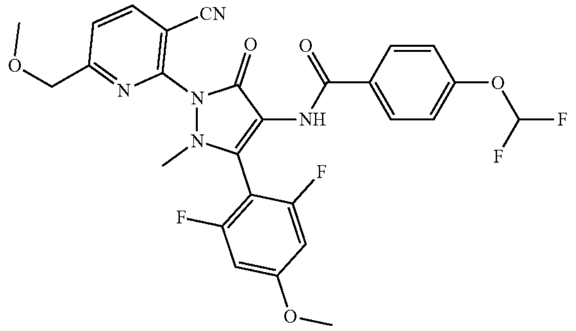 [SMILES: COCc1ccc(C#N)c(-n2c(=O)c(NC(=O)c3ccc(OC(F)F)cc3)c(-c3c(F)cc(OC)cc3F)n2C)n1] | 1.66 A 572.1 |
| 194 | N-{2-[3-cyano-6-(2-fluoropropan-2-yl)pyridin-2-yl]-5-(2,6-difluoro-4-methoxyphenyl)-1-methyl-3-oxo-2,3-dihydro-1H-pyrazol-4-yl}-4-(difluoromethoxy)benzamide | 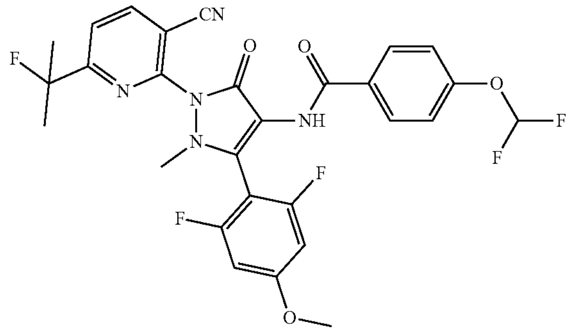 [SMILES: COc1cc(F)c(-c2c(NC(=O)c3ccc(OC(F)F)cc3)c(=O)n(-c3nc(C(C)(C)F)ccc3C#N)n2C)c(F)c1] | 1.94 A 588.3 |
| 195 | N-[5-(2,6-difluoro-4-methoxyphenyl)-2-[6-(hydroxymethyl)-3-(trifluoromethyl)pyridin-2-yl]-1-methyl-3-oxo-2,3-dihydro-1H-pyrazol-4-yl]-4-(difluoromethoxy)benzamide | 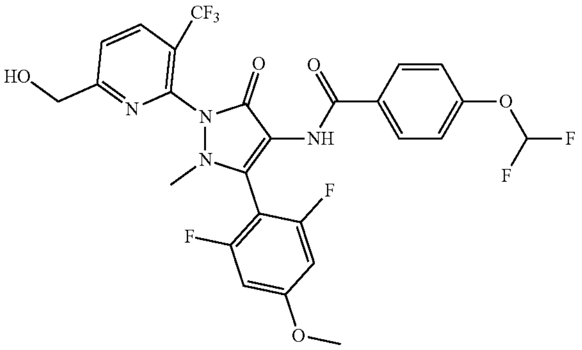 [SMILES: COc1cc(F)c(-c2c(NC(=O)c3ccc(OC(F)F)cc3)c(=O)n(-c3nc(CO)ccc3C(F)(F)F)n2C)c(F)c1] | 1.66 B 601.3 |

TABLE 2-continued

| $^1$H NMR data for the examples in Table 2: | | | |
|---|---|---|---|
| Ex. No. | Name | Structure | LC/MS Rt (min) Method M + H |
| 196 | N-[5-(2,6-difluoro-4-methoxyphenyl)-2-[6-(methoxymethyl)-3-(trifluoromethyl)pyridin-2-yl]-1-methyl-3-oxo-2,3-dihydro-1H-pyrazol-4-yl]-4-(difluoromethoxy)benzamide | 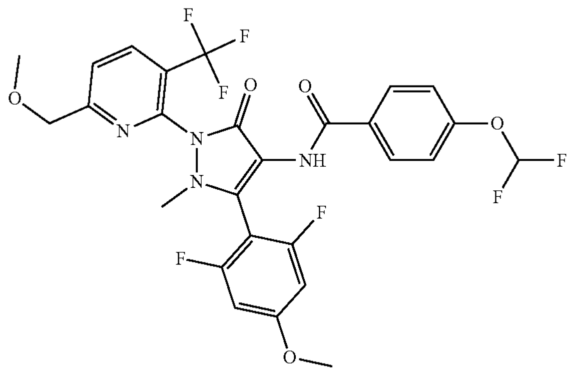 [SMILES: COCc1ccc(C(F)(F)F)c(-n2c(=O)c(NC(=O)c3ccc(OC(F)F)cc3)c(-c3c(F)cc(OC)cc3F)n2C)n1] | 1.82 B 615.2 |
| 197 | N-[2-(3-chloropyridin-2-yl)-5-(2,6-difluoro-4-methoxyphenyl)-1-methyl-3-oxo-2,3-dihydro-1H-pyrazol-4-yl]-4-(difluoromethoxy)benzamide | 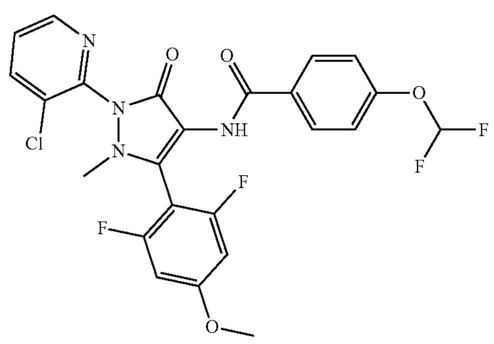 [SMILES: COc1cc(F)c(-c2c(NC(=O)c3ccc(OC(F)F)cc3)c(=O)n(-c3ncccc3Cl)n2C)c(F)c1] | 1.67 A 537.3 |
| 198 | N-[2-(2-chloro-5-methoxyphenyl)-5-(2,6-difluoro-4-methoxyphenyl)-1-methyl-3-oxo-2,3-dihydro-1H-pyrazol-4-yl]-4-(difluoromethoxy)benzamide | 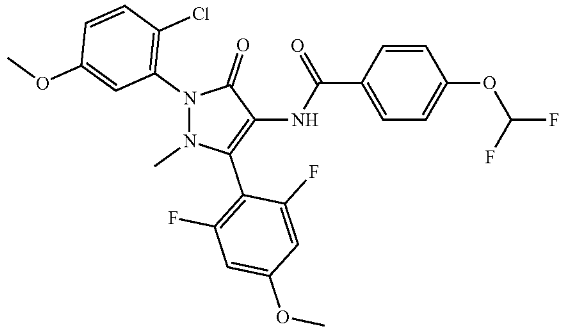 [SMILES: COc1cc(F)c(-c2c(NC(=O)c3ccc(OC(F)F)cc3)c(=O)n(-c3cc(OC)ccc3Cl)n2C)c(F)c1] | 0.91 C 566.0 |
| 199 | N-[2-(3-cyano-4-cyclohexylpyridin-2-yl)-5-(2,6-difluoro-4-methoxyphenyl)-1methyl-3-oxo-2,3-dihydro-1H-pyrazol-4-yl]-4-(difluoromethoxy)benzamide | 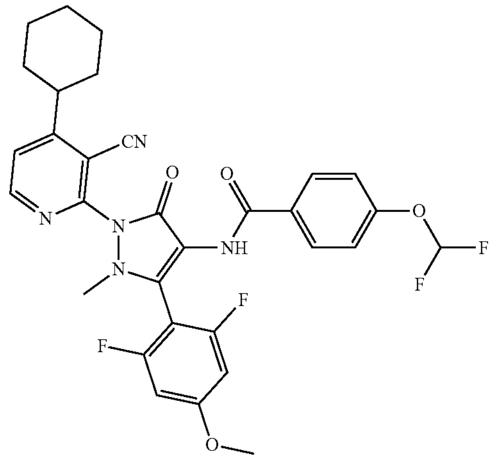 [SMILES: COc1cc(F)c(-c2c(NC(=O)c3ccc(OC(F)F)cc3)c(=O)n(-c3nccc(C4CCCCC4)c3C#N)n2C)c(F)c1] | 1.03 C 610.3 |

TABLE 2-continued

$^1$H NMR data for the examples in Table 2:

| Ex. No. | Name | Structure | LC/MS Rt (min) Method M + H |
|---|---|---|---|
| 200 | N-{2-[3-chloro-6-(methoxymethyl)pyridin-2-yl]-5-(2,6-difluoro-4-methoxyphenyl)-1-methyl-3-oxo-2,3-dihydro-1H-pyrazol-4-yl}-4-(difluoromethoxy)benzamide | 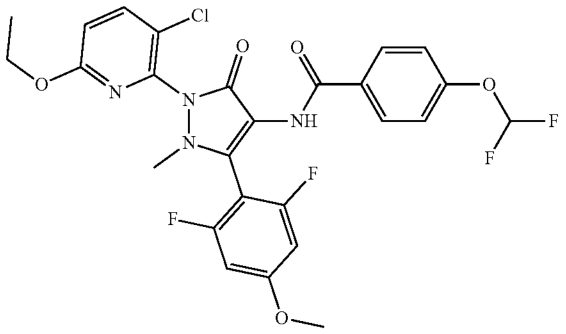 [SMILES: CCOc1ccc(Cl)c(-n2c(=O)c(NC(=O)c3ccc(OC(F)F)cc3)c(-c3c(F)cc(OC)cc3F)n2C)n1] | 0.86 C 581.3 |
| 201 | N-[2-(3-cyano-4-methylpyridin-2-yl)-5-(2,6-difluoro-4-methoxyphenyl)-1-methyl-3-oxo-2,3-dihydro-1H-pyrazol-4-yl]-4-(difluoromethoxy)benzamide | 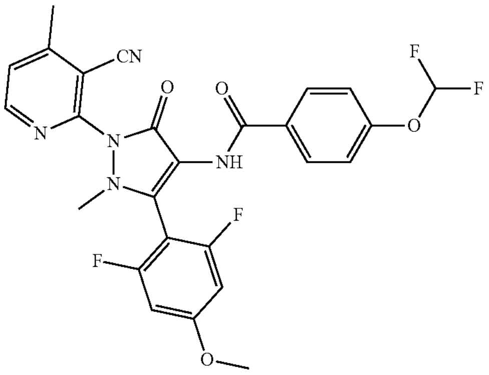 [SMILES: COc1cc(F)c(-c2c(NC(=O)c3ccc(OC(F)F)cc3)c(=O)n(-c3nccc(C)c3C#N)n2C)c(F)c1] | 8.64 B 615.2 |
| 202 | N-{2-[3-cyano-6-(4-methylpiperazin-1-yl)pyridin-2-yl]-5-(2,6-difluoro-4-methoxyphenyl)-1-methyl-3-oxo-2,3-dihydro-1H-pyrazol-4-yl}-4-(difluoromethoxy)benzamide | 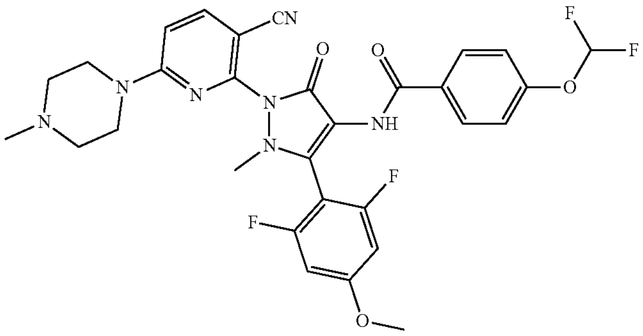 [SMILES: COc1cc(F)c(-c2c(NC(=O)c3ccc(OC(F)F)cc3)c(=O)n(-c3nc(N4CCN(C)CC4)ccc3C#N)n2C)c(F)c1] | 1.75 A 626.0 |
| 203 | N-{2-[6-chloro-3-(3-hydroxy-3-methylazetidin-1-yl)pyridin-2-yl]-5-(2,6-difluoro-4-methoxyphenyl)-1-methyl-3-oxo-2,3-dihydro-1H-pyrazol-4-yl}-4-(difluoromethoxy)benzamide | 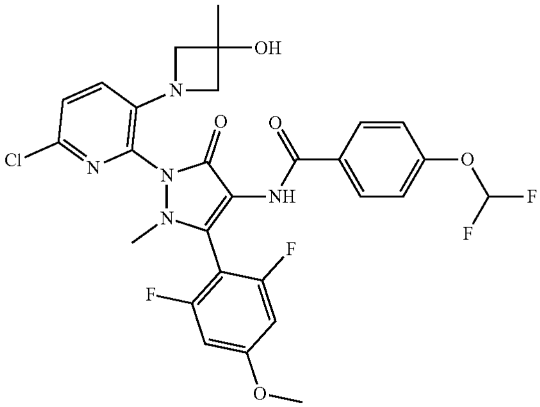 [SMILES: COc1cc(F)c(-c2c(NC(=O)c3ccc(OC(F)F)cc3)c(=O)n(-c3nc(Cl)ccc3N3CC(C)(O)C3)n2C)c(F)c1] | 1.70 A 622.1 |

TABLE 2-continued

| ¹H NMR data for the examples in Table 2: | | | |
|---|---|---|---|
| Ex. No. | Name | Structure | LC/MS Rt (min) Method M + H |
| 204 | N-[5-(2,6-difluoro-4-methoxyphenyl)-2-{6-[(dimethylamino)methyl]pyridin-2-yl}-1-methyl-3-oxo-2,3-dihydro-1H-pyrazol-4-yl]-4-(difluoromethoxy)benzamide | 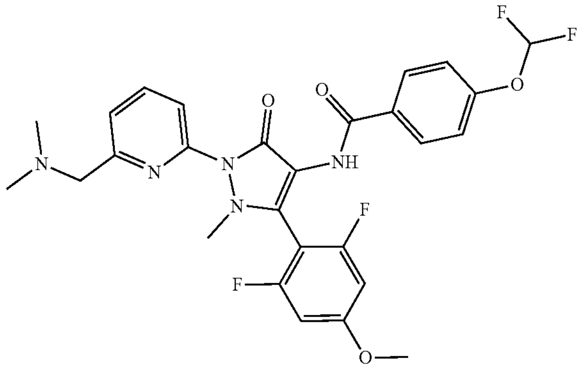 [SMILES: COc1cc(F)c(-c2c(NC(=O)c3ccc(OC(F)F)cc3)c(=O)n(-c3cccc(CN(C)C)n3)n2C)c(F)c1] | 1.34 A 560.0 |
| 205 | N-[5-(2,6-difluoro-4-methoxyphenyl)-1-methyl-2-{6-[(4-methylpiperazin-1-yl)methyl]pyridin-2-yl}-3-oxo-2,3-dihydro-1H-pyrazol-4-yl]-4-(difluoromethoxy)benzamide | 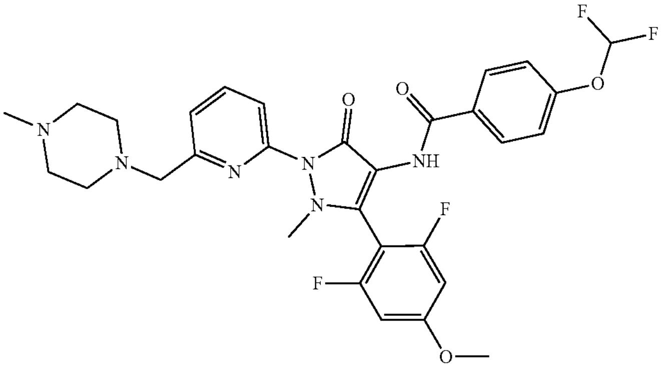 [SMILES: COc1cc(F)c(-c2c(NC(=O)c3ccc(OC(F)F)cc3)c(=O)n(-c3cccc(CN4CCN(C)CC4)n3)n2C)c(F)c1] | 1.32 A 615.1 |
| 206 | N-[5-(2,6-difluoro-4-methoxyphenyl)-2-{6-[4-(2-methanesulfonylethyl)piperazin-1-yl]pyridin-2-yl}-1-methyl-3-oxo-2,3-dihydro-1H-pyrazol-4-yl]-4-(difluoromethoxy)benzamide | 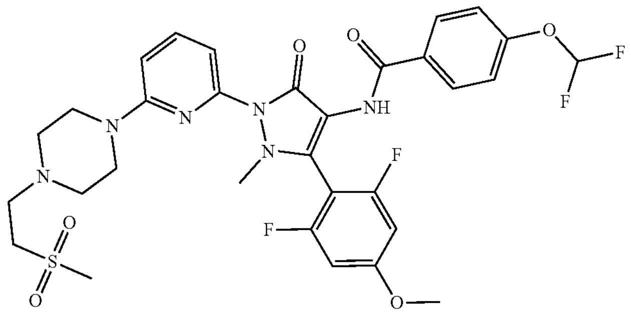 [SMILES: COc1cc(F)c(-c2c(NC(=O)c3ccc(OC(F)F)cc3)c(=O)n(-c3cccc(N4CCN(CCS(C)(=O)=O)CC4)n3)n2C)c(F)c1] | 1.41 B 693.0 |
| 207 | N-(2-{6-[4-(cyclopropylmethyl)piperazin-1-yl]pyridin-2-yl}-5-(2,6-difluoro-4-methoxyphenyl)-1-methyl-3-oxo-2,3-dihydro-1H-pyrazol-4-yl)-4-(difluoromethoxy)benzamide | 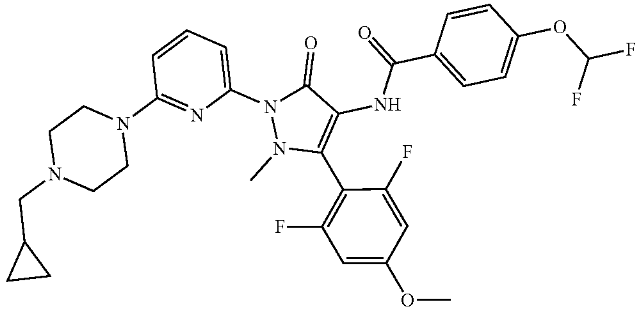 [SMILES: COc1cc(F)c(-c2c(NC(=O)c3ccc(OC(F)F)cc3)c(=O)n(-c3cccc(N4CCN(CC5CC5)CC4)n3)n2C)c(F)c1] | 1.57 B 641.3 |

TABLE 2-continued $^{1}$H NMR data for the examples in Table 2:

| Ex. No. | Name | Structure | LC/MS Rt (min) Method M + H |
|---|---|---|---|
| 208 | N-[5-(2,6-difluoro-4-methoxyphenyl)-2-{6-[4-(3-hydroxypropyl)piperazin-1-yl]pyridin-2-yl}-1-methyl-3-oxo-2,3-dihydro-1H-pyrazol 4-yl]-4-(difluoromethoxy)benzamide | 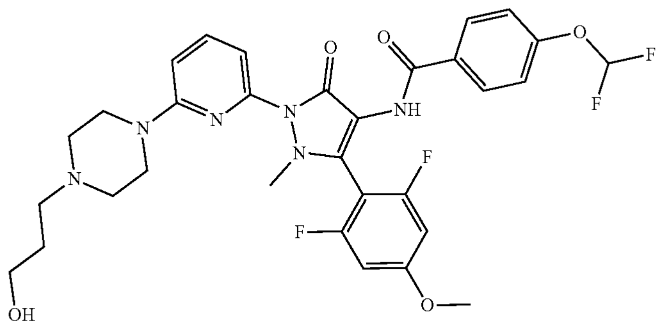 [SMILES: COc1cc(F)c(-c2c(NC(=O)c3ccc(OC(F)F)cc3)c(=O)n(-c3cccc(N4CCN(CCCO)CC4)n3)n2C)c(F)c1] | 1.47 A 645.0 |
| 209 | N-{2-[6-chloro-3-(dimethylamino)pyridin-2-yl]-5-(2,6-difluoro-4-methoxyphenyl)-1-methyl-3-oxo-2,3-dihydro-1H-pyrazol-4-yl}-4-(difluoromethoxy)benzamide | 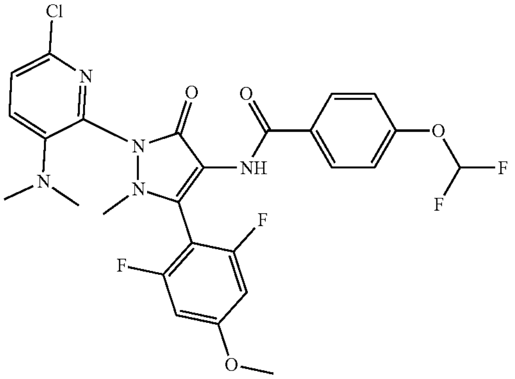 [SMILES: COc1cc(F)c(-c2c(NC(=O)c3ccc(OC(F)F)cc3)c(=O)n(-c3nc(Cl)ccc3N(C)C)n2C)c(F)c1] | 1.86 A 580.1 |
| 210 | N-[5-(2,6-difluoro-4-methoxyphenyl)-2-[3-fluoro-6-(3-hydroxy-3-methylazetidin-1-yl)pyridin-2-yl]-1-methyl-3-oxo-2,3-dihydro-1H-pyrazol-4-yl]-4-(difluoromethoxy)benzamide | 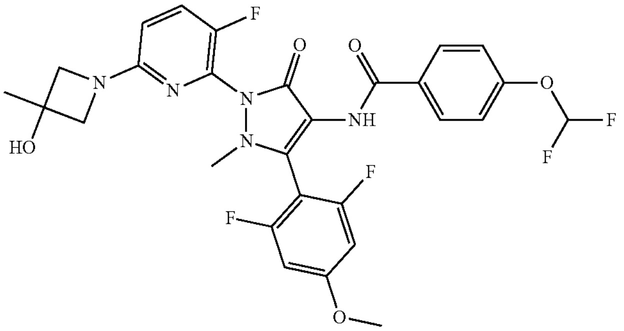 [SMILES: COc1cc(F)c(-c2c(NC(=O)c3ccc(OC(F)F)cc3)c(=O)n(-c3nc(N4CC(C)(O)C4)ccc3F)n2C)c(F)c1] | 1.70 A 606.1 |
| 211 | N-[5-(2,6-difluoro-4-methoxyphenyl)-2-[3-(3-hydroxy-3-methylazetidin-1-yl)pyridin-2-yl]-1-methyl-3-oxo-2,3-dihydro-1H-pyrazol-4-yl]-4-(difluoromethoxy)benzamide | 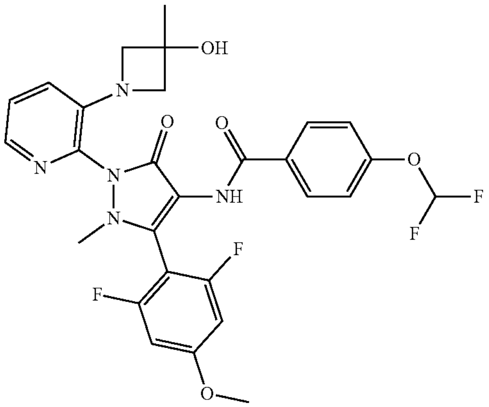 [SMILES: COc1cc(F)c(-c2c(NC(=O)c3ccc(OC(F)F)cc3)c(=O)n(-c3ncccc3N3CC(C)(O)C3)n2C)c(F)c1] | 1.42 B 588.0 |

TABLE 2-continued

| $^1$H NMR data for the examples in Table 2: | | | |
|---|---|---|---|
| Ex. No. | Name | Structure | LC/MS Rt (min) Method M + H |
| 212 | N-[5-(2,6-difluoro-4-methoxyphenyl)-2-{6-[4-(2-methoxyethyl)piperazin-1-yl]pyridin-2-yl}-1-methyl-3-oxo-2,3-dihydro-1H-pyrazol-4-yl]-4-(difluoromethoxy)benzamide | 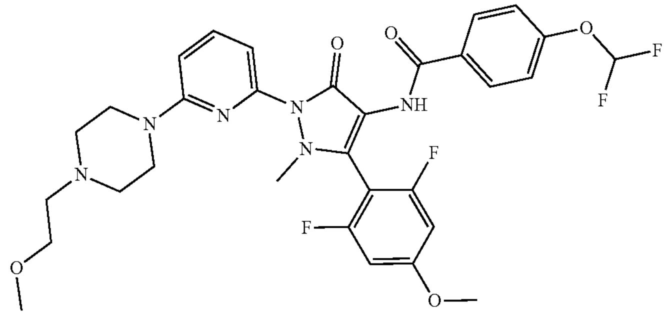 [SMILES: COCCN1CCN(c2cccc(-n3c(=O)c(NC(=O)c4ccc(OC(F)F)cc4)c(-c4c(F)cc(OC)cc4F)n3C)n2)CC1] | 1.50 B 645.3 |
| 213 | N-[5-(2,6-difluoro-4-methoxyphenyl)-2-[6-(4-methanesulfonylpiperazin-1-yl)pyridin-2-yl]-1-methyl-3-oxo-2,3-dihydro-1H-pyrazol-4-yl]-4-(difluoromethoxy)benzamide | 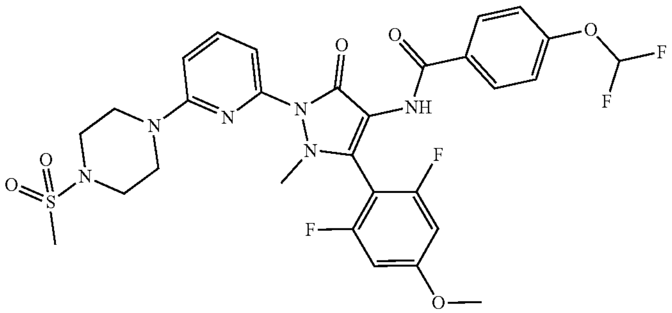 [SMILES: COc1cc(F)c(-c2c(NC(=O)c3ccc(OC(F)F)cc3)c(=O)n(-c3cccc(N4CCN(S(C)(=O)=O)CC4)n3)n2C)c(F)c1] | 1.67 A 665.3 |
| 214 | N-[5-(2,6-difluoro-4-methoxyphenyl)-1-methyl-3-oxo-2-[6-(3-oxopiperazin-1-yl)-3-(trifluoromethyl)pyridin-2-yl]-2,3-dihydro-1H-pyrazol-4-yl]-4-(difluoromethoxy)benzamide | 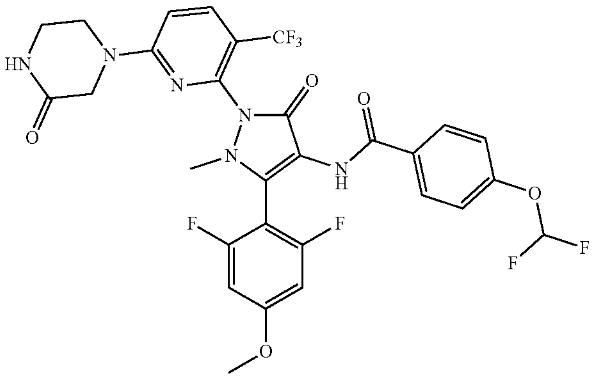 [SMILES: COc1cc(F)c(-c2c(NC(=O)c3ccc(OC(F)F)cc3)c(=O)n(-c3nc(N4CCNC(=O)C4)ccc3C(F)(F)F)n2C)c(F)c1] | 1.72 A 669.0 |
| 215 | N-{2-[6-chloro-3-(methylamino)pyridin-2-yl]-5-(2,6-difluoro-4-methoxyphenyl)-1-methyl-3-oxo-2,3-dihydro-1H-pyrazol-4-yl}-4-(difluoromethoxy)benzamide | 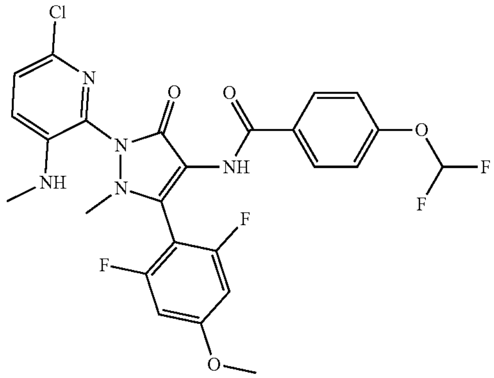 [SMILES: CNc1ccc(Cl)nc1-n1c(=O)c(NC(=O)c2ccc(OC(F)F)cc2)c(-c2c(F)cc(OC)cc2F)n1C] | 1.94 A 566.2 |

TABLE 2-continued

| $^{1}$H NMR data for the examples in Table 2: | | | |
|---|---|---|---|
| Ex. No. | Name | Structure | LC/MS Rt (min) Method M + H |
| 216 | (2S)-1-{6-[3-(2,6-difluoro-4-methoxyphenyl)-4-[4-(difluoromethoxy)benzamido]-2-methyl-5-oxo-2,5-dihydro-1H-pyrazol-1-yl]-5-(trifluoromethyl)pyridin-2-yl}pyrrolidine-2-carboxamide | 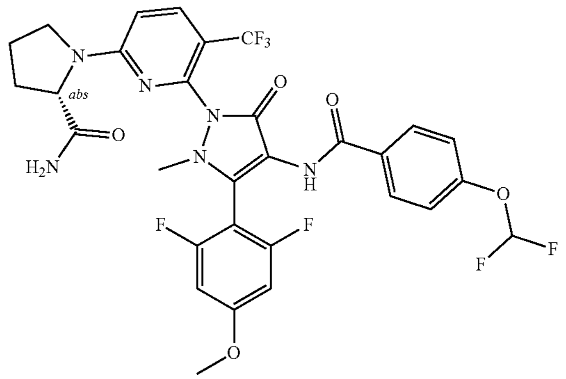 [SMILES: COc1cc(F)c(-c2c(NC(=O)c3ccc(OC(F)F)cc3)c(=O)n(-c3nc(N4CCC[C@H]4C(N)=O)ccc3C(F)(F)F)n2C)c(F)c1] | 1.8 A 683 |
| 217 | N-{2-[6-chloro-3-(4-methylpiperazin-1-yl)pyridin-2-yl]-5-(2,6-difluoro-4-methoxyphenyl)-1-methyl-3-oxo-2,3-dihydro-1H-pyrazol-4-yl}-4-(difluoromethoxy)benzamide | 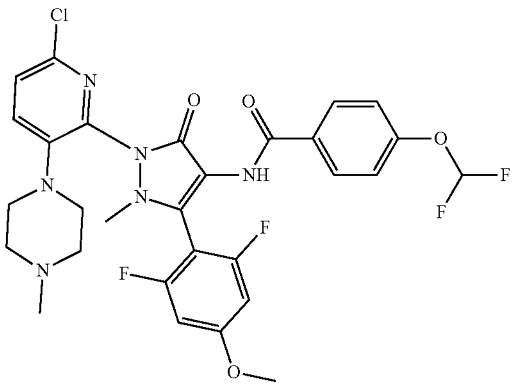 [SMILES: COc1cc(F)c(-c2c(NC(=O)c3ccc(OC(F)F)cc3)c(=O)n(-c3nc(Cl)ccc3N3CCN(C)CC3)n2C)c(F)c1] | 1.53 A 635.1 |
| 218 | N-[5-(2,6-difluoro-4-methoxyphenyl)-2-[6-(3,3-dimethylazetidin-1-yl)pyridin-2-yl]-1-methyl-3-oxo-2,3-dihydro-1H-pyrazol-4-yl]-4-(difluoromethoxy)benzamide | 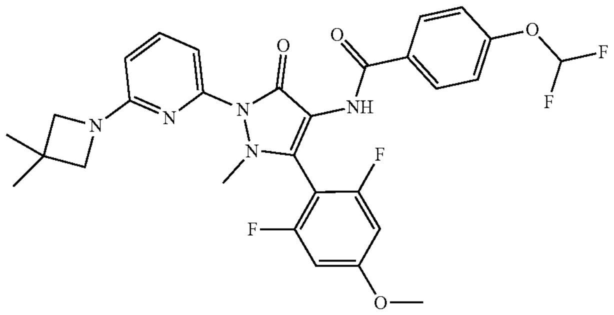 [SMILES: COc1cc(F)c(-c2c(NC(=O)c3ccc(OC(F)F)cc3)c(=O)n(-c3cccc(N4CC(C)(C)C4)n3)n2C)c(F)c1] | 2.17 A 586.3 |
| 219 | N-[5-(2,6-difluoro-4-methoxyphenyl)-2-[3-fluoro-6-(4-methylpiperazin-1-yl)pyridin-2-yl]-1-methyl-3-oxo-2,3-dihydro-1H-pyrazol-4-yl]-4-(difluoromethoxy)benzamide | 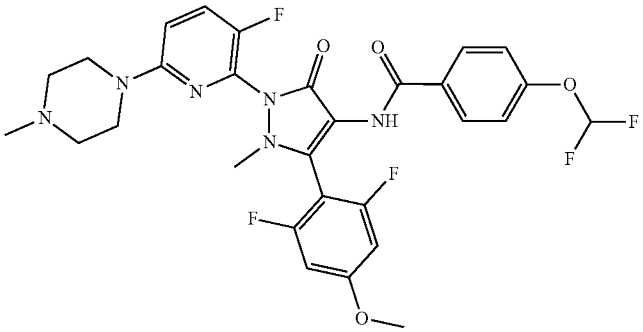 [SMILES: COc1cc(F)c(-c2c(NC(=O)c3ccc(OC(F)F)cc3)c(=O)n(-c3nc(N4CCN(C)CC4)ccc3F)n2C)c(F)c1] | 0.74 C 619.4 |

TABLE 2-continued

| $^1$H NMR data for the examples in Table 2: | | | |
|---|---|---|---|
| Ex. No. | Name | Structure | LC/MS Rt (min) Method M + H |
| 220 | N-[5-(2,6-difluoro-4-methoxyphenyl)-1-methyl-2-[6-(4-methyl-3-oxopiperazin-1-yl)-3-(trifluoromethyl)pyridin-2-yl]-3-oxo-2,3-dihydro-1H-pyrazol-4-yl]-4-(difluoromethoxy)benzamide | 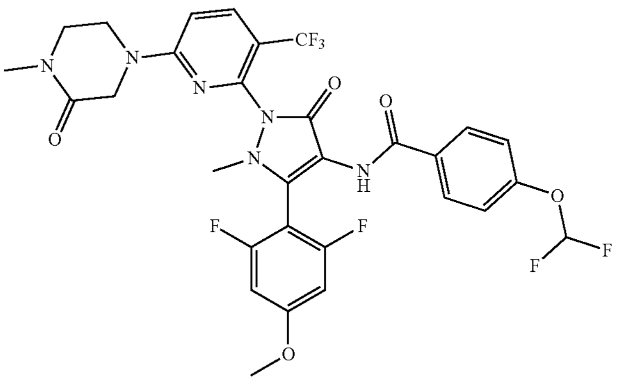 [SMILES: COc1cc(F)c(-c2c(NC(=O)c3ccc(OC(F)F)cc3)c(=O)n(-c3nc(N4CCN(C)C(=O)C4)ccc3C(F)(F)F)n2C)c(F)c1] | 1.74 A 683.1 |
| 221 | N-(5-(3-chloro-4-methoxyphenyl)-1-methyl-3-oxo-2-(3-(trifluoromethyl)pyridin-2-yl)-2,3-dihydro-1H-pyrazol-4-yl)-4-(difluoromethoxy)benzamide | 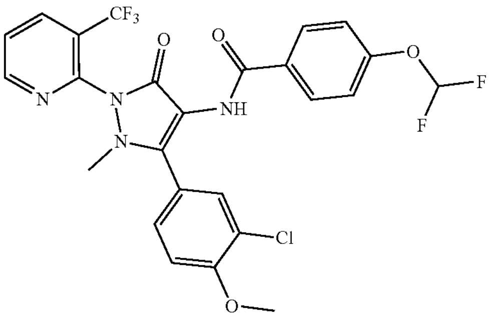 [SMILES: COc1ccc(-c2c(NC(=O)c3ccc(OC(F)F)cc3)c(=O)n(-c3ncccc3C(F)(F)F)n2C)cc1Cl] | 1.79 B 569.0 |
| 222 | N-{2-[6-chloro-3-(trifluoromethyl)pyridin-2-yl]-5-(2,6-difluoro-4-methoxyphenyl)-1-methyl-3-oxo-2,3-dihydro-1H-pyrazol-4-yl}-4-(difluoromethoxy)benzamide | 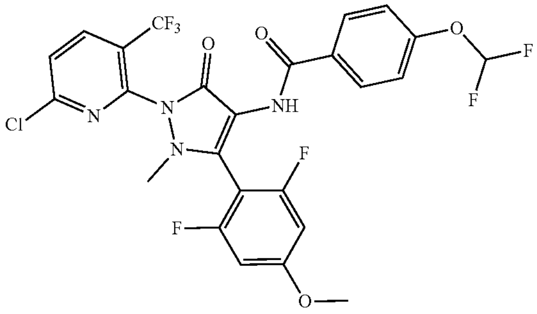 [SMILES: COc1cc(F)c(-c2c(NC(=O)c3ccc(OC(F)F)cc3)c(=O)n(-c3nc(Cl)ccc3C(F)(F)F)n2C)c(F)c1] | 1.87 A 605.1 |
| 223 | 4-(difluoromethoxy)-N-(1-methyl-5-(1-methyl-1H-indazol-5-yl)-3-oxo-2-(3-(trifluoromethyl)pyridin-2-yl)-2,3-dihydro-1H-pyrazol-4-yl)benzamide | 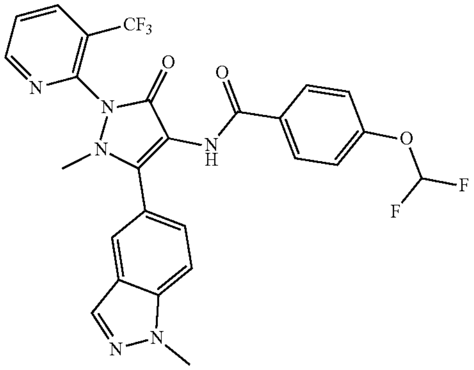 [SMILES: Cn1ncc2cc(-c3c(NC(=O)c4ccc(OC(F)F)cc4)c(=O)n(-c4ncccc4C(F)(F)F)n3C)ccc21] | 1.60 B 559.3 |

TABLE 2-continued

| $^1$H NMR data for the examples in Table 2: | | | |
|---|---|---|---|
| Ex. No. | Name | Structure | LC/MS Rt (min) Method M + H |
| 224 | N-[5-(2,6-difluoro-4-methoxyphenyl)-1-methyl-2-[4-(4-methylpiperazin-1-yl)-3-(trifluoromethyl)pyridin-2-yl]-3-oxo-2,3-dihydro-1H-pyrazol-4-yl]-4-(difluoromethoxy)benzamide | 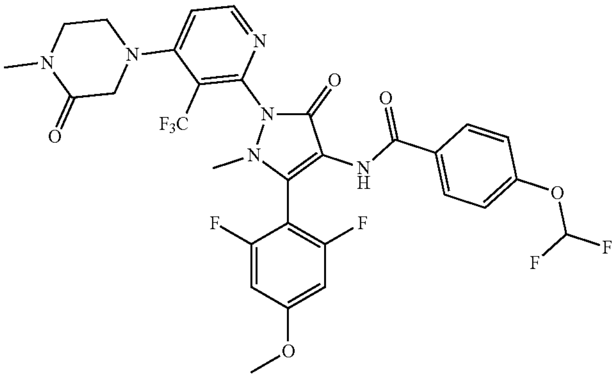 [SMILES: COc1cc(F)c(-c2c(NC(=O)c3ccc(OC(F)F)cc3)c(=O)n(-c3nccc(N4CCN(C)C(=O)C4)c3C(F)(F)F)n2C)c(F)c1] | 1.79 A 669.1 |
| 225 | N-[5-(2,6-difluoro-4-methoxyphenyl)-2-{6-[(2-hydroxyethyl)amino]-3-(trifluoromethyl)pyridin-2-yl}-1-methyl-3-oxo-2,3-dihydro-1H-pyrazol-4-yl]-4-(difluoromethoxy)benzamide | 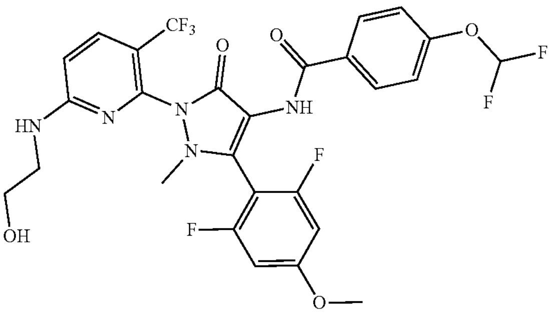 [SMILES: COc1cc(F)c(-c2c(NC(=O)c3ccc(OC(F)F)cc3)c(=O)n(-c3nc(NCCO)ccc3C(F)(F)F)n2C)c(F)c1] | 1.78 A 630.2 |
| 226 | N-(2-{6-[(carbamoylmethyl)amino]-3-(trifluoromethyl)pyridin-2-yl}-5-(2,6-difluoro-4-methoxyphenyl)-1-methyl-3-oxo-2,3-dihydro-1H-pyrazol-4-yl)-4-(difluoromethoxy)benzamide | 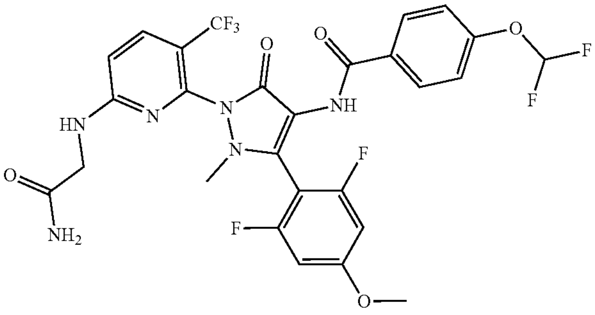 [SMILES: COc1cc(F)c(-c2c(NC(=O)c3ccc(OC(F)F)cc3)c(=O)n(-c3nc(NCC(N)=O)ccc3C(F)(F)F)n2C)c(F)c1] | 1.62 A 643.1 |
| 227 | N-[5-(2,6-difluoro-4-methoxyphenyl)-1-methyl-2-[6-(methylamino)-3-(trifluoromethyl)pyridin-2-yl]-3-oxo-2,3-dihydro-1H-pyrazol-4-yl]-4-(difluoromethoxy)benzamide | 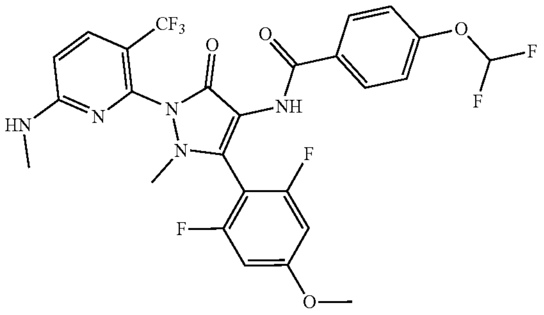 [SMILES: CNc1ccc(C(F)(F)F)c(-n2c(=O)c(NC(=O)c3ccc(OC(F)F)cc3)c(-c3c(F)cc(OC)cc3F)n2C)n1] | 1.83 A 600.0 |

TABLE 2-continued

| Ex. No. | Name | Structure | LC/MS Rt (min) Method M + H |
|---|---|---|---|
| | $^1$H NMR data for the examples in Table 2: | | |
| 228 | N-[5-(2,6-difluoro-4-methoxyphenyl)-2-{6-[(1,3-dimethyl-1H-pyrazol-4-yl)amino]-3-(trifluoromethyl)pyridin-2-yl}-1-methyl-3-oxo-2,3-dihydro-1H-pyrazol-4-yl]-4-(difluoromethoxy)benzamide | 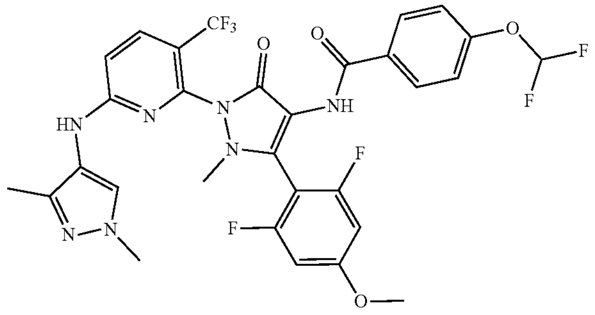 [SMILES: COc1cc(F)c(-c2c(NC(=O)c3ccc(OC(F)F)cc3)c(=O)n(-c3nc(Nc4cn(C)nc4C)ccc3C(F)(F)F)n2C)c(F)c1] | 1.82 A 680.2 |
| 229 | N-[2-(6-{[(cyclopropylcarbamoyl) methy]amino}-3-(trifluoromethyl)pyridin-2-yl)-5-(2,6-difluoro-4-methoxyphenyl)-1-methyl-3-oxo-2,3-dihydro-1H-pyrazol-4-yl]-4-(difluoromethoxy)benzamide | 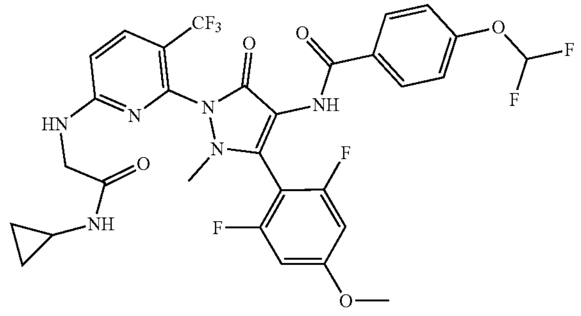 [SMILES: COc1cc(F)c(-c2c(NC(=O)c3ccc(OC(F)F)cc3)c(=O)n(-c3nc(NCC(=O)NC4CC4)ccc3C(F)(F)F)n2C)c(F)c1] | 1.72 A 683.3 |
| 230 | 4-(difluoromethoxy)-N-[5-(2-fluoro-6-hydroxy-4-methoxyphenyl)-2-{6-[(2-hydroxyethyl)amino]-3-(trifluoromethyl)pyridin-2-yl}-1-methyl-3-oxo-2,3-dihydro-1H-pyrazol-4-yl]benzamide | 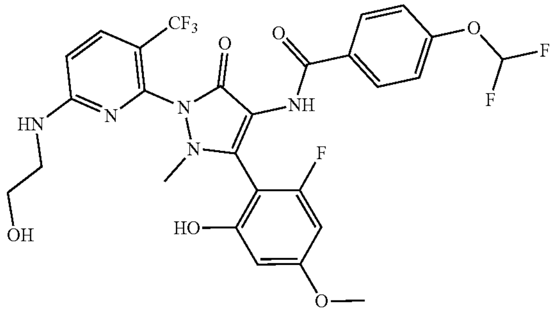 [SMILES: COc1cc(O)c(-c2c(NC(=O)c3ccc(OC(F)F)cc3)c(=O)n(-c3nc(NCCO)ccc3C(F)(F)F)n2C)c(F)c1] | 0.94 C 628.3 |
| 231 | N-[5-(2,6-difluoro-4-methoxyphenyl)-2-(6-{[1-(hydroxymethyl)cyclopropyl] amino}-3-(trifluoromethyl)pyridin-2-yl)-1-methyl-3-oxo-2,3-dihydro-1H-pyrazol-4-yl]-4-(difluoromethoxy)benzamide | 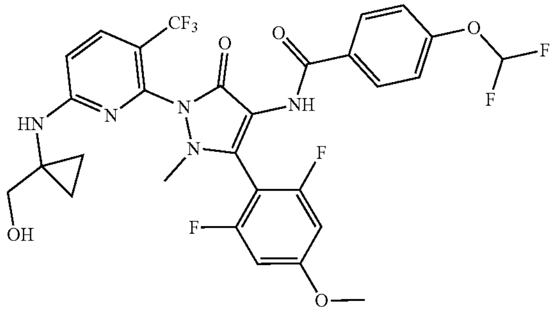 [SMILES: COc1cc(F)c(-c2c(NC(=O)c3ccc(OC(F)F)cc3)c(=O)n(-c3nc(NC4(CO)CC4)ccc3C(F)(F)F)n2C)c(F)c1] | 1.74 A 656.6 |

TABLE 2-continued

| $^1$H NMR data for the examples in Table 2: | | | |
|---|---|---|---|
| Ex. No. | Name | Structure | LC/MS Rt (min) Method M + H |
| 232 | N-[5-(2,6-difluoro-4-methoxyphenyl)-1-methyl-2-(6-{[(1S)-1-(methylcarbamoyl)ethyl]amino}-3-(trifluoromethyl)pyridin-2-yl)-3-oxo-2,3-dihydro-1H-pyrazol-4-yl]-4-(difluoromethoxy)benzamide | 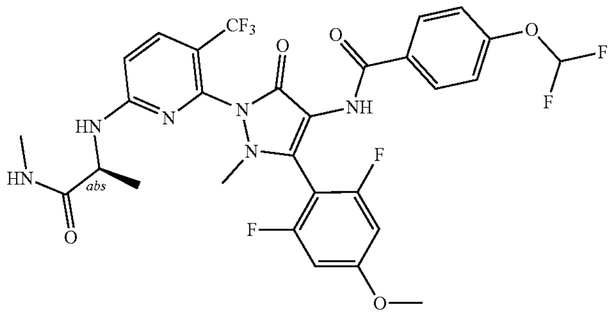 [SMILES: CNC(=O)[C@H](C)Nc1ccc(C(F)(F)F)c(-n2c(=O)c(NC(=O)c3ccc(OC(F)F)cc3)c(-c3c(F)cc(OC)cc3F)n2C)n1] | 1.78 A 671.1 |
| 233 | 4-(difluoromethoxy)-N-[5-(2-fluoro-6-hydroxy-4-methoxyphenyl)-1-methyl-2-[6-(methylamino)-3-(trifluoromethyl)pyridin-2-yl]-3-oxo-2,3-dihydro-1H-pyrazol-4-yl]benzamide | 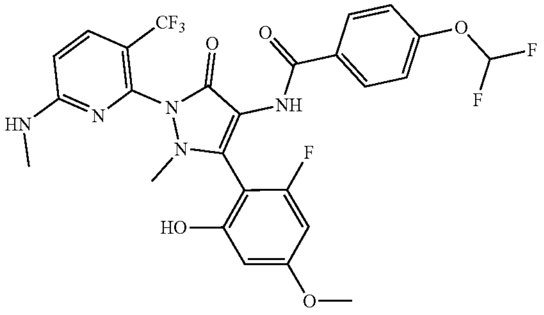 [SMILES: CNc1ccc(C(F)(F)F)c(-n2c(=O)c(NC(=O)c3ccc(OC(F)F)cc3)c(-c3c(O)cc(OC)cc3F)n2C)n1] | 0.98 C 598.3 |
| 234 | N-[5-(2,6-difluoro-4-methoxyphenyl)-1-methyl-3-oxo-2-{6-[(1H-1,2,4-triazol-5-yl)amino]-3-(trifluoromethyl)pyridin-2-yl}-2,3-dihydro-1H-pyrazol-4-yl]-4-(difluoromethoxy)benzamide | 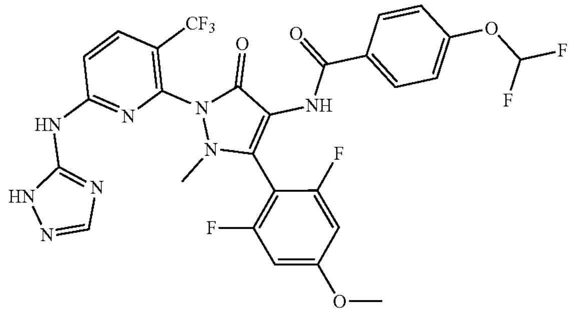 [SMILES: COc1cc(F)c(-c2c(NC(=O)c3ccc(OC(F)F)cc3)c(=O)n(-c3nc(Nc4ncn[nH]4)ccc3C(F)(F)F)n2C)c(F)c1] | 1.80 A 653.0 |
| 235 | N-[5-(2,6-difluoro-4-methoxyphenyl)-2-{6-[(2-methoxyethyl)amino]-3-(trifluoromethyl)pyridin-2-yl}-1-methyl-3-oxo-2,3-dihydro-1H-pyrazol-4-yl]-4-(difluoromethoxy)benzamide | 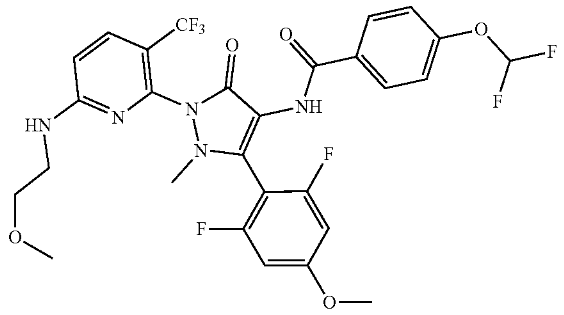 [SMILES: COCCNc1ccc(C(F)(F)F)c(-n2c(=O)c(NC(=O)c3ccc(OC(F)F)cc3)c(-c3c(F)cc(OC)cc3F)n2C)n1] | 1.90 A 644.0 |

TABLE 2-continued $^{1}$H NMR data for the examples in Table 2:

| Ex. No. | Name | Structure | LC/MS Rt (min) Method M + H |
|---|---|---|---|
| 236 | N-[5-(2,6-difluoro-4-methoxyphenyl)-2-(6-{[(2R)-1-hydroxypropan-2-yl]amino}-3-(trifluoromethyl)pyridin-2-yl)-1-methyl-3-oxo-2,3-dihydro-1H-pyrazol-4-yl]-4-(difluoromethoxy)benzamide | 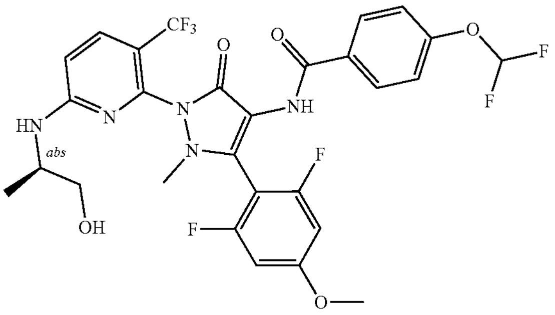 [SMILES: COc1cc(F)c(-c2c(NC(=O)c3ccc(OC(F)F)cc3)c(=O)n(-c3nc(N[C@H](C)CO)ccc3C(F)(F)F)n2C)c(F)c1] | 1.72 A 644.2 |
| 237 | N-[5-(2,6-difluoro-4-methoxyphenyl)-2-(6-{[(2S)-1-hydroxypropan-2-yl]amino}-3-(trifluoromethyl)pyridin-2-yl)-1-methyl-3-oxo-2,3-dihydro-1H-pyrazol-4-yl]-4-(difluoromethoxy)benzamide | 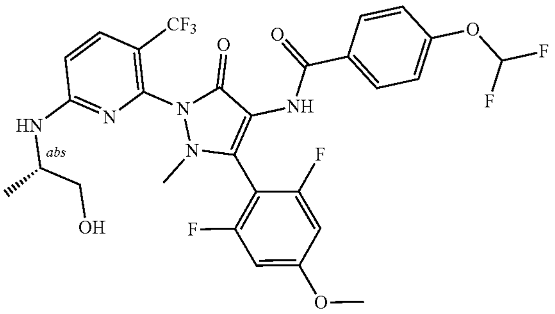 [SMILES: COc1cc(F)c(-c2c(NC(=O)c3ccc(OC(F)F)cc3)c(=O)n(-c3nc(N[C@@H](C)CO)ccc3C(F)(F)F)n2C)c(F)c1] | 1.78 B 644.1 |
| 238 | N-[5-(2,6-difluoro-4-methoxyphenyl)-1-methyl-2-(6-{[(methylcarbamoyl)methyl]amino}-3-(trifluoromethyl)pyridin-2-yl)-3-oxo-2,3-dihydro-1H-pyrazol-4-yl]-4-(difluoromethoxy)benzamide | 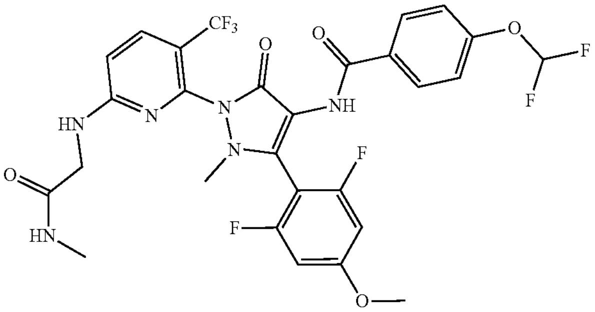 [SMILES: CNC(=O)CNc1ccc(C(F)(F)F)c(-n2c(=O)c(NC(=O)c3ccc(OC(F)F)cc3)c(-c3c(F)cc(OC)cc3F)n2C)n1] | 1.62 A 656.9 |
| 239 | N-(2-{3-chloro-6-[4-(2,2,2-trifluoroethyl)piperazin-1-yl]pyridin-2-yl}-5-(2,6-difluoro-4-methoxyphenyl)-1-methyl-3-oxo-2,3-dihydro-1H-pyrazol-4-yl)-4-(difluoromethoxy)benzamide | 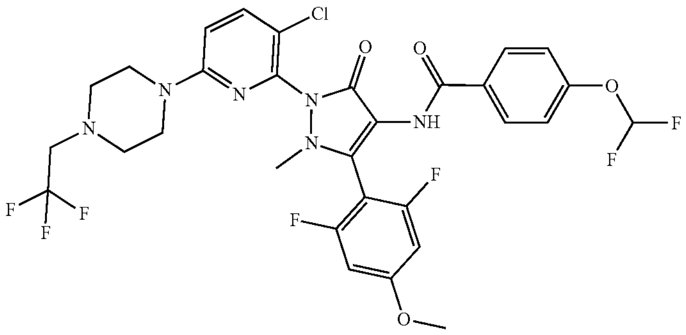 [SMILES: COc1cc(F)c(-c2c(NC(=O)c3ccc(OC(F)F)cc3)c(=O)n(-c3nc(N4CCN(CC(F)(F)F)CC4)ccc3Cl)n2C)c(F)c1] | 2.13 A 703.3 |

TABLE 2-continued

| $^1$H NMR data for the examples in Table 2: | | | |
|---|---|---|---|
| Ex. No. | Name | Structure | LC/MS Rt (min) Method M + H |
| 240 | N-(2-{3-chloro-6-[4-(2,2-difluoroethyl)piperazin-1-yl]pyridin-2-yl}-5-(2,6-difluoro-4-methoxyphenyl)-1-methyl-3-oxo-2,3-dihydro-1H-pyrazol-4-yl)-4-(difluoromethoxy)benzamide | 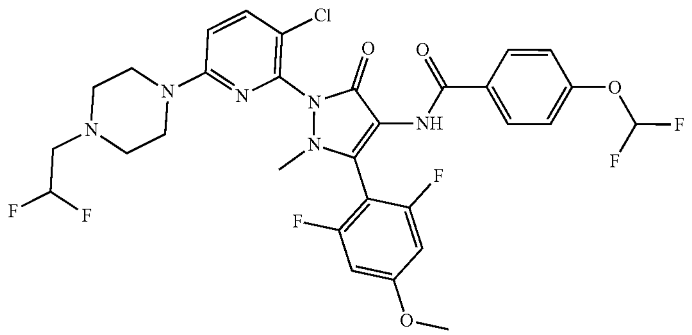 [SMILES: COc1cc(F)c(-c2c(NC(=O)c3ccc(OC(F)F)cc3)c(=O)n(-c3nc(N4CCN(CC(F)F)CC4)ccc3Cl)n2C)c(F)c1] | 1.99 A 685.1 |
| 241 | N-[5-(2,6-difluoro-4-methoxyphenyl)-1-methyl-2-[6-(N-methylmethanesulfonamido)-3-(trifluoromethyl)pyridin-2-yl]-3-oxo-2,3-dihydro-1H-pyrazol-4-yl]-4-(difluoromethoxy)benzamide | 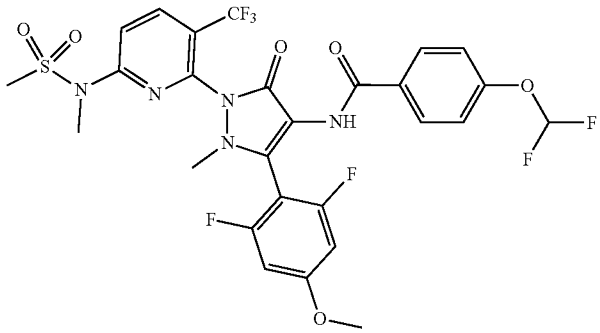 [SMILES: COc1cc(F)c(-c2c(NC(=O)c3ccc(OC(F)F)cc3)c(=O)n(-c3nc(N(C)S(C)(=O)=O)ccc3C(F)(F)F)n2C)c(F)c1] | 1.88 E 678.1 |
| 242 | N-[2-(3,6-dichloropyridin-2-yl)-5-(2,6-difluoro-4-methoxyphenyl)-1-methyl-3-oxo-2,3-dihydro-1H-pyrazol-4-yl]-4-(difluoromethoxy)benzamide | 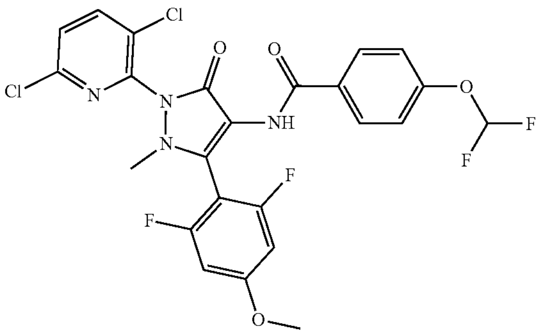 [SMILES: COc1cc(F)c(-c2c(NC(=O)c3ccc(OC(F)F)cc3)c(=O)n(-c3nc(Cl)ccc3Cl)n2C)c(F)c1] | 1.93 A 571.2 |
| 243 | N-[2-(6-{[(1R)-1-cyclopropylethyl]amino}-3-(trifluoromethyl)pyridin-2-yl)-5-(2,6-difluoro-4-methoxyphenyl)-1-methyl-3-oxo-2,3-dihydro-1H-pyrazol-4-yl]-4-(difluoromethoxy)benzamide | 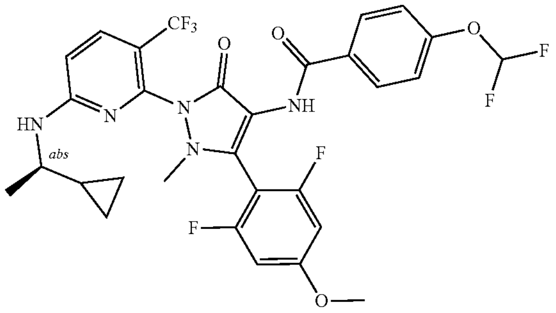 [SMILES: COc1cc(F)c(-c2c(NC(=O)c3ccc(OC(F)F)cc3)c(=O)n(-c3nc(N[C@H](C)C4CC4)ccc3C(F)(F)F)n2C)c(F)c1] | 2.21 B 654.3 |

TABLE 2-continued

| $^{1}$H NMR data for the examples in Table 2: | | | |
|---|---|---|---|
| Ex. No. | Name | Structure | LC/MS Rt (min) Method M + H |
| 244 | N-[5-(2,6-difluoro-4-methoxyphenyl)-2-[3-ethyl-6-(4-methylpiperazin-1-yl)pyridin-2-yl]-1-methyl-3-oxo-2,3-dihydro-1H-pyrazol-4-yl]-4-(difluoromethoxy)benzamide | 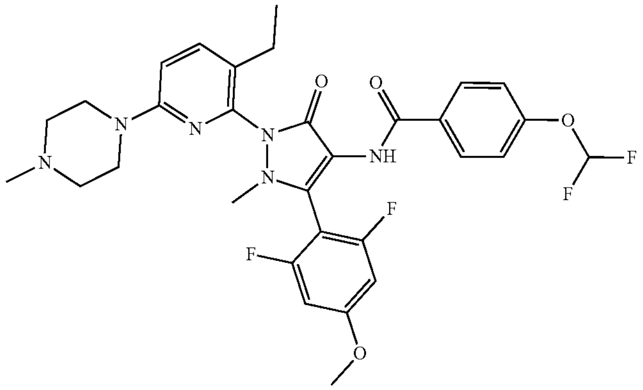 [SMILES: CCc1ccc(N2CCN(C)CC2)nc1-n1c(=O)c(NC(=O)c2ccc(OC(F)F)cc2)c(-c2c(F)cc(OC)cc2F)n1C] | 1.59 B 629.1 |
| 245 | N-[2-(3-chloropyridin-2-yl)-5-(4-methoxyphenyl)-1-methyl-3-oxo-2,3-dihydro-1H-pyrazol-4-yl]-4-(difluoromethoxy)benzamide | 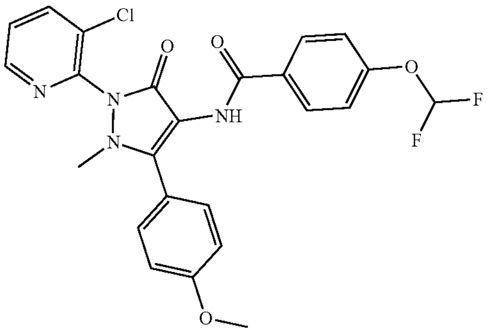 [SMILES: COc1ccc(-c2c(NC(=O)c3ccc(OC(F)F)cc3)c(=O)n(-c3ncccc3Cl)n2C)cc1] | 1.62 A 501.1 |
| 246 | 4-(difluoromethoxy)-N-(5-(4-methoxy-3-methylphenyl)-1-methyl-3-oxo-2-(3-(trifluoromethyl)pyridin-2-yl)-2,3-dihydro-1H-pyrazol-4-yl)benzamide | 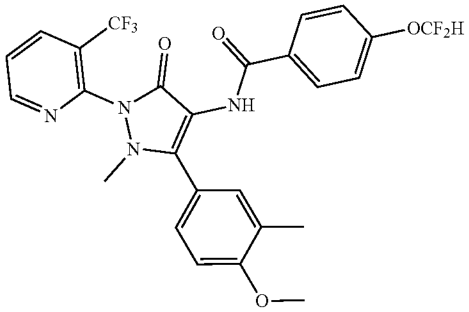 | 1.84 A 549.2 |
| 247 | N-{2-[3-chloro-6-(4-methanesulfonylpiperazin-1-yl)pyridin-2-yl]-5-(2,6-difluoro-4-methoxyphenyl)-1-methyl-3-oxo-2,3-dihydro-1H-pyrazol-4-yl}-4-(difluoromethoxy)benzamide | 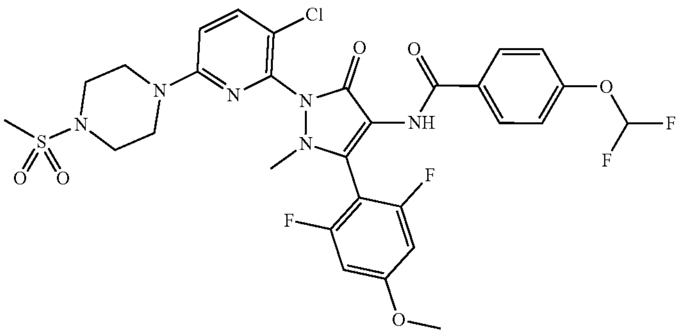 [SMILES: COc1cc(F)c(-c2c(NC(=O)c3ccc(OC(F)F)cc3)c(=O)n(-c3nc(N4CCN(S(C)(=O)=O)CC4)ccc3Cl)n2C)c(F)c1] | 1.74 B 698.9 |

TABLE 2-continued

| Ex. No. | Name | Structure | LC/MS Rt (min) Method M + H |
|---|---|---|---|
| | $^1$H NMR data for the examples in Table 2: | | |
| 248 | N-[2-(6-chloro-3-ethoxypyridin-2-yl)-5-(2,6-difluoro-4-methoxyphenyl)-1-methyl-3-oxo-2,3-dihydro-1H-pyrazol-4-yl]-4-(difluoromethoxy)benzamide | 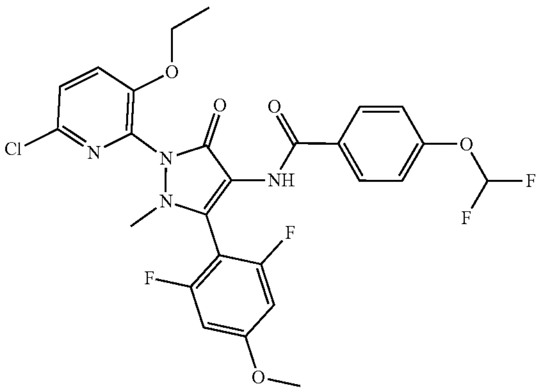 [SMILES: CCOc1ccc(Cl)nc1-n1c(=O)c(NC(=O)c2ccc(OC(F)F)cc2)c(-c2c(F)cc(OC)cc2F)n1C] | 1.82 B 580.9 |
| 249 | N-[5-(4-chlorophenyl)-1-methyl-3-oxo-2-[3-(trifluoromethyl)pyridin-2-yl]-2,3-dihydro-1H-pyrazol-4-yl]-4-(difluoromethoxy)benzamide | 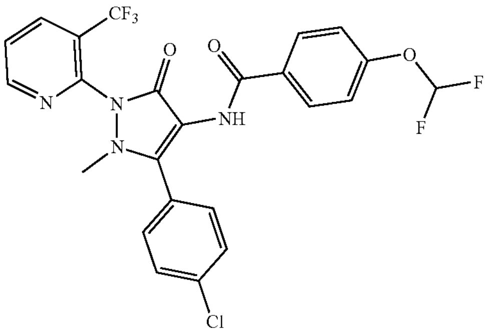 [SMILES: Cn1c(-c2ccc(Cl)cc2)c(NC(=O)c2ccc(OC(F)F)cc2)c(=O)n1-c1ncccc1C(F)(F)F] | 1.96 A 539.2 |
| 250 | 4-(difluoromethoxy)-N-[5-(4-methoxyphenyl)-1-methyl-3-oxo-2-[3-(trifluoromethyl)pyridin-2-yl]-2,3-dihydro-1H-pyrazol-4-yl]benzamide | 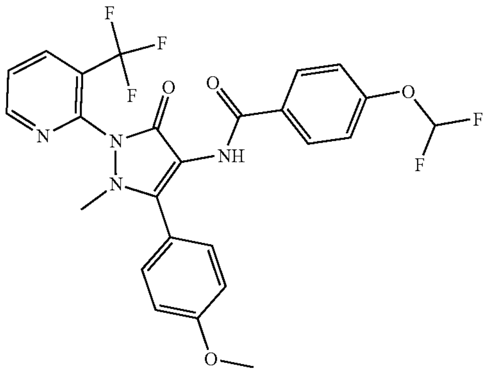 [SMILES: COc1ccc(-c2c(NC(=O)c3ccc(OC(F)F)cc3)c(=O)n(-c3ncccc3C(F)(F)F)n2C)cc1] | 1.67 A 535.2 |
| 251 | N-{2-[6-(cyclopropylamino)-3-(trifluoromethyl)pyridin-2-yl]-5-(2,6-difluoro-4-methoxyphenyl)-1-methyl-3-oxo-2,3-dihydro-1H-pyrazol-4-yl}-4-(difluoromethoxy)benzamide | 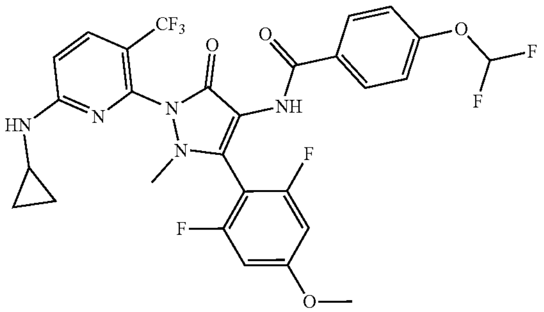 [SMILES: COc1cc(F)c(-c2c(NC(=O)c3ccc(OC(F)F)cc3)c(=O)n(-c3nc(NC4CC4)ccc3C(F)(F)F)n2C)c(F)c1] | 2.06 A 626.3 |

TABLE 2-continued

| $^1$H NMR data for the examples in Table 2: | | | |
|---|---|---|---|
| Ex. No. | Name | Structure | LC/MS Rt (min) Method M + H |
| 252 | N-[5-(2,6-difluoro-4-methoxyphenyl)-2-(6-{[(dimethylcarbamoyl)methyl]-amino}-3-(trifluoromethyl)pyridin-2-yl)-1-methyl-3-oxo-2,3-dihydro-1H-pyrazol-4-yl]-4-(difluoromethoxy)benzamide | 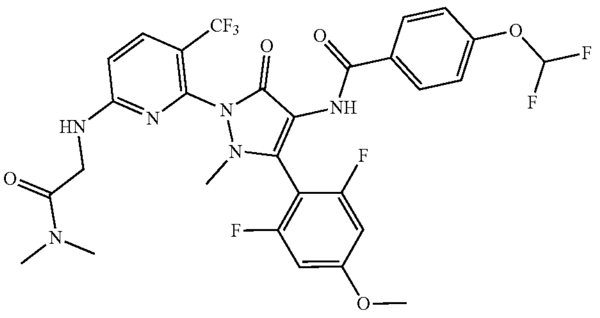 [SMILES: COc1cc(F)c(-c2c(NC(=O)c3ccc(OC(F)F)cc3)c(=O)n(-c3nc(NCC(=O)N(C)C)ccc3C(F)(F)F)n2C)c(F)c1] | 1.82 A 671.3 |
| 253 | N-[5-(2,6-difluoro-4-methoxyphenyl)-1-methyl-2-{6-[(oxetan-3-yl)amino]-3-(trifluoromethyl)pyridin-2-yl}-3-oxo-2,3-dihydro-1H-pyrazol-4-yl]-4-(difluoromethoxy)benzamide | 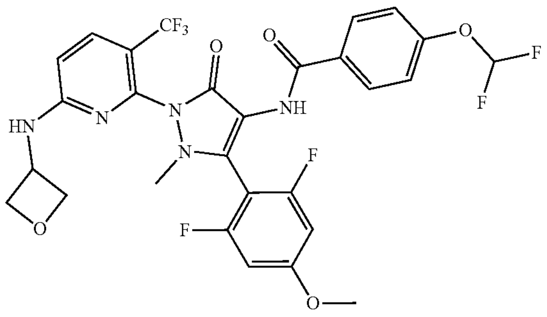 [SMILES: COc1cc(F)c(-c2c(NC(=O)c3ccc(OC(F)F)cc3)c(=O)n(-c3nc(NC4COC4)ccc3C(F)(F)F)n2C)c(F)c1] | 1.73 B 642.2 |
| 254 | N-[5-(2,6-difluoro-4-methoxyphenyl)-1-methyl-3-oxo-2-(6-{[(3R)-oxolan-3-yl]amino}-3-(trifluoromethyl)pyridin-2-yl)-2,3-dihydro-1H-pyrazol-4-yl]-4-(difluoromethoxy)benzamide | 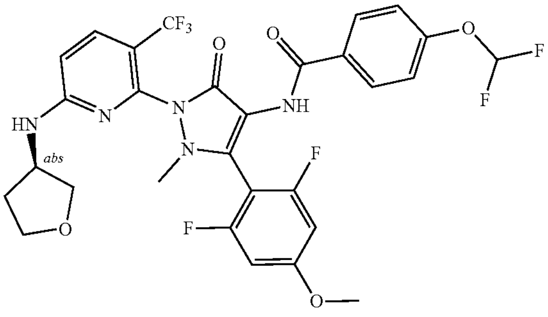 [SMILES: COc1cc(F)c(-c2c(NC(=O)c3ccc(OC(F)F)cc3)c(=O)n(-c3nc(N[C@@H]4CCOC4)ccc3C(F)(F)F)n2C)c(F)c1] | 1.88 A 656.0 |
| 255 | N-[5-(2,6-difluoro-4-methoxyphenyl)-1-methyl-3-oxo-2-{[(3S)-oxolan-3-yl]amino}-3-(trifluoromethyl)pyridin-2-yl)-2,3-dihydro-1H-pyrazol-4-yl]-4-(difluoromethoxy)benzamide | 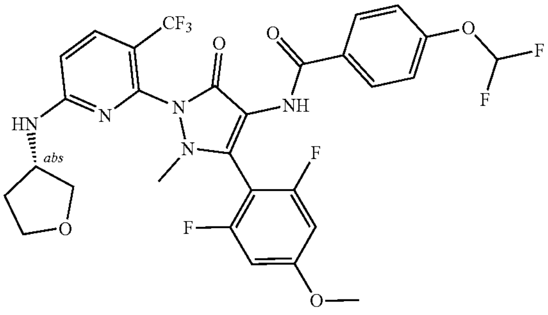 [SMILES: COc1cc(F)c(-c2c(NC(=O)c3ccc(OC(F)F)cc3)c(=O)n(-c3nc(N[C@H]4CCOC4)ccc3C(F)(F)F)n2C)c(F)c1] | 1.93 B 656.3 |

TABLE 2-continued

| $^1$H NMR data for the examples in Table 2: | | | |
|---|---|---|---|
| Ex. No. | Name | Structure | LC/MS Rt (min) Method M + H |
| 256 | N-[5-(2,6-difluoro-4-methoxyphenyl)-2-{6-[(1-hydroxy-2-methylpropan-2-yl)amino]-3-(trifluoromethyl)pyridin-2-yl}-1-methyl-3-oxo-2,3-dihydro-1H-pyrazol-4-yl]-4-(difluoromethoxy)benzamide | 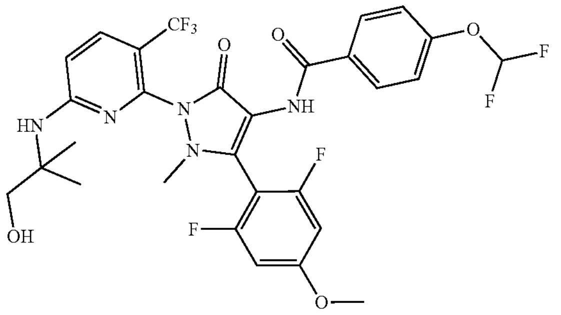 [SMILES: COc1cc(F)c(-c2c(NC(=O)c3ccc(OC(F)F)cc3)c(=O)n(-c3nc(NC(C)(C)CO)ccc3C(F)(F)F)n2C)c(F)c1] | 1.88 A 658.1 |
| 257 | N-[5-(2,6-difluoro-4-methoxyphenyl)-2-[6-methoxy-3-(trifluoromethyl)pyridin-2-yl]-1-methyl-3-oxo-2,3-dihydro-1H-pyrazol-4-yl]-4-(difluoromethoxy)benzamide | 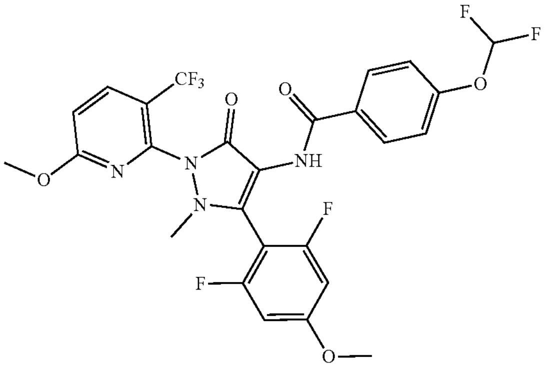 [SMILES: COc1cc(F)c(-c2c(NC(=O)c3ccc(OC(F)F)cc3)c(=O)n(-c3nc(OC)ccc3C(F)(F)F)n2C)c(F)c1] | 1.88 B 600.9 |
| 258 | N-[5-(2,6-difluoro-4-methoxyphenyl)-2-{6-[(2S)-2-(hydroxymethyl)pyrrolidin-1-yl]-3-(trifluoromethyl)pyridin-2-yl}-1-methyl-3-oxo-2,3-dihydro-1H-pyrazol-4-yl]-4-(difluoromethoxy)benzamide | 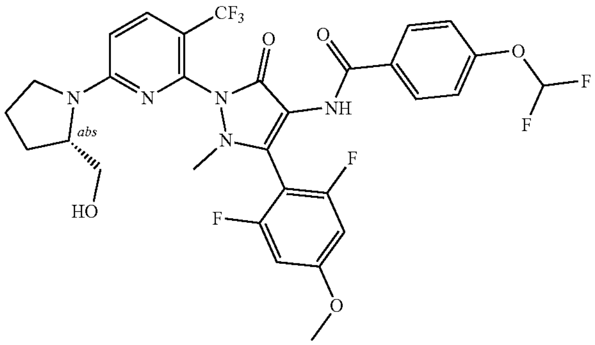 [SMILES: COc1cc(F)c(-c2c(NC(=O)c3ccc(OC(F)F)cc3)c(=O)n(-c3nc(N4CCC[C@H]4CO)ccc3C(F)(F)F)n2C)c(F)c1] | 1.88 B 670.2 |
| 259 | methyl (2S)-1-{6-[3-(2,6-difluoro-4-methoxyphenyl)-4-[4-(difluoromethoxy)benzamido]-2-methyl-5-oxo-2,5-dihydro-1H-pyrazol-1-yl]-5-(trifluoromethyl)pyridin-2-yl}pyrrolidine-2-carboxylate | 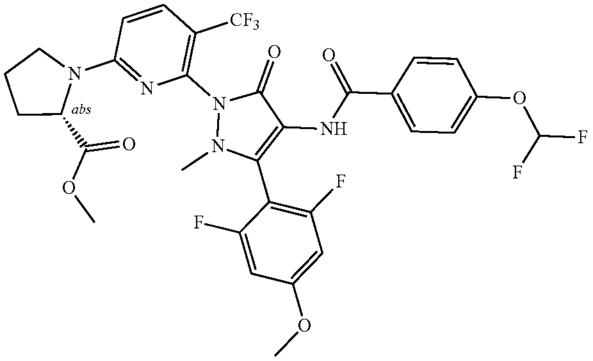 [SMILES: COC(=O)[C@@H]1CCCN1c1ccc(C(F)(F)F)c(-n2c(=O)c(NC(=O)c3ccc(OC(F)F)cc3)c(-c3c(F)cc(OC)cc3F)n2C)n1] | 2.01 B 697.9 |

TABLE 2-continued $^{1}$H NMR data for the examples in Table 2:

| Ex. No. | Name | Structure | LC/MS Rt (min) Method M + H |
|---|---|---|---|
| 260 | N-[5-(2,6-difluoro-4-methoxyphenyl)-1-methyl-2-(6-{methyl[(methylcarbamoyl)methyl]amino}-3-(trifluoromethyl)pyridin-2-yl)-3-oxo-2,3-dihydro-1H-pyrazol-4-yl]-4-(difluoromethoxy)benzamide | 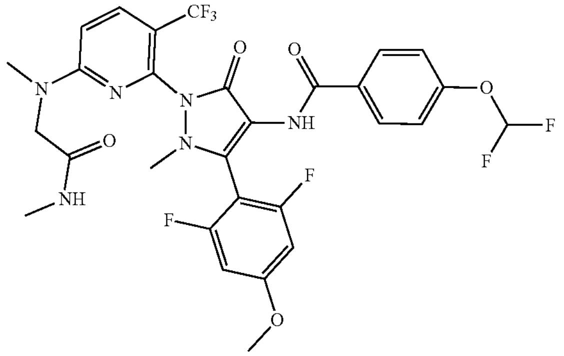 [SMILES: CNC(=O)CN(C)c1ccc(C(F)(F)F)c(-n2c(=O)c(NC(=O)c3ccc(OC(F)F)cc3)c(-c3c(F)cc(OC)cc3F)n2C)n1] | 1.61<br>A<br>671.4 |
| 261 | N-[5-(2,6-difluoro-4-methoxyphenyl)-2-{6-[(2-hydroxy-2-methylpropyl)(methyl)amino]-3-(trifluoromethyl)pyridin-2-yl}-1-methyl-3-oxo-2,3-dihydro-1H-pyrazol-4-yl]-4-(difluoromethoxy)benzamide | 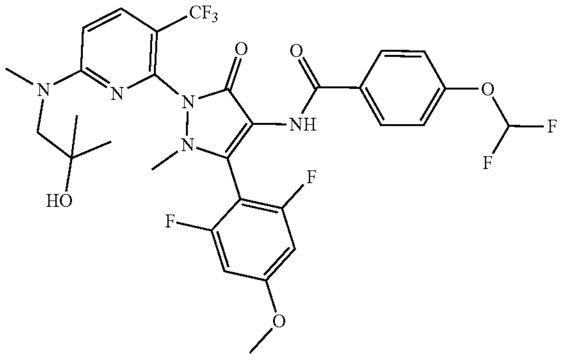 [SMILES: COc1cc(F)c(-c2c(NC(=O)c3ccc(OC(F)F)cc3)c(=O)n(-c3nc(N(C)CC(C)(C)O)ccc3C(F)(F)F)n2C)c(F)c1] | 1.92<br>B<br>672.1 |
| 262 | N-[2-(3-chloropyridin-2-yl)-5-(2-fluoro-4-methoxyphenyl)-1-methyl-3-oxo-2,3-dihydro-1H-pyrazol-4-yl]-4-(difluoromethoxy)benzamide | 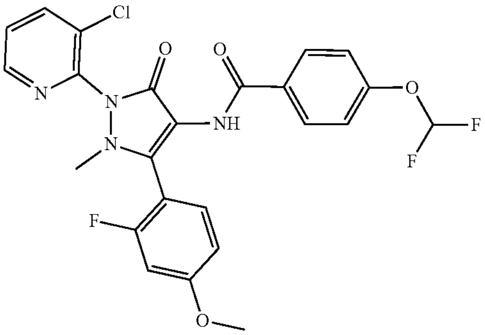 [SMILES: COc1ccc(-c2c(NC(=O)c3ccc(OC(F)F)cc3)c(=O)n(-c3ncccc3Cl)n2C)c(F)c1] | 1.65<br>B<br>519.1 |
| 263 | 4-(difluoromethoxy)-N-[5-(2-fluoro-4-methoxyphenyl)-1-methyl-3-oxo-2-[3-(trifluoromethyl)pyridin-2-yl]-2,3-dihydro-1H-pyrazol-4-yl]benzamide | 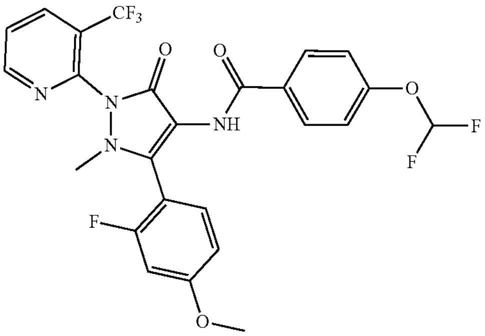 | 1.63<br>B<br>553.1 |

TABLE 2-continued

| $^1$H NMR data for the examples in Table 2: | | | |
|---|---|---|---|
| Ex. No. | Name | Structure | LC/MS Rt (min) Method M + H |
| 264 | N-(2-{6-[(cyclopropylmethyl)amino]-3-(trifluoromethyl)pyridin-2-yl}-5-(2,6-difluoro-4-methoxyphenyl)-1-methyl-3-oxo-2,3-dihydro-1H-pyrazol-4-yl)-4-(difluoromethoxy)benzamide | 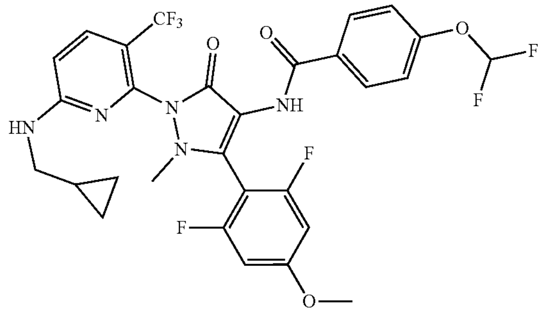 [SMILES: COc1cc(F)c(-c2c(NC(=O)c3ccc(OC(F)F)cc3)c(=O)n(-c3nc(NCC4CC4)ccc3C(F)(F)F)n2C)c(F)c1] | 2.03<br>A<br>640.1 |
| 265 | N-{2-[6-(tert-butylamino)-3-(trifluoromethyl)pyridin-2-yl]-5-(2,6-difluoro-4-methoxyphenyl)-1-methyl-3-oxo-2,3-dihydro-1H-pyrazol-4-yl}-4-(difluoromethoxy)benzamide | 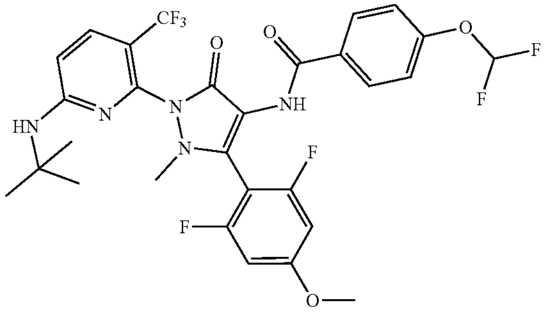 [SMILES: COc1cc(F)c(-c2c(NC(=O)c3ccc(OC(F)F)cc3)c(=O)n(-c3nc(NC(C)(C)C)ccc3C(F)(F)F)n2C)c(F)c1] | 2.13<br>B<br>642.1 |
| 266 | N-[5-(2,6-difluoro-4-methoxyphenyl)-1-methyl-2-{6-[(1-methylcyclopropyl)amino]-3-(trifluoromethyl)pyridin-2-yl}-3-oxo-2,3-dihydro-1H-pyrazol-4-yl]-4-(difluoromethoxy)benzamide | 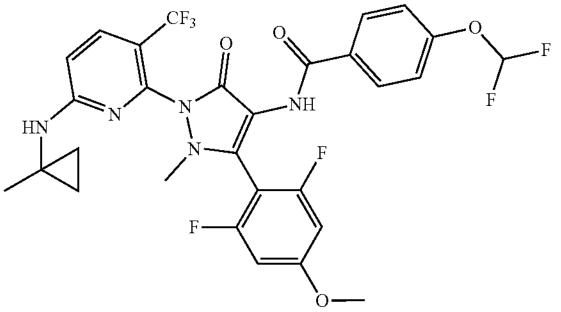 [SMILES: COc1cc(F)c(-c2c(NC(=O)c3ccc(OC(F)F)cc3)c(=O)n(-c3nc(NC4(C)CC4)ccc3C(F)(F)F)n2C)c(F)c1] | 2.10<br>min,<br>B<br>640.0 |
| 267 | N-{2-[6-(dicyclopropylamino)-3-(trifluoromethyl)pyridin-2-yl]-5-(2,6-difluoro-4-methoxyphenyl)-1-methyl-3-oxo-2,3-dihydro-1H-pyrazol-4-yl}-4-(difluoromethoxy)benzamide | 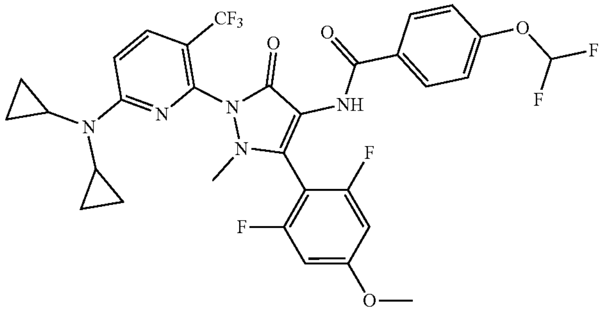 [SMILES: COc1cc(F)c(-c2c(NC(=O)c3ccc(OC(F)F)cc3)c(=O)n(-c3nc(N(C4CC4)C4CC4)ccc3C(F)(F)F)n2C)c(F)c1] | 2.17<br>B<br>666.1 |

TABLE 2-continued

| $^1$H NMR data for the examples in Table 2: | | | |
|---|---|---|---|
| Ex. No. | Name | Structure | LC/MS Rt (min) Method M + H |
| 268 | N-[5-(2,6-difluoro-4-methoxyphenyl)-2-[6-(4-methanesulfonylpiperazin-1-yl)-3-(trifluoromethyl)pyridin-2-yl]-1-methyl-3-oxo-2,3-dihydro-1H-pyrazol-4-yl]-4-(difluoromethoxy)benzamide | 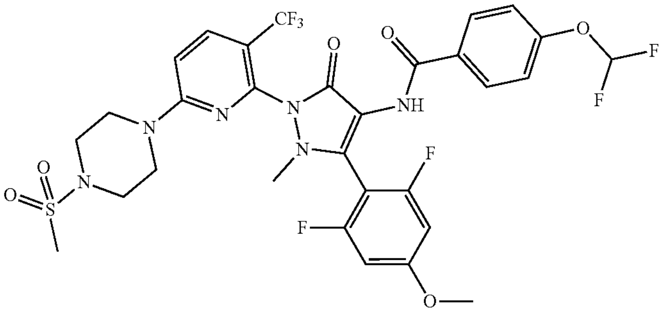 [SMILES: COc1cc(F)c(-c2c(NC(=O)c3ccc(OC(F)F)cc3)c(=O)n(-c3nc(N4CCN(S(C)(=O)=O)CC4)ccc3C(F)(F)F)n2C)c(F)c1] | 1.86 A 732.9 |
| 269 | N-[5-(2,6-difluoro-4-methoxyphenyl)-1-methyl-3-oxo-2-{6-[4-(2,2,2-trifluoroethyl)piperazin-1-yl]-3-(trifluoromethyl)pyridin-2-yl}-2,3-dihydro-1H-pyrazol-4-yl]-4-(difluoromethoxy)benzamide | 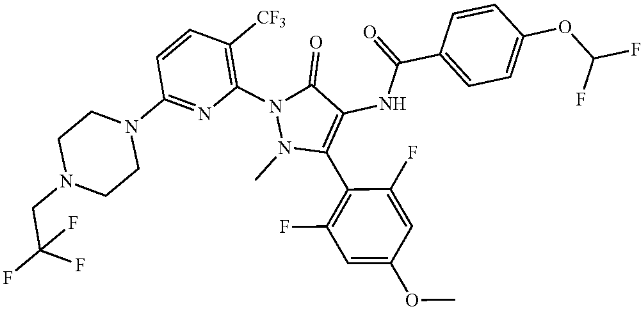 [SMILES: COc1cc(F)c(-c2c(NC(=O)c3ccc(OC(F)F)cc3)c(=O)n(-c3nc(N4CCN(CC(F)(F)F)CC4)ccc3C(F)(F)F)n2C)c(F)c1] | 2.15 B 737.0 |
| 270 | N-[5-(2,6-difluoro-4-methoxyphenyl)-2-{6-[4-(2,2-difluoroethyl)piperazin-1-yl]-3-(trifluoromethyl)pyridin-2-yl}-1-methyl-3-oxo-2,3-dihydro-1H-pyrazol-4-yl]-4-(difluoromethoxy)benzamide | 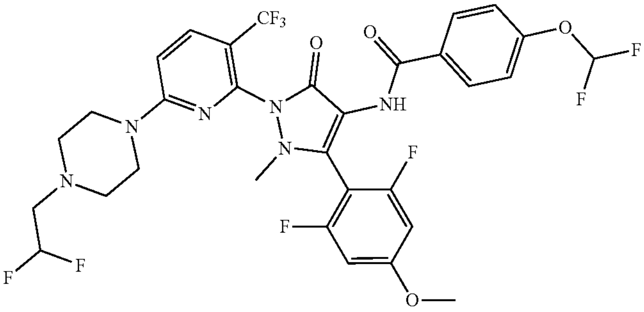 [SMILES: COc1cc(F)c(-c2c(NC(=O)c3ccc(OC(F)F)cc3)c(=O)n(-c3nc(N4CCN(CC(F)F)CC4)ccc3C(F)(F)F)n2C)c(F)c1] | 2.05 A 718.9 |
| 271 | N-[5-(2,6-difluoro-4-methoxyphenyl)-2-{6-[(2-hydroxy-2-methylpropyl)amino]-3-(trifluoromethyl)pyridin-2-yl}-1-methyl-3-oxo-2,3-dihydro-1H-pyrazol-4-yl]-4-(difluoromethoxy)benzamide | 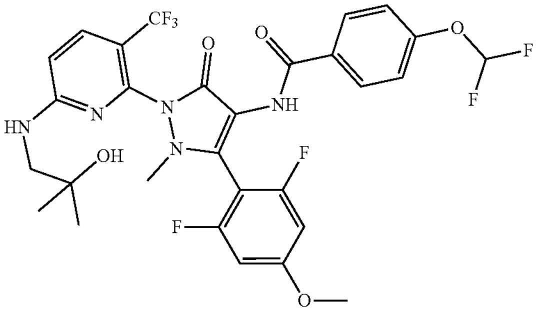 [SMILES: COc1cc(F)c(-c2c(NC(=O)c3ccc(OC(F)F)cc3)c(=O)n(-c3nc(NCC(C)(C)O)ccc3C(F)(F)F)n2C)c(F)c1] | 1.91 A 658.4 |

TABLE 2-continued

| $^1$H NMR data for the examples in Table 2: | | | |
|---|---|---|---|
| Ex. No. | Name | Structure | LC/MS Rt (min) Method M + H |
| 272 | N-[5-(2,6-difluoro-4-methoxyphenyl)-2-(6-{[(2S)-2-hydroxypropyl]amino}-3-(trifluoromethyl)pyridin-2-yl)-1-methyl-3-oxo-2,3-dihydro-1H-pyrazol-4-yl]-4-(difluoromethoxy)benzamide | 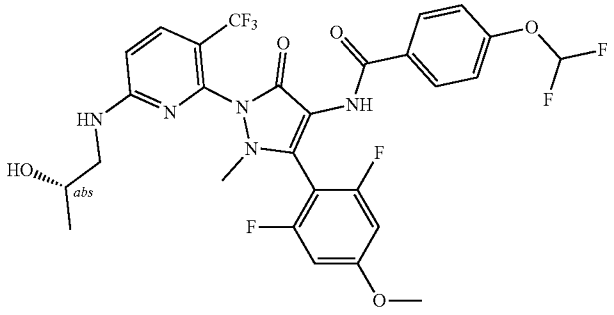 [SMILES: COc1cc(F)c(-c2c(NC(=O)c3ccc(OC(F)F)cc3)c(=O)n(-c3nc(NC[C@H](C)O)ccc3C(F)(F)F)n2C)c(F)c1] | 1.76 A 644.3 |
| 273 | N-[5-(2,6-difluoro-4-methoxyphenyl)-2-(6-{(2R)-2-hydroxypropyl]amino}-3-(trifluoromethyl)pyridin-2-yl)-1-methyl-3-oxo-2,3-dihydro-1H-pyrazol-4-yl]-4-(difluoromethoxy)benzamide | 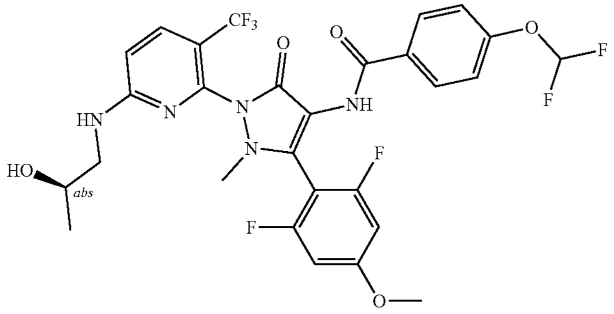 [SMILES: COc1cc(F)c(-c2c(NC(=O)c3ccc(OC(F)F)cc3)c(=O)n(-c3nc(NC[C@@H](C)O)ccc3C(F)(F)F)n2C)c(F)c1] | 1.85 B 644.1 |
| 274 | N-[5-(2,6-difluoro-4-methoxyphenyl)-1-methyl-3-oxo-2-(6-{[(2S)-3,3,3-trifluoro-2-hydroxypropyl]amino}-3-(trifluoromethyl)pyridin-2-yl)-2,3-dihydro-1H-pyrazol-4-yl]-4-(difluoromethoxy)benzamide | 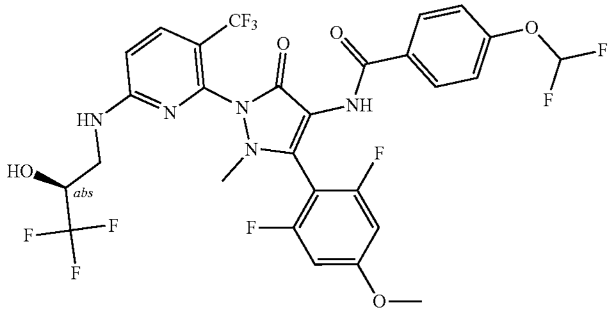 [SMILES: COc1cc(F)c(-c2c(NC(=O)c3ccc(OC(F)F)cc3)c(=O)n(-c3nc(NC[C@H](O)C(F)(F)F)ccc3C(F)(F)F)n2C)c(F)c1] | 1.95 A 697.9 |
| 275 | N-[5-(2,6-difluoro-4-methoxyphenyl)-2-[6-(2-hydroxypropan-2-yl)-3-(trifluoromethyl)pyridin-2-yl]-1-methyl-3-oxo-2,3-dihydro-1H-pyrazol-4-yl]-4-(difluoromethoxy)benzamide | 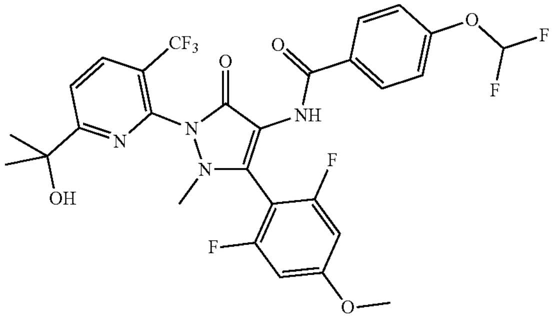 [SMILES: COc1cc(F)c(-c2c(NC(=O)c3ccc(OC(F)F)cc3)c(=O)n(-c3nc(C(C)(C)O)ccc3C(F)(F)F)n2C)c(F)c1] | 1.84 A 629.1 |

TABLE 2-continued

| $^1$H NMR data for the examples in Table 2: | | | |
|---|---|---|---|
| Ex. No. | Name | Structure | LC/MS Rt (min) Method M + H |
| 276 | N-{2-[3-chloro-6-(2-hydroxypropan-2-yl)pyridin-2-yl]-5-(2,6-difluoro-4-methoxyphenyl)-1-methyl-3-oxo-2,3-dihydro-1H-pyrazol-4-yl}-4-(difluoromethoxy)benzamide | 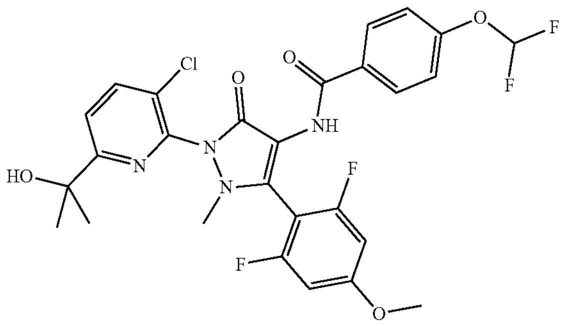 [SMILES: COc1cc(F)c(-c2c(NC(=O)c3ccc(OC(F)F)cc3)c(=O)n(-c3nc(C(C)(C)O)ccc3Cl)n2C)c(F)c1] | 1.75 A 595.1 |
| 277 | N-[5-(4-cyclopropylphenyl)-1-methyl-3-oxo-2-[3-(trifluoromethyl)pyridin-2-yl]-2,3-dihydro-1H-pyrazol-4-yl]-4-(difluoromethoxy)benzamide | 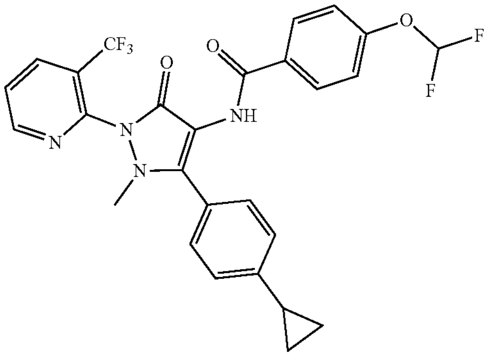 [SMILES: Cn1c(-c2ccc(C3CC3)cc2)c(NC(=O)c2ccc(OC(F)F)cc2)c(=O)n1-c1ncccc1C(F)(F)F] | 1.97 A 544.9 |
| 278 | N-[5-(2,6-difluoro-4-methoxyphenyl)-2-[6-(2-methoxyethoxy)-3-(trifluoromethyl)pyridin-2-yl]-1-methyl-3-oxo-2,3-dihydro-1H-pyrazol-4-yl]-4-(difluoromethoxy)benzamide | 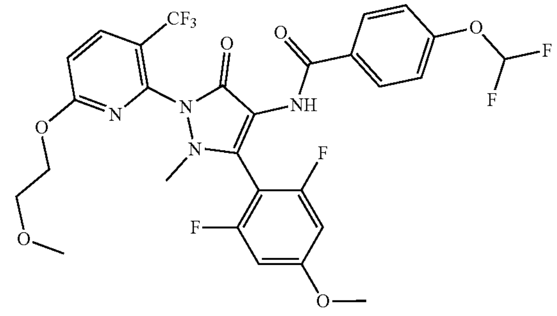 [SMILES: COCCOc1ccc(C(F)(F)F)c(-n2c(=O)c(NC(=O)c3ccc(OC(F)F)cc3)c(-c3c(F)cc(OC)cc3F)n2C)n1] | 1.91 A 645.4 |
| 279 | N-(2-{6-[(2-carbamoyl-2,2-dimethylethyl)amino]-3-(trifluoromethyl)pyridin-2-yl}-5-(2,6-difluoro-4-methoxyphenyl)-1-methyl-3-oxo-2,3-dihydro-1H-pyrazol-4-yl)-4-(difluoromethoxy)benzamide | 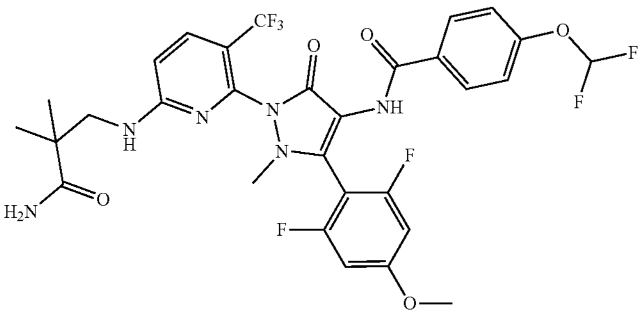 [SMILES: COc1cc(F)c(-c2c(NC(=O)c3ccc(OC(F)F)cc3)c(=O)n(-c3nc(NCC(C)(C)C(N)=O)ccc3C(F)(F)F)n2C)c(F)c1] | 1.82 A 685.2 |

TABLE 2-continued

| Ex. No. | Name | Structure | LC/MS Rt (min) Method M + H |
|---|---|---|---|
| | $^1$H NMR data for the examples in Table 2: | | |
| 280 | N-[5-(2,6-difluoro-4-methoxyphenyl)-2-{6-[(3S)-3-hydroxypyrrolidin-1-yl]-3-(trifluoromethyl)pyridin-2-yl}-1-methyl-3-oxo-2,3-dihydro-1H-pyrazol-4-yl]-4-(difluoromethoxy)benzamide | 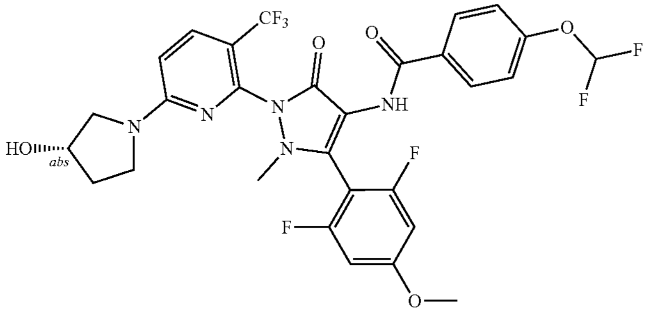 [SMILES: COc1cc(F)c(-c2c(NC(=O)c3ccc(OC(F)F)cc3)c(=O)n(-c3nc(N4CC[C@H](O)C4)ccc3C(F)(F)F)n2C)c(F)c1] | 1.85<br>A<br>655.8 |
| 281 | 4-(difluoromethoxy)-N-{5-[4-(difluoromethoxy)phenyl]-1-methyl-3-oxo-2-[3-(trifluoromethyl)pyridin-2-yl]-2,3-dihydro-1H-pyrazol-4-yl}benzamide | 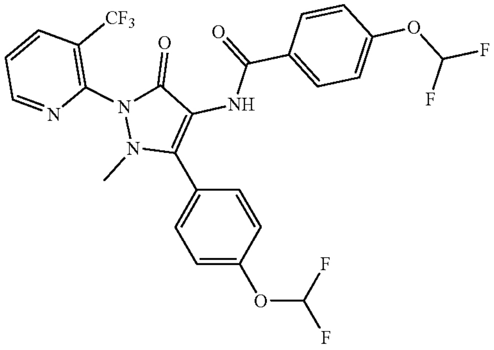 [SMILES: Cn1c(-c2ccc(OC(F)F)cc2)c(NC(=O)c2ccc(OC(F)F)cc2)c(=O)n1-c1ncccc1C(F)(F)F] | 1.84<br>A<br>571.2 |
| 282 | N-[5-(2,6-difluoro-4-methoxyphenyl)-2-[6-(3-hydroxy-3-methylpyrrolidin-1-yl)-3-(trifluoromethyl)pyridin-2-yl]-1-methyl-3-oxo-2,3-dihydro-1H-pyrazol-4-yl]-4-(difluoromethoxy)benzamide | 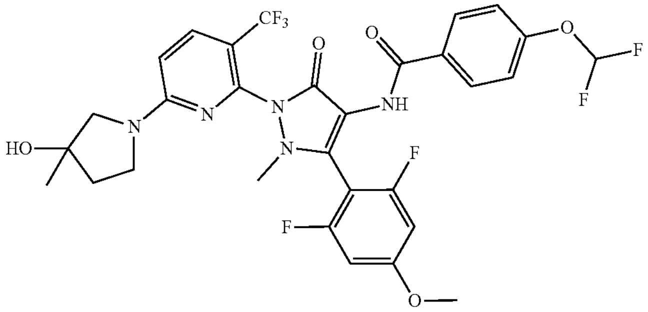 [SMILES: COc1cc(F)c(-c2c(NC(=O)c3ccc(OC(F)F)cc3)c(=O)n(-c3nc(N4CCC(C)(O)C4)ccc3C(F)(F)F)n2C)c(F)c1] | 1.76<br>A<br>670.0 |
| 283 | N-[5-(2,6-difluoro-4-methoxyphenyl)-2-(6-{[(1-hydroxycyclopropyl)methyl]amino}-3-(trifluoromethyl)pyridin-2-yl)-1-methyl-3-oxo-2,3-dihydro-1H-pyrazol-4-yl]-4-(difluoromethoxy)benzamide | 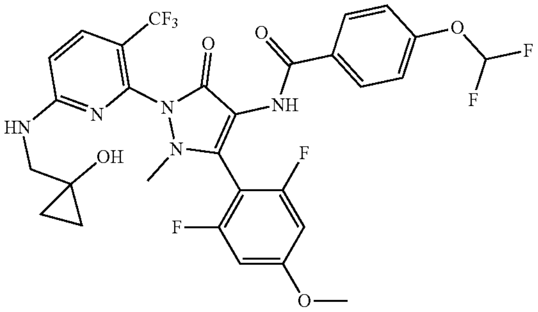 [SMILES: COc1cc(F)c(-c2c(NC(=O)c3ccc(OC(F)F)cc3)c(=O)n(-c3nc(NCC4(O)CC4)ccc3C(F)(F)F)n2C)c(F)c1] | 1.85<br>B<br>656.2 |

TABLE 2-continued

| Ex. No. | Name | Structure | LC/MS Rt (min) Method M + H |
|---|---|---|---|
| | $^1$H NMR data for the examples in Table 2: | | |
| 284 | N-[5-(2,6-difluoro-4-methoxyphenyl)-2-[6-(3-hydroxy-3-methylpyrrolidin-1-yl)-3-(trifluoromethyl)pyridin-2-yl]-1-methyl-3-oxo-2,3-dihydro-1H-pyrazol-4-yl]-4-(difluoromethoxy)benzamide | 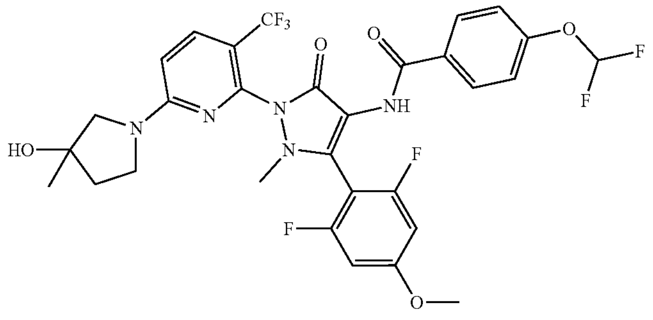 [SMILES: COc1cc(F)c(-c2c(NC(=O)c3ccc(OC(F)F)cc3)c(=O)n(-c3nc(N4CCC(C)(O)C4)ccc3C(F)(F)F)n2C)c(F)c1] | 1.76 A 670.0 |
| 285 | N-[5-(2,6-difluoro-4-methoxyphenyl)-2-[6-(2-hydroxyethoxy)-3-(trifluoromethyl)pyridin-2-yl]-1-methyl-3-oxo-2,3-dihydro-1H-pyrazol-4-yl]-4-(difluoromethoxy)benzamide | 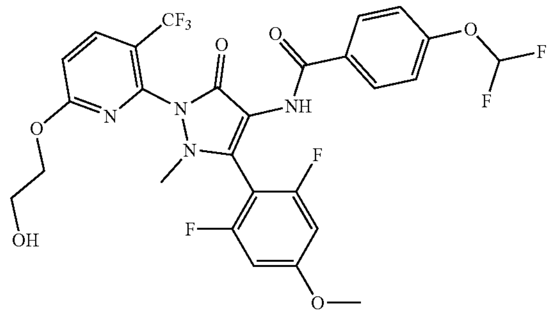 [SMILES: COc1cc(F)c(-c2c(NC(=O)c3ccc(OC(F)F)cc3)c(=O)n(-c3nc(OCCO)ccc3C(F)(F)F)n2C)c(F)c1] | 1.74 A 631.1 |
| 286 | N-[5-(2,6-difluoro-4-methoxyphenyl)-2-[6-ethoxy-3-(trifluoromethyl)pyridin-2-yl]-1-methyl-3-oxo-2,3-dihydro-1H-pyrazol-4-yl]-4-(difluoromethoxy)benzamide | 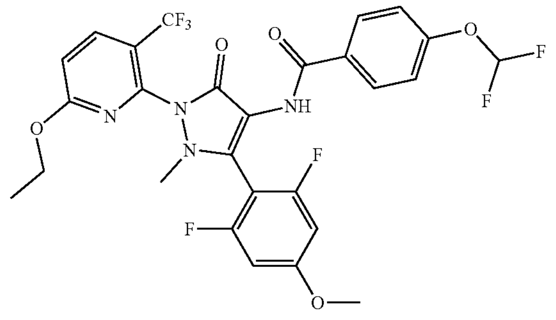 [SMILES: CCOc1ccc(C(F)(F)F)c(-n2c(=O)c(NC(=O)c3ccc(OC(F)F)cc3)c(-c3c(F)cc(OC)cc3F)n2C)n1] | 2.04 A 615.3 |
| 287 | N-{2-[6-(cyclopropylmethoxy)-3-(trifluoromethyl)pyridin-2-yl]-5-(2,6-difluoro-4-methoxyphenyl)-1-methyl-3-oxo-2,3-dihydro-1H-pyrazol-4-yl}-4-(difluoromethoxy)benzamide | 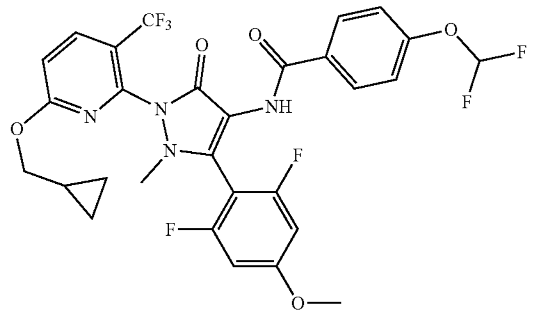 [SMILES: COc1cc(F)c(-c2c(NC(=O)c3ccc(OC(F)F)cc3)c(=O)n(-c3nc(OCC4CC4)ccc3C(F)(F)F)n2C)c(F)c1] | 2.04 A 641.2 |

TABLE 2-continued

| $^1$H NMR data for the examples in Table 2: | | | |
|---|---|---|---|
| Ex. No. | Name | Structure | LC/MS Rt (min) Method M + H |
| 288 | N-[5-(2,6-difluoro-4-methoxyphenyl)-2-[6-(2-hydroxy-2-methylpropoxy)-3-(trifluoromethyl)pyridin-2-yl]-1-methyl-3-oxo-2,3-dihydro-1H-pyrazol-4-yl]-4-(difluoromethoxy)benzamide | 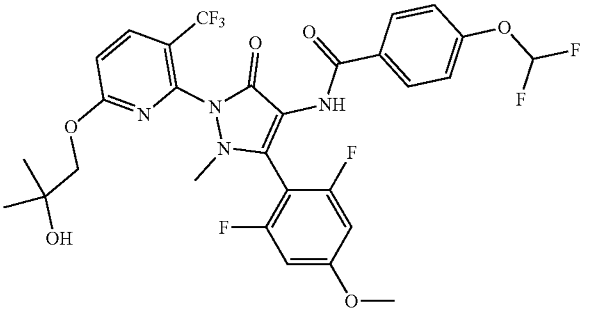 [SMILES: COc1cc(F)c(-c2c(NC(=O)c3ccc(OC(F)F)cc3)c(=O)n(-c3nc(OCC(C)(C)O)ccc3C(F)(F)F)n2C)c(F)c1] | 1.86 A 659.1 |
| 289 | methyl 2-({6-[3-(2,6-difluoro-4-methoxyphenyl)-4-[4-(difluoromethoxy)benzamido]-2-methyl-5-oxo-2,5-dihydro-1H-pyrazol-1-yl]-5-(trifluoromethyl)pyridin-2-yl}oxy)acetate | 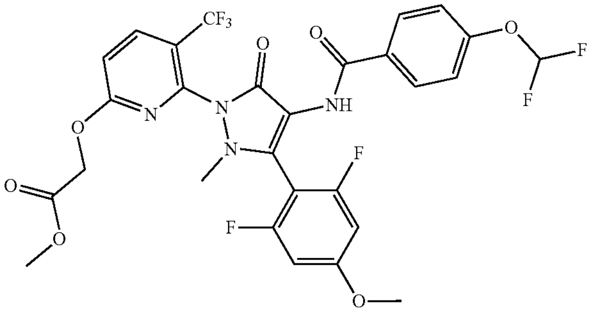 [SMILES: COC(=O)COc1ccc(C(F)(F)F)c(-n2c(=O)c(NC(=O)c3ccc(OC(F)F)cc3)c(-c3c(F)cc(OC)cc3F)n2C)n1] | 1.90 A find 659.1 |
| 290 | N-[5-(2,6-difluoro-4-methoxyphenyl)-2-[6-({[1-(hydroxymethyl)cyclobutyl]-methyl}amino)-3-(trifluoromethyl)pyridin-2-yl]-1-methyl-3-oxo-2,3-dihydro-1H-pyrazol-4-yl]-4-(difluoromethoxy)benzamide | 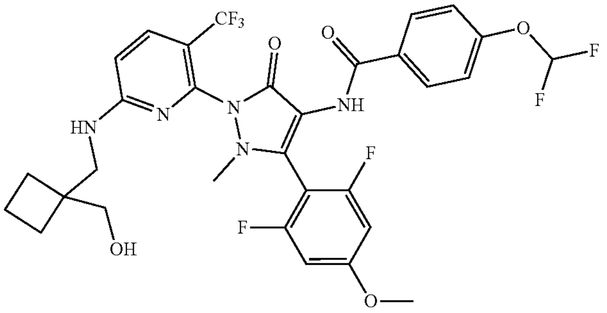 [SMILES: COc1cc(F)c(-c2c(NC(=O)c3ccc(OC(F)F)cc3)c(=O)n(-c3nc(NCC4(CO)CCC4)ccc3C(F)(F)F)n2C)c(F)c1] | 1.95 A 683.9 |
| 291 | N-{2-[3-cyano-6-(2-hydroxypropan-2-yl)pyridin-2-yl]-5-(2,6-difluoro-4-methoxyphenyl)-1-methyl-3-oxo-2,3-dihydro-1H-pyrazol-4-yl}-4-(difluoromethoxy)benzamide | 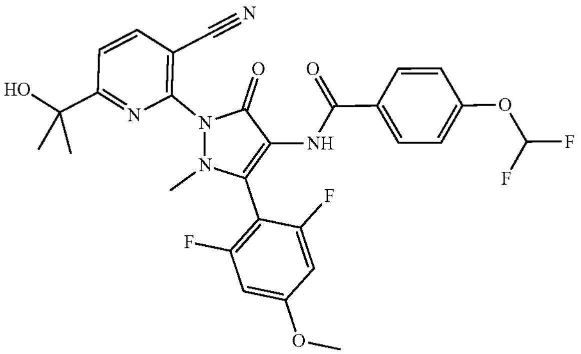 [SMILES: COc1cc(F)c(-c2c(NC(=O)c3ccc(OC(F)F)cc3)c(=O)n(-c3nc(C(C)(C)O)ccc3C#N)n2C)c(F)c1] | 1.83 A 586.3 |

TABLE 2-continued

| $^1$H NMR data for the examples in Table 2: | | | |
|---|---|---|---|
| Ex. No. | Name | Structure | LC/MS Rt (min) Method M + H |
| 292 | N-[5-(2,6-difluoro-4-methoxyphenyl)-2-{6-[(3R)-3-(hydroxymethyl)pyrrolidin-1-yl]-3-(trifluoromethyl)pyridin-2-yl}-1-methyl-3-oxo-2,3-dihydro-1H-pyrazol-4-yl]-4-(difluoromethoxy)benzamide | 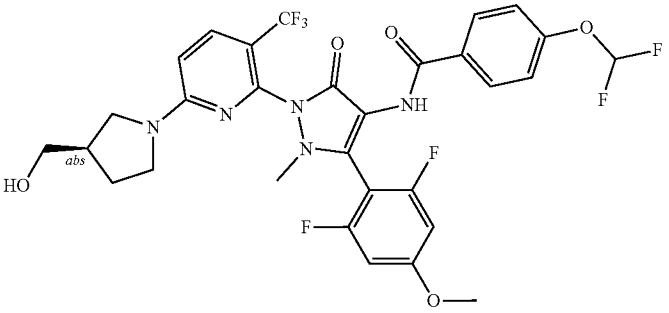 [SMILES: COc1cc(F)c(-c2c(NC(=O)c3ccc(OC(F)F)cc3)c(=O)n(-c3nc(N4CC[C@@H](CO)C4)ccc3C(F)(F)F)n2C)c(F)c1] | 1.86 A 667.9 |
| 293 | 4-(difluoromethoxy)-N-[5-(3-fluoro-4-methoxyphenyl)-1-methyl-3-oxo-2-[3-(trifluoromethyl)pyridin-2-yl]-2,3-dihydro-1H-pyrazol-4-yl]benzamide | 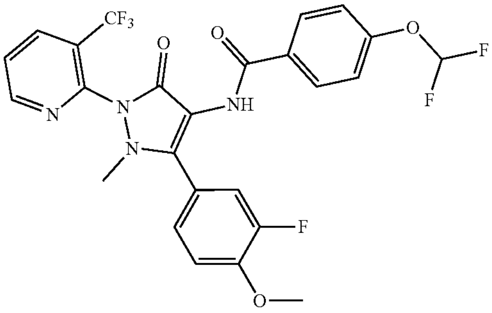 [SMILES: COc1ccc(-c2c(NC(=O)c3ccc(OC(F)F)cc3)c(=O)n(-c3ncccc3C(F)(F)F)n2C)cc1F] | 1.76 B 552.8 |
| 294 | N-[2-(3-chloropyridin-2-yl)-5-(3-fluoro-4-methoxyphenyl)-1-methyl-3-oxo-2,3-dihydro-1H-pyrazol-4-yl]-4-(difluoromethoxy)benzamide | 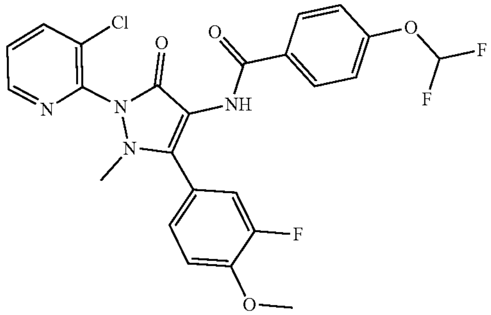 [SMILES: COc1ccc(-c2c(NC(=O)c3ccc(OC(F)F)cc3)c(=O)n(-c3ncccc3Cl)n2C)cc1F] | 1.67 A 519.3 |
| 295 | N-{2-[6-chloro-3-(trifluoromethyl)pyridin-2-yl]-5-(2-fluoro-4-methoxyphenyl)-1-methyl-3-oxo-2,3-dihydro-1H-pyrazol-4-yl}-4-(difluoromethoxy)benzamide | 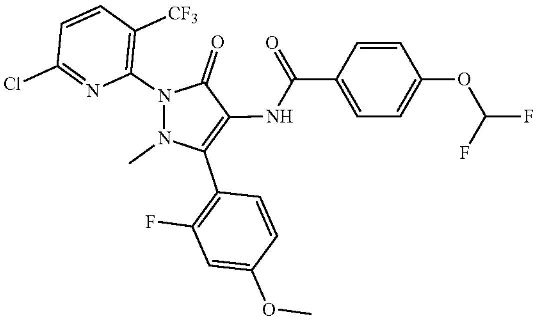 [SMILES: COc1ccc(-c2c(NC(=O)c3ccc(OC(F)F)cc3)c(=O)n(-c3nc(Cl)ccc3C(F)(F)F)n2C)c(F)c1] | 1.93 A 587.1 |

TABLE 2-continued

| Ex. No. | Name | Structure | LC/MS Rt (min) Method M + H |
|---|---|---|---|
| | | $^1$H NMR data for the examples in Table 2: | |
| 296 | N-[2-(3,6-dichloropyridin-2-yl)-5-(2-fluoro-6-hydroxy-4-methoxyphenyl)-1-methyl-3-oxo-2,3-dihydro-1H-pyrazol-4-yl]-4-(difluoromethoxy)benzamide | 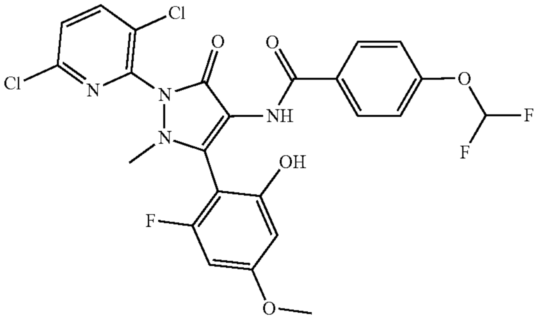 [SMILES: COc1cc(O)c(-c2c(NC(=O)c3ccc(OC(F)F)cc3)c(=O)n(-c3nc(Cl)ccc3Cl)n2C)c(F)c1] | 1.64 A 569.1 |
| 297 | N-[5-(2,6-difluoro-4-methoxyphenyl)-1-methyl-3-oxo-2-[6-(2-oxopyrrolidin-1-yl)-3-(tifluoromethyl)pyridin-2-yl]-2,3-dihydro-1H-pyrazol-4-yl]-4-(difluoromethoxy)benzamide | 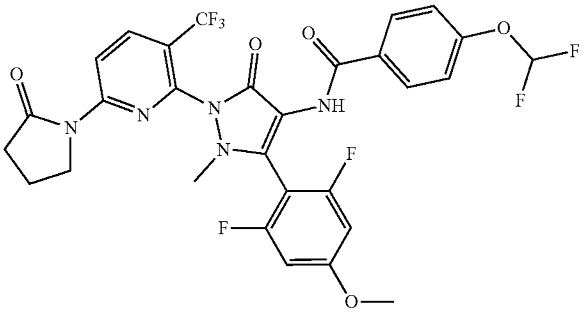 [SMILES: COc1cc(F)c(-c2c(NC(=O)c3ccc(OC(F)F)cc3)c(=O)n(-c3nc(N4CCCC4=O)ccc3C(F)(F)F)n2C)c(F)c1] | 1.93 A 653.9 |
| 298 | N-{2-[3-chloro-6-(2-hydroxy-2-methylpropoxy)pyridin-2-yl]-5-(2,6-difluoro-4-methoxyphenyl)-1-methyl-3-oxo-2,3-dihydro-1H-pyrazol-4-yl}-4-(difluoromethoxy)benzamide | 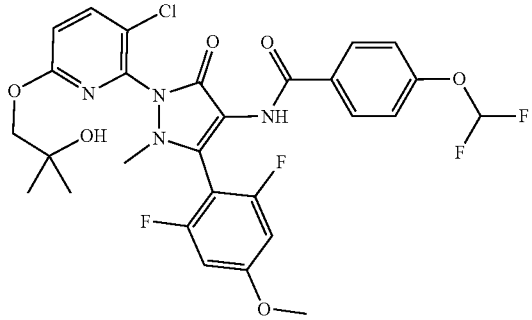 [SMILES: COc1cc(F)c(-c2c(NC(=O)c3ccc(OC(F)F)cc3)c(=O)n(-c3nc(OCC(C)(C)O)ccc3Cl)n2C)c(F)c1] | 1.76 B 625.1 |
| 299 | N-[2-(3-chloro-6-{6-hydroxy-2-azaspiro[3.3]heptan-2-yl}pyridin-2-yl)-5-(2,6-difluoro-4-methoxyphenyl)-1-methyl-3-oxo-2,3-dihydro-1H-pyrazol-4-yl]-4-(difluoromethoxy)benzamide | 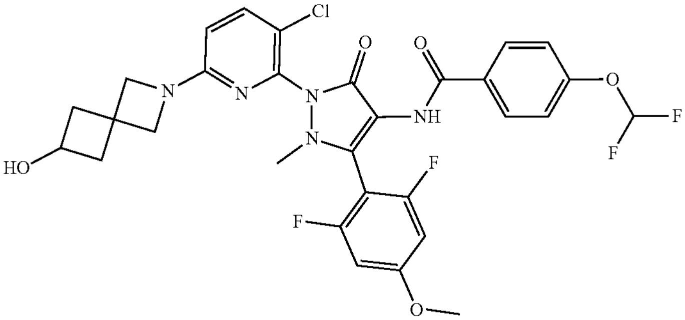 [SMILES: COc1cc(F)c(-c2c(NC(=O)c3ccc(OC(F)F)cc3)c(=O)n(-c3nc(N4CC5(CC(O)C5)C4)ccc3Cl)n2C)c(F)c1] | 1.71 B 648.1 |

TABLE 2-continued

| $^1$H NMR data for the examples in Table 2: | | | |
|---|---|---|---|
| Ex. No. | Name | Structure | LC/MS Rt (min) Method M + H |
| 300 | N-{2-[3-chloro-6-(3-hydroxyazetidin-1-yl)pyridin-2-yl]-5-(2,6-difluoro-4-methoxyphenyl)-1-methyl-3-oxo-2,3-dihydro-1H-pyrazol-4-yl}-4-(difluoromethoxy)benzamide | 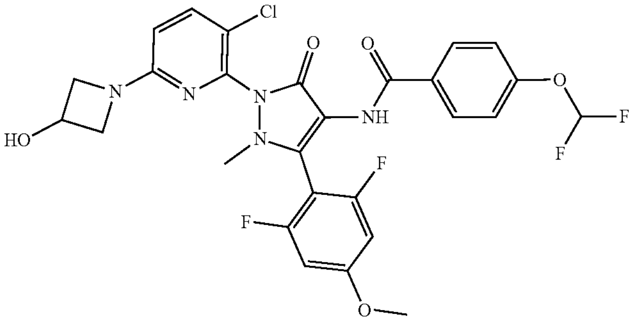 [SMILES: COc1cc(F)c(-c2c(NC(=O)c3ccc(OC(F)F)cc3)c(=O)n(-c3nc(N4CC(O)C4)ccc3Cl)n2C)c(F)c1] | 1.68 B 607.8 |
| 301 | 4-(difluoromethoxy)-N-{1-methyl-3-oxo-5-[4-(trifluoromethyl)phenyl]-2-[3-(trifluoromethyl)pyridin-2-yl]-2,3-dihydro-1H-pyrazol-4-yl}benzamide | 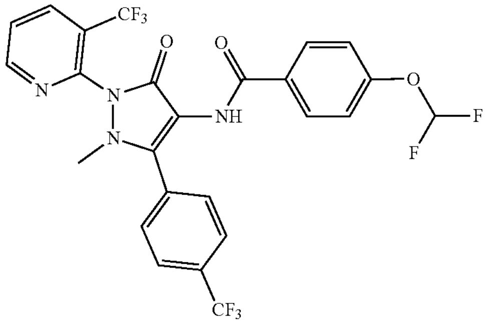 [SMILES: Cn1c(-c2ccc(C(F)(F)F)cc2)c(NC(=O)c2ccc(OC(F)F)cc2)c(=O)n1-c1ncccc1C(F)(F)F] | 1.98 B 573.1 |
| 302 | N-[5-(2,6-difluoro-4-methoxyphenyl)-1-methyl-3-oxo-2-[3-(trifluoromethyl)-6-[2-(trifluoromethyl)pyrrolidin-1-yl]pyridin-2-yl]-2,3-dihydro-1H-pyrazol-4-yl]-4-(difluoromethoxy)benzamide | 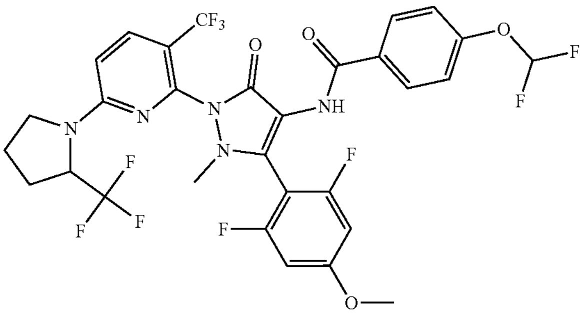 [SMILES: COc1cc(F)c(-c2c(NC(=O)c3ccc(OC(F)F)cc3)c(=O)n(-c3nc(N4CCCC4C(F)(F)F)ccc3C(F)(F)F)n2C)c(F)c1] | 2.23 A 708 |
| 303 | 1-{6-[3-(2,6-difluoro-4-methoxyphenyl)-4-[4-(difluoromethoxy)benzamido]-2-methyl-5-oxo-2,5-dihydro-1H-pyrazol-1-yl]-5-(trifluoromethyl)pyridin-2-yl}pyrrolidine-3-carboxamide | 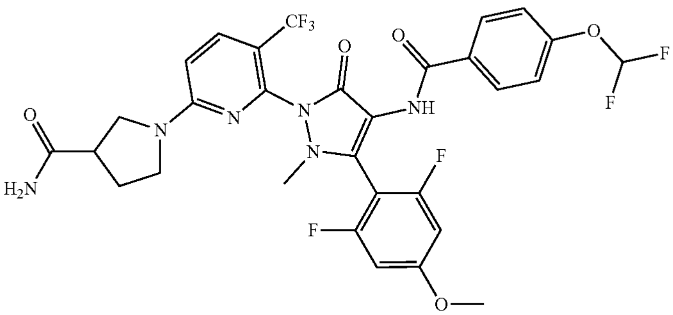 [SMILES: COc1cc(F)c(-c2c(NC(=O)c3ccc(OC(F)F)cc3)c(=O)n(-c3nc(N4CCC(C(N)=O)C4)ccc3C(F)(F)F)n2C)c(F)c1] | 1.73 A 683.1 |

TABLE 2-continued

| $^1$H NMR data for the examples in Table 2: | | | |
|---|---|---|---|
| Ex. No. | Name | Structure | LC/MS Rt (min) Method M + H |
| 304 | 4-(difluoromethoxy)-N-{1-methyl-3-oxo-5-[4-(trifluoromethoxy)phenyl]-2-[3-(trifluoromethyl)pyridin-2-yl]-2,3-dihydro-1H-pyrazol-4-yl}benzamide | 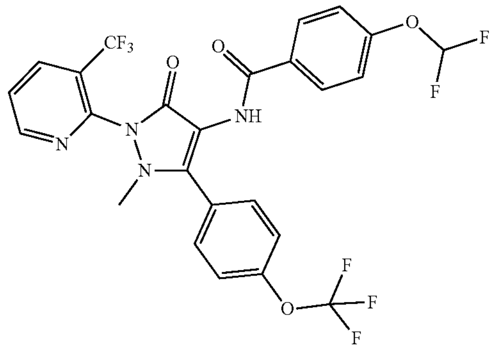 [SMILES: Cn1c(-c2ccc(OC(F)(F)F)cc2)c(NC(=O)c2ccc(OC(F)F)cc2)c(=O)n1-c1ncccc1C(F)(F)F] | 2.03 A 589.0 |
| 305 | 1-{6-[3-(2,6-difluoro-4-methoxyphenyl)-4-[4-(difluoromethoxy)benzamido]-2-methyl-5-oxo-2,5-dihydro-1H-pyrazol-1-yl]-5-(trifluoromethyl)pyridin-2-yl}pyrrolidine-3-carboxamide | 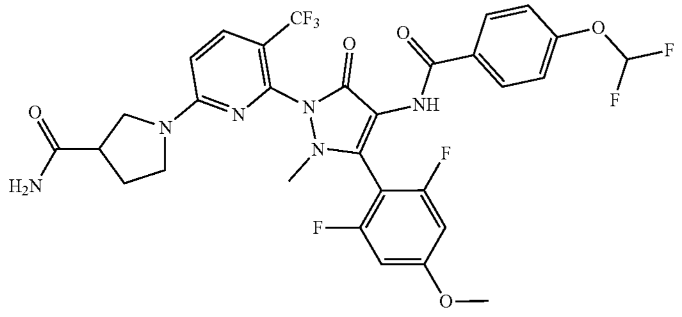 [SMILES: COc1cc(F)c(-c2c(NC(=O)c3ccc(OC(F)F)cc3)c(=O)n(-c3nc(N4CCC(C(N)=O)C4)ccc3C(F)(F)F)n2C)c(F)c1] | 1.73 B 683.2 |
| 306 | N-(2-{6-[(8aR)-octahydropyrrolo[1,2-a]piperazin-2-yl]-3-(trifluoromethyl)pyridin-2-yl}-5-(2,6-difluoro-4-methoxyphenyl)-1-methyl-3-oxo-2,3-dihydro-1H-pyrazol-4-yl)-4-(difluoromethoxy)benzamide | 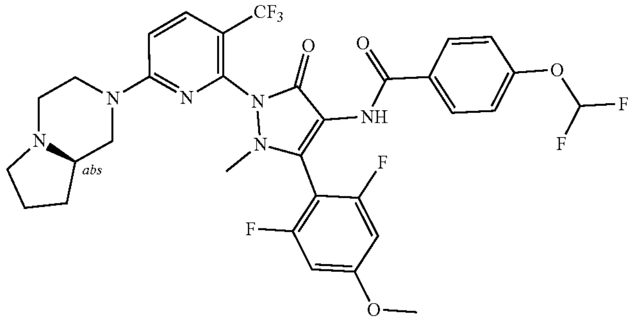 [SMILES: COc1cc(F)c(-c2c(NC(=O)c3ccc(OC(F)F)cc3)c(=O)n(-c3nc(N4CCN5CCC[C@@H]5C4)ccc3C(F)(F)F)n2C)c(F)c1] | 1.92 A 695.3 |
| 307 | N-{2-[3-chloro-6-(3-hydroxy-3-methylazetidin-1-yl)pyridin-2-yl]-5-(2,6-difluoro-4-methoxyphenyl)-1-methyl-3-oxo-2,3-dihydro-1H-pyrazol-4-yl}-4-(difluoromethoxy)benzamide | 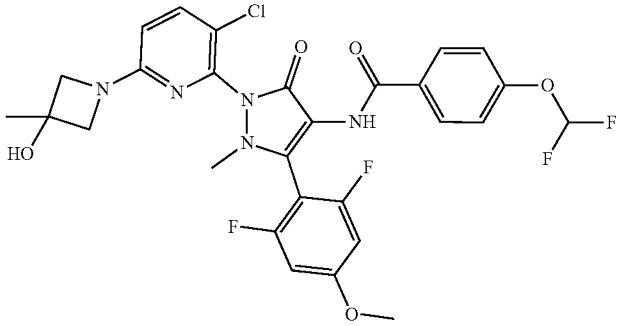 [SMILES: COc1cc(F)c(-c2c(NC(=O)c3ccc(OC(F)F)cc3)c(=O)n(-c3nc(N4CC(C)(O)C4)ccc3Cl)n2C)c(F)c1] | 1.84 A 622.0 |

TABLE 2-continued

| $^1$H NMR data for the examples in Table 2: | | | |
|---|---|---|---|
| Ex. No. | Name | Structure | LC/MS Rt (min) Method M + H |
| 308 | N-[5-(2,6-difluoro-4-methoxyphenyl)-2-(6-{6-hydroxy-2-azaspiro[3.3]heptan-2-yl}-3-(trifluoromethyl)pyridin-2-yl)-1-methyl-3-oxo-2,3-dihydro-1H-pyrazol-4-yl]-4-(difluoromethoxy)benzamide | 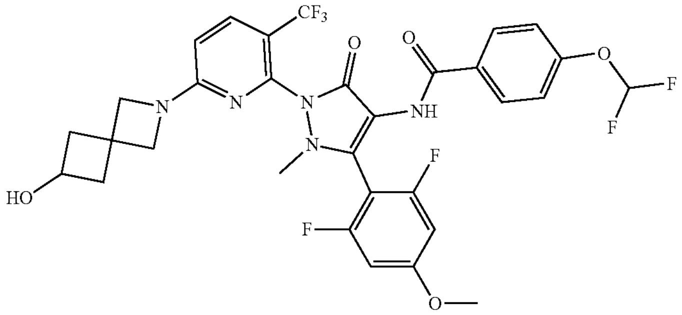 [SMILES: COc1cc(F)c(-c2c(NC(=O)c3ccc(OC(F)F)cc3)c(=O)n(-c3nc(N4CC5(CC(O)C5)C4)ccc3C(F)(F)F)n2C)c(F)c1] | 1.87<br>B<br>682.3 |
| 309 | N-[5-(2,6-difluoro-4-methoxyphenyl)-2-[3-ethyl-6-(2-hydroxy-2-methylpropoxy)pyridin-2-yl]-1-methyl-3-oxo-2,3-dihydro-1H-pyrazol-4-yl]-4-(difluoromethoxy)benzamide | 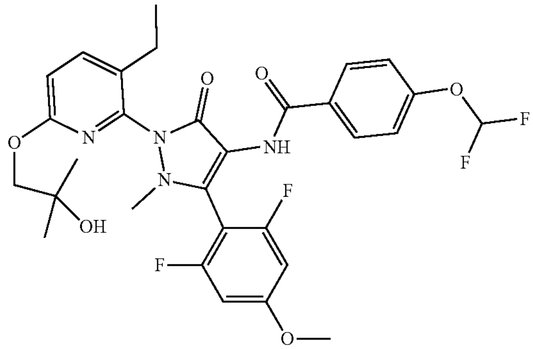 [SMILES: CCc1ccc(OCC(C)(C)O)nc1-n1c(=O)c(NC(=O)c2ccc(OC(F)F)cc2)c(-c2c(F)cc(OC)cc2F)n1C] | 1.80<br>B<br>618.9 |
| 310 | N-[5-(2,6-difluoro-4-methoxyphenyl)-2-[3-ethyl-6-(3-hydroxy-3-methylazetidin-1-yl)pyridin-2-yl]-1-methyl-3-oxo-2,3-dihydro-1H-pyrazol-4-yl]-4-(difluoromethoxy)benzamide | 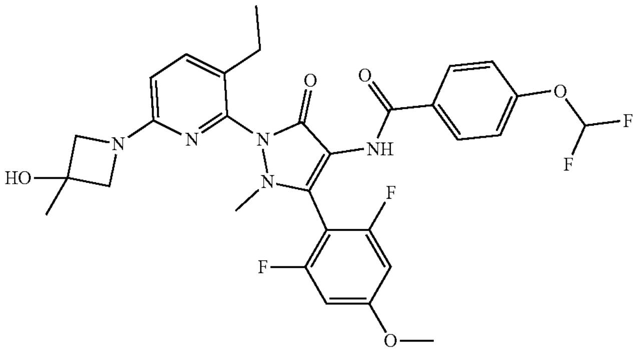 [SMILES: CCc1ccc(N2CC(C)(O)C2)nc1-n1c(=O)c(NC(=O)c2ccc(OC(F)F)cc2)c(-c2c(F)cc(OC)cc2F)n1C] | 1.76<br>B<br>616.1 |
| 311 | N-{2-[3-cyano-6-(3-hydroxy-3-methylazetidin-1-yl)pyridin-2-yl]-5-(2,6-difluoro-4-methoxyphenyl)-1-methyl-3-oxo-2,3-dihydro-1H-pyrazol-4-yl}-4-(difluoromethoxy)benzamide | 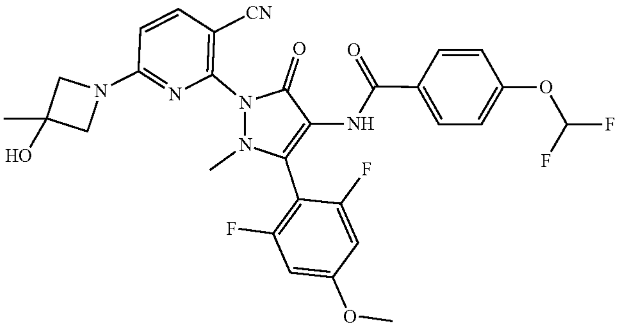 [SMILES: COc1cc(F)c(-c2c(NC(=O)c3ccc(OC(F)F)cc3)c(=O)n(-c3nc(N4CC(C)(O)C4)ccc3C#N)n2C)c(F)c1] | 1.69<br>B<br>613.3 |

TABLE 2-continued

| $^1$H NMR data for the examples in Table 2: | | | |
|---|---|---|---|
| Ex. No. | Name | Structure | LC/MS Rt (min) Method M + H |
| 312 | N-[5-(2,6-difluoro-4-methoxyphenyl)-2-[6-(3-hydroxy-3-methylazetidin-1-yl)pyridin-2-yl]-1-methyl-3-oxo-2,3-dihydro-1H-pyrazol-4-yl]-4-(difluoromethoxy)benzamide | 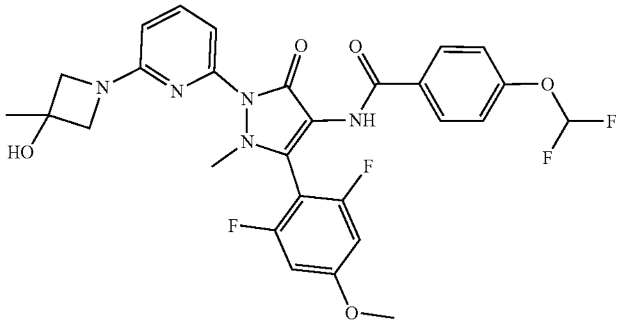 [SMILES: COc1cc(F)c(-c2c(NC(=O)c3ccc(OC(F)F)cc3)c(=O)n(-c3cccc(N4CC(C)(O)C4)n3)n2C)c(F)c1] | 1.68 B 588.3 |
| 313 | 4-(difluoromethoxy)-N-[5-(2-fluoro-4-methoxyphenyl)-2-[6-(4-hydroxy-4-methylpiperidin-1-yl)-3-(trifluoromethyl)pyridin-2-yl]-1-methyl-3-oxo-2,3-dihydro-1H-pyrazol-4-yl]benzamide | 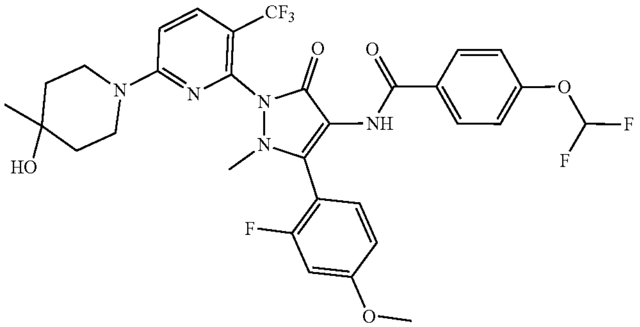 [SMILES: COc1ccc(-c2c(NC(=O)c3ccc(OC(F)F)cc3)c(=O)n(-c3nc(N4CCC(C)(O)CC4)ccc3C(F)(F)F)n2C)c(F)c1] | 1.90 A 666.1 |
| 314 | N-[5-(2,6-difluoro-4-methoxyphenyl)-2-[6-(4-hydroxy-4-methylpiperidin-1-yl)-3-(trifluoromethyl)pyridin-2-yl]-1-methyl-3-oxo-2,3-dihydro-1H-pyrazol-4-yl]-4-(difluoromethoxy)benzamide | 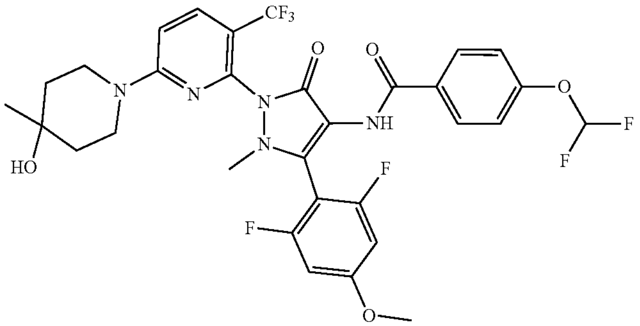 [SMILES: COc1cc(F)c(-c2c(NC(=O)c3ccc(OC(F)F)cc3)c(=O)n(-c3nc(N4CCC(C)(O)CC4)ccc3C(F)(F)F)n2C)c(F)c1] | 1.94 A 684.2 |
| 315 | 4-(difluoromethoxy)-N-{5-[4-(difluoromethoxy)phenyl]-2-(6-methoxypyridin-2-yl)-1-methyl-3-oxo-2,3-dihydro-1H-pyrazol-4-yl}benzamide | 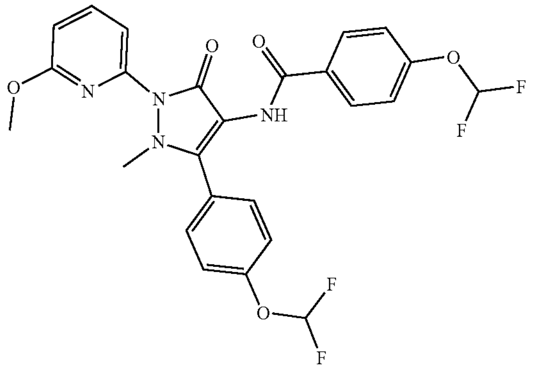 [SMILES: COc1cccc(-n2c(=O)c(NC(=O)c3ccc(OC(F)F)cc3)c(-c3ccc(OC(F)F)cc3)n2C)n1] | 1.95 B 533.3 |

TABLE 2-continued

| $^1$H NMR data for the examples in Table 2: | | | |
|---|---|---|---|
| Ex. No. | Name | Structure | LC/MS Rt (min) Method M + H |
| 316 | N-{2-[3-chloro-6-(1-methanesulfonylpiperidin-4-yl)pyridin-2-yl]-5-(2,6-difluoro-4-methoxyphenyl)-1-methyl-3-oxo-2,3-dihydro-1H-pyrazol-4-yl}-4-(difluoromethoxy)benzamide | 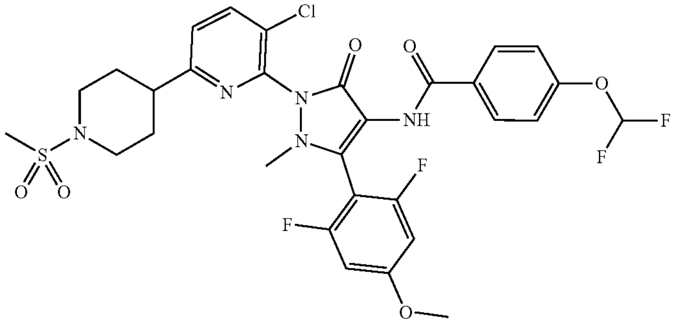 [SMILES: COc1cc(F)c(-c2c(NC(=O)c3ccc(OC(F)F)cc3)c(=O)n(-c3nc(C4CCN(S(C)(=O)=O)CC4)ccc3Cl)n2C)c(F)c1] | 1.81 B 698 |
| 317 | N-{2-[6-chloro-3-(trifluoromethyl)pyridin-2-yl]-5-[4-(difluoromethoxy)phenyl]-1-methyl-3-oxo-2,3-dihydro-1H-pyrazol-4-yl}-4-(difluoromethoxy)benzamide | 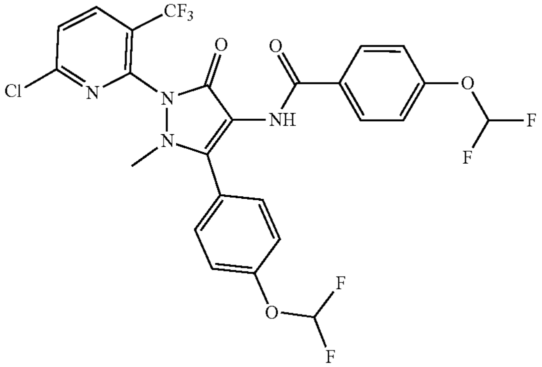 [SMILES: Cn1c(-c2ccc(OC(F)F)cc2)c(NC(=O)c2ccc(OC(F)F)cc2)c(=O)n1-c1nc(Cl)ccc1C(F)(F)F] | 2.01 A 605.3 |
| 318 | N-[5-(2,6-difluoro-4-methoxyphenyl)-2-[6-methanesulfonyl-3-(trifluoromethyl)pyridin-2-yl]-1-methyl-3-oxo-2,3-dihydro-1H-pyrazol-4-yl]-4-(difluoromethoxy)benzamide | 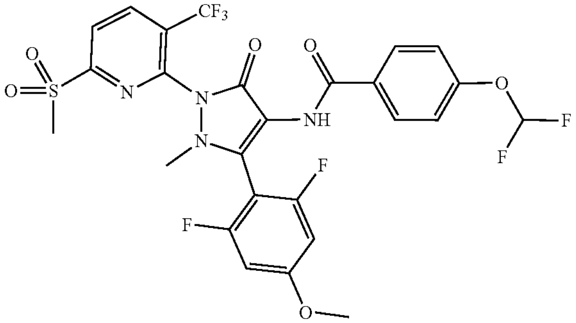 [SMILES: COc1cc(F)c(-c2c(NC(=O)c3ccc(OC(F)F)cc3)c(=O)n(-c3nc(S(C)(=O)=O)ccc3C(F)(F)F)n2C)c(F)c1] | 1.84 A 649.3 |
| 320 | N-(5-(2,6-Difluoro-4-methoxyphenyl)-1-methyl-2-(6-methyl-4-((tetrahydrofuran-3-yl)oxy)pyridin-2-yl)-3-oxo-2,3-dihydro-1H-pyrazol-4-yl)-4-(difluoromethoxy)benzamide | 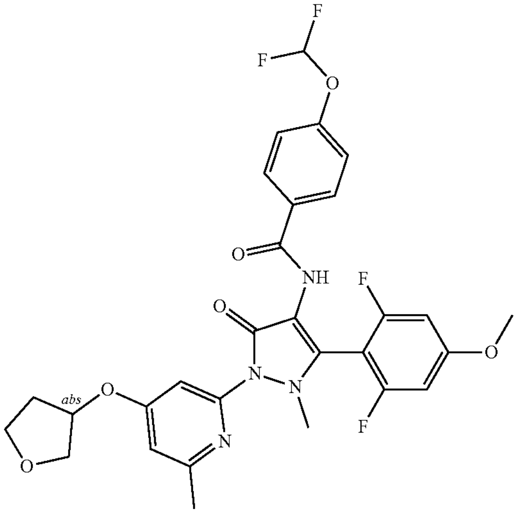 [SMILES: COc1cc(F)c(-c2c(NC(=O)c3ccc(OC(F)F)cc3)c(=O)n(-c3cc(OC4CCOC4)cc(C)n3)n2C)c(F)c1] | 1.63 C 603.2 |

TABLE 2-continued

| $^1$H NMR data for the examples in Table 2: | | | |
|---|---|---|---|
| Ex. No. | Name | Structure | LC/MS Rt (min) Method M + H |
| 321 | N-(5-(2,6-Difluoro-4-methoxyphenyl)-1-methyl-2-(6-methyl-4-((tetrahydrofuran-3-yl)oxy)pyridin-2-yl)-3-oxo-2,3-dihydro-1H-pyrazol-4-yl)-4-(difluoromethoxy)benzamide | 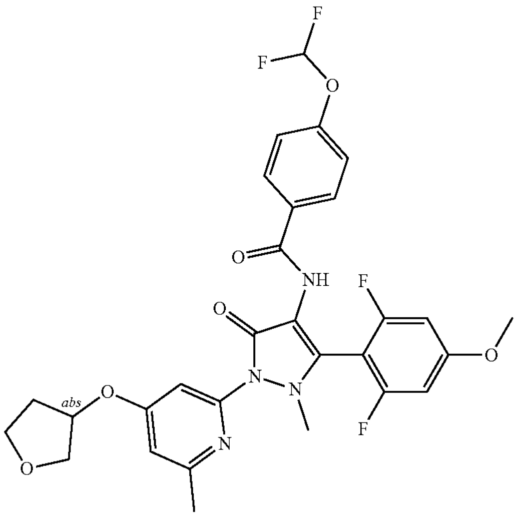 [SMILES: COc1cc(F)c(-c2c(NC(=O)c3ccc(OC(F)F)cc3)c(=O)n(-c3cc(OC4CCOC4)cc(C)n3)n2C)c(F)c1] | 1.63<br>C<br>603.2 |
| 322 | N-(5-(2,6-Difluoro-4-methoxyphenyl)-2-(6-(2-hydroxy-2-methylpropoxy)-4-methylpyridin-2-yl)-1-methyl-3-oxo-2,3-dihydro-1H-pyrazol-4-yl)-4-(difluoromethoxy)benzamide | 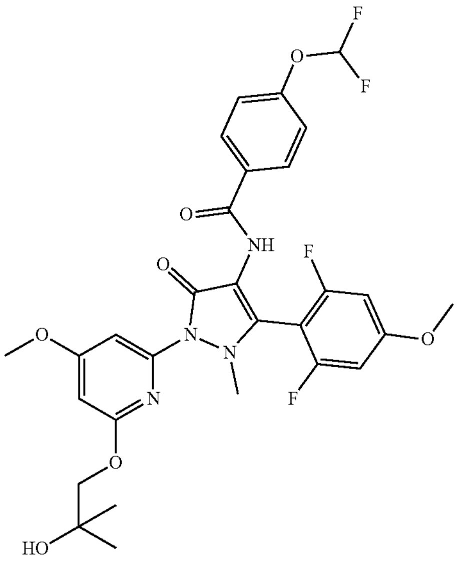 | 1.86<br>D<br>621.2 |

TABLE 2-continued

| $^1$H NMR data for the examples in Table 2: | | | |
|---|---|---|---|
| Ex. No. | Name | Structure | LC/MS Rt (min) Method M + H |
| 323 | N-(5-(2,6-Difluoro-4-methoxyphenyl)-1-methyl-2-(6-methyl-4-(piperidin-4-yl)pyridin-2-yl)-3-oxo-2,3-dihydro-1H-pyrazol-4-yl)-4-(difluoromethoxy)benzamide | 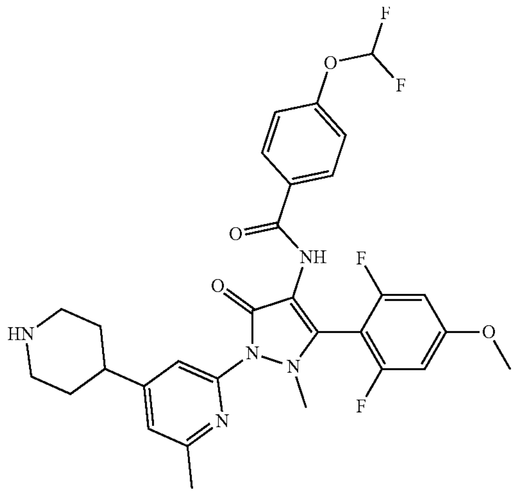 [SMILES: COc1cc(F)c(-c2c(NC(=O)c3ccc(OC(F)F)cc3)c(=O)n(-c3cc(C4CCNCC4)cc(C)n3)n2C)c(F)c1] | 1.37 C 600.2 |
| 324 | N-(5-(2,6-Difluoro-4-methoxyphenyl)-1-methyl-2-(6-methyl-4-(1-methylpiperidin-4-yl)pyridin-2-yl)-3-oxo-2,3-dihydro-1H-pyrazol-4-yl)-4-(difluoromethoxy)benzamide | 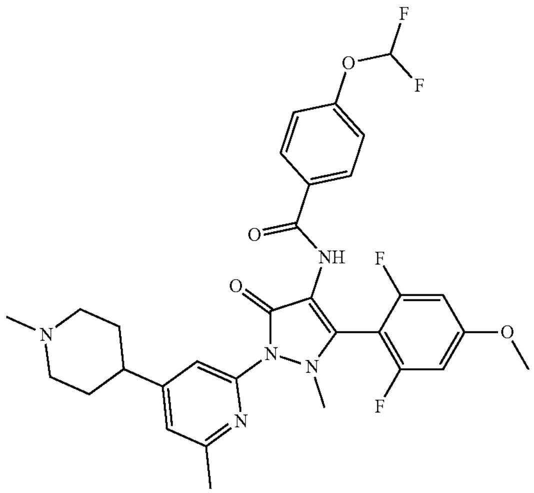 | 1.37 C 614.2 |
| 325 | N-(5-(2,6-Difluoro-4-methoxyphenyl)-2-(6-(3-hydroxy-2-(hydroxymethyl)-2-methylpropoxy)-4-methoxypyridin-2-yl)-1-methyl-3-oxo-2,3-dihydro-1H-pyrazol-4-yl)-4-(difluoromethoxy)benzamide | 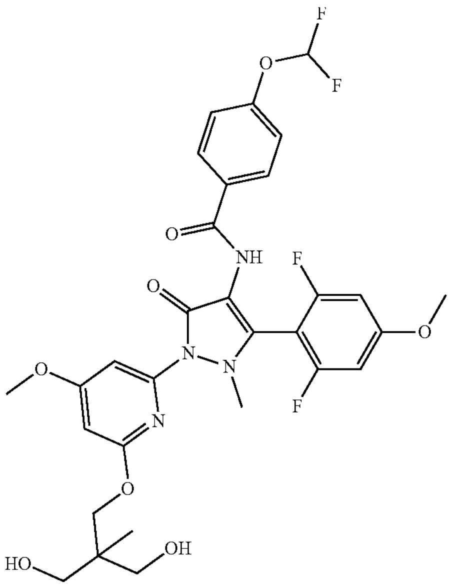 | 1.46 D 651.2 |

TABLE 2-continued

| $^1$H NMR data for the examples in Table 2: | | | |
|---|---|---|---|
| Ex. No. | Name | Structure | LC/MS Rt (min) Method M + H |
| 326 | N-(5-(2,6-Difluoro-4-methoxyphenyl)-2-(6-hydroxy-4-methoxypyridin-2-yl)-1-methyl-3-oxo-2,3-dihydro-1H-pyrazol-4-yl)-4-(difluoromethoxy)benzamide | 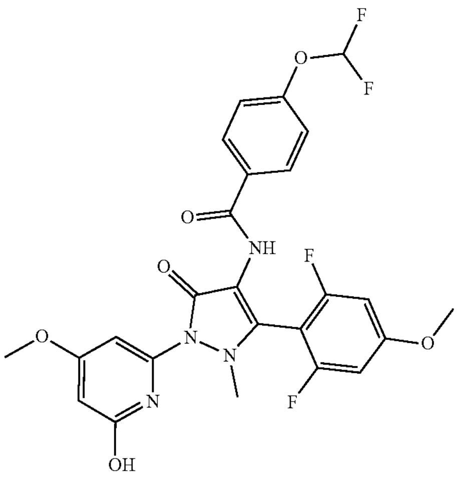 | 1.37<br>D<br>549.1 |
| 327 | N-(5-(2,6-Difluoro-4-methoxyphenyl)-1-methyl-2-(6-methyl-4-((3-methyloxetan-3-yl)methoxy)pyridin-2-yl)-3-oxo-2,3-dihydro-1H-pyrazol-4-yl)-4-(difluoromethoxy)benzamide | 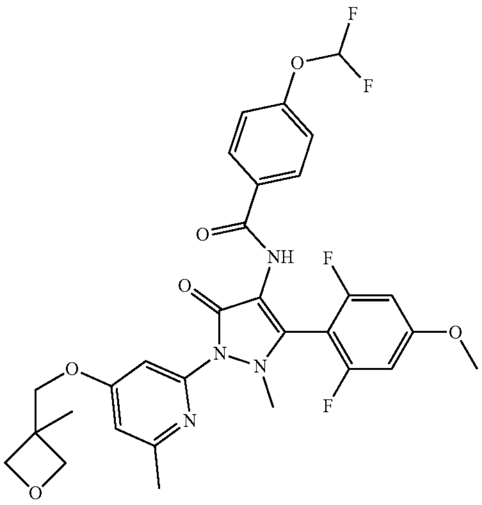 [SMILES: COc1cc(F)c(-c2c(NC(=O)c3ccc(OC(F)F)cc3)c(=O)n(-c3cc(OCC4(C)COC4)cc(C)n3)n2C)c(F)c1] | 1.67<br>C<br>617.2 |
| 328 | N-(2-(4-Cyano-6-methylpyridin-2-yl)-5-(2,6-difluoro-4-methoxyphenyl)-1-methyl-3-oxo-2,3-dihydro-1H-pyrazol-4-yl)-4-(difluoromethoxy)benzamide | 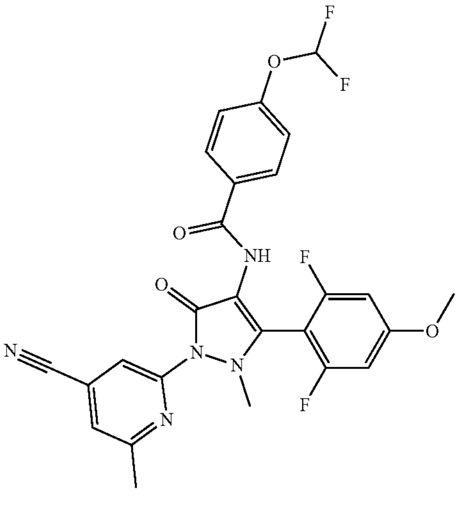 [SMILES: COc1cc(F)c(-c2c(NC(=O)c3ccc(OC(F)F)cc3)c(=O)n(-c3cc(C#N)cc(C)n3)n2C)c(F)c1] | 1.69<br>C<br>542.1 |

TABLE 2-continued
| ¹H NMR data for the examples in Table 2: | | | |
|---|---|---|---|
| Ex. No. | Name | Structure | LC/MS Rt (min) Method M + H |
| 329 | N-(5-(2,6-Difluoro-4-methoxyphenyl)-2-(6-(3-hydroxypropoxy)-4-methoxypyridin-2-yl)-1-methyl-3-oxo-2,3-dihydro-1H-pyrazol-4-yl)-4-(difluoromethoxy)benzamide | 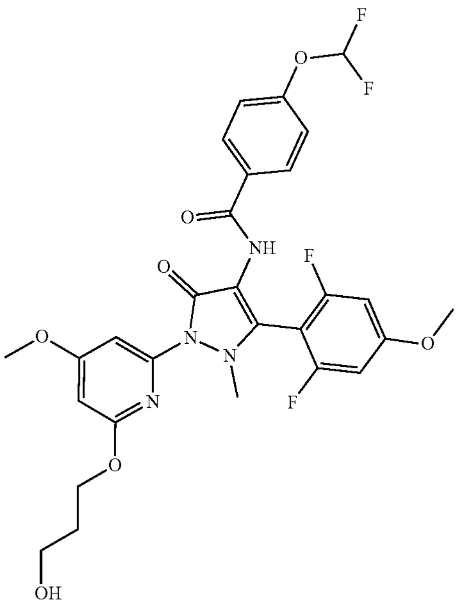 | 1.55 D 607.2 |
| 330 | N-(5-(2,6-Difluoro-4-methoxyphenyl)-2-(2-methoxypyridin-3-yl)-1-methyl-3-oxo-2,3-dihydro-1H-pyrazol-4-yl)-4-(difluoromethoxy)benzamide | 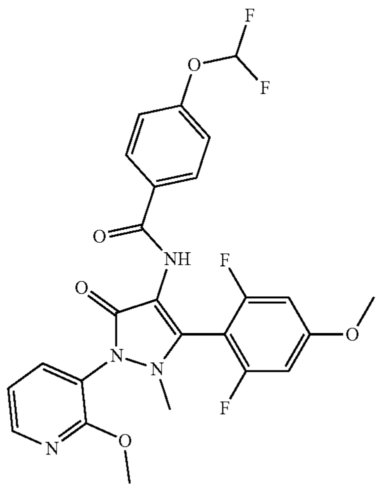 [SMILES: COc1cc(F)c(-c2c(NC(=O)c3ccc(OC(F)F)cc3)c(=O)n(-c3cccnc3OC)n2C)c(F)c1] | 1.21 D 533.1 |

TABLE 2-continued
| $^1$H NMR data for the examples in Table 2: | | | |
|---|---|---|---|
| Ex. No. | Name | Structure | LC/MS Rt (min) Method M + H |
| 331 | N-(5-(2,6-Difluoro-4-methoxyphenyl)-2-(6-(2-hydroxyethoxy)-4-methylpyridin-2-yl)-1-methyl-3-oxo-2,3-dihydro-1H-pyrazol-4-yl)-4-(difluoromethoxy)benzamide | 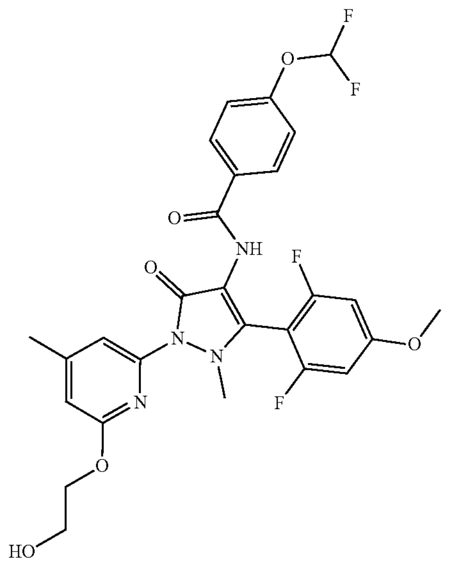 [SMILES: COc1cc(F)c(-c2c(NC(=O)c3ccc(OC(F)F)cc3)c(=O)n(-c3cc(C)cc(OCCO)n3)n2C)c(F)c1] | 1.57<br>D<br>577.1 |
| 332 | N-(5-(2,6-Difluoro-4-methoxyphenyl)-2-(6-(2-hydroxyethoxy)-4-methoxypyridin-2-yl)-1-methyl-3-oxo-2,3-dihydro-1H-pyrazol-4-yl)-4-(difluoromethoxy)benzamide | 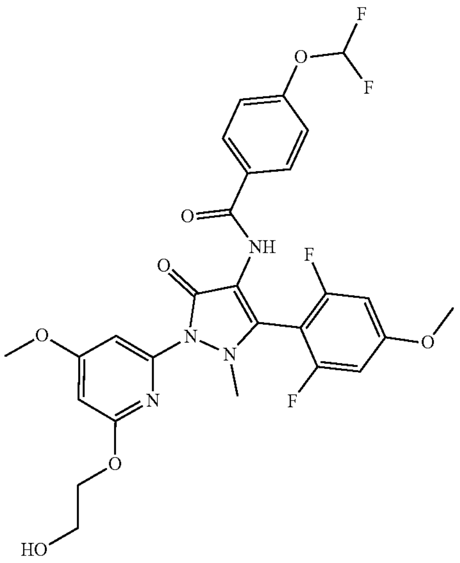 | 1.50<br>D<br>593.1 |

TABLE 2-continued
| Ex. No. | Name | Structure | LC/MS Rt (min) Method M + H |
|---|---|---|---|
| $^1$H NMR data for the examples in Table 2: | | | |
| 333 | N-(5-(2,6-Difluoro-4-methoxyphenyl)-2-(6-(2-hydroxyethoxy)pyridin-2-yl)-1-methyl-3-oxo-2,3-dihydro-1H-pyrazol-4-yl)-4-(difluoromethoxy)benzamide | 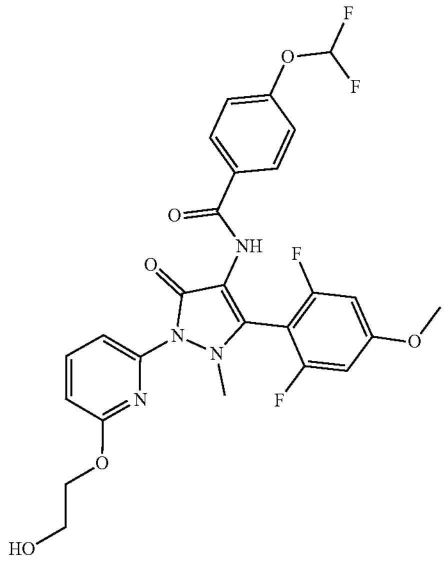 [SMILES: COc1cc(F)c(-c2c(NC(=O)c3ccc(OC(F)F)cc3)c(=O)n(-c3cccc(OCCO)n3)n2C)c(F)c1] | 1.49 D 563.1 |
| 334 | N-(5-(2,6-Difluoro-4-methoxyphenyl)-1-methyl-3-oxo-2-(5-((tetrahydrofuran-3-yl)methoxy)-6-(trifluoromethyl)pyridin-2-yl)-2,3-dihydro-1H-pyrazol-4-yl)-4-(difluoromethoxy)benzamide | 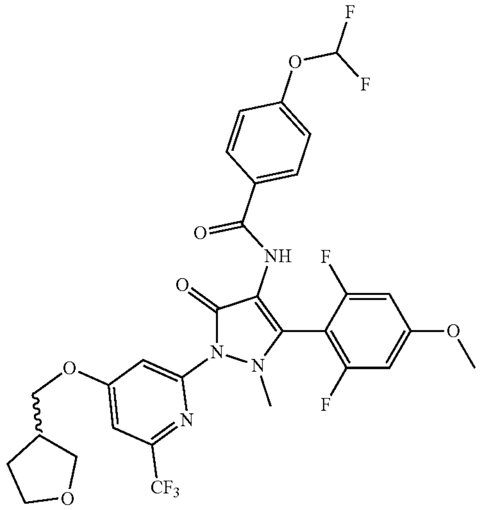 [SMILES: COc1cc(F)c(-c2c(NC(=O)c3ccc(OC(F)F)cc3)c(=O)n(-c3cc(OCC4CCOC4)cc(C(F)(F)F)n3)n2C)c(F)c1] | 2.16 C 671.2 |

TABLE 2-continued
| $^1$H NMR data for the examples in Table 2: | | | |
|---|---|---|---|
| Ex. No. | Name | Structure | LC/MS Rt (min) Method M + H |
| 335 | N-(5-(2,6-Difluoro-4-methoxyphenyl)-2-(4-methoxy-6-(2-(methylsulfonyl)ethoxy)pyridin-2-yl)-1-methyl-3-oxo-2,3-dihydro-1H-pyrazol-4-yl)-4-(difluoromethoxy)benzamide | 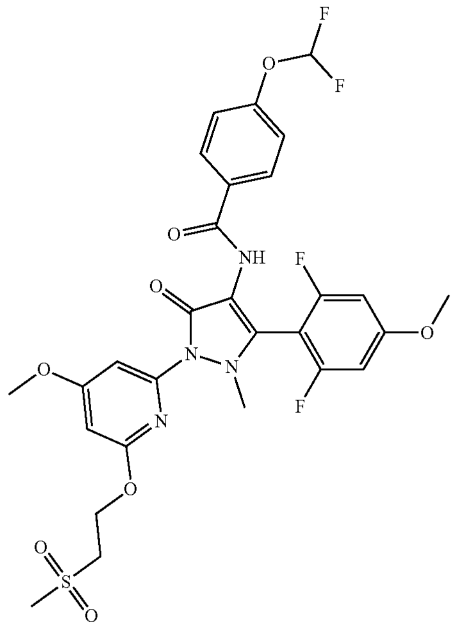 | 1.63 D 655.1 |
| 336 | N-(5-(2,6-Difluoro-4-methoxyphenyl)-2-(6-(2-hydroxyethoxy)-4-(hydroxymethyl)pyridin-2-yl)-1-methyl-3-oxo-2,3-dihydro-1H-pyrazol-4-yl)-4-(difluoromethoxy)benzamide | 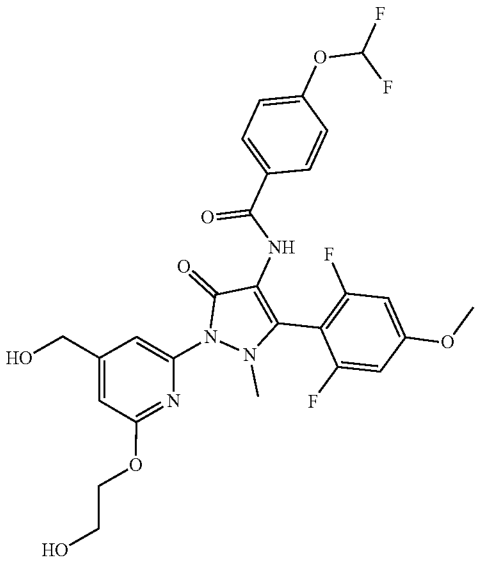 [SMILES: COc1cc(F)c(-c2c(NC(=O)c3ccc(OC(F)F)cc3)c(=O)n(-c3cc(CO)cc(OCCO)n3)n2C)c(F)c1] | 1.41 D 593.1 |

TABLE 2-continued

| $^1$H NMR data for the examples in Table 2: | | | |
|---|---|---|---|
| Ex. No. | Name | Structure | LC/MS Rt (min) Method M + H |
| 337 | N-(5-(2,6-Difluoro-4-methoxyphenyl)-2-(6-((1,1-dioxidotetrahydro-2H-thiopyran-4-yl)methoxy)-4-methoxypyridin-2-yl)-1-methyl-3-oxo-2,3-dihydro-1H-pyrazol-4-yl)-4-(difluoromethoxy)benzamide | 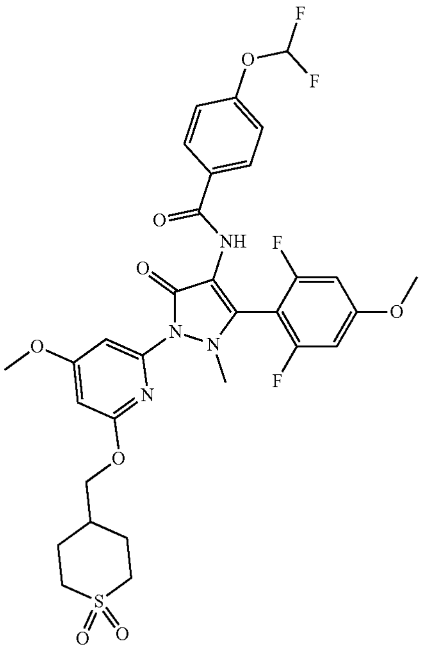 | 1.74<br>D<br>695.2 |
| 338 | N-(5-(2,6-Difluoro-4-methoxyphenyl)-2-(6-(1-(2-hydroxyethyl)piperidin-3-yl)-4-methoxypyridin-2-yl)-1-methyl-3-oxo-2,3-dihydro-1H-pyrazol-4-yl)-4-(difluoromethoxy)benzamide | 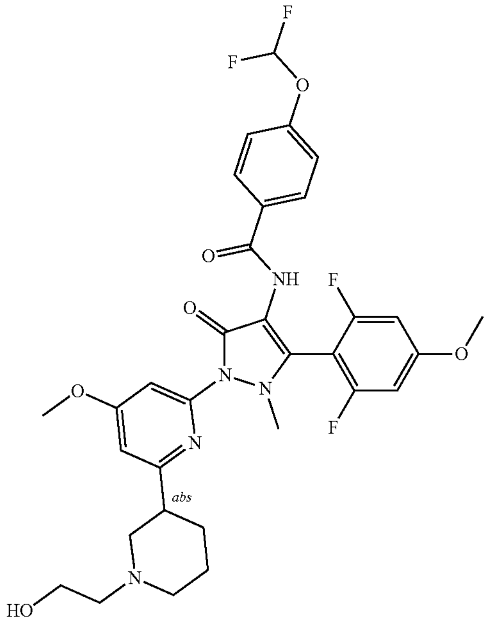 [SMILES: COc1cc(C2CCCN(CCO)C2)nc(-n2c(=O)c(NC(=O)c3ccc(OC(F)F)cc3)c(-c3c(F)cc(OC)cc3F)n2C)c1] | 1.44<br>D<br>660.2 |

TABLE 2-continued

| $^1$H NMR data for the examples in Table 2: | | | |
|---|---|---|---|
| Ex. No. | Name | Structure | LC/MS Rt (min) Method M + H |
| 339 | N-(5-(2,6-Difluoro-4-methoxyphenyl)-2-(4-methoxy-6-((tetrahydrofuran-2-yl)methoxy)pyridin-2-yl)-1-methyl-3-oxo-2,3-dihydro-1H-pyrazol-4-yl)-4-(difluoromethoxy)benzamide | 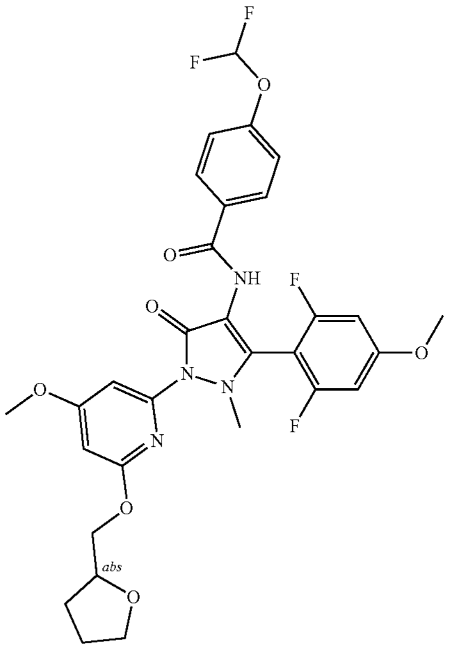 | 1.91 D 633.2 |
| 340 | N-(5-(2,6-Difluoro-4-methoxyphenyl)-2-(6-(1-(2-hydroxyethyl)piperidin-3-yl)-4-methoxypyridin-2-yl)-1-methyl-3-oxo-2,3-dihydro-1H-pyrazol-4-yl)-4-(difluoromethoxy)benzamide | 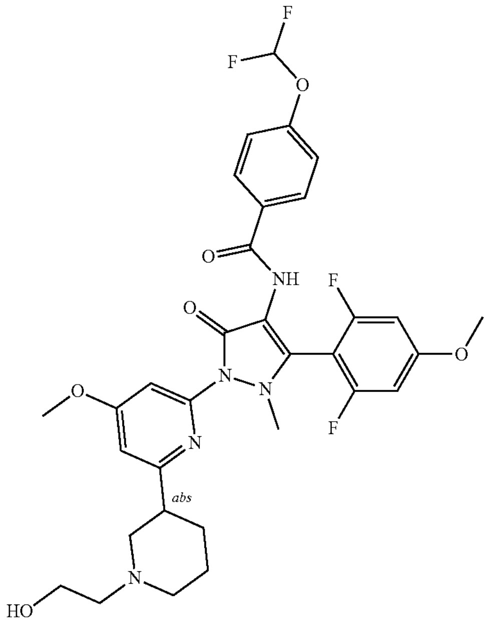 [SMILES: COc1cc(C2CCCN(CCO)C2)nc(-n2c(=O)c(NC(=O)c3ccc(OC(F)F)cc3)c(-c3c(F)cc(OC)cc3F)n2C)c1] | 1.44 D 660.2 |

TABLE 2-continued
| $^1$H NMR data for the examples in Table 2: | | | |
|---|---|---|---|
| Ex. No. | Name | Structure | LC/MS Rt (min) Method M + H |
| 341 | N-(2-(4-Cyano-6-(trifluoromethyl)pyridin-2-yl)-5-(2,6-difluoro-4-methoxyphenyl)-1-methyl-3-oxo-2,3-dihydro-1H-pyrazol-4-yl)-4-(difluoromethoxy)benzamide | 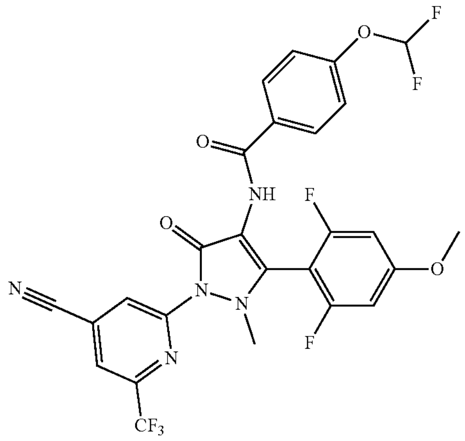 [SMILES: COc1cc(F)c(-c2c(NC(=O)c3ccc(OC(F)F)cc3)c(=O)n(-c3cc(C#N)cc(C(F)(F)F)n3)n2C)c(F)c1] | 2.09<br>C<br>596.1 |
| 342 | N-(5-(2,6-Difluoro-4-methoxyphenyl)-2-(4-methoxy-6-(1-methylpiperidin-3-yl)pyridin-2-yl)-1-methyl-3-oxo-2,3-dihydro-1H-pyrazol-4-yl)-4-(difluoromethoxy)benzamide | 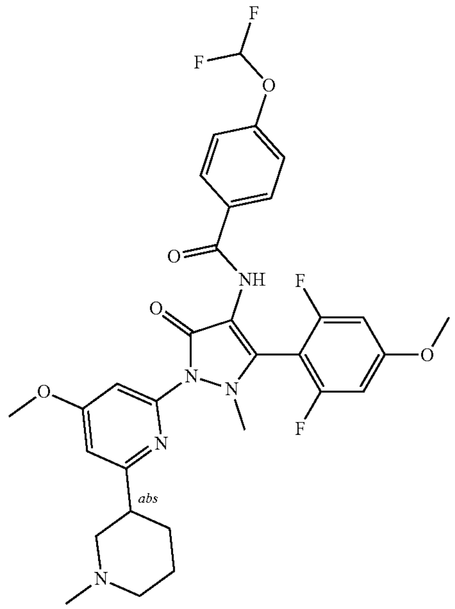 | 1.47<br>D<br>630.2 |

TABLE 2-continued

| $^1$H NMR data for the examples in Table 2: | | | |
|---|---|---|---|
| Ex. No. | Name | Structure | LC/MS Rt (min) Method M + H |
| 343 | N-(5-(2,6-Difluoro-4-methoxyphenyl)-2-(4-methoxy-6-(1-methylpiperidin-3-yl)pyridin-2-yl)-1-methyl-3-oxo-2,3-dihydro-1H-pyrazol-4-yl)-4-(difluoromethoxy)benzamide | 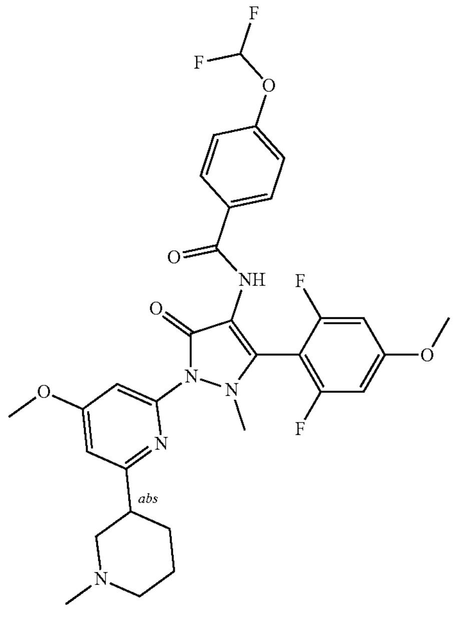 | 1.46<br>D<br>630.2 |
| 344 | N-(5-(2,6-Difluoro-4-methoxyphenyl)-2-(4-methoxy-6-((3-methyloxetan-3-yl)methoxy)pyridin-2-yl)-1-methyl-3-oxo-2,3-dihydro-1H-pyrazol-4-yl)-4-(difluoromethoxy)benzamide | 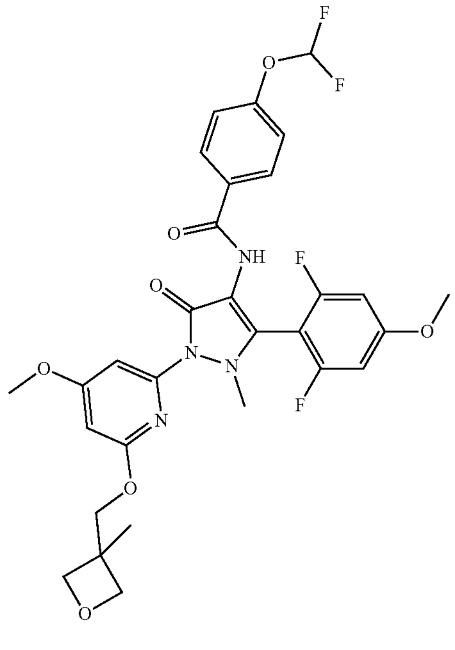 | 1.86<br>D<br>631.1 |

TABLE 2-continued
| $^1$H NMR data for the examples in Table 2: | | | |
|---|---|---|---|
| Ex. No. | Name | Structure | LC/MS Rt (min) Method M + H |
| 345 | N-(5-(2,6-Difluoro-4-methoxyphenyl)-2-(4-methoxy-6-(tetrahydro-2H-pyran-4-yl)pyridin-2-yl)-1-methyl-3-oxo-2,3-dihydro-1H-pyrazol-4-yl)-4-(difluoromethoxy)benzamide | 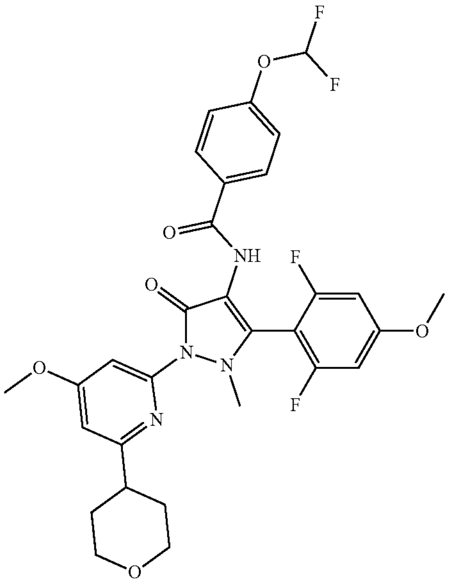 | 1.80 D 617.2 |
| 346 | N-(5-(2,6-Difluoro-4-methoxyphenyl)-2-(4-methoxy-6-(piperidin-3-yl)pyridin-2-yl)-1-methyl-3-oxo-2,3-dihydro-1H-pyrazol-4-yl)-4-(difluoromethoxy)benzamide | 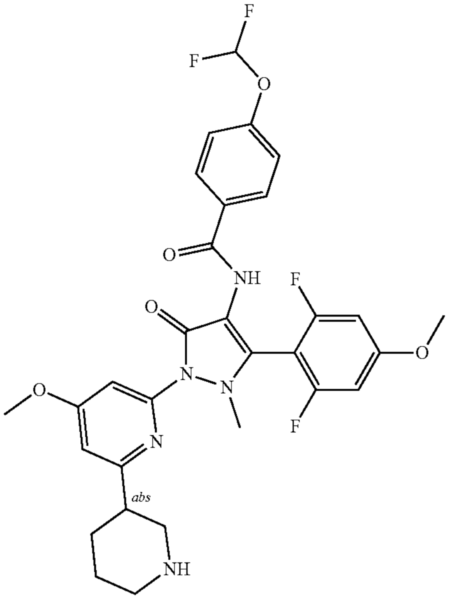 | 1.35 D 616.2 |

TABLE 2-continued

| Ex. No. | Name | Structure | LC/MS Rt (min) Method M + H |
|---|---|---|---|
| | $^1$H NMR data for the examples in Table 2: | | |
| 347 | N-(5-(2,6-Difluoro-4-methoxyphenyl)-2-(4-methoxy-6-(piperidin-3-yl)pyridin-2-yl)-1-methyl-3-oxo-2,3-dihydro-1H-pyrazol-4-yl)-4-(difluoromethoxy)benzamide | 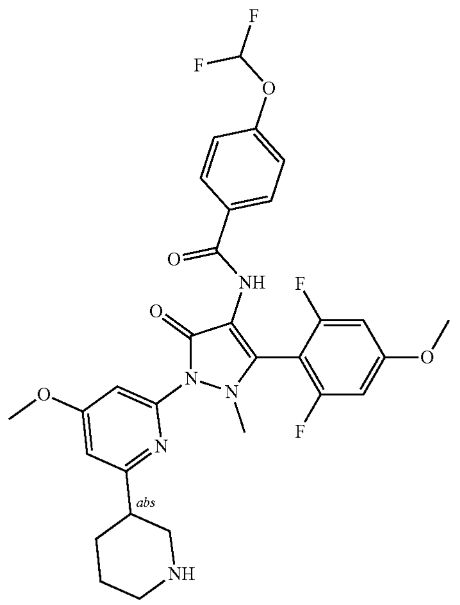 | 1.36<br>D<br>616.2 |
| 348 | N-(5-(2,6-Difluoro-4-methoxyphenyl)-2-(4-(2-hydroxyethoxy)-6-(trifluoromethyl)pyridin-2-yl)-1-methyl-3-oxo-2,3-dihydro-1H-pyrazol-4-yl)-4-(difluoromethoxy)benzamide | 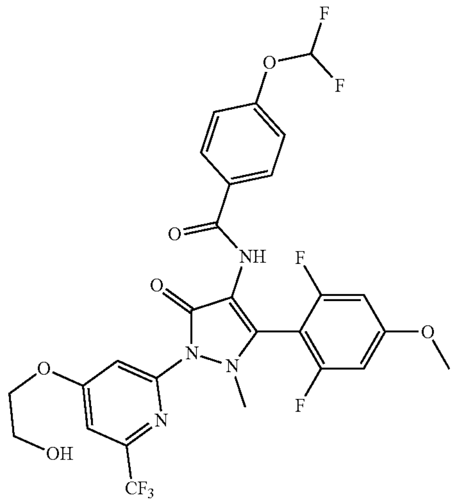 [SMILES: COc1cc(F)c(-c2c(NC(=O)c3ccc(OC(F)F)cc3)c(=O)n(-c3cc(OCCO)cc(C(F)(F)F)n3)n2C)c(F)c1] | 1.83<br>C<br>631.2 |

TABLE 2-continued

| $^1$H NMR data for the examples in Table 2: | | | |
|---|---|---|---|
| Ex. No. | Name | Structure | LC/MS Rt (min) Method M + H |
| 349 | N-(5-(2,6-Difluoro-4-methoxyphenyl)-1-methyl-2-(4-((3-methyloxetan-3-yl)methoxy)-6-(trifluoromethyl)pyridin-2-yl)-3-oxo-2,3-dihydro-1H-pyrazol-4-yl)-4-(difluoromethoxy)benzamide | 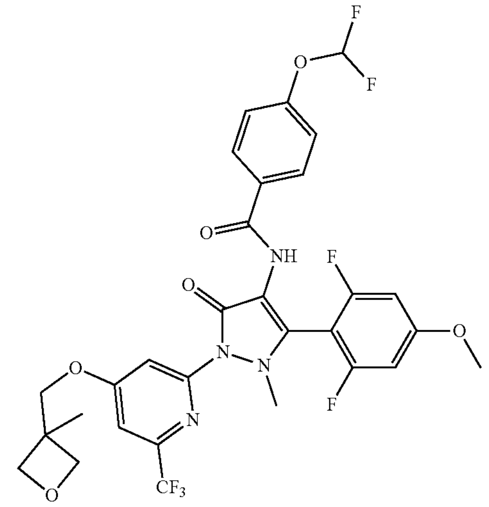 [SMILES: COc1cc(F)c(-c2c(NC(=O)c3ccc(OC(F)F)cc3)c(=O)n(-c3cc(OCC4(C)COC4)cc(C(F)(F)F)n3)n2C)c(F)c1] | 2.19<br>C<br>671.2 |
| 350 | N-(5-(2,6-Difluoro-4-methoxyphenyl)-2-(4-methoxy-6-((tetrahydrofuran-2-yl)methoxy)pyridin-2-yl)-1-methyl-3-oxo-2,3-dihydro-1H-pyrazol-4-yl)-4-(difluoromethoxy)benzamide | 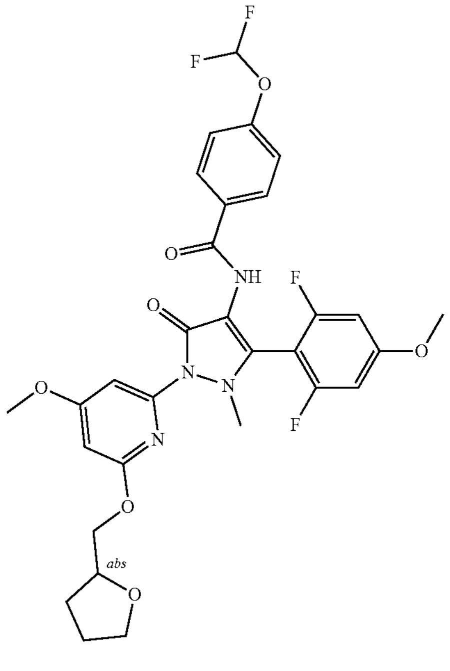 | 1.91<br>D<br>633.2 |

TABLE 2-continued

| $^1$H NMR data for the examples in Table 2: | | | |
|---|---|---|---|
| Ex. No. | Name | Structure | LC/MS Rt (min) Method M + H |
| 351 | N-(5-(2,6-Difluoro-4-methoxyphenyl)-2-(4-methoxy-6-((tetrahydrofuran-3-yl)methoxy)pyridin-2-yl)-1-methyl-3-oxo-2,3-dihydro-1H-pyrazol-4-yl)-4-(difluoromethoxy)benzamide | 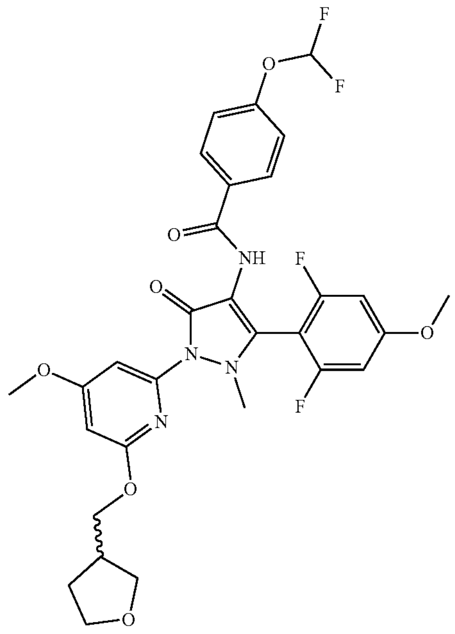 | 1.86<br>D<br>633.2 |
| 352 | N-(5-(2,6-Difluoro-4-methoxyphenyl)-1-methyl-2-(4-methyl-6-((tetrahydrofuran-3-yl)methoxy)pyridin-2-yl)-3-oxo-2,3-dihydro-1H-pyrazol-4-yl)-4-(difluoromethoxy)benzamide | 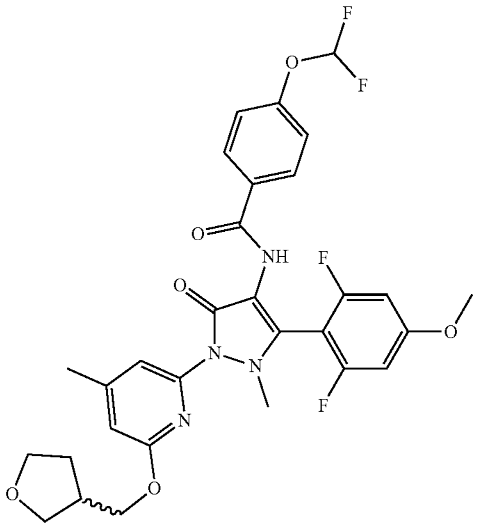 [SMILES: COc1cc(F)c(-c2c(NC(=O)c3ccc(OC(F)F)cc3)c(=O)n(-c3cc(C)cc(OCC4CCOC4)n3)n2C)c(F)c1] | 1.89<br>D<br>617.2 |

TABLE 2-continued

| $^1$H NMR data for the examples in Table 2: | | | |
|---|---|---|---|
| Ex. No. | Name | Structure | LC/MS Rt (min) Method M + H |
| 353 | N-(5-(2,6-Difluoro-4-methoxyphenyl)-1-methyl-2-(4-methyl-6-((3-methyloxetan-3-yl)methoxy)pyridin-2-yl)-3-oxo-2,3-dihydro-1H-pyrazol-4-yl)-4-(difluoromethoxy)benzamide | 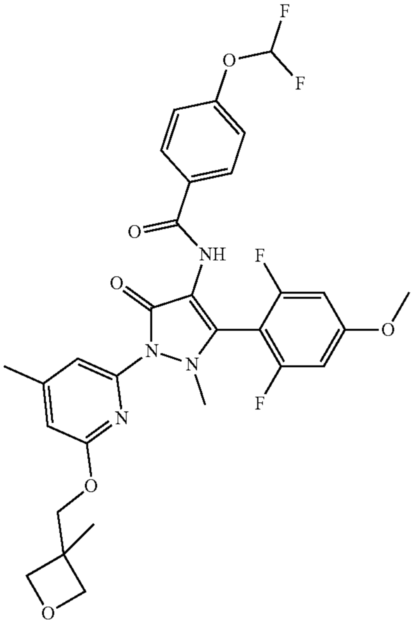 | 1.89<br>D<br>617.2 |
| 354 | N-(5-(2,6-Difluoro-4-methoxyphenyl)-2-(4-methoxy-6-((1R,4R)-5-methyl-2,5-diazabicyclo[2.2.1]heptan-2-yl)pyridin-2-yl)-1-methyl-3-oxo-2,3-dihydro-1H-pyrazol-4-yl)-4-(difluoromethoxy)benzamide | 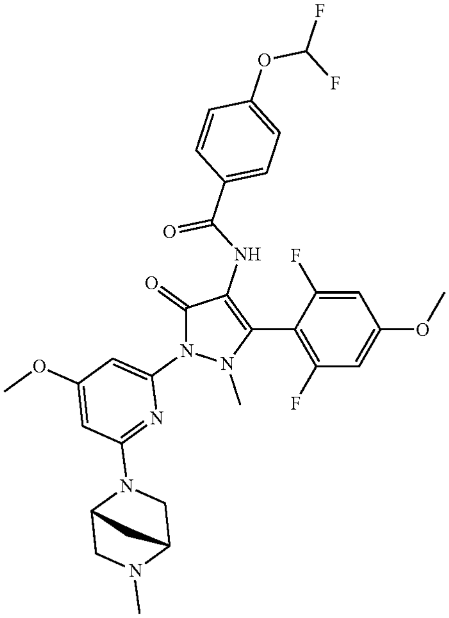 | 1.36<br>D<br>643.2 |

TABLE 2-continued

| Ex. No. | Name | Structure | LC/MS Rt (min) Method M + H |
|---|---|---|---|
| | $^1$H NMR data for the examples in Table 2: | | |
| 355 | N-(5-(2,6-Difluoro-4-methoxyphenyl)-2-(4-methoxy-6-((tetrahydrofuran-3-yl)oxy)pyridin-2-yl)-1-methyl-3-oxo-2,3-dihydro-1H-pyrazol-4-yl)-4-(difluoromethoxy)benzamide | 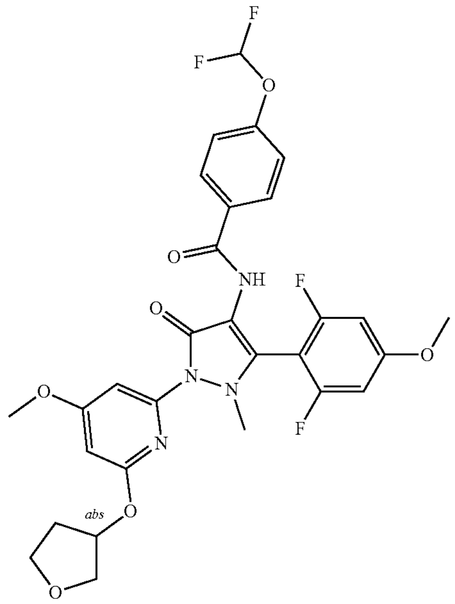 | 1.84<br>D<br>619.2 |
| 356 | N-(5-(2,6-Difluoro-4-methoxyphenyl)-2-(4-methoxy-6-((tetrahydrofuran-3-yl)oxy)pyridin-2-yl)-1-methyl-3-oxo-2,3-dihydro-1H-pyrazol-4-yl)-4-(difluoromethoxy)benzamide | 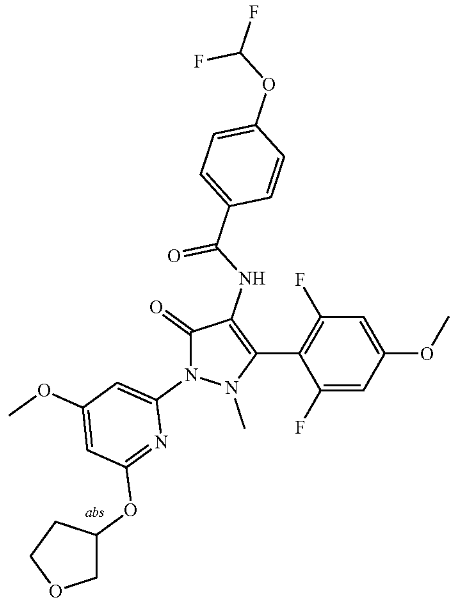 | 1.83<br>D<br>619.2 |

TABLE 2-continued
| $^1$H NMR data for the examples in Table 2: | | | |
|---|---|---|---|
| Ex. No. | Name | Structure | LC/MS Rt (min) Method M + H |
| 357 | N-(2-(3-Cyano-6-methylpyridin-2-yl)-5-(2,6-difluoro-4-methoxyphenyl)-1-methyl-3-oxo-2,3-dihydro-1H-pyrazol-4-yl)-4-(difluoromethoxy)benzamide | 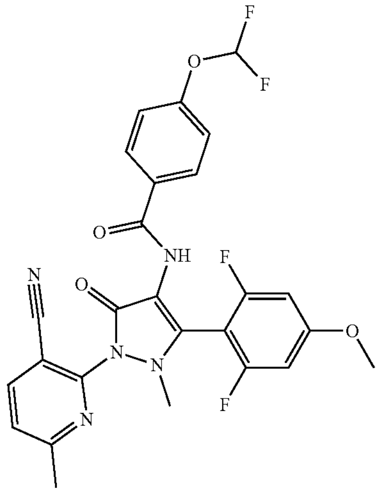 [SMILES: COc1cc(F)c(-c2c(NC(=O)c3ccc(OC(F)F)cc3)c(=O)n(-c3nc(C)ccc3C#N)n2C)c(F)c1] | 1.68 C 542.2 |
| 358 | N-(5-(2,6-Difluoro-4-methoxyphenyl)-1-methyl-2-(3-((3-methyloxetan-3-yl)methoxy)-6-(trifluoromethyl)pyridin-2-yl)-3-oxo-2,3-dihydro-1H-pyrazol-4-yl)-4-(difluoromethoxy)benzamide | 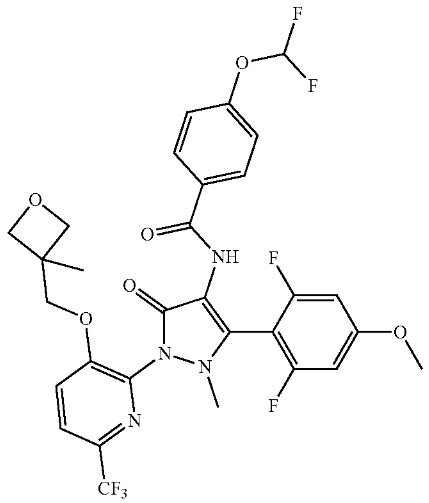 [SMILES: COc1cc(F)c(-c2c(NC(=O)c3ccc(OC(F)F)cc3)c(=O)n(-c3nc(C(F)(F)F)ccc3OCC3(C)COC3)n2C)c(F)c1] | 1.76 C 671.2 |

TABLE 2-continued
| Ex. No. | Name | Structure | LC/MS Rt (min) Method M + H |
|---|---|---|---|
| | $^1$H NMR data for the examples in Table 2: | | |
| 359 | N-(5-(2,6-Difluoro-4-methoxyphenyl)-1-methyl-2-(4-methyl-6-((tetrahydrofuran-3-yl)oxy)pyridin-2-yl)-3-oxo-2,3-dihydro-1H-pyrazol-4-yl)-4-(difluoromethoxy)benzamide | 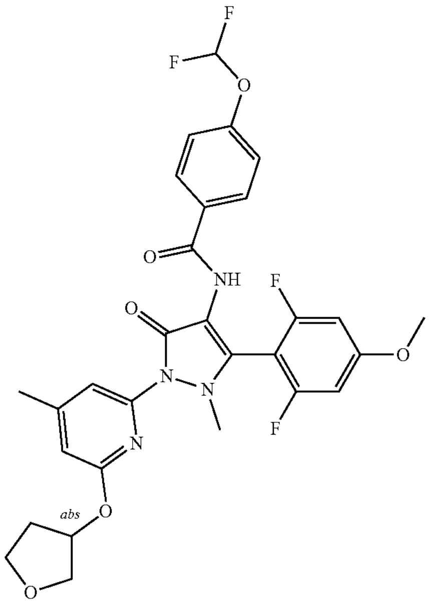 [SMILES: COc1cc(F)c(-c2c(NC(=O)c3ccc(OC(F)F)cc3)c(=O)n(-c3cc(C)cc(OC4CCOC4)n3)n2C)c(F)c1] | 1.84 D 603.2 |
| 360 | N-(5-(2,6-Difluoro-4-methoxyphenyl)-1-methyl-2-(4-methyl-6-((tetrahydrofuran-3-yl)oxy)pyridin-2-yl)-3-oxo-2,3-dihydro-1H-pyrazol-4-yl)-4-(difluoromethoxy)benzamide | 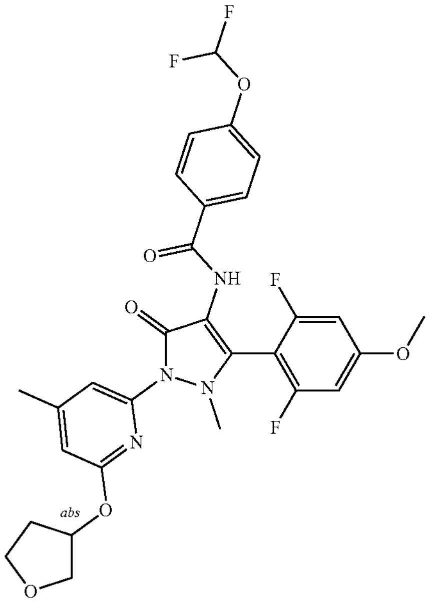 [SMILES: COc1cc(F)c(-c2c(NC(=O)c3ccc(OC(F)F)cc3)c(=O)n(-c3cc(C)cc(OC4CCOC4)n3)n2C)c(F)c1] | 1.84 D 603.2 |

TABLE 2-continued
| $^1$H NMR data for the examples in Table 2: | | | |
|---|---|---|---|
| Ex. No. | Name | Structure | LC/MS Rt (min) Method M + H |
| 361 | N-(5-(2,6-Difluoro-4-methoxyphenyl)-1-methyl-2-(4-methyl-6-(1-methylpyridin-4-yl)pyridin-2-yl)-3-oxo-2,3-dihydro-1H-pyrazol-4-yl)-4-(difluoromethoxy)benzamide | 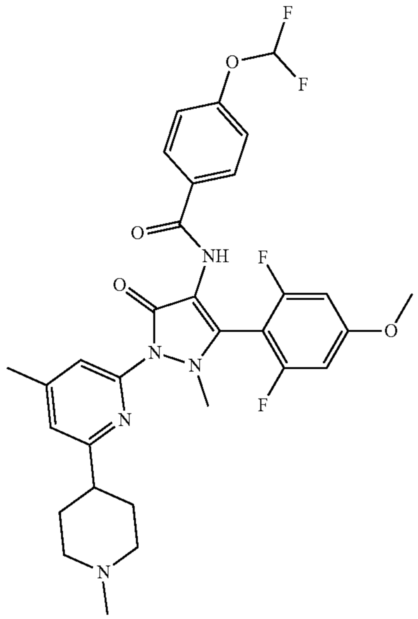 | 1.34<br>D<br>614.2 |
| 362 | N-(2-(6-Cyano-4-methylpyridin-2-yl)-5-(2,6-difluoro-4-methoxyphenyl)-1-methyl-3-oxo-2,3-dihydro-1H-pyrazol-4-yl)-4-(difluoromethoxy)benzamide | 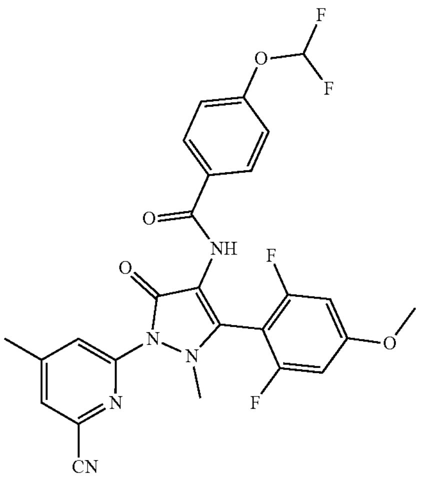 | 1.80<br>D<br>542.2 |

TABLE 2-continued
| $^1$H NMR data for the examples in Table 2: | | | |
|---|---|---|---|
| Ex. No. | Name | Structure | LC/MS Rt (min) Method M + H |
| 363 | N-(5-(2,6-Difluoro-4-methoxyphenyl)-2-(4-methoxy-6-(1-methylpiperidin-4-yl)pyridin-2-yl)-1-methyl-3-oxo-2,3-dihydro-1H-pyrazol-4-yl)-4-(difluoromethoxy)benzamide | 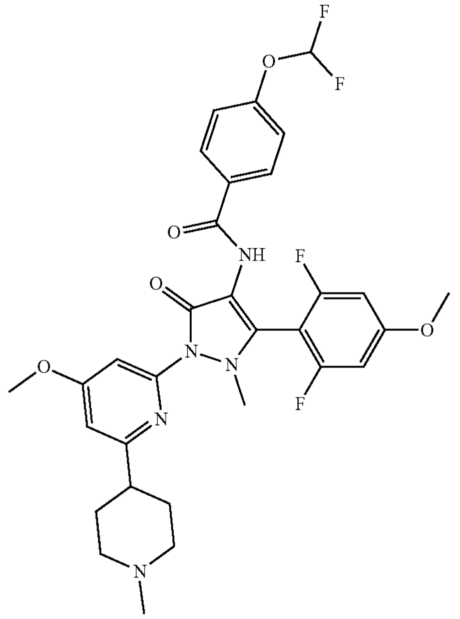 | 1.34<br>D<br>630.2 |
| 364 | N-(5-(2,6-Difluoro-4-methoxyphenyl)-2-(4-methoxy-6-morpholinopyridin-2-yl)-1-methyl-3-oxo-2,3-dihydro-1H-pyrazol-4-yl)-4-(difluoromethoxy)benzamide | 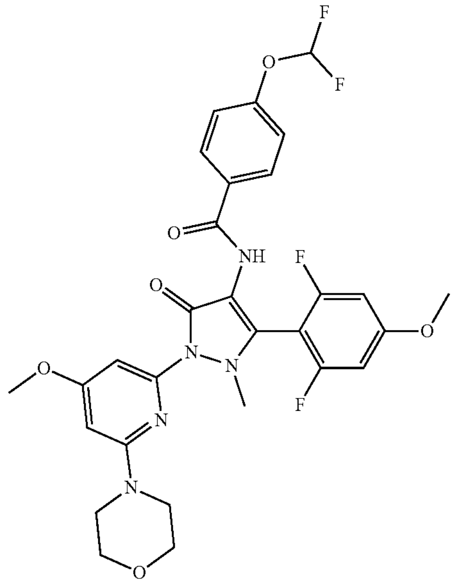 | 1.70<br>C<br>618.3 |

TABLE 2-continued

| $^1$H NMR data for the examples in Table 2: | | | |
|---|---|---|---|
| Ex. No. | Name | Structure | LC/MS Rt (min) Method M + H |
| 365 | N-(5-(2,6-Difluoro-4-methoxyphenyl)-2-(6-(1-(2,2-difluoroethyl)piperidin-4-yl)-4-methoxypyridin-2-yl)-1-methyl-3-oxo-2,3-dihydro-1H-pyrazol-4-yl)-4-(difluoromethoxy)benzamide | 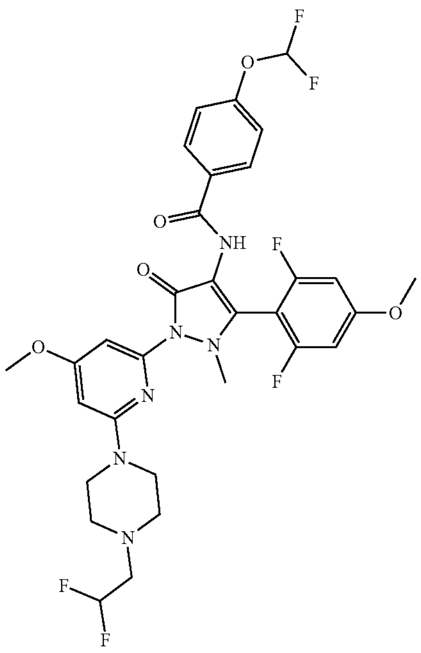 | 1.91<br>D<br>680.2 |
| 366 | N-(5-(2,6-Difluoro-4-methoxyphenyl)-2-(4-methoxy-6-(1-(methylsulfonyl)piperidin-4-yl)pyridin-2-yl)-1-methyl-3-oxo-2,3-dihydro-1H-pyrazol-4-yl)-4-(difluoromethoxy)benzamide | 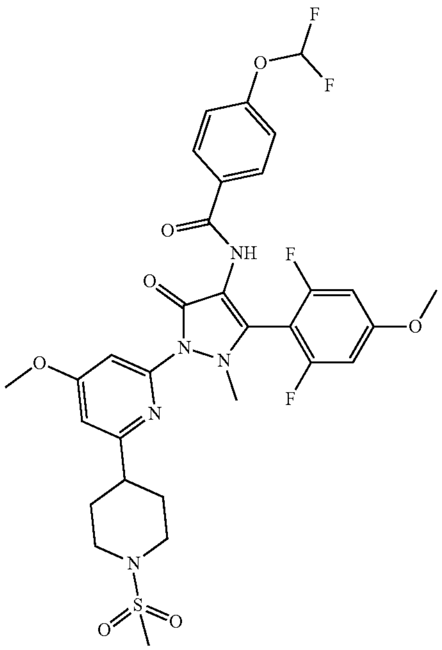 | 1.68<br>D<br>694.2 |

TABLE 2-continued

| $^1$H NMR data for the examples in Table 2: | | | |
|---|---|---|---|
| Ex. No. | Name | Structure | LC/MS Rt (min) Method M + H |
| 367 | N-(5-(2,6-Difluoro-4-methoxyphenyl)-2-(4-methoxy-6-(piperidin-4-yl)pyridin-2-yl)-1-methyl-3-oxo-2,3-dihydro-1H-pyrazol-4-yl)-4-(difluoromethoxy)benzamide | 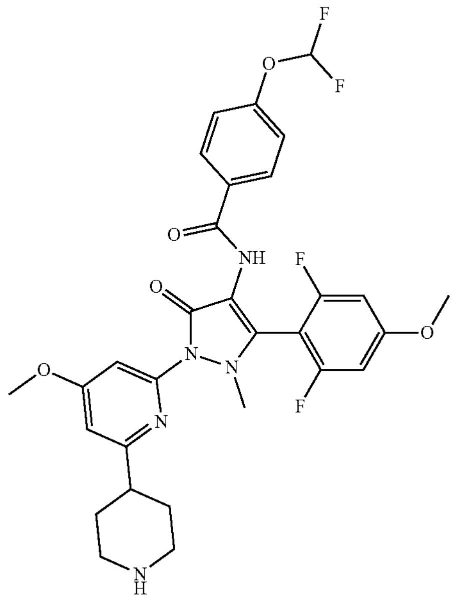 | 1.31<br>D<br>616.1 |
| 368 | N-(5-(2,6-Difluoro-4-methoxyphenyl)-2-(6-(1-(2-hydroxyethyl)piperidin-4-yl)-4-methoxypyridin-2-yl)-1-methyl-3-oxo-2,3-dihydro-1H-pyrazol-4-yl)-4-(difluoromethoxy)benzamide | 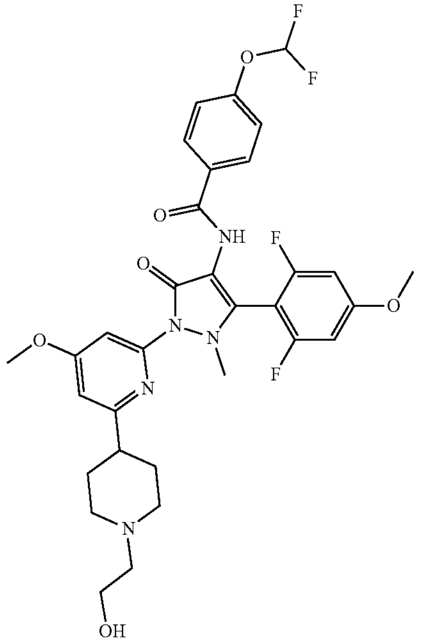 | 1.32<br>D<br>660.3 |

TABLE 2-continued

| Ex. No. | Name | Structure | LC/MS Rt (min) Method M + H |
|---|---|---|---|
| | $^1$H NMR data for the examples in Table 2: | | |
| 369 | N-(5-(2,6-Difluoro-4-methoxyphenyl)-1-methyl-3-oxo-2-(3-((tetrahydrofuran-3-yl)methoxy)-6-(trifluoromethyl)pyridin-2-yl)-2,3-dihydro-1H-pyrazol-4-yl)-4-(difluoromethoxy)benzamide | 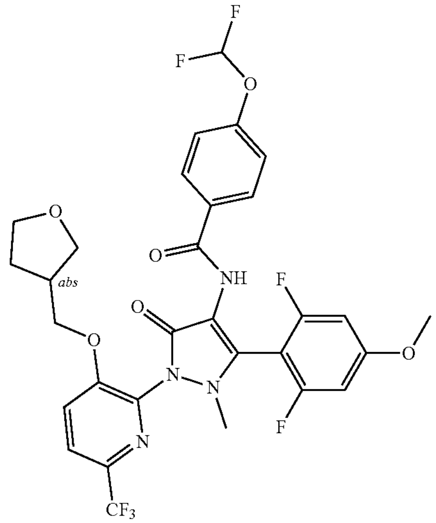 [SMILES: COc1cc(F)c(-c2c(NC(=O)c3ccc(OC(F)F)cc3)c(=O)n(-c3nc(C(F)(F)F)ccc3OCC3CCOC3)n2C)c(F)c1] | 1.67 D 671.1 |
| 370 | N-(5-(2,6-Difluoro-4-methoxyphenyl)-1-methyl-3-oxo-2-(3-((tetrahydrofuran-3-yl)methoxy)-6-(trifluoromethyl)pyridin-2-yl)-2,3-dihydro-1H-pyrazol-4-yl)-4-(difluoromethoxy)benzamide | 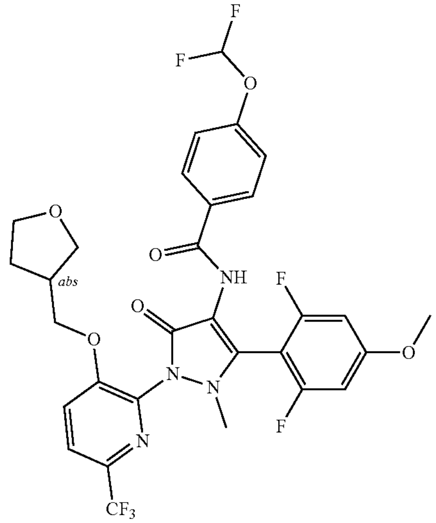 [SMILES: COc1cc(F)c(-c2c(NC(=O)c3ccc(OC(F)F)cc3)c(=O)n(-c3nc(C(F)(F)F)ccc3OCC3CCOC3)n2C)c(F)c1] | 1.76 C 671.1 |
| 371 | N-(5-(2,6-Difluoro-4-methoxyphenyl)-2-(3-methoxy-6-(trifluoromethyl)pyridin-2-yl)-1-methyl-3-oxo-2,3-dihydro-1H-pyrazol-4-yl)-4-(difluoromethoxy)benzamide | 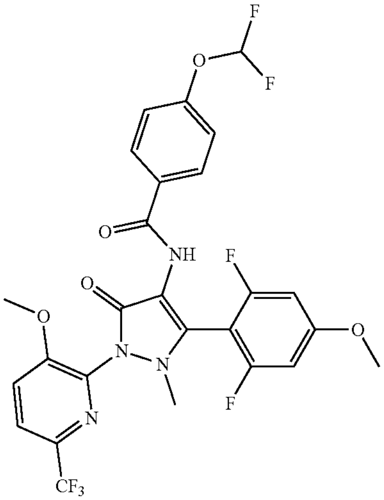 | 1.72 C 601.1 |

TABLE 2-continued

| $^1$H NMR data for the examples in Table 2: | | | |
|---|---|---|---|
| Ex. No. | Name | Structure | LC/MS Rt (min) Method M + H |
| 372 | N-(5-(2,6-Difluoro-4-methoxyphenyl)-2-(3-(2-hydroxyethoxy)-6-(trifluoromethyl)pyridin-2-yl)-1-methyl-3-oxo-2,3-dihydro-1H-pyrazol-4-yl)-4-(difluoromethoxy)benzamide | 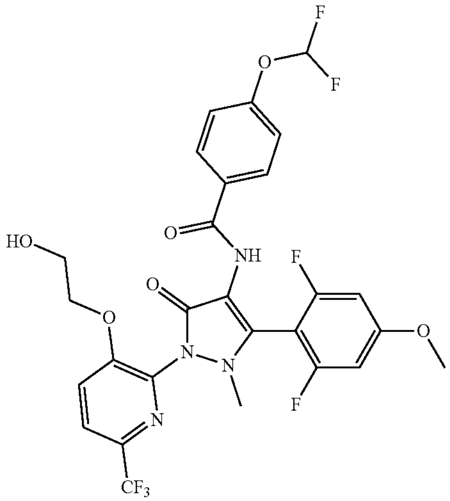 [SMILES: COc1cc(F)c(-c2c(NC(=O)c3ccc(OC(F)F)cc3)c(=O)n(-c3nc(C(F)(F)F)ccc3OCCO)n2C)c(F)c1] | 1.65 C 631.1 |
| 373 | (S)-N-(5-(2,6-Difluoro-4-methoxyphenyl)-2-(3-(2-hydroxypropoxy)-6-(trifluoromethyl)pyridin-2-yl)-1-methyl-3-oxo-2,3-dihydro-1H-pyrazol-4-yl)-4-(difluoromethoxy)benzamide | 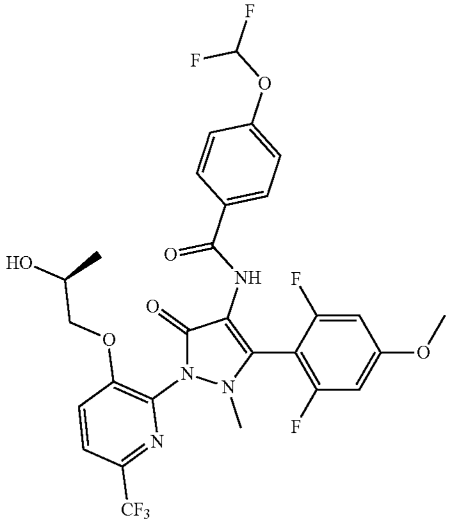 [SMILES: COc1cc(F)c(-c2c(NC(=O)c3ccc(OC(F)F)cc3)c(=O)n(-c3nc(C(F)(F)F)ccc3OC[C@H](C)O)n2C)c(F)c1] | 1.49 C 645.2 |
| 374 | N-(5-(2,6-Difluoro-4-methoxyphenyl)-2-(3-((2-hydroxyethyl)amino)-6-(trifluoromethyl)pyridin-2-yl)-1-methyl-3-oxo-2,3-dihydro-1H-pyrazol-4-yl)-4-(difluoromethoxy)benzamide | 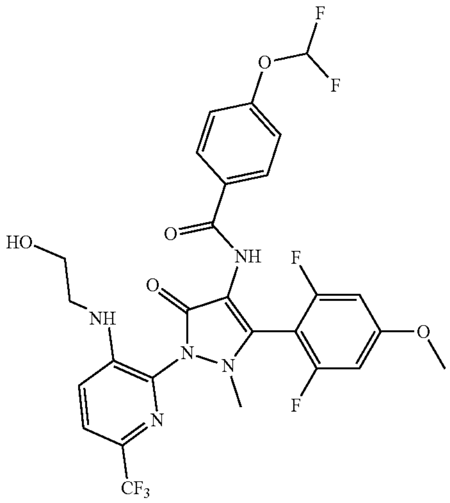 | 1.49 C 600.2 |

TABLE 2-continued

| $^1$H NMR data for the examples in Table 2: | | | |
|---|---|---|---|
| Ex. No. | Name | Structure | LC/MS Rt (min) Method M + H |
| 375 | N-(5-(2,6-Difluoro-4-methoxyphenyl)-2-(3-((2-hydroxyethyl)(methyl)amino)-6-(trifluoromethyl)pyridin-2-yl)-1-methyl-3-oxo-2,3-dihydro-1H-pyrazol-4-yl)-4-(difluoromethoxy)benzamide | 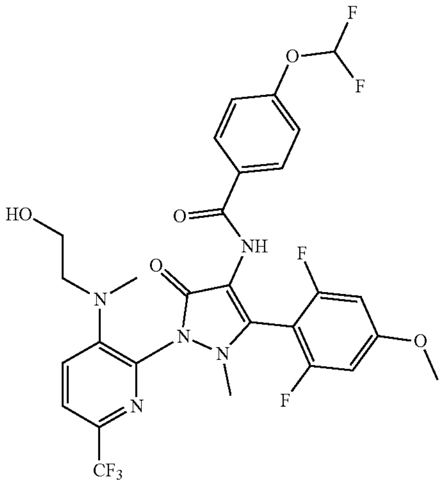 [SMILES: COc1cc(F)c(-c2c(NC(=O)c3ccc(OC(F)F)cc3)c(=O)n(-c3nc(C(F)(F)F)ccc3N(C)CCO)n2C)c(F)c1] | 1.52<br>C<br>644.1 |
| 376 | N-(5-(2,6-Difluoro-4-methoxyphenyl)-2-(4-methoxy-6-methylpyridin-2-yl)-1-methyl-3-oxo-2,3-dihydro-1H-pyrazol-4-yl)-4-(difluoromethoxy)benzamide | 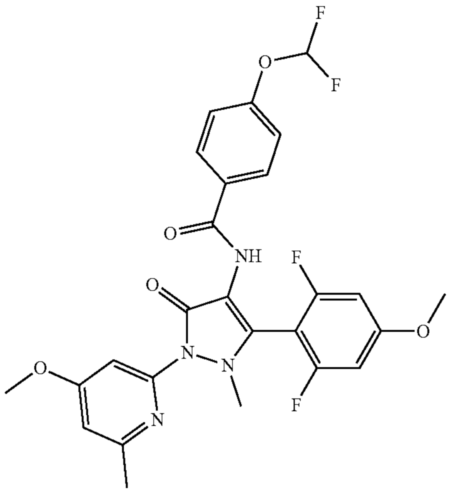 | 1.56<br>D<br>547.1 |

TABLE 2-continued
| $^{1}H$ NMR data for the examples in Table 2: | | | |
|---|---|---|---|
| Ex. No. | Name | Structure | LC/MS Rt (min) Method M + H |
| 377 | N-(5-(2,6-Difluoro-4-methoxyphenyl)-2-(6-(2-hydroxy-2-methylpropoxy)-4-isopropoxypyridin-2-yl)-1-methyl-3-oxo-2,3-dihydro-1H-pyrazol-4-yl)-4-(difluoromethoxy)benzamide | 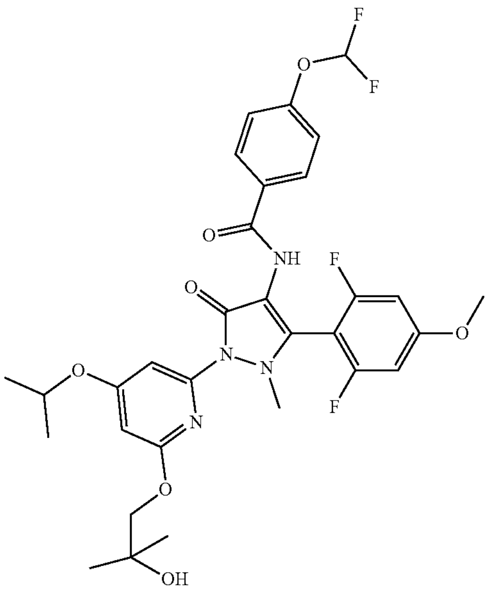 [SMILES: COc1cc(F)c(-c2c(NC(=O)c3ccc(OC(F)F)cc3)c(=O)n(-c3cc(OC(C)C)cc(OCC(C)(C)O)n3)n2C)c(F)c1] | 1.82 D 649.2 |
| 378 | N-(5-(2,6-Difluoro-4-methoxyphenyl)-2-(6-(2-hydroxyethoxy)-4-isopropoxypyridin-2-yl)-1-methyl-3-oxo-2,3-dihydro-1H-pyrazol-4-yl)-4-(difluoromethoxy)benzamide | 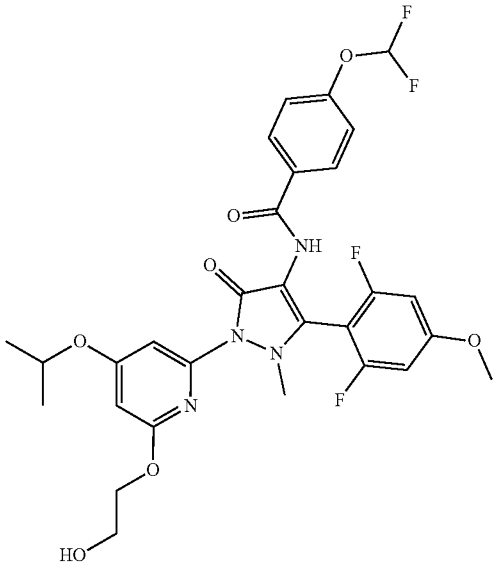 [SMILES: COc1cc(F)c(-c2c(NC(=O)c3ccc(OC(F)F)cc3)c(=O)n(-c3cc(OC(C)C)cc(OCCO)n3)n2C)c(F)c1] | 1.65 D 621.2 |

TABLE 2-continued

| Ex. No. | Name | Structure | LC/MS Rt (min) Method M + H |
|---|---|---|---|
| | $^1$H NMR data for the examples in Table 2: | | |
| 379 | N-(5-(2,6-Difluoro-4-methoxyphenyl)-2-(6-(3-hydroxy-3-methylbutoxy)-4-methoxypyridin-2-yl)-1-methyl-3-oxo-2,3-dihydro-1H-pyrazol-4-yl)-4-(difluoromethoxy)benzamide | 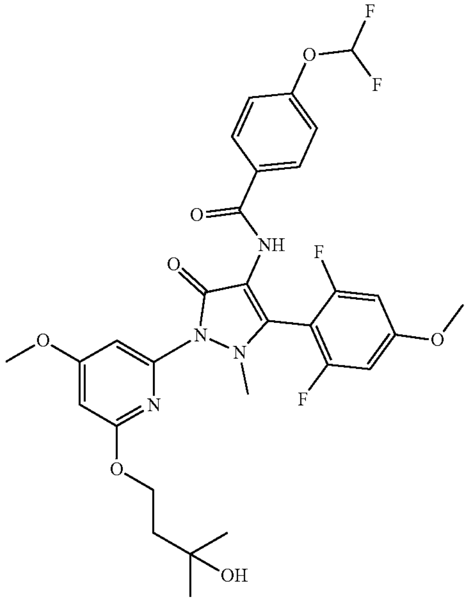 | 1.67<br>D<br>635.2 |
| 380 | N-(5-(2,6-Difluoro-4-methoxyphenyl)-2-(4-methoxy-6-(3,3,3-trifluoro-2-hydroxypropoxy)pyridin-2-yl)-1-methyl-3-oxo-2,3-dihydro-1H-pyrazol-4-yl)-4-(difluoromethoxy)benzamide | 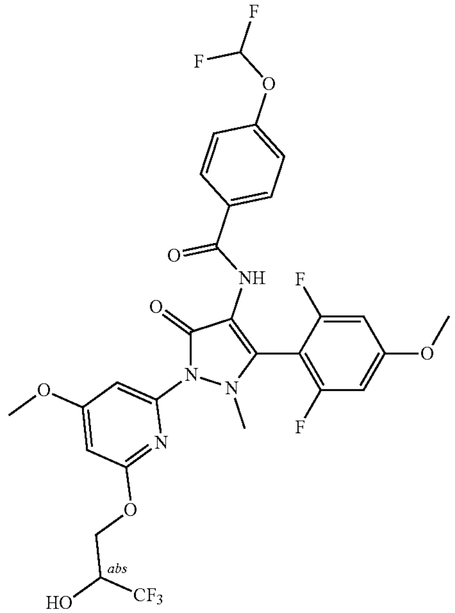 | 1.76<br>D<br>661.3 |

TABLE 2-continued

| $^1$H NMR data for the examples in Table 2: | | | |
|---|---|---|---|
| Ex. No. | Name | Structure | LC/MS Rt (min) Method M + H |
| 381 | N-(5-(2,6-Difluoro-4-methoxyphenyl)-2-(4-methoxy-6-((1,1,1-trifluoro-3-hydroxypropan-2-yl)oxy)pyridin-2-yl)-1-methyl-3-oxo-2,3-dihydro-1H-pyrazol-4-yl)-4-(difluoromethoxy)benzamide | 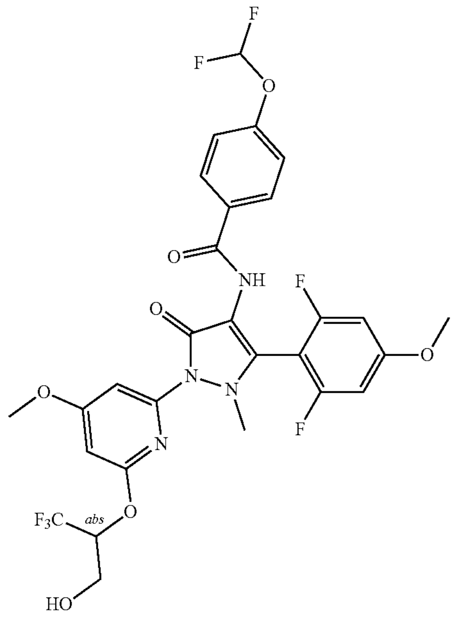 | 1.78 D 661.1 |
| 382 | N-(5-(2,6-Difluoro-4-methoxyphenyl)-2-(6-((1-hydroxy-3-methoxypropan-2-yl)oxy)-4-methoxypyridin-2-yl)-1-methyl-3-oxo-2,3-dihydro-1H-pyrazol-4-yl)-4-(difluoromethoxy)benzamide | 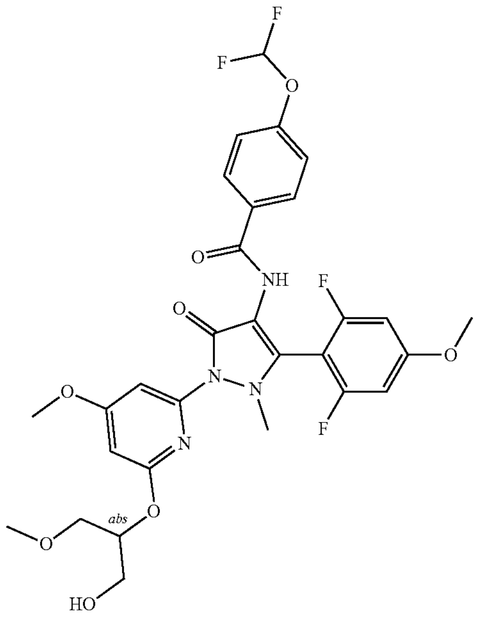 | 1.53 D 637.2 |

TABLE 2-continued

| $^1$H NMR data for the examples in Table 2: | | | |
|---|---|---|---|
| Ex. No. | Name | Structure | LC/MS Rt (min) Method M + H |
| 383 | N-(5-(2,6-Difluoro-4-methoxyphenyl)-2-(4-methoxy-6-(3,3,3-trifluoro-2-hydroxypropoxy)pyridin-2-yl)-1-methyl-3-oxo-2,3-dihydro-1H-pyrazol-4-yl)-4-(difluoromethoxy)benzamide | 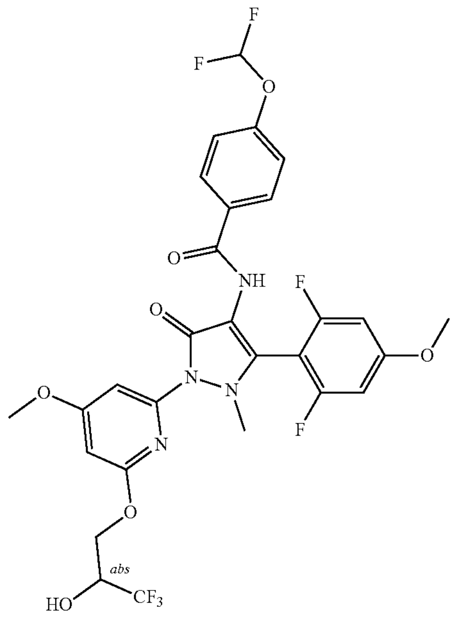 | 1.76 D 661.1 |
| 384 | N-(5-(2,6-Difluoro-4-methoxyphenyl)-2-(6-((3-(hydroxymethyl)oxetan-3-yl)methoxy)-4-methoxypyridin-2-yl)-1-methyl-3-oxo-2,3-dihydro-1H-pyrazol-4-yl)-4-(difluoromethoxy)benzamide | 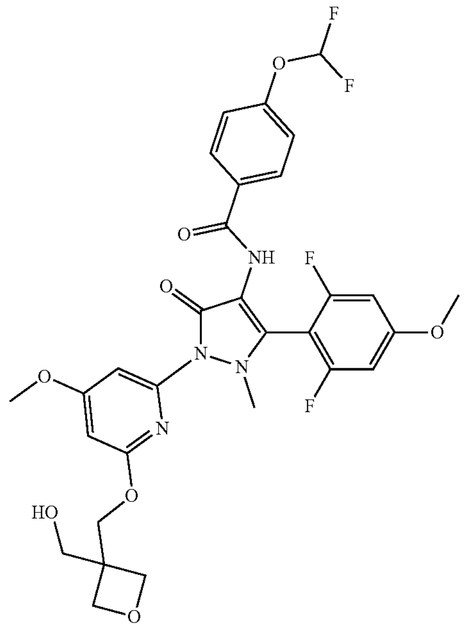 | 1.45 D 649.2 |

TABLE 2-continued

| $^1$H NMR data for the examples in Table 2: | | | |
|---|---|---|---|
| Ex. No. | Name | Structure | LC/MS Rt (min) Method M + H |
| 385 | N-(5-(2,6-Difluoro-4-methoxyphenyl)-2-(6-(2-fluoro-2-methylpropoxy)-4-methoxypyridin-2-yl)-1-methyl-3-oxo-2,3-dihydro-1H-pyrazol-4-yl)-4-(difluoromethoxy)benzamide | 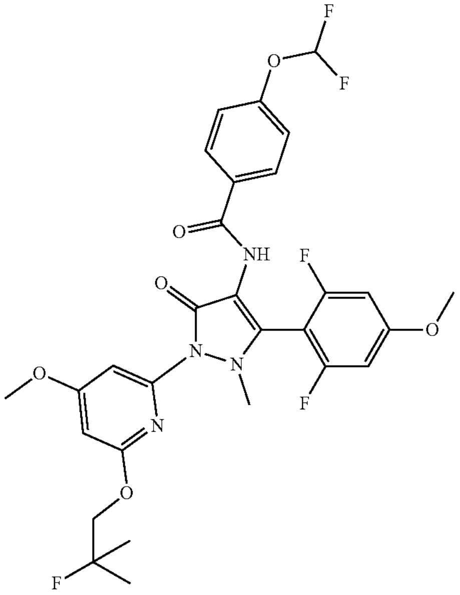 | 1.96<br>D<br>623.2 |
| 386 | N-(5-(2,6-Difluoro-4-methoxyphenyl)-2-(6-((1-hydroxy-3-methoxypropan-2-yl)oxy)-4-methoxypyridin-2-yl)-1-methyl-3-oxo-2,3-dihydro-1H-pyrazol-4-yl)-4-(difluoromethoxy)benzamide | 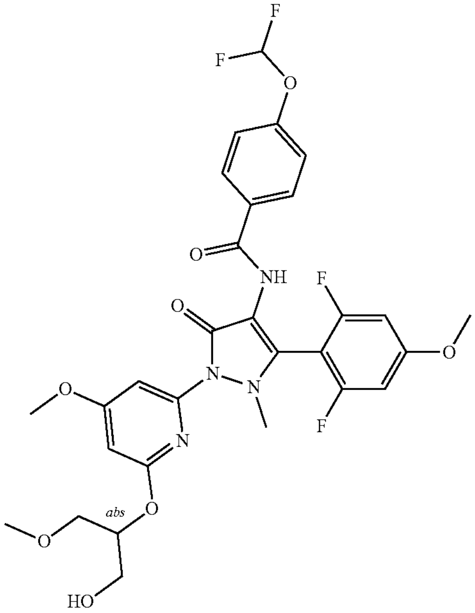 | 1.94<br>D<br>637.2 |

TABLE 2-continued
| $^1$H NMR data for the examples in Table 2: | | | |
|---|---|---|---|
| Ex. No. | Name | Structure | LC/MS Rt (min) Method M + H |
| 387 | N-(5-(2,6-Difluoro-4-methoxyphenyl)-2-(6-(2,2-difluoropropoxy)-4-methoxypyridin-2-yl)-1-methyl-3-oxo-2,3-dihydro-1H-pyrazol-4-yl)-4-(difluoromethoxy)benzamide | 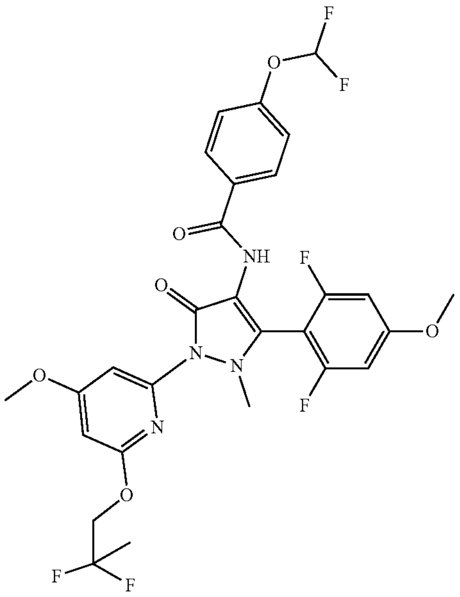 | 1.94 D 627.1 |
| 388 | N-(5-(2,6-Difluoro-4-methoxyphenyl)-2-(5-(2-hydroxyethoxy)pyridin-2-yl)-1-methyl-3-oxo-2,3-dihydro-1H-pyrazol-4-yl)-4-(difluoromethoxy)benzamide | 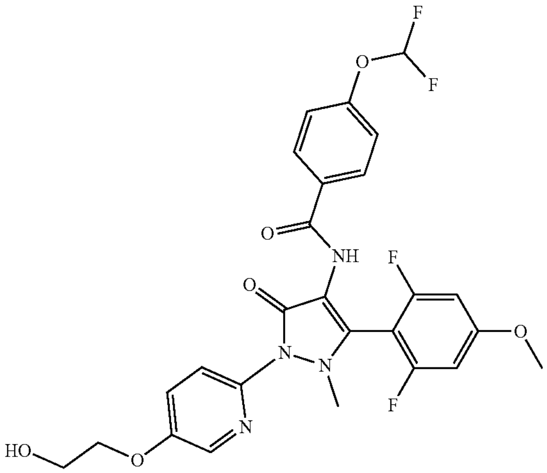 [SMILES: COc1cc(F)c(-c2c(NC(=O)c3ccc(OC(F)F)cc3)c(=O)n(-c3ccc(OCCO)cn3)n2C)c(F)c1] | 1.38 C 563.1 |

TABLE 2-continued

| $^1$H NMR data for the examples in Table 2: | | | |
|---|---|---|---|
| Ex. No. | Name | Structure | LC/MS Rt (min) Method M + H |
| 389 | N-(5-(2,6-Difluoro-4-methoxyphenyl)-2-(4-methoxy-6-(2,2,2-trifluoroethoxy)pyridin-2-yl)-1-methyl-3-oxo-2,3-dihydro-1H-pyrazol-4-yl)-4-(difluoromethoxy)benzamide | 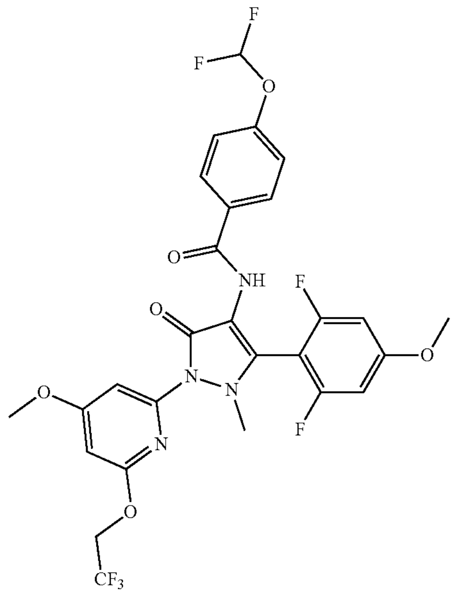 | 1.96<br>D<br>631.2 |
| 390 | N-(5-(2,6-Difluoro-4-methoxyphenyl)-2-(4-methoxy-6-((1,1,1-trifluoro-3-hydroxypropan-2-yl)oxy)pyridin-2-yl)-1-methyl-3-oxo-2,3-dihydro-1H-pyrazol-4-yl)-4-(difluoromethoxy)benzamide | 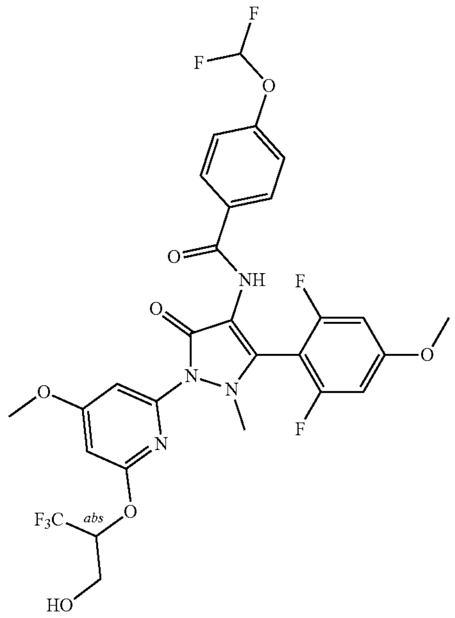 | 1.78<br>D<br>661.1 |

TABLE 2-continued
| $^1$H NMR data for the examples in Table 2: | | | |
|---|---|---|---|
| Ex. No. | Name | Structure | LC/MS Rt (min) Method M + H |
| 391 | N-(5-(2,6-Difluoro-4-methoxyphenyl)-1-methyl-2-(6-methyl-4-((tetrahydrofuran-2-yl)methoxy)pyridin-2-yl)-3-oxo-2,3-dihydro-1H-pyrazol-4-yl)-4-(difluoromethoxy)benzamide | 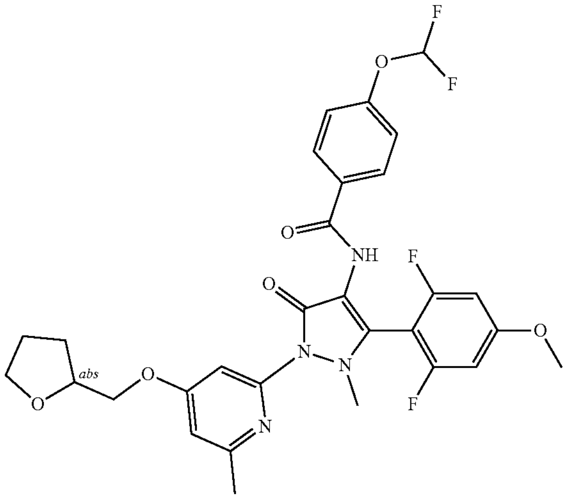 [SMILES: COc1cc(F)c(-c2c(NC(=O)c3ccc(OC(F)F)cc3)c(=O)n(-c3cc(OCC4CCCO4)cc(C)n3)n2C)c(F)c1] | 1.68 C 617.2 |
| 392 | N-(5-(2,6-Difluoro-4-methoxyphenyl)-2-(6-(2-hydroxy-2-methylpropoxy)pyridin-2-yl)-1-methyl-3-oxo-2,3-dihydro-1H-pyrazol-4-yl)-4-(difluoromethoxy)benzamide | 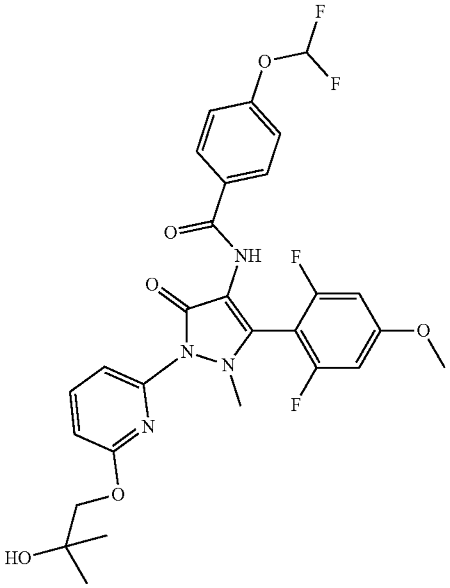 [SMILES: COc1cc(F)c(-c2c(NC(=O)c3ccc(OC(F)F)cc3)c(=O)n(-c3cccc(OCC(C)(C)O)n3)n2C)c(F)c1] | 1.64 C 591.2 |

TABLE 2-continued

| Ex. No. | Name | Structure | LC/MS Rt (min) Method M + H |
|---|---|---|---|
| | | $^1$H NMR data for the examples in Table 2: | |
| 393 | N-(5-(2,6-Difluoro-4-methoxyphenyl)-2-(4-(2-hydroxypropoxy)-6-methylpyridin-2-yl)-1-methyl-3-oxo-2,3-dihydro-1H-pyrazol-4-yl)-4-(difluoromethoxy)benzamide | 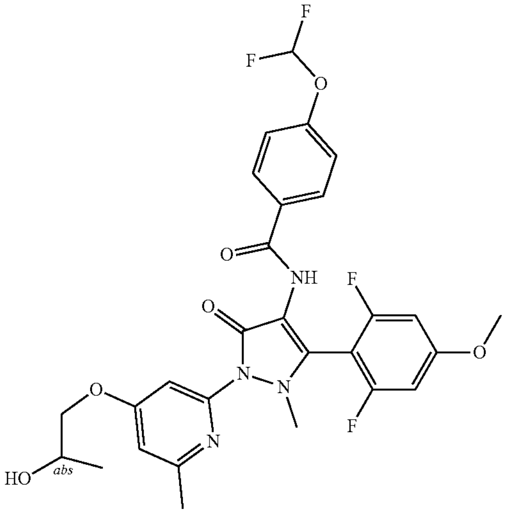 [SMILES: COc1cc(F)c(-c2c(NC(=O)c3ccc(OC(F)F)cc3)c(=O)n(-c3cc(OCC(C)O)cc(C)n3)n2C)c(F)c1] | 1.49 C 591.2 |
| 394 | N-(5-(2,6-Difluoro-4-methoxyphenyl)-2-(4-(2-hydroxypropoxy)-6-methylpyridin-2-yl)-1-methyl-3-oxo-2,3-dihydro-1H-pyrazol-4-yl)-4-(difluoromethoxy)benzamide | 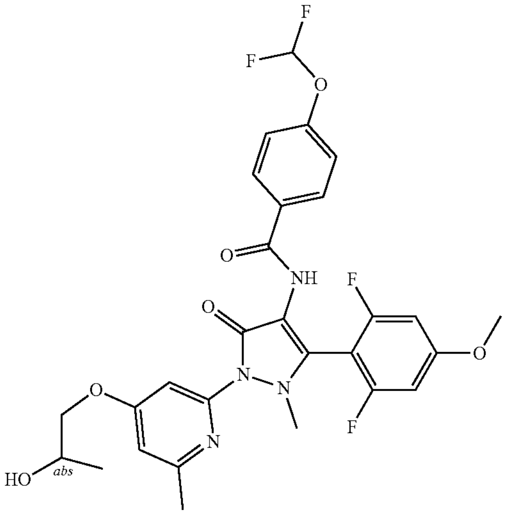 [SMILES: COc1cc(F)c(-c2c(NC(=O)c3ccc(OC(F)F)cc3)c(=O)n(-c3cc(OCC(C)O)cc(C)n3)n2C)c(F)c1] | 1.49 C 591.2 |
| 395 | N-(5-(2,6-Difluoro-4-methoxyphenyl)-1-methyl-2-(1-methyl-2-oxo-1,2-dihydropyridin-3-yl)-3-oxo-2,3-dihydro-1H-pyrazol-4-yl)-4-(difluoromethoxy)benzamide | 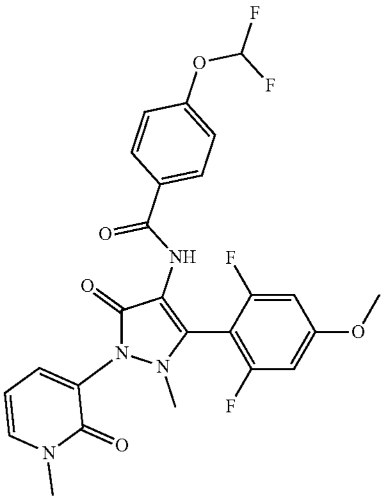 [SMILES: COc1cc(F)c(-c2c(NC(=O)c3ccc(OC(F)F)cc3)c(=O)n(-c3cccn(C)c3=O)n2C)c(F)c1] | 1.20 D 533.1 |

TABLE 2-continued

| ¹H NMR data for the examples in Table 2: | | | |
|---|---|---|---|
| Ex. No. | Name | Structure | LC/MS Rt (min) Method M + H |
| 396 | N-(5-(2,6-Difluoro-4-methoxyphenyl)-1-methyl-2-(6-methyl-4-((tetrahydrofuran-2-yl)methoxy)pyridin-2-yl)-3-oxo-2,3-dihydro-1H-pyrazol-4-yl)-4-(difluoromethoxy)benzamide | 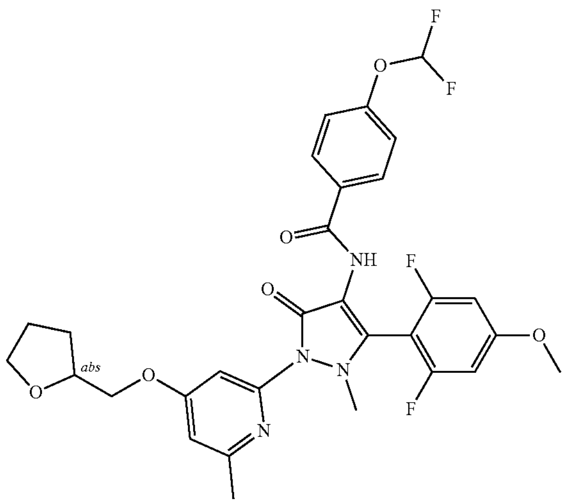 [SMILES: COc1cc(F)c(-c2c(NC(=O)c3ccc(OC(F)F)cc3)c(=O)n(-c3cc(OCC4CCCO4)cc(C)n3)n2C)c(F)c1] | 1.68 C 617.2 |
| 397 | N-(5-(2,6-difluoro-4-(methoxy-d3)phenyl)-2-(4-(difluoromethyl)pyridin-2-yl)-1-methyl-3-oxo-2,3-dihydro-1H-pyrazol-4-yl)-4-(difluoromethoxy)benzamide | 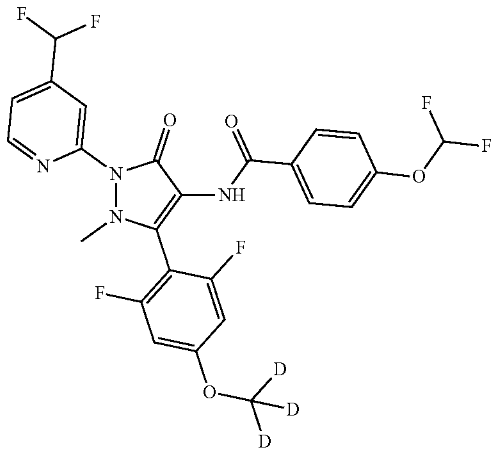 [SMILES: [2H]C([2H])([2H])Oc1cc(F)c(-c2c(NC(=O)c3ccc(OC(F)F)cc3)c(=O)n(-c3cc(C(F)F)ccn3)n2C)c(F)c1] | 1.81 E 556.1 |
| 398 | N-(5-(4-chloro-2,6-difluorophenyl)-2-(6-(2-hydroxyethoxy)-4-isopropoxypyridin-2-yl)-1-methyl-3-oxo-2,3-dihydro-1H-pyrazol-4-yl)-4-(trifluoromethoxy)benzamide | 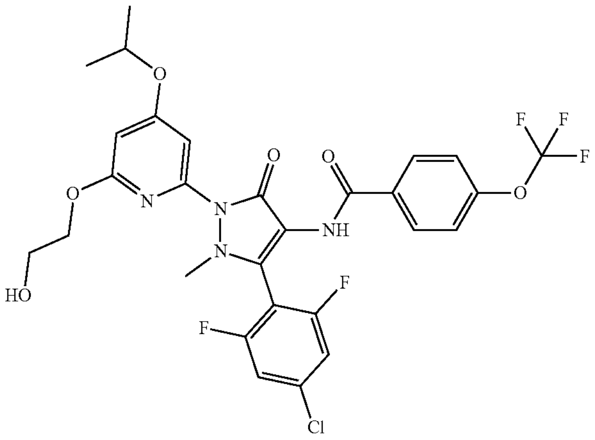 [SMILES: CC(C)Oc1cc(OCCO)nc(-n2c(=O)c(NC(=O)c3ccc(OC(F)(F)F)cc3)c(-c3c(F)cc(Cl)cc3F)n2C)c1] | 2.04 E 643.0 |

TABLE 2-continued

| $^1$H NMR data for the examples in Table 2: | | | |
|---|---|---|---|
| Ex. No. | Name | Structure | LC/MS Rt (min) Method M + H |
| 399 | N-(5-(4-chloro-2,6-difluorophenyl)-2-(6-(2-hydroxyethoxy)-4-isopropoxypyridin-2-yl)-1-methyl-3-oxo-2,3-dihydro-1H-pyrazol-4-yl)-4-(difluoromethoxy)benzamide | 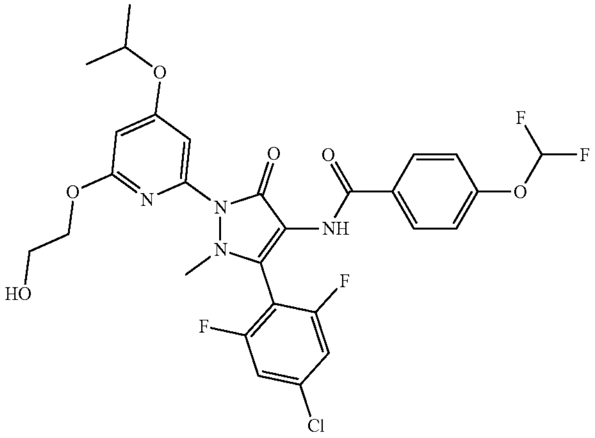 [SMILES: CC(C)Oc1cc(OCCO)nc(-n2c(=O)c(NC(=O)c3ccc(OC(F)F)cc3)c(-c3c(F)cc(Cl)cc3F)n2C)c1] | 1.88 E 625.1 |
| 400 | 4-(difluoromethoxy)-N-(5-(4-(difluoromethoxy)-2,6-difluorophenyl)-2-(6-(2-hydroxy-2-methylpropoxy)-4-methylpyridin-2-yl)-1-methyl-3-oxo-2,3-dihydro-1H-pyrazol-4-yl)benzamide | 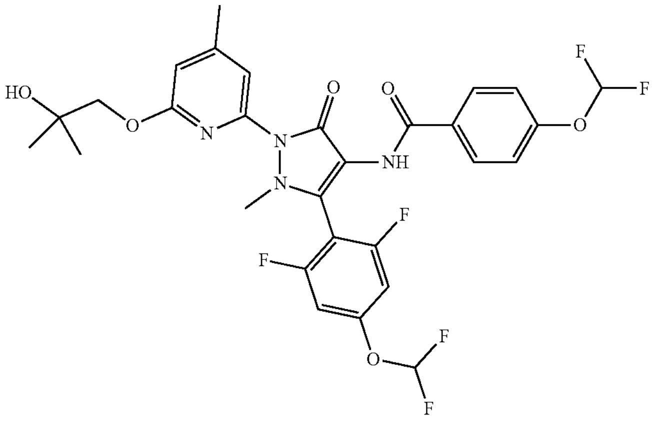 [SMILES: Cc1cc(OCC(C)(C)O)nc(-n2c(=O)c(NC(=O)c3ccc(OC(F)F)cc3)c(-c3c(F)cc(OC(F)F)cc3F)n2C)c1] | 1.95 E 641.1 |
| 401 | N-(5-(2,6-difluoro-4-(trifluoromethyl)phenyl)-2-(6-(2-hydroxypropan-2-yl)pyridin-2-yl)-1-methyl-3-oxo-2,3-dihydro-1H-pyrazol-4-yl)-4-(difluoromethoxy)benzamide | 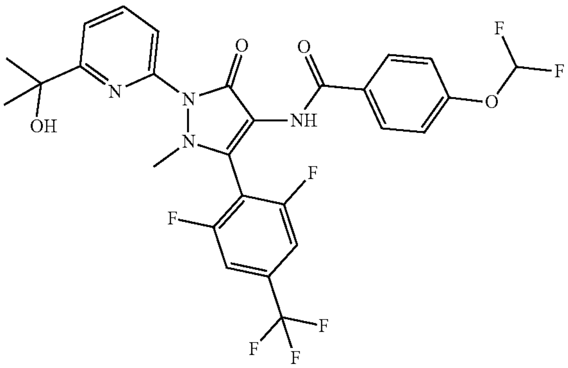 [SMILES: Cn1c(-c2c(F)cc(C(F)(F)F)cc2F)c(NC(=O)c2ccc(OC(F)F)cc2)c(=O)n1-c1cccc(C(C)(C)O)n1] | 1.96 E 599.0 |

TABLE 2-continued

| $^1$H NMR data for the examples in Table 2: | | | |
|---|---|---|---|
| Ex. No. | Name | Structure | LC/MS Rt (min) Method M + H |
| 402 | N-(5-(2,6-difluoro-4-(methoxy-d3)phenyl)-1-methyl-3-oxo-2-(4-(trifluoromethyl)pyridin-2-yl)-2,3-dihydro-1H-pyrazol-4-yl)-4-(trifluoromethoxy)benzamide | 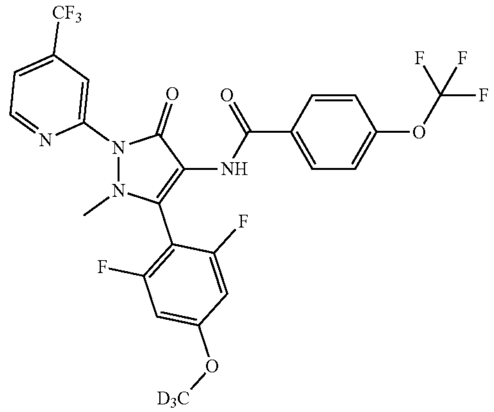 [SMILES: [2H]C([2H])([2H])Oc1cc(F)c(-c2c(NC(=O)c3ccc(OC(F)(F)F)cc3)c(=O)n(-c3cc(C(F)(F)F)ccn3)n2C)c(F)c1] | 2.11 E 592.1 |
| 403 | N-(5-(4-ethyl-2,6-difluorophenyl)-2-(6-(2-hydroxypropan-2-yl)pyridin-2-yl)-1-methyl-3-oxo-2,3-dihydro-1H-pyrazol-4-yl)-4-(trifluoromethoxy)benzamide | 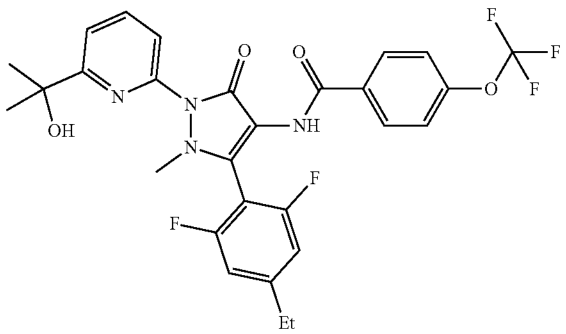 [SMILES: CCc1cc(F)c(-c2c(NC(=O)c3ccc(OC(F)(F)F)cc3)c(=O)n(-c3cccc(C(C)(C)O)n3)n2C)c(F)c1] | 2.05 E 577.2 |
| 404 | N-(5-(2,6-difluoro-4-(methoxy-d3)phenyl)-2-(6-(2-hydroxypropan-2-yl)pyridin-2-yl)-1-methyl-3-oxo-2,3-dihydro-1H-pyrazol-4-yl)-4-(difluoromethoxy)benzamide | 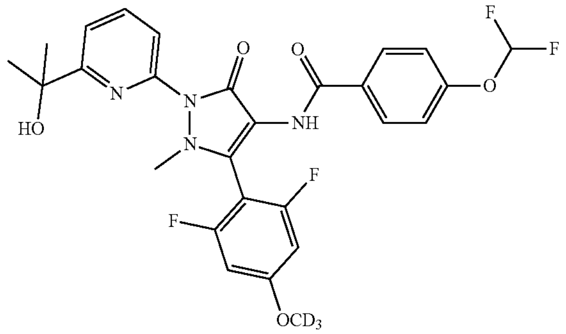 | 2.05 E 564.1 |
| 405 | N-(5-(2,6-difluoro-4-(methoxy-d3)phenyl)-2-(6-(2-hydroxypropan-2-yl)pyridin-2-yl)-1-methyl-3-oxo-2,3-dihydro-1H-pyrazol-4-yl)-4-(trifluoromethoxy)benzamide | 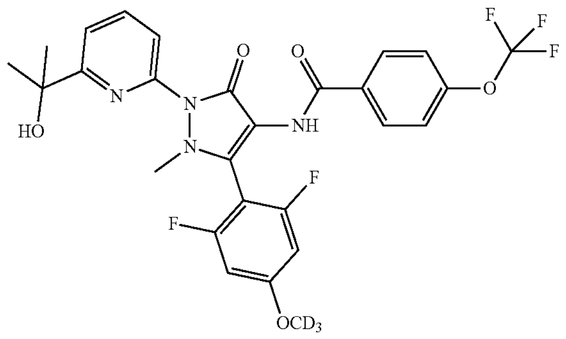 | 1.83 E 582.2 |

TABLE 2-continued

| $^1$H NMR data for the examples in Table 2: | | | |
|---|---|---|---|
| Ex. No. | Name | Structure | LC/MS Rt (min) Method M + H |
| 406 | N-(5-(4-chloro-2,6-difluorophenyl)-2-(6-(2-hydroxypropan-2-yl)pyridin-2-yl)-1-methyl-3-oxo-2,3-dihydro-1H-pyrazol-4-yl)-4-(trifluoromethoxy)benzamide | 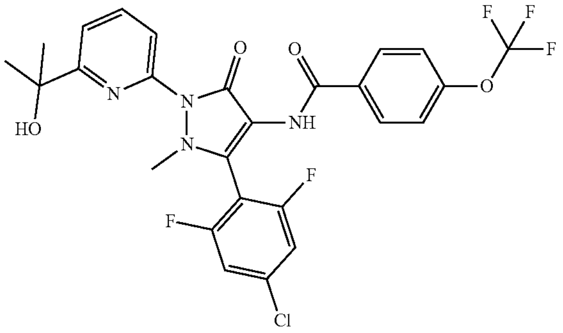 [SMILES: Cn1c(-c2c(F)cc(Cl)cc2F)c(NC(=O)c2ccc(OC(F)(F)F)cc2)c(=O)n1-c1cccc(C(C)(C)O)n1] | 2.01 E 583.1 |
| 407 | N-(5-(4-chloro-2,6-difluorophenyl)-2-(6-(2-hydroxypropan-2-yl)pyridin-2-yl)-1-methyl-3-oxo-2,3-dihydro-1H-pyrazol-4-yl)-4-(trifluoromethoxy)benzamide | 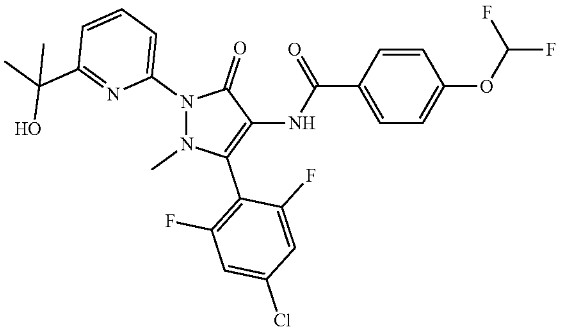 [SMILES: Cn1c(-c2c(F)cc(Cl)cc2F)c(NC(=O)c2ccc(OC(F)F)cc2)c(=O)n1-c1cccc(C(C)(C)O)n1] | 1.82 E 565.1 |
| 408 | N-(5-(4-chloro-2,6-difluorophenyl)-2-(6-(2-hydroxy-2-methylpropoxy)-4-isopropoxypyridin-2-yl)-1-methyl-3-oxo-2,3-dihydro-1H-pyrazol-4-yl)-4-(trifluoromethoxy)benzamide | 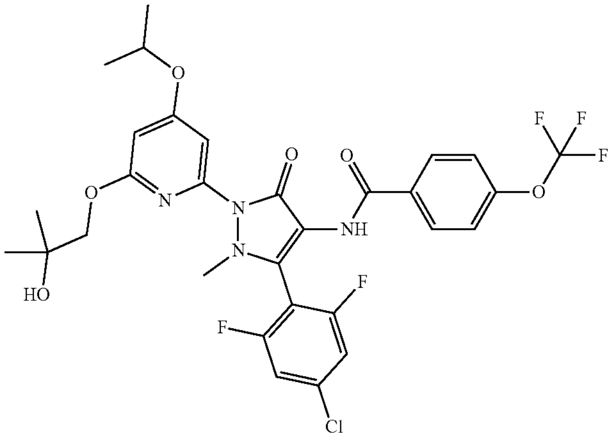 [SMILES: CC(C)Oc1cc(OCC(C)(C)O)nc(-n2c(=O)c(NC(=O)c3ccc(OC(F)(F)F)cc3)c(-c3c(F)cc(Cl)cc3F)n2C)c1] | 2.28 E 671.2 |

$^1$H NMR data for the examples in Table 2:

Example 2

$^1$H NMR (500 MHz, DMSO-$d_6$) δ 9.87 (s, 1H), 7.93 (br d, J=7.9 Hz, 2H), 7.69-7.56 (m, 1H), 7.44 (br d, J=8.2 Hz, 2H), 7.34-7.16 (m, 3H), 6.90 (br d, J=10.4 Hz, 2H), 3.72 (br s, 3H), 2.96 (s, 3H).

Example 3

$^1$H NMR (500 MHz, $CD_3OD$) δ 7.87 (br d, J=6.1 Hz, 2H), 7.39-7.23 (m, 3H), 7.21-7.12 (m, 2H), 7.05-6.68 (m, 3H), 3.85 (s, 3H), 3.07 (s, 3H), 2.39 (s, 3H), 2.16 (s, 3H).

Example 4

$^1$H NMR (500 MHz, $CD_3OD$) δ 7.92 (br d, J=7.0 Hz, 2H), 7.65-7.42 (m, 5H), 7.33 (br d, J=7.9 Hz, 2H), 6.76 (br d, J=10.8 Hz, 2H), 3.86 (s, 3H), 3.10 (s, 3H).

Example 5

$^1$H NMR (500 MHz, $CD_3OD$) δ 7.98 (br d, J=7.2 Hz, 2H), 7.74 (br d, J=8.2 Hz, 2H), 7.59 (t, J=7.8 Hz, 2H), 7.54-7.50 (m, 2H), 7.50-7.43 (m, 1H), 6.77 (d, J=10.0 Hz, 2H), 3.86 (s, 3H), 3.11 (s, 3H).

Example 6

$^1$H NMR (500 MHz, DMSO-d6) δ 7.89 (br d, J=7.7 Hz, 2H), 7.43-7.09 (m, 8H), 6.81 (br d, J=10.4 Hz, 2H), 5.13 (s, 2H), 3.80 (s, 3H), 3.09 (s, 3H).

Example 7

$^1$H NMR (500 MHz, DMSO-d6) δ 9.64 (s, 1H), 7.98 (br d, J=8.5 Hz, 2H), 7.66-7.53 (m, 6H), 7.39-7.19 (m, 4H), 7.11 (br d, J=8.5 Hz, 2H), 3.81 (s, 3H), 2.96 (s, 3H)

Example 8

$^1$H NMR (500 MHz, DMSO-d6) δ 7.89 (br d, J=8.2 Hz, 2H), 7.69-7.55 (m, 1H), 7.46-7.11 (m, 6H), 6.91 (br d, J=10.7 Hz, 2H), 2.96 (s, 3H), 2.55 (s, 3H).

Example 9

$^1$H NMR (500 MHz, $CD_3OD$) δ 7.80 (br d, J=7.2 Hz, 2H), 7.62-7.54 (m, 2H), 7.53-7.42 (m, 5H), 6.75 (br d, J=10.9 Hz, 2H), 3.86 (s, 3H), 3.09 (s, 3H).

Example 10

$^1$H NMR (500 MHz, DMSO-d6) δ 9.86 (s, 1H), 7.95 (br d, J=7.9 Hz, 2H), 7.52-7.37 (m, 6H), 6.93 (br d, J=10.7 Hz, 2H), 3.83 (s, 3H), 2.94 (s, 3H).

Example 11

$^1$H NMR (500 MHz, DMSO-d6) δ 7.82 (br s, 2H), 7.71-7.58 (m, 1H), 7.59-7.48 (m, 2H), 7.39-7.17 (m, 3H), 6.91 (br d, J=10.4 Hz, 2H), 3.82 (s, 3H), 2.96 (s, 3H).

Example 12

$^1$H NMR (500 MHz, DMSO-d6) δ 9.75 (s, 1H), 7.91 (br d, J=8.2 Hz, 2H), 7.50-7.40 (m, 4H), 7.33 (t, J=73.9 Hz, 1H), 7.25 (br d, J=8.2 Hz, 2H), 6.93 (br d, J=10.7 Hz, 2H), 3.83 (s, 3H), 2.93 (s, 3H).

Example 13

$^1$H NMR (500 MHz, $CD_3OD$) δ 7.83 (br d, J=7.8 Hz, 2H), 7.16 (d, J=8.7 Hz, 2H), 6.86 (t, J=73.6 Hz, 1H), 6.71 (d, J=9.9 Hz, 2H), 3.84 (s, 3H), 3.45 (s, 3H), 3.00 (quin, J=5.2 Hz, 1H), 1.22-1.16 (m, 4H).

Example 14

$^1$H NMR (500 MHz, $CD_3OD$) δ 7.87 (br d, J=7.2 Hz, 2H), 7.45 (br t, J=6.6 Hz, 1H), 7.20 (br dd, J=14.5, 8.7 Hz, 4H), 7.06-6.66 (m, 3H), 3.85 (s, 3H), 3.07 (s, 3H), 2.27 (s, 3H).

Example 15

$^1$H NMR (500 MHz, DMSO-d6) δ 9.80 (br s, 1H), 7.84 (br d, J=7.9 Hz, 2H), 7.53 (br d, J=8.2 Hz, 2H), 7.49-7.39 (m, 4H), 6.92 (br d, J=10.4 Hz, 2H), 3.82 (s, 3H), 2.93 (s, 3H).

Example 16

$^1$H NMR (500 MHz, $CD_3OD$) δ 7.70 (br d, J=7.3 Hz, 2H), 7.61-7.40 (m, 5H), 7.18-7.08 (m, 2H), 6.88-6.67 (m, 2H), 3.85 (s, 3H), 3.08 (s, 3H), 2.01-1.89 (m, 1H), 1.08-0.96 (m, 2H), 0.73 (br d, J=3.2 Hz, 2H).

Example 17

$^1$H NMR (500 MHz, DMSO-d6) δ 8.00 (br d, J=7.4 Hz, 2H), 7.82 (br d, J=8.2 Hz, 2H), 7.52-7.45 (m, 2H), 7.44-7.37 (m, 2H), 6.89 (br d, J=10.4 Hz, 2H), 3.83 (s, 3H), 2.95 (s, 3H).

Example 18

$^1$H NMR (500 MHz, $CD_3OD$) δ 7.84 (br d, J=7.6 Hz, 2H), 7.17 (d, J=8.6 Hz, 2H), 7.04-6.63 (m, 3H), 3.84 (s, 3H), 3.79-3.73 (m, 1H), 3.28 (s, 3H), 1.56 (d, J=7.0 Hz, 6H).

Example 19

$^1$H NMR (500 MHz, $CD_3OD$) δ 7.92 (br d, J=5.9 Hz, 2H), 7.66-7.42 (m, 7H), 6.93-6.65 (m, 3H), 3.86 (s, 3H), 3.10 (s, 3H).

Example 20

$^1$H NMR (500 MHz, $CD_3OD$) δ 7.87 (br s, 2H), 7.61-7.54 (m, 2H), 7.51 (br d, J=7.3 Hz, 2H), 7.49-7.44 (m, 1H), 7.15 (br t, J=8.1 Hz, 2H), 6.75 (br d, J=10.8 Hz, 2H), 3.86 (s, 3H), 3.09 (s, 3H).

Example 21

$^1$H NMR (500 MHz, $CDCl_3$) δ 7.92 (br s, 1H), 7.82 (br d, J=8.0 Hz, 2H), 7.14 (br d, J=8.5 Hz, 2H), 6.74-6.40 (m, 3H), 4.69 (s, 2H), 4.27 (q, J=7.0 Hz, 2H), 3.84 (s, 3H), 3.16 (s, 3H), 1.32 (t, J=7.2 Hz, 3H).

Example 22

$^1$H NMR (500 MHz, $CD_3OD$) δ 7.80 (br d, J=8.1 Hz, 2H), 7.64-7.40 (m, 5H), 7.03-6.89 (m, 2H), 6.81-6.70 (m, 2H), 3.87-3.82 (m, 6H), 3.08 (s, 3H).

Example 23

$^1$H NMR (500 MHz, $CD_3OD$) δ 10.42 (br s, 1H), 9.31 (br s, 1H), 8.77 (br d, J=7.7 Hz, 2H), 8.74-8.69 (m, 2H), 8.59 (s, 1H), 8.45-8.32 (m, 2H), 8.27 (br d, J=7.7 Hz, 2H), 8.24-8.19 (m, 1H), 7.69 (br d, J=11.2 Hz, 2H), 7.38 (s, 1H), 4.64 (s, 3H), 3.76 (s, 3H).

Example 24

$^1$H NMR (500 MHz, $CD_3OD$) δ 8.67-8.56 (m, 1H), 8.15 (s, 1H), 7.89 (br d, J=7.7 Hz, 1H), 7.53 (s, 5H), 6.75 (d, J=10.1 Hz, 2H), 3.86 (s, 3H), 3.10 (s, 3H).

Example 25

$^1$H NMR (500 MHz, $CD_3OD$) δ 8.81-8.73 (m, 1H), 8.21-8.15 (m, 1H), 7.63-7.42 (m, 6H), 6.77 (d, J=10.0 Hz, 2H), 3.87 (s, 3H), 3.11 (s, 3H).

Example 26

$^1$H NMR (500 MHz, DMSO-$d_6$) δ 9.80 (s, 1H), 7.95 (br d, J=8.5 Hz, 2H), 7.74-7.67 (m, 1H), 7.47-7.37 (m, 4H), 6.90 (br d, J=10.7 Hz, 2H), 3.81 (s, 3H), 2.98 (s, 3H).

Example 27

$^1$H NMR (500 MHz, DMSO-$d_6$) δ 9.69 (br s, 1H), 7.94-7.87 (m, 2H), 7.74-7.67 (m, 1H), 7.41 (br t, J=8.5 Hz, 2H), 7.30 (t, J=73.6 Hz, 1H), 7.23 (br d, J=8.5 Hz, 2H), 6.90 (br d, J=10.7 Hz, 2H), 3.81 (s, 3H), 2.97 (s, 3H).

Example 28

$^1$H NMR (500 MHz, DMSO-$d_6$) δ 9.81 (br s, 1H), 7.94 (br d, J=8.2 Hz, 2H), 7.57 (br d, J=6.1 Hz, 1H), 7.51-7.40 (m, 5H), 6.90 (br d, J=10.7 Hz, 2H), 3.81 (s, 3H), 2.93 (s, 3H).

Example 29

$^1$H NMR (500 MHz, DMSO-$d_6$) δ 9.59 (s, 1H), 7.91 (br d, J=8.3 Hz, 2H), 7.65-7.54 (m, 1H), 7.54-7.40 (m, 3H), 7.29 (t, J=73.6 Hz, 1H), 7.24 (br d, J=8.5 Hz, 2H), 6.89 (br d, J=10.4 Hz, 2H), 3.84 (s, 3H), 2.94 (s, 3H).

Example 30

$^1$H NMR (500 MHz, DMSO-$d_6$) δ 9.77 (br s, 1H), 7.85 (br d, J=7.9 Hz, 2H), 7.60-7.46 (m, 5H), 7.45-7.38 (m, 1H), 6.91 (br d, J=10.4 Hz, 2H), 3.82 (s, 3H), 2.93 (s, 3H).

Example 31

$^1$H NMR (500 MHz, DMSO-$d_6$) δ 9.78 (br s, 1H), 7.86 (br d, J=7.9 Hz, 2H), 7.77-7.67 (m, 1H), 7.54 (br d, J=8.2 Hz, 2H), 7.42 (br t, J=8.5 Hz, 2H), 6.92 (br d, J=10.4 Hz, 2H), 3.82 (s, 3H), 2.98 (s, 3H).

Example 32

$^1$H NMR (500 MHz, DMSO-$d_6$) δ 9.81 (s, 1H), 8.51 (br d, J=4.0 Hz, 1H), 8.04 (br t, J=8.9 Hz, 1H), 7.95 (br d, J=7.9 Hz, 2H), 7.69-7.59 (m, 1H), 7.45 (br d, J=7.9 Hz, 2H), 6.92 (br d, J=10.7 Hz, 2H), 3.82 (s, 3H), 3.04 (s, 3H).

Example 33

$^1$H NMR (500 MHz, DMSO-$d_6$) δ 9.71 (s, 1H), 8.96 (br d, J=4.6 Hz, 1H), 8.48 (br d, J=7.9 Hz, 1H), 7.95-7.86 (m, 2H), 7.86-7.78 (m, 1H), 7.31 (t, J=73.6 Hz, 1H), 7.22 (br d, J=8.2 Hz, 2H), 7.00-6.80 (m, 2H), 3.81 (s, 3H), 2.95 (s, 3H).

Example 35

$^1$H NMR (500 MHz, DMSO-$d_6$) δ 9.87 (br s, 1H), 7.97 (br d, J=8.2 Hz, 2H), 7.85 (br d, J=7.9 Hz, 1H), 7.62-7.58 (m, 1H), 7.56-7.52 (m, 1H), 7.45 (br d, J=8.2 Hz, 2H), 6.92 (br s, 2H), 3.82 (s, 3H), 2.91 (s, 3H).

Example 36

$^1$H NMR (500 MHz, DMSO-$d_6$) δ 9.84 (s, 1H), 7.85 (br d, J=7.9 Hz, 2H), 7.64 (br d, J=8.9 Hz, 2H), 7.54 (br d, J=8.2 Hz, 2H), 7.47 (br d, J=8.5 Hz, 2H), 6.93 (br d, J=10.4 Hz, 2H), 3.83 (s, 3H), 2.94 (s, 3H).

Example 37

$^1$H NMR (500 MHz, DMSO-$d_6$) δ 9.67 (br s, 1H), 7.87 (br d, J=7.9 Hz, 2H), 7.61 (br d, J=8.2 Hz, 1H), 7.43 (br t, J=7.9 Hz, 1H), 7.30 (br d, J=7.6 Hz, 1H), 7.23 (t, J=73.6 Hz, 1H), 7.22 (br d, J=7.9 Hz, 2H), 6.87 (br t, J=10.7 Hz, 2H), 3.86 (br s, 3H), 2.90 (s, 3H), 2.23 (br s, 3H).

Example 38

$^1$H NMR (500 MHz, $CD_3OD$) δ 7.92 (br d, J=8.6 Hz, 2H), 7.59 (d, J=7.7 Hz, 2H), 7.53 (s, 3H), 7.32 (dd, J=15.4, 8.0 Hz, 4H), 3.10 (s, 3H).

Example 40

$^1$H NMR (500 MHz, $CD_3OD$) δ 8.67 (d, J=2.2 Hz, 1H), 8.15 (dd, J=8.7, 2.4 Hz, 1H), 7.91-7.83 (m, 3H), 7.19 (d, J=8.7 Hz, 2H), 6.88 (t, J=73.6 Hz, 1H), 6.76 (d, J=10.0 Hz, 2H), 3.86 (s, 3H), 3.31 (s, 3H).

Example 41

$^1$H NMR (500 MHz, $CD_3OD$) δ 8.62 (dd, J=4.7, 1.5 Hz, 1H), 8.15 (dd, J=8.2, 1.4 Hz, 1H), 7.91 (br d, J=7.1 Hz, 2H), 7.60 (dd, J=8.1, 4.7 Hz, 1H), 7.32 (br d, J=8.3 Hz, 2H), 6.76 (d, J=10.3 Hz, 2H), 3.86 (s, 3H), 3.16 (s, 3H).

Example 43

$^1$H NMR (500 MHz, $CD_3OD$) δ 8.57 (d, J=2.4 Hz, 1H), 8.02 (dd, 2.5 Hz, 1H), 7.92 (d, J=8.8 Hz, 1H), 7.80 (br d, J=8.2 Hz, 2H), 7.44 (d, J=8.5 Hz, 2H), 6.76 (d, J=10.0 Hz, 2H), 3.86 (s, 3H), 3.31 (s, 3H).

Example 46

$^1$H NMR (500 MHz, $CD_3OD$) δ 7.90-7.85 (m, 3H), 7.64 (d, J=8.1 Hz, 1H), 7.27 (d, J=7.6 Hz, 1H), 7.19 (d, J=8.7 Hz, 2H), 6.88 (t, J=73.6, 1H), 6.76 (d, J=9.9 Hz, 2H), 3.86 (s, 3H), 3.31 (s, 3H), 2.59 (s, 3H).

Example 47

$^1$H NMR (500 MHz, $CD_3OD$) δ 8.41 (d, J=1.9 Hz, 1H), 7.87 (br d, J=8.3 Hz, 2H), 7.77-7.62 (m, 2H), 7.18 (d, J=8.6 Hz, 2H), 7.04-6.70 (m, 3H), 3.86 (s, 3H), 3.26 (s, 3H), 2.10-2.00 (m, 1H), 1.15-1.06 (m, 2H), 0.90-0.73 (m, 2H).

Example 48

$^1$H NMR (500 MHz, DMSO-d6) δ 9.83-9.63 (m, 1H), 8.42 (s, 1H), 7.84 (br s, 3H), 7.75 (d, J=8.2 Hz, 1H), 7.54 (br d, J=8.2 Hz, 2H), 6.93 (br d, J=10.7 Hz, 2H), 3.83 (s, 3H), 3.17 (m, 3H), 2.36 (s, 3H).

Example 49

$^1$H NMR (500 MHz, $CD_3OD$) δ 8.52-8.37 (m, 1H), 7.87 (br d, J=8.4 Hz, 3H), 7.72 (br d, J=8.2 Hz, 1H), 7.18 (d, J=8.6 Hz, 2H), 7.05-6.69 (m, 3H), 3.85 (s, 3H), 3.26 (s, 3H), 2.41 (s, 3H).

Example 50

$^1$H NMR (500 MHz, $CD_3OD$) δ 8.43 (br s, 1H), 7.95-7.89 (m, 2H), 7.87-7.68 (m, 2H), 7.32 (br d, J=8.3 Hz, 2H), 6.76 (d, J=10.0 Hz, 2H), 3.86 (s, 3H), 3.27 (s, 3H), 2.42 (s, 3H).

Example 51

$^1$H NMR (500 MHz, DMSO-$d_6$) δ 9.60 (s, 1H), 8.93-8.88 (m, 1H), 8.31 (dd, J=8.6, 2.3 Hz, 1H), 8.00 (d, J=8.5 Hz,

1H), 7.96-7.88 (m, 2H), 7.79 (d, J=7.5 Hz, 2H), 7.54 (t, J=7.6 Hz, 2H), 7.50-7.41 (m, 1H), 7.28 (t, J=73.6 Hz, 1H), 7.25 (d, J=8.7 Hz, 2H), 6.91 (br d, J=10.4 Hz, 2H), 3.85 (s, 3H), 3.24 (s, 3H).

Example 52

$^1$H NMR (500 MHz, $CD_3OD$) δ 8.41 (d, J=1.8 Hz, 1H), 7.92 (br d, J=8.2 Hz, 2H), 7.73-7.68 (m, 1H), 7.68-7.64 (m, 1H), 7.32 (br d, J=8.2 Hz, 2H), 6.76 (d, J=10.0 Hz, 2H), 3.86 (s, 3H), 3.28-3.25 (m, 3H), 2.07-1.98 (m, 1H), 1.15-1.05 (m, 2H), 0.86-0.77 (m, 2H).

Example 53

$^1$H NMR (500 MHz, DMSO-$d_6$) δ 9.51 (s, 1H), 8.42 (s, 1H), 7.72 (br d, J=8.2 Hz, 3H), 7.63 (br d, J=8.5 Hz, 1H), 7.13 (br d, J=7.9 Hz, 2H), 6.91 (br d, J=10.4 Hz, 2H), 3.82 (s, 3H), 3.13 (s, 3H), 2.06-1.99 (m, 1H), 1.97-1.92 (m, 1H), 1.07-0.96 (m, 4H), 0.79 (br d, J=4.9 Hz, 2H), 0.72 (br d, J=4.9 Hz, 2H).

Example 55

$^1$H NMR (500 MHz, $CD_3OD$) δ 8.87 (dd, J=4.8, 1.6 Hz, 1H), 8.39 (dd, J=7.8, 1.7 Hz, 1H), 7.86 (br d, J=8.3 Hz, 2H), 7.63 (dd, J=7.8, 4.9 Hz, 1H), 7.18 (d, J=8.7 Hz, 2H), 7.04-6.67 (m, 3H), 3.87 (s, 3H), 3.26 (s, 3H).

Example 56

$^1$H NMR (500 MHz, $CDCl_3$) δ 8.85 (dd, J=4.8, 1.8 Hz, 1H), 8.20 (dd, J=7.7, 1.7 Hz, 1H), 7.92-7.78 (m, 3H), 7.45 (dd, J=7.8, 4.8 Hz, 1H), 7.25 (d, J=8.3 Hz, 2H), 6.61 (d, J=9.9 Hz, 2H), 3.86 (s, 3H), 3.20 (s, 3H).

Example 60

$^1$H NMR (500 MHz, DMSO-d6) δ 9.75 (br s, 1H), 8.55 (d, J=8.9 Hz, 1H), 8.14 (d, J=8.8 Hz, 1H), 8.04 (t, J=6.9 Hz, 2H), 7.92 (d, J=8.2 Hz, 2H), 7.82 (t, J=7.5 Hz, 1H), 7.63 (t, J=7.5 Hz, 1H), 7.54-7.13 (m, 3H), 6.96 (d, J=10.4 Hz, 2H), 3.84 (s, 3H), 3.31 (s, 3H).

Example 61

$^1$H NMR (500 MHz, DMSO-d6) δ 9.75 (s, 1H), 8.99 (s, 1H), 8.49 (s, 1H), 7.91 (br d, J=8.2 Hz, 2H), 7.54-7.12 (m, 3H), 6.94 (br d, J=10.7 Hz, 2H), 3.83 (s, 3H), 3.20 (s, 3H), 2.58 (s, 3H).

Example 62

$^1$H NMR (500 MHz, DMSO-d6) δ 9.78 (s, 1H), 8.92-8.81 (m, 1H), 8.25 (s, 1H), 7.90 (d, J=6.5 Hz, 2H), 7.75 (d, J=2.7 Hz, 1H), 7.51-7.10 (m, 3H), 6.95 (dd, J=10.4, 2.9 Hz, 2H), 3.83 (d, J=2.4 Hz, 3H), 3.23 (d, J=2.1 Hz, 3H).

Example 63

$^1$H NMR (500 MHz, DMSO-d6) δ 9.88 (s, 1H), 8.87 (d, J=5.0 Hz, 1H), 8.24 (s, 1H), 7.95 (d, J=8.2 Hz, 2H), 7.74 (d, J=5.0 Hz, 1H), 7.47 (d, J=7.9 Hz, 2H), 6.95 (d, J=11.8 Hz, 2H), 3.83 (s, 3H), 3.23 (s, 3H).

Example 64

$^1$H NMR (500 MHz, DMSO-d6) δ 9.82 (s, 1H), 9.53 (s, 1H), 8.21-8.06 (m, 2H), 7.99-7.81 (m, 4H), 7.49-7.12 (m, 3H), 6.96 (d, J=10.4 Hz, 2H), 3.84 (s, 3H), 3.33 (s, 3H).

Example 65

$^1$H NMR (500 MHz, DMSO-d6) δ 9.66 (s, 1H), 7.90 (d, J=8.2 Hz, 2H), 7.54-7.41 (m, 1H), 7.38-7.12 (m, 3H), 7.08 (s, 1H), 6.92 (d, J=10.1 Hz, 2H), 3.82 (s, 3H), 3.16 (s, 3H), 2.55 (s, 6H).

Example 66

$^1$H NMR (500 MHz, DMSO-d6) δ 9.78 (s, 1H), 7.95 (d, J=8.5 Hz, 2H), 7.55-7.32 (m, 3H), 7.08 (s, 1H), 6.93 (d, J=10.4 Hz, 2H), 3.83 (s, 3H), 3.17 (s, 3H), 2.49 (s, 3H), 2.38 (s, 3H).

Example 67

$^1$H NMR (500 MHz, DMSO-d6) δ 9.75 (s, 1H), 8.25-8.15 (m, 1H), 8.10-8.01 (m, 1H), 7.95-7.81 (m, 2H), 7.66 (d, J=7.7 Hz, 1H), 7.49-7.00 (m, 4H), 6.92 (d, J=10.0 Hz, 2H), 3.87-3.60 (m, 3H), 3.22 (s, 3H).

Example 68

$^1$H NMR (500 MHz, DMSO-d6) δ 9.86 (s, 1H), 8.21 (t, J=7.8 Hz, 1H), 8.07 (d, J=8.2 Hz, 1H), 7.94 (d, J=8.1 Hz, 2H), 7.66 (d, J=7.5 Hz, 1H), 7.46 (d, J=8.2 Hz, 2H), 7.22-6.87 (m, 3H), 3.91-3.56 (m, 3H), 3.22 (s, 3H).

Example 69

$^1$H NMR (500 MHz, DMSO-d6) δ 9.76 (s, 1H), 8.39 (d, J=1.7 Hz, 1H), 8.15 (t, J=8.0 Hz, 1H), 7.92 (br d, J=8.5 Hz, 2H), 7.81-7.70 (m, 2H), 7.55-7.13 (m, 3H), 7.02-6.88 (m, 2H), 6.47 (d, J=2.2 Hz, 1H), 3.84 (s, 3H), 3.26 (s, 3H), 2.32 (s, 3H).

Example 70

$^1$H NMR (500 MHz, DMSO-d6) δ 9.88 (s, 1H), 8.40 (d, J=2.2 Hz, 1H), 8.15 (t, J=8.0 Hz, 1H), 7.97 (d, J=8.3 Hz, 2H), 7.82-7.69 (m, 2H), 7.48 (d, J=8.2 Hz, 2H), 6.97 (d, J=10.5 Hz, 2H), 6.47 (d, J=2.4 Hz, 1H), 3.84 (s, 3H), 3.27 (s, 3H), 2.32 (s, 3H).

Example 71

$^1$H NMR (500 MHz, DMSO-d6) δ 9.77 (s, 1H), 8.77-8.64 (m, 1H), 8.26 (s, 1H), 7.90 (d, J=7.9 Hz, 2H), 7.52-7.14 (m, 3H), 6.94 (d, J=10.7 Hz, 2H), 3.99 (s, 3H), 3.83 (s, 3H), 3.26 (s, 3H).

Example 72

$^1$H NMR (500 MHz, DMSO-d6) δ 9.73 (s, 1H), 8.17-8.06 (m, 3H), 8.00-7.83 (m, 4H), 7.61-7.44 (m, 3H), 7.35-7.14 (m, 3H), 6.96 (br d, J=10.4 Hz, 2H), 3.84 (s, 3H), 3.30 (s, 3H).

Example 73

$^1$H NMR (500 MHz, DMSO-$d_6$) δ 9.84 (s, 1H), 8.17-8.08 (m, 3H), 7.96 (br d, J=7.3 Hz, 3H), 7.88 (d, J=8.2 Hz, 1H), 7.59-7.53 (m, 2H), 7.52-7.43 (m, 3H), 6.97 (br d, J=10.1 Hz, 2H), 3.84 (s, 3H), 3.31 (s, 3H).

Example 74

$^1$H NMR (500 MHz, DMSO-d6) δ 9.80 (s, 1H), 7.98-7.84 (m, 3H), 7.50-7.40 (m, 3H), 6.92 (br d, J=10.4 Hz, 2H), 6.79 (d, J=8.2 Hz, 1H), 3.91 (s, 3H), 3.82 (s, 3H), 3.24 (s, 3H).

Example 75

$^1$H NMR (500 MHz, DMSO-d6) δ 9.69 (s, 1H), 7.98-7.82 (m, 3H), 7.44 (d, J=7.3 Hz, 1H), 7.34-7.10 (m, 3H), 6.92 (d, J=10.7 Hz, 2H), 6.79 (d, J=7.9 Hz, 1H), 3.91 (s, 3H), 3.82 (s, 3H), 3.24 (s, 3H).

Example 76

$^1$H NMR (500 MHz, DMSO-d6) δ 9.76 (s, 1H), 8.76 (d, J=5.0 Hz, 1H), 8.09 (s, 1H), 7.91 (d, J=8.3 Hz, 2H), 7.55 (d, J=4.9 Hz, 1H), 7.49-7.08 (m, 4H), 6.94 (d, J=10.2 Hz, 2H), 3.83 (s, 3H), 3.20 (s, 3H).

Example 77

$^1$H NMR (500 MHz, DMSO-d6) δ 9.66 (s, 1H), 8.21 (s, 1H), 7.88 (d, J=8.5 Hz, 2H), 7.47-7.06 (m, 4H), 6.90 (d, J=10.4 Hz, 2H), 3.93 (s, 3H), 3.81 (s, 3H), 3.15 (s, 3H), 2.15 (s, 3H).

Example 78

$^1$H NMR (500 MHz, DMSO-d6) δ 9.72 (s, 1H), 7.98-7.80 (m, 3H), 7.51-7.16 (m, 4H), 6.95 (br d, J=10.4 Hz, 2H), 6.76 (d, J=8.1 Hz, 1H), 4.36 (q, J=7.0 Hz, 2H), 3.83 (s, 3H), 3.23 (s, 3H), 1.37 (t, J=7.0 Hz, 3H).

Example 79

$^1$H NMR (500 MHz, DMSO-d6) δ 9.66 (s, 1H), 7.91 (br d, J=8.2 Hz, 2H), 7.75 (t, J=7.9 Hz, 1H), 7.51-7.11 (m, 4H), 6.93 (br d, J=10.4 Hz, 2H), 6.77 (d, J=8.2 Hz, 1H), 3.82 (s, 3H), 3.77-3.69 (m, 4H), 3.53-3.47 (m, 2H), 3.44-3.33 (m, 2H), 3.19 (s, 3H).

Example 80

$^1$H NMR (500 MHz, DMSO-d6) δ 9.65 (s, 1H), 7.90 (d, J=8.2 Hz, 2H), 7.68 (t, J=7.9 Hz, 1H), 7.24 (d, J=8.5 Hz, 2H), 7.30 (t, J=73.9 Hz, 1H), 7.01 (d, J=7.6 Hz, 1H), 6.92 (d, J=10.1 Hz, 2H), 6.74 (d, J=8.5 Hz, 1H), 3.82 (s, 3H), 3.63-3.39 (m, 4H), 3.19 (s, 3H), 1.67-1.47 (m, 6H).

Example 81

$^1$H NMR (500 MHz, DMSO-d6) δ 9.68 (s, 1H), 8.01 (t, J=7.9 Hz, 1H), 7.89 (d, J=8.5 Hz, 2H), 7.72 (d, J=7.9 Hz, 1H), 7.47-7.41 (m, 1H), 7.32-7.12 (m, 3H), 6.91 (d, J=10.4 Hz, 2H), 4.61 (s, 2H), 3.82 (s, 3H), 3.56 (br s, 1H), 3.18 (s, 3H).

Example 82

$^1$H NMR (500 MHz, DMSO-d6) δ 9.66 (s, 1H), 7.89 (d, J=8.5 Hz, 2H), 7.67 (t, J=8.0 Hz, 1H), 7.24 (d, J=8.5 Hz, 2H), 7.23 (t, J=73.5 Hz, 1H), 6.99 (d, J=7.7 Hz, 1H), 6.90 (d, J=10.3 Hz, 2H), 6.57 (d, J=8.4 Hz, 1H), 3.81 (s, 3H), 3.22 (s, 3H), 3.05 (s, 6H).

Example 83

$^1$H NMR (500 MHz, DMSO-d6) δ 9.69 (s, 1H), 7.91 (d, J=8.5 Hz, 2H), 7.72 (t, J=8.0 Hz, 1H), 7.25 (d, J=8.6 Hz, 2H), 7.29 (t, J=75.1 Hz, 1H), 7.10 (d, J=7.7 Hz, 1H), 6.94 (d, J=10.4 Hz, 2H), 6.78 (d, J=8.4 Hz, 1H), 3.83 (s, 3H), 3.19 (s, 3H), 2.45 (br s, 4H), 2.25 (s, 3H), 1.92 (s, 4H).

Example 84

$^1$H NMR (500 MHz, DMSO-d6) δ 9.91 (s, 1H), 9.72 (s, 1H), 8.04-7.96 (m, 2H), 7.91 (d, J=8.3 Hz, 2H), 7.54-7.50 (m, 1H), 7.25 (d, J=8.4 Hz, 2H), 7.50-7.16 (m, 1H), 6.94 (d, J=10.7 Hz, 2H), 3.83 (s, 3H), 3.21 (s, 3H), 1.27 (s, 9H).

Example 86

$^1$H NMR (500 MHz, DMSO-d6) δ 9.69 (s, 1H), 8.00 (t, J=7.9 Hz, 1H), 7.91 (d, J=8.5 Hz, 2H), 7.74 (d, J=7.9 Hz, 1H), 7.47 (d, J=7.0 Hz, 1H), 7.36-7.14 (m, 3H), 6.93 (d, J=10.4 Hz, 2H), 5.52 (d, J=4.6 Hz, 1H), 4.85-4.72 (m, 1H), 3.83 (s, 3H), 3.21 (s, 3H), 1.43 (d, J=6.4 Hz, 3H).

Example 89

$^1$H NMR (500 MHz, DMSO-d6) δ 9.66 (s, 1H), 7.89 (br d, J=8.2 Hz, 2H), 7.48-7.10 (m, 5H), 6.92 (br d, J=10.4 Hz, 2H), 5.41 (s, 1H), 3.90 (s, 3H), 3.82 (s, 3H), 3.22 (s, 3H), 1.46 (s, 6H).

Example 90

$^1$H NMR (500 MHz, DMSO-d6) δ 9.69 (s, 1H), 7.91 (d, J=8.6 Hz, 2H), 7.30 (d, J=1.9 Hz, 1H), 7.25 (d, J=8.7 Hz, 2H), 7.34 (t, J=73.8 Hz, 1H), 7.02 (s, 1H), 6.93 (d, J=10.2 Hz, 2H), 5.61 (t, J=5.8 Hz, 1H), 4.57 (d, J=5.8 Hz, 2H), 3.92 (s, 3H), 3.83 (s, 3H), 3.19 (s, 3H).

Example 92

$^1$H NMR (500 MHz, DMSO-d6) δ 9.63 (s, 1H), 7.89 (d, J=8.2 Hz, 2H), 7.47-7.10 (m, 3H), 6.91 (d, J=10.7 Hz, 2H), 6.69 (s, 1H), 6.28 (s, 1H), 4.21-4.07 (m, 2H), 3.85 (s, 3H), 3.81 (s, 3H), 3.65-3.59 (m, 2H), 3.18 (s, 3H), 2.49-2.40 (m, 2H), 1.15 (d, J=6.1 Hz, 6H).

Example 93

$^1$H NMR (500 MHz, DMSO-d6) δ 9.65 (s, 1H), 7.88 (d, J=8.4 Hz, 2H), 7.24 (d, J=8.6 Hz, 2H), 7.46-7.09 (m, 1H), 6.91 (d, J=11.0 Hz, 2H), 6.66 (s, 1H), 6.28 (s, 1H), 4.13 (d, J=13.0 Hz, 2H), 3.84 (s, 3H), 3.80 (s, 3H), 3.18 (s, 3H), 2.62 (t, J=11.9 Hz, 2H), 2.23-2.13 (m, 5H), 1.08 (d, J=6.1 Hz, 6H).

Example 94

$^1$H NMR (500 MHz, DMSO-d6) δ 9.64 (s, 1H), 7.89 (d, J=7.8 Hz, 2H), 7.24 (d, J=8.6 Hz, 2H), 7.32 (t, J=84.6 Hz, 1H), 6.91 (d, J=10.4 Hz, 2H), 6.65 (s, 1H), 6.58 (d, J=1.9 Hz, 1H), 6.00 (d, J=1.3 Hz, 1H), 3.81 (s, 3H), 3.78 (s, 3H), 3.62-3.59 (m, 2H), 3.33 (q, J=5.7 Hz, 2H), 3.20 (s, 3H), 1.91 (s, 1H).

Example 95

$^1$H NMR (500 MHz, DMSO-d6) δ 9.64 (s, 1H), 7.88 (d, J=8.0 Hz, 2H), 7.46-7.10 (m, 4H), 6.89 (d, J=10.4 Hz, 2H), 6.63 (d, J=1.9 Hz, 1H), 5.86 (s, 1H), 4.40 (br s, 1H), 3.83 (br s, 3H), 3.79-3.78 (m, 3H), 3.73 (br d, J=1.4 Hz, 1H), 3.54-3.42 (m, 2H), 3.35 (br d, J=10.4 Hz, 1H), 3.24 (s, 3H), 2.09-1.97 (m, 1H), 1.94-1.86 (m, 1H).

Example 96

$^1$H NMR (500 MHz, DMSO-d6) δ 9.65 (s, 1H), 7.90 (d, J=8.6 Hz, 2H), 7.24 (d, J=8.6 Hz, 2H), 7.52-7.13 (m, 1H), 6.92 (d, J=10.3 Hz, 2H), 6.76-6.67 (m, 1H), 5.86 (d, J=1.4 Hz, 1H), 3.93-3.78 (m, 8H), 3.57-3.50 (m, 3H), 3.22 (s, 3H), 1.45 (s, 3H).

Example 97

$^1$H NMR (500 MHz, DMSO-d6) δ 9.63 (s, 1H), 7.90 (d, J=8.2 Hz, 2H), 7.24 (d, J=8.5 Hz, 2H), 7.31 (t, J=71.4 Hz, 1H), 6.91 (d, J=10.1 Hz, 2H), 6.67 (d, J=1.5 Hz, 1H), 5.86 (d, J=1.5 Hz, 1H), 4.40 (br s, 1H), 3.84 (s, 3H), 3.81 (s, 3H), 3.81-3.78 (m, 1H), 3.59-3.49 (m, 1H), 3.49-3.42 (m, 2H), 3.41-3.30 (m, 1H), 3.25 (s, 3H), 2.09-1.97 (m, 1H), 1.94-1.83 (m, 1H).

Example 98

$^1$H NMR (500 MHz, DMSO-d6) δ 9.63 (s, 1H), 7.89 (d, J=8.5 Hz, 2H), 7.24 (d, J=8.5 Hz, 2H), 7.30 (t, J=72.6 Hz, 1H), 6.91 (d, J=10.7 Hz, 2H), 6.72 (s, 1H), 5.94 (s, 1H), 5.45 (d, J=56.2 Hz, 1H), 3.85 (s, 3H), 3.81 (s, 3H), 3.78-3.38 (m, 4H), 3.24 (s, 3H), 2.33-2.06 (m, 2H).

Example 99

$^1$H NMR (500 MHz, DMSO-$d_6$) δ 9.67 (s, 1H), 7.91 (d, J=8.7 Hz, 2H), 7.25 (d, J=8.6 Hz, 2H), 7.53-7.14 (m, 1H), 6.93 (d, J=10.4 Hz, 2H), 6.79 (s, 1H), 6.02 (d, J=1.5 Hz, 1H), 3.87 (s, 3H), 3.82 (s, 3H), 3.94-3.75 (m, 2H), 3.67 (br t, J=7.3 Hz, 2H), 3.24 (s, 3H), 2.63-2.54 (m, 2H).

Example 100

$^1$H NMR (500 MHz, DMSO-d6) δ 9.71 (s, 1H), 7.91 (d, J=8.6 Hz, 2H), 7.32-7.28 (m, 1H), 7.26 (d, J=8.6 Hz, 2H), 7.32 (t, J=75.4 Hz, 1H), 7.06 (s, 1H), 6.95 (dd, J=10.5, 3.8 Hz, 2H), 3.90 (s, 3H), 3.82 (s, 3H), 3.48-3.46 (m, 1H), 3.27 (s, 3H), 2.55-2.53 (m, 2H), 2.34-2.24 (m, 2H), 2.05-1.82 (m, 2H).

Example 101

$^1$H NMR (500 MHz, DMSO-d6) δ 9.69 (s, 1H), 7.94 (d, J=8.2 Hz, 2H), 7.29 (d, J=8.5 Hz, 2H), 7.36 (t, J=75.4 Hz, 1H), 6.96 (d, J=10.4 Hz, 2H), 6.80 (s, 1H), 6.33 (s, 1H), 3.90 (s, 3H), 3.86 (s, 3H), 3.68-3.49 (m, 4H), 3.23 (s, 3H), 2.59 (s, 3H), 2.34 (s, 4H).

Example 102

$^1$H NMR (500 MHz, DMSO-d6) δ 9.65 (s, 1H), 7.91 (d, J=8.5 Hz, 2H), 7.66 (t, J=7.9 Hz, 1H), 7.25 (d, J=8.5 Hz, 2H), 7.33 (t, J=73.5 Hz, 1H), 7.02 (d, J=7.6 Hz, 1H), 6.93 (d, J=10.1 Hz, 2H), 6.38 (d, J=8.2 Hz, 1H), 5.04 (d, J=3.7 Hz, 1H), 4.42 (br d, J=1.8 Hz, 1H), 3.83 (s, 3H), 3.63-3.40 (m, 4H), 3.25 (s, 3H), 2.11-2.00 (m, 1H), 1.97-1.84 (m, 1H).

Example 103

$^1$H NMR (500 MHz, DMSO-d6) δ 9.70 (s, 1H), 7.93 (d, J=8.6 Hz, 2H), 7.71 (t, J=8.0 Hz, 1H), 7.26 (d, J=8.6 Hz, 2H), 7.36 (t, J=72.5 Hz, 1H), 7.06 (d, J=7.7 Hz, 1H), 6.96 (d, J=10.4 Hz, 2H), 6.80 (d, J=8.5 Hz, 1H), 4.17 (br d, J=12.5 Hz, 2H), 3.83 (s, 3H), 3.19 (s, 3H), 2.64 (br t, J=11.9 Hz, 2H), 2.20 (m, 5H), 1.10 (d, J=6.1 Hz, 6H).

Example 104

$^1$H NMR (500 MHz, DMSO-d6) δ 9.67 (s, 1H), 7.91 (d, J=8.9 Hz, 2H), 7.81 (t, J=7.9 Hz, 1H), 7.28-7.22 (m, 3H), 7.32 (t, J=78.4 Hz, 1H), 6.93 (d, J=10.1 Hz, 2H), 6.53 (d, J=7.9 Hz, 1H), 4.45 (t, J=12.4 Hz, 4H), 3.83 (s, 3H), 3.22 (s, 3H).

Example 105

$^1$H NMR (500 MHz, DMSO-d6) δ 9.64 (s, 1H), 7.91 (d, J=8.5 Hz, 2H), 7.25 (d, J=8.5 Hz, 2H), 7.32 (t, J=73.5 Hz, 1H), 6.92 (d, J=10.4 Hz, 2H), 6.71 (s, 1H), 6.21 (s, 1H), 4.52 (br s, 2H), 3.84 (s, 3H), 3.82 (s, 3H), 3.20 (s, 3H), 2.65-2.58 (m, 2H), 2.32-2.23 (m, 2H), 2.13 (s, 3H), 1.97-1.81 (m, 4H).

Example 106

$^1$H NMR (500 MHz, DMSO-d6) δ 9.66 (s, 1H), 7.91 (d, J=8.7 Hz, 2H), 7.25 (d, J=8.7 Hz, 2H), 7.34 (t, J=73.7 Hz, 1H), 6.93 (d, J=10.2 Hz, 2H), 6.74 (s, 1H), 5.87 (s, 1H), 4.51 (quin, J=5.5 Hz, 1H), 4.25-4.18 (m, 2H), 3.84 (s, 3H), 3.82 (s, 3H), 3.74 (dd, J=8.8, 4.5 Hz, 2H), 3.70-3.61 (m, 1H), 3.22 (s, 3H), 1.12 (d, J=6.1 Hz, 6H).

Example 107

$^1$H NMR (500 MHz, DMSO-d6) δ 9.70 (s, 1H), 7.92 (d, J=8.8 Hz, 2H), 7.83 (t, J=8.1 Hz, 1H), 7.26 (d, J=8.5 Hz, 2H), 7.22 (d, J=7.7 Hz, 1H), 7.35 (t, J=73.2 Hz, 1H), 6.94 (d, J=10.2 Hz, 2H), 6.91 (d, J=8.5 Hz, 1H), 4.40 (br d, J=13.5 Hz, 2H), 3.84 (s, 3H), 3.81-3.76 (m, 3H), 3.63 (br d, J=11.3 Hz, 2H), 3.38-3.29 (m, 2H), 3.26 (br s, 2H), 3.21-3.16 (m, 5H).

Example 109

$^1$H NMR (500 MHz, DMSO-d6) δ 9.70 (s, 1H), 7.89 (br d, J=7.9 Hz, 2H), 7.23 (br d, J=8.2 Hz, 2H), 7.30 (t, J=74.0 Hz, 1H), 7.03 (s, 3H), 6.89 (br s, 2H), 3.81 (s, 3H), 2.91 (s, 3H), 2.35 (s, 6H).

Example 110

$^1$H NMR (500 MHz, DMSO-d6) δ 9.90-9.69 (m, 1H), 7.93-7.86 (m, 3H), 7.83 (br d, J=4.9 Hz, 1H), 7.78 (br d, J=4.9 Hz, 2H), 7.24 (br d, J=8.5 Hz, 2H), 7.30 (t, J=74.0 Hz, 1H), 6.92 (br d, J=10.4 Hz, 2H), 3.82 (s, 3H), 2.96 (s, 3H).

Example 111

$^1$H NMR (500 MHz, DMSO-d6) δ 9.71 (s, 1H), 8.02-7.79 (m, 2H), 7.48-7.39 (m, 1H), 7.24 (br d, J=8.5 Hz, 2H), 7.18 (t, J=74.0 Hz, 1H), 7.15 (br d, J=5.8 Hz, 2H), 7.07 (br d,

J=7.9 Hz, 1H), 6.91 (br d, J=10.4 Hz, 2H), 3.81 (s, 3H), 2.91 (s, 3H), 2.15-1.96 (m, 1H), 1.12-0.94 (m, 2H), 0.78-0.63 (m, 2H).

Example 112

$^1$H NMR (500 MHz, DMSO-d6) δ 9.76 (s, 1H), 7.91 (br d, J=8.5 Hz, 2H), 7.52-7.46 (m, 1H), 7.25 (d, J=8.6 Hz, 2H), 7.30 (t, J=74.0 Hz, 1H), 7.05-6.96 (m, 3H), 6.93 (d, J=10.4 Hz, 2H), 3.83 (s, 6H), 2.94 (s, 3H).

Example 113

$^1$H NMR (500 MHz, DMSO-d6) δ 9.78 (s, 1H), 8.00 (s, 1H), 7.95 (br d, J=6.7 Hz, 1H), 7.91 (br d, J=8.5 Hz, 2H), 7.79-7.67 (m, 2H), 7.25 (d, J=8.5 Hz, 2H), 7.32 (t, J=74.0 Hz, 1H), 6.93 (br d, J=10.4 Hz, 2H), 3.91 (s, 3H), 3.83 (s, 3H), 2.94 (s, 3H).

Example 114

$^1$H NMR (500 MHz, DMSO-d6) δ 9.79 (s, 1H), 7.91 (br d, J=8.5 Hz, 2H), 7.68-7.58 (m, 1H), 7.53 (d, J=1.8 Hz, 1H), 7.50-7.44 (m, 1H), 7.41 (br d, J=7.9 Hz, 1H), 7.36-7.12 (m, 3H), 6.94 (br d, J=10.1 Hz, 2H), 3.83 (s, 3H), 2.96 (s, 3H).

Example 115

$^1$H NMR (500 MHz, DMSO-d6) δ 9.84 (s, 1H), 8.30 (d, J=5.6 Hz, 1H), 7.89 (br d, J=8.4 Hz, 2H), 7.24 (br d, J=8.6 Hz, 2H), 7.50-7.15 (m, 1H), 7.14-7.08 (m, 1H), 6.93 (br d, J=10.4 Hz, 2H), 6.86 (s, 1H), 3.90 (s, 3H), 3.82 (s, 3H), 2.96 (s, 3H).

Example 116

$^1$H NMR (500 MHz, DMSO-d6) δ 9.87 (s, 1H), 8.53 (d, J=5.6 Hz, 1H), 7.88 (br d, J=8.7 Hz, 2H), 7.60 (d, J=1.7 Hz, 1H), 7.50 (dd, J=5.6, 1.8 Hz, 1H), 7.28 (t, J=74.0 Hz, 1H), 7.24 (d, J=8.8 Hz, 2H), 6.92 (d, J=10.6 Hz, 2H), 3.82 (s, 3H), 2.98 (s, 3H). 16 out of 17 protons observed.

Example 117

$^1$H NMR (500 MHz, DMSO-d6) δ 9.79 (s, 1H), 7.89 (d, J=8.5 Hz, 2H), 7.28 (d, J=14.6 Hz, 2H), 7.26-7.21 (m, 3H), 7.30 (t, J=74.0 Hz, 1H), 6.92 (d, J=10.4 Hz, 2H), 3.91 (s, 3H), 3.82 (s, 3H), 2.98-2.89 (m, 3H).

Example 118

$^1$H NMR (500 MHz, DMSO-d6) δ 9.84-9.67 (m, 1H), 7.90 (br d, J=7.2 Hz, 2H), 7.46 (t, J=7.9 Hz, 1H), 7.24 (br d, J=8.2 Hz, 2H), 7.34-7.13 (m, 1H), 7.01-6.87 (m, 5H), 4.08 (q, J=7.1 Hz, 2H), 3.82 (s, 3H), 2.93 (s, 3H), 1.36 (br t, J=6.9 Hz, 3H).

Example 119

$^1$H NMR (500 MHz, DMSO-d6) δ 9.80 (s, 1H), 7.89 (br d, J=8.4 Hz, 2H), 7.76 (s, 1H), 7.70 (s, 1H), 7.60 (s, 1H), 7.24 (d, J=8.6 Hz, 2H), 7.32 (t, J=74.0 Hz, 1H), 6.93 (d, J=10.5 Hz, 2H), 3.82 (s, 3H), 3.07 (dt, J=13.7, 6.9 Hz, 1H), 2.95 (s, 3H), 1.26 (d, J=6.8 Hz, 6H).

Example 120

$^1$H NMR (500 MHz, DMSO-d6) δ 9.81 (s, 1H), 7.89 (br t, J=6.6 Hz, 4H), 7.78 (s, 1H), 7.24 (br d, J=8.5 Hz, 2H), 7.29 (t, J=74.0 Hz, 1H), 6.92 (br d, J=10.7 Hz, 2H), 3.91 (s, 3H), 3.82 (s, 3H), 2.95 (s, 3H).

Example 121

$^1$H NMR (500 MHz, DMSO-d6) δ 9.73 (s, 1H), 7.89 (br d, J=8.3 Hz, 2H), 7.45-7.44 (m, 1H), 7.24 (d, J=8.6 Hz, 1H), 7.31 (t, J=74.0 Hz, 1H), 6.91 (d, J=10.4 Hz, 2H), 6.81 (s, 1H), 6.80 (d, J=14.0 Hz, 2H), 3.81 (s, 3H), 3.79 (s, 3H), 2.92 (s, 3H), 2.36 (s, 3H).

Example 122

$^1$H NMR (500 MHz, DMSO-d6) δ 9.79 (s, 1H), 7.90 (br d, J=8.2 Hz, 2H), 7.29 (s, 1H), 7.26-7.23 (m, 3H), 7.22 (s, 1H), 7.31 (t, J=74.0 Hz, 1H), 6.93 (br d, J=10.7 Hz, 2H), 4.19 (q, J=7.0 Hz, 2H), 3.82 (s, 3H), 2.96 (s, 3H), 1.38 (t, J=6.9 Hz, 3H).

Example 123

$^1$H NMR (500 MHz, DMSO-d6) δ 9.81 (s, 1H), 7.88 (br d, J=8.5 Hz, 2H), 7.59-7.52 (m, J=7.6 Hz, 2H), 7.40 (s, 1H), 7.24 (d, J=8.5 Hz, 2H), 7.29 (t, J=74.0 Hz, 1H), 6.92 (br d, J=10.7 Hz, 2H), 3.82 (s, 3H), 2.96 (s, 3H).

Example 124

$^1$H NMR (500 MHz, DMSO-d6) δ 9.79 (s, 1H), 7.90 (br d, J=8.3 Hz, 2H), 7.24 (d, J=8.6 Hz, 2H), 7.31 (t, J=74.0 Hz, 1H), 7.10-7.03 (m, 2H), 6.97-6.89 (m, 3H), 3.85 (s, 3H), 3.82 (s, 3H), 2.95 (s, 3H).

Example 125

$^1$H NMR (500 MHz, DMSO-d6) δ 9.78 (s, 1H), 7.90 (br d, J=7.9 Hz, 2H), 7.24 (br d, J=8.6 Hz, 2H), 7.32 (t, J=74.0 Hz, 1H), 6.92 (br d, J=10.6 Hz, 2H), 6.87-6.76 (m, 3H), 4.68 (spt, J=5.7 Hz, 1H), 3.82 (s, 3H), 2.95 (s, 3H), 1.30 (d, J=5.9 Hz, 6H).

Example 126

$^1$H NMR (500 MHz, DMSO-d6) δ 9.91-9.76 (m, 1H), 7.88 (br d, J=7.5 Hz, 2H), 7.57 (s, 1H), 7.47 (d, J=1.3 Hz, 1H), 7.36 (s, 1H), 7.24 (d, J=8.3 Hz, 2H), 7.30 (t, J=74.0 Hz, 1H), 6.92 (br d, J=10.7 Hz, 2H), 3.81 (s, 3H), 3.00 (s, 3H), 2.96 (s, 3H), 2.95-2.92 (m, 3H).

Example 127

$^1$H NMR (500 MHz, DMSO-d6) δ 9.88-9.76 (m, 1H), 7.88 (br d, J=8.2 Hz, 2H), 7.62 (d, J=1.5 Hz, 1H), 7.46 (d, J=1.8 Hz, 2H), 7.26-7.19 (m, 1H), 7.25 (t, J=74.0 Hz, 2H), 6.91 (br d, J=10.4 Hz, 2H), 3.81 (s, 3H), 2.95 (s, 3H).

Example 128

$^1$H NMR (500 MHz, DMSO-d6) δ 9.85 (s, 1H), 9.05 (s, 1H), 8.92 (d, J=1.7 Hz, 1H), 8.25 (s, 1H), 7.89 (br d, J=8.3

Hz, 2H), 7.24 (d, J=8.6 Hz, 2H), 7.29 (t, J=74.0 Hz, 1H), 6.93 (br d, J=10.7 Hz, 2H), 3.93 (s, 3H), 3.82 (s, 3H), 2.98 (s, 3H).

Example 129

$^1$H NMR (500 MHz, DMSO-d6) δ 9.79 (s, 1H), 8.38-8.17 (m, 2H), 7.89 (br d, J=8.6 Hz, 2H), 7.50-7.11 (m, 4H), 6.97-6.84 (m, 2H), 3.91 (s, 3H), 3.81 (s, 3H), 2.97 (s, 3H).

Example 130

$^1$H NMR (500 MHz, DMSO-d6) δ 9.84 (s, 1H), 8.67-8.58 (m, 2H), 8.01 (s, 1H), 7.89 (br d, J=8.1 Hz, 2H), 7.24 (d, J=8.6 Hz, 2H), 7.31 (t, J=74.0 Hz, 1H), 6.93 (br d, J=10.5 Hz, 2H), 3.82 (s, 3H), 2.99 (s, 3H).

Example 131

$^1$H NMR (500 MHz, DMSO-d6) δ 9.84 (s, 1H), 7.88 (br d, J=5.2 Hz, 3H), 7.77 (s, 1H), 7.70 (s, 1H), 7.24 (br d, J=8.7 Hz, 2H), 7.27 (t, J=74.0 Hz, 1H), 6.92 (br d, J=10.3 Hz, 2H), 3.81 (s, 3H), 2.96 (s, 3H).

Example 132

$^1$H NMR (500 MHz, DMSO-d6) δ 9.75 (s, 1H), 7.87 (d, J=8.2 Hz, 2H), 7.23 (d, J=8.5 Hz, 2H), 7.26 (t, J=74.0 Hz, 1H), 6.99-6.71 (m, 5H), 3.82 (s, 3H), 3.80 (s, 3H), 2.94 (s, 3H).

Example 133

$^1$H NMR (500 MHz, DMSO-d6) δ 9.83 (s, 1H), 7.89 (br d, J=8.2 Hz, 2H), 7.83 (s, 1H), 7.69 (br d, J=8.6 Hz, 1H), 7.58 (br d, J=9.5 Hz, 1H), 7.24 (br d, J=8.7 Hz, 2H), 7.29 (t, J=74.0 Hz, 1H), 6.93 (br d, J=10.6 Hz, 2H), 4.36 (q, J=7.0 Hz, 2H), 3.81 (s, 3H), 2.96 (s, 3H), 1.33 (t, J=7.1 Hz, 3H).

Example 134

$^1$H NMR (500 MHz, DMSO-d6) δ 9.76 (s, 1H), 7.90 (br d, J=8.5 Hz, 2H), 7.32-7.19 (m, 5H), 7.32 (t, J=74.0 Hz, 1H), 6.93 (br d, J=10.4 Hz, 2H), 3.83 (s, 3H), 2.94 (s, 3H), 2.41 (s, 3H).

Example 136

$^1$H NMR (500 MHz, DMSO-d6) δ 9.68 (s, 1H), 7.94 (br dd, J=19.0, 8.9 Hz, 3H), 7.24 (d, J=8.6 Hz, 2H), 7.33 (t, J=73.6 Hz, 1H), 6.99-6.82 (m, 3H), 3.82 (s, 3H), 3.13 (s, 6H), 2.98 (s, 3H).

Example 137

$^1$H NMR (500 MHz, DMSO-d6) δ 9.67 (s, 1H), 7.99-7.87 (m, 3H), 7.24 (br d, J=8.5 Hz, 2H), 7.33 (t, J=73.9 Hz, 1H), 7.02-6.84 (m, 3H), 4.69-4.52 (m, 2H), 3.82 (s, 3H), 2.99 (s, 3H), 2.65 (br d, J=10.7 Hz, 2H), 2.19 (br t, J=10.1 Hz, 2H), 2.13 (s, 3H), 1.96 (br d, J=7.6 Hz, 2H), 1.93-1.86 (m, 2H).

Example 138

$^1$H NMR (500 MHz, DMSO-d6) δ 9.66 (s, 1H), 7.96 (d, J=8.9 Hz, 1H), 7.91 (d, J=8.5 Hz, 2H), 7.23 (d, J=8.5 Hz, 2H), 7.32 (t, J=73.2 Hz, 1H), 6.90 (dd, J=18.0, 11.9 Hz, 2H), 6.63 (d, J=8.9 Hz, 1H), 5.79 (s, 1H), 4.01-3.88 (m, 4H), 3.82 (s, 3H), 2.96 (s, 3H), 1.46 (s, 3H).

Example 139

$^1$H NMR (500 MHz, DMSO-d6) δ 9.67 (s, 1H), 7.92 (br dd, J=8.7, 5.6 Hz, 3H), 7.27-7.21 (m, 2H), 7.34 (t, J=76.0 Hz, 1H), 7.00-6.84 (m, 3H), 3.83 (s, 3H), 3.78-3.52 (m, 8H), 3.08 (s, 2H), 2.97 (s, 3H).

Example 140

$^1$H NMR (500 MHz, DMSO-d6) δ 9.66 (s, 1H), 8.00-7.93 (m, 1H), 7.89 (br d, J=8.7 Hz, 2H), 7.25-7.19 (m, J=8.6 Hz, 2H), 7.30 (t, J=74.0 Hz, 1H), 6.98-6.78 (m, 2H), 6.62 (d, J=8.8 Hz, 1H), 4.53 (br t, J=4.5 Hz, 1H), 4.37-4.27 (m, 2H), 3.91-3.82 (m, 2H), 3.80 (s, 3H), 3.71-3.60 (m, 1H), 2.94 (s, 3H), 1.11 (d, J=6.1 Hz, 6H).

Example 141

$^1$H NMR (500 MHz, DMSO-d6) δ 9.74 (s, 1H), 7.98 (d, J=8.9 Hz, 1H), 7.86 (br d, J=8.2 Hz, 2H), 7.53 (br d, J=8.2 Hz, 2H), 7.00-6.84 (m, 2H), 6.64 (d, J=8.5 Hz, 1H), 4.55 (br d, J=4.9 Hz, 1H), 4.33 (br s, 2H), 3.94-3.85 (m, 2H), 3.83 (s, 3H), 3.68 (dt, J=12.2, 6.1 Hz, 1H), 2.97 (s, 3H), 1.13 (d, J=6.1 Hz, 6H).

Example 142

$^1$H NMR (500 MHz, $CD_3CN$) δ 8.23 (d, J=4.1 Hz, 1H), 8.13 (br s, 1H), 7.84 (br d, J=7.7 Hz, 2H), 7.66 (d, J=8.3 Hz, 1H), 7.48 (dd, J=8.3, 4.4 Hz, 1H), 7.21 (br d, J=8.5 Hz, 2H), 6.77 (d, J=10.2 Hz, 2H), 6.87 (t, J=79.0 Hz, 1H), 3.87 (s, 3H), 3.18 (s, 3H), 2.93 (s, 6H).

Example 143

$^1$H NMR (500 MHz, DMSO-d6) δ 9.68 (br s, 1H), 7.96-7.87 (m, 2H), 7.83 (d, J=9.0 Hz, 1H), 7.32 (br s, 1H), 7.26-7.21 (m, J=8.3 Hz, 2H), 7.02 (br d, J=9.2 Hz, 1H), 6.91 (br s, 1H), 3.82 (s, 3H), 3.63-3.50 (m, 4H), 3.00 (s, 3H), 2.45-2.36 (m, 4H), 2.22 (s, 3H).

Example 144

$^1$H NMR (500 MHz, DMSO-d6) δ 9.62 (s, 1H), 7.93 (br d, J=8.5 Hz, 2H), 7.47 (d, J=8.5 Hz, 1H), 7.24 (br d, J=8.5 Hz, 2H), 7.33 (t, J=73.6 Hz, 1H), 7.20-7.15 (m, 1H), 6.93 (br d, J=12.2 Hz, 2H), 4.67 (s, 4H), 4.13-4.08 (m, 2H), 4.04 (br d, J=8.5 Hz, 2H), 3.82 (s, 3H), 2.98 (s, 3H).

Example 145

$^1$H NMR (500 MHz, DMSO-d6) δ 9.71 (br s, 1H), 8.00-7.88 (m, 3H), 7.49-7.24 (br d, J=6.4 Hz, 1H), 7.19 (br s, 1H), 6.92 (br s, 2H), 6.79 (dd, J=8.8, 3.5 Hz, 2H), 4.48 (br t, J=11.9 Hz, 4H), 3.83 (s, 3H), 3.01 (s, 3H)

Example 146

$^1$H NMR (500 MHz, $CDCl_3$+$CD_3OD$) δ 7.77 (br d, J=8.5 Hz, 2H), 7.64 (t, J=8.3 Hz, 1H), 7.39 (dd, J=8.7, 2.9 Hz, 1H), 7.06 (br d, J=8.5 Hz, 2H), 6.56-6.47 (m, 2H), 6.52 (t, J=73.2 Hz, 1H), 3.76 (s, 3H), 3.14 (s, 3H).

Example 147

$^1$H NMR (500 MHz, DMSO-d6) δ 9.68 (s, 1H), 7.93 (br d, J=8.5 Hz, 2H), 7.79 (d, J=9.2 Hz, 2H), 7.49-7.19 (s, 1H), 7.24 (br d, J=8.5 Hz, 1H), 6.92 (br s, 1H), 6.82 (d, J=9.2 Hz, 2H), 3.84 (s, 3H), 3.07 (s, 6H), 3.02 (s, 3H)

Example 148

$^1$H NMR (500 MHz, DMSO-d6) δ 9.74 (s, 1H), 7.87 (br d, J=8.2 Hz, 2H), 7.44-7.08 (m, 6H), 6.89 (br d, J=10.7 Hz, 2H), 5.47 (s, 1H), 3.80 (s, 3H), 2.95 (s, 3H), 1.45 (s, 6H).

Example 150

$^1$H NMR (500 MHz, DMSO-d6) δ 9.72 (s, 1H), 8.00 (t, J=7.9 Hz, 1H), 7.93 (d, J=8.5 Hz, 2H), 7.72 (d, J=8.2 Hz, 1H), 7.68 (d, J=7.9 Hz, 1H), 7.26 (d, J=8.5 Hz, 2H), 7.35 (t, J=74.8 Hz, 1H), 6.95 (d, J=10.4 Hz, 2H), 3.92 (br t, J=5.8 Hz, 2H), 3.84 (s, 3H), 3.22 (s, 3H), 1.97-1.80 (m, 4H). two protons of the piperidinone group obscured by the solvent peak Example 151

$^1$H NMR (500 MHz, $CD_3OD$) δ 8.47 (d, J=5.2 Hz, 1H), 7.97 (br d, J=8.8 Hz, 2H), 7.74 (s, 1H), 7.38 (br d, J=8.3 Hz, 2H), 7.31 (d, J=5.2 Hz, 1H), 6.82 (d, J=9.9 Hz, 2H), 3.89 (s, 3H), 3.32 (s, 3H), 2.52 (s, 3H).

Example 152

$^1$H NMR (400 MHz, $CDCl_3$) 8.46 (d, J=5.3 Hz, 1H), 8.11 (d, J=1.8 Hz, 1H), 7.81 (d, J=8.8 Hz, 2H), 7.24 (m, 1H), 7.14 (d, J=8.8 Hz, 2H), 6.77-6.29 (m, 3H), 3.84 (s, 3H), 3.31 (s, 3H).

Example 154

$^1$H NMR (500 MHz, DMSO-$d_6$) δ 9.82 (s, 1H), 8.95 (br d, J=4.0 Hz, 1H), 8.48 (br d, J=7.9 Hz, 1H), 7.94 (br d, J=8.2 Hz, 2H), 7.84-7.77 (m, 1H), 7.43 (br d, J=7.9 Hz, 2H), 7.00-6.80 (m, 2H), 3.81 (s, 3H), 2.94 (s, 3H)

Example 155

$^1$H NMR (500 MHz, DMSO-$d_6$) δ 9.86 (s, 1H), 8.35-8.27 (m, 1H), 8.27-8.21 (m, 1H), 7.95 (br d, J=8.2 Hz, 2H), 7.86 (br d, J=7.3 Hz, 1H), 7.46 (br d, J=8.2 Hz, 2H), 6.94 (br d, J=10.4 Hz, 2H), 3.83 (s, 3H), 3.23 (s, 3H).

Example 156

$^1$H NMR (500 MHz, DMSO-d6) δ 9.75 (s, 1H), 8.33-8.27 (m, 1H), 8.27-8.20 (m, 1H), 7.90 (br d, J=8.2 Hz, 2H), 7.85 (br d, J=7.3 Hz, 1H), 7.32 (t, J=73.6 Hz, 1H), 7.24 (br d, J=8.5 Hz, 2H), 6.93 (br d, J=10.7 Hz, 2H), 3.82 (s, 3H), 3.22 (s, 3H).

Example 157

$^1$H NMR (500 MHz, DMSO-d6) δ 9.85 (s, 1H), 8.87 (d, J=7.9 Hz, 1H), 8.15 (d, J=8.2 Hz, 1H), 7.91 (br d, J=8.5 Hz, 2H), 7.29 (t, J=73.6 Hz 1H), 7.24 (br d, J=8.5 Hz, 2H), 6.94 (br d, J=10.7 Hz, 2H), 3.82 (s, 3H), 3.19 (s, 3H).

Example 158

$^1$H NMR (500 MHz, DMSO-d6) δ 9.73 (s, 1H), 8.57 (dd, J=4.6, 1.2 Hz, 1H), 7.97 (d, J=7.9 Hz, 1H), 7.93 (br d, J=8.2 Hz, 2H), 7.66 (dd, J=8.2, 4.9 Hz, 1H), 7.33 (dt, J=73.6, 14.3 Hz, 1H), 7.25 (d, J=8.5 Hz, 2H), 6.94 (d, J=10.7 Hz, 2H), 3.84 (s, 3H), 3.02 (s, 3H).

Example 159

$^1$H NMR (500 MHz, $CDCl_3$) δ 8.31 (d, J=8.0 Hz, 1H), 7.83 (br d, J=8.3 Hz, 2H), 7.71 (br s, 1H), 7.67 (d, J=8.3 Hz, 1H), 7.16 (br d, J=8.5 Hz, 2H), 6.60 (br d, J=9.9 Hz, 2H), 6.57 (t, J=73.2 Hz, 1H), 3.86 (s, 3H), 3.11 (s, 3H).

Example 160

$^1$H NMR (400 MHz, $CD_3OD$ containing $CDCl_3$) δ 7.99 (d, J=8.4 Hz, 1H), 7.87 (br d, J=8.6 Hz, 2H), 7.27 (d, J=8.1 Hz, 1H), 7.16 (d, J=8.8 Hz, 2H), 6.70 (t, J=73.3 Hz, 1H), 6.64 (br s, 2H), 3.86 (s, 3H), 3.16 (s, 3H), 2.16-2.07 (m, 1H), 1.15-0.97 (m, 4H).

Example 161

$^1$H NMR (400 MHz, DMSO-d6) δ 9.79 (s, 1H), 8.35 (d, J=8.1 Hz, 1H), 7.92 (d, J=8.8 Hz, 2H), 7.59 (d, J=8.1 Hz, 1H), 7.34 (t, J=73.5 Hz, 1H), 7.24 (d, J=8.8 Hz, 2H), 6.98-6.93 (m, 2H), 3.84 (s, 3H), 3.11 (s, 3H), 2.38-2.31 (m, 1H), 1.24-1.05 (m, 4H).

Example 162

$^1$H NMR (500 MHz, $CDCl_3$) δ 7.98 (d, J=2.2 Hz, 1H), 7.83 (d, J=8.8 Hz, 2H), 7.79-7.68 (m, 1H), 7.19-7.10 (m, 3H), 6.63-6.58 (m, 2H), 6.58 (t, J=73.5 Hz, 1H), 4.01 (s, 3H), 3.86 (s, 3H), 3.40 (s, 3H).

Example 163

$^1$H NMR (400 MHz, $CD_3OD$) δ 7.93 (s, 3H), 7.70 (d, J=8.0 Hz, 1H), 7.31 (d, J=7.5 Hz, 1H), 7.24-7.19 (m, 2H), 7.16-6.75 (m, 3H), 3.88 (s, 3H), 3.37 (s, 3H), 2.91 (q, J=7.5 Hz, 2H), 1.37 (t, J=7.6 Hz, 3H).

Example 164

$^1$H NMR (500 MHz, $CD_3OD$) δ 8.62 (dd, J=4.6, 1.4 Hz, 1H), 8.15 (dd, J=8.2, 1.4 Hz, 1H), 7.79 (br d, J=7.7 Hz, 2H), 7.59 (dd, J=8.1, 4.7 Hz, 1H), 7.43 (d, J=8.5 Hz, 2H), 6.75 (d, J=10.3 Hz, 2H), 3.86 (s, 3H), 3.16 (s, 3H).

Example 165

$^1$H NMR (500 MHz, $CD_3OD$) δ 8.66 (dd, J=4.6, 1.3 Hz, 1H), 8.31 (dd, J=8.1, 1.4 Hz, 1H), 7.86 (br d, J=8.0 Hz, 2H), 7.51 (dd, J=8.1, 4.7 Hz, 1H), 7.18 (d, J=8.6 Hz, 2H), 7.04-6.67 (m, 3H), 3.86 (s, 3H), 3.15 (s, 3H).

Example 166

$^1$H NMR (500 MHz, DMSO-d6) δ 9.67 (br s, 1H), 8.51 (br d, J=3.7 Hz, 1H), 8.03-7.84 (m, 3H), 7.62-7.14 (m, 4H), 7.01-6.84 (m, 2H), 3.83 (s, 3H), 2.97 (s, 3H), 2.82-2.70 (m, 2H), 1.21 (br t, J=7.5 Hz, 3H).

Example 167

$^1$H NMR (500 MHz, $CD_3OD$) δ 7.92 (br d, J=7.9 Hz, 2H), 7.80 (t, J=7.8 Hz, 1H), 7.60 (d, J=7.9 Hz, 1H), 7.32 (br d,

J=8.3 Hz, 2H), 7.26 (d, J=7.7 Hz, 2H), 6.76 (d, J=10.0 Hz, 2H), 3.86 (s, 3H), 3.30 (br s, 3H), 2.20-2.10 (m, 1H), 1.11-0.93 (m, 4H).

Example 168

$^1$H NMR (400 MHz, $CD_3OD$) δ 8.08 (t, J=8.0 Hz, 1H), 7.92 (d, J=8.6 Hz, 2H), 7.76 (d, J=7.8 Hz, 1H), 7.55 (t, J=72.8 Hz, 1H), 7.22 (d, J=8.7 Hz, 2H), 7.00 (d, J=8.1 Hz, 1H), 7.03-6.98 (m, 1H), 6.86-6.79 (m, 1H), 6.96 (t, J=73.5 Hz, 1H), 3.89 (s, 3H), 3.36 (s, 3H)

Example 169

$^1$H NMR (400 MHz, $CD_3OD$) δ 8.09 (t, J=8.0 Hz, 1H), 7.97 (d, J=8.7 Hz, 2H), 7.81-7.31 (m, 4H), 7.01 (d, J=8.0 Hz, 1H), 6.83 (d, J=10.0 Hz, 2H), 3.89 (s, 3H), 3.37 (s, 3H).

Example 170

$^1$H NMR (500 MHz, $CD_3OD$) δ 8.79 (br d, J=4.1 Hz, 1H), 8.08 (br d, J=8.2 Hz, 1H), 7.96-7.85 (m, 3H), 7.33 (br d, J=8.2 Hz, 2H), 6.77 (br d, J=11.3 Hz, 2H), 3.87 (s, 3H), 3.11 (s, 3H).

Example 171

$^1$H NMR (500 MHz, $CD_3OD$) δ 7.89 (d, J=8.7 Hz, 2H), 7.70 (dd, J=7.8, 1.6 Hz, 1H), 7.66 (dd, J=7.4, 1.8 Hz, 1H), 7.63-7.54 (m, 2H), 7.19 (d, J=8.6 Hz, 2H), 7.09-6.74 (m, 3H), 3.85 (s, 3H), 3.13 (s, 3H)

Example 172

$^1$H NMR (500 MHz, $CD_3OD$) δ 7.94 (d, J=8.7 Hz, 2H), 7.75-7.64 (m, 2H), 7.64-7.55 (m, 2H), 7.35 (br d, J=8.3 Hz, 2H), 6.78 (br d, J=10.6 Hz, 2H), 3.85 (s, 3H), 3.14 (s, 3H).

Example 173

$^1$H NMR (500 MHz, DMSO-d6) δ 9.86 (s, 1H), 8.05 (d, J=7.6 Hz, 1H), 7.97-7.84 (m, 3H), 7.65 (t, J=7.5 Hz, 1H), 7.50 (d, J=7.9 Hz, 1H), 7.46-7.14 (m, 3H), 6.92 (br d, J=9.2 Hz, 2H), 3.82 (s, 3H), 2.94 (s, 3H).

Example 174

$^1$H NMR (500 MHz, $CD_3OD$) 8.01 δ 7.88 (m, 4H), 7.74-7.61 (m, 2H), 7.35 (br d, J=8.2 Hz, 2H), 6.80 (br d, J=10.5 Hz, 2H), 3.86 (s, 3H), 3.12 (s, 3H).

Example 175

$^1$H NMR (400 MHz, $CD_3OD$) δ 7.91 (br d, J=8.6 Hz, 2H), 7.54 (m, 3H), 7.21 (d, J=8.8 Hz, 2H), 7.14-6.74 (m, 3H), 3.88 (s, 3H), 3.14 (s, 3H).

Example 176

$^1$H NMR (500 MHz, $CD_3OD$) δ 7.89 (br d, J=8.6 Hz, 2H), 7.76 (d, J=2.1 Hz, 1H), 7.71-7.66 (m, 1H), 7.65-7.60 (m, 1H), 7.19 (br d, J=8.6 Hz, 2H), 7.11-6.72 (m, 3H), 3.85 (s, 3H), 3.13 (s, 3H).

Example 177

$^1$H NMR (400 MHz, $CD_3OD$) δ 7.92 (br d, J=8.6 Hz, 2H), 7.67-7.59 (m, 1H), 7.42-7.36 (m, 2H), 7.30-7.12 (m, 3H), 6.96 (d, J=9.0 Hz, 1H), 6.84-6.76 (m, 2H), 6.82 (s, 1H), 3.88 (s, 3H), 3.14 (s, 3H).

Example 178

$^1$H NMR (500 MHz, $CD_3OD$) δ 8.01-7.86 (m, 3H), 7.56-7.45 (m, 2H), 7.19 (d, J=8.6 Hz, 2H), 7.14-6.68 (m, 3H), 3.86 (s, 3H), 3.12 (s, 3H).

Example 179

$^1$H NMR (500 MHz, $CD_3OD$) δ 8.15 (d, J=8.0 Hz, 1H), 8.08-7.99 (m, 2H), 7.89 (br d, J=8.6 Hz, 2H), 7.20 (d, J=8.7 Hz, 2H), 7.11-6.76 (m, 3H), 3.86 (s, 3H), 3.12 (s, 3H).

Example 180

$^1$H NMR (500 MHz, DMSO-d6) 9.73 (br s, 1H), 8.53-8.43 (m, 1H), 7.91 (br d, J=7.3 Hz, 2H), 7.60 (br d, J=4.4 Hz, 1H), 7.51-7.12 (m, 3H), 6.98-6.82 (m, 2H), 3.89-3.76 (m, 3H), 3.65 (br s, 3H), 2.96 (s, 3H).

Example 182

$^1$H NMR (500 MHz, $CD_3OD$) δ 8.00-7.94 (m, 1H), 7.92-7.83 (m, 2H), 7.19 (br d, J=8.3 Hz, 2H), 7.11-6.90 (m, 2H), 6.85-6.69 (m, 2H), 3.96 (s, 3H), 3.85 (s, 3H), 3.22 (s, 3H).

Example 183

$^1$H NMR (500 MHz, $CD_3OD$) δ 7.89 (t, J=8.5 Hz, 3H), 7.40-7.16 (m, 4H), 7.13-6.72 (m, 3H), 3.96 (s, 3H), 3.86 (s, 3H), 3.13 (s, 3H).

Example 184

$^1$H NMR (500 MHz, $CD_3OD$) δ 7.89 (d, J=8.6 Hz, 2H), 7.56-7.47 (m, 1H), 7.38-7.30 (m, 1H), 7.25-7.22 (m, 1H), 7.21-7.16 (m, 2H), 7.09-6.74 (m, 3H), 3.98 (s, 3H), 3.85 (s, 3H), 3.12 (s, 3H).

Example 185

$^1$H NMR (500 MHz, $CD_3OD$) δ 7.96 (d, J=8.8 Hz, 1H), 7.89 (d, J=8.7 Hz, 2H), 7.20 (s, 2H), 7.12-6.91 (m, 2H), 6.85-6.68 (m, 2H), 3.96 (s, 3H), 3.85 (s, 3H), 3.22 (s, 3H).

Example 186

$^1$H NMR (500 MHz, METHANOL-d4) δ 7.89 (br d, J=8.6 Hz, 2H), 7.72 (dd, 5.3 Hz, 1H), 7.53 (dd, J=8.3, 2.7 Hz, 1H), 7.45-7.36 (m, 1H), 7.19 (d, J=8.6 Hz, 2H), 7.09-6.73 (m, 3H), 3.85 (s, 3H), 3.14 (s, 3H) Example 187:

$^1$H NMR (500 MHz, $CD_3OD$) δ 7.89 (br d, J=8.5 Hz, 2H), 7.75-7.67 (m, 1H), 7.57-7.49 (m, 1H), 7.44-7.35 (m, 1H), 7.19 (d, J=8.6 Hz, 2H), 7.12-6.75 (m, 3H), 3.85 (s, 3H), 3.14 (s, 3H).

Example 188

$^1$H NMR (500 MHz, $CD_3OD$) δ 8.04 (dd, J=8.6, 5.6 Hz, 1H), 7.89 (br d, J=8.5 Hz, 2H), 7.54-7.42 (m, 2H), 7.25-7.14 (m, 2H), 7.11-6.76 (m, 3H), 3.86 (s, 3H), 3.13-3.12 (m, 3H).

Example 189

$^1$H NMR (500 MHz, $CD_3OD$) δ 7.99-7.93 (m, 1H), 7.91-7.85 (m, 3H), 7.59 (t, J=8.0 Hz, 1H), 7.20 (d, J=8.7 Hz, 2H), 7.12-6.76 (m, 3H), 3.86 (s, 3H), 3.13 (s, 3H).

Example 190

$^1$H NMR (500 MHz, $CD_3OD$) δ 8.30 (d, J=8.2 Hz, 1H), 7.89 (br d, J=8.7 Hz, 2H), 7.69 (d, J=8.2 Hz, 1H), 7.19 (br d, J=8.7 Hz, 2H), 7.09-6.76 (m, 3H), 3.87 (s, 3H), 3.32 (s, 3H), 1.43 (s, 9H).

Example 191

$^1$H NMR (500 MHz, $CD_3OD$) δ 8.81 (d, J=5.3 Hz, 1H), 7.92 (s, 2H), 7.68 (d, J=5.3 Hz, 1H), 7.21 (br d, J=8.8 Hz, 2H), 7.11-6.79 (m, 3H), 4.08-3.96 (m, 1H), 3.89 (s, 3H), 3.28 (s, 3H), 2.65-2.56 (m, 2H), 2.44-2.35 (m, 2H), 2.28-2.17 (m, 2H).

Example 192

$^1$H NMR (500 MHz, $CD_3OD$) δ 8.36-8.30 (m, 1H), 7.90-7.86 (m, 2H), 7.84-7.80 (m, 1H), 7.19 (s, 2H), 7.10-6.69 (m, 3H), 3.86 (s, 3H), 3.63 (q, J=7.0 Hz, 2H), 3.23 (s, 3H), 1.45 (br d, J=6.3 Hz, 4H), 1.28 (t, J=7.0 Hz, 3H).

Example 193

$^1$H NMR (500 MHz, $CD_3OD$) δ 8.40 (d, J=8.0 Hz, 1H), 7.88 (br d, J=8.5 Hz, 2H), 7.72 (d, J=8.1 Hz, 1H), 7.18 (br d, J=8.5 Hz, 2H), 7.09-6.64 (m, 3H), 4.69 (s, 2H), 3.86 (s, 3H), 3.53 (s, 3H), 3.28 (s, 3H).

Example 194

$^1$H NMR (500 MHz, $CD_3OD$) δ 8.52-8.39 (m, 1H), 7.88 (br d, J=8.6 Hz, 2H), 7.84-7.77 (m, 1H), 7.19 (br d, J=8.4 Hz, 2H), 7.09-6.75 (m, 3H), 3.86 (s, 3H), 3.30 (s, 3H), 1.76 (s, 3H), 1.72 (s, 3H).

Example 195

$^1$H NMR (500 MHz, $CD_3OD$) δ 8.43 (d, J=8.2 Hz, 1H), 7.93 (d, J=8.2 Hz, 1H), 7.87 (br d, J=8.5 Hz, 2H), 7.18 (br d, J=8.4 Hz, 2H), 7.10-6.72 (m, 3H), 4.82 (br d, J=8.4 Hz, 2H), 3.85 (s, 3H), 3.14 (s, 3H).

Example 196

$^1$H NMR (500 MHz, $CD_3OD$) δ 8.43 (d, J=8.2 Hz, 1H), 7.90-7.86 (m, 3H), 7.18 (br d, J=8.6 Hz, 2H), 7.10-6.73 (m, 3H), 4.69 (s, 2H), 3.85 (s, 3H), 3.53 (s, 3H), 3.14 (s, 3H).

Example 197

$^1$H NMR (500 MHz, $CDCl_3$) δ 8.60 (d, J=4.7 Hz, 1H), 7.97 (d, J=8.0 Hz, 1H), 7.83 (br d, J=8.0 Hz, 3H), 7.41 (ddd, J=8.0, 4.7, 0.8 Hz, 1H), 7.15 (d, J=8.5 Hz, 2H), 6.80-6.39 (m, 3H), 3.85 (s, 3H), 3.41 (t, J=7.0 Hz, 3H). Example 200

$^1$H NMR (500 MHz, $CDCl_3$) δ 7.96 (d, J=8.3 Hz, 1H), 7.84 (br d, J=8.5 Hz, 2H), 7.57 (d, J=8.3 Hz, 1H), 7.18-7.14 (m, 2H), 6.47-6.46 (m, 1H), 6.76-6.40 (m, 2H), 4.64 (s, 2H), 3.85 (s, 3H), 3.53 (s, 3H), 3.07 (s, 3H).

Example 201

$^1$H NMR (400 MHz, $CD_3OD$) δ 8.75-8.68 (m, 1H), 7.90 (br d, J=8.8 Hz, 2H), 7.57 (dd, J=5.1, 0.7 Hz, 1H), 7.21 (d, J=8.6 Hz, 2H), 7.15-6.69 (m, 3H), 3.88 (s, 3H), 3.29 (s, 3H), 2.72 (s, 3H).

Example 202

$^1$H NMR (500 MHz, DMSO-$d_6$, ws) δ 9.82 (s, 1H), 8.17 (d, J=8.8 Hz, 1H), 7.91 (d, J=8.6 Hz, 2H), 7.25 (br d, J=8.5 Hz, 2H), 7.26 (t, J=73.4 Hz, 1H), 7.10 (d, J=9.0 Hz, 1H), 6.94 (d, J=10.6 Hz, 2H), 3.83 (s, 3H), 3.14 (s, 3H), 2.54 (s, 3H).

Example 203

$^1$H NMR (500 MHz, DMSO-d6) δ 9.61 (s, 1H), 7.90 (d, J=8.5 Hz, 2H), 7.46 (d, J=8.5 Hz, 1H), 7.23 (d, J=8.5 Hz, 2H), 7.18 (d, J=8.9 Hz, 1H), 7.31 (t, J=73.2 Hz, 1H), 6.90 (d, J=10.4 Hz, 2H), 3.80 (s, 3H), 3.90-3.65 (m, 4H), 2.96 (s, 3H), 1.76 (s, 1H), 1.41 (s, 3H).

Example 204

$^1$H NMR (500 MHz, DMSO-d6) δ 9.76 (s, 1H), 8.23-8.08 (m, 1H), 7.92 (d, J=8.2 Hz, 3H), 7.53 (d, J=7.6 Hz, 1H), 7.27 (d, J=8.5 Hz, 2H), 7.35 (t, J=73.5 Hz, 1H), 6.96 (d, J=10.4 Hz, 2H), 4.47 (br s, 2H), 3.85 (s, 3H), 3.22 (s, 3H), 2.89 (s, 6H).

Example 205

$^1$H NMR (500 MHz, DMSO-d6) δ 9.70 (s, 1H), 7.98 (t, J=8.0 Hz, 1H), 7.91 (d, J=8.5 Hz, 2H), 7.76 (d, J=8.0 Hz, 1H), 7.39 (d, J=7.6 Hz, 1H), 7.25 (d, J=8.0 Hz, 2H), 7.33 (t, J=73.4 Hz, 1H), 6.94 (d, J=10.9 Hz, 2H), 3.83 (s, 3H), 3.65 (s, 2H), 3.21 (s, 3H), 2.49-2.32 (m, 8H), 2.18 (s, 3H).

Example 206

$^1$H NMR (500 MHz, DMSO-d6) δ 9.68 (s, 1H), 7.91 (d, J=8.6 Hz, 2H), 7.73 (m, 1H), 7.25 (d, J=8.7 Hz, 2H), 7.33 (t, J=73.6 Hz, 1H), 7.10 (d, J=7.7 Hz, 1H), 6.93 (d, J=10.4 Hz, 2H), 6.79 (d, J=8.4 Hz, 1H), 3.83 (s, 3H), 3.63-3.45 (m, 4H), 3.39-3.29 (m, 2H), 3.19 (s, 3H), 3.06 (s, 3H), 2.84-2.73 (m, 2H), 2.62-2.57 (m, 4H).

Example 207

$^1$H NMR (500 MHz, DMSO-d6) δ 9.71 (s, 1H), 7.91 (br d, J=8.3 Hz, 2H), 7.82 (m, 1H), 7.26 (d, J=8.8 Hz, 2H), 7.53-7.16 (m, 2H), 6.99-6.87 (m, 3H), 3.83 (s, 3H), 3.61-3.30 (m, 4H), 3.20 (s, 3H), 3.12-2.90 (m, 4H), 2.57 (br s, 2H), 1.17-1.02 (m, 1H), 0.71-0.61 (m, 2H), 0.43-0.33 (m, 2H).

Example 208

$^1$H NMR (500 MHz, DMSO-d6) δ 9.67 (s, 1H), 7.92 (d, J=8.2 Hz, 2H), 7.72 (m, 1H), 7.25 (d, J=8.5 Hz, 2H), 7.34 (t, J=72.3 Hz, 1H), 7.10 (d, J=7.6 Hz, 1H), 6.94 (d, J=10.1

Hz, 2H), 6.77 (d, J=8.2 Hz, 1H), 3.83 (s, 3H), 3.54 (br s, 4H), 3.47 (t, J=6.3 Hz, 2H), 3.20 (s, 3H), 2.50-2.45 (m, 4H), 2.40 (br t, J=7.2 Hz, 2H), 1.92 (s, 1H), 1.64 (quin, J=6.7 Hz, 2H).

Example 209

$^1$H NMR (500 MHz, DMSO-d6) δ 9.61 (s, 1H), 7.90 (d, J=8.5 Hz, 2H), 7.60 (d, J=8.9 Hz, 1H), 7.50 (d, J=8.5 Hz, 1H), 7.23 (br d, J=8.5 Hz, 2H), 7.32 (t, J=74.5 Hz, 1H), 6.90 (m, 2H), 3.81 (s, 3H), 2.99 (s, 3H), 2.81 (s, 6H).

Example 210

$^1$H NMR (500 MHz, DMSO-d6) δ 9.66 (s, 1H), 7.90 (br d, J=8.2 Hz, 2H), 7.74 (m, 1H), 7.23 (d, J=8.5 Hz, 2H), 7.34 (t, J=73.3 Hz, 1H), 6.92 (br d, J=10.7 Hz, 2H), 6.56 (m, 1H), 3.90 (s, 1H), 3.82 (s, 3H), 3.83 (dd, J=26.3, 8.0 Hz, 2H), 3.79-3.78 (m, 1H), 3.04 (s, 3H), 1.44 (s, 3H).

Example 211

$^1$H NMR (500 MHz, DMSO-d6, ws) δ 9.60 (s, 1H), 7.96 (d, J=4.0 Hz, 1H), 7.92 (d, J=8.2 Hz, 2H), 7.37 (m, 1H), 7.23 (d, J=8.2 Hz, 2H), 7.32 (t, J=73.8 Hz, 1H), 7.09 (d, J=8.2 Hz, 1H), 6.90 (d, J=10.4 Hz, 2H), 3.89 (s, 1H), 3.81 (s, 3H), 3.76 (br d, J=7.3 Hz, 1H), 3.70-3.64 (m, 1H), 2.94 (s, 3H), 1.42 (s, 3H)

Example 212

$^1$H NMR (500 MHz, DMSO-d6) δ 9.67 (s, 1H), 7.90 (d, J=8.4 Hz, 2H), 7.72 (m, 1H), 7.24 (d, J=8.4 Hz, 2H), 7.30 (t, J=73.5 Hz, 1H), 7.08 (d, J=7.6 Hz, 1H), 6.91 (d, J=10.3 Hz, 2H), 6.76 (d, J=8.3 Hz, 1H), 3.81 (s, 3H), 3.72-3.61 (m, 6H), 3.59-3.46 (m, 2H), 3.25 (s, 3H), 3.19 (s, 3H), 2.61-2.56 (m, 4H).

Example 213

$^1$H NMR (500 MHz, DMSO-d6) δ 9.68 (s, 1H), 7.91 (d, J=8.5 Hz, 2H), 7.77 (m, 1H), 7.25 (d, J=8.7 Hz, 2H), 7.32 (t, J=73.7 Hz, 1H), 7.13 (d, J=7.7 Hz, 1H), 6.93 (d, J=10.3 Hz, 2H), 6.84 (d, J=8.5 Hz, 1H), 3.82 (s, 3H), 3.74-3.62 (m, 4H), 3.27-3.20 (m, 4H), 3.19 (s, 3H), 2.91 (s, 3H).

Example 214

$^1$H NMR (500 MHz, DMSO-d6) δ 9.66 (s, 1H), 8.21 (br s, 1H), 8.03 (d, J=9.2 Hz, 1H), 7.90 (br d, J=8.2 Hz, 2H), 7.22 (br d, J=8.5 Hz, 2H), 7.31 (t, J=74.0 Hz, 1H), 7.04 (d, J=9.2 Hz, 1H), 6.98-6.75 (m, 2H), 4.13 (s, 2H), 3.81 (s, 4H), 2.97 (s, 3H).

Example 215

$^1$H NMR (500 MHz, DMSO-d6) δ 9.66 (s, 1H), 7.90 (br d, J=8.5 Hz, 2H), 7.24 (d, J=8.5 Hz, 2H), 7.63-7.16 (m, 3H), 6.91 (d, J=10.7 Hz, 2H), 5.90 (d, J=4.9 Hz, 1H), 3.82 (s, 3H), 2.98 (s, 3H), 2.78 (d, J=4.9 Hz, 3H).

Example 217

$^1$H NMR (500 MHz, DMSO-d6, ws) δ 9.80 (s, 1H), 8.01 (d, J=8.5 Hz, 1H), 7.93 (br d, J=8.5 Hz, 2H), 7.75 (d, J=8.5 Hz, 1H), 7.25 (d, J=8.9 Hz, 2H), 7.33 (t, J=73.8 Hz, 1H), 6.93 (m, 2H), 3.82 (s, 3H), 3.01 (s, 3H), 2.83 (s, 3H).

Example 218

$^1$H NMR (500 MHz, DMSO-d6) δ 9.65 (s, 1H), 7.92 (d, J=8.5 Hz, 2H), 7.68 (m, 1H), 7.25 (d, J=8.9 Hz, 2H), 7.34 (t, J=74.8 Hz, 1H), 7.10 (d, J=7.6 Hz, 1H), 6.93 (d, J=10.1 Hz, 2H), 6.30 (d, J=8.2 Hz, 1H), 3.83 (s, 3H), 3.70 (s, 4H), 3.23 (s, 3H), 1.31 (s, 6H).

Example 219

$^1$H NMR (500 MHz, $CD_3OD$) δ 7.89 (d, J=8.8 Hz, 2H), 7.76 (m, 1H), 7.20 (d, J=8.5 Hz, 2H), 7.15 (dd, J=9.2, 2.3 Hz, 1H), 6.93 (t, J=73.5 Hz, 1H), 6.81-6.75 (m, 2H), 4.47 (br d, J=12.1 Hz, 2H), 3.86 (s, 3H), 3.61 (br d, J=10.5 Hz, 2H), 3.25 (s, 3H), 3.28-3.15 (m, 4H), 2.96 (s, 3H).

Example 220

$^1$H NMR (500 MHz, DMSO-d6) δ 9.68 (s, 1H), 8.04 (d, J=9.1 Hz, 1H), 7.91 (br d, J=8.2 Hz, 2H), 7.28-7.20 (m, 1H), 7.33 (t, J=74.0 Hz, 1H), 7.09 (d, J=9.0 Hz, 1H), 7.28-7.02 (m, 1H), 6.99-6.84 (m, 2H), 4.27-4.12 (m, 2H), 3.91 (d, J=3.3 Hz, 2H), 3.82 (s, 3H), 3.59-3.37 (m, 1H), 3.07-2.98 (m, 1H), 2.97 (s, 3H), 2.91 (s, 3H).

Example 221

$^1$H NMR (500 MHz, DMSO-d6) δ 9.65 (s, 1H), 8.96 (d, J=4.0 Hz, 1H), 8.48 (d, J=7.6 Hz, 1H), 7.94 (d, J=8.5 Hz, 2H), 7.81 (dd, J=7.9, 4.8 Hz, 1H), 7.64 (d, J=2.0 Hz, 1H), 7.54 (dd, J=8.5, 1.9 Hz, 1H), 7.27 (br d, J=8.6 Hz, 2H), 7.49-7.18 (m, 2H), 3.90 (s, 3H), 2.99 (s, 3H)

Example 222

$^1$H NMR (500 MHz, DMSO-d6) δ 9.77 (s, 1H), 8.54 (d, J=8.4 Hz, 1H), 7.96 (d, J=8.2 Hz, 1H), 7.91 (d, J=8.4 Hz, 2H), 7.24 (d, J=8.6 Hz, 2H), 7.33 (t, J=76.7 Hz, 1H), 7.01-6.85 (m, 2H), 3.83 (s, 3H), 3.00 (s, 3H).

Example 223

$^1$H NMR (500 MHz, DMSO-d6) δ 9.68 (s, 1H), 8.99 (br d, J=3.7 Hz, 1H), 8.51 (br d, J=7.6 Hz, 1H), 8.20 (s, 1H), 8.05 (s, 1H), 7.95 (br d, J=8.5 Hz, 2H), 7.87-7.74 (m, 2H), 7.59 (br d, J=8.9 Hz, 1H), 7.26 (br d, J=8.5 Hz, 2H), 7.33 (t, J=73.5 Hz, 1H), 4.08 (s, 3H), 3.02 (s, 3H)

Example 224

$^1$H NMR (500 MHz, DMSO-d6, ws) δ 9.80 (s, 1H), 8.52 (d, J=5.0 Hz, 1H), 7.90 (br d, J=8.4 Hz, 2H), 7.23 (br d, J=8.6 Hz, 2H), 7.32 (t, J=74.0 Hz, 1H), 6.98-6.86 (m, 3H), 3.82 (s, 3H), 2.90 (s, 3H), 2.44 (br s, 4H), 2.22 (s, 3H).

Example 225

$^1$H NMR (500 MHz, DMSO-d6) δ 9.68 (s, 1H), 7.92 (d, J=8.5 Hz, 2H), 7.87-7.78 (m, 1H), 7.74 (br s, 1H), 7.23 (d, J=8.5 Hz, 2H), 7.34 (t, J=70.8 Hz, 1H), 6.98-6.83 (m, 2H), 6.76 (d, J=8.7 Hz, 1H), 4.83-4.68 (m, 1H), 3.82 (s, 3H), 3.57 (q, J=5.3 Hz, 2H), 3.48-3.36 (m, 2H), 2.97 (s, 3H).

Example 226

$^{1}$H NMR (500 MHz, DMSO-d6, ws) δ 9.64 (s, 1H), 7.96-7.79 (m, 4H), 7.46 (d, J=6.4 Hz, 1H), 7.31-7.19 (m, 3H), 7.19-7.10 (m, 1H), 7.05 (m, 1H), 6.97-6.77 (m, 2H), 3.81 (s, 3H), 2.99 (s, 3H).

Example 227

$^{1}$H NMR (500 MHz, DMSO-d6) δ 9.65 (s, 1H), 7.90 (d, J=8.2 Hz, 2H), 7.89-7.79 (m, 1H), 7.64 (q, J=4.4 Hz, 1H), 7.23 (d, J=8.5 Hz, 2H), 7.30 (t, J=73.5 Hz, 1H), 6.89 (dd, J=19.1, 11.7 Hz, 2H), 6.69 (d, J=8.9 Hz, 1H), 3.81 (s, 3H), 2.98 (s, 3H), 2.84 (d, J=4.9 Hz, 3H).

Example 228

$^{1}$H NMR (500 MHz, DMSO-d6) δ 9.73 (s, 1H), 9.34-9.19 (m, 1H), 8.07-7.86 (m, 4H), 7.23 (d, J=8.5 Hz, 2H), 7.31 (t, J=79.0 Hz, 1H), 7.00 (br d, J=11.6 Hz, 2H), 6.89 (d, J=11.3 Hz, 1H), 3.83 (s, 3H), 3.77 (s, 3H), 3.01 (s, 3H), 2.18 (br s, 3H).

Example 229

41 NMR (500 MHz, DMSO-d6) δ 9.63 (s, 1H), 8.12-8.02 (m, 1H), 7.94-7.85 (m, 3H), 7.82 (s, 1H), 7.22 (d, J=8.5 Hz, 2H), 7.29 (t, J=76.9 Hz, 1H), 6.94-6.75 (m, 3H), 3.81 (s, 3H), 3.60 (br d, J=7.3 Hz, 2H), 2.96 (s, 3H), 2.62 (td, J=7.2, 3.8 Hz, 1H), 0.68-0.52 (m, 2H), 0.48-0.32 (m, 2H).

Example 230

1H NMR (500 MHz, Acetonitrile-d3) δ 8.17 (br s, 1H), 7.92-7.79 (m, 3H), 7.20 (d, J=8.3 Hz, 2H), 6.88 (t, J=73.2 Hz, 1H), 6.73-6.69 (m, J=5.8, 3.3 Hz, 1H), 6.49-6.37 (m, 2H), 6.37-6.17 (m, 1H), 5.48 (s, 1H), 4.67-4.43 (m, 1H), 3.80 (s, 3H), 3.73-3.64 (m, 2H), 3.55-3.39 (m, 2H), 3.06 (s, 3H).

Example 231

$^{1}$H NMR (500 MHz, DMSO-d6, ws) δ 9.68 (s, 1H), 8.06 (s, 1H), 7.92 (d, J=7.9 Hz, 2H), 7.23 (d, J=8.5 Hz, 2H), 7.33 (t, J=73.9 Hz, 1H), 6.96-6.86 (m, 3H), 3.82 (s, 3H), 2.96 (br s, 3H), 1.92 (s, 1H), 0.91-0.79 (m, 2H), 0.74-0.66 (m, 2H).

Example 232

$^{1}$H NMR (500 MHz, DMSO-d6) δ 9.74-9.56 (m, 1H), 8.02-7.78 (m, 4H), 7.26-7.19 (m, 2H), 7.30 (t, J=74.2 Hz, 1H), 7.06-6.75 (m, 3H), 4.53-4.17 (m, 1H), 3.81 (s, 3H), 3.01-2.87 (m, 3H), 2.63-2.56 (m, 3H), 1.34 (br d, J=6.4 Hz, 3H).

Example 233

$^{1}$H NMR (500 MHz, Acetonitrile-d3) δ 8.19-8.01 (m, 1H), 7.91-7.78 (m, 3H), 7.21 (d, J=8.5 Hz, 2H), 6.87 (t, J=74.8 Hz, 1H), 6.67 (d, J=5.8 Hz, 1H), 6.49-6.38 (m, 2H), 6.01 (br s, 1H), 3.81 (s, 3H), 3.06 (s, 3H), 2.92 (d, J=4.7 Hz, 3H).

Example 234

$^{1}$H NMR (500 MHz, DMSO-d6) 9.84 (s, 1H), δ 8.59 (d, J=8.9 Hz, 1H), 8.00 (d, J=8.8 Hz, 1H), 7.92 (d, J=8.5 Hz, 2H), 7.76 (s, 1H), 7.69 (s, 2H), 7.25 (d, J=8.9 Hz, 2H), 7.32 (t, J=73.9 Hz, 1H), 6.92 (d, J=10.7 Hz, 2H), 3.84 (s, 3H), 3.03 (s, 3H).

Example 235

$^{1}$H NMR (500 MHz, DMSO-d6) δ 9.65 (s, 1H), 7.90 (d, J=8.4 Hz, 2H), 7.86-7.79 (m, 1H), 7.79-7.69 (m, 1H), 7.22 (d, J=8.4 Hz, 2H), 7.47-7.15 (m, 1H), 6.95-6.83 (m, 2H), 6.75 (d, J=8.6 Hz, 1H), 3.81 (s, 3H), 3.63-3.57 (m, 2H), 3.52-3.35 (m, 2H), 3.27 (s, 3H), 2.97 (s, 3H).

Example 236

$^{1}$H NMR (500 MHz, DMSO-d6) δ 9.68 (s, 1H), 7.91 (d, J=8.1 Hz, 2H), 7.86-7.78 (m, 1H), 7.76-7.63 (m, 1H), 7.23 (d, J=8.5 Hz, 2H), 7.32 (t, J=70.0 Hz, 1H), 6.99-6.84 (m, 2H), 6.78 (dd, J=8.2, 4.2 Hz, 1H), 4.87-4.76 (m, 1H), 3.88-3.76 (m, 4H), 3.51-3.50 (m, 2H), 2.96 (s, 3H), 1.10 (d, J=5.4 Hz, 3H).

Example 237

$^{1}$H NMR (500 MHz, DMSO-d6) δ 9.66 (d, J=4.9 Hz, 1H), 7.91 (d, J=8.5 Hz, 2H), 7.86-7.75 (m, 1H), 7.56 (m, 1H), 7.22 (d, J=8.5 Hz, 2H), 7.32 (t, J=73.2 Hz, 1H), 6.96-6.84 (m, 2H), 6.73 (dd, J=8.9, 4.3 Hz, 1H), 3.90 (s, 4H), 3.51-3.36 (m, 2H), 2.96 (s, 3H), 1.79 (s, 1H), 1.14 (t, J=7.2 Hz, 3H).

Example 238

$^{1}$H NMR (500 MHz, DMSO-d6) δ 9.66 (s, 1H), 8.04-7.78 (m, 5H), 7.23 (d, J=8.7 Hz, 2H), 7.34 (t, J=73.6 Hz, 1H), 7.01-6.73 (m, 3H), 4.03-3.82 (m, 2H), 3.81 (s, 3H), 2.95 (s, 3H), 2.60 (d, J=4.5 Hz, 3H).

Example 239

$^{1}$H NMR (500 MHz, DMSO-d6) δ 9.65 (s, 1H), 7.90 (d, J=8.2 Hz, 2H), 7.82 (d, J=8.9 Hz, 1H), 7.22 (d, J=8.2 Hz, 2H), 7.30 (t, J=73.2 Hz, 1H), 7.01 (d, J=9.2 Hz, 1H), 6.96-6.83 (m, 2H), 3.81 (s, 3H), 3.57-3.51 (m, 2H), 3.49-3.42 (m, 2H), 3.23 (q, J=9.9 Hz, 2H), 2.99 (s, 3H), 2.71 (s, 4H)

Example 240

$^{1}$H NMR (500 MHz, DMSO-d6) δ 9.67 (s, 1H), 7.91 (br d, J=8.9 Hz, 2H), 7.83 (d, J=8.9 Hz, 1H), 7.23 (br d, J=8.2 Hz, 2H), 7.32 (t, J=73.8 Hz, 1H), 7.02 (d, J=9.2 Hz, 1H), 6.91 (br t, J=12.1 Hz, 2H), 6.18 (tt, J=55.8, 4.3 Hz, 1H), 3.81 (s, 3H), 3.54 (br s, 4H), 2.99 (s, 3H), 2.79 (td, J=15.6, 4.1 Hz, 2H), 2.63 (br t, J=4.0 Hz, 4H).

Example 242

$^{1}$H NMR (500 MHz, DMSO-d6) δ 9.74 (s, 1H), 8.29 (d, J=8.4 Hz, 1H), 7.89 (br d, J=8.6 Hz, 2H), 7.74 (d, J=8.4 Hz, 1H), 7.23 (d, J=8.5 Hz, 2H), 7.30 (t, J=73.6 Hz, 1H), 6.91 (br s, 2H), 3.81 (s, 3H), 2.99 (s, 3H).

Example 243

$^{1}$H NMR (500 MHz, DMSO-d6) δ 9.66 (s, 1H), 7.90 (d, J=8.2 Hz, 2H), 7.79 (d, J=7.9 Hz, 1H), 7.74-7.62 (m, 1H), 7.22 (d, J=8.5 Hz, 2H), 7.31 (t, J=77.8 Hz, 1H), 6.93 (m, 1H), 6.86 (d, J=11.3 Hz, 1H), 6.68 (dd, J=17.4, 8.9 Hz, 1H), 3.80 (s, 3H), 2.94 (s, 3H), 1.37-1.24 (m, 1H), 1.21 (d, J=6.4 Hz, 3H), 1.03-0.82 (m, 1H), 0.52-0.30 (m, 3H), 0.26-0.07 (m, 1H).

Example 244

$^1$H NMR (500 MHz, DMSO-d6) δ 9.63 (s, 1H), 7.92 (d, J=8.6 Hz, 2H), 7.67 (d, J=8.7 Hz, 1H), 7.24 (d, J=8.4 Hz, 2H), 7.34 (t, J=72.5 Hz, 1H), 7.00-6.86 (m, 3H), 3.82 (s, 3H), 3.62-3.32 (m, 4H), 3.00 (s, 3H), 2.68-2.54 (m, 2H), 2.46-2.36 (m, 4H), 2.24 (s, 3H), 1.13 (t, J=7.4 Hz, 3H).

Example 245

$^1$H NMR (500 MHz, DMSO-d6) δ 9.63 (s, 1H), 8.68-8.62 (m, 1H), 8.25 (d, J=7.9 Hz, 1H), 7.98 (d, J=8.9 Hz, 2H), 7.62 (m, 1H), 7.55 (d, J=8.5 Hz, 2H), 7.29 (d, J=8.5 Hz, 2H), 7.36 (t, J=73.9 Hz, 1H), 7.11 (d, J=8.9 Hz, 2H), 3.81 (s, 3H), 2.99 (s, 3H).

Example 246

$^1$H NMR (500 MHz, DMSO-d6) δ 9.60 (s, 1H), 8.97 (d, J=3.7 Hz, 1H), 8.49 (d, J=8.2 Hz, 1H), 7.97 (d, J=8.5 Hz, 2H), 7.81 (t, J=6.1 Hz, 1H)), 7.45 (br d, J=8.2 Hz, 1H), 7.40 (s, 1H), 7.30-7.26 (d, J=8.9 Hz, 3H), 7.11 (d, J=8.5 Hz, 1H), 3.90 (s, 3H), 3.00 (s, 3H), 2.19 (s, 3H).

Example 247

$^1$H NMR (500 MHz, DMSO-d6) δ 9.66 (s, 1H), 7.90 (br d, J=8.5 Hz, 2H), 7.87 (d, J=8.9 Hz, 1H), 7.22 (d, J=8.5 Hz, 2H), 7.30 (t, J=72.9 Hz, 1H), 7.07 (d, J=9.2 Hz, 1H), 6.96-6.84 (m, 2H), 3.81 (s, 3H), 3.67 (br d, J=3.4 Hz, 4H), 3.25-3.19 (m, 4H), 3.00 (s, 3H), 2.89 (s, 3H).

Example 248

$^1$H NMR (500 MHz, DMSO-d6) δ 9.64 (s, 1H), 7.91 (d, J=8.5 Hz, 2H), 7.86 (d, J=8.9 Hz, 1H), 7.67 (d, J=8.9 Hz, 1H), 7.23 (d, J=8.5 Hz, 2H), 7.33 (t, J=73.6 Hz, 1H), 6.91 (d, J=10.7 Hz, 2H), 4.20 (q, J=6.8 Hz, 2H), 3.81 (s, 3H), 2.95 (s, 3H), 1.31 (t, J=7.0 Hz, 3H).

Example 249

$^1$H NMR (500 MHz, DMSO-d6) δ 9.64 (s, 1H), 8.97-8.83 (m, 1H), 8.44 (d, J=7.9 Hz, 1H), 7.89 (d, J=8.5 Hz, 1H), 7.78 (dd, J=8.1, 4.4 Hz, 1H), 7.69-7.53 (m, 5H), 7.22 (d, J=8.5 Hz, 1H), 7.29 (t, J=73.5 Hz, 1H), 2.98-2.88 (m, 3H), 2.64 (s, 3H)

Example 250

$^1$H NMR (500 MHz, DMSO-d6) δ 9.65 (s, 1H), 9.00 (d, J=3.7 Hz, 1H), 8.52 (d, J=7.3 Hz, 1H), 8.00 (d, J=8.9 Hz, 2H), 7.84 (m, 1H), 7.58 (d, J=8.5 Hz, 2H), 7.31 (d, J=8.9 Hz, 1H), 7.53 (t, J=73.5 Hz, 1H), 7.15 (d, J=8.9 Hz, 2H), 3.02 (s, 3H), 2.59 (m, 3H)

Example 251

$^1$H NMR (500 MHz, DMSO-d6) δ 9.70 (s, 1H), 8.12-7.94 (m, 2H), 7.91 (d, J=8.6 Hz, 2H), 7.23 (d, J=8.6 Hz, 2H), 7.33 (t, J=73.7 Hz, 1H), 7.00-6.81 (m, 3H), 3.81 (s, 3H), 3.00 (s, 3H), 2.99-2.94 (m, 1H), 0.78 (br d, J=5.9 Hz, 2H), 0.58-0.43 (m, 2H).

Example 252

$^1$H NMR (500 MHz, DMSO-d6) δ 9.67 (s, 1H), 7.98-7.80 (m, 4H), 7.23 (d, J=8.5 Hz, 2H), 7.32 (t, J=69.9 Hz, 1H), 6.95 (d, J=11.6 Hz, 1H), 6.88 (d, J=10.3 Hz, 2H), 4.33-4.21 (m, 1H), 4.11-3.97 (m, 1H), 3.82 (s, 3H), 3.04 (s, 3H), 2.95 (s, 3H), 2.85 (s, 3H).

Example 253

$^1$H NMR (500 MHz, DMSO-d6) δ 9.69 (s, 1H), 8.43 (d, J=3.7 Hz, 1H), 7.97-7.86 (m, 3H), 7.29-7.21 (m, 2H), 7.54-7.16 (m, 1H), 6.98 (d, J=10.4 Hz, 1H), 6.89 (d, J=10.4 Hz, 1H), 6.74 (d, J=8.2 Hz, 1H), 4.91-4.77 (m, 3H), 4.61-4.42 (m, 2H), 3.86-3.80 (m, 3H), 2.96 (s, 3H).

Example 254

$^1$H NMR (500 MHz, DMSO-d6) δ 9.71-9.66 (m, 1H), 8.02-7.82 (m, 4H), 7.23 (d, J=8.4 Hz, 2H), 7.32 (t, J=79.1 Hz, 1H), 7.00-6.83 (m, 2H), 6.74 (d, J=8.9 Hz, 1H), 4.39-4.27 (m, 1H), 3.97-3.84 (m, 2H), 3.82 (s, 3H), 3.78-3.70 (m, 1H), 3.62-3.53 (m, 1H), 3.02-2.95 (m, 3H), 2.26-2.17 (m, 1H), 1.93-1.78 (m, 1H).

Example 255

$^1$H NMR (500 MHz, DMSO-d6) δ 9.66 (br s, 1H), 7.99-7.80 (m, 4H), 7.22 (d, J=8.5 Hz, 2H), 7.28 (t, J=73.5 Hz, 1H), 6.99-6.82 (m, 2H), 6.73 (d, J=8.8 Hz, 1H), 4.36-4.21 (m, 1H), 3.95-3.82 (m, 2H), 3.82-3.78 (m, 3H), 3.69-3.65 (m, 2H), 2.97 (s, 3H), 2.30-2.15 (m, 1H), 1.92-1.77 (m, 1H).

Example 256

$^1$H NMR (500 MHz, DMSO-d6) δ 9.67 (s, 1H), 7.91 (d, J=8.6 Hz, 2H), 7.75 (d, J=8.9 Hz, 1H), 7.50-7.04 (m, 5H), 6.99-6.91 (m, 1H), 6.90-6.83 (m, 1H), 6.75 (br d, J=8.9 Hz, 1H), 3.81 (s, 3H), 3.00 (s, 3H), 2.96 (s, 2H), 1.31 (s, 6H).

Example 257

$^1$H NMR (500 MHz, DMSO-d6) δ 9.69 (s, 1H), 8.28 (d, J=8.8 Hz, 1H), 7.89 (d, J=7.9 Hz, 2H), 7.23 (d, J=8.4 Hz, 2H), 7.18 (d, J=8.8 Hz, 1H), 7.26 (t, J=76.3 Hz, 1H), 6.97-6.82 (m, 2H), 3.95 (s, 3H), 3.81 (s, 3H), 3.01 (s, 3H).

Example 260

$^1$H NMR (500 MHz, DMSO-d6) δ 9.62 (s, 1H), 7.97 (d, J=9.2 Hz, 1H), 7.87 (d, J=8.2 Hz, 3H), 7.21 (d, J=8.5 Hz, 2H), 7.26 (t, J=174.0 Hz, 1H), 6.93-6.81 (m, 3H), 4.40-4.26 (m, 1H), 4.04 (d, J=17.4 Hz, 1H), 3.79 (s, 3H), 3.11 (s, 3H), 2.93 (s, 3H), 2.58 (d, J=4.3 Hz, 3H).

Example 261

$^1$H NMR (500 MHz, DMSO-d6, ws) δ 9.64 (s, 1H), 7.89 (d, J=8.5 Hz, 2H), 7.21 (d, J=8.5 Hz, 2H), 7.27 (m, 2H), 6.96-6.81 (m, 3H), 3.80 (s, 3H), 3.16 (s, 3H), 2.92 (s, 2H), 1.12 (s, 3H), 1.08 (br s, 3H).

Example 262

$^1$H NMR (500 MHz, DMSO-d6) δ 9.60 (s, 1H), 8.62 (m, 1H), 8.21 (dd, J=8.1, 1.4 Hz, 1H), 7.91 (d, J=8.9 Hz, 2H), 7.59 (dd, J=7.9, 4.6 Hz, 1H), 7.50-7.41 (m, 1H), 7.30-7.04 (m, 4H), 7.00 (m, 1H), 6.92 (m, 1H), 3.79 (s, 3H), 2.95 (s, 3H).

Example 263

$^1$H NMR (500 MHz, DMSO-d6) δ 9.61 (s, 1H), 8.94 (d, J=3.6 Hz, 1H), 8.46 (d, J=7.3 Hz, 1H), 7.90 (d, J=8.7 Hz, 2H), 7.79 (m, 1H), 7.45 (m, 1H), 7.23 (d, J=8.5 Hz, 2H), 7.28 (m, 1H), 7.00 (m, 1H), 6.92 (m, 1H), 3.79 (s, 3H), 2.94 (s, 3H).

Example 264

$^1$H NMR (500 MHz, DMSO-d6) δ 9.65 (s, 1H), 7.90 (d, J=8.5 Hz, 2H), 7.81 (m, 2H), 7.22 (d, J=8.5 Hz, 2H), 7.31 (t, J=78.7 Hz, 1H), 6.97-6.81 (m, 2H), 6.72 (d, J=8.9 Hz, 1H), 3.81 (s, 3H), 3.51-3.02 (m, 2H), 2.95 (s, 3H), 1.14-0.94 (m, 1H), 0.45 (br d, J=7.9 Hz, 2H), 0.32-0.11 (m, 2H).

Example 265

$^1$H NMR (500 MHz, DMSO-d6) δ 9.66 (s, 1H), 7.92 (d, J=8.2 Hz, 2H), 7.76 (d, J=8.5 Hz, 1H), 7.37 (s, 1H), 7.23 (d, J=8.2 Hz, 2H), 7.32 (t, J=73.9 Hz, 1H), 6.98-6.83 (m, 2H), 6.70 (d, J=8.9 Hz, 1H), 3.82 (s, 3H), 2.96 (s, 3H), 1.40 (s, 9H).

Example 266

$^1$H NMR (500 MHz, DMSO-d6) δ 9.70 (s, 1H), 8.22-8.06 (m, 1H), 8.04-7.95 (m, 1H), 7.93 (d, J=8.5 Hz, 2H), 7.24 (d, J=8.5 Hz, 2H), 7.34 (t, J=74.2 Hz, 1H), 6.98-6.76 (m, 3H), 3.83 (s, 3H), 3.06-2.90 (m, 3H), 1.37 (s, 3H), 0.73 (d, J=8.9 Hz, 4H).

Example 267

$^1$H NMR (500 MHz, DMSO-d6) δ 9.66 (s, 1H), 8.02 (d, J=8.8 Hz, 1H), 7.91 (d, J=8.2 Hz, 2H), 7.24 (d, J=8.5 Hz, 2H), 7.32 (t, J=81.8 Hz, 1H), 7.13 (d, J=8.9 Hz, 1H), 7.01-6.80 (m, 2H), 3.82 (s, 3H), 3.03 (s, 3H), 2.76-2.66 (m, 2H), 1.05-0.76 (m, 6H), 0.66-0.48 (m, 2H).

Example 268

$^1$H NMR (500 MHz, DMSO-d6) δ 9.66 (s, 1H), 8.04 (d, J=9.2 Hz, 1H), 7.90 (d, J=8.5 Hz, 2H), 7.23 (d, J=8.2 Hz, 2H), 7.47-7.08 (m, 2H), 6.97-6.81 (m, 2H), 3.81 (s, 3H), 3.72-3.55 (m, 4H), 3.24 (br t, J=4.7 Hz, 4H), 2.99 (s, 3H), 2.90 (s, 3H).

Example 269

$^1$H NMR (500 MHz, DMSO-d6) δ 9.66 (s, 1H), 8.00 (d, J=9.2 Hz, 1H), 7.91 (d, J=8.5 Hz, 2H), 7.24 (d, J=8.5 Hz, 2H), 7.31 (t, J=73.5 Hz, 1H), 7.09 (d, J=9.2 Hz, 1H), 6.98-6.82 (m, 2H), 3.82 (s, 3H), 3.73-3.40 (m, 4H), 3.26 (q, J=10.1 Hz, 2H), 2.98 (s, 3H), 2.74 (br t, J=4.4 Hz, 4H).

Example 270

$^1$H NMR (500 MHz, DMSO-d6) δ 9.64 (s, 1H), 7.99 (d, J=8.9 Hz, 1H), 7.89 (d, J=8.5 Hz, 2H), 7.23 (d, J=8.5 Hz, 2H), 7.27 (t, J=71.7 Hz, 1H), 7.07 (d, J=9.2 Hz, 1H), 6.89 (dd, J=19.7, 11.7 Hz, 2H), 6.16 (t, J=56.5 Hz, 1H), 3.81 (s, 3H), 3.76-3.62 (m, 4H), 2.99 (s, 3H), 2.81 (td, J=15.7, 4.3 Hz, 2H), 2.68-2.60 (m, 4H).

Example 271

$^1$H NMR (500 MHz, DMSO-d6) δ 9.66 (s, 1H), 7.91 (d, J=8.5 Hz, 2H), 7.82 (d, J=7.6 Hz, 1H), 7.61-7.52 (m, 1H), 7.23 (d, J=8.2 Hz, 2H), 7.30 (t, J=73.9 Hz, 1H), 6.99-6.77 (m, 3H), 3.82 (s, 3H), 3.64-3.44 (m, 2H), 3.22-3.10 (m, 1H), 2.95 (s, 3H), 1.14 (d, J=8.9 Hz, 6H).

Example 272

$^1$H NMR (500 MHz, DMSO-d6) δ 9.67 (s, 1H), 7.92 (d, J=8.5 Hz, 2H), 7.83 (d, J=2.7 Hz, 1H), 7.75-7.62 (m, 1H), 7.24 (d, J=8.9 Hz, 2H), 7.32 (t, J=73.2 Hz, 1H), 6.98-6.83 (m, 2H), 6.78 (dd, J=8.7, 3.8 Hz, 1H), 4.81 (br d, J=4.3 Hz, 1H), 3.82 (s, 3H), 3.53-3.38 (m, 1H), 3.18 (d, J=5.2 Hz, 2H), 2.97 (s, 3H), 1.14-1.06 (m, 3H).

Example 273

$^1$H NMR (500 MHz, DMSO-d6) δ 9.65 (s, 1H), 7.90 (d, J=8.5 Hz, 2H), 7.86-7.77 (m, 1H), 7.73-7.59 (m, 1H), 7.23 (d, J=8.5 Hz, 2H), 7.29 (t, J=73.5 Hz, 1H), 6.98-6.81 (m, 2H), 6.78 (dd, J=8.9, 3.4 Hz, 1H), 3.81 (s, 3H), 3.65-3.49 (m, 1H), 3.32-3.15 (m, 1H), 3.15-3.05 (m, 1H), 2.97 (s, 3H), 1.92 (s, 1H), 1.10 (t, J=5.0 Hz, 3H).

Example 274

$^1$H NMR (500 MHz, DMSO-d6) δ 9.63 (s, 1H), 7.94-7.78 (m, 4H), 7.22 (d, J=8.2 Hz, 2H), 7.27 (t, J=69.6 Hz, 1H), 6.93-6.76 (m, 3H), 4.21 (br d, J=2.4 Hz, 1H), 3.81 (s, 3H), 3.74-3.58 (m, 1H), 3.54-3.14 (m, 1H), 2.98 (br d, J=7.6 Hz, 3H), 1.92 (s, 1H).

Example 275

$^1$H NMR (500 MHz, DMSO-d6) δ 9.66 (br s, 1H), 8.42 (d, J=8.3 Hz, 1H), 7.98 (d, J=8.2 Hz, 1H), 7.88 (d, J=8.0 Hz, 2H), 7.21 (br d, J=8.4 Hz, 2H), 7.26 (t, J=73.3 Hz, 1H), 6.96-6.80 (m, 2H), 5.79-5.68 (m, 1H), 3.80 (s, 3H), 2.96 (s, 3H), 1.47 (s, 6H).

Example 276

$^1$H NMR (500 MHz, DMSO-d6) δ 9.66 (s, 1H), 8.15 (d, J=8.5 Hz, 1H), 7.88 (d, J=8.2 Hz, 2H), 7.79 (d, J=8.5 Hz, 1H), 7.22 (d, J=8.5 Hz, 2H), 7.26 (t, J=73.6 Hz, 1H), 6.94-6.83 (m, 2H), 5.62 (s, 1H), 3.80 (s, 3H), 2.98 (s, 3H), 1.45 (s, 6H).

Example 277

$^1$H NMR (500 MHz, DMSO-d6) δ 9.61 (s, 1H), 8.95 (d, J=4.6 Hz, 1H), 8.47 (d, J=8.0 Hz, 1H), 7.94 (br d, J=8.5 Hz, 2H), 7.79 (dd, J=7.6, 5.1 Hz, 1H), 7.45 (br d, J=8.2 Hz, 2H), 7.24 (br dd, J=14.1, 8.4 Hz, 5H), 2.96 (s, 3H), 2.54 (s, 3H), 2.02-1.89 (m, 1H), 0.99 (br dd, J=8.3, 2.0 Hz, 2H), 0.78-0.66 (m, 2H)

Example 278

$^1$H NMR (500 MHz, $CD_3OD$) δ 7.95-7.84 (m, 3H), 7.21 (d, J=8.5 Hz, 2H), 6.89 (d, J=9.9 Hz, 2H), 6.97 (t, J=74.0 Hz,

1H), 6.85-6.79 (m, 1H), 4.37-4.19 (m, 2H), 3.89 (s, 3H), 3.84-3.72 (m, 1H), 3.67-3.60 (m, 1H), 3.37 (s, 3H), 3.27 (s, 3H).

Example 279

$^1$H NMR (500 MHz, DMSO-d6) δ 9.66 (s, 1H), 7.91 (d, J=8.2 Hz, 2H), 7.81 (d, J=0.9 Hz, 1H), 7.46 (s, 1H), 7.34-7.12 (m, 4H), 7.07-6.78 (m, 4H), 3.82 (s, 3H), 3.60-3.41 (m, 2H), 2.95 (s, 3H), 1.13 (s, 6H).

Example 280

$^1$H NMR (500 MHz, DMSO-d6) δ 9.66 (br s, 1H), 7.99-7.84 (m, 3H), 7.24 (d, J=8.2 Hz, 2H), 7.31 (t, J=74.2 Hz, 1H), 6.97-6.83 (m, 2H), 6.72 (d, J=8.2 Hz, 1H), 5.32-5.02 (m, 1H), 4.52-4.32 (m, 1H), 3.82 (s, 3H), 3.59-3.41 (m, 4H), 2.99 (s, 3H), 2.19-1.84 (m, 2H).

Example 281

$^1$H NMR (500 MHz, DMSO-d6) δ 9.68 (s, 1H), 8.98 (d, J=4.3 Hz, 1H), 8.50 (d, J=8.2 Hz, 1H), 7.96 (d, J=8.5 Hz, 2H), 7.83 (m, 1H), 7.67 (d, J=8.5 Hz, 2H), 7.53-7.14 (m, 6H), 3.00 (s, 3H)

Example 282

$^1$H NMR (500 MHz, DMSO-d6) δ 9.66 (br s, 1H), 8.00-7.85 (m, 3H), 7.23 (d, J=8.5 Hz, 2H), 7.32 (t, J=74.1 Hz, 1H), 6.98-6.84 (m, 2H), 6.74-6.59 (m, 1H), 5.07-4.82 (m, 1H), 3.82 (s, 3H), 3.62-3.38 (m, 4H), 2.98 (s, 3H), 2.03-1.85 (m, 2H), 1.37 (s, 3H).

Example 283

$^1$H NMR (500 MHz, DMSO-d6) δ 9.69 (s, 1H), 8.00-7.75 (m, 3H), 7.24 (d, J=5.8 Hz, 2H), 7.34 (t, J=71.1 Hz, 1H), 7.09 (d, J=38.1 Hz, 1H), 6.95 (d, J=11.6 Hz, 1H), 6.89 (d, J=11.6 Hz, 1H), 6.83 (d, J=9.2 Hz, 1H), 4.34-4.04 (m, 2H), 3.83 (s, 3H), 2.99-2.86 (m, 3H), 0.98 (t, J=7.2 Hz, 1H), 0.68-0.51 (m, 4H).

Example 284

$^1$H NMR (500 MHz, DMSO-d6) δ 9.66 (br s, 1H), 8.00-7.85 (m, 3H), 7.23 (d, J=8.5 Hz, 2H), 7.32 (t, J=74.1 Hz, 1H), 6.98-6.84 (m, 2H), 6.74-6.59 (m, 1H), 5.07-4.82 (m, 1H), 3.82 (s, 3H), 3.62-3.38 (m, 4H), 2.98 (s, 3H), 2.03-1.85 (m, 2H), 1.37 (s, 3H).

Example 285

$^1$H NMR (500 MHz, DMSO-d6) δ 9.73 (s, 1H), 8.30 (d, J=8.9 Hz, 1H), 7.93 (d, J=8.5 Hz, 2H), 7.25 (d, J=8.5 Hz, 2H), 7.34 (t, J=73.9 Hz, 1H), 7.19 (d, J=7.6 Hz, 1H), 7.03-6.82 (m, 2H), 4.46-4.31 (m, 2H), 3.84 (s, 3H), 3.78 (q, J=4.9 Hz, 2H), 3.49-3.39 (m, 1H), 3.01 (s, 3H).

Example 286

$^1$H NMR (500 MHz, DMSO-d6) δ 9.89-9.76 (m, 1H), 7.92 (d, J=8.5 Hz, 2H), 7.87 (d, J=9.8 Hz, 1H), 7.24 (d, J=8.6 Hz, 2H), 7.33 (t, J=75.2 Hz, 1H), 6.97-6.90 (m, 2H), 6.82 (d, J=9.8 Hz, 1H), 3.82 (s, 3H), 3.81-3.62 (m, 2H), 3.05 (s, 3H), 1.23 (br t, J=6.9 Hz, 3H).

Example 287

$^1$H NMR (500 MHz, DMSO-d6) δ 9.82 (s, 1H), 7.94 (d, J=8.9 Hz, 2H), 7.89 (d, J=10.1 Hz, 1H), 7.26 (d, J=7.9 Hz, 2H), 7.35 (t, J=80.0 Hz, 1H), 6.95 (d, J=10.7 Hz, 2H), 6.85 (d, J=9.5 Hz, 1H), 3.84 (s, 3H), 4.04-3.69 (m, 2H), 3.08 (s, 3H), 1.33-1.14 (m, 1H), 0.56-0.28 (m, 4H).

Example 288

$^1$H NMR (500 MHz, DMSO-d6) δ 9.72 (s, 1H), 8.30 (d, J=8.9 Hz, 1H), 7.92 (d, J=8.2 Hz, 2H), 7.25 (d, J=8.2 Hz, 2H), 7.20 (d, J=8.5 Hz, 1H), 7.31 (t, J=73.9 Hz, 1H), 7.04-6.78 (m, 2H), 4.28-4.02 (m, 2H), 3.83 (s, 3H), 3.53 (br s, 1H), 3.00 (s, 3H), 1.22 (s, 6H).

Example 289

$^1$H NMR (500 MHz, $CD_3OD$) δ 8.31 (d, J=8.8 Hz, 1H), 7.89 (d, J=8.8 Hz, 2H), 7.28 (d, J=8.8 Hz, 1H), 7.21 (d, J=8.5 Hz, 2H), 7.00 (t, J=74.8 Hz, 1H), 6.86-6.76 (m, 2H), 5.17 (d, J=16.0 Hz, 2H), 3.88 (s, 3H), 3.79 (s, 3H), 3.13 (s, 3H

Example 290

$^1$H NMR (500 MHz, DMSO-d6) δ 9.65 (s, 1H), 7.90 (d, J=8.4 Hz, 2H), 7.84-7.73 (m, 1H), 7.63-7.55 (m, 1H), 7.22 (d, J=8.5 Hz, 2H), 7.31 (t, J=50.8 Hz, 1H), 6.96-6.80 (m, 2H), 6.77 (d, J=8.8 Hz, 1H), 4.80-4.53 (m, 1H), 3.80 (s, 3H), 3.39 (d, J=4.0 Hz, 2H), 3.30-3.12 (m, 2H), 2.94 (s, 3H), 1.88-1.67 (m, 6H).

Example 291

$^1$H NMR (500 MHz, DMSO-d6) δ 9.77 (s, 1H), 8.47 (d, J=8.2 Hz, 1H), 7.88 (d, J=7.9 Hz, 2H), 7.84 (d, J=7.9 Hz, 1H), 7.22 (d, J=8.2 Hz, 2H), 7.27 (t, J=73.2 Hz, 1H), 6.92 (d, J=10.7 Hz, 2H), 3.81 (s, 3H), 3.14 (s, 3H), 2.97 (s, 1H), 1.47 (br s, 6H).

Example 292

$^1$H NMR (500 MHz, DMSO-d6) δ 9.65 (s, 1H), 7.96-7.87 (m, 3H), 7.24 (d, J=8.5 Hz, 2H), 7.31 (t, J=73.5 Hz, 1H), 6.90 (m, 2H), 6.71 (d, J=8.9 Hz, 1H), 4.91-4.83 (m, 1H), 3.82 (s, 3H), 3.61-3.49 (m, 2H), 3.48-3.39 (m, 2H), 3.29-3.15 (m, 2H), 2.99 (s, 3H), 2.50-2.38 (m, 1H), 2.14-2.00 (m, 1H), 1.87-1.72 (m, 1H).

Example 293

$^1$H NMR (500 MHz, DMSO-d6) δ 9.67 (s, 1H), 8.97 (d, J=4.0 Hz, 1H), 8.50 (d, J=7.6 Hz, 1H), 7.96 (d, J=8.5 Hz, 2H), 7.83 (m, 1H), 7.50-7.40 (m, 2H), 7.39-7.34 (m, 1H), 7.32-7.14 (m, 3H), 3.90 (s, 3H), 3.02 (s, 3H).

Example 294

$^1$H NMR (500 MHz, DMSO-d6) δ 9.66 (s, 1H), 8.65 (d, J=4.0 Hz, 1H), 8.24 (d, J=7.3 Hz, 1H), 7.97 (d, J=8.9 Hz, 2H), 7.62 (m, 1H), 7.50-7.04 (m, 6H), 3.89 (s, 3H), 3.01 (s, 3H).

Example 295

$^1$H NMR (500 MHz, DMSO-d6) δ 9.64 (s, 1H), 8.51 (d, J=8.4 Hz, 1H), 7.96-7.87 (m, 3H), 7.46 (m, 1H), 7.24 (d,

J=8.4 Hz, 2H), 7.30 (t, J=73.8 Hz, 1H), 7.02 (br d, J=12.5 Hz, 1H), 6.93 (br d, J=8.5 Hz, 1H), 3.80 (s, 3H), 2.98 (s, 3H).

Example 296

$^1$H NMR (500 MHz, DMSO-d6) Shift 8.26 (d, J=8.5 Hz, 1H), 8.07 (d, J=8.5 Hz, 1H), 7.90 (d, J=8.2 Hz, 2H), 7.70 (d, J=8.2 Hz, 1H), 7.22 (d, J=8.2 Hz, 2H), 7.30 (t, J=73.7 Hz, 1H), 6.40-6.14 (m, 2H), 3.70 (s, 3H), 2.95 (s, 3H)

Example 297

$^1$H NMR (500 MHz, DMSO-d6) δ 9.72 (s, 1H), 8.58 (d, J=8.5 Hz, 1H), 8.43 (d, J=8.9 Hz, 1H), 7.92 (d, J=7.3 Hz, 2H), 7.25 (d, J=8.5 Hz, 2H), 7.34 (t, J=72.6 Hz, 1H), 7.01-6.86 (m, 2H), 4.10-3.93 (m, 2H), 3.84 (s, 3H), 3.03 (s, 3H), 2.76-2.60 (m, 2H), 2.17-2.01 (m, 2H).

Example 298

$^1$H NMR (500 MHz, DMSO-d6) δ 9.70 (s, 1H), 8.43 (s, 1H), 8.06 (d, J=8.8 Hz, 1H), 7.91 (d, J=7.9 Hz, 2H), 7.23 (d, J=8.2 Hz, 1H), 7.32 (t, J=73.8 Hz, 1H), 7.06 (d, J=8.5 Hz, 1H), 6.99-6.83 (m, 2H), 4.13-3.98 (m, 2H), 3.81 (s, 3H), 3.00 (s, 3H), 1.20 (s, 6H).

Example 299

$^1$H NMR (500 MHz, DMSO-d6) δ 9.66 (s, 1H), 7.90 (d, J=8.2 Hz, 2H), 7.77 (m, 1H), 7.28-7.25 (m, 1H), 7.22 (d, J=8.5 Hz, 2H), 7.31 (t, J=73.8 Hz, 1H), 7.18-7.14 (m, 1H), 7.05 (s, 1H), 6.95-6.82 (m, 2H), 6.51 (d, J=8.8 Hz, 1H), 4.00 (t, J=7.1 Hz, 1H), 3.97 (s, 1H), 3.92 (s, 1H), 3.81 (s, 3H), 2.97 (s, 3H), 2.49-2.43 (m, 2H), 2.02 (m, 2H).

Example 300

$^1$H NMR (500 MHz, DMSO-d6) δ 9.64 (s, 1H), 8.44-8.19 (m, 1H), 7.89 (d, J=8.5 Hz, 2H), 7.78 (d, J=8.5 Hz, 1H), 7.22 (d, J=8.2 Hz, 2H), 7.28 (t, J=73.6 Hz, 1H), 6.88 (s, 2H), 6.56 (d, J=8.9 Hz, 1H), 4.59 (m, 1H), 4.20 (m, 2H), 3.80 (s, 3H), 3.76-3.68 (m, 2H), 2.98 (s, 3H), 2.91 (d, J=4.9 Hz, 1H).

Example 301

$^1$H NMR (500 MHz, DMSO-d6) δ 9.75 (s, 1H), 9.02-8.92 (m, 1H), 8.50 (d, J=7.3 Hz, 1H), 8.08-7.77 (m, 7H), 7.26 (br d, J=8.5 Hz, 2H), 7.29 (t, J=73.2 Hz, 1H), 3.00 (br s, 3H)

Example 302

$^1$H NMR (500 MHz, DMSO-d6) δ 9.70 (br s, 1H), 8.17-8.07 (m, 1H), 7.92 (d, J=8.5 Hz, 2H), 7.25 (d, J=8.5 Hz, 2H), 7.32 (t, J=61.3 Hz, 1H), 7.05-6.84 (m, 3H), 5.13-4.96 (m, 1H), 3.83 (s, 3H), 3.77-3.65 (m, 1H), 3.53-3.36 (m, 1H), 3.03-2.94 (m, 3H), 2.29-2.04 (m, 4H).

Example 303

$^1$H NMR (500 MHz, DMSO-d6) δ 9.67 (s, 1H), 7.96 (d, J=9.2 Hz, 1H), 7.93 (d, J=8.5 Hz, 2H), 7.57 (s, 1H), 7.24 (d, J=8.2 Hz, 2H), 7.33 (t, J=73.5 Hz, 1H), 7.01 (s, 1H), 6.98-6.84 (m, 2H), 6.73 (d, J=8.5 Hz, 1H), 3.91 (s, 1H), 3.83 (s, 3H), 3.57-3.38 (m, 2H), 3.19 (d, J=4.6 Hz, 1H), 3.14-3.05 (m, 1H), 3.00 (s, 3H), 2.28-2.04 (m, 2H).

Example 304

$^1$H NMR (500 MHz, DMSO-d6) δ 9.71 (s, 1H), 8.98 (d, J=4.0 Hz, 1H), 8.50 (d, J=7.6 Hz, 1H), 7.95 (d, J=8.5 Hz, 2H), 7.83 (m, 1H), 7.74 (br d, J=8.9 Hz, 2H), 7.57 (d, J=8.2 Hz, 2H), 7.27 (br d, J=8.2 Hz, 2H), 7.32 (t, J=73.2 Hz, 1H), 3.00 (s, 3H)

Example 305

$^1$H NMR (500 MHz, DMSO-d6) δ 9.67 (s, 1H), 7.96 (d, J=9.2 Hz, 1H), 7.93 (d, J=8.5 Hz, 2H), 7.57 (s, 1H), 7.24 (d, J=8.2 Hz, 2H), 7.33 (t, J=73.5 Hz, 1H), 7.01 (s, 1H), 6.98-6.84 (m, 2H), 6.73 (d, J=8.5 Hz, 1H), 3.91 (s, 1H), 3.83 (s, 3H), 3.57-3.38 (m, 2H), 3.19 (d, J=4.6 Hz, 1H), 3.14-3.05 (m, 1H), 3.00 (s, 3H), 2.28-2.04 (m, 2H).

Example 306

$^1$H NMR (500 MHz, DMSO-d6) δ 9.65 (s, 1H), 7.97 (d, J=9.0 Hz, 1H), 7.90 (d, J=8.2 Hz, 2H), 7.22 (d, J=8.5 Hz, 2H), 7.29 (t, J=77.0 Hz, 1H), 7.09 (d, J=9.0 Hz, 1H), 6.99-6.81 (m, 2H), 4.56-4.45 (m, 1H), 4.40-4.23 (m, 1H), 3.81 (s, 3H), 3.12-2.99 (m, 2H), 2.97 (s, 3H), 2.78-2.60 (m, 1H), 2.21-2.06 (m, 2H), 2.03-1.94 (m, 1H), 1.89-1.80 (m, 1H), 1.80-1.62 (m, 2H), 1.46-1.33 (m, 1H)

Example 307

$^1$H NMR (500 MHz, DMSO-d6) δ 9.65 (s, 1H), 7.90 (d, J=8.2 Hz, 2H), 7.79 (d, J=8.9 Hz, 1H), 7.22 (d, J=8.2 Hz, 2H), 7.30 (t, J=73.5 Hz, 1H), 6.96-6.83 (m, 2H), 6.57 (d, J=8.9 Hz, 1H), 5.72 (br s, 1H), 3.91-3.81 (m, 4H), 3.80 (s, 3H), 2.98 (s, 3H), 1.44 (s, 3H).

Example 308

$^1$H NMR (500 MHz, DMSO-d6) δ 9.66 (s, 1H), 7.94 (d, J=8.9 Hz, 1H), 7.91 (d, J=8.2 Hz, 2H), 7.23 (d, J=8.5 Hz, 2H), 7.27 (t, J=73.5 Hz, 1H), 6.96-6.82 (m, 2H), 6.57 (d, J=8.9 Hz, 1H), 4.09-3.99 (m, 4H), 3.82 (s, 3H), 3.32 (br t, J=6.9 Hz, 1H), 2.96 (s, 3H), 2.05 (br dd, J=11.4, 7.8 Hz, 4H).

Example 309

$^1$H NMR (500 MHz, DMSO-d6) δ 9.66 (s, 1H), 7.93 (d, J=7.9 Hz, 2H), 7.86 (d, J=8.5 Hz, 1H), 7.25 (d, J=8.5 Hz, 2H), 7.33 (t, J=77.5 Hz, 1H), 7.01-6.85 (m, 3H), 4.13-3.94 (m, 2H), 3.83 (s, 3H), 3.53-3.30 (m, 1H), 3.01 (s, 3H), 2.73-2.56 (m, 2H), 1.21 (s, 6H), 1.17 (br t, J=7.5 Hz, 3H).

Example 310

$^1$H NMR (500 MHz, DMSO-d6) δ 9.61 (s, 1H), 7.92 (d, J=8.0 Hz, 2H), 7.64 (d, J=8.5 Hz, 1H), 7.23 (d, J=8.4 Hz, 2H), 7.33 (t, J=73.2 Hz, 1H), 7.03-6.83 (m, 2H), 6.54 (d, J=8.5 Hz, 1H), 5.71-5.51 (m, 1H), 4.02-3.69 (m, 7H), 3.45-3.42 (m, 2H), 2.99 (s, 3H), 1.45 (s, 3H), 1.11 (br t, J=7.3 Hz, 3H).

Example 311

$^1$H NMR (500 MHz, DMSO-d6) δ 9.63 (s, 1H), 7.88 (d, J=8.2 Hz, 2H), 7.67 (m, 1H), 7.23 (d, J=8.5 Hz, 2H), 7.29 (t, J=73.4 Hz, 1H), 7.07 (d, J=7.3 Hz, 1H), 6.90 (d, J=10.4 Hz, 2H), 6.33 (d, J=8.2 Hz, 1H), 3.89-3.81 (m, 4H), 3.81 (s, 3H), 3.20 (s, 3H), 1.44 (s, 3H).

Example 312

$^1$H NMR (500 MHz, DMSO-d6) δ 9.63 (s, 1H), 7.88 (d, J=8.2 Hz, 2H), 7.67 (m, 1H), 7.23 (d, J=8.5 Hz, 2H), 7.29

(t, J=73.4 Hz, 1H), 7.07 (d, J=7.3 Hz, 1H), 6.90 (d, J=10.4 Hz, 2H), 6.33 (d, J=8.2 Hz, 1H), 3.89-3.81 (m, 4H), 3.81 (s, 3H), 3.20 (s, 3H), 1.44 (s, 3H)

Example 313

$^1$H NMR (500 MHz, DMSO-d6, ws) δ 9.56 (s, 1H), 7.95-7.89 (m, 3H), 7.43 (m, 1H), 7.24 (d, J=8.2 Hz, 2H), 7.33 (t, J=73.8 Hz, 1H), 7.08-6.99 (m, 2H), 6.93 (m, 1H), 4.05-3.94 (m, 1H), 3.80 (s, 3H), 2.97 (s, 3H), 1.59-1.43 (m, 4H), 1.16 (s, 3H).

Example 314

$^1$H NMR (500 MHz, DMSO-d6) δ 9.64 (s, 1H), 7.96-7.85 (m, 3H), 7.22 (d, J=8.7 Hz, 2H), 7.30 (t, J=73.6 Hz, 1H), 7.05 (d, J=9.0 Hz, 1H), 6.92 (d, J=10.2 Hz, 1H), 6.87 (d, J=11.7 Hz, 1H), 4.03-3.93 (m, 1H), 3.80 (s, 3H), 3.16 (d, J=5.1 Hz, 4H), 2.96 (s, 3H), 1.59-1.43 (m, 4H), 1.15 (s, 3H).

Example 315

$^1$H NMR (500 MHz, DMSO-d6) δ 9.70 (s, 1H), 7.98 (d, J=8.5 Hz, 2H), 7.91 (m, 1H), 7.72 (br d, J=8.5 Hz, 2H), 7.55 (d, J=7.6 Hz, 1H), 7.30 (d, J=8.5 Hz, 2H), 7.52-7.19 (m, 4H), 6.78 (d, J=7.9 Hz, 1H), 3.99 (s, 3H), 3.26 (s, 3H)

Example 316

$^1$H NMR (500 MHz, DMSO-d6) δ 9.69 (s, 1H), 8.15 (d, J=8.2 Hz, 1H), 7.90 (d, J=8.2 Hz, 2H), 7.54 (d, J=8.2 Hz, 1H), 7.23 (d, J=8.5 Hz, 2H), 7.31 (t, J=73.5 Hz, 1H), 6.99-6.84 (m, 2H), 3.81 (s, 3H), 3.67 (d, J=12.2 Hz, 2H), 2.99 (s, 3H), 2.89 (s, 3H), 2.99-2.81 (m, 3H), 2.02 (d, J=12.2 Hz, 2H), 1.83-1.68 (m, 2H)

Example 317

$^1$H NMR (500 MHz, DMSO-d6) δ 8.04 (s, 1H), 8.00 (d, J=8.9 Hz, 2H), 7.74 (d, J=8.2 Hz, 1H), 7.63 (d, J=8.9 Hz, 2H), 7.31 (d, J=8.2 Hz, 2H), 7.35 (d, J=8.2 Hz, 2H), 7.40 (t, J=73.5 Hz, 1H), 7.30 (t, J=73.6 Hz, 1H), 6.72 (d, J=7.9 Hz, 1H), 3.79 (s, 3H).

Example 320

$^1$H NMR (400 MHz, DMSO-d6) δ=9.68 (br s, 1H), 7.91 (d, J=8.8 Hz, 2H), 7.34 (t, J=76.0 Hz, 1H), 7.26-7.23 (m, 3H), 6.93 (d, J=10.3 Hz, 2H), 6.85 (d, J=1.8 Hz, 1H), 5.26-5.05 (m, 1H), 3.97-3.89 (m, 1H), 3.89-3.82 (m, 5H), 3.82-3.73 (m, 1H), 3.21 (s, 3H), 2.48 (s, 3H), 2.35-2.19 (m, 1H), 2.07-1.96 (m, 1H).

Example 321

$^1$H NMR (400 MHz, DMSO-d6) δ=9.68 (br s, 1H), 7.91 (d, J=8.8 Hz, 2H), 7.34 (t, J=76.0 Hz, 1H), 7.26-7.23 (m, 3H), 6.93 (d, J=10.3 Hz, 2H), 6.85 (d, J=1.8 Hz, 1H), 5.26-5.05 (m, 1H), 3.97-3.89 (m, 1H), 3.89-3.82 (m, 5H), 3.82-3.73 (m, 1H), 3.21 (s, 3H), 2.48 (s, 3H), 2.35-2.19 (m, 1H), 2.07-1.96 (m, 1H).

Example 322

$^1$H NMR (400 MHz, DMSO-d6) δ=9.86-9.31 (m, 1H), 7.91 (d, J=8.4 Hz, 2H), 7.34 (t, J=73.6 Hz, 1H), 7.25 (d, J=8.4 Hz, 2H), 7.04 (d, J=2.0 Hz, 1H), 6.95 (d, J=10.0 Hz, 2H), 6.36 (d, J=2.0 Hz, 1H), 4.67 (s, 1H), 4.07 (s, 2H), 3.88 (s, 3H), 3.83 (s, 3H), 3.23 (s, 3H), 1.21 (s, 6H).

Example 323

$^1$H NMR (400 MHz, DMSO-d6) δ=9.66 (br s, 1H), 7.91 (d, J=8.8 Hz, 2H), 7.56 (s, 1H), 7.34 (t, J=72.5 Hz, 1H), 7.28-7.20 (m, 2H), 7.11 (s, 1H), 6.93 (d, J=10.0 Hz, 2H), 3.83 (s, 3H), 3.18 (s, 3H), 3.11-3.07 (m, 2H), 2.75-2.59 (m, 3H), 1.88-1.83 (m, 4H), 1.83-1.70 (m, 2H), 1.61-1.57 (m, 2H).

Example 324

$^1$H NMR (400 MHz, DMSO-d6) δ=9.65 (s, 1H), 7.90 (d, J=8.8 Hz, 2H), 7.57 (s, 1H), 7.34 (t, J=71.3 Hz, 1H), 7.24 (d, J=8.8 Hz, 2H), 7.14 (s, 1H), 6.93 (d, J=10.0 Hz, 2H), 3.83 (s, 3H), 3.17 (s, 3H), 2.91-2.87 (m, 2H), 2.61-2.52 (m, 1H), 2.20 (s, 3H), 2.02-1.97 (m, 2H), 1.89 (s, 3H), 1.85-1.76 (m, 2H), 1.74-1.59 (m, 2H).

Example 325

$^1$H NMR (400 MHz, DMSO-d6) δ=9.67 (s, 1H), 7.90 (d, J=8.8 Hz, 2H), 7.33 (t, J=73.5 Hz, 1H), 7.24 (d, J=8.8 Hz, 2H), 7.02 (d, J=2.0 Hz, 1H), 6.93 (d, J=10.0 Hz, 2H), 6.32 (d, J=2.0 Hz, 1H), 4.47 (t, J=5.3 Hz, 2H), 4.13 (s, 2H), 3.87 (s, 3H), 3.82 (s, 3H), 3.38-3.35 (m, 4H), 3.22 (s, 3H), 0.90 (s, 3H).

Example 326

$^1$H NMR (400 MHz, DMSO-d6) δ=11.12 (br s, 1H), 9.67 (s, 1H), 7.90 (d, J=8.5 Hz, 2H), 7.34 (t, J=73.5 Hz, 1H), 7.24 (d, J=8.8 Hz, 2H), 6.92 (d, J=10.0 Hz, 2H), 6.91-6.74 (m, 1H), 6.13 (s, 1H), 3.88 (s, 3H), 3.83 (s, 3H), 3.16 (s, 3H).

Example 327

$^1$H NMR (400 MHz, DMSO-d6) δ=9.65 (s, 1H), 7.91 (d, J=8.8 Hz, 2H), 7.34 (t, J=72.5 Hz, 1H), 7.29 (d, J=2.0 Hz, 1H), 7.24 (d, J=8.8 Hz, 2H), 6.97-6.88 (m, 3H), 4.51 (d, J=5.8 Hz, 2H), 4.33 (d, J=5.8 Hz, 2H), 4.20 (s, 2H), 3.83 (s, 3H), 3.19 (s, 3H), 2.48 (s, 3H), 1.38 (s, 3H).

Example 328

$^1$H NMR (400 MHz, DMSO-d6) δ=9.75 (s, 1H), 8.11 (s, 1H), 7.91 (d, J=8.8 Hz, 2H), 7.71 (s, 1H), 7.25 (d, J=8.8 Hz, 2H), 7.34 (t, J=74.6 Hz, 1H), 6.94 (d, J=10.0 Hz, 2H), 3.83 (s, 3H), 3.22 (s, 3H), 2.61 (s, 3H).

Example 329

$^1$H NMR (400 MHz, DMSO-d6) δ=9.67 (s, 1H), 7.91 (d, J=8.8 Hz, 2H), 7.34 (t, J=73.8 Hz, 1H), 7.25 (d, J=8.8 Hz, 2H), 7.05 (d, J=2.0 Hz, 1H), 6.93 (d, J=10.0 Hz, 2H), 6.34 (d, J=1.8 Hz, 1H), 4.51 (br s, 1H), 4.35 (t, J=6.4 Hz, 2H), 3.87 (s, 3H), 3.82 (s, 3H), 3.56 (t, J=6.4 Hz, 2H), 3.23 (s, 3H), 1.92-1.86 (m, 2H).

Example 330

$^1$H NMR (400 MHz, DMSO-d6) δ=9.56 (s, 1H), 7.94-7.89 (m, 3H), 7.71 (dd, J=7.3, 2.0 Hz, 1H), 7.32 (t, J=73.5

Hz, 1H), 7.22 (d, J=8.8 Hz, 2H), 6.88 (d, J=10.5 Hz, 2H), 6.4 (t, J=6.9 Hz, 1H), 3.8 (s, 3H), 3.53 (s, 3H), 2.99 (s, 3H).

Example 331

$^1$H NMR (400 MHz, DMSO-d6) δ=9.67 (s, 1H), 7.91 (d, J=8.8 Hz, 2H), 7.33 (t, J=74.0 Hz, 1H), 7.28-7.24 (m, 3H), 6.93 (d, J=10.3 Hz, 2H), 6.62 (s, 1H), 4.85 (t, J=5.1 Hz, 1H), 4.30 (t, J=5.1 Hz, 2H), 3.82 (s, 3H), 3.74 (q, J=5.1 Hz, 2H), 3.19 (s, 3H), 2.37 (s, 3H).

Example 332

$^1$H NMR (400 MHz, DMSO-d6) δ=9.68 (s, 1H), 7.91 (br d, J=8.8 Hz, 2H), 7.33 (t, J=73.6 Hz, 1H), 7.24 (d, J=8.8 Hz, 2H), 7.07 (d, J=1.8 Hz, 1H), 6.94 (d, J=10.3 Hz, 2H), 6.35 (d, J=1.8 Hz, 1H), 4.84 (t, J=5.4 Hz, 1H), 4.31 (t, J=5.4 Hz, 2H), 3.88 (s, 3H), 3.83 (s, 3H), 3.74 (q, J=5.4 Hz, 2H), 3.23 (s, 3H).

Example 333

$^1$H NMR (400 MHz, DMSO-d6) δ=9.69 (s, 1H), 7.94-7.81 (m, 3H), 7.45 (d, J=7.8 Hz, 1H), 7.33 (t, J=73.8 Hz, 1H), 7.24 (d, J=8.5 Hz, 2H), 6.94 (d, J=10.3 Hz, 2H), 6.77 (d, J=8.3 Hz, 1H), 4.87 (t, J=5.5 Hz, 1H), 4.32 (t, J=5.5 Hz, 2H), 3.83 (s, 3H), 3.76 (q, J=5.5 Hz, 2H), 3.22 (s, 3H).

Example 334

$^1$H NMR (400 MHz, DMSO-d6) δ=9.72 (s, 1H), 7.90 (d, J=8.5 Hz, 2H), 7.74 (d, J=2.0 Hz, 1H), 7.47 (d, J=2.0 Hz, 1H), 7.34 (t, J=74.0 Hz, 1H), 7.25 (d, J=8.8 Hz, 2H), 6.95 (d, J=10.3 Hz, 2H), 4.27-4.13 (m, 2H), 3.86-3.73 (m, 5H), 3.69-3.65 (m, 1H), 3.60-3.55 (m, 1H), 3.22 (s, 3H), 2.76-2.71 (m, 1H), 2.11-2.00 (m, 1H), 1.74-1.70 (m, 1H).

Example 335

$^1$H NMR (400 MHz, DMSO-d6) δ=9.70 (s, 1H), 7.91 (d, J=8.8 Hz, 2H), 7.34 (t, J=72.8 Hz, 1H), 7.25 (d, J=8.8 Hz, 2H), 7.11 (d, J=2.0 Hz, 1H), 6.94 (d, J=10.3 Hz, 2H), 6.42 (d, J=2.0 Hz, 1H), 4.68 (t, J=5.5 Hz, 2H), 3.89 (s, 3H), 3.83 (s, 3H), 3.67 (t, J=5.5 Hz, 2H), 3.23 (s, 3H), 3.08 (s, 3H).

Example 336

$^1$H NMR (400 MHz, DMSO-d6) δ=9.68 (s, 1H), 7.91 (d, J=8.8 Hz, 2H), 7.34 (t, J=73.8 Hz, 1H), 7.27-7.24 (m, 2H), 7.09 (d, J=2.0 Hz, 1H), 7.01-6.86 (m, 2H), 6.70 (s, 1H), 5.52 (br s, 1H), 4.86 (br s, 1H), 4.58 (s, 2H), 4.31 (t, J=5.0 Hz, 2H), 3.83 (s, 3H), 3.74 (br t, J=5.0 Hz, 2H), 3.20 (s, 3H).

Example 337

$^1$H NMR (400 MHz, DMSO-d6) δ=9.68 (s, 1H), 7.94-7.83 (m, 2H), 7.34 (t, J=74.8 Hz, 2H), 7.25 (d, J=8.8 Hz, 2H), 7.05 (d, J=2.0 Hz, 1H), 6.94 (d, J=10.0 Hz, 2H), 6.37 (d, J=2.0 Hz, 1H), 4.21 (d, J=6.0 Hz, 2H), 3.87 (s, 3H), 3.83 (s, 3H), 3.22-3.16 (m, 5H), 3.12-3.06 (m, 2H), 2.15-2.07 (m, 3H), 1.80-1.76 (m, 2H).

Example 338

$^1$H NMR (400 MHz, DMSO-d6) δ=9.66 (s, 1H), 7.91 (d, J=8.8 Hz, 2H), 7.34 (t, J=75.3 Hz, 1H), 7.29-7.23 (m, 3H), 6.95 (d, J=10.5 Hz, 2H), 6.91 (d, J=2.0 Hz, 1H), 4.39 (s, 1H), 3.90 (s, 3H), 3.84 (s, 3H), 3.55-3.52 (m, 2H), 3.24 (s, 3H), 3.07-3.02 (m, 1H), 2.96-2.86 (m, 2H), 2.43 (t, J=6.3 Hz, 2H), 2.02-1.86 (m, 3H), 1.69-1.55 (m, 3H).

Example 339

$^1$H NMR (400 MHz, DMSO-d6) δ=9.68 (s, 1H), 7.91 (d, J=8.8 Hz, 2H), 7.34 (t, J=75.3 Hz, 1H), 7.25 (d, J=8.8 Hz, 2H), 7.05 (d, J=2.0 Hz, 1H), 6.94 (d, J=10.5 Hz, 2H), 6.36 (d, J=2.0 Hz, 1H), 4.33-4.16 (m, 3H), 3.88 (s, 3H), 3.80 (s, 3H), 3.82-3.81 (m, 1H), 3.72-3.64 (m, 1H), 3.22 (s, 3H), 2.05-1.80 (m, 3H), 1.71-1.60 (m, 1H).

Example 340

$^1$H NMR (400 MHz, DMSO-d6) δ=9.66 (s, 1H), 7.91 (d, J=8.8 Hz, 2H), 7.34 (t, J=75.3 Hz, 1H), 7.29-7.23 (m, 3H), 6.95 (d, J=10.5 Hz, 2H), 6.91 (d, J=2.0 Hz, 1H), 4.39 (s, 1H), 3.90 (s, 3H), 3.84 (s, 3H), 3.55-3.52 (m, 2H), 3.24 (s, 3H), 3.07-3.03 (m, 1H), 2.96-2.86 (m, 2H), 2.43 (t, J=6.3 Hz, 2H), 2.02-1.86 (m, 3H), 1.69-1.55 (m, 3H).

Example 341

$^1$H NMR (400 MHz, DMSO-d6) δ=9.82 (s, 1H), 8.68 (s, 1H), 8.43 (s, 1H), 7.92 (d, J=8.8 Hz, 2H), 7.35 (t, J=75.1 Hz, 1H), 7.26 (d, J=8.8 Hz, 2H), 6.97 (d, J=10.3 Hz, 2H), 3.84 (s, 3H), 3.24 (s, 3H).

Example 342

$^1$H NMR (400 MHz, DMSO-d6) δ=9.66 (s, 1H), 7.91 (d, J=8.5 Hz, 2H), 7.34 (t, J=74.0 Hz, 1H), 7.30 (d, J=2.0 Hz, 1H), 7.25 (d, J=8.8 Hz, 2H), 6.95 (d, J=10.5 Hz, 2H), 6.90 (d, J=2.0 Hz, 1H), 3.90 (s, 3H), 3.84 (s, 3H), 3.23 (s, 3H), 3.05-2.91 (m, 2H), 2.87-2.78 (m, 1H), 2.26 (br s, 3H), 2.26-2.23 (m, 1H), 2.03-1.85 (m, 2H), 1.80-1.71 (m, 1H), 1.69-1.49 (m, 2H).

Example 343

$^1$H NMR (400 MHz, DMSO-d6) δ=9.66 (s, 1H), 7.91 (d, J=8.5 Hz, 2H), 7.34 (t, J=72.8 Hz, 1H), 7.30 (d, J=2.0 Hz, 1H), 7.25 (d, J=8.8 Hz, 2H), 6.95 (d, J=10.5 Hz, 2H), 6.90 (d, J=2.0 Hz, 1H), 3.90 (s, 3H), 3.84 (s, 3H), 3.23 (s, 3H), 3.04-2.90 (m, 2H), 2.88-2.78 (m, 1H), 2.26 (br s, 3H), 2.26-2.23 (m, 1H), 1.91 (br s, 2H), 1.78-1.72 (m, 1H), 1.70-1.46 (m, 2H).

Example 344

$^1$H NMR (400 MHz, DMSO-d6) δ=9.69 (s, 1H), 7.91 (d, J=9.0 Hz, 2H), 7.34 (t, J=72.8 Hz, 1H), 7.25 (d, J=8.8 Hz, 2H), 7.06 (d, J=2.0 Hz, 1H), 6.95 (d, J=10.5 Hz, 2H), 6.41 (d, J=2.0 Hz, 1H), 4.51 (d, J=6.0 Hz, 2H), 4.39 (s, 2H), 4.31 (d, J=6.0 Hz, 2H), 3.89 (s, 3H), 3.83 (s, 3H), 3.23 (s, 3H), 1.38 (s, 3H).

Example 345

$^1$H NMR (400 MHz, DMSO-d6) δ=9.68 (s, 1H), 7.92 (d, J=8.8 Hz, 2H), 7.35 (t, J=74.3 Hz, 1H), 7.33 (d, J=2.0 Hz, 1H), 7.26 (d, J=8.8 Hz, 2H), 6.95 (d, J=10.3 Hz, 2H), 6.88 (d, J=2.0 Hz, 1H), 4.04-3.93 (m, 2H), 3.90 (s, 3H), 3.84 (s, 3H), 3.53-3.40 (m, 2H), 3.24 (s, 3H), 3.01-2.90 (m, 1H), 1.90-1.73 (m, 4H).

Example 346

$^{1}$H NMR (400 MHz, DMSO-d6) δ=9.66 (s, 1H), 7.90 (d, J=8.5 Hz, 2H), 7.35 (t, J=73.6 Hz, 1H), 7.29 (d, J=2.0 Hz, 1H), 7.24 (d, J=8.5 Hz, 2H), 6.94 (d, J=10.5 Hz, 2H), 6.83 (d, J=2.0 Hz, 1H), 3.88 (s, 3H), 3.83 (s, 3H), 3.23 (s, 3H), 3.14-3.08 (m, 1H), 2.97-2.88 (m, 2H), 2.80-2.72 (m, 2H), 2.68-2.63 (m, 1H), 1.86-1.61 (m, 4H).

Example 347

$^{1}$H NMR (400 MHz, DMSO-d6) δ=9.68 (s, 1H), 7.91 (d, J=8.5 Hz, 2H), 7.35 (t, J=73.6 Hz, 1H), 7.29 (d, J=2.0 Hz, 1H), 7.24 (d, J=8.5 Hz, 2H), 6.94 (d, J=10.5 Hz, 2H), 6.83 (d, J=2.0 Hz, 1H), 3.88 (s, 3H), 3.83 (s, 3H), 3.23 (s, 3H), 3.14-3.08 (m, 1H), 2.97-2.88 (m, 2H), 2.80-2.72 (m, 2H), 2.68-2.63 (m, 1H), 1.86-1.61 (m, 4H).

Example 348

$^{1}$H NMR (400 MHz, DMSO-d6) δ=9.73 (s, 1H), 7.91 (d, J=8.8 Hz, 2H), 7.74 (d, J=2.0 Hz, 1H), 7.45 (d, J=2.0 Hz, 1H), 7.34 (t, J=73.0 Hz, 1H), 7.25 (d, J=8.8 Hz, 2H), 6.95 (d, J=10.3 Hz, 2H), 5.01 (t, J=5.5 Hz, 1H), 4.28 (t, J=4.8 Hz, 2H), 3.83 (s, 3H), 3.81-3.75 (m, 2H), 3.23 (s, 3H).

Example 349

$^{1}$H NMR (400 MHz, DMSO-d6) δ=9.72 (s, 1H), 7.91 (d, J=8.8 Hz, 2H), 7.78 (d, J=2.0 Hz, 1H), 7.52 (d, J=4.2 Hz, 1H), 7.33 (t, J=74.0 Hz, 1H), 7.24 (d, J=8.8 Hz, 2H), 6.95 (d, J=10.0 Hz, 2H), 4.54 (d, J=5.8 Hz, 2H), 4.42-4.28 (m, 4H), 3.83 (s, 3H), 3.23 (s, 3H), 1.40 (s, 3H).

Example 350

$^{1}$H NMR (400 MHz, DMSO-d6) δ=9.68 (s, 1H), 7.91 (d, J=8.5 Hz, 2H), 7.34 (t, J=75.3 Hz, 1H), 7.25 (d, J=8.8 Hz, 2H), 7.05 (d, J=2.0 Hz, 1H), 6.94 (d, J=10.5 Hz, 2H), 6.36 (d, J=2.0 Hz, 1H), 4.33-4.16 (m, 3H), 3.88 (s, 3H), 3.84-3.76 (m, 3H), 3.82-3.81 (m, 1H), 3.72-3.64 (m, 1H), 3.22 (s, 3H), 2.05-1.80 (m, 3H), 1.71-1.60 (m, 1H).

Example 351

$^{1}$H NMR (400 MHz, DMSO-d6) δ=9.67 (s, 1H), 7.91 (d, J=8.8 Hz, 2H), 7.34 (t, J=73.5 Hz, 1H), 7.25 (d, J=8.8 Hz, 2H), 7.05 (d, J=2.0 Hz, 1H), 6.94 (d, J=10.3 Hz, 2H), 6.36 (d, J=2.0 Hz, 1H), 4.29 (dd, J=10.6, 6.6 Hz, 1H), 4.19 (dd, J=10.6, 7.8 Hz, 1H), 3.87 (s, 3H), 3.85-3.74 (m, 5H), 3.71-3.62 (m, 1H), 3.56-3.52 (m, 1H), 3.31 (s, 3H), 2.77-2.63 (m, 1H), 2.08-1.97 (m, 1H), 1.72-1.57 (m, 1H).

Example 352

$^{1}$H NMR (400 MHz, DMSO-d6) δ=9.69 (s, 1H), 7.92 (br d, J=8.6 Hz, 2H), 7.35 (t, J=73.4 Hz, 1H), 7.30-7.18 (m, 3H), 6.95 (d, J=11.0 Hz, 2H), 6.64 (s, 1H), 4.34-4.25 (m, 1H), 4.19 (dd, J=10.4, 8.0 Hz, 1H), 3.87 (s, 3H), 3.86-3.73 (m, 2H), 3.69-3.64 (m, 1H), 3.56-3.52 (m, 1H), 3.2 (s, 3H) 2.74-2.70 (m, 1H), 2.38 (s, 3H), 2.08-1.94 (m, 1H), 1.68-1.64 (m, 1H).

Example 353

$^{1}$H NMR (400 MHz, DMSO-d6) δ=9.68 (s, 1H), 7.91 (d, J=8.8 Hz, 2H), 7.34 (t, J=75.8 Hz, 1H), 7.30 (s, 1H), 7.25 (d, J=8.8 Hz, 2H), 6.94 (d, J=10.0 Hz, 2H), 6.69 (s, 1H), 4.51 (d, J=5.9 Hz, 2H), 4.38 (s, 2H), 4.31 (d, J=5.9 Hz, 2H), 3.83 (s, 3H), 3.21 (s, 3H), 2.39 (s, 3H), 1.37 (s, 3H).

Example 354

$^{1}$H NMR (400 MHz, DMSO-d6) δ=9.64 (s, 1H), 7.91 (br d, J=8.8 Hz, 2H), 7.34 (t, J=75.8 Hz, 1H), 7.24 (br d, J=8.8 Hz, 2H), 6.93 (d, J=10.5 Hz, 2H), 6.71 (d, J=1.5 Hz, 1H), 5.96 (br s, 1H), 4.64 (br s, 1H), 3.86 (s, 3H), 3.83 (s, 3H), 3.52-3.48 (m, 2H), 3.22 (s, 3H), 2.95-2.84 (m, 2H), 2.61-2.41 (m, 1H), 2.30 (s, 3H), 1.91-1.83 (m, 2H).

Example 355

$^{1}$H NMR (400 MHz, DMSO-d6) δ=9.71 (s, 1H), 7.92 (d, J=8.8 Hz, 2H), 7.35 (t, J=73.6 Hz, 1H), 7.26 (d, J=8.8 Hz, 2H), 7.07 (d, J=2.0 Hz, 1H), 6.95 (d, J=10.5 Hz, 2H), 6.37 (d, J=2.0 Hz, 1H), 5.47-5.42 (m, 1H), 4.01-3.96 (m, 1H), 3.90-3.85 (m, 4H), 3.84-3.76 (m, 5H), 3.21 (s, 3H), 2.31-2.22 (m, 1H), 2.10-2.02 (m, 1H).

Example 356

$^{1}$H NMR (400 MHz, DMSO-d6) δ=9.71 (s, 1H), 7.92 (d, J=8.8 Hz, 2H), 7.35 (t, J=73.6 Hz, 1H), 7.26 (d, J=8.8 Hz, 2H), 7.07 (d, J=2.0 Hz, 1H), 6.95 (d, J=10.5 Hz, 2H), 6.37 (d, J=2.0 Hz, 1H), 5.47-5.42 (m, 1H), 4.01-3.96 (m, 1H), 3.90-3.85 (m, 4H), 3.84-3.76 (m, 5H), 3.21 (s, 3H), 2.31-2.22 (m, 1H), 2.10-2.02 (m, 1H).

Example 357

$^{1}$H NMR (400 MHz, DMSO-d6) δ=9.81 (s, 1H), 8.43 (d, J=8.1 Hz, 1H), 7.92 (d, J=8.6 Hz, 2H), 7.55 (d, J=8.1 Hz, 1H), 7.34 (t, J=73.6 Hz, 1H), 7.24 (d, J=8.6 Hz, 2H), 6.95 (d, J=10.5 Hz, 2H), 3.84 (s, 3H), 3.14 (s, 3H), 2.65 (s, 3H).

Example 358

$^{1}$H NMR (400 MHz, DMSO-d6) δ=9.66 (s, 1H), 8.13 (d, J=8.8 Hz, 1H), 7.99 (d, J=8.8 Hz, 1H), 7.91 (d, J=8.8 Hz, 2H), 7.24 (d, J=8.6 Hz, 2H), 7.33 (t, J=74.0 Hz, 1H), 6.96-6.84 (m, 2H), 4.48 (d, J=6.0 Hz, 2H), 4.36-4.22 (m, 4H), 3.81 (s, 3H), 2.93 (s, 3H), 1.28 (s, 3H).

Example 359

$^{1}$H NMR (400 MHz, DMSO-d6) δ=9.71 (s, 1H), 7.92 (d, J=8.6 Hz, 2H), 7.35 (t, J=73.8 Hz, 1H), 7.30 (s, 1H), 7.26 (d, J=8.6 Hz, 2H), 6.95 (d, J=10.5 Hz, 2H), 6.64 (s, 1H), 5.45-5.41 (m, 1H), 3.99 (dd, J=10.3, 4.9 Hz, 1H), 3.90-3.74 (m, 6H), 3.19 (s, 3H), 2.38 (s, 3H), 2.31-2.21 (m, 1H), 2.10-1.99 (m, 1H).

Example 360

$^{1}$H NMR (400 MHz, DMSO-d6) δ=9.71 (s, 1H), 7.92 (d, J=8.8 Hz, 2H), 7.35 (t, J=73.4 Hz, 1H), 7.30 (s, 1H), 7.26 (d, J=8.6 Hz, 2H), 6.95 (d, J=10.8 Hz, 2H), 6.64 (s, 1H), 5.47-5.37 (m, 1H), 3.99 (dd, J=10.1, 4.8 Hz, 1H), 3.90-3.73 (m, 6H), 3.19 (s, 3H), 2.38 (s, 3H), 2.30-2.21 (m, 1H), 2.11-1.99 (m, 1H).

Example 361

$^{1}$H NMR (400 MHz, DMSO-d6) δ=9.68 (s, 1H), 7.91 (d, J=8.6 Hz, 2H), 7.56 (s, 1H), 7.35 (t, J=73.4 Hz, 1H), 7.25 (d,

J=8.6 Hz, 2H), 7.10 (s, 1H), 6.94 (d, J=10.0 Hz, 2H), 3.83 (s, 3H), 3.21 (s, 3H), 2.96-2.90 (m, 2H), 2.66-2.59 (m, 2H), 2.40 (s, 3H), 2.26 (br s, 3H), 2.11-2.06 (m, 2H), 1.86-1.82 (m, 3H).

Example 362

$^1$H NMR (400 MHz, DMSO-d6) δ=9.75 (s, 1H), 8.07 (s, 1H), 7.96-7.83 (m, 3H), 7.35 (t, J=73.6 Hz, 1H), 7.26 (d, J=8.8 Hz, 2H), 6.96 (d, J=10.0 Hz, 2H), 3.84 (s, 3H), 3.18 (s, 3H), 2.5 (s, 3H).

Example 363

$^1$H NMR (400 MHz, DMSO-d6) δ=9.65 (s, 1H), 7.91 (d, J=8.5 Hz, 2H), 7.34 (t, J=72.1 Hz, 1H), 7.31 (d, J=2.0 Hz, 1H), 7.25 (d, J=8.5 Hz, 2H), 6.94 (d, J=10.0 Hz, 2H), 6.86 (d, J=2.0 Hz, 1H), 3.89 (s, 3H), 3.84 (s, 3H), 3.24 (s, 3H), 2.90-2.86 (m, 2H), 2.66-2.60 (m, 1H), 2.20 (s, 3H), 2.02-1.93 (m, 2H), 1.86-1.77 (m, 4H).

Example 364

$^1$H NMR (400 MHz, DMSO-d6) δ=9.66 (s, 1H), 7.91 (d, J=8.8 Hz, 2H), 7.35 (t, J=75.3 Hz, 1H), 7.25 (d, J=8.8 Hz, 2H), 6.94 (d, J=10.0 Hz, 2H), 6.81 (d, J=1.5 Hz, 1H), 6.29 (d, J=1.5 Hz, 1H), 3.86 (s, 3H), 3.83 (s, 3H), 3.76-3.66 (m, 4H), 3.56-3.41 (m, 4H), 3.20 (s, 3H).

Example 365

$^1$H NMR (400 MHz, DMSO-d6) δ=9.66 (s, 1H), 7.92 (d, J=8.8 Hz, 2H), 7.35 (t, J=73.6 Hz, 1H), 7.32 (d, J=2.0 Hz, 1H), 7.26 (d, J=8.6 Hz, 2H), 6.94 (d, J=10.3 Hz, 2H), 6.87 (d, J=2.0 Hz, 1H), 6.18 (tt, J=55.5, 5.6 Hz, 1H), 3.90 (s, 3H), 3.84 (s, 3H), 3.24 (s, 3H), 3.05-3.00 (m, 2H), 2.82-2.63 (m, 3H), 2.35-2.16 (m, 2H), 1.90-1.66 (m, 4H).

Example 366

$^1$H NMR (400 MHz, DMSO-d6) δ=9.67 (s, 1H), 7.92 (d, J=8.6 Hz, 2H), 7.33 (t, J=73.6 Hz, 1H), 7.28-7.24 (m, 3H), 7.00-6.82 (m, 3H), 3.91 (s, 3H), 3.84 (s, 3H), 3.69 (br d, J=12.0 Hz, 2H), 3.24 (s, 3H), 2.91 (s, 3H), 2.89-2.80 (m, 3H), 2.00 (br d, J=12.2 Hz, 2H), 1.91-1.76 (m, 2H).

Example 367

$^1$H NMR (400 MHz, DMSO-d6) δ=9.67 (s, 1H), 7.99-7.84 (m, 2H), 7.35 (t, J=75.1 Hz, 1H), 7.33 (d, J=2.0 Hz, 1H), 7.26 (d, J=8.8 Hz, 2H), 6.94 (d, J=10.0 Hz, 2H), 6.84 (d, J=2.2 Hz, 1H), 3.90 (s, 3H), 3.84 (s, 3H), 3.80-3.33 (br s, 1H), 3.24 (s, 3H), 3.19-3.13 (m, 2H), 2.90-2.81 (m, 1H), 2.80-2.70 (m, 2H), 1.94-1.83 (m, 2H), 1.82-1.70 (m, 2H).

Example 368

$^1$H NMR (400 MHz, DMSO-d6) δ=9.66 (s, 1H), 7.91 (d, J=8.6 Hz, 2H), 7.35 (t, J=75.1 Hz, 1H), 7.32 (d, J=2.0 Hz, 1H), 7.25 (d, J=8.6 Hz, 2H), 6.94 (d, J=10.0 Hz, 2H), 6.87 (d, J=2.2 Hz, 1H), 4.64-4.39 (m, 1H), 3.90 (s, 3H), 3.84 (s, 3H), 3.62-3.54 (m, 2H), 3.24 (s, 3H), 3.17-3.03 (m, 2H), 2.76-2.72 (m, 1H), 2.63-2.56 (m, 3H), 2.31-2.19 (m, 1H), 1.95-1.80 (m, 4H).

Example 369

$^1$H NMR (400 MHz, DMSO-d6) δ=9.66 (s, 1H), 8.09 (d, J=8.5 Hz, 1H), 7.97 (d, J=8.5 Hz, 1H), 7.91 (d, J=8.8 Hz, 2H), 7.33 (t, J=74.3 Hz, 1H), 7.24 (d, J=8.8 Hz, 2H), 6.98-6.86 (m, 2H), 4.21-4.16 (m, 1H), 4.13-4.05 (m, 1H), 3.82 (s, 3H), 3.77-3.68 (m, 2H), 3.66-3.58 (m, 1H), 3.55-3.50 (m, 1H), 2.95 (s, 3H), 2.67-2.60 (m, 1H), 2.05-1.92 (m, 1H), 1.66-1.60 (m, 1H).

Example 370

$^1$H NMR (400 MHz, DMSO-d6) δ=9.66 (s, 1H), 8.09 (d, J=8.5 Hz, 1H), 7.97 (d, J=8.5 Hz, 1H), 7.91 (d, J=8.8 Hz, 2H), 7.33 (t, J=74.3 Hz, 1H), 7.24 (d, J=8.8 Hz, 2H), 6.98-6.86 (m, 2H), 4.21-4.16 (m, 1H), 4.13-4.05 (m, 1H), 3.82 (s, 3H), 3.77-3.68 (m, 2H), 3.66-3.58 (m, 1H), 3.55-3.50 (m, 1H), 2.95 (s, 3H), 2.67-2.60 (m, 1H), 2.05-1.92 (m, 1H), 1.66-1.60 (m, 1H).

Example 371

$^1$H NMR (400 MHz, DMSO-d6) δ=9.68 (s, 1H), 8.10 (d, J=8.8 Hz, 1H), 7.98 (d, J=8.6 Hz, 1H), 7.92 (d, J=8.6 Hz, 2H), 7.34 (t, J=74.1 Hz, 1H), 7.24 (d, J=8.6 Hz, 2H), 6.92 (d, J=10.5 Hz, 2H), 4.00 (s, 3H), 3.83 (s, 3H), 2.98 (s, 3H).

Example 372

$^1$H NMR (400 MHz, DMSO-d6) δ=9.69 (s, 1H), 8.10-7.98 (m, 2H), 7.92 (d, J=8.8 Hz, 2H), 7.34 (t, J=73.8 Hz, 1H), 7.25 (d, J=8.6 Hz, 2H), 6.99-6.86 (m, 2H), 4.85 (t, J=5.8 Hz, 1H), 4.34 (t, J=4.8 Hz, 2H), 3.83 (s, 3H), 3.74 (q, J=5.8 Hz, 2H), 3.04 (s, 3H).

Example 373

$^1$H NMR (400 MHz, DMSO-d6) δ=9.68 (s, 1H), 8.10-8.00 (m, 2H), 7.92 (br d, J=8.8 Hz, 2H), 7.34 (t, J=73.8 Hz, 1H), 7.24 (d, J=8.6 Hz, 2H), 6.99-6.86 (m, 2H), 4.93 (d, J=3.9 Hz, 1H), 4.22-4.15 (m, 1H), 4.14-4.04 (m, 1H), 4.03-3.94 (m, 1H), 3.83 (s, 3H), 3.03 (s, 3H), 1.33-1.07 (2d, J=3.9 Hz, 3H). (Mixture of interconvertible atropisomers)

Example 374

$^1$H NMR (400 MHz, DMSO-d6) δ=9.69 (br s, 1H), 8.11-8.03 (m, 1H), 8.03-7.95 (m, 1H), 7.92 (br d, J=8.8 Hz, 2H), 7.34 (t, J=74.1 Hz, 1H), 7.24 (d, J=8.8 Hz, 2H), 6.93 (d, J=10.5 Hz, 2H), 4.22 (t, J=5.3 Hz, 2H), 3.83 (s, 3H), 3.40-3.10 (br s, 2H), 3.00 (s, 3H), 2.89 (t, J=5.3 Hz, 2H).

Example 375

$^1$H NMR (400 MHz, DMSO-d6) δ=9.81 (s, 1H), 8.65-8.44 (s, 1H), 8.17-8.13 (m, 2H), 8.01-7.90 (m, 2H), 7.36 (t, J=73.4 Hz, 1H), 7.30 (d, J=8.8 Hz, 2H), 7.06-6.93 (m, 2H), 4.72-4.57 (m, 2H), 3.86 (s, 3H), 3.49-3.42 (m, 2H), 3.17 (s, 3H), 2.72 (br s, 3H).

Example 376

$^1$H NMR (400 MHz, DMSO-d6) δ=9.66 (s, 1H), 7.91 (d, J=8.5 Hz, 2H), 7.35 (t, J=73.3 Hz, 1H), 7.29-7.20 (m, 3H), 6.93 (d, J=10.0 Hz, 2H), 6.88 (d, J=2.0 Hz, 1H), 3.89 (s, 3H), 3.84 (s, 3H), 3.20 (s, 3H), 2.48 (s, 3H).

Example 377

$^1$H NMR (400 MHz, DMSO-d6) δ=9.67 (s, 1H), 7.91 (d, J=8.8 Hz, 2H), 7.34 (t, J=75.6 Hz, 1H), 7.24 (d, J=8.8 Hz,

2H), 6.99 (m, 3H), 6.94 (d, J=10.3 Hz, 1H), 4.78 (sept, J=6.0 Hz, 1H), 4.63 (s, 1H), 4.06 (s, 2H), 3.82 (s, 3H), 3.22 (s, 3H), 1.33 (d, J=6.0 Hz, 6H), 1.20 (s, 6H).

Example 378

$^1$H NMR (400 MHz, DMSO-d6) δ=9.68 (s, 1H), 7.91 (d, J=8.8 Hz, 2H), 7.34 (t, J=73.5 Hz, 1H), 7.25 (d, J=8.8 Hz, 2H), 7.02 (d, J=1.8 Hz, 1H), 6.94 (d, J=10.3 Hz, 2H), 6.31 (d, J=1.8 Hz, 1H), 4.84 (t, J=5.4 Hz, 1H), 4.78 (sept, J=6.0 Hz, 1H), 4.30 (t, J=5.4 Hz, 2H), 3.83 (s, 3H), 3.74 (q, J=5.4 Hz, 2H), 3.23 (s, 3H), 1.33 (d, J=6.0 Hz, 6H).

Example 379

$^1$H NMR (400 MHz, DMSO-d6) δ=9.68 (s, 1H), 7.91 (d, J=8.8 Hz, 2H), 7.34 (t, J=72.3 Hz, 1H), 7.24 (d, J=8.8 Hz, 2H), 7.04 (d, J=1.8 Hz, 1H), 6.93 (d, J=10.0 Hz, 2H), 6.31 (d, J=1.8 Hz, 1H), 4.41 (t, J=7.4 Hz, 2H), 4.36 (s, 1H), 3.87 (s, 3H), 3.82 (s, 3H), 3.23 (s, 3H), 1.86 (t, J=7.4 Hz, 2H), 1.17 (s, 6H).

Example 380

$^1$H NMR (400 MHz, DMSO-d6) δ=9.70 (s, 1H), 7.91 (d, J=8.8 Hz, 2H), 7.34 (t, J=74.8 Hz, 1H), 7.24 (d, J=8.8 Hz, 2H), 7.09 (d, J=1.8 Hz, 1H), 6.94 (d, J=10.5 Hz, 2H), 6.63 (br d, J=6.3 Hz, 1H), 6.39 (d, J=1.8 Hz, 1H), 4.58 (dd, J=11.4, 3.9 Hz, 1H), 4.52-4.43 (m, 1H), 4.35 (dd, J=11.4, 7.0 Hz, 1H), 3.88 (s, 3H), 3.82 (s, 3H), 3.19 (s, 3H).

Example 381

$^1$H NMR (400 MHz, DMSO-d6) δ=9.70 (s, 1H), 7.91 (d, J=8.8 Hz, 2H), 7.35 (t, J=72.3 Hz, 1H), 7.25 (d, J=8.8 Hz, 2H), 7.09 (d, J=2.0 Hz, 1H), 6.94 (d, J=10.5 Hz, 2H), 6.66-6.56 (m, 1H), 6.39 (d, J=2.0 Hz, 1H), 4.61-4.58 (m, 1H), 4.53-4.43 (m, 1H), 4.40-4.31 (m, 1H), 3.89 (s, 3H), 3.83 (s, 3H), 3.20 (s, 3H).

Example 382

$^1$H NMR (400 MHz, DMSO-d6) δ=9.70 (s, 1H), 7.91 (d, J=8.8 Hz, 2H), 7.34 (t, J=73.5 Hz, 1H), 7.24 (d, J=8.8 Hz, 2H), 7.04 (d, J=1.8 Hz, 1H), 6.93 (d, J=10.5 Hz, 2H), 6.33 (d, J=1.8 Hz, 1H), 5.25 (quin, J=5.1 Hz, 1H), 4.89 (br s, 1H), 3.87 (s, 3H), 3.82 (s, 3H), 3.68-3.55 (m, 4H), 3.28 (s, 3H), 3.20 (s, 3H).

Example 383

$^1$H NMR (400 MHz, DMSO-d6) δ=9.70 (s, 1H), 7.91 (d, J=8.8 Hz, 2H), 7.34 (t, J=74.8 Hz, 1H), 7.24 (d, J=8.8 Hz, 2H), 7.09 (d, J=1.8 Hz, 1H), 6.94 (d, J=10.5 Hz, 2H), 6.63 (br d, J=6.3 Hz, 1H), 6.39 (d, J=1.8 Hz, 1H), 4.58 (dd, J=11.4, 3.9 Hz, 1H), 4.52-4.43 (m, 1H), 4.35 (dd, J=11.4, 7.0 Hz, 1H), 3.88 (s, 3H), 3.82 (s, 3H), 3.19 (s, 3H).

Example 384

$^1$H NMR (400 MHz, DMSO-d6) δ=9.67 (s, 1H), 7.91 (d, J=8.8 Hz, 2H), 7.34 (t, J=74.8 Hz, 1H), 7.24 (d, J=8.5 Hz, 2H), 7.06 (d, J=2.0 Hz, 1H), 6.93 (d, J=10.3 Hz, 2H), 6.39 (d, J=2.0 Hz, 1H), 4.99 (t, J=5.4 Hz, 1H), 4.47 (s, 2H), 4.45-4.42 (m, 2H), 4.41-4.37 (m, 2H), 3.88 (s, 3H), 3.82 (s, 3H), 3.71 (d, J=5.4 Hz, 2H), 3.23 (s, 3H).

Example 385

$^1$H NMR (400 MHz, DMSO-d6) δ=9.69 (s, 1H), 7.91 (d, J=8.8 Hz, 2H), 7.35 (t, J=73.0 Hz, 1H), 7.25 (d, J=8.8 Hz, 2H), 7.06 (d, J=2.0 Hz, 1H), 6.93 (d, J=10.3 Hz, 2H), 6.44 (d, J=2.0 Hz, 1H), 4.38 (d, J=20.0 Hz, 2H), 3.90 (s, 3H), 3.83 (s, 3H), 3.32 (s, 3H), 1.44 (d, J=19.0 Hz, 6H).

Example 386

$^1$H NMR (400 MHz, DMSO-d6) δ=9.69 (s, 1H), 7.91 (d, J=8.8 Hz, 2H), 7.34 (t, J=71.5 Hz, 1H), 7.26 (d, J=8.8 Hz, 2H), 7.04 (d, J=2.0 Hz, 1H), 6.93 (d, J=10.5 Hz, 2H), 6.33 (d, J=2.0 Hz, 1H), 5.25 (quin, J=5.2 Hz, 1H), 4.89 (br s, 1H), 3.87 (s, 3H), 3.82 (s, 3H), 3.68-3.56 (m, 4H), 3.28 (s, 3H), 3.20 (s, 3H).

Example 387

$^1$H NMR (400 MHz, DMSO-d6) δ=9.69 (s, 1H), 7.91 (d, J=8.8 Hz, 2H), 7.35 (t, J=72.3 Hz, 1H), 7.25 (d, J=8.5 Hz, 2H), 7.11 (d, J=1.8 Hz, 1H), 6.95 (d, J=10.3 Hz, 2H), 6.49 (d, J=2.0 Hz, 1H), 4.60 (t, J=12.9 Hz, 2H), 3.90 (s, 3H), 3.83 (s, 3H), 3.21 (s, 3H), 1.76 (t, J=19.1 Hz, 3H).

Example 388

$^1$H NMR (400 MHz, DMSO-d6) δ=9.67 (s, 1H), 8.31 (d, J=3.0 Hz, 1H), 7.91 (d, J=8.5 Hz, 2H), 7.77-7.71 (m, 1H), 7.69-7.63 (m, 1H), 7.34 (t, J=73.0 Hz, 1H), 7.24 (d, J=8.8 Hz, 2H), 6.92 (d, J=10.3 Hz, 2H), 4.61-4.50 (br s, 1H), 4.13 (t, J=4.9 Hz, 2H), 3.82 (s, 3H), 3.76 (t, J=4.9 Hz, 2H), 3.11 (s, 3H).

Example 389

$^1$H NMR (400 MHz, DMSO-d6) δ=9.69 (s, 1H), 7.91 (d, J=8.8 Hz, 2H), 7.34 (t, J=73.3 Hz, 1H), 7.25 (d, J=8.5 Hz, 2H), 7.14 (d, J=1.8 Hz, 1H), 6.94 (d, J=10.3 Hz, 2H), 6.56 (d, J=1.8 Hz, 1H), 5.02 (q, J=9.0 Hz, 2H), 3.91 (s, 3H), 3.83 (s, 3H), 3.20 (s, 3H).

Example 390

$^1$H NMR (400 MHz, DMSO-d6) δ=9.70 (s, 1H), 7.91 (d, J=8.8 Hz, 2H), 7.35 (t, J=72.3 Hz, 1H), 7.25 (d, J=8.8 Hz, 2H), 7.09 (d, J=2.0 Hz, 1H), 6.99-6.88 (m, 2H), 6.66-6.56 (m, 1H), 6.39 (d, J=2.0 Hz, 1H), 4.61-4.57 (m, 1H), 4.53-4.43 (m, 1H), 4.40-4.31 (m, 1H), 3.89 (s, 3H), 3.83 (s, 3H), 3.20 (s, 3H).

Example 391

$^1$H NMR (400 MHz, DMSO-d6) δ=9.66 (s, 1H), 7.91 (d, J=8.8 Hz, 2H), 7.34 (t, J=73.5 Hz, 1H), 7.29-7.21 (m, 3H), 6.93 (d, J=10.3 Hz, 2H), 6.88 (d, J=2.0 Hz, 1H), 4.25-4.17 (m, 1H), 4.15-4.09 (m, 1H), 4.08-4.01 (m, 1H), 3.88-3.77 (m, 1H), 3.83 (s, 3H), 3.75-3.66 (m, 1H), 3.20 (s, 3H), 2.47 (s, 3H), 2.07-1.98 (m, 1H), 1.95-1.77 (m, 2H), 1.74-1.63 (m, 1H).

Example 392

$^1$H NMR (400 MHz, DMSO-d6) δ=9.69 (s, 1H), 7.96-7.83 (m, 3H), 7.44 (d, J=7.5 Hz, 1H), 7.34 (t, J=74.6 Hz,

1H), 7.25 (d, J=8.8 Hz, 2H), 6.94 (d, J=10.3 Hz, 2H), 6.79 (d, J=8.3 Hz, 1H), 4.65 (br s, 1H), 4.09 (s, 2H), 3.83 (s, 3H), 3.22 (s, 3H), 1.21 (s, 6H).

Example 393

$^1$H NMR (400 MHz, DMSO-d6) δ=9.66 (br s, 1H), 7.91 (d, J=8.8 Hz, 2H), 7.34 (t, J=72.0 Hz, 1H), 7.29-7.18 (m, 3H), 6.92 (d, J=10.0 Hz, 2H), 6.86 (d, J=2.0 Hz, 1H), 5.02 (br s, 1H), 4.05-3.91 (m, 3H), 3.82 (s, 3H), 3.19 (s, 3H), 2.47 (s, 3H), 1.16 (d, J=6.0 Hz, 3H).

Example 394

$^1$H NMR (400 MHz, DMSO-d6) δ=9.66 (br s, 1H), 7.91 (d, J=8.8 Hz, 2H), 7.34 (t, J=72.0 Hz, 1H), 7.29-7.18 (m, 3H), 6.92 (d, J=10.0 Hz, 2H), 6.86 (d, J=2.0 Hz, 1H), 5.02 (br s, 1H), 4.05-3.91 (m, 3H), 3.82 (s, 3H), 3.19 (s, 3H), 2.47 (s, 3H), 1.16 (d, J=6.0 Hz, 3H).

Example 395

$^1$H NMR (400 MHz, DMSO-d6) δ=9.57 (s, 1H), 7.96-7.89 (m, 2H), 7.72 (dd, J=7.0, 2.0 Hz, 1H), 7.33 (t, J=73.5 Hz, 1H), 7.25-7.20 (m, 2H), 7.12-7.08 (m, 1H), 6.99-6.95 (m, 1H), 6.93-6.85 (m, 1H), 6.41 (t, J=6.9 Hz, 1H), 3.82 (s, 3H), 3.54 (s, 3H), 3.00 (s, 3H).

Example 396

$^1$H NMR (400 MHz, DMSO-d6) δ=9.66 (s, 1H), 7.91 (d, J=8.8 Hz, 2H), 7.34 (t, J=73.5 Hz, 1H), 7.29-7.21 (m, 3H), 6.93 (d, J=10.3 Hz, 2H), 6.88 (d, J=2.0 Hz, 1H), 4.25-4.17 (m, 1H), 4.15-4.09 (m, 1H), 4.08-4.01 (m, 1H), 3.88-3.77 (m, 1H), 3.83 (s, 3H), 3.75-3.66 (m, 1H), 3.20 (s, 3H), 2.47 (s, 3H), 2.07-1.98 (m, 1H), 1.95-1.77 (m, 2H), 1.74-1.63 (m, 1H).

Example 397

$^1$H NMR (500 MHz, DMSO-d6) δ 9.74 (s, 1H), 8.76 (d, J=5.0 Hz, 1H), 8.09 (s, 1H), 7.90 (br d, J=8.4 Hz, 2H), 7.54 (br d, J=4.9 Hz, 1H), 7.31 (t, J=73.6 Hz, 1H), 7.25 (br d, J=8.2 Hz, 2H), 7.22 (t, J=55.0 Hz, 1H), 6.93 (br d, J=10.8 Hz, 2H), 3.20 (s, 2H).

Example 398

$^1$H NMR (500 MHz, DMSO-d6) δ 9.93 (s, 1H), 7.95 (br d, J=8.5 Hz, 2H), 7.60 (br d, J=7.9 Hz, 2H), 7.47 (br d, J=8.2 Hz, 2H), 7.00 (d, J=1.2 Hz, 1H), 6.33 (d, J=1.5 Hz, 1H), 4.83-4.73 (m, 1H), 4.29 (t, J=4.9 Hz, 2H), 3.74 (q, J=5.1 Hz, 2H), 3.25 (s, 3H), 1.33 (d, J=5.8 Hz, 6H).

Example 399

$^1$H NMR (500 MHz, DMSO-d6) δ 9.81 (s, 1H), 7.90 (br d, J=8.6 Hz, 2H), 7.59 (d, J=7.9 Hz, 2H), 7.33 (s, 1H), 7.25 (d, J=8.5 Hz, 2H), 7.00 (d, J=1.7 Hz, 1H), 6.32 (d, J=1.6 Hz, 1H), 4.83-4.73 (m, 1H), 4.29 (t, J=5.0 Hz, 2H), 3.77-3.70 (m, 2H), 3.24 (s, 3H), 1.33 (d, J=6.0 Hz, 6H)

Example 400

$^1$H NMR (500 MHz, DMSO-d6) δ 7.91 (br d, J=8.9 Hz, 2H), 7.42 (t, J=72.6 Hz, 1H), 7.34 (t, J=73.9 Hz, 1H), 7.29-7.22 (m, 5H), 6.66 (s, 1H), 4.07 (s, 2H), 3.21 (s, 3H), 2.39 (s, 3H), 1.21 (s, 6H).

Example 401

$^1$H NMR (500 MHz, DMSO-d6) δ 9.90 (s, 1H), 8.01 (t, J=8.0 Hz, 1H), 7.90 (br d, J=8.5 Hz, 2H), 7.87 (br d, J=7.9 Hz, 2H), 7.74 (br d, J=8.0 Hz, 1H), 7.63 (d, J=7.7 Hz, 1H), 7.33 (t, J=72.3 Hz, 1H), 7.25 (br d, J=8.5 Hz, 2H), 3.43 (s, 3H), 1.50 (s, 6H).

Example 402

$^1$H NMR (500 MHz, DMSO-d6) δ 9.87 (br s, 1H), 8.87 (br s, 1H), 8.24 (br s, 1H), 7.95 (br d, J=5.2 Hz, 2H), 7.74 (br s, 1H), 7.46 (br d, J=6.1 Hz, 2H), 6.93 (br d, J=12.2 Hz, 2H), 3.62 (br s, 3H), 3.23 (br s, 3H).

Example 403

$^1$H NMR (500 MHz, DMSO-d6) δ 9.82 (s, 1H), 8.06-7.93 (m, 3H), 7.73 (d, J=7.9 Hz, 1H), 7.62 (d, J=7.6 Hz, 1H), 7.47 (br d, J=7.9 Hz, 2H), 7.18 (br d, J=9.8 Hz, 2H), 3.23 (s, 3H), 2.68 (q, J=7.4 Hz, 2H), 1.50 (s, 6H), 1.16-1.16 (m, 1H), 1.20 (t, J=7.5 Hz, 2H).

Example 404

$^1$H NMR (500 MHz, DMSO-d6) δ 9.69 (s, 1H), 7.99 (br t, J=7.8 Hz, 1H), 7.92 (br d, J=8.2 Hz, 2H), 7.74 (br d, J=7.9 Hz, 1H), 7.61 (br d, J=7.9 Hz, 1H), 7.34 (t, J=1.0 Hz, 1H), 7.26 (br d, J=8.5 Hz, 2H), 6.94 (br t, J=10.4 Hz, 2H), 3.91 (s, 3H), 3.24 (s, 3H), 1.50 (s, 6H)

Example 405

$^1$H NMR (500 MHz, DMSO-d6) δ 9.81 (s, 1H), 8.01-7.92 (m, 3H), 7.74 (d, J=7.9 Hz, 1H), 7.61 (d, J=7.9 Hz, 1H), 7.47 (br d, J=8.2 Hz, 2H), 6.95 (br d, J=10.4 Hz, 2H), 3.24 (s, 3H), 1.50 (s, 6H)

Example 406

$^1$H NMR (500 MHz, DMSO-d6) δ 9.94 (s, 1H), 8.00 (br t, J=7.9 Hz, 1H), 7.95 (br d, J=8.2 Hz, 2H), 7.73 (br d, J=7.9 Hz, 1H), 7.61 (br dd, J=15.9, 7.9 Hz, 3H), 7.47 (br d, J=8.2 Hz, 2H), 3.26 (s, 3H), 1.50 (s, 6H)

Example 407

$^1$H NMR (500 MHz, CHLOROFORM-d) δ 7.96-7.88 (m, 2H), 7.83 (d, J=8.7 Hz, 2H), 7.37 (br d, J=8.5 Hz, 1H), 7.16 (d, J=8.6 Hz, 2H), 7.10 (d, J=7.4 Hz, 2H), 6.57 (t, J=75.9 Hz, 1H), 3.24 (s, 3H), 1.62 (s, 6H)

Example 408

$^1$H NMR (500 MHz, DMSO-d6) δ 7.95 (br d, J=8.5 Hz, 2H), 7.60 (br d, J=7.9 Hz, 2H), 7.47 (br d, J=8.2 Hz, 2H), 6.98 (s, 1H), 6.33 (s, 1H), 4.79 (dt, J=12.1, 6.0 Hz, 1H), 4.06 (s, 2H), 3.25 (s, 3H), 1.34 (d, J=6.1 Hz, 6H), 1.21 (s, 6H)

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

We claim:

1. A compound of formula I

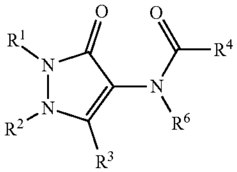

I or a pharmaceutically acceptable salt thereof, wherein $R^1$ is alkyl, haloalkyl, hydroxyalkyl, alkoxyalkyl, alkoxycarbonylalkyl, cycloalkyl, ($Ar^1$)alkyl, or $Ar^1$;

$Ar^1$ is cycloalkyl, piperidinyl, phenyl, pyridinyl, pyridazinyl, pyrimidinyl, pyrazinyl, pyrrolyl, furanyl, thienyl, pyrazolyl, isoxazolyl, isothiazolyl, imidazolyl, oxazolyl, thiazolyl, triazolyl, oxadiazolyl, thiadiazolyl, quinolinyl, isoquinolinyl, or quinoxalinyl and, is substituted with 0-2 $R^{5a}$ and 0-2 $R^{5b}$;

$R^2$ is alkyl or haloalkyl;

$R^3$ is phenyl or pyridinyl, and is substituted with 1 $R^{3a}$ and 0-2 $R^{3b}$;

$R^{3a}$ is halo, alkyl, haloalkyl, alkoxy, deuteroalkoxy, haloalkoxy, or cycloalkyl substituent in the para-position with respect to the pyrazol-3-one moiety;

$R^{3b}$ is halo, alkyl, hydroxy, or haloalkyl;

or $R^{3a}$ and the adjacent $R^{3b}$, together with the two carbon atoms they are attached to, form a 3-6 membered heterocycle comprising carbon atoms and 1-3 heteroatoms selected from N, NH, O, S, and substituted with 0-3 halo, hydroxy, alkyl, haloalkyl, or alkoxycarbonyl;

$R^4$ is phenyl or pyridinyl, and is substituted with 1 $R^{4a}$ and 0-2 $R^{4b}$;

$R^{4a}$ is halo, alkyl, cycloalkyl, haloalkyl, alkoxy, haloalkoxy, or pyrazolyl substituent in the para-position with respect to the amide moiety;

$R^{4b}$ is halo or haloalkyl;

$R^{5a}$ and $R^{5b}$ are independently cyano, halo, alkyl, haloalkyl, alkoxyalkyl, hydroxy, hydroxyalkyl, alkoxy, alkoxyalkoxy, hydroxyalkoxy, haloalkoxy, hydroxyhaloalkoxy, hydroxyalkoxyalkoxy, alkylsulfonylalkoxy, carboxamide, alkoxycarbonyl, alkylaminoalkyl, alkoxycarbonylalkoxy, hydroxyalkylcycloalkylalkyl, alkylsulfonyl, aminocarbonylalkyl, —$NR^7R^8$, cycloalkyl substituted with 0-3 halo, hydroxy, alkyl, or alkoxy, phenyl substituted with 0-3 halo, hydroxy, or alkyl, 4-8 membered heterocyclyl comprising carbon atoms and 1-3 heteroatoms selected from N, NH, O, S, and substituted with 0-3 halo, alkyl, hydroxyalkyl, haloalkyl, alkoxycarbonyl, or alkylsulfonyl, heterocyclyloxy, heterocyclylalkyl, or heterocyclylalkoxy, wherein the heterocyclyl moiety of the heterocyclyloxy, heterocyclylalkyl, and heterocyclylalkoxy comprises 4-8 carbon atoms and 1-3 heteroatoms selected from N, NH, O, S, and substituted with 0-3 halo, hydroxy, hydroxyalkyl, alkyl, or haloalkyl;

$R^6$ is hydrogen or lower alkyl;

$R^7$ and $R^8$ are independently hydrogen, alkyl, haloalkyl, hydroxyalkyl, halohydroxyalkyl, alkoxyalkyl, aminocarbonylalkyl, alkylsulfonyl; alkylaminocarbonylalkyl, cycloalkylaminocarbonylalkyl, cycloalkylalkyl, hydroxycycloalkylalkyl, hydroxyalkylcycloalkylalkyl, cycloalkylalkyl, cycloalkyl, wherein each cycloalkyl is substituted with 0-3 halo, hydroxy, or alkyl, or hydroxyalkyl, or 5-8 membered heterocyclyl comprising carbon atoms and 1-3 heteroatoms selected from N, NH, O, S, and substituted with 0-3 halo, hydroxy, alkyl, haloalkyl, or alkoxycarbonyl;

or $R^7$ and $R^8$, together with the nitrogen to which they are attached, form a 5-12 membered heterocycle comprising carbon atoms and 0-3 additional heteroatoms selected from N, NH, O, S, and substituted with 0-5 halo, hydroxy, alkyl, alkoxy, oxo, haloalkyl, cycloalkylalkyl, hydroxyalkyl, alkoxyalkyl, alkylsulfonyl, alkylsulfonylalkyl, aminocarbonyl, or alkoxycarbonyl;

provided that when $Ar^1$ is triazolyl, oxadiazolyl, or thiadiazolyl, $Ar^1$ is substituted with 0-1 $R^{5a}$ and 0-1 $R^{5b}$.

2. The compound of claim 1 or a pharmaceutically acceptable salt thereof, wherein $R^1$ is $Ar^1$.

3. The compound of claim 1 or a pharmaceutically acceptable salt thereof, wherein $R^3$ is phenyl substituted with 1 $R^{3a}$ and 0-2 $R^{3b}$;

$R^{3a}$ is halo, alkyl, haloalkyl, alkoxy, or deuteroalkoxy substituent in the para-position with respect to the pyrazol-3-one moiety; and $R^{3b}$ is halo or haloalkyl.

4. The compound of claim 1 or a pharmaceutically acceptable salt thereof, wherein $R^4$ is phenyl or pyridinyl substituted with 1 $R^{4a}$ in the para-position with respect to the amide moiety and 0-2 $R^{4b}$;

$R^{4a}$ is halo, alkyl, cycloalkyl, haloalkyl, alkoxy, or haloalkoxy; and $R^{4b}$ is halo or haloalkyl.

5. The compound of claim 1, having formula II

II

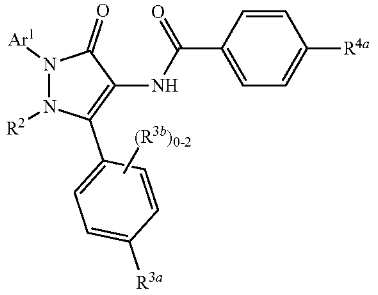

or a pharmaceutically acceptable salt thereof, wherein $Ar^1$ is

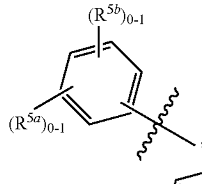

,

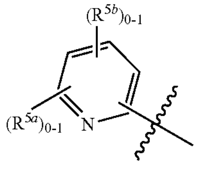

, or

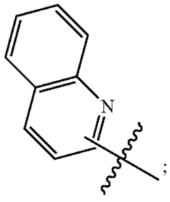

;

$R^2$ is alkyl or haloalkyl;

$R^{3a}$ is halo, alkyl, haloalkyl, alkoxy, deuteroalkoxy, haloalkoxy or cycloalkyl;

$R^{3b}$ is halo, alkyl, hydroxy, or haloalkyl;

or $R^{3a}$ and the adjacent $R^{3b}$, together with the two carbon atoms they are attached to, form a 3-6 membered heterocycle comprising carbon atoms and 1-3 heteroatoms selected from N, NH, O, S, and substituted with 0-3 halo, hydroxy, alkyl, haloalkyl, or alkoxycarbonyl;

$R^{4a}$ is halo, alkyl, cycloalkyl, haloalkyl, alkoxy, haloalkoxy, or pyrazolyl;

$R^{5a}$ and $R^{5b}$ are independently cyano, halo, alkyl, haloalkyl, alkoxyalkyl, hydroxy, hydroxyalkyl, alkoxy, alkoxyalkoxy, hydroxyalkoxy, haloalkoxy, hydroxyhaloalkoxy, hydroxyalkoxyalkoxy, alkylsulfonylalkoxy, carboxamide, alkoxycarbonyl, alkylaminoalkyl, alkoxycarbonylalkoxy, hydroxyalkylcycloalkylalkyl, alkylsulfonyl, aminocarbonylalkyl, —$NR^7R^8$, cycloalkyl substituted with 0-3 halo, hydroxy, alkyl, or alkoxy, phenyl substituted with 0-3 halo, hydroxy, or alkyl, 4-8 membered heterocyclyl comprising carbon atoms and 1-3 heteroatoms selected from N, O, NH, S, and substituted with 0-3 halo, alkyl, hydroxyalkyl, haloalkyl, alkoxycarbonyl, or alkylsulfonyl, heterocyclyloxy, heterocyclylalkyl or heterocyclylalkoxy wherein the heterocyclyl moiety of the heterocyclyloxy and heterocyclylalkoxy comprises 4-8 carbon atoms and 1-3 heteroatoms selected from N, NH, O, S, and substituted with 0-3 halo, hydroxy, hydroxyalkyl, alkyl, or haloalkyl; and $R^7$ and $R^8$ are independently hydrogen, alkyl, haloalkyl, hydroxyalkyl, halohydroxyalkyl, alkoxyalkyl, aminocarbonylalkyl, alkylsulfonyl; alkylaminocarbonylalkyl, cycloalkylaminocarbonylalkyl, cycloalkylalkyl, hydroxycycloalkylalkyl, hydroxyalkylcycloalkylalkyl, cycloalkylalkyl, cycloalkyl, wherein each cycloalkyl is substituted with 0-3 halo, hydroxy, or alkyl, or hydroxyalkyl, or 5-8 membered heterocyclyl comprising carbon atoms and 1-3 heteroatoms selected from N, NH, O, S, and substituted with 0-3 halo, hydroxy, alkyl, haloalkyl, or alkoxycarbonyl;

or $R^7$ and $R^8$, together with the nitrogen to which they are attached, form a 5-12 membered heterocycle comprising carbon atoms and 0-3 additional heteroatoms selected from N, NH, O, S and substituted with 0-5 halo, hydroxy, alkyl, alkoxy, oxo, haloalkyl, cycloalkylalkyl, hydroxyalkyl, alkoxyalkyl, alkylsulfonyl, alkylsulfonylalkyl, aminocarbonyl, or alkoxycarbonyl.

6. The compound of claim 5 or a pharmaceutically acceptable salt thereof, wherein $Ar^1$ is

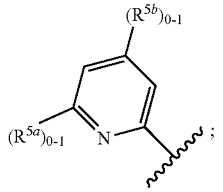

$R^{5a}$ is cyano, halo, alkyl, haloalkyl, alkoxyalkyl, hydroxyalkyl, alkoxy, haloalkoxy, carboxamide, alkoxycarbonyl, —$NR^7R^8$, cycloalkyl substituted with 0-1 halo, hydroxy, alkyl, or alkoxy, phenyl substituted with 0-1 halo, hydroxy, or alkyl, or 5-8 membered heterocyclyl comprising carbon atoms and 1-3 heteroatoms selected from N, NH, O, S, and substituted with 0-1 halo, hydroxy, or alkyl;

$R^{5b}$ is cyano, halo, alkyl, haloalkyl, alkoxyalkyl, hydroxyalkyl, alkoxy, haloalkoxy, carboxamide, alkoxycarbonyl, or cycloalkyl; and $R^7$ and $R^8$ are independently hydrogen, alkyl, haloalkyl, or hydroxyalkyl; or $R^7$ and $R^8$, together with the nitrogen to which they are attached, form a heterocycle with 0-3 additional heteroatoms selected from N, NH, O, S, and substituted with 0-3 halo, hydroxy, alkyl, alkoxy, or oxo.

7. The compound of claim 6 or a pharmaceutically acceptable salt thereof, wherein $Ar^1$ is

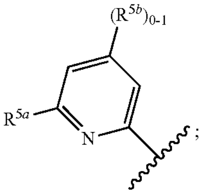

$R^{5a}$ is alkyl, hydroxyalkyl, —$NR^7R^8$, cyclobutyl substituted with 0-1 halo, hydroxy, alkyl, alkoxy, or phenyl;

$R^{5b}$ is alkoxy; and $R^7$ and $R^8$ are independently alkyl or hydroxyalkyl; or $R^7$ and $R^8$, together with the nitrogen to which they are attached, form a heterocycle with 0-2 additional nitrogen atoms and substituted with 0-3 halo, hydroxy, alkyl, alkoxy, or oxo.

8. The compound of claim 7 or a pharmaceutically acceptable salt thereof, wherein $R^{5a}$ is —$NR^7R^8$; and $R^7$ and $R^8$ are independently alkyl or hydroxyalkyl; or $R^7$ and $R^8$, together with the nitrogen to which they are attached form

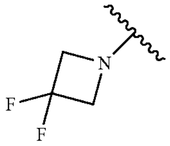 , 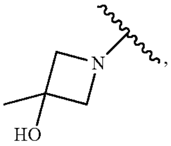 ,

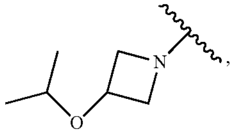 , 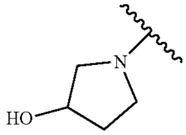 ,

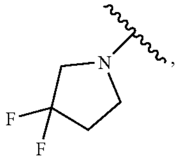 , 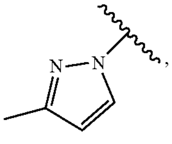 ,

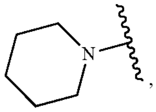 , 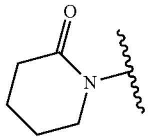 , 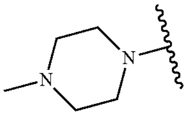 ,

-continued

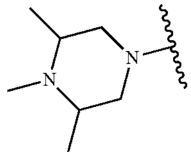, 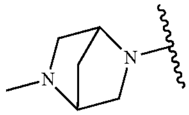,

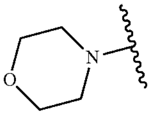, or 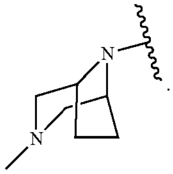.

9. The compound of claim 5, or a pharmaceutically acceptable salt thereof, wherein $Ar^1$ is

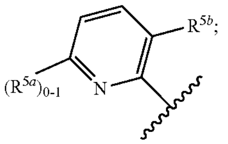

$R^{5a}$ is cyano, halo, alkyl, haloalkyl, hydroxyalkyl, alkoxy, haloalkoxy, —$NR^7R^8$, or cycloalkyl substituted with 0-1 alkoxy;

$R^{5b}$ is cyano, halo, alkyl, or haloalkyl; and $R^7$ and $R^8$ are independently alkyl or hydroxyalkyl; or $R^7$ and $R^8$, together with the nitrogen to which they are attached, form

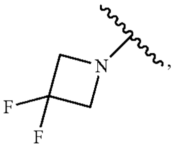, 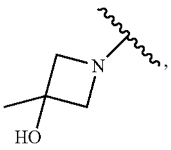,

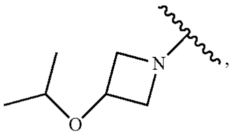, 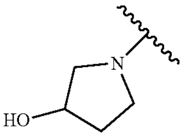,

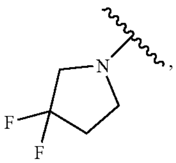, 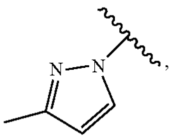,

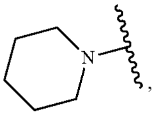, 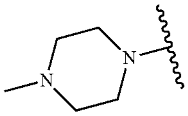,

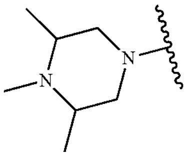, 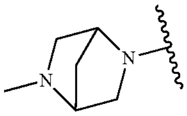,

-continued

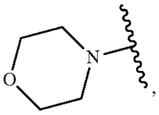, or 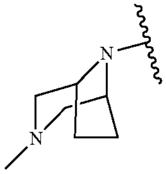.

10. The compound of claim 5, or a pharmaceutically acceptable salt thereof, wherein $Ar^1$ is

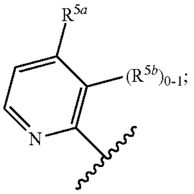

$R^{5a}$ is cyano, halo, alkyl, haloalkyl, alkoxyalkyl, hydroxyalkyl, alkoxy, or haloalkoxy; and $R^{5b}$ is cyano, halo, alkyl, haloalkyl, alkoxyalkyl, hydroxyalkyl, alkoxy, or haloalkoxy.

11. The compound of claim 5, or a pharmaceutically acceptable salt thereof, wherein $Ar^1$ is

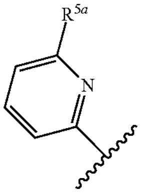 or 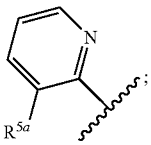;

and $R^{5a}$ is alkyl, haloalkyl, hydroxyalkyl, alkoxy, haloalkoxy, or cycloalkyl.

12. The compound of claim 5, or a pharmaceutically acceptable salt thereof, wherein $Ar^1$ is

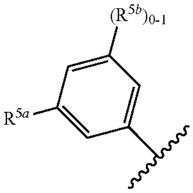

$R^{5a}$ is halo, alkoxy, haloalkoxy, carboxamide, alkoxycarbonyl, or cycloalkyl substituted with 0-1 hydroxy; and $R^{5b}$ is cyano, halo, alkyl, haloalkyl, alkoxyalkyl, hydroxyalkyl, alkoxy, haloalkoxy, carboxamide, alkoxycarbonyl, or cycloalkyl.

13. The compound of claim 5, or a pharmaceutically acceptable salt thereof, wherein $Ar^1$ is

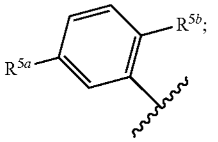

$R^{5a}$ is cyano, halo, alkyl, haloalkyl, alkoxyalkyl, hydroxyalkyl, or alkoxy; and $R^{5b}$ is cyano, halo, alkyl, or haloalkyl.

14. The compound of claim 5, or a pharmaceutically acceptable salt thereof, wherein $Ar^1$ is

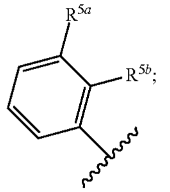

$R^{5a}$ is halo; and $R^{5b}$ is halo.

15. The compound of claim 5, or a pharmaceutically acceptable salt thereof, wherein $Ar^1$ is

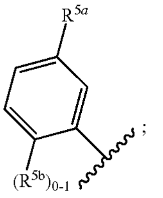

$R^{5a}$ is halo, alkyl, alkoxy, or haloalkoxy; and $R^{5b}$ is halo, alkyl, haloalkyl, alkoxyalkyl, hydroxyalkyl, alkoxy, or haloalkoxy.

16. The compound of claim 5, having formula III

III

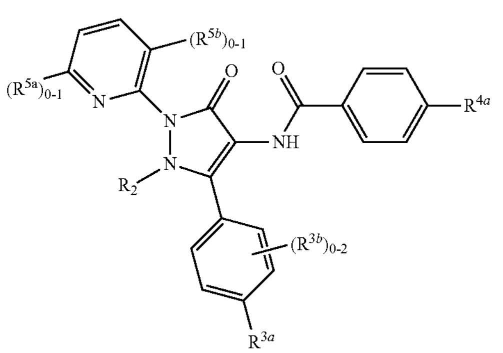

or a pharmaceutically acceptable salt thereof, wherein $R^2$ is alkyl or haloalkyl;

$R^{3a}$ is halo, alkyl, haloalkyl, alkoxy, deuteroalkoxy, haloalkoxy or cycloalkyl;

$R^{3b}$ is halo, alkyl, hydroxy, or haloalkyl; or $R^{3a}$ and the adjacent $R^{3b}$, together with the two carbon atoms they are attached to, form a 3-6 membered heterocycle comprising carbon atoms and 1-3 heteroatoms selected from N, NH, O, S, and substituted with 0-3 halo, hydroxy, alkyl, haloalkyl, or alkoxycarbonyl;

$R^{4a}$ is halo, alkyl, cycloalkyl, haloalkyl, alkoxy, haloalkoxy, or pyrazolyl;

$R^{5a}$ is halo, hydroxyalkyl, alkoxy, alkoxyalkoxy, hydroxyalkoxy, alkylaminoalkyl, alkoxycarbonylalkoxy, hydroxyalkylcycloalkylalkyl, alkylsulfonyl, aminocarbonylalkyl, —$NR^7R^8$, 5-8 membered heterocyclyl comprising carbon atoms and 1-3 heteroatoms selected from N, NH, O, S, and substituted with 0-3 halo, hydroxy, alkyl, haloalkyl, alkoxycarbonyl, or alkylsulfonyl, or heterocyclylalkyl wherein the heterocyclyl comprises 5-8 carbon atoms and 1-3 heteroatoms selected from N, NH, O, S, and substituted with 0-3 halo, hydroxy, alkyl, or haloalkyl;

$R^{5b}$ is cyano, halo, alkyl, alkoxy, or haloalkyl; and $R^7$ and $R^8$ are independently hydrogen, alkyl, haloalkyl, hydroxyalkyl, halohydroxyalkyl, alkoxyalkyl, aminocarbonylalkyl, alkylsulfonyl; alkylaminocarbonylalkyl, cycloalkylaminocarbonylalkyl, cycloalkylalkyl, hydroxycycloalkylalkyl, hydroxyalkylcycloalkylalkyl, cycloalkyl, wherein each cycloalkyl is substituted with 0-3 halo, hydroxy, or alkyl, or hydroxyalkyl, or 5-8 membered heterocyclyl comprising carbon atoms and 1-3 heteroatoms selected from N, NH, O, S, and substituted with 0-3 halo, hydroxy, alkyl, haloalkyl, or alkoxycarbonyl;

or $R^7$ and $R^8$, together with the nitrogen to which they are attached, form a 5-12 membered heterocycle comprising carbon atoms and 0-3 additional heteroatoms selected from N, NH, O, S and substituted with 0-5 halo, hydroxy, alkyl, alkoxy, oxo, haloalkyl, cycloalkylalkyl, hydroxyalkyl, alkoxyalkyl, alkylsulfonyl, alkylsulfonylalkyl, aminocarbonyl, or alkoxycarbonyl.

17. The compound of claim 16, having formula IV

IV

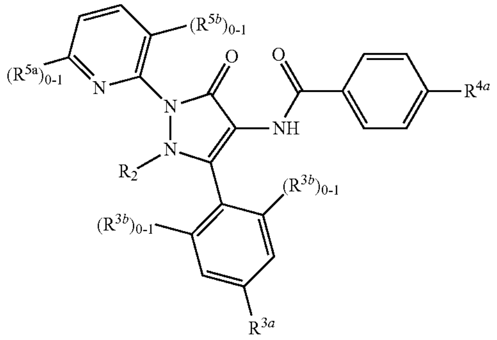

or a pharmaceutically acceptable salt thereof, wherein $R^{5a}$ is halo, hydroxyalkyl, alkoxy, alkoxyalkoxy, hydroxyalkoxy, hydroxyalkylcycloalkylalkyl, aminocarbonylalkyl, —$NR^7R^8$, or

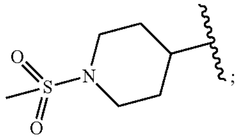 [SMILES: *C1CCN(S(C)(=O)=O)CC1];

$R^{5b}$ is halo or haloalkyl; and $R^7$ and $R^8$ are independently hydrogen, alkyl, hydroxyalkyl, halohydroxyalkyl, alkoxyalkyl, aminocarbonylalkyl, hydroxycycloalkylalkyl, hydroxyalkylcycloalkylalkyl, cycloalkylalkyl, cycloalkyl,

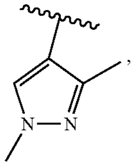, or 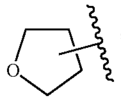;

or $R^7$ and $R^8$, together with the nitrogen to which they are attached form

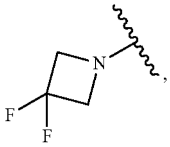, 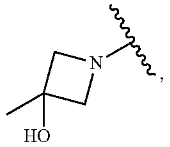,

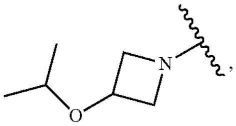, 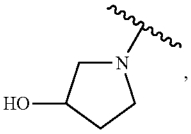,

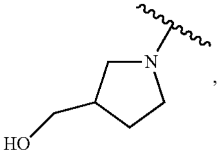, 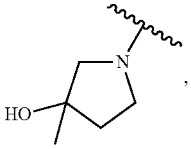,

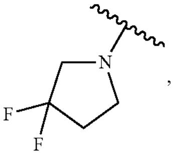, 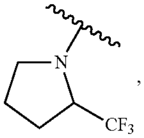, 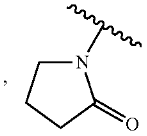,

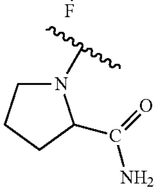, 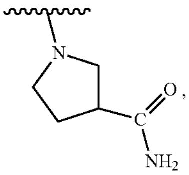, 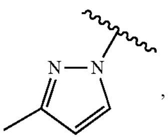,

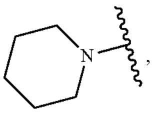, 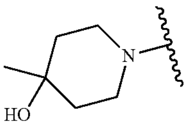, 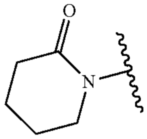,

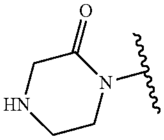, 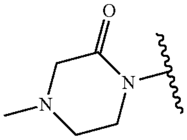,

-continued

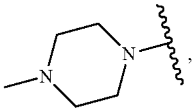, 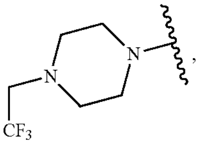,

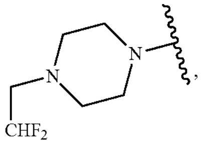, 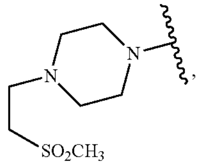,

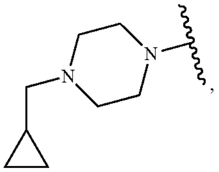, 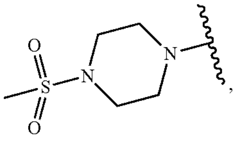,

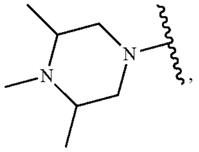, 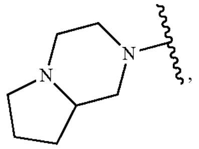, or

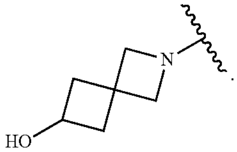.

18. The compound of claim 17, having formula V

V

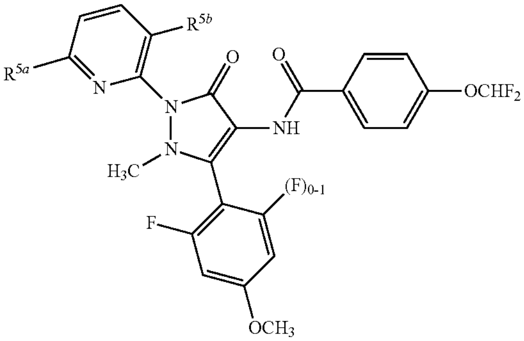

or a pharmaceutically acceptable salt thereof, wherein $R^{5a}$ is halo, hydroxyalkyl, alkoxyalkoxy, hydroxyalkoxy, —$NR^7R^8$, or

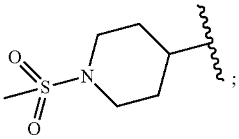 [SMILES: *C1CCN(S(C)(=O)=O)CC1];

$R^{5b}$ is Cl or $CF_3$;

$R^7$ is hydrogen; and $R^8$ is alkyl, hydroxyalkyl, halohydroxyalkyl, alkoxyalkyl, aminocarbonylalkyl, hydroxycycloalkylalkyl, hydroxyalkylcycloalkylalkyl, cycloalkylalkyl, cycloalkyl,

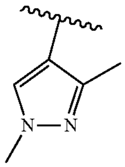, or 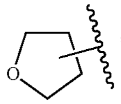;

or $R^7$ and $R^8$, together with the nitrogen to which they are attached form

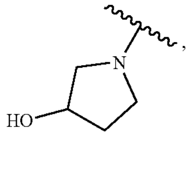, 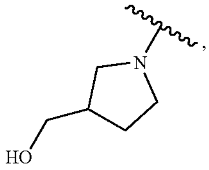,

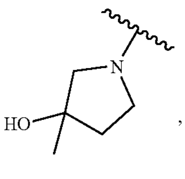, 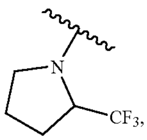, 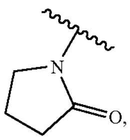,

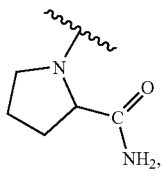, 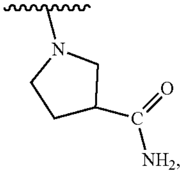,

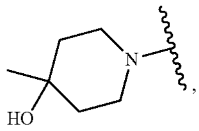, 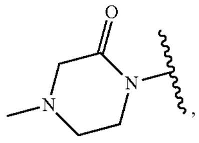,

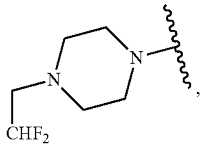, 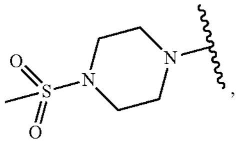, or

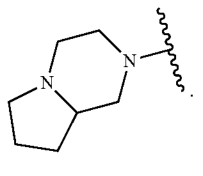.

19. The compound of claim 5, having formula VI

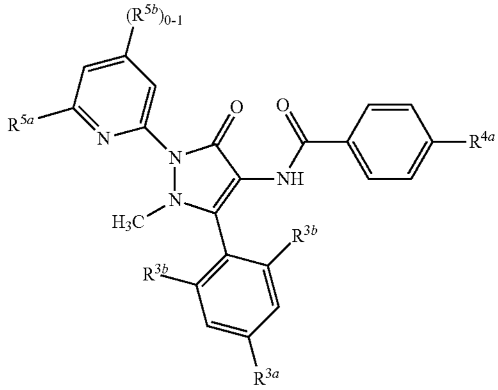
VI or a pharmaceutically acceptable salt thereof, wherein $R^{3a}$ is halo, alkyl, haloalkyl, alkoxy, haloalkoxy, or deuteroalkoxy;

$R^{3b}$ is halo;

$R^{4a}$ is haloalkoxy;

$R^{5a}$ is cyano, halo, alkyl, haloalkyl, hydroxyalkyl, alkoxyalkoxy, hydroxyalkoxy, hydroxyhaloalkoxy, hydroxyalkoxyalkoxy, alkylsylfonylalkoxy, 5-8 membered heterocyclyl comprising carbon atoms and 1-3 heteroatoms selected from N, NH, O, S, and substituted with 0-3 halo, alkyl, hydroxyalkyl, haloalkyl, or alkylsulfonyl, or heterocyclylalkoxy wherein the heterocyclyl comprises 5-8 carbon atoms and 1-3 heteroatoms selected from N, NH, O, S, and substituted with 0-3 halo, hydroxy, hydroxyalkyl, alkyl, or haloalkyl; and $R^{5b}$ is cyano, alkyl, hydroxyalkyl, alkoxy, hydroxyalkoxy, 5-8 membered heterocyclyl comprising carbon atoms and 1-3 heteroatoms selected from N, NH, O, S, and substituted with 0-3 halo, alkyl, or heterocyclyloxy wherein the heterocyclyl moiety comprises 5-8 carbon atoms and 1-3 heteroatoms selected from N, NH, O, S, and substituted with alkyl, heterocyclyl substituted with 0-1 alkyl.

20. The compound of claim 19, or a pharmaceutically acceptable salt thereof, wherein $R^{5a}$ is

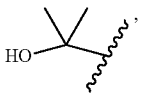, 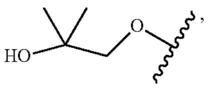, 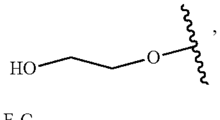,

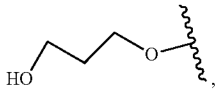, 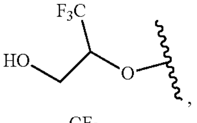,

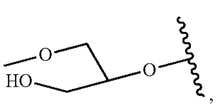, 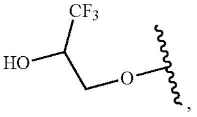,

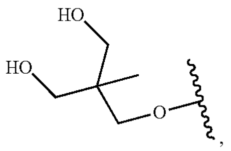, 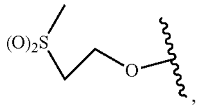,

-continued

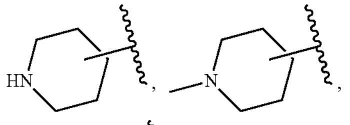

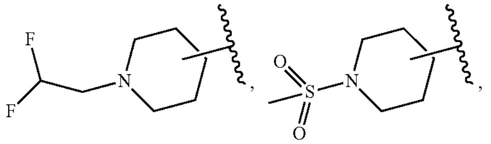

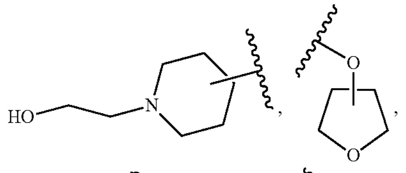

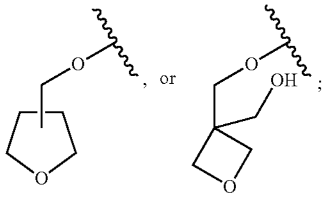

and $R^{5b}$ is —$OCH_3$ or $CH_3$.

21. The compound of claim 19, having formula VII

VII

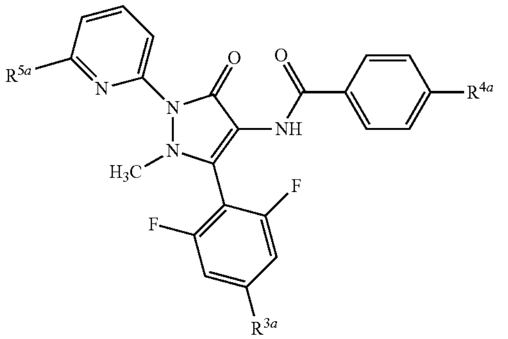

or a pharmaceutically acceptable salt thereof, wherein $R^{3a}$ is Cl, $CF_3$, $CH_3$, $CH_3CH_2$, $CD_3$, $OCH_3$, $OCF_3$, $OCF_2$, or $OCD_3$;

$R^{4a}$ is $OCF_3$ or $OCF_2$; and $R^{5a}$ is

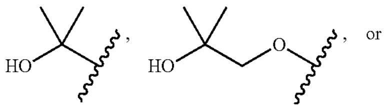

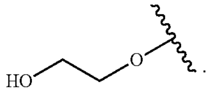

22. The compound of claim 5, having formula VIII

VIII

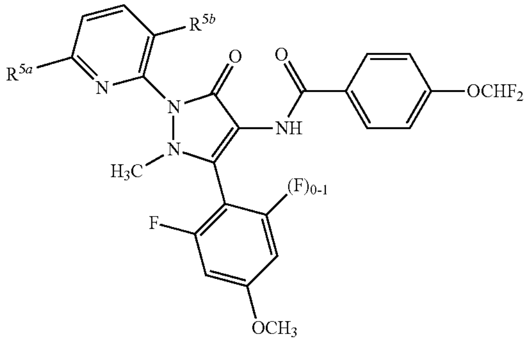

or a pharmaceutically acceptable salt thereof, wherein $R^{5a}$ is cyano, alkyl, or haloalkyl;

$R^{5b}$ is cyano, alkyl, hydroxyalkyl, alkoxy, hydroxyalkoxy, —$NR^7R^8$,

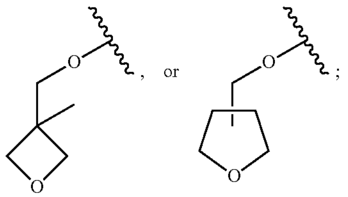

$R^7$ is hydrogen or alkyl; and $R^8$ is alkyl.

23. A pharmaceutical composition comprising a compound of claim 1, or a pharmaceutically acceptable salt thereof, and a pharmaceutically acceptable carrier, diluent, or excipient.

24. A method for treating a heart disease comprising administering a therapeutically effective amount of a pharmaceutical composition of claim 23 to a patient in need thereof.

25. The method of claim 24 wherein the heart disease is selected from the group consisting of angina pectoris, unstable angina, myocardial infarction, heart failure, acute coronary disease, acute heart failure, chronic heart failure, and cardiac iatrogenic damage.

26. The method of claim 25 wherein the heart failure is selected from the group consisting of congestive heart failure, systolic heart failure, diastolic heart failure, heart failure with reduced ejection fraction ($HF_REF$), heart failure with preserved ejection fraction ($HF_PEF$), acute heart failure, chronic heart failure of ischemic and non-ischemic origin.

27. A compound of claim 1, having FPR2 $EC_{50}$ values≤0.005 μM.

* * * * *